US010640495B2

(12) United States Patent
Yukimasa et al.

(10) Patent No.: US 10,640,495 B2
(45) Date of Patent: May 5, 2020

(54) HETEROCYCLE DERIVATIVES HAVING TRKA INHIBITORY ACTIVITY

(71) Applicant: Shionogi & Co., Ltd., Osaka (JP)

(72) Inventors: Akira Yukimasa, Osaka (JP); Kenichiroh Nakamura, Osaka (JP); Masanao Inagaki, Osaka (JP); Kazuya Kano, Osaka (JP); Motohiro Fujiu, Osaka (JP); Hiroki Yamaguchi, Osaka (JP); Kayoko Hata, Osaka (JP); Takatsugu Inoue, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 15/741,875

(22) PCT Filed: Jul. 6, 2016

(86) PCT No.: PCT/JP2016/069968
§ 371 (c)(1),
(2) Date: Jan. 4, 2018

(87) PCT Pub. No.: WO2017/006953
PCT Pub. Date: Jan. 12, 2017

(65) Prior Publication Data

US 2018/0201607 A1 Jul. 19, 2018

(30) Foreign Application Priority Data

Jul. 7, 2015 (JP) ................................ 2015-135844
Jan. 13, 2016 (JP) ................................ 2016-004010

(51) Int. Cl.
*C07D 405/14* (2006.01)
*C07D 405/12* (2006.01)
(Continued)

(52) U.S. Cl.
CPC ........ *C07D 405/14* (2013.01); *A61K 31/4155* (2013.01); *A61K 31/422* (2013.01);
(Continued)

(58) Field of Classification Search
CPC .. C07D 405/12; C07D 405/14; C07D 231/38; C07D 403/14; C07D 413/14;
(Continued)

(56) References Cited

U.S. PATENT DOCUMENTS 4,855,316 A 8/1989 Horwell et al.
4,906,655 A 3/1990 Horwell et al.
(Continued)

FOREIGN PATENT DOCUMENTS

EP 0 372 466 A2 6/1990
EP 2 842 955 A1 3/2015
(Continued)

OTHER PUBLICATIONS

Prokof'ev et al., 12 (No. 6) Vestinik Moskovskogo Universiteta, Seriya Matematiki, Mekhanik, Astronomi, Fizik, Khimi 215-24 (1957) (Year: 1957).*
(Continued)

*Primary Examiner* — Timothy R Rozof
(74) *Attorney, Agent, or Firm* — Sterne, Kessler, Goldstein & Fox P.L.L.C.

(57) ABSTRACT

The present invention provides a compound having a TrkA inhibitory activity or a pharmaceutically acceptable salt thereof.

The present invention relates to a compound represented by Formula (I):

(I)

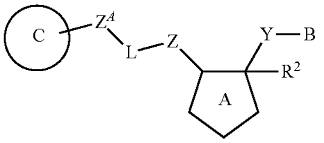

wherein -L- is —C(═X)—, or the like, —Z— is —$NR^5$—, or the like, —$Z^A$— is —$NR^{5A}$—, or the like, B is substituted or unsubstituted aromatic carbocyclyl, or the like, Y is a single bond, or the like, the ring C is a substituted or unsubstituted aromatic heterocycle, or the like, $R^2$ is a hydrogen atom, or the like, and the group represented by

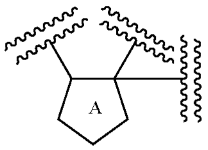

is a group represented by Formula:

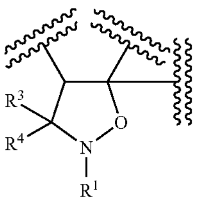

, 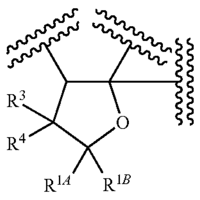 ,

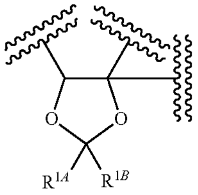

, 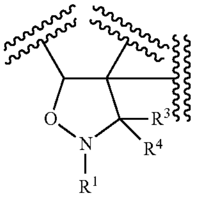 , (Continued)

-continued

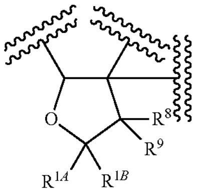

,

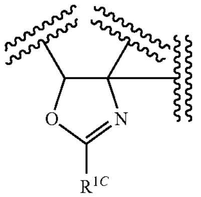

, or

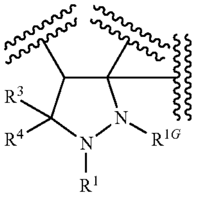

, or a pharmaceutically acceptable salt thereof, and a pharmaceutical composition comprising the same.

20 Claims, No Drawings

(51) Int. Cl.

| | |
|---|---|
| ***A61K 31/4155*** | (2006.01) |
| ***A61K 31/427*** | (2006.01) |
| ***A61K 31/433*** | (2006.01) |
| ***A61K 31/437*** | (2006.01) |
| ***A61K 31/4439*** | (2006.01) |
| ***A61K 31/454*** | (2006.01) |
| ***A61K 31/506*** | (2006.01) |
| ***A61K 31/519*** | (2006.01) |
| ***C07D 231/38*** | (2006.01) |
| ***C07D 403/14*** | (2006.01) |
| ***C07D 413/14*** | (2006.01) |
| ***C07D 417/14*** | (2006.01) |
| ***C07D 471/04*** | (2006.01) |
| ***C07D 487/04*** | (2006.01) |
| ***C07D 487/08*** | (2006.01) |
| ***C07D 491/048*** | (2006.01) |
| ***C07D 491/056*** | (2006.01) |
| ***C07D 491/08*** | (2006.01) |
| ***C07D 491/107*** | (2006.01) |
| ***C07D 498/04*** | (2006.01) |
| ***C07F 7/18*** | (2006.01) |
| ***A61K 31/422*** | (2006.01) |

(52) U.S. Cl.

CPC .......... *A61K 31/433* (2013.01); *A61K 31/437* (2013.01); *A61K 31/4439* (2013.01); *A61K 31/454* (2013.01); *A61K 31/506* (2013.01); *A61K 31/519* (2013.01); *C07D 231/38* (2013.01); *C07D 403/14* (2013.01); *C07D 405/12* (2013.01); *C07D 413/14* (2013.01); *C07D 417/14* (2013.01); *C07D 471/04* (2013.01); *C07D 487/04* (2013.01); *C07D 487/08* (2013.01); *C07D 491/048* (2013.01); *C07D 491/056* (2013.01); *C07D 491/08* (2013.01); *C07D 491/107* (2013.01); *C07D 498/04* (2013.01); *C07F 7/1804* (2013.01)

(58) Field of Classification Search

CPC .. C07D 417/14; C07D 471/04; C07D 487/04; C07D 487/08; C07D 491/048; C07D 491/056; C07D 491/08; C07D 491/107; C07D 498/04; C07F 7/1804; A61K 31/4155; A61K 31/427; A61K 31/433; A61K 31/437; A61K 31/4439; A61K 31/454; A61K 31/506; A61K 31/519

See application file for complete search history.

(56) References Cited

U.S. PATENT DOCUMENTS

| | | | |
|---|---|---|---|
| 2015/0111865 | A1 | 4/2015 | Takeuchi et al. |
| 2016/0000783 | A1 | 1/2016 | Takeuchi et al. |
| 2016/0280684 | A1 | 9/2016 | Takeuchi et al. |
| 2017/0027939 | A1 | 2/2017 | Takeuchi et al. |
| 2017/0240512 | A1 | 8/2017 | Yukimasa et al. |
| 2017/0340634 | A1 | 11/2017 | Takeuchi et al. |

FOREIGN PATENT DOCUMENTS

| | | | |
|---|---|---|---|
| JP | 1 96191 | | 4/1989 |
| WO | WO 97/22619 | | 6/1997 |
| WO | WO 99/16431 | | 4/1999 |
| WO | WO 00/35452 | | 6/2000 |
| WO | WO 02/02525 | A2 | 1/2002 |
| WO | WO 03/103677 | A1 | 12/2003 |
| WO | WO 2004/110993 | A2 | 12/2004 |
| WO | WO 2005/026113 | A1 | 3/2005 |
| WO | WO 2005/110994 | A2 | 11/2005 |
| WO | WO 2009/074260 | A1 | 6/2009 |
| WO | WO 2009/131196 | A1 | 10/2009 |
| WO | WO 2012/158413 | A2 | 11/2012 |
| WO | WO 2012/174199 | A1 | 12/2012 |
| WO | WO 2014/052563 | A2 | 4/2014 |
| WO | WO 2014/053965 | A1 | 4/2014 |
| WO | WO 2014/053967 | A1 | 4/2014 |
| WO | WO 2014/053968 | A1 | 4/2014 |
| WO | WO 2014/053968 | A8 | 4/2014 |
| WO | WO 2014/078322 | A1 | 5/2014 |
| WO | WO 2014/078323 | A1 | 5/2014 |
| WO | WO 2014/078325 | A1 | 5/2014 |
| WO | WO 2014/078328 | A1 | 5/2014 |
| WO | WO 2014/078331 | A1 | 5/2014 |
| WO | WO 2014/078372 | A1 | 5/2014 |
| WO | WO 2014/078378 | A1 | 5/2014 |
| WO | WO 2014/078408 | A1 | 5/2014 |
| WO | WO 2014/078417 | A1 | 5/2014 |
| WO | WO 2014/078454 | A1 | 5/2014 |
| WO | WO 2014/129431 | A1 | 8/2014 |
| WO | WO 2015/035278 | A1 | 3/2015 |
| WO | WO 2015/039333 | A1 | 3/2015 |
| WO | WO 2015/039334 | A1 | 3/2015 |
| WO | WO 2015/042085 | A2 | 3/2015 |
| WO | WO 2015/042088 | A1 | 3/2015 |
| WO | WO 2015/159175 | A1 | 10/2015 |
| WO | WO 2015/170218 | A1 | 11/2015 |
| WO | WO 2015/175788 | A1 | 11/2015 |
| WO | WO 2016/116900 | A1 | 7/2016 |
| WO | WO 2017/135399 | A1 | 8/2017 |

OTHER PUBLICATIONS

Allen, S., et al., "Clinical relevance of the neurotrophins and their receptors," *Clinical Science* 110: 175-191, Biochemical Society, Great Britain (2006).

Benson, S., et al., "Second-Generation Total Synthesis of Spirastrellolide F Methyl Ester: The Alkyne Route," *Angewandte Chemie* 50: 8739-8744, Wiley-VCH, Germany (2011).

Chao, M., "Neurotrophins and Their Receptors: A Convergence Point for Many Signalling Pathways," *Nature Neuroscience* 4: 299-309, Nature Publishing Group, United Kingdom (2003).

Chennamadhavuni, D., et al., "A solvent-free approach to glycosyl amides: toward the synthesis of α-N-galactosyl ceramides," *Tetrahedron Letters* 56: 3583-3586, Elsevier Ltd., United States (2015).

Ellis, C., et al., "Synthesis and evaluation of thiazepines as interleukin-1β converting enzyme (ICE) inhibitors," *Bioorganic & Medicinal Chemistry Letters* 16: 4728-4732, Elsevier, Netherlands (2006).

(56) References Cited

OTHER PUBLICATIONS

Geng, H., et al., "Synthesis of the Revised Structure of Acortatarin A," *European Journal of Organic Chemistry* 2014: 6227-6241, Wiley, Germany (2014).
Ghilardi, J., et al., "Administration of a tropomyosin receptor kinase inhibitor attenuates sarcoma-induced nerve sprouting, neuroma formation and bone cancer pain," *Molecular Pain* 6: 87(12 pages), BioMed Central, United Kingdom (2010).
Ghilardi, J., et al., "Sustained blockade of neurotrophin receptors TrkA, TrkB and TrkC reduces non-malignant skeletal pain but not the maintenance of sensory and sympathetic nerve fibers," *Bone* 48: 389-398, Elsevier, Netherlands (2011).
Halfpenny, P., et al., "Highly Selective k-Opioid Analgesics. 2. Synthesis and Structure-Activity Relationships of Novel N-[(2-Aminocyclohexyl)aryl] acetamide Derivatives," *Journal of Medicinal Chemistry* 32:1620-1626, American Chemical Society, United States (1989).
Halfpenny, P., et al., "Highly Selective k-Opioid Analgesics. 3. Synthesis and Structure-Activity Relationships of Novel N-[2-(1-Pryyolidinyl)-4- or -5 substituted-cyclohexyl] arylacetamide Derivatives," *Journal of Medicinal Chemistry* 33:286-291, American Chemical Society, United States (1990).
Indo, Y., "Nerve growth factor and the physiology of pain: lessons from congenital insensitivity to pain with anhidrosis," *Clinical Genetics* 82: 341-350, Wiley-Blackwell, United States (2012).
Mantyh, P., et al., "Antagonism of Nerve Growth Factor-TrkA Signaling and the Relief of Pain," *Anesthesiology* 115: 189-204, Lippincott Williams & Wilkins, United States (2011).
McCarthy, C., et al., Tropomyosin receptor kinase inhibitors: a patent update 2009-2013, *Expert Opinion on Therapeutic Patents* 24: 731-744, Taylor & Francis, United Kingdom (2014).
McKelvey, L., et al., "Nerve growth factor-mediated regulation of pain signaling and proposed new intervention strategies in clinical pain management," *Journal of Neurochemistry* 24: 276-289, International Society for Neurochemistry, Wiley (2013).
Meyer, J., et al., "Remarkable leukemogenic potency and quality of a constitutively active neurotrophin receptor, ΔTrkA," *Leukemia* 21: 2171-2180, Nature Publishing Group, United Kingdom (2007).
Pinski, J., et al., "Trk Receptor Inhibition Induces Apoptosis of Proliferating but not Quiescent Human Osteoblasts," *Cancer Research* 62: 986-989, United Kingdom (2002).
Stachel, S., et al., "Maximizing Diversity from a Kinase Screen: Identification of Novel and Selective pan-Trk Inhibitors for Chronic Pain," *Journal of Medicinal Chemistry* 57: 5800-5816, ACS Publications, United States (2014).
Truzzi, F., et al., "Neutrophins in healthy and diseased skin," *Dermato-Endocrinology* 3: 32-36, Taylor & Francis, United Kingdom (2011).
Vaishnavi, A., et al., "Oncogenic and drug-sensitive NTRK1 rearrangements in lung cancer," *Nature Medicine* 19: 1469-1472, Nature Publishing Group, United Kingdom (2013).
Wang, T., et al., "Trk kinase inhibitors as new treatments for cancer and pain," *Expert Opinion on Therapeutic Patents* 19: 305-319, Taylor & Francis, United Kingdom (2009).
Wang, Y., et al., "Synthesis and evaluation of unsaturated caprolactams as interleukin-1β converting enzyme (ICE) inhibitors," *Bioorganic & Medicinal Chemistry Letters* 15: 1311-1322, Elsevier, Netherlands (2007).
Notification of Transmittal of the Translation of the International Preliminary Report on Patentability for International Application No. PCT/JP2016/069968, International Searching Authority, Netherlands, dated Jan. 18, 2018, 1 page.
International Preliminary Report on Patentability for International Application No. PCT/JP2016/069968, International Bureau of WIPO, Switzerland, dated Jan. 9, 2018, 1 page.
English Translation of Written Opinion for International Application No. PCT/JP2016/069968, International Bureau of WIPO, Switzerland, dated Oct. 11, 2016, 8 pages.
Ashraf, S., et al., "Selective Inhibition of Tropomyosin-receptor-kinase A (TrkA) reduces pain and joint damage in two rat models of inflammatory arthritis," Arthritis Research & Therapy 18(97): p. 11, Springer, Netherlands (2016).
Gura, Trish., "Systems for Identifying New Drugs Are Often Faulty," Science Magazine 278(5340):1041-1042, American Association for the Advancement of Science, United States (1997).
Herbrich, S.M., et al., "Characterization of TRKA signaling in acute myeloid leukemia," Oncotarget 9(53):30092-30105, Impact Journals, United States (2018).
Johnson, Ji., et al., "Relationships between drug activity in NCI preclinical in vitro and in vivo models and early clinical trials," British Journal of Cancer 84(10): 1424-1431, Cancer Research Campaign, United Kingdom (2001).
Pearce, H.L., et al., "Failure modes in anticancer drug discovery and development," Cancer Drug Design and Discovery (18.2): 424-435, Elsevier, Netherlands (2008).
Schulz, W., "Chapter 1: An Introduction to Human Cancers," Molecular Biology of Human Cancers, An Advanced Student's Textbook: p. 25, Springer, Netherlands (2007).
Simone, Joseph V., "Oncology," Part XIV, 154: 1004-1010, Cecil Textbook of Medicine, 20th ed. vol. 1., W.B. Saunders Company, United States (1997).
Extended European Search Report for EP Application No. EP16821422.9, Munich, Germany, dated Feb. 13, 2019, 10 pages.
Golisade, A., et al., "Improving an Antitrypanosomal Lead Applying Nucleophilic Substitution on a Safety Catch Linker," Bioorganic & Medicinal Chemistry 10(1):159-165, Elsevier, Netherlands (2002).
Li, H., et al., "Synthesis of 2'-Amino-2'-deoxyuridine modified by 1,8-Naphthalimide," Synthetic Communications 36(4):1933-40, Taylor & Francis Group, England (2006).
Kawai, K., et al., "Excess electron transfer in DNA Studied by Pulse Radiolysis and γ-Radiolysis of Naphthalimide and lodouridine Modified ODN," J Phys Chem 107(36):12838-12841, American Chemical Society, United States (2006).
Kosiova, I., et al., "Synthesis of coumarin or ferrocene labeled nucleosides via Staudinger ligation," Beilsten Journal of Organic Chemistry 2(1):23, Beilstein-Institut, Germany (2006).
Noe, C.R. et al., "Novel Three-Atom 2'-5' Linkages in Antisense Nucleotides: Synthesis and Pairing Properties of Dinucleotides with a Carboxylic Ester Linkage," Arch Pharm 328:743-744, Elsevier, Netherlands (1995).
Notz, W., et al., "De Novo Synthesis of a Methylene-Bridged Neu5Ac-α-(2,3)-Gal C-Disaccharide," J. Org. Chem. 66(12):4250-4260, American Chemical Society, United States (2001).

* cited by examiner

HETEROCYCLE DERIVATIVES HAVING TRKA INHIBITORY ACTIVITY

TECHNICAL FIELD

The present invention relates to a compound that has a TrkA inhibitory activity and is useful in the treatment and/or prevention of TrkA mediated disorders, or a pharmaceutically acceptable salt thereof, and a pharmaceutical composition comprising the same.

BACKGROUND ART

The tropomyosin receptor kinase (Trk) is a family of receptor tyrosine kinases and has a function as a receptor of neurotrophin (NT). Three major subtypes of Trk receptors are TrkA high-affinity receptor for nerve growth factor (NGF), TrkB high-affinity receptor for brain-derived neutrophic factor (BDNF) and NT-4/5, and TrkC high-affinity receptor for NT-3. All receptors involve in various physiological function in vivo. TrkA is mainly expressed in peripheral and central nerves, and involves in neuronal development and differentiation, and maintenance of neuronal functions. The gene mutation in TrkA is associated with painless anhidrosis in human (Patent Documents 1, 2 and Non-patent Documents 1 to 3). The activation of NGF-TrkA signal produces hypralgesia (Non-patent Documents 4 to 6). Clinical and non-clinical researches regarding anti-NGF antibodies and non-clinical researches regarding Trk inhibitors reveal the involvement of NGF-TrkA signal or NT-Trk signal in the pain of osteoarthritis, rheumatoid arthritis, bone fracture, interstitial cystitis, chronic pancreatitis and prostatitis in addition to nociceptive pain such as chronic low back pain, neuropathic pain such as diabetic peripheral neuropathic pain, acute pain sucha as postoperative pain and chronic pain such as pelvic pain and cancer pain (Patent Documents 1, 2 and Non-patent documents 7, 8).

Trk receptors are also expressed in several types of cancer cells such as neuroblastoma, prostate cancer, lung cancer, breast cancer, gastric cancer and pancreatic cancer, and involve in the proliferation and migration of cancer cells. The fusion protein combined with TrkA kinase domain causes the proliferation of lung cancer cells. Trk inhibitor is shown to suppress the proliferation and metastasis of cancer cells in animal model. (Patent Document 1 and Non-patent Documents 9 to 12). Furthermore, Trk receptors are expressed in mast cells, eosinophils, immunocompetent cells such as T and B cells and keratinocytes, and NGF-trkA signal or NT-Trk signal involves in inflammatory bowel diseases such as ulcerative colitis and Crohn's disease, allergic diseases such as asthma and rhinitis, and skin diseases such as psoriasis, atopic dermatitis and pruritus (Patent Documents 1, 2). In addition, the inhibition of NGF-TrkA signal improves the overactive bladder (Patent Document 1). NT-Trk signal also involves in Sjogren's syndrome (Patent Document 1) and endometriosis (Patent Document 1). TrkA receptor plays a critical role in the infection process of the parasitic infection of *Trypanosoma cruzi* (Chagas disease) (Patent Document 1). Therefore, the compounds having an inhibitory activity for TrkA will be effective for various diseases including nociceptive pain, neuropathic pain, cancer, inflammatory diseases, allergic diseases and dermatological diseases.

The compounds that have an inhibitory activity for TrkA are disclosed in Patent Documents 1 to 16 and Non-patent Documents 6, 13 to 14. However, the compounds related to the present invention are not indicated and suggested in any of the documents.

PRIOR ART REFERENCES

Patent Document

[Patent Document 1] International Publication No. 2014/078325 pamphlet

[Patent Document 2] International Publication No. 2013/161919 pamphlet

[Patent Document 3] International Publication No. 2012/158413 pamphlet

[Patent Document 4] International Publication No. 2014/078454 pamphlet

[Patent Document 5] International Publication No. 2014/078417 pamphlet

[Patent Document 6] International Publication No. 2014/078408 pamphlet

[Patent Document 7] International Publication No. 2014/078378 pamphlet

[Patent Document 8] International Publication No. 2014/078372 pamphlet

[Patent Document 9] International Publication No. 2014/078331 pamphlet

[Patent Document 10] International Publication No. 2014/078328 pamphlet

[Patent Document 11] International Publication No. 2014/078323 pamphlet

[Patent Document 12] International Publication No. 2014/078322 pamphlet

[Patent Document 13] International Publication No. 2014/053967 pamphlet

[Patent Document 14] International Publication No. 2014/053965 pamphlet

[Patent Document 15] International Publication No. 2014/053968 pamphlet

[Patent Document 16] International Publication No. 2015/175788 pamphlet

[Non-patent Document 1] Clinical Science, Vol. 110, 175-191(2006)

[Non-patent Document 2] Nature Reviews Neuroscience, Vol. 4, 299-309(2003)

[Non-patent Document 3] Clinical Genetics, Vol. 82, 341-350(2012)

[Non-patent Document 4] Anesthesiology, Vol. 115, 189-204(2011)

[Non-patent Document 5] Journal of Neurochemistry, Vol. 124, 276-289(2013)

[Non-patent Document 6] Expert Opinion on Therapeutic Patents, Vol. 24, 731-744(2014)

[Non-patent Document 7] Bone, Vol. 48, 389-398(2011)

[Non-patent Document 8] Molecular Pain, Vol. 6, 87(2010)

[Non-patent Document 9] Dermato-Endocrinology, Vol. 3, 32-36(2011)

[Non-patent Document 10] Leukemia, Vol. 21, 2171-2180 (2007)

[Non-patent Document 11] Cancer Research, Vol. 62, 986-989(2002)

[Non-patent Document 12] Nature Medicine, Vol. 19, 1469-1472(2013)

[Non-patent Document 13] Journal of Medicinal Chemistry, Vol. 57, 5800-5816(2014)

[Non-patent Document 14] Expert Opinion on Therapeutic Patents, Vol. 19, 305-319(2009)

SUMMARY OF THE INVENTION

Problems to be Solved by the Invention

The purpose of the present invention is to provide a compound that has a TrkA inhibitory activity or a pharmaceutically acceptable salt thereof, or a pharmaceutical composition comprising the same.

Means for Solving the Problem

The present invention relates to a compound that has a TrkA inhibitory activity and is useful in the treatment and/or prevention of TrkA mediated disorders, or a pharmaceutically acceptable salt thereof.

The present invention relates to the following 1") to 19" and 101") to 107").

1") A compound represented by Formula (I):

[Chemical Formula 1]

(I)

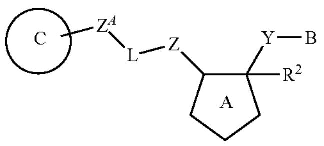

wherein the group represented by Formula:

[Chemical Formula 2]

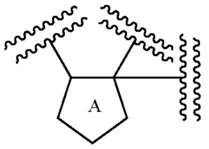

is a group represented by Formula:

[Chemical Formula 3]

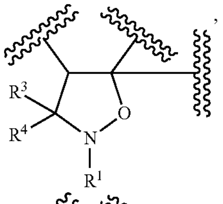
,
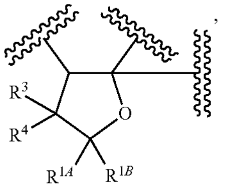
,
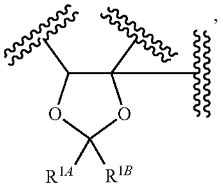
,
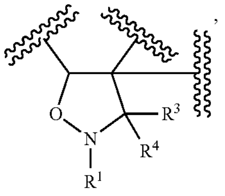
,

-continued

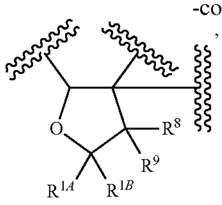
,
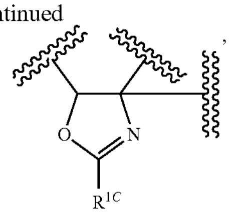
, or
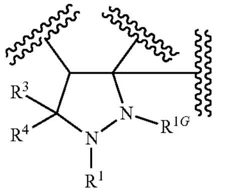

wherein $R^1$ is a hydrogen atom, cyano, substituted or unsubstituted alkyl, substituted or unsubstituted alkenyl, substituted or unsubstituted acyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

each of $R^{1A}$ and $R^{1C}$ is substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{1B}$ is a hydrogen atom, hydroxy, halogen, substituted or unsubstituted alkyl, substituted or unsubstituted alkenyl, substituted or unsubstituted acyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or $R^{1A}$ and $R^{1B}$ may be taken together to form a group represented by $=CR^{1D}R^{1E}$, oxo, a group represented by $=N-O-R^{1F}$, substituted or unsubstituted non-aromatic carbocycle, or substituted or unsubstituted non-aromatic heterocycle;

$R^{1D}$ and $R^{1E}$ are each independently hydrogen, substituted or unsubstituted alkyl, substituted or unsubstituted alkyloxy, or substituted or unsubstituted alkyloxycarbonyl;

$R^{1F}$ is a hydrogen atom, substituted or unsubstituted alkyl, substituted or unsubstituted alkenyl, or substituted or unsubstituted alkynyl;

$R^{1G}$ is a hydrogen atom or substituted or unsubstituted alkyl;

$R^3$ and $R^4$ are each independently a hydrogen atom, substituted or unsubstituted alkyl, substituted or unsubstituted alkenyl, substituted or unsubstituted alkynyl, substituted or unsubstituted alkyloxycarbonyl, or substituted or unsubstituted carbamoyl;

$R^8$ is a hydrogen atom, halogen, hydroxy, substituted or unsubstituted alkyl, substituted or unsubstituted alkenyl, substituted or unsubstituted alkynyl, or substituted or unsubstituted alkyloxy; and $R^9$ is a hydrogen atom, halogen, hydroxy, substituted or unsubstituted alkyl, substituted or unsubstituted alkenyl, substituted or unsubstituted alkynyl, or substituted or unsubstituted alkyloxy, or $R^8$ and $R^9$ may be taken together to form oxo;

-L- is —C(=X)— or —$SO_2$—;

=X is =O, =S, =$NR^{10}$ or =$CR^{11}R^{12}$;

—Z— is —$NR^5$—, —O— or —$CR^6R^7$—;

—$Z^A$— is —$NR^{5A}$— or —$CR^{6A}R^{7A}$—;

—Y— is a single bond, or substituted or unsubstituted alkylene which may be intervened by oxygen atom(s);

B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy;

the ring C is a substituted or unsubstituted aromatic heterocycle or a substituted or unsubstituted non-aromatic heterocycle;

$R^2$ is a hydrogen atom, substituted or unsubstituted alkyl, substituted or unsubstituted alkyloxy, cyano, carboxy, substituted or unsubstituted alkyloxycarbonyl, substituted or unsubstituted carbamoyl, halogen or hydroxy;

$R^5$ and $R^{5A}$ are each independently a hydrogen atom or substituted or unsubstituted alkyl;

$R^6$, $R^{6A}$, $R^7$ and $R^{7A}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, or substituted or unsubstituted amino;

$R^{10}$ is substituted or unsubstituted alkyl, substituted or unsubstituted acyl, substituted or unsubstituted alkyloxycarbonyl, substituted or unsubstituted alkylsulfonyl, nitro, substituted or unsubstituted alkyloxy, or hydroxy;

$R^{11}$ is a hydrogen atom, cyano, substituted or unsubstituted acyl, substituted or unsubstituted alkyloxycarbonyl, substituted or unsubstituted carbamoyl, substituted or unsubstituted alkylsulfonyl, or nitro; and $R^{12}$ is a hydrogen atom or cyano;

provided that the ring C is not

[Chemical Formula 4]

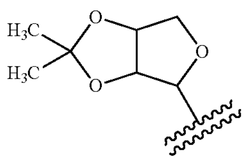

when —Z— is —O—, -L is —C(=O)—, and —$Z^A$— is —$CH_2$—, or a pharmaceutically acceptable salt thereof.

2") The compound according to the above item 1"), wherein —Y— is a single bond, -L- is —C(=X)—, and $R^1$ is cyano, substituted or unsubstituted alkyl, substituted or unsubstituted alkenyl, substituted or unsubstituted acyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

3") The compound according to the above item 1") or 2"), wherein —Z— is —$NR^5$— or —$CR^6R^7$—, or a pharmaceutically acceptable salt thereof.

4") The compound according to the above item 2") or 3"), wherein —Z— is —$NR^5$—, -L- is —C(=O)—, and —$Z^A$— is —$NR^{5A}$—, or a pharmaceutically acceptable salt thereof.

5") The compound according to the above item 4"), wherein each of $R^5$ and $R^{5A}$ is a hydrogen atom, or a pharmaceutically acceptable salt thereof.

6") The compound according to any one of the above items 1") to 5"), wherein B is substituted or unsubstituted aromatic carbocyclyl or substituted or unsubstituted aromatic heterocyclyl, or a pharmaceutically acceptable salt thereof.

7") The compound according to any one of the above items 1") to 6"), wherein $R^2$ is a hydrogen atom or substituted or unsubstituted alkyl, or a pharmaceutically acceptable salt thereof.

8") The compound according to any one of the above items 2") to 7"), wherein the group represented by Formula:

[Chemical Formula 5]

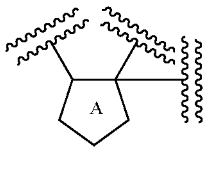

is represented by Formula:

[Chemical Formula 6]

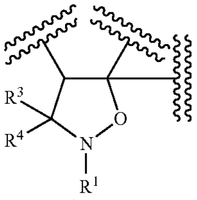
,
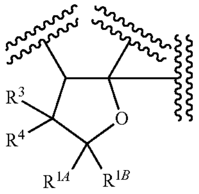
, or
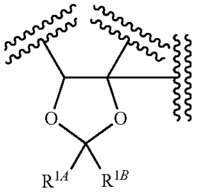
, wherein $R^1$, $R^{1A}$, $R^{1B}$, $R^3$ and $R^4$ are the same as the above item 1"), or a pharmaceutically acceptable salt.

9") The compound according to any one of the above items 1") to 8"), wherein $R^1$ is substituted or unsubstituted alkyl, $R^{1A}$ is substituted or unsubstituted alkyl, and $R^{1B}$ is a hydrogen atom, or a pharmaceutically acceptable salt.

10") The compound according to any one of the above items 1") to 9"), wherein $R^3$ and $R^4$ are hydrogen atoms, or a pharmaceutically acceptable salt.

11") The compound according to any one of the above items 1") to 10"), wherein the ring C is a substituted or unsubstituted aromatic heterocycle, or a pharmaceutically acceptable salt thereof.

12") The compound according to any one of the above items 1") to 11"), wherein the ring C is substituted or unsubstituted pyrazole, or its pharmaceutically acceptable salt thereof.

13") The compound according to the above items 1") to 12"), wherein the ring C is a ring represented by Formula:

[Chemical Formula 7]

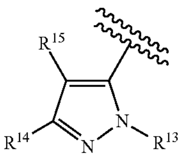

wherein R13 is a hydrogen atom, substituted or unsubstituted alkyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{14}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl; and $R^{15}$ is a hydrogen atom, halogen, cyano, substituted or unsubstituted alkyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl; or $R^{14}$ and $R^{15}$ may be taken together to form a substituted or unsubstituted aromatic carbocycle, a substituted or unsubstituted aromatic heterocycle, a substituted or unsubstituted non-aromatic carbocycle, or a substituted or unsubstituted non-aromatic heterocycle, or a pharmaceutically acceptable salt thereof.

14") The compound according to the above item 13"), wherein $R^{13}$ is substituted or unsubstituted aromatic carbocyclyl, substituted or unsubstituted alkyl, or substituted or unsubstituted non-aromatic carbocyclyl, $R^{14}$ is substituted or unsubstituted aromatic heterocyclyl, substituted or unsubstituted alkyloxy, substituted or unsubstituted aromatic carbocyclyl, or substituted or unsubstituted non-aromatic heterocyclyl, and $R^{15}$ is a hydrogen atom or substituted or unsubstituted alkyl, or a pharmaceutically acceptable salt thereof.

15") The compound according to the above item 1"), wherein the compound is selected from the group consisting of Examples I-65, I-211, I-236, I-237, I-319, I-325, I-536, I-551, I-556 and I-558, or a pharmaceutically acceptable salt thereof.

16") A pharmaceutical composition comprising the compound according to any one of the above items 1") to 15"), or a pharmaceutically acceptable salt thereof.

17") The pharmaceutical composition according to the above item 16"), wherein the composition has a TrkA inhibitory activity.

18") A method for treating or preventing a disease related to TrkA comprising administering the compound according to any one of the above items 1") to 15"), or a pharmaceutically acceptable salt thereof.

19") The compound according to any one of the above items 1") to 15"), or a pharmaceutically acceptable salt thereof, for use in a method for treating or preventing a disease related to TrkA.

101") A pharmaceutical composition comprising the compound according to any one of the above items 1") to 15"), or a pharmaceutically acceptable salt thereof, for oral administration.

102") The pharmaceutical composition according to the above item 101"), which is a tablet, powder, granule, capsule, pill, film, suspension, emulsion, elixir, syrup, lemonade, spirit, aromatic water, extract, decoction or tincture.

103") The pharmaceutical composition according to the above item 102"), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, micro capsule or sustained-release capsule.

104") A pharmaceutical composition comprising the compound according to any one of the above items 1") to 15"), or a pharmaceutically acceptable salt thereof, for parenteral administration.

105") The pharmaceutical composition according to the above item (104"), for dermal, subcutaneous, intravenous, intraarterial, intramuscular, intraperitoneal, transmucosal, inhalation, transnasal, ophthalmic, inner ear or vaginal administration.

106") The pharmaceutical composition according to the above item 104") or 105"), which is an injection, infusion, eye drop, nose drop, ear drop, aerosol, inhalation, lotion, impregnation, liniment, mouthwash, enema, ointment, plaster, jelly, cream, patch, cataplasm, external powder or suppository.

107") A pharmaceutical composition comprising the compound according to any one of the above items 1") to 15"), or a pharmaceutically acceptable salt thereof, for a pediatric or geriatric patient.

In addition, the present invention relates to the following items 1') to 19') and 101') to 107').

1') A compound represented by Formula (I):

[Chemical Formula 8]

(I)

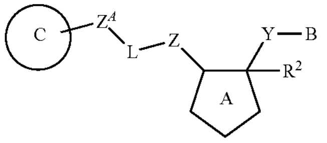

wherein the group represented by Formula:

[Chemical Formula 9]

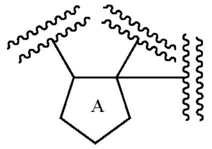

is a group represented by Formula:

[Chemical Formula 10]

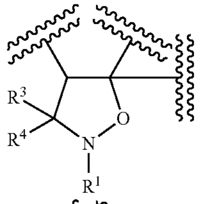,
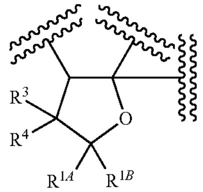,
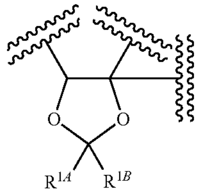,
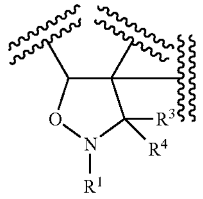,
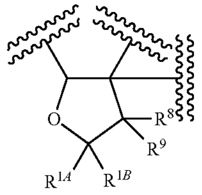,
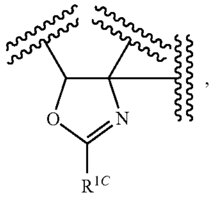, or
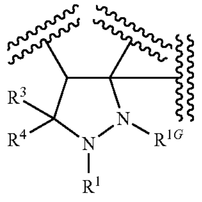, wherein $R^1$ is cyano, substituted or unsubstituted alkyl, substituted or unsubstituted alkenyl, substituted or unsubstituted acyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

each of $R^{1A}$ and $R^{1C}$ is substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{1B}$ is a hydrogen atom, hydroxy, halogen, substituted or unsubstituted alkyl, substituted or unsubstituted alkenyl, substituted or unsubstituted acyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or $R^{1A}$ and $R^{1B}$ may be taken together to form a group represented by $=CR^{1D}R^{1E}$, oxo, a group represented by $=N—O—R^{1F}$, a substituted or unsubstituted non-aromatic carbocycle, or a substituted or unsubstituted non-aromatic heterocycle;

$R^{1D}$ and $R^{1E}$ are each independently hydrogen, substituted or unsubstituted alkyl, substituted or unsubstituted alkyloxy, or substituted or unsubstituted alkyloxycarbonyl;

$R^{1F}$ is a hydrogen atom, substituted or unsubstituted alkyl, substituted or unsubstituted alkenyl, or substituted or unsubstituted alkynyl;

$R^{1G}$ is a hydrogen atom or substituted or unsubstituted alkyl;

$R^3$ and $R^4$ are each independently a hydrogen atom, substituted or unsubstituted alkyl, substituted or unsubstituted alkenyl, substituted or unsubstituted alkynyl, substituted or unsubstituted alkyloxycarbonyl, or substituted or unsubstituted carbamoyl;

$R^8$ is a hydrogen atom, halogen, hydroxy, substituted or unsubstituted alkyl, substituted or unsubstituted alkenyl, substituted or unsubstituted alkynyl, or substituted or unsubstituted alkyloxy; and $R^9$ is a hydrogen atom, halogen, hydroxy, substituted or unsubstituted alkyl, substituted or unsubstituted alkenyl, substituted or unsubstituted alkynyl, or substituted or unsubstituted alkyloxy, or $R^8$ and $R^9$ may be taken together to form oxo;

-L- is $—C(=X)—$ or $—SO_2—$;

$=X$ is $=O$, $=S$, $=NR^{10}$ or $=CR^{11}R^{12}$;

$—Z—$ is $—NR^5—$, $—O—$ or $—CR^6R^7—$;

$—Z^A—$ is $—NR^{5A}—$ or $—CR^{6A}R^{7A}—$;

—Y— is a single bond, or substituted or unsubstituted alkylene which may be intervened by oxygen atom(s);

B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy;

the ring C is a substituted or unsubstituted aromatic heterocycle or a substituted or unsubstituted non-aromatic heterocycle;

$R^2$ is a hydrogen atom, substituted or unsubstituted alkyl, substituted or unsubstituted alkyloxy, cyano, carboxy, substituted or unsubstituted alkyloxycarbonyl, substituted or unsubstituted carbamoyl, halogen or hydroxy;

$R^5$ and $R^{5A}$ are each independently a hydrogen atom or substituted or unsubstituted alkyl;

$R^6$, $R^{6A}$, $R^7$ and $R^{7A}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, or substituted or unsubstituted amino;

$R^{10}$ is substituted or unsubstituted alkyl, substituted or unsubstituted acyl, substituted or unsubstituted alkyloxycarbonyl, substituted or unsubstituted alkylsulfonyl, nitro, substituted or unsubstituted alkyloxy, or hydroxy;

$R^{11}$ is a hydrogen atom, cyano, substituted or unsubstituted acyl, substituted or unsubstituted alkyloxycarbonyl, substituted or unsubstituted carbamoyl, substituted or unsubstituted alkylsulfonyl, or nitro; and $R^{12}$ is a hydrogen atom or cyano;

provided that the ring C is not

[Chemical Formula 11]

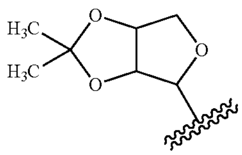

when —Z— is —O—, -L is $—C(=O)—$, and $—Z^A—$ is $—CH_2—$, or a pharmaceutically acceptable salt thereof.

2') The compound according to the above item 1'), wherein —Y— is a single bond, and -L- is $—C(=X)—$, or a pharmaceutically acceptable salt thereof.

3') The compound according to the above item 1') or 2'), wherein —Z— is $—NR^5—$ or $—CR^6R^7—$, or a pharmaceutically acceptable salt thereof.

4') The compound according to the above item 2') or 3'), wherein —Z— is $—NR^5—$, -L- is $—C(=O)—$, and $—Z^A—$ is $—NR^{5A}—$ or a pharmaceutically acceptable salt thereof.

5') The compound according to the above item 4'), wherein each of $R^5$ and $R^{5A}$ is a hydrogen atom, or a pharmaceutically acceptable salt thereof.

6') The compound according to any one of the above items 1') to 5'), wherein B is substituted or unsubstituted aromatic carbocyclyl or substituted or unsubstituted aromatic heterocyclyl, or a pharmaceutically acceptable salt thereof.

7') The compound according to any one of the above items 1') to 6'), wherein $R^2$ is a hydrogen atom or substituted or unsubstituted alkyl, or a pharmaceutically acceptable salt thereof.

8') The compound according to any one of the above items 1') to 7'), wherein the group represented by Formula:

[Chemical Formula 12]

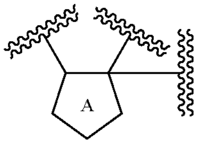

is represented by Formula:

[Chemical Formula 13]

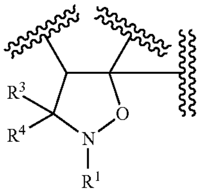,

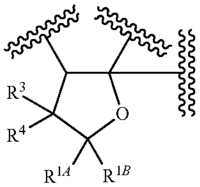

or

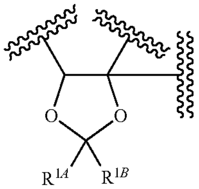, wherein $R^1$, $R^{1A}$, $R^{1B}$, $R^3$ and $R^4$ are the same as the above item 1'), or a pharmaceutically acceptable salt.

9') The compound according to any one of the above items 1') to 8'), wherein $R^1$ is substituted or unsubstituted alkyl, $R^{1A}$ is substituted or unsubstituted alkyl, and $R^{1B}$ is a hydrogen atom, or a pharmaceutically acceptable salt.

10') The compound according to any one of the above items 1') to 9'), wherein each of $R^3$ and $R^4$ is hydrogen atoms, or a pharmaceutically acceptable salt.

11') The compound according to any one of the above items 1') to 10'), wherein the ring C is a substituted or unsubstituted aromatic heterocycle, or a pharmaceutically acceptable salt thereof.

12') The compound according to any one of the above items 1') to 11'), wherein the ring C is substituted or unsubstituted pyrazole, or a pharmaceutically acceptable salt thereof.

13') The compound according to any one of the above items 1') to 12'), wherein the ring C is a ring represented by Formula:

[Chemical Formula 14]

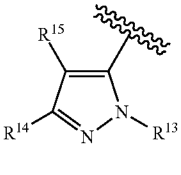

wherein $R^{13}$ is a hydrogen atom, substituted or unsubstituted alkyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{14}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl; and $R^{15}$ is a hydrogen atom, halogen, cyano, substituted or unsubstituted alkyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl; or $R^{14}$ and $R^{15}$ may be taken together to form a substituted or unsubstituted aromatic carbocycle, a substituted or unsubstituted aromatic heterocycle, a substituted or unsubstituted non-aromatic carbocycle, or a substituted or unsubstituted non-aromatic heterocycle, or a pharmaceutically acceptable salt thereof.

14') The compound according to the above item 13'), wherein $R^{13}$ is substituted or unsubstituted aromatic carbocyclyl, substituted or unsubstituted alkyl, or substituted or unsubstituted non-aromatic carbocyclyl, $R^{14}$ is substituted or unsubstituted aromatic heterocyclyl, substituted or unsubstituted alkyloxy, substituted or unsubstituted aromatic carbocyclyl, or substituted or unsubstituted non-aromatic heterocyclyl, and $R^{15}$ is a hydrogen atom or substituted or unsubstituted alkyl, or a pharmaceutically acceptable salt thereof.

15') A pharmaceutical composition comprising the compound according to any one of the above items 1') to 14'), or a pharmaceutically acceptable salt thereof.

16') The pharmaceutical composition according to the above item 15'), wherein the composition has a TrkA inhibitory activity.

17') A method for treating or preventing a disease related to TrkA comprising administering the compound according to any one of the above items 1') to 14'), or a pharmaceutically acceptable salt thereof.

18') The compound according to any one of the above items 1') to 14'), or a pharmaceutically acceptable salt thereof, for use in a method for treating or preventing a disease related to TrkA.

19') Use of the compound according to any one of the above items 1') to 14'), or a pharmaceutically acceptable salt thereof, for the manufacture of a medicament for treating or preventing a disease related to TrkA.

101') A pharmaceutical composition comprising the compound according to any one of the above items 1') to 14'), or a pharmaceutically acceptable salt thereof, for oral administration.

102') The pharmaceutical composition according to the above item 101'), which is a tablet, powder, granule, capsule, pill, film, suspension, emulsion, elixir, syrup, lemonade, spirit, aromatic water, extract, decoction or tincture.

103') The pharmaceutical composition according to the above item 102'), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, micro capsule or sustained-release capsule.

104') A pharmaceutical composition comprising the compound according to any one of the above items 1') to 14'), or a pharmaceutically acceptable salt thereof, for parenteral administration.

105') The pharmaceutical composition according to the above item 104'), for dermal, subcutaneous, intravenous, intraarterial, intramuscular, intraperitoneal, transmucosal, inhalation, transnasal, ophthalmic, inner ear or vaginal administration.

106') The pharmaceutical composition according to the above item 104') or 105'), which is injection, infusion, eye drop, nose drop, ear drop, aerosol, inhalation, lotion, impregnation, liniment, mouthwash, enema, ointment, plaster, jelly, cream, patch, cataplasm, external powder or suppository.

107') A pharmaceutical composition comprising the compound according to any one of the above items 1') to 14'), or a pharmaceutically acceptable salt thereof, for a pediatric or geriatric patient.

In addition, the present invention relates to the following items 1) to 17) and 101) to 107).

1) A compound represented by Formula (I):

[Chemical Formula 15]

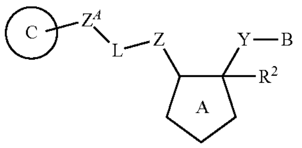

(I)

wherein the group represented by Formula:

[Chemical Formula 16]

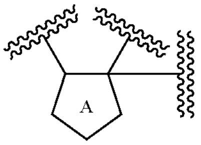

is a group represented by Formula:

[Chemical Formula 17]

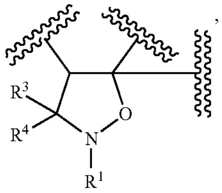,
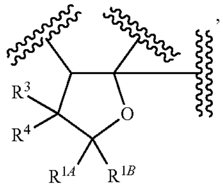,
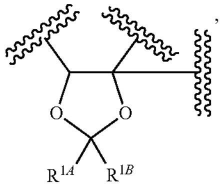,
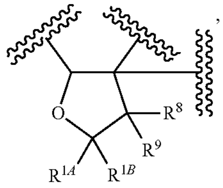,
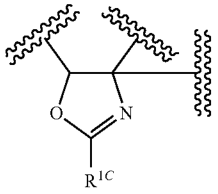
or
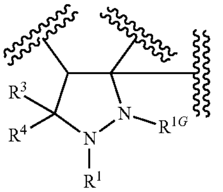

wherein $R^1$ is cyano, substituted or unsubstituted alkyl, substituted or unsubstituted alkenyl, substituted or unsubstituted acyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

each of $R^{1A}$ and $R^{1C}$ is substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{1B}$ is a hydrogen atom, hydroxy, halogen, substituted or unsubstituted alkyl, substituted or unsubstituted alkenyl, substituted or unsubstituted acyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or $R^{1A}$ and $R^{1B}$ may be taken together to form a group represented by $=CR^{1D}R^{1E}$, oxo, a group represented by $=N—O—R^{1F}$, a substituted or unsubstituted non-aromatic carbocycle, or a substituted or unsubstituted non-aromatic heterocycle;

$R^{1D}$ and $R^{1E}$ are each independently hydrogen, substituted or unsubstituted alkyl, substituted or unsubstituted alkyloxy, or substituted or unsubstituted alkyloxycarbonyl;

$R^{1F}$ is a hydrogen atom, substituted or unsubstituted alkyl, substituted or unsubstituted alkenyl, or substituted or unsubstituted alkynyl;

$R^{1G}$ is a hydrogen atom or substituted or unsubstituted alkyl;

$R^3$ and $R^4$ are each independently a hydrogen atom, substituted or unsubstituted alkyl, substituted or unsubstituted alkenyl, substituted or unsubstituted alkynyl, substituted or unsubstituted alkyloxycarbonyl, or substituted or unsubstituted carbamoyl;

$R^8$ is a hydrogen atom, halogen, hydroxy, substituted or unsubstituted alkyl, substituted or unsubstituted alkenyl, substituted or unsubstituted alkynyl, or substituted or unsubstituted alkyloxy; and $R^9$ is a hydrogen atom, halogen, hydroxy, substituted or unsubstituted alkyl, substituted or unsubstituted alkenyl, substituted or unsubstituted alkynyl, or substituted or unsubstituted alkyloxy, or $R^8$ and $R^9$ may be taken together to form oxo;

-L- is —C(=X)— or $—SO_2—$;

=X is =O, =S, $=NR^{10}$ or $=CR^{11}R^{12}$;

—Z— is $—NR^5—$, —O— or $—CR^6R^7—$;

$—Z^A—$ is $—NR^{5A}—$ or $—CR^{6A}R^{7A}—$;

—Y— is a single bond, or substituted or unsubstituted alkylene which may be intervened by oxygen atom(s);

B is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy;

the ring C is a substituted or unsubstituted aromatic heterocycle or a substituted or unsubstituted non-aromatic heterocycle;

$R^2$ is a hydrogen atom, substituted or unsubstituted alkyl, substituted or unsubstituted alkyloxy, cyano, carboxy, substituted or unsubstituted alkyloxycarbonyl, substituted or unsubstituted carbamoyl, halogen or hydroxy;

$R^5$ and $R^{5A}$ are each independently a hydrogen atom or substituted or unsubstituted alkyl;

$R^6$, $R^{6A}$, $R^7$ and $R^{7A}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, or substituted or unsubstituted amino;

$R^{10}$ is substituted or unsubstituted alkyl, substituted or unsubstituted acyl, substituted or unsubstituted alkyloxycarbonyl, substituted or unsubstituted alkylsulfonyl, nitro, substituted or unsubstituted alkyloxy, or hydroxy;

$R^{11}$ is a hydrogen atom, cyano, substituted or unsubstituted acyl, substituted or unsubstituted alkyloxycarbonyl, substituted or unsubstituted alkylcarbamoyl, substituted or unsubstituted alkylsulfonyl, or nitro; and $R^{12}$ is a hydrogen atom or cyano;

provided that the ring C is not

[Chemical Formula 18]

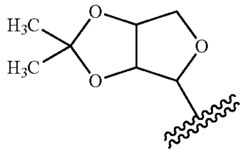

when —Z— is —O—, -L is —C(=O)—, and $—Z^A—$ is $—CH_2—$, or a pharmaceutically acceptable salt thereof.

2) The compound according to the above item 1), wherein —Y— is a single bond, and -L- is —C(=X)—, or a pharmaceutically acceptable salt thereof.

3) The compound according to the above item 1) or 2), wherein —Z— is $—NR^5—$ or $—CR^6R^7—$, or a pharmaceutically acceptable salt thereof.

4) The compound according to the above item 2) or 3), wherein —Z— is $—NR^5—$, -L- is —C(=O)—, and $—Z^A—$ is $—NR^{5A}—$, or a pharmaceutically acceptable salt thereof.

5) The compound according to the above item 4), wherein each of $R^5$ and $R^{5A}$ is a hydrogen atom, or a pharmaceutically acceptable salt thereof.

6) The compound according to any one of the above items 2) to 5), wherein B is substituted or unsubstituted aromatic carbocyclyl or substituted or unsubstituted aromatic heterocyclyl, or a pharmaceutically acceptable salt thereof.

7) The compound according to any one of the above items 2) to 6), wherein $R^2$ is a hydrogen atom or substituted or unsubstituted alkyl, or a pharmaceutically acceptable salt thereof.

8) The compound according to any one of the above items 2) to 7), wherein the group represented by Formula:

[Chemical Formula 19]

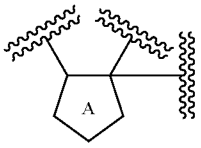

is represented by Formula:

[Chemical Formula 20]

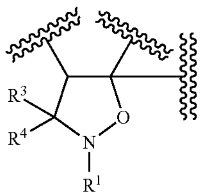,

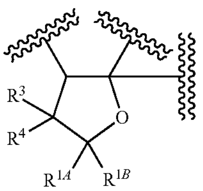

or

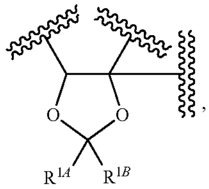, wherein $R^1$, $R^{1A}$, $R^{1B}$, $R^3$ and $R^4$ are the same as the above item 1), or a pharmaceutically acceptable salt.

9) The compound according to any one of the above items 2) to 8), wherein $R^1$ is substituted or unsubstituted alkyl, $R^{1A}$ is substituted or unsubstituted alkyl, and $R^{1B}$ is a hydrogen atom, or a pharmaceutically acceptable salt.

10) The compound according to any one of the above items 2) to 9), wherein each of $R^3$ and $R^4$ is hydrogen atoms, or a pharmaceutically acceptable salt.

11) The compound according to any one of the above items 2) to 10), wherein the ring C is a substituted or unsubstituted aromatic heterocycle, or a pharmaceutically acceptable salt thereof.

12) The compound according to any one of the above items 2) to 11), wherein the ring C is substituted or unsubstituted pyrazole, or a pharmaceutically acceptable salt thereof.

13) A pharmaceutical composition comprising the compound according to any one of the above items 1) to 12), or a pharmaceutically acceptable salt thereof.

14) The pharmaceutical composition according to the above item 13), wherein the composition has a TrkA inhibitory activity.

15) A method for treating or preventing a disease related to TrkA comprising administering the compound according to any one of the above items 1) to 12), or a pharmaceutically acceptable salt thereof.

16) The compound according to any one of the above items 1) to 12), or a pharmaceutically acceptable salt thereof, for use in a method for treating or preventing a disease related to TrkA.

17) Use of the compound according to any one of the above items 1) to 12), or a pharmaceutically acceptable salt thereof, for the manufacture of a medicament for treating or preventing a disease related to TrkA.

101) A pharmaceutical composition comprising the compound according to any one of the above items 1) to 12), or a pharmaceutically acceptable salt thereof, for oral administration.

102) The pharmaceutical composition according to the above item 101), which is a tablet, powder, granule, capsule, pill, film, suspension, emulsion, elixir, syrup, lemonade, spirit, aromatic water, extract, decoction or tincture.

103) The pharmaceutical composition according to the above item 102), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, micro capsule or sustained-release capsule.

104) A pharmaceutical composition comprising the compound according to any one of the above items 1) to 12), or a pharmaceutically acceptable salt thereof, for parenteral administration.

105) The pharmaceutical composition according to the above item (104), for dermal, subcutaneous, intravenous, intraarterial, intramuscular, intraperitoneal, transmucosal, inhalation, transnasal, ophthalmic, inner ear or vaginal administration.

106) The pharmaceutical composition according to the above item 104) or 105), which is an injection, infusion, eye drop, nose drop, ear drop, aerosol, inhalation, lotion, impregnation, liniment, mouthwash, enema, ointment, plaster, jelly, cream, patch, cataplasm, external powder or suppository.

107) A pharmaceutical composition comprising the compound according to any one of the above items 1) to 12), or a pharmaceutically acceptable salt thereof, for a pediatric or geriatric patient.

Effect of the Invention

The present invention provides a compound useful in the treatment and/or prevention of TrkA mediated disorder, or a pharmaceutically acceptable salt thereof. The compound of the present invention shows an excellent TrkA kinase inhibitory activity as described in the following test examples. Thereby, a pharmaceutical composition comprising a compound of the present invention, or a pharmaceutically acceptable salt thereof, is available for therapeutic agent and/or prophylactic agent for pain associated with osteoarthritis, rheumatoid arthritis, fracture, interstitial cystitis, chronic pancreatitis and prostate inflammation; and nociceptive pain as typified by chronic low back pain, diabetic peripheral neuropathy pain, postoperative pain, pelvic pain and cancer pain; neuropathic pain, acute pain, chronic pain, cancer, inflammatory disease, allergic disease, dermatological disease and the like.

A compound of the present invention is the one having utility as a medicament. Herein, utility as a medicament includes the following points: the compound has good solubility; good metabolic stability; the induction of a drug-metabolizing enzyme is low; the inhibition of a drug-metabolizing enzyme which metabolizes another drug is low; the compound has high oral absorbency; the inhibition of hERG is low; the clearance is low; and/or the half-life is sufficiently long to express the efficacy; or the like.

MODE FOR CARRYING OUT THE INVENTION

Hereinafter, the present invention is described with reference to embodiments. It should be understood that, throughout the present specification, the expression of a singular form includes the concept of its plural form unless specified otherwise. Accordingly, it should be understood that an article in singular form (for example, in the English language, "a," "an," and "the") includes the concept of its plural form unless specified otherwise. Furthermore, it should be understood that the terms used herein are used in a meaning normally used in the art unless specified otherwise. Thus, unless defined otherwise, all technical and scientific terms used herein have the same meaning as those generally understood by those skilled in the art in the field to which the present invention pertains. If there is a contradiction, the present specification (including definitions) precedes.

Terms used in this description are explained below. Each term, unless otherwise indicated, has the same meaning when it is used alone or together with other terms.

The term "halogen" includes a fluorine atom, a chlorine atom, a bromine atom and an iodine atom. A fluorine atom and a chlorine atom are especially preferable.

The term "alkyl" includes a C1 to C15, preferably C1 to C10, more preferably C1 to C6 and further preferably C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

The term "alkenyl" includes a C2 to C15, preferably a C2 to C10, more preferably a C2 to C6 and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, and pentadecenyl.

A preferred embodiment of "alkenyl" is vinyl, allyl, propenyl, isopropenyl or butenyl.

The term "alkynyl" includes a C2 to C10, preferably a C2 to C8, more preferably a C2 to C6 and further preferably a C2 to C4 linear or branched hydrocarbon group having one or more triple bond(s) at any position(s). Furthermore, it may have double bond(s) at any position(s). Examples include ethynyl, propynyl, butynyl, pentynyl, hexynyl, heptynyl, octynyl, nonynyl, and decynyl.

A preferred embodiment of "alkynyl" is ethynyl, propynyl, butynyl or pentynyl.

The term "alkylene" includes a C1 to C15, preferably a C1 to C10, more preferably a C1 to C6 and further preferably a C1 to C4 liner or branched divalent hydrocarbon group. Examples include methylene, ethylene, trimethylene, propylene, tetramethylene, pentamethylene, and hexamethylene.

The term "aromatic carbocyclyl" means a cyclic aromatic hydrocarbon group which is monocyclic or polycyclic having two or more rings. Examples include phenyl, naphthyl, anthryl, and phenanthryl.

A preferred embodiment of "aromatic carbocyclyl" is phenyl.

The term "aromatic carbocycle" means a cyclic aromatic hydrocarbon ring which is monocyclic or polycyclic having two or more rings. Examples include a benzene ring, a naphthalene ring, an anthracene ring, and a phenanthrene ring.

A preferred embodiment of "aromatic carbocycle" is a benzene ring and a naphthalene ring.

Examples of an aromatic carbocycle which may be formed by $R^{14}$ and $R^{15}$ together include the ring $Q^4$ as follows:

[Chemical Formula 21]

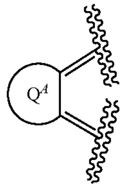

wherein examples of the ring $Q^4$ include a 6-membered aromatic carbocycle.

The term "non-aromatic carbocyclyl" means a cyclic saturated hydrocarbon group or a cyclic unsaturated non-aromatic hydrocarbon group, which is monocyclic or polycyclic having two or more rings. The "non-aromatic carbocyclyl" which is polycyclic having two or more rings includes a fused ring group wherein a non-aromatic carbocyclyl, which is monocyclic or polycyclic having two or more rings, is fused with a ring of the above "aromatic carbocyclyl".

In addition, examples of the "non-aromatic carbocyclyl" also include a group having a bridge or a group to form a spiro ring as follows:

[Chemical Formula 22]

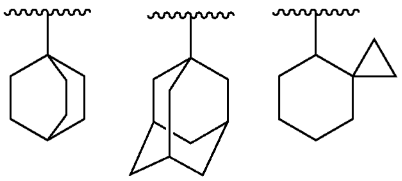

The non-aromatic carbocyclyl which is monocyclic is preferably C3 to C16, more preferably C3 to C12 and further preferably C4 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl.

Examples of non-aromatic carbocyclyl, which is polycyclic having two or more rings, include indanyl, indenyl, acenaphthyl, tetrahydronaphthyl, and fluorenyl.

The term "non-aromatic carbocycle" means a cyclic saturated hydrocarbon ring or a cyclic unsaturated non-aromatic hydrocarbon ring, which is monocyclic or polycyclic having two or more rings. The "non-aromatic carbocycle", which is polycyclic having two or more rings, includes a fused ring wherein the non-aromatic carbocycle, which is monocyclic or polycyclic having two or more rings, is fused with a ring of the above "aromatic carbocycle".

In addition, examples of the "non-aromatic carbocycle" also include a ring having a bridge or a ring to form a spiro ring as follows:

[Chemical Formula 23]

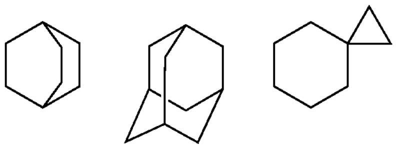

The non-aromatic carbocycle which is monocyclic is preferably C3 to C16, more preferably C3 to C12 and further preferably C4 to C8 carbocyclyl. Examples include cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, and cyclohexadiene.

Examples of a non-aromatic carbocycle, which is polycyclic having two or more rings, include indane, indene, acenaphthene, tetrahydronaphthalene, and fluorene.

Examples of a non-aromatic carbocycle which may be formed by $R^{1A}$ and $R^{1B}$ together include a ring as follows:

[Chemical Formula 24]

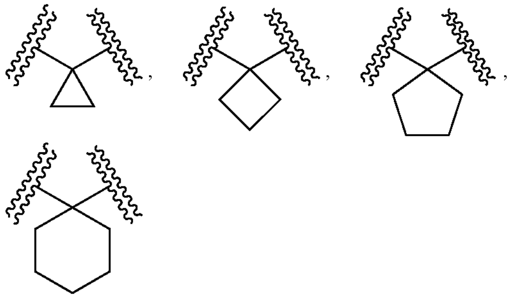

Examples of a non-aromatic carbocycle which may be formed by $R^{14}$ and $R^{15}$ together include a ring $Q^B$ as follows:

[Chemical Formula 25]

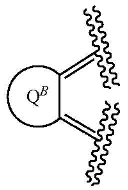

wherein examples of the ring $Q^B$ include a 5- to 8-membered non-aromatic carbocycle.

The term “aromatic heterocyclyl” means an aromatic cyclyl, which is monocyclic or polycyclic having two or more rings, containing one or more, same or different heteroatom(s) selected independently from O, S and N. The “aromatic heterocyclyl”, which is polycyclic having two or more rings, includes a fused ring group wherein an aromatic heterocyclyl, which is monocyclic or polycyclic having two or more rings, is fused with a ring of the above “aromatic carbocyclyl”.

The aromatic heterocyclyl, which is monocyclic, is preferably a 5- to 8-membered ring and more preferably a 5- to 6-membered ring. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, and thiadiazolyl.

Examples of aromatic heterocyclyl, which is bicyclic, include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, and thiazolopyridyl.

Examples of aromatic heterocyclyl, which is bicyclic, include a group as follows:

[Chemical Formula 26]

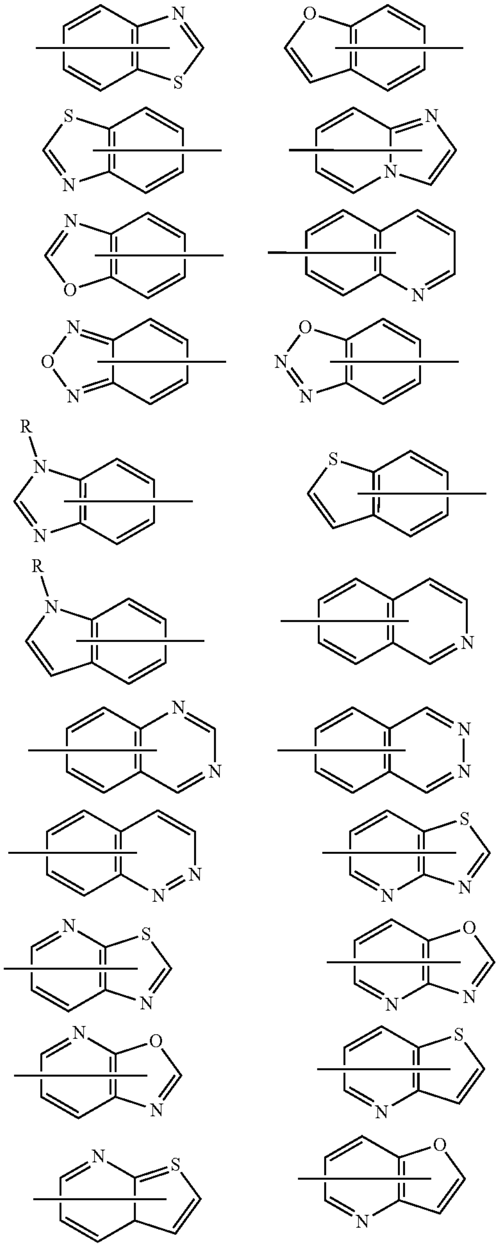

-continued

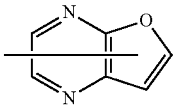

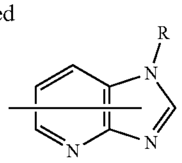

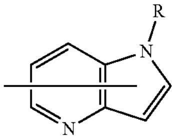

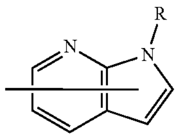

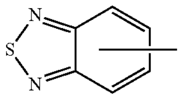

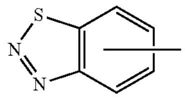

wherein R is a hydrogen atom, $CH_3$, $CH_2CF_3$, in the case that one of the binding group attaches to one ring, it may be attached to a connectable annular atom on the ring, in the case that one of the binding group attached to two rings, it may be attached to a connectable annular atom on the two rings.

Examples of aromatic heterocyclyl, which is polycyclic having three or more rings, include carbazolyl, acridinyl, xanthenyl, phenothiazinyl, phenoxathiinyl, phenoxazinyl, and dibenzofuryl.

The term "aromatic heterocycle" means an aromatic ring, which is monocyclic or polycyclic having two or more rings, containing one or more, same or different heteroatom(s) selected independently from O, S and N.

The "aromatic heterocycle", which is polycyclic having two or more rings, includes a fused ring wherein an aromatic heterocycle, which is monocyclic or polycyclic having two or more rings, is fused with a ring of the above "aromatic carbocycle".

The aromatic heterocycle, which is monocyclic, is preferably a 5- to 8-membered ring and more preferably a 5- or 6-membered ring. Examples include pyrrole, imidazole, pyrazole, pyridine, pyridazine, pyrimidine, pyrazine, pyridone, triazole, triazine, tetrazole, furan, thiophen, isoxazole, oxazole, oxadiazole, isothiazole, thiazole, and thiadiazole.

Examples of an aromatic heterocycle, which is bicyclic, include, indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, oxazolopyridine, and thiazolopyridine.

Examples of an aromatic heterocycle, which is polycyclic having three or more rings, include carbazole, acridine, xanthene, phenothiazine, phenoxathiine, phenoxazine, and dibenzofuran.

Examples of an aromatic heterocycle which may be formed by $R^{14}$ and $R^{15}$ together include the ring $Q^C$ as follows:

[Chemical Formula 27]

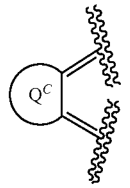

wherein examples of the ring $Q^C$ include a 5- or 6-membered aromatic heterocycle containing one or more, same or different heteroatom(s) selected independently from O, S and N.

The term "non-aromatic heterocyclyl" means a non-aromatic cyclyl, which is monocyclic or polycyclic having two or more rings, containing one or more, same or different heteroatom(s) selected independently from O, S and N. The "non-aromatic heterocyclyl", which is polycyclic having two or more rings, includes an above-mentioned non-aromatic heterocyclyl fused with a ring of the above "aromatic carbocyclyl", "non-aromatic carbocyclyl" and/or "aromatic heterocyclyl". The "non-aromatic heterocyclyl", which is polycyclic having two or more rings, includes an aromatic heterocyclyl, which is monocyclic or polycyclic having two or more rings, fused with a ring of the above "non-aromatic carbocyclyl" and/or "aromatic heterocyclyl".

In addition, examples of the "non-aromatic heterocyclyl" also include a group having a bridge or a group to form a spiro ring as follows:

[Chemical Formula 28]

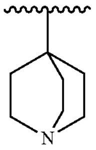

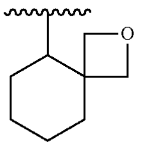

The non-aromatic heterocyclyl, which is monocyclic, is preferably a 3- to 8-membered and more preferably a 5- to 6-membered ring. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolynyl, oxepanyl, thiolanyl, thiinyl, and thiazinyl.

Examples of non-aromatic heterocyclyl, which is polycyclic having two or more rings, include indolinyl, isoindolinyl, chromanyl, and isochromanyl.

The term "non-aromatic heterocycle" means a cyclic non-aromatic ring, which is monocyclic or polycyclic having two or more rings, containing one or more, same or different heteroatom(s) selected from O, S and N.

The "non-aromatic heterocycle", which is polycyclic having two or more rings, includes an above-mentioned non-aromatic heterocycle fused with a ring of the above "aromatic carbocycle", "non-aromatic carbocycle" and/or "aromatic heterocycle".

In addition, the "non-aromatic heterocycle" also includes a ring having a bridge or a ring to form a spiro ring as follows:

[Chemical Formula 29]

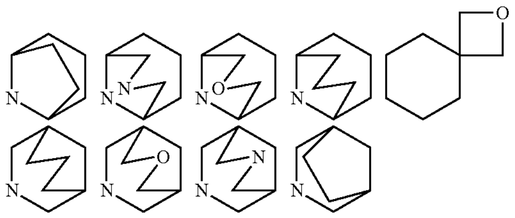

The non-aromatic heterocycle which is non-bridged is preferably a 3 to 8-membered ring, more preferably a 4 to 8-membered ring, and further preferably a 5 or 6-membered ring.

The non-aromatic heterocycle which is bridged is preferably a 6 to 10-membered ring and more preferably a 8 or 9-membered ring. Herein, a number of members mean a number of all annular atoms of a bridged non-aromatic heterocycle.

The non-aromatic heterocycle which is monocyclic is preferably a 3 to 8-membered ring, and more preferably a 5 or 6-membered ring. Examples include dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyran, dihydrothiazole, tetrahydrothiazole, tetrahydroisothiazole, dihydrooxazine, hexahydroazepine, tetrahydrodiazepine, tetrahydropyridazine, hexahydropyrimidine, dioxolane, dioxazine, aziridine, dioxoline, oxepane, thiolane, thiine, and thiazine.

Examples of a non-aromatic heterocycle, which is polycyclic having two or more rings, include indoline, isoindoline, chromane, and isochromane.

Examples of a non-aromatic heterocycle which may be formed by $R^{1A}$ and $R^{1B}$ together include a ring as follows:

[Chemical Formula 30]

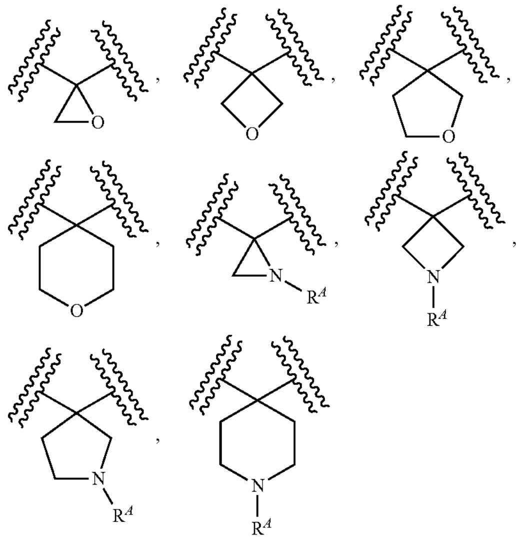

wherein $R^A$ is substituted or unsubstituted alkyl, substituted or unsubstituted alkenyl, substituted or unsubstituted alkyloxycarbonyl, or substituted or unsubstituted alkylcarbonyl.

Examples of a non-aromatic heterocycle which may be formed by $R^{14}$ and $R^{15}$ together include the ring $Q^D$ as follows:

[Chemical Formula 31]

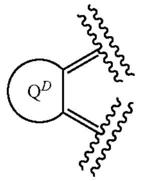

wherein examples of the ring $Q^D$ include a 5- to 8-membered non-aromatic heterocycle containing one or more, same or different heteroatom(s) selected independently from O, S and N.

The term "hydroxyalkyl" means a group wherein one or more hydrogen atom(s) attached to a carbon atom of the above "alkyl" is replaced with a hydroxyl group. Examples include hydroxymethyl, 1-hydroxyethyl, 2-hydroxyethyl, 1-hydroxypropyl, 2-hydroxypropyl, and 1,2-dihydroxyethyl.

A preferred embodiment of "hydroxyalkyl" is hydroxymethyl.

The term "alkyloxy" means a group wherein the above "alkyl" is bonded to an oxygen atom. Examples include methoxy, ethoxy, n-propyloxy, isopropyloxy, n-butyloxy, tert-butyloxy, isobutyloxy, sec-butyloxy, pentyloxy, isopentyloxy, and hexyloxy.

A preferred embodiment of "alkyloxy" is methoxy, ethoxy, n-propyloxy, isopropyloxy, and tert-butyloxy.

The term "alkenyloxy" means a group wherein the above "alkenyl" is bonded to an oxygen atom. Examples include vinyloxy, allyloxy, 1-propenyloxy, 2-butenyloxy, 2-pentenyloxy, 2-hexenyloxy, 2-heptenyloxy, and 2-octenyloxy.

The term "alkynyloxy" means a group wherein the above "alkynyl" is bonded to an oxygen atom. Examples include ethynyloxy, 1-propynyloxy, 2-propynyloxy, 2-butynyloxy, 2-pentynyloxy, 2-hexynyloxy, 2-heptynyloxy, and 2-octynyloxy.

The term "haloalkyl" includes a group wherein one or more hydrogen atom(s) attached to a carbon atom of the above "alkyl" is replaced with the above "halogen". Examples include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, and 1,1,1-trifluoropropan-2-yl.

A preferred embodiment of "haloalkyl" is trifluoromethyl and trichloromethyl.

The term "haloalkyloxy" means a group wherein the above "haloalkyl" is bonded to an oxygen atom. Examples include monofluoromethoxy, monofluoroethoxy, trifluoromethoxy, trichloromethoxy, trifluoroethoxy, and trichloroethoxy.

A preferred embodiment of "haloalkyloxy" is trifluoromethoxy and trichloromethoxy.

The term "alkyloxyalkyl" means a group wherein the above "alkyloxy" is bonded to the above "alkyl". Examples include methoxymethyl, methoxyethyl, and ethoxymethyl.

The term "alkyloxyalkyloxy" means a group wherein the above "alkyloxy" is bonded to the above "alkyloxy". Examples include methoxymethoxy, methoxyethoxy, ethoxymethoxy, and ethoxyethoxy.

The term "alkylcarbonyl" means a group wherein the above "alkyl" is bonded to a carbonyl group. Examples include methylcarbonyl, ethylcarbonyl, propylcarbonyl, isopropylcarbonyl, tert-butylcarbonyl, isobutylcarbonyl, sec-butylcarbonyl, pentylcarbonyl, isopentylcarbonyl, and hexylcarbonyl.

A preferred embodiment of "alkylcarbonyl" is methylcarbonyl, ethylcarbonyl and n-propylcarbonyl.

The term "alkenylcarbonyl" means a group wherein the above "alkenyl" is bonded to a carbonyl group. Examples include ethylenylcarbonyl and propenylcarbonyl.

The term "alkynylcarbonyl" means a group wherein the above "alkynyl" is bonded to a carbonyl group. Examples include ethynylcarbonyl and propynylcarbonyl.

The term "alkylamino" means a group wherein one or two hydrogen atom(s) attached to a nitrogen atom of an amino group is(are) replaced with the above "alkyl". Examples include methylamino, dimethylamino, ethylamino, diethylamino, isopropylamino, N,N-diisopropylamino, and N-methyl-N-ethylamino.

A preferred embodiment of "alkylamino" is methylamino and ethylamino.

The term "alkylsulfonyl" means a group wherein the above "alkyl" is bonded to a sulfonyl group. Examples include methylsulfonyl, ethylsulfonyl, propylsulfonyl, isopropylsulfonyl, tert-butylsulfonyl, isobutylsulfonyl, and sec-butylsulfonyl.

A preferred embodiment of "alkylulfonyl" is methylsulfonyl and ethylsulfonyl.

The term "alkenylsulfonyl" means a group wherein the above "alkenyl" is bonded to a sulfonyl group. Examples include ethylenylsulfonyl, and propenylsulfonyl.

The term "alkynylsulfonyl" means a group wherein the above "alkynyl" is bonded to a sulfonyl group. Examples include ethynylsulfonyl, and propynylsulfonyl.

The term "alkylcarbonylamino" means a group wherein one or two hydrogen atom(s) attached to a nitrogen atom of an amino group is(are) replaced with the above "alkylcarbonyl". Examples include methylcarbonylamino, dimethylcarbonylamino, ethylcarbonylamino, diethylcarbonylamino, propylcarbonylamino, isopropylcarbonylamino, N,N-diisopropylcarbonylamino, tert-butylcarbonylamino, isobutylcarbonylamino, and sec-butylcarbonylamino.

The term "alkylsulfonylamino" means a group wherein one or two hydrogen atom(s) attached to a nitrogen atom of an amino group is(are) replaced with the above "alkylsulfonyl". Examples include methylsulfonylamino, dimethylsulfonylamino, ethylsulfonylamino, diethylsulfonylamino, propylsulfonylamino, isopropylsulfonylamino, N,N-diisopropylsulfonylamino, tert-butylsulfonylamino, isobutylsulfonylamino, and sec-butylsulfonylamino.

A preferred embodiment of "alkylsulfonylamino" is methylsulfonylamino and ethylsulfonylamino.

The term "alkylimino" means a group wherein a hydrogen atom attached to a nitrogen atom of an imino group is replaced with the above "alkyl". Examples include methylimino, ethylimino, n-propylimino, and isopropylimino.

The term "alkenylimino" means a group wherein a hydrogen atom attached to a nitrogen atom of an imino group is replaced with the above "alkenyl". Examples include ethylenylimino, and propenylimino.

The term "alkynylimino" means a group wherein a hydrogen atom attached to a nitrogen atom of an imino group is replaced with the above "alkynyl". Examples include ethynylimino, and propynylimino.

The term "alkylcarbonylimino" means a group wherein a hydrogen atom attached to a nitrogen atom of an imino group is replaced with the above "alkylcarbonyl". Examples include methylcarbonylimino, ethylcarbonylimino, n-propylcarbonylimino, and isopropylcarbonylimino.

The term "alkenylcarbonylimino" means a group wherein a hydrogen atom attached to a nitrogen atom of an imino group is replaced with the above "alkenylcarbonyl". Examples include ethylenylcarbonylimino, and propenylcarbonylimino.

The term "alkynylcarbonylimino" means a group wherein a hydrogen atom attached to a nitrogen atom of an imino group is replaced with the above "alkynylcarbonyl". Examples include ethynylcarbonylimino and propynylcarbonylimino.

The term "alkyloxyimino" means a group wherein a hydrogen atom attached to a nitrogen atom of an imino group is replaced with the above "alkyloxy". Examples include methyloxyimino, ethyloxyimino, n-propyloxyimino, and isopropyloxyimino.

The term "alkenyloxyimino" means a group wherein a hydrogen atom attached to a nitrogen atom of an imino group is replaced with the above "alkenyloxy". Examples include ethylenyloxyimino, and propenyloxyimino.

The term "alkynyloxyimino" means a group wherein a hydrogen atom attached to a nitrogen atom of an imino group is replaced with the above "alkynyloxy". Examples include ethynyloxyimino, and propynyloxyimino.

The term "alkylcarbonyloxy" means a group wherein the above "alkylcarbonyl" is bonded to an oxygen atom. Examples include methylcarbonyloxy, ethylcarbonyloxy, propylcarbonyloxy, isopropylcarbonyloxy, tert-butylcarbonyloxy, isobutylcarbonyloxy, and sec-butylcarbonyloxy.

A preferred embodiment of "alkylcarbonyloxy" is methylcarbonyloxy and ethylcarbonyloxy.

The term "alkenylcarbonyloxy" means a group wherein the above "alkenylcarbonyl" is bonded to an oxygen atom. Examples include ethylenylcarbonyloxy and propenylcarbonyloxy.

The term "alkynylcarbonyloxy" means a group wherein the above "alkynylcarbonyl" is bonded to an oxygen atom. Examples include ethynylcarbonyloxy and propynylcarbonyloxy.

The term "alkyloxycarbonyl" means a group wherein the above "alkyloxy" is bonded to a carbonyl group. Examples include methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl, and hexyloxycarbonyl.

A preferred embodiment of "alkyloxycarbonyl" is methyloxycarbonyl, ethyloxycarbonyl and propyloxycarbonyl.

The term "alkenyloxycarbonyl" means a group wherein the above "alkenyloxy" is bonded to a carbonyl group. Examples include ethylenyloxycarbonyl and propenyloxycarbonyl.

The term "alkynyloxycarbonyl" means a group wherein the above "alkynyloxy" is bonded to a carbonyl group. Examples include ethynyloxycarbonyl and propynyloxycarbonyl.

The term "alkylsulfanyl" means a group wherein a hydrogen atom attached to a sulfur atom of a sulfanyl group is replaced with the above "alkyl". Examples include methylsulfanyl, ethylsulfanyl, n-propylsulfanyl, and isopropylsulfanyl.

The term “alkenylsulfanyl” means a group wherein a hydrogen atom attached to a sulfur atom of a sulfanyl group is replaced with the above “alkenyl”. Examples include ethylenylsulfanyl, and propenylsulfanyl.

The term “alkynylsulfanyl” means a group wherein a hydrogen atom attached to a sulfur atom of a sulfanyl group is replaced with the above “alkynyl”. Examples include ethynylsulfanyl, and propynylsulfanyl.

The term “alkylsulfinyl” means a group wherein the above “alkyl” is bonded to a sulfinyl group. Examples include methylsulfinyl, ethylsulfinyl, n-propylsulfinyl, and isopropylsulfinyl.

The term “alkenylsulfinyl” means a group wherein the above “alkenyl” is bonded to a sulfinyl group. Examples include ethylenylsulfinyl, and propenylsulfinyl The term “alkynylsulfinyl” means a group wherein the above “alkynyl” is bonded to a sulfinyl group. Examples include ethynylsulfinyl and propynylsulfinyl.

The term “alkylcarbamoyl” means a group wherein one or two hydrogen atom(s) attached to a nitrogen atom of a carbamoyl group is(are) replaced with the above “alkyl”. Examples include methylcarbamoyl, dimethylcarbamoyl, ethylcarbamoyl, and diethylcarbamoyl.

The term “alkylsulfamoyl” means a group wherein one or two hydrogen atom(s) attached to a nitrogen atom of a sulfamoyl group is(are) replaced with the above “alkyl”. Examples include methylsulfamoyl, dimethylsulfamoyl, dimethylsulfamoyl, and diethylsulfamoyl.

The term “trialkylsilyl” means a group wherein three of the above “alkyl” are bonded to a silyl atom. Three alkyl groups may be the same or different. Examples include trimethylsilyl, triethylsilyl, and tert-butyldimethylsilyl.

The alkyl part of “aromatic carbocyclylalkyl”, “non-aromatic carbocyclylalkyl”, “aromatic heterocyclylalkyl”, and “non-aromatic heterocyclylalkyl”, “aromatic carbocyclylalkyloxy”, “non-aromatic carbocyclylalkyloxy”, “aromatic heterocyclylalkyloxy”, and “non-aromatic heterocyclylalkyloxy”, “aromatic carbocyclylalkyloxycarbonyl”, “non-aromatic carbocyclylalkyloxycarbonyl”, “aromatic heterocyclylalkyloxycarbonyl”, and “non-aromatic heterocyclylalkyloxycarbonyl”, “aromatic carbocyclylalkyloxyalkyl”, “non-aromatic carbocyclylalkyloxyalkyl”, “aromatic heterocyclylalkyloxyalkyl”, and “non-aromatic heterocyclylalkyloxyalkyl”, and “aromatic carbocyclylalkylamino”, “non-aromatic carbocyclylalkylamino”, “aromatic heterocyclylalkylamino”, and “non-aromatic heterocyclylalkylamino” is also the same as above “alkyl”.

The term “aromatic carbocyclylalkyl” means an alkyl substituted with one or more “aromatic carbocyclyl” described above. Examples include benzyl, phenethyl, phenylpropyl, benzhydryl, trityl, naphthylmethyl, and a group of the following formula:

[Chemical Formula 32]

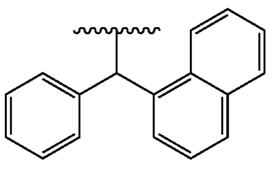

A preferred embodiment of “aromatic carbocyclylalkyl” is benzyl, phenethyl or benzhydryl.

The term “non-aromatic carbocyclylalkyl” means an alkyl substituted with one or more “non-aromatic carbocyclyl” described above. The “non-aromatic carbocyclylalkyl” also includes “non-aromatic carbocyclylalkyl” wherein the alkyl part is substituted with the above “aromatic carbocyclyl”. Examples include cyclopropylmethyl, cyclobutylmethyl, cyclopenthylmethyl, cyclohexylmethyl, and a group of the following formula:

[Chemical Formula 33]

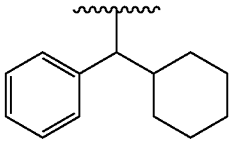

The term “aromatic heterocyclylalkyl” means an alkyl substituted with one or more “aromatic heterocyclyl” described above. The “aromatic heterocyclylalkyl” also includes “aromatic heterocyclylalkyl” wherein the alkyl part is substituted with the above “aromatic carbocyclyl” and/or “non-aromatic carbocyclyl”. Examples include pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl, and groups of the following formulae:

[Chemical Formula 34]

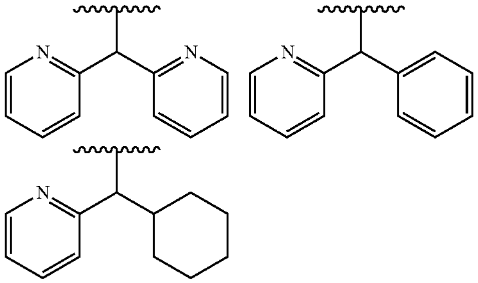

The term “non-aromatic heterocyclylalkyl” means an alkyl substituted with one or more “non-aromatic heterocyclyl” described above. The “non-aromatic heterocyclylalkyl” also includes “non-aromatic heterocyclylalkyl” wherein the alkyl part is substituted with the above “aromatic carbocyclyl”, “non-aromatic carbocyclyl” and/or “aromatic heterocyclyl”. Examples include tetrahydropyranylmethyl, morpholinylethyl, piperidinylmethyl, piperazinylmethyl, and groups of the following formulae:

[Chemical Formula 35]

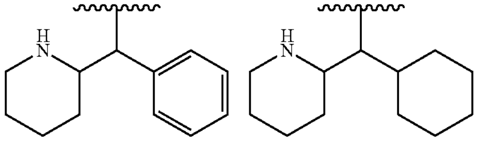

-continued

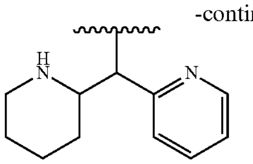

The term "aromatic carbocyclylalkyloxy" means an alkyloxy substituted with one or more "aromatic carbocyclyl" described above. Examples include benzyloxy, phenethyloxy, phenylpropyloxy, benzhydryloxy, trityloxy, naphthylmethyloxy, and a group of the following formula:

[Chemical Formula 36]

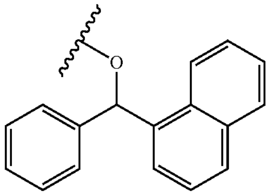

The term "non-aromatic carbocyclylalkyloxy" means an alkyloxy substituted with one or more "non-aromatic carbocyclyl" described above. The "non-aromatic carbocyclylalkyloxy" also includes "non-aromatic carbocyclylalkyloxy" wherein the alkyl part is substituted with the above "aromatic carbocyclyl". Examples include cyclopropylmethyloxy, cyclobutylmethyloxy, cyclopenthylmethyloxy, cyclohexylmethyloxy, and a group of the following formula:

[Chemical Formula 37]

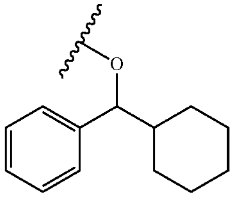

The term "aromatic heterocyclylalkyloxy" means an alkyloxy substituted with one or more "aromatic heterocyclyl" described above. The "aromatic heterocyclylalkyloxy" also includes "aromatic heterocyclylalkyloxy" wherein the alkyl part is substituted with the above "aromatic carbocyclyl" and/or "non-aromatic carbocyclyl". Examples include pyridylmethyloxy, furanylmethyloxy, imidazolylmethyloxy, indolylmethyloxy, benzothiophenylmethyloxy, oxazolylmethyloxy, isoxazolylmethyloxy, thiazolylmethyloxy, isothiazolylmethyloxy, pyrazolylmethyloxy, isopyrazolylmethyloxy, pyrrolidinylmethyloxy, benzoxazolylmethyloxy, and groups of the following formulae:

[Chemical Formula 38]

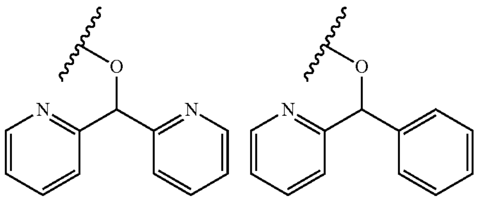

-continued

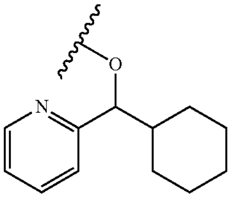

The term "non-aromatic heterocyclylalkyloxy" means an alkyloxy substituted with one or more "non-aromatic heterocyclyl" described above. The "non-aromatic heterocyclylalkyloxy" also includes "non-aromatic heterocyclylalkyloxy" wherein the alkyl part is substituted with the above "aromatic carbocyclyl", "non-aromatic carbocyclyl" and/or "aromatic heterocyclyl". Examples include tetrahydropyranylmethyloxy, morpholinylmethyloxy, morpholinylethyloxy, piperidinylmethyloxy, piperazinylmethyloxy, and groups of the following formulae:

[Chemical Formula 39]

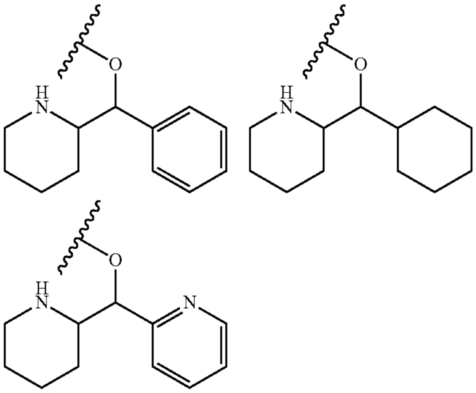

The term "aromatic carbocyclylalkyloxycarbonyl" means an alkyloxycarbonyl substituted with one or more "aromatic carbocyclyl" described above. Examples include benzyloxycarbonyl, phenethyloxycarbonyl, phenylpropyloxycarbonyl, benzhydryloxycarbonyl, trityloxycarbonyl, naphthylmethyloxycarbonyl, and a group of the following formula:

[Chemical Formula 40]

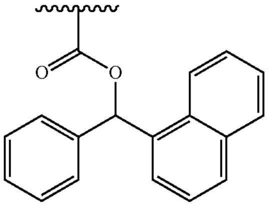

The term "non-aromatic carbocyclylalkyloxycarbonyl" means an alkyloxycarbonyl substituted with one or more "non-aromatic carbocyclyl" described above. The "non-aromatic carbocyclylalkyloxycarbonyl" also includes "non-aromatic carbocyclylalkyloxycarbonyl" wherein the alkyl part is substituted with the above "aromatic carbocyclyl". Examples include cyclopropylmethyloxycarbonyl, cyclobutylmethyloxycarbonyl, cyclopenthylmethyloxycarbonyl, cyclohexylmethyloxycarbonyl, and a group of the following formula:

[Chemical Formula 41]

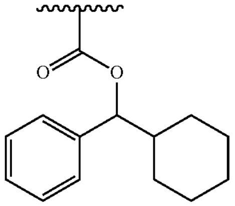

The term "aromatic heterocyclylalkyloxycarbonyl" means an alkyloxycarbonyl substituted with one or more "aromatic heterocyclyl" described above. The "aromatic heterocyclylalkyloxycarbonyl" also include "aromatic heterocyclylalkyloxycarbonyl" wherein the alkyl part is substituted with the above "aromatic carbocyclyl" and/or "non-aromatic carbocyclyl". Examples include pyridylmethyloxycarbonyl, furanylmethyloxycarbonyl, imidazolylmethyloxycarbonyl, indolylmethyloxycarbonyl, benzothiophenylmethyloxycarbonyl, oxazolylmethyloxycarbonyl, isoxazolylmethyloxycarbonyl, thiazolylmethyloxycarbonyl, isothiazolylmethyloxycarbonyl, pyrazolylmethyloxycarbonyl, isopyrazolylmethyloxycarbonyl, pyrrolidinylmethyloxycarbonyl, benzoxazolylmethyloxycarbonyl, and groups of the following formulae:

[Chemical Formula 42]

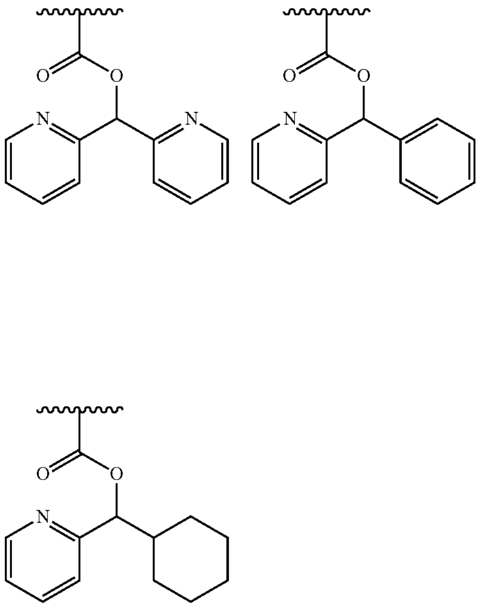

The term "non-aromatic heterocyclylalkyloxycarbonyl" means an alkyloxycarbonyl substituted with one or more "non-aromatic heterocyclyl" described above. The "non-aromatic heterocyclylalkyloxycarbonyl" also includes "non-aromatic heterocyclylalkyloxycarbonyl" wherein the alkyl part is substituted with the above "aromatic carbocyclyl", "non-aromatic carbocyclyl" and/or "aromatic heterocyclyl". Examples include tetrahydropyranylmethyloxy, morpholinylmethyloxy, morpholinylethyloxy, piperidinylmethyloxy, piperazinylmethyloxy, and groups of the following formulae:

[Chemical Formula 43]

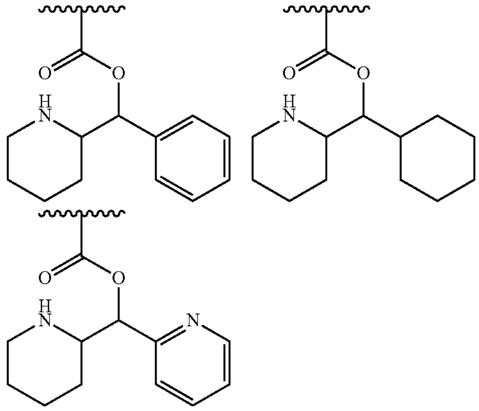

The term "aromatic carbocyclylalkyloxyalkyl" means an alkyloxyalkyl substituted with one or more "aromatic carbocyclyl" described above. Examples include benzyloxymethyl, phenethyloxymethyl, phenylpropyloxymethyl, benzhydryloxymethyl, trityloxymethyl, naphthylmethyloxymethyl, and a group of the following formula:

[Chemical Formula 44]

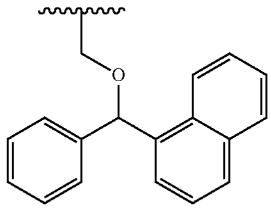

The term "non-aromatic carbocyclylalkyloxyalkyl" means an alkyloxyalkyl substituted with one or more "non-aromatic carbocyclyl" described above. The "non-aromatic carbocyclylalkyloxyalkyl" also includes "non-aromatic carbocyclylalkyloxyalkyl" wherein the alkyl part bonded to the non-aromatic carbocycle is substituted with the above "aromatic carbocyclyl". Examples include cyclopropylmethyloxymethyl, cyclobutylmethyloxymethyl, cyclopenthylmethyloxymethyl, cyclohexylmethyloxymethyl, and a group of the following formula:

[Chemical Formula 45]

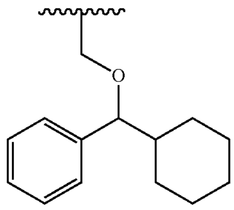

The term "aromatic heterocyclylalkyloxyalkyl" means an alkyloxyalkyl substituted with one or more "aromatic heterocyclyl" described above. The "aromatic heterocyclylalkyloxyalkyl" also includes "aromatic heterocyclylalkyloxyalkyl" wherein the alkyl part bonded to the aromatic heterocycle is substituted with the above "aromatic carbocyclyl" and/or "non-aromatic carbocyclyl". Examples include pyridylmethyloxymethyl, furanylmethyloxymethyl, imidazolylmethyloxymethyl, indolylmethyloxymethyl, benzothiophenylmethyloxymethyl, oxazolylmethyloxymethyl, isoxazolylmethyloxymethyl, thiazolylmethyloxymethyl, isothiazolylmethyloxymethyl, pyrazolylmethyloxymethyl, isopyrazolylmethyloxymethyl, pyrrolidinylmethyloxymethyl, benzoxazolylmethyloxymethyl, and groups of the following formulae:

[Chemical Formula 46]

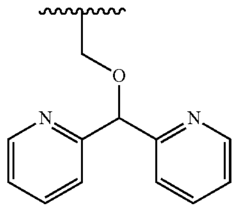

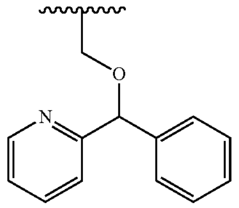

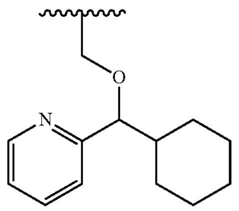

The term "non-aromatic heterocyclylalkyloxyalkyl" means an alkyloxyalkyl substituted with one or more "non-aromatic heterocyclyl" described above. The "non-aromatic heterocyclylalkyloxyalkyl" also includes "non-aromatic heterocyclylalkyloxyalkyl" wherein the alkyl part bonded to the non-aromatic heterocycle is substituted with the above "aromatic carbocyclyl", "non-aromatic carbocyclyl" and/or "aromatic heterocyclyl". Examples include tetrahydropyranylmethyloxymethyl, morpholinylmethyloxymethyl, morpholinylethyloxymethyl, piperidinylmethyloxymethyl, piperazinylmethyloxymethyl, and groups of the following formulae:

[Chemical Formula 47]

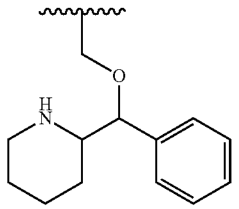

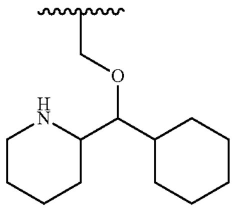

-continued

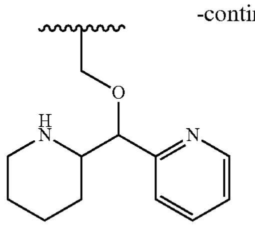

The term "aromatic carbocyclylalkylamino" means a group wherein one or two hydrogen atom(s) attached to a nitrogen atom of an amino group is(are) replaced with the above "aromatic carbocyclylalkyl". Examples include benzylamino, phenethylamino, phenylpropylamino, benzhydrylamino, tritylamino, naphthylmethylamino, and dibenzylamino.

The term "non-aromatic carbocyclylalkylamino" means a group wherein one or two hydrogen atom(s) attached to a nitrogen atom of an amino group is(are) replaced with the above "non-aromatic carbocyclylalkyl". Examples include cyclopropylmethylamino, cyclobutylmethylamino, cyclopentylmethylamino, and cyclohexylmethylamino.

The term "aromatic heterocyclylalkylamino" means a group wherein one or two hydrogen atom(s) attached to a nitrogen atom of an amino group is(are) replaced with the above "aromatic heterocyclylalkyl". Examples include pyridylmethylamino, furanylmethylamino, imidazolylmethylamino, indolylmethylamino, benzothiophenylmethylamino, oxazolylmethylamino, isoxazolylmethylamino, thiazolylmethylamino, isothiazolylmethylamino, pyrazolylmethylamino, isopyrazolylmethylamino, pyrrolylmethylamino, and benzoxazolylmethylamino.

The term "non-aromatic heterocyclylalkylamino" means a group wherein one or two hydrogen atom(s) attached to a nitrogen atom of an amino group is(are) replaced with the above "non-aromatic heterocyclylalkyl". Examples include tetrahydropyranylmethylamino, morpholinylethylamino, piperidinylmethylamino, and piperazinylmethylamino.

The aromatic carbocycle part of "aromatic carbocyclyloxy", "aromatic carbocyclylcarbonyl", "aromatic carbocyclyloxycarbonyl", "aromatic carbocyclylsulfanyl", and "aromatic carbocyclylsulfonyl" is also the same as above "aromatic carbocyclyl".

The term "aromatic carbocyclyloxy" means a group wherein the "aromatic carbocycle" is bonded to an oxygen atom. Examples include phenyloxy and naphthyloxy.

The term "aromatic carbocyclylcarbonyl" means a group wherein the "aromatic carbocycle" is bonded to a carbonyl group. Examples include phenylcarbonyl and naphthylcarbonyl.

The term "aromatic carbocyclyloxycarbonyl" means a group wherein the above "aromatic carbocyclyloxy" is bonded to a carbonyl group. Examples include phenyloxycarbonyl and naphthyloxycarbonyl.

The term "aromatic carbocyclylsulfanyl" means a group wherein a hydrogen atom attached to a sulfur atom of a sulfanyl group is replaced with the "aromatic carbocycle". Examples include phenylsulfanyl and naphthylsulfanyl.

The term "aromatic carbocyclylsulfonyl" means a group wherein the "aromatic carbocycle" is bonded to a sulfonyl group. Examples include phenylsulfonyl and naphthylsulfonyl.

The non-aromatic carbocycle part of "non-aromatic carbocyclyloxy", "non-aromatic carbocyclylcarbonyl", "non-aromatic carbocyclyloxycarbonyl", "non-aromatic carbocyclylsulfanyl", and "non-aromatic carbocyclylsulfonyl" is also the same as above "non-aromatic carbocyclyl".

The term "non-aromatic carbocyclyloxy" means a group wherein the "non-aromatic carbocycle" is bonded to an oxygen atom. Examples include cyclopropyloxy, cyclohexyloxy, and cyclohexenyloxy.

The term "non-aromatic carbocyclylcarbonyl" means a group wherein the "non-aromatic carbocycle" is bonded to a carbonyl group. Examples include cyclopropylcarbonyl, cyclohexylcarbonyl, and cyclohexenylcarbonyl.

The term "non-aromatic carbocyclyloxycarbonyl" means a group wherein the above "non-aromatic carbocyclyloxy" is bonded to a carbonyl group. Examples include cyclopropyloxycarbonyl, cyclohexyloxycarbonyl, and cyclohexenyloxycarbonyl.

The term "non-aromatic carbocyclylsulfanyl" means a group wherein a hydrogen atom attached to a sulfur atom of a sulfanyl group is replaced with the "non-aromatic carbocycle". Examples include cyclopropylsulfanyl, cyclohexylsulfanyl, and cyclohexenylsulfanyl.

The term "non-aromatic carbocyclylsulfonyl" means a group wherein the "non-aromatic carbocycle" is bonded to a sulfonyl group. Examples include cyclopropylsulfonyl, cyclohexylsulfonyl, and cyclohexenylsulfonyl.

The aromatic heterocycle part of "aromatic heterocyclyloxy", "aromatic heterocyclylcarbonyl", "aromatic heterocyclyloxycarbonyl", "aromatic heterocyclylsulfanyl", and "aromatic heterocyclylsulfonyl" is also the same as above "aromatic heterocyclyl".

The term "aromatic heterocyclyloxy" means a group wherein the "aromatic heterocycle" is bonded to an oxygen atom. Examples include pyridyloxy and oxazolyloxy.

The term "aromatic heterocyclylcarbonyl" means a group wherein the "aromatic heterocycle" is bonded to a carbonyl group. Examples include pyridylcarbonyl and oxazolylcarbonyl.

The term "aromatic heterocyclyloxycarbonyl" means a group wherein the above "aromatic heterocyclyloxy" is bonded to a carbonyl group. Examples include pyridyloxycarbonyl and oxazolyloxycarbonyl.

The term "aromatic heterocyclylsulfanyl" means a group wherein a hydrogen atom attached to a sulfur atom of a sulfanyl group is replaced with the "aromatic heterocycle". Examples include pyridylsulfanyl and oxazolylsulfanyl.

The term "aromatic heterocyclylsulfonyl" means a group wherein the "aromatic heterocycle" is bonded to a sulfonyl group. Examples include pyridylsulfonyl and oxazolylsulfonyl.

The non-aromatic heterocycle part of "non-aromatic heterocyclyloxy", "non-aromatic heterocyclylcarbonyl", "non-aromatic heterocyclyloxycarbonyl", "non-aromatic heterocyclylsulfanyl", and "non-aromatic heterocyclylsulfonyl" is also the same as above "non-aromatic heterocyclyl".

The term "non-aromatic heterocyclyloxy" means a group wherein the "non-aromatic heterocycle" is bonded to an oxygen atom. Examples include piperidinyloxy and tetrahydrofuryloxy.

The term "non-aromatic heterocyclylcarbonyl" means a group wherein the "non-aromatic heterocycle" is bonded to a carbonyl group. Examples include piperidinylcarbonyl, and tetrahydrofurylcarbonyl.

The term "non-aromatic heterocyclyloxycarbonyl" means a group wherein the above "non-aromatic heterocyclyloxy" is bonded to a carbonyl group. Examples include piperidinyloxycarbonyl, and tetrahydrofuryloxycarbonyl.

The term "non-aromatic heterocyclylsulfanyl" means a group wherein a hydrogen atom attached to a sulfur atom of a sulfanyl group is replaced with the "non-aromatic heterocycle". Examples include piperidinylsulfanyl and tetrahydrofurylsulfanyl.

The term "non-aromatic heterocyclylsulfonyl" means a group wherein the "non-aromatic heterocycle" is bonded to a sulfonyl group. Examples include piperidinylsulfonyl and tetrahydrofurylsulfonyl.

The term "acyl" includes "formyl", "alkylcarbonyl", "alkenylcarbonyl", "alkynylcarbonyl", "aromatic heterocyclylcarbonyl", "non-aromatic heterocyclylcarbonyl", "aromatic heterocyclylcarbonyl" and "non-aromatic heterocyclylcarbonyl".

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylcarbonyl", "substituted or unsubstituted alkenylcarbonyl", "substituted or unsubstituted alkynylcarbonyl", "substituted or unsubstituted alkylamino", "substituted or unsubstituted alkenylamino", "substituted or unsubstituted alkylsulfonyl", "substituted or unsubstituted alkenylsulfonyl", "substituted or unsubstituted alkynylsulfonyl", "substituted or unsubstituted alkylcarbonylamino", "substituted or unsubstituted alkenylcarbonylamino", "substituted or unsubstituted alkylsulfonylamino", "substituted or unsubstituted alkenylsulfonylamino", "substituted or unsubstituted alkylimino", "substituted or unsubstituted alkenylimino", "substituted or unsubstituted alkynylimino", "substituted or unsubstituted alkylcarbonylimino", "substituted or unsubstituted alkenylcarbonylimino", "substituted or unsubstituted alkynylcarbonylimino", "substituted or unsubstituted alkyloxyimino", "substituted or unsubstituted alkenyloxyimino", "substituted or unsubstituted alkynyloxyimino", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfanyl", "substituted or unsubstituted alkenylsulfanyl", "substituted or unsubstituted alkynylsulfanyl", "substituted or unsubstituted sulfinyl", "substituted or unsubstituted alkylsulfinyl", "substituted or unsubstituted alkenylsulfinyl", "substituted or unsubstituted alkynylsulfinyl", "substituted or unsubstituted carbamoyl", "substituted or unsubstituted alkylcarbamoyl", "substituted or unsubstituted alkenylcarbamoyl", "substituted or unsubstituted alkynylcarbamoyl", "substituted or unsubstituted sulfamoyl", "substituted or unsubstituted alkylsulfamoyl", "substituted or unsubstituted alkenylsulfamoyl" and "substituted or unsubstituted alkynylsulfamoyl" include the following substituents. A carbon atom at any positions may be bonded to one or more group(s) selected from the following substituents.

A substituent: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydrazino, ureido, amidino, guanidino, trialkylsilyl, alkyloxy, alkenyloxy, alkynyloxy, haloalkyloxy, alkylcarbonyl, alkenylcarbonyl, alkynylcarbonyl, alkylamino, dialkylamino, alkylsulfonyl, alkenylsulfonyl, alkynylsulfonyl, alkylcarbonylamino, alkylcarbonylamino, alkylsulfonylamino, alkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, alkylcarbamoyl, alkenylcarbamoyl, alkynylcarbamoyl, alkylsulfamoyl, alkenylsulfamoyl, alkynylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, and non-aromatic heterocyclylsulfonyl.

The substituents on the ring of "aromatic carbocycle", "non-aromatic carbocycle", "aromatic heterocycle", and "non-aromatic heterocycle" part of "substituted or unsubstituted aromatic carbocyclyl", "substituted or unsubstituted non-aromatic carbocyclyl", "substituted or unsubstituted aromatic heterocyclyl" and "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", and "substituted or unsubstituted non-aromatic heterocyclyloxy", "substituted or unsubstituted aromatic carbocyclylcarbonyl", "substituted or unsubstituted non-aromatic carbocyclylcarbonyl", "substituted or unsubstituted aromatic heterocyclylcarbonyl", and "substituted or unsubstituted non-aromatic heterocyclylcarbonyl", "substituted or unsubstituted aromatic carbocyclylcarbonyloxy", "substituted or unsubstituted non-aromatic carbocyclylcarbonyloxy", "substituted or unsubstituted aromatic heterocyclylcarbonyloxy", and "substituted or unsubstituted non-aromatic heterocyclylcarbonyloxy", "substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", and "substituted or unsubstituted non-aromatic heterocyclyloxycarbonyl", "substituted or unsubstituted aromatic carbocyclylsulfanyl", "substituted or unsubstituted non-aromatic carbocyclylsulfanyl", "substituted or unsubstituted aromatic heterocyclylsulfanyl", and "substituted or unsubstituted non-aromatic heterocyclylsulfanyl", and "substituted or unsubstituted aromatic carbocyclylsulfonyl", "substituted or unsubstituted non-aromatic carbocyclylsulfonyl", "substituted or unsubstituted aromatic heterocyclylsulfonyl", and "substituted or unsubstituted non-aromatic heterocyclylsulfonyl" include the following substituents. An atom at any position(s) on the ring may be bonded to one or more group(s) selected from the following substituents.

A substituent: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydrazino, ureido, amidino, guanidino, trialkylsilyl, alkyl, alkenyl, alkynyl, haloalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, alkylamino, dialkylamino, alkylsulfonyl, alkenylsulfonyl, alkynylsulfonyl, alkylcarbonylamino, alkylcarbonylamino, alkylsulfonylamino, alkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, alkylcarbamoyl, alkenylcarbamoyl, alkynylcarbamoyl, alkylsulfamoyl, alkenylsulfamoyl, alkynylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkyloxyalkyl, non-aromatic carbocyclylalkyloxyalkyl, aromatic heterocyclylalkyloxyalkyl, non-aromatic heterocyclylalkyloxyalkyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, and non-aromatic heterocyclylsulfonyl.

Additionally, "substituted or unsubstituted non-aromatic carbocyclyl" and "substituted or unsubstituted non-aromatic heterocyclyl" may be substituted with "oxo". In this case, it means a group wherein two hydrogen atoms on the same carbon atom are substituted as below.

[Chemical Formula 48]

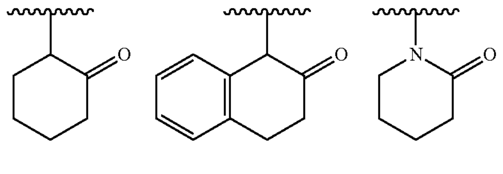

-continued

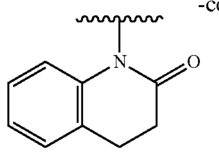

The non-aromatic carbocycle or non-aromatic heterocycle part of the above "substituted or unsubstituted non-aromatic carbocyclyloxy", "substituted or unsubstituted non-aromatic heterocyclyloxy", "substituted or unsubstituted non-aromatic carbocyclylcarbonyl", "substituted or unsubstituted non-aromatic heterocyclylcarbonyl", "substituted or unsubstituted non-aromatic carbocyclyloxycarbonyl", "substituted or unsubstituted non-aromatic heterocyclyloxycarbonyl", "substituted or unsubstituted non-aromatic carbocyclylsulfanyl", "substituted or unsubstituted non-aromatic heterocyclylsulfanyl", "substituted or unsubstituted non-aromatic carbocyclylsulfonyl", and "substituted or unsubstituted non-aromatic heterocyclylsulfonyl" may be substituted with "oxo" as described above.

The substituent of "substituted or unsubstituted alkyl" in $R^1$ includes, for example, substituted or unsubstituted aromatic heterocyclyl;
hydroxy;
substituted or unsubstituted alkyloxy;
substituted or unsubstituted non-aromatic carbocyclyl;
substituted or unsubstituted non-aromatic heterocyclyl;
substituted or unsubstituted amino; and
halogen. It may be substituted with one or more group(s) selected from the above substituents.

The substituent of "substituted or unsubstituted alkyl" in $R^1$ includes, for example, alkyloxy.

The substituent of "substituted or unsubstituted alkyl" in $R^{1A}$ includes, for example, substituted or unsubstituted aromatic heterocycle;
hydroxy; and
substituted or unsubstituted alkyloxy. It may be substituted with one or more group(s) selected from the above substituents.

The substituent of "substituted or unsubstituted alkyl" in $R^{1A}$ includes, for example, alkyloxy.

The substituent of "substituted or unsubstituted aromatic carbocyclyl" in B includes, for example, halogen; and
substituted or unsubstituted alkyl. It may be substituted with one or more group(s) selected from the above substituents.

The substituent of "substituted or unsubstituted aromatic carbocyclyl" in B includes, for example, halogen; and
substituted alkyl (the substituent: hydroxy, halogen) or unsubstituted alkyl.

The substituent of "substituted or unsubstituted aromatic heterocyclyl" in B includes, for example, halogen;
substituted or unsubstituted alkyl; and
substituted or unsubstituted alkyloxy. It may be substituted with one or more group(s) selected from the above substituents.

The substituent of "substituted or unsubstituted aromatic heterocyclyl" in B includes, for example, halogen; and
substituted alkyl (the substituent: hydroxy, halogen).

The substituent of "substituted or unsubstituted aromatic heterocycle" in the ring C includes, for example, substituted or unsubstituted aromatic carbocyclyl;
substituted or unsubstituted aromatic heterocyclyl;
substituted or unsubstituted non-aromatic heterocyclyl;
substituted or unsubstituted non-aromatic carbocyclyl;
substituted or unsubstituted alkyl; and
substituted or unsubstituted alkyloxy. It may be substituted with one or more group(s) selected from the above substituents.

The substituent of "substituted or unsubstituted aromatic heterocycle" in the ring C includes, for example, substituted or unsubstituted phenyl;
substituted or unsubstituted pyrazolyl;
substituted or unsubstituted indazolyl;
substituted or unsubstituted pyrimidinyl;
substituted or unsubstituted pyridyl;
substituted or unsubstituted piperazinyl;
substituted or unsubstituted tetrahydropyridinyl;
substituted or unsubstituted triazolopyrimidinyl;
substituted or unsubstituted triazolopyridinyl;
substituted or unsubstituted pyrazolopyridinyl;
substituted or unsubstituted oxazolopyridinyl;
substituted or unsubstituted isoxazolopyridinyl;
substituted or unsubstituted imidazopyridinyl;
substituted or unsubstituted pyridonyl;
substituted or unsubstituted dihydropyridinyl;
substituted or unsubstituted dihydropyrazolopyridinyl;
substituted or unsubstituted alkyl;
substituted or unsubstituted alkyloxy;
substituted or unsubstituted cyclopropyl;
substituted or unsubstituted cyclobutyl;
substituted or unsubstituted pyridopyrazinyl;
substituted or unsubstituted naphthyridinyl;
substituted or unsubstituted pyrrolopyrazolyl;
substituted or unsubstituted furopyridinyl;
substituted or unsubstituted dihydrobenzisothiazole dioxide-yl;
substituted or unsubstituted pyridooxazinyl;
substituted or unsubstituted thiazolyl;
substituted or unsubstituted pyrrolopyridinyl; and
substituted or unsubstituted dihydropyridazinyl. It may be substituted with one or more group(s) selected from the above substituents.

The substituent of "substituted or unsubstituted pyrazole" in the ring C includes, for example, substituted or unsubstituted aromatic carbocyclyl;
substituted or unsubstituted aromatic heterocyclyl;
substituted or unsubstituted non-aromatic heterocyclyl;
substituted or unsubstituted alkyl; and
substituted or unsubstituted alkyloxy. It may be substituted with one or more group(s) selected from the above substituents.

The substituent of "substituted or unsubstituted pyrazole" in the ring C includes, for example, substituted or unsubstituted phenyl;
substituted or unsubstituted pyrazolyl;
substituted or unsubstituted imidazolyl;
substituted or unsubstituted indazolyl;
substituted or unsubstituted pyrimidinyl;
substituted or unsubstituted pyridinyl;
substituted or unsubstituted piperazinyl;
substituted or unsubstituted tetrahydropyridinyl;
substituted or unsubstituted triazolopyrimidinyl;
substituted or unsubstituted triazolopyridinyl;
substituted or unsubstituted pyrazolopyridinyl;
substituted or unsubstituted oxazolopyridinyl;

substituted or unsubstituted isoxazolopyridinyl;
substituted or unsubstituted imidazopyridinyl;
substituted or unsubstituted pyridonyl;
substituted or unsubstituted dihydropyridinyl;
substituted or unsubstituted dihydropyrazolopyridinyl;
substituted or unsubstituted alkyl;
substituted or unsubstituted alkyloxy;
substituted or unsubstituted cyclopropyl;
substituted or unsubstituted cyclobutyl;
substituted or unsubstituted pyridopyrazinyl;
substituted or unsubstituted naphthyridinyl;
substituted or unsubstituted pyrrolopyrazolyl;
substituted or unsubstituted furopyridinyl;
substituted or unsubstituted dihydrobenzisothiazole dioxide-yl;
substituted or unsubstituted pyridooxazinyl;
substituted or unsubstituted thiazolyl;
substituted or unsubstituted pyrrolopyridinyl;
substituted or unsubstituted dihydropyridazinyl;
substituted or unsubstituted dihydroimidazopyridinyl;
substituted or unsubstituted dihydrooxazolopyridinyl;
substituted or unsubstituted dihydronaphthyridinyl;
substituted or unsubstituted tetrahydropyrrolopyrazolyl;
substituted or unsubstituted dihydrofuropyridinyl;
substituted or unsubstituted dihydroisoxazolopyridinyl;
substituted or unsubstituted dihydropyridooxazinyl; and
substituted or unsubstituted dihydropyrrolopyridinyl. It may be substituted with one or more group(s) selected from the above substituents.

The substituent of “substituted or unsubstituted aromatic heterocycle” in the ring C includes, for example,
substituted or unsubstituted aromatic carbocyclyl;
substituted or unsubstituted aromatic heterocyclyl;
substituted or unsubstituted non-aromatic heterocyclyl;
substituted or unsubstituted non-aromatic carbocyclyl;
substituted or unsubstituted alkyl;
substituted or unsubstituted alkyloxy; and
substituted or unsubstituted carbamoyl. It may be substituted with one or more group(s) selected from the above substituents.

The substituent of “substituted or unsubstituted pyrazole” in the ring C includes, for example,
substituted or unsubstituted phenyl;
substituted or unsubstituted pyrazolyl;
substituted or unsubstituted imidazolyl;
substituted or unsubstituted indazolyl;
substituted or unsubstituted pyrimidinyl;
substituted or unsubstituted pyridinyl;
substituted or unsubstituted piperazinyl;
substituted or unsubstituted tetrahydropyridinyl;
substituted or unsubstituted triazolopyrimidinyl;
substituted or unsubstituted triazolopyridinyl;
substituted or unsubstituted pyrazolopyridinyl;
substituted or unsubstituted oxazolopyridinyl;
substituted or unsubstituted isoxazolopyridinyl;
substituted or unsubstituted imidazopyridinyl;
substituted or unsubstituted pyridonyl;
substituted or unsubstituted dihydropyridinyl;
substituted or unsubstituted dihydropyrazolopyridinyl;
substituted or unsubstituted alkyl;
substituted or unsubstituted alkyloxy;
substituted or unsubstituted cyclopropyl;
substituted or unsubstituted cyclobutyl;
substituted or unsubstituted pyridopyrazinyl;
substituted or unsubstituted naphthyridinyl;
substituted or unsubstituted pyrrolopyrazolyl;
substituted or unsubstituted furopyridinyl;
substituted or unsubstituted dihydrobenzisothiazole dioxide-yl;
substituted or unsubstituted pyridooxazinyl;
substituted or unsubstituted thiazolyl;
substituted or unsubstituted pyrrolopyridinyl;
substituted or unsubstituted dihydropyridazinyl;
substituted or unsubstituted dihydroimidazopyridinyl;
substituted or unsubstituted dihydrooxazolopyridinyl;
substituted or unsubstituted dihydronaphthyridinyl;
substituted or unsubstituted tetrahydropyrrolopyrazolyl;
substituted or unsubstituted dihydrofuropyridinyl;
substituted or unsubstituted dihydroisoxazolopyridinyl;
substituted or unsubstituted dihydropyridooxazinyl;
substituted or unsubstituted dihydropyrrolopyridinyl;
substituted or unsubstituted pyrazolopyrazinyl;
substituted or unsubstituted azetidinyl;
substituted or unsubstituted pyrazinyl;
substituted or unsubstituted dioxolopyridinyl;
substituted or unsubstituted dihydrodioxinopyridinyl;
substituted or unsubstituted dihydropyridinonyl; and
substituted or unsubstituted carbamoyl. It may be substituted with one or more group(s) selected from the above substituents.

The substituent of “substituted or unsubstituted aromatic heterocyclyl” in $R^{13}$ includes, for example, halogen.

The substituent of “substituted or unsubstituted aromatic carbocyclyl” in $R^{13}$ includes, for example, halogen.

The substituent of “substituted or unsubstituted alkyl” in $R^{13}$ includes, for example, dialkylamino; aromatic carbocyclyl; and hydroxy. It may be substituted with one or more group(s) selected from the above substituents.

The substituent of “substituted or unsubstituted alkyl” in $R^{15}$ includes, for example, halogen and hydroxy.

The substituent of “substituted or unsubstituted aromatic heterocyclyl”, “substituted or unsubstituted aromatic carbocyclyl”, “substituted or unsubstituted non-aromatic heterocyclyl”, or “substituted or unsubstituted non-aromatic carbocyclyl” in $R^{14}$ includes, for example,
carboxy;
oxo;
hydroxy;
halogen;
cyano;
substituted alkyl (the substituent: halogen, hydroxy, alkylcarbonyloxy, amino) or unsubstituted alkyl;
substituted alkyloxy (the substituent: halogen, hydroxy, amino, alkylamino, dialkylamino) or unsubstituted alkyloxy;
substituted alkyloxycarbonyl (the substituent: halogen, hydroxy, aromatic carbocyclyl) or unsubstituted alkyloxycarbonyl;
substituted carbamoyl (the substituent: non-aromatic heterocyclyl, non-aromatic carbocyclyl, alkyl, haloalkyl, hydroxyalkyl, alkyloxyalkyl, hydroxy, alkyloxy, haloalkyloxy, hydroxyalkyloxy, aminoalkyl, alkylaminoalkyl, dialkylaminoalkyl) or unsubstituted carbamoyl;
substituted acyl (the substituent: halogen, hydroxy, amino, alkylamino, dialkylamino) or unsubstituted acyl;
substituted amino (the substituent: alkyl, alkyloxycarbonyl, non-aromatic carbocyclyl) or unsubstituted amino;
substituted imino (the substituent: sulfoxy, alkylsulfoxy, dialkylsulfoxy);
substituted non-aromatic carbocyclyl (the substituent: alkyl, halogen, hydroxy, amino, alkylamino, dialkylamino) or unsubstituted non-aromatic carbocyclyl;

substituted non-aromatic heterocyclyl (the substituent: alkyl, halogen, hydroxy, phenylcarbonyloxy, amino, alkylamino, dialkylamino) or unsubstituted non-aromatic heterocyclyl;

substituted sulfonyl (the substituent: amino, alkylamino, dialkylamino, alkyl);

substituted sulfanyl (the substituent: alkyl) or unsubstituted sulfanyl;

substituted aromatic heterocyclyl (the substituent: alkyl, hydroxy, halogen, amino, alkylamino, dialkylamino) or unsubstituted aromatic heterocyclyl; and substituted aromatic carbocyclyl (the substituent: alkyl, hydroxy, halogen, amino, alkylamino, dialkylamino) or unsubstituted aromatic heterocyclyl. It may be substituted with one or more group(s) selected from the above substituents.

The substituent of "substituted or unsubstituted alkyloxy" in $R^{14}$ includes, for example, halogen; hydroxy; amino; alkylamino; and dialkylamino.

The substituent of "substituted or unsubstituted aromatic heterocyclyl", "substituted or unsubstituted aromatic carbocyclyl", "substituted or unsubstituted non-aromatic heterocyclyl", or "substituted or unsubstituted non-aromatic carbocyclyl" in $R^{14}$ includes, for example, carboxy;

oxo;

hydroxy;

halogen;

cyano;

substituted alkyl (the substituent: halogen, hydroxy, alkylcarbonyloxy, amino, alkylamino, dialkylamino, non-aromatic heterocyclyl, alkyloxycarbonyl, dialkylcarbamoyl, alkylcarbamoyl, acyl, aromatic carbocyclyl, alkylsilyloxy, alkyloxy, dialkylsulfonylamino) or unsubstituted alkyl;

substituted alkyloxy (the substituent: halogen, hydroxy, amino, alkylamino, dialkylamino, alkyloxy, non-aromatic carbocyclyl) or unsubstituted alkyloxy;

substituted alkyloxycarbonyl (the substituent: halogen, hydroxy, aromatic carbocyclyl) or unsubstituted alkyloxycarbonyl;

substituted carbamoyl (the substituent: non-aromatic heterocyclyl, non-aromatic carbocyclyl, alkyl, haloalkyl, hydroxyalkyl, alkyloxyalkyl, hydroxy, alkyloxy, haloalkyloxy, hydroxyalkyloxy, aminoalkyl, alkylaminoalkyl, dialkylaminoalkyl) or unsubstituted carbamoyl;

substituted acyl (the substituent: halogen, hydroxy, amino, alkylamino, dialkylamino, non-aromatic heterocyclyl) or unsubstituted acyl;

substituted amino (the substituent: alkyl, alkyloxycarbonyl, non-aromatic carbocyclyl, haloalkyl, alkyloxyalkyl, dialkylaminoalkyl) or unsubstituted amino;

substituted imino (the substituent: sulfoxy, alkylsulfoxy, dialkylsulfoxy);

substituted non-aromatic carbocyclyl (the substituent: alkyl, halogen, hydroxy, amino, alkylamino, dialkylamino) or unsubstituted non-aromatic carbocyclyl;

substituted non-aromatic heterocyclyl (the substituent: alkyl, halogen, hydroxy, phenylcarbonyloxy, amino, alkylamino, dialkylamino, alkyloxy, alkyloxycarbonyl, alkylcarbonylamino, cyanoalkyl, acyl, alkyloxycarbonylamino, oxo, non-aromatic heterocyclyl, hydroxyacyl) or unsubstituted non-aromatic heterocyclyl;

substituted sulfonyl (the substituent: amino, alkylamino, dialkylamino, alkyl);

substituted sulfanyl (the substituent: alkyl) or unsubstituted sulfanyl;

substituted aromatic heterocyclyl (the substituent: alkyl, hydroxy, halogen, amino, alkylamino, dialkylamino) or unsubstituted aromatic heterocyclyl;

substituted aromatic carbocyclyl (the substituent: alkyl, hydroxy, halogen, amino, alkylamino, dialkylamino) or unsubstituted aromatic heterocyclyl;

substituted non-aromatic heterocyclyloxy (the substituent: alkyl) or unsubstituted non-aromatic heterocyclyloxy; and substituted non-aromatic carbocyclyloxy or unsubstituted non-aromatic carbocyclyloxy. It may be substituted with one or more group(s) selected from the above substituents.

The substituent of "substituted or unsubstituted alkyloxy" in $R^{14}$ includes, for example, halogen; hydroxy; alkyloxy; amino; alkylamino; dialkylamino; unsubstituted carbamoyl; substituted carbamoyl (the substituent: alkyl, non-aromatic carbocyclyl, aminoalkyl, alkylaminoalkyl, dialkylaminoalkyl, hydroxyalkyl); unsubstituted non-aromatic heterocyclyl; substituted non-aromatic heterocyclyl (the substituent: halogen, acyl, alkyl, alkyloxycarbonyl, alkyloxy, hydroxy, amino, alkylamino, dialkylamino, hydroxyacyl, alkyloxyacyl, oxo); unsubstituted aromatic heterocyclyl; substituted aromatic heterocyclyl (the substituent: alkyl, alkyloxy); and non-aromatic carbocyclyl. It may be substituted with one or more group(s) selected from the above substituents.

The substituent of "substituted or unsubstituted non-aromatic heterocyclyloxy" in $R^{14}$ includes, for example, halogen, acyl, alkyl, alkyloxycarbonyl, alkyloxy, hydroxy, amino, alkylamino, and dialkylamino. It may be substituted with one or more group(s) selected from the above substituents.

The substituent of "substituted or unsubstituted aromatic heterocyclyloxy" in $R^{14}$ includes, for example, halogen; alkyl; and haloalkyl. It may be substituted with one or more group(s) selected from the above substituents.

The substituent of "substituted or unsubstituted carbamoyl" in $R^{14}$ includes, for example, unsubstituted alkyl; and substituted alkyl (the substituent: hydroxy, aromatic heterocyclyl).

The substituent of "substituted or unsubstituted alkyl" in $R^{14}$ includes, for example, amino; alkylamino; dialkylamino; hydroxy; halogen; and alkylsilyloxy.

It may be substituted with one or more group(s) selected from the above substituents.

Embodiments of the present invention are exemplified below.

A compound represented by Formula (IA):

[Chemical Formula 49]

(IA)

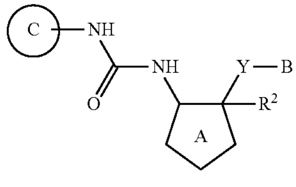

wherein each symbol in the formula is the same as above, or a pharmaceutically acceptable salt thereof.

Embodiments of the group represented by Formula:

[Chemical Formula 50]

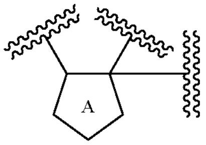

Y, B, $R^2$ and ring C are exemplified below. The embodiment of compounds represented by Formula (IA) includes the compounds indicated by all possible combination of the following each substituent.

The group represented by Formula:

[Chemical Formula 51]

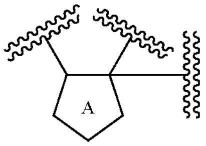

includes a group represented by Formula:

[Chemical Formula 52]

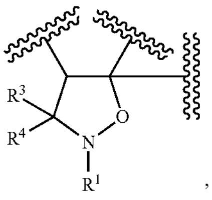
,
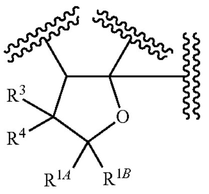
or
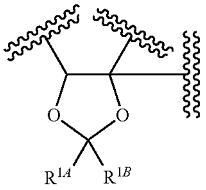
, wherein $R^1$, $R^{1A}$, $R^{1B}$, $R^3$ and $R^4$ are the same as above. (hereinafter, referred to as A-1)

The group represented by Formula:

[Chemical Formula 53]

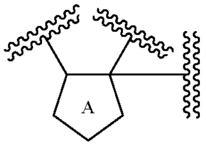

includes a group represented by Formula:

[Chemical Formula 54]

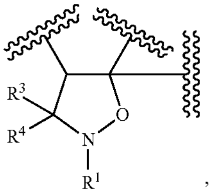
,
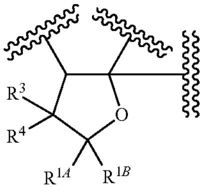
or
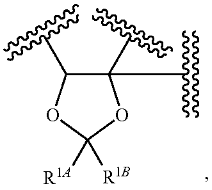
, wherein $R^1$, $R^{1A}$ and $R^{1B}$ are the same as above, and each of $R^3$ and $R^4$ is a hydrogen atom. (hereinafter, referred to as A-2)

Y includes a single bond or substituted or unsubstituted alkylene which may be intervened by an oxygen atom. (hereinafter, referred to as B-1)

Y includes a single bond. (hereinafter, referred to as B-2)

B includes substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted alkyl, or substituted or unsubstituted alkyloxy. (hereinafter, referred to as C-1)

B includes substituted or unsubstituted aromatic carbocyclyl, or substituted or unsubstituted aromatic heterocyclyl. (hereinafter, referred to as C-2)

B includes aromatic carbocyclyl substituted with halogen or aromatic heterocyclyl substituted with halogen. (hereinafter, referred to as C-3)

Ring C includes a substituted or unsubstituted aromatic heterocycle or a substituted or unsubstituted non-aromatic heterocycle. (hereinafter, referred to as D-1)

Ring C includes a substituted or unsubstituted aromatic heterocycle. (hereinafter, referred to as D-2)

Ring C includes substituted or unsubstituted pyrazole. (hereinafter, referred to as D-3)

Ring C includes pyrazole substituted with substituted or unsubstituted phenyl. (hereinafter, referred to as D-4)

Ring C includes pyrazole substituted with substituted or unsubstituted alkyl. (hereinafter, referred to as D-5)

Ring C includes pyrazole substituted with substituted or unsubstituted pyrazolyl. (hereinafter, referred to as D-6)

Ring C includes a ring as follows. (hereinafter, referred to as D-7)

Formula:

[Chemical Formula 55]

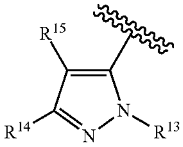

wherein $R^{13}$ is substituted or unsubstituted aromatic carbocyclyl, substituted or unsubstituted alkyl, or substituted or unsubstituted non-aromatic carbocyclyl, $R^{14}$ is substituted or unsubstituted aromatic heterocyclyl, substituted or unsubstituted alkyloxy, substituted or unsubstituted aromatic carbocyclyl, or substituted or unsubstituted non-aromatic heterocyclyl, and $R^{15}$ is a hydrogen atom, substituted or unsubstituted alkyl or halogen.

Ring C includes a ring as follows. (hereinafter, referred to as D-8)

Formula:

[Chemical Formula 56]

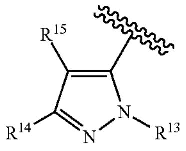

wherein $R^{13}$ is substituted or unsubstituted aromatic carbocyclyl, $R^{14}$ is substituted or unsubstituted aromatic heterocyclyl, substituted or unsubstituted alkyloxy, or substituted or unsubstituted non-aromatic heterocyclyl, and $R^{15}$ is substituted or unsubstituted alkyl or halogen.

$R^1$ includes substituted or unsubstituted alkyl. (hereinafter, referred to as E-1)

$R^1$ includes alkyl substituted with substituted or unsubstituted alkoxy. (hereinafter, referred to as E-2)

$R^1$ includes alkyl substituted with alkoxy. (hereinafter, referred to as E-3)

$R^1$ includes C2-C6 alkyl substituted with substituted or unsubstituted C1-C3 alkoxy. (hereinafter, referred to as E-4)

$R^1$ includes C2-C6 alkyl substituted with C1-C3 alkoxy. (hereinafter, referred to as E-5)

$R^{1A}$ includes substituted or unsubstituted alkyl, and $R^{1B}$ includes a hydrogen atom. (hereinafter, referred to as E-6)

$R^{1A}$ includes alkyl substituted with substituted or unsubstituted alkoxy, and $R^{1B}$ includes a hydrogen atom. (hereinafter, referred to as E-7)

$R^{1A}$ includes alkyl substituted with alkoxy, and $R^{1B}$ includes a hydrogen atom. (hereinafter, referred to as E-8)

$R^{1A}$ includes C2-C6 alkyl substituted with substituted or unsubstituted C1-C3 alkoxy, and $R^{1B}$ includes a hydrogen atom. (hereinafter, referred to as E-9)

$R^{1A}$ includes C2-C6 alkyl substituted with C1-C3 alkoxy, and $R^{1B}$ includes a hydrogen atom. (hereinafter, referred to as E-10)

The compounds of Formula (I) or Formula (IA) are not limited to specific isomers but include all possible isomers (e.g., keto-enol isomers, imine-enamine isomers, diastereoisomers, enantiomers, or rotamers), racemates or mixtures thereof.

One or more hydrogen, carbon and/or other atom(s) in the compounds of Formula (I) or Formula (IA) may be replaced with isotopes of hydrogen, carbon and/or other atoms respectively. Examples of isotopes include hydrogen, carbon, nitrogen, oxygen, phosphorus, sulfur, fluorine, iodine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds of Formula (I) or Formula (IA) include the compounds replaced with these isotopes. The compounds replaced with the above isotopes are useful as medicines and include all of radiolabeled compounds of the compound of Formula (I) or Formula (IA). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the compounds of Formula (I) or Formula (IA) can be prepared using well-known methods in this field of the invention. For example, a tritium-labeled compound of Formula (I) or Formula (IA) can be prepared by introducing a tritium to a certain compound of Formula (I) or Formula (IA) through a catalytic dehalogenation reaction using a tritium. This method comprises reacting an appropriately-halogenated precursor of the compound of Formula (I) or Formula (IA) with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$.

The pharmaceutically acceptable salts of the compounds of Formula (I) or Formula (IA) include, for example, salts with alkaline metal (e.g., lithium, sodium, or potassium), alkaline earth metal (e.g., calcium or barium), magnesium, transition metal (e.g., zinc or iron), ammonia, organic bases (e.g., trimethylamine, triethylamine, dicyclohexylamine, ethanolamine, diethanolamine, triethanolamine, meglumine, diethanolamine, ethylenediamine, pyridine, picoline, or quinoline), amino acids, or salts with inorganic acids (e.g., hydrochloric acid, sulfuric acid, nitric acid, carbonic acid, hydrobromic acid, phosphoric acid, or hydroiodic acid) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, or ethanesulfonic acid). Especially, salts with hydrochloric acid, sulfuric acid, phosphoric acid, tartaric acid, methanesulfonic acid and the like are included. These salts can be formed by the usual methods.

The compounds of Formula (I) or Formula (IA) of the present invention or pharmaceutically acceptable salts thereof may form solvates (e.g., hydrates), co-crystal and/or crystal polymorphs. The present invention encompasses those various solvates, co-crystal and crystal polymorphs. "Solvates" may be those wherein any numbers of solvent molecules (e.g., water molecules) are coordinated with the compounds of Formula (I) or Formula (IA). When the compounds of Formula (I) or Formula (IA) or pharmaceutically acceptable salts thereof are allowed to stand in the atmosphere, the compounds may absorb water, resulting in attachment of adsorbed water or formation of hydrates. Recrystallization of the compounds of Formula (I) or Formula (IA) or pharmaceutically acceptable salts thereof may produce crystal polymorphs. "Co-crystal" means that a compound of Formula (I) or Formula (IA) or a salt thereof and a counter-molecule exist in the same crystal lattice, and it can be formed with any number of counter-molecules.

The compounds of Formula (I) or Formula (IA) of the present invention or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds of Formula (I) or Formula (IA) through enzymatic oxidation, reduction, hydrolysis or the like under physiological conditions in vivo, compounds that are converted to the compounds of Formula (I) or Formula (IA) through hydrolysis by gastric acid etc., and the like. Methods for selecting and preparing suitable prodrug derivatives are described in, for example, "Design of Prodrugs, Elsevier, Amsrdam, 1985". Prodrugs themselves may have some activity.

When the compounds of Formula (I) or Formula (IA) or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride and mixed anhydride, or with a condensing agent. For example, they include $CH_3COO—$, $C_2H_5COO—$, tert-BuCOO—, $C_{15}H_{31}COO—$, PhCOO—, (m-NaOOCPh)COO—, $NaOOCCH_2CH_2COO—$, $CH_3CH(NH_2)COO—$, $CH_2N(CH_3)_2COO—$, $CH_3SO_3—$, $CH_3CH_2SO_3—$, $CF_3SO_3—$, $CH_2FSO_3—$, $CF_3CH_2SO_3—$, p-$CH_3O$-$PhSO_3—$, $PhSO_3—$ and p-$CH_3PhSO_3—$.

General procedures for the synthesis of the compounds of the present invention are described below. Starting materials and reaction reagents used in such synthesis are commercially available or can be synthesized according to methods well known in the art using compounds commercially available. Further, extraction, purification and the like may be performed in accordance with the methods carried out in the art.

In the following all steps, when a substituent which impedes a reaction, e.g. hydroxy, mercapto, amino, formyl, carbonyl, carboxy, is possessed, the substituent is protected by the method described in Protective Groups in organic Synthesis, and Theodora W Greene (John Wiley & Sons, hereinafter referred to as literature A) in advance, and the protecting group may be removed at a desirable stage. In addition, in the all steps, an order of steps to be implemented may be appropriately changed, and each intermediate may be isolated, and used in a next step. All of reaction time, reaction temperature, solvents, reagents, protecting groups, etc. are mere exemplification and not limited as long as they do not cause an adverse effect on a reaction.

For example, the compounds represented by Formula (I) of the present invention can be prepared by the general synthetic methods described below.

[Chemical Formula 57]

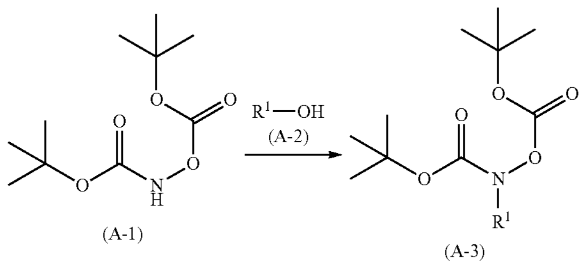

(A-1)

(A-3)

-continued

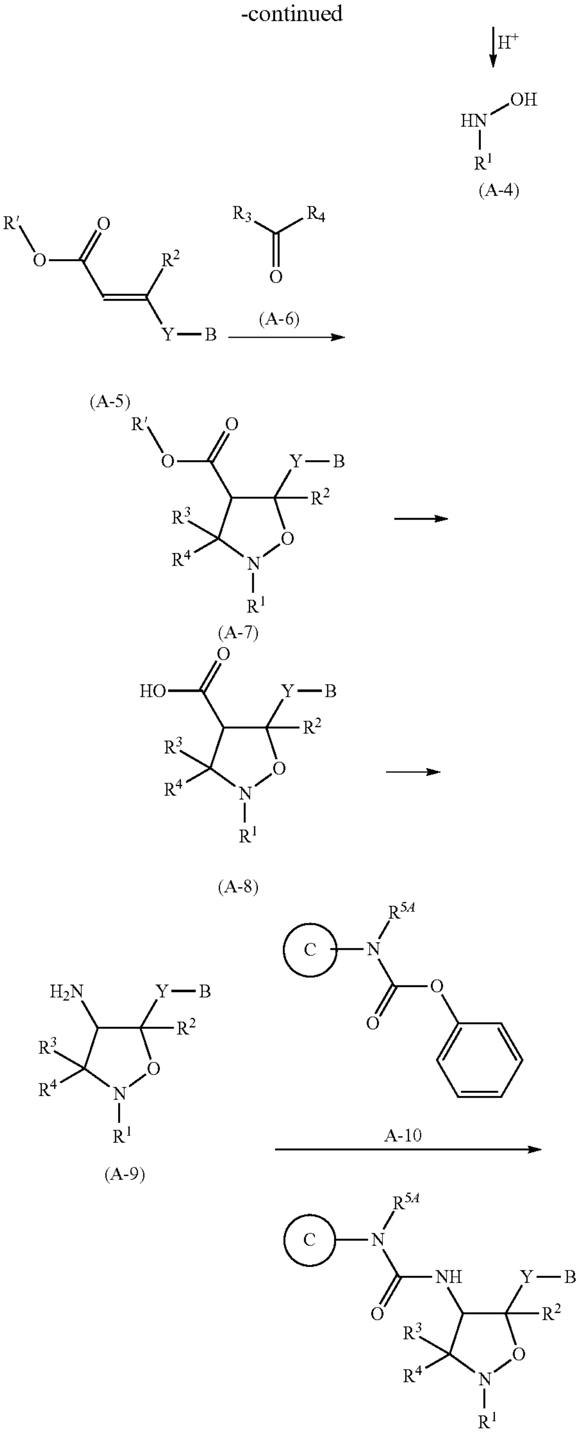

(A-4)

(A-5)

(A-7)

(A-8)

(A-9)

(I-A)

wherein each symbol in the formula is the same as above, R' is C1-C4 alkyl, and X' is halogen.

(Method A)

(Step 1)

Compound (A-3) can be obtained by reacting Compound (A-1) with Compound (A-2) in the presence of phosphine and azodicarboxylic acid ester.

Compound (A-1) is commercially available or can be synthesized according to the known methods.

Compound (A-2) is commercially available or can be synthesized according to the known methods. It can be used at 1 to 3 mol equivalent(s) relative to Compound (A-1).

As the phosphine, triphenylphosphine, tributylphosphine, trimethylphosphine and the like are exemplified, and it can be used at 1 to 3 mol equivalent(s) relative to Compound (A-1).

As the azodicarboxylic acid ester, diethyl azodicarboxylate, diisopropyl azodicarboxylate and the like are exemplified, and it can be used at 1 to 3 mol equivalent(s) relative to Compound (A-1).

The reaction temperature is 0° C. to the reflux temperature of the solvent, preferably room temperature to 50° C.

The reaction time is 0.1 to 24 hour(s), preferably 0.5 to 12 hour(s).

As the reaction solvent, dichloromethane, THF, toluene and the like are exemplified, and it can be used alone or in combination.

(Step 2)

Compound (A-4) can be obtained by deprotection of the Boc group of Compound (A-3) which is obtained in the above step 1. For example, the method disclosed in the above literature A can be used.

(Step 3)

Compound (A-7) can be obtained by reacting Compound (A-4), Compound (A-5) and Compound (A-6) in the presence of a base.

Compound (A-5) is commercially available or can be synthesized according to the known methods. It can be used at 1 to 3 mol equivalent(s) relative to Compound (A-4).

Compound (A-6) is commercially available or can be synthesized according to the known methods. It can be used at 1 to 5 mol equivalent(s) relative to Compound (A-4).

As the base, triethylamine, diisopropylethylamine, N-methylmorpholine and the like are exemplified, and it can be used at 1 to 5 mol equivalent(s) relative to Compound (A-4).

The reaction temperature is room temperature to the reflux temperature of the solvent, preferably 0 to 80° C.

The reaction time is 0.1 to 24 hour(s), preferably 0.5 to 12 hour(s).

As the reaction solvent, xylene, toluene and the like are exemplified, and it can be used alone or in combination.

(Step 4)

Compound (A-8) can be obtained by deprotection of protecting group for carboxyl group of Compound (A-7) which is obtained in the above step 2. For example, the method disclosed in the above literature A can be used.

(Step 5)

The carboxyl group of Compound (A-8) which is obtained in the above step 4 can be converted to an amino group by Curtius rearrangement.

As the reagent used for Curtius rearrangement, DPPA and the like are exemplified, and it can be used at 1 to 5 mol equivalent(s) relative to Compound (A-8).

The reaction temperature is room temperature to the reflux temperature of the solvent, preferably 50 to 100° C.

The reaction time is 0.1 to 24 hour(s), preferably 0.5 to 12 hour(s).

As the reaction solvent, 2-(trimethylsilyl)ethanol, t-BuOH, benzyl alcohol and the like can be used.

As the reaction solvent, toluene, benzene and the like can be also used. In this case, carbamate can be obtained by adding the above alcohol after preparation of isocyanate.

The above alcohol can be used at 1 to 5 mol equivalent(s) relative to Compound (A-8).

The obtained carbamate can be deprotected in accordance with the method described in the above literature A to give Compound (A-9).

(Step 6)

Compound (I-A) can be obtained by reacting Compound (A-9) with Compound (A-10) in the presence of a base.

Compound (A-10) can be synthesized in accordance with the method described in WO2012/158413. It can be used at 1 to 1.5 mol equivalent(s) relative to Compound (A-9).

As the base, pyridine, triethylamine, diisopropylethylamine, N-methylmorpholine and the like are exemplified, and it can be used at 1 to 5 mol equivalent(s) relative to Compound (A-9).

The reaction temperature is 0° C. to the reflux temperature of the solvent, preferably room temperature to 50° C.

The reaction time is 0.1 to 24 hour(s), preferably 0.5 to 12 hour(s).

As the reaction solvent, dichloromethane, chloroform, THF, toluene, DMF, DMSO, dioxane and the like are exemplified, and it can be used alone or in combination.

[Chemical Formula 58]

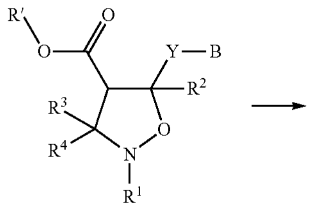

(A-7)

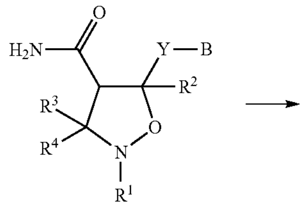

(A-8-1)

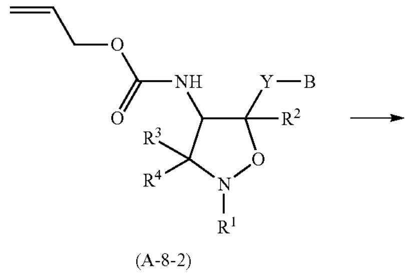

(A-8-2)

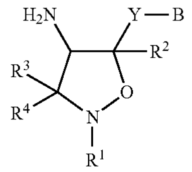

(A-9)

wherein each symbol in the formula is the same as above, and R' is C1-C4 alkyl.

(Method A') Synthesis of Compound (A-9) from Compound (A-7)

(Step 1)

Compound (A-8-1) can be obtained by treating Compound (A-7) which is obtained in step 3 of the above Method A with a solution of ammonia in methanol.

The solution of ammonia in methanol can be used at 10 to 100 mol equivalents relative to Compound (A-7).

The reaction temperature is room temperature to the reflux temperature of the solvent, preferably room temperature to 40° C.

The reaction time is 0.1 to 120 hour(s), preferably 0.5 to 72 hour(s).

(Step 2)

Compound (A-8-2) can be obtained by reacting Compound (A-8-1) with allyl alcohol and iodobenzene diacetate.

The allyl alcohol can be used at 10 to 50 mol equivalents relative to Compound (A-8-1).

The iodobenzene diacetate can be used at 1 to 5 mol equivalent(s) relative to Compound (A-8-1).

The reaction temperature is 50° C. to the reflux temperature of the solvent, preferably 60 to 80° C.

The reaction time is 0.1 to 24 hour(s), preferably 0.5 to 12 hour(s).

As the reaction solvent, 1,2-dichloroethane, toluene, xylene and the like are exemplified, and it can be used alone or in combination.

(Step 3)

Compound (A-9) can be obtained by reacting Compound (A-8-2) with amine in the presence of a palladium catalyst.

As the palladium catalyst, tetrakis(triphenylphosphine) palladium is exemplified, and it can be used at 0.01 to 0.1 mol equivalent relative to Compound (A-8-2).

As the amine, diethylamine, morpholine and the like are exemplified, and it can be used at 1 to 5 mol equivalent(s) relative to Compound (A-8-2).

The reaction temperature is room temperature to the reflux temperature of the solvent, preferably 0 to 80° C.

The reaction time is 0.1 to 24 hour(s), preferably 0.5 to 12 hour(s).

As the reaction solvent, xylene, toluene and the like are exemplified, and it can be used alone or in combination.

[Chemical Formula 59]

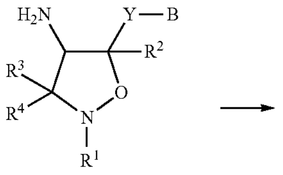

(A-9)

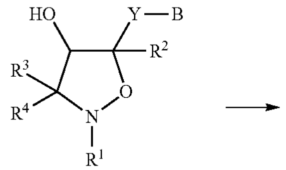

(B-1)

-continued

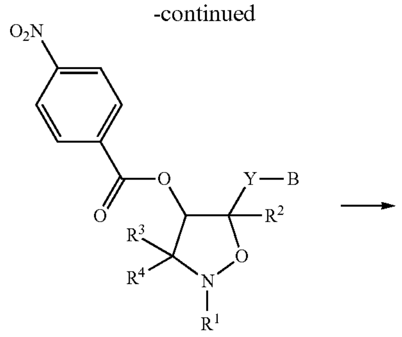

(B-2)

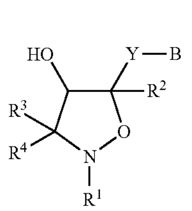

(B-3)

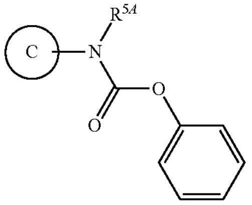

(A-10)

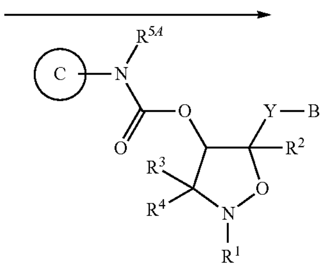

(I-B)

wherein each symbol in the formula is the same as above.

(Method B)

(Step 1)

Compound (B-1) can be synthesized by reacting Compound (A-9) with a sodium nitritein the presence of an acid.

Compound (A-9) can be synthesized in accordance with the above Method A.

Examples of the acid include hydrochloric acid and acetic acid, and it can be used at 1 to 5 mol equivalent relative to Compound (A-9).

Sodium nitrite can be used at 1 to 5 mol equivalent(s) relative to Compound (A-9).

The reaction temperature is 0° C. to the reflux temperature of the solvent, preferably room temperature to 80° C.

The reaction time is 0.1 to 72 hour(s), preferably 0.5 to 60 hour(s).

Examples of the reaction solvent include dichloromethane, chloroform, THF, toluene, DMF, DMSO, NMP, and dioxane, and it can be used alone or in combination.

(Step 2)

Compound (B-2) can be obtained by reacting Compound (B-1) with paranitrobenzoic acid in the presence of phosphine and azodicarboxylic acid ester.

The paranitrobenzoic acid can be used at 1 to 5 mol equivalent(s) relative to Compound (B-1).

As the phosphine, triphenylphosphine, tributylphosphine, trimethylphosphine and the like are exemplified, and it can be used at 1 to 3 mol equivalent(s) relative to Compound (B-1).

As the azodicarboxylic acid ester, diethyl azodicarboxylate, diisopropyl azodicarboxylate and the like are exemplified, and it can be used at 1 to 3 mol equivalent(s) relative to Compound (B-1).

The reaction temperature is 0° C. to the reflux temperature of the solvent, preferably room temperature to 50° C.

The reaction time is 0.1 to 24 hour(s), preferably 0.5 to 12 hour(s).

As the reaction solvent, dichloromethane, THF, toluene and the like are exemplified, and it can be used alone or in combination.

(Step 3)

Compound (B-3) can be obtained by deprotection of protecting group for carboxyl group of Compound (B-2) which is obtained in the above step 2. For example, the method disclosed in the above literature A can be used.

(Step 4)

Compound (I-B) can be obtained from Compound (B-3) which is obtained in the above step 3 in accordance with step 6 of the above Method A.

(Alternative Method)

Compound (I-B) in which carbamate is stereoinverted can be obtained from Compound (B-1) which is obtained in step 1 of the above Method B in accordance with step 6 of the above Method A.

[Chemical Formula 60]

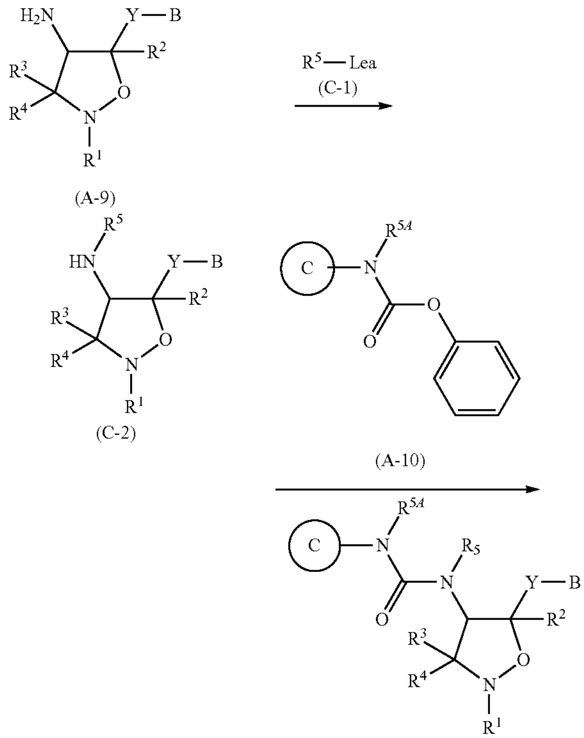

(A-9) (C-1) (C-2) (A-10) (I-C)

wherein each symbol in the formula is the same as above,

Lea is a leaving group, such as halogen, tosylate, and mesylate.

(Method C)

(Step 1)

Compound (C-2) can be obtained by reacting Compound (A-9) with Compound (C-1) in the presence of a base.

Compound (A-9) can be synthesized in accordance with the above Method A.

Compound (C-1) is commercially available or can be synthesized according to the methods well known in the art and used at 1 to 1.5 mol equivalent(s) relative to Compound (A-9).

Examples of the base include pyridine, triethylamine, diisopropylethylamine, and N-methylmorpholine, and it can be used at 1 to 5 mol equivalent(s) relative to Compound (A-9).

The reaction temperature is 0° C. to the reflux temperature of the solvent, preferably room temperature to 100° C.

The reaction time is 0.1 to 72 hour(s), preferably 0.5 to 60 hour(s).

Examples of the reaction solvent include dichloromethane, chloroform, THF, toluene, DMF, DMSO, NMP, and dioxane, and it can be used alone or in combination.

(Step 2)

Compound (I-C) can be obtained from Compound (C-2) which is obtained in the above step 1 in accordance with step 6 of the above Method A.

[Chemical Formula 61]

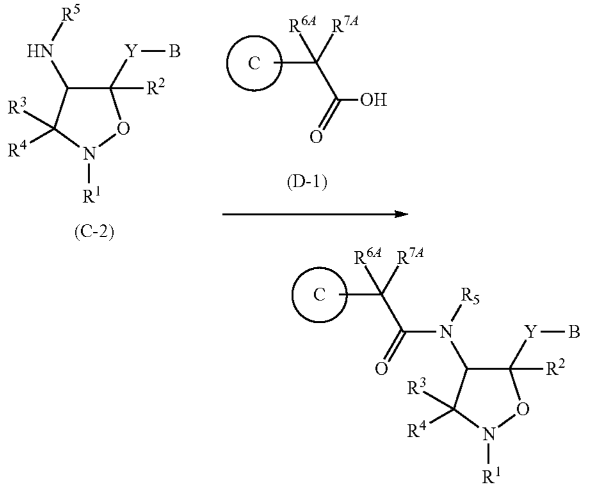

(C-2) (D-1) (I-D)

wherein each symbol in the formula is the same as above.

(Method D)

Compound (I-D) can be obtained by reacting Compound (C-2) with Compound (D-1) in the presence of a condensing agent and a base.

Compound (C-2) can be synthesized in accordance with the above Method A and Method C.

Compound (D-1) is commercially available or can be synthesized according to the known methods. It can be used at 1 to 3 mol equivalent(s) relative to Compound (C-2).

As the condensing agent, HATU, COMU, EDC and the like are exemplified, and it can be used at 1 to 5 mol equivalent(s) relative to Compound (C-2).

As the base, pyridine, triethylamine, diisopropylethylamine, N-methylmorpholine and the like are exemplified, and it can be used at 1 to 5 mol equivalent(s) relative to Compound (C-2).

The reaction temperature is −20° C. to the reflux temperature of the solvent, preferably −10 to 50° C.

The reaction time is 0.1 to 24 hour(s), preferably 0.5 to 12 hour(s).

As the reaction solvent, dichloromethane, chloroform, THF, toluene, DMF, DMSO, NMP, dioxane and the like are exemplified, and it can be used alone or in combination.

[Chemical Formula 62]

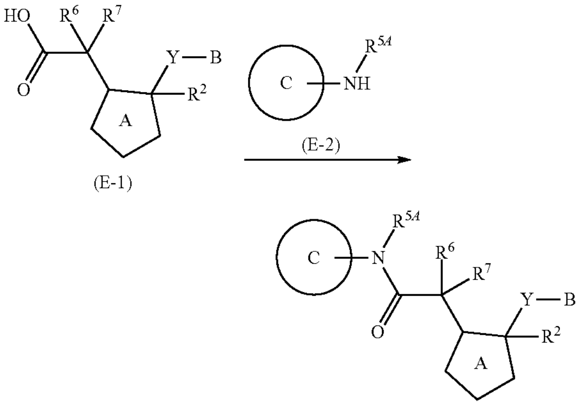

(E-1) (E-2) (I-E)

wherein each symbol in the formula is the same as above.

(Method E)

Compound (I-E) can be obtained in accordance with the above Method D.

Compound (E-1) is commercially available or can be synthesized according to the known methods.

Compound (E-2) is commercially available or can be synthesized according to the known methods.

[Chemical Formula 63]

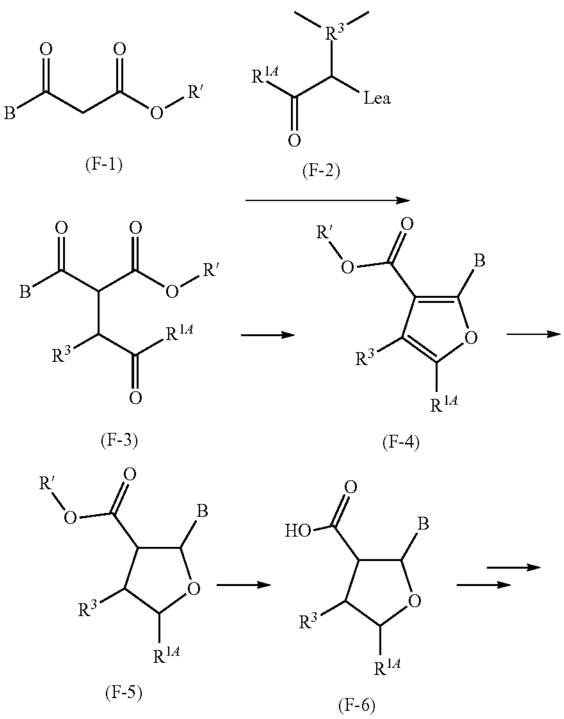

(F-1) (F-2) (F-3) (F-4) (F-5) (F-6)

-continued

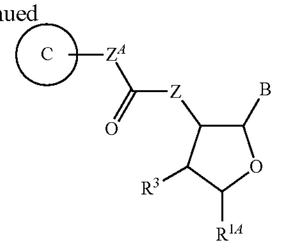

(I-F)

wherein each symbol in the formula is the same as above, Lea is a leaving group, such as halogen, tosylate, mesylate and the like, and R' is C1-C4 alkyl.

(Method F)

(Step 1)

Compound (F-3) can be obtained by reacting Compound (F-1) with Compound (F-2) in the presence of a base. A catalyst can be also present.

Compound (F-1) is commercially available or can be synthesized according to the known methods.

Compound (F-2) is commercially available or can be synthesized according to the known methods. It can be used at 1 to 3 mol equivalent(s) relative to Compound (F-1).

As the base, sodium hydride, potassium tert-butoxide and the like are exemplified, and it can be used at 1 to 1.5 mol equivalent(s) relative to Compound (F-1).

As the catalyst, sodium iodide, potassium iodide and the like are exemplified, and it can be used at 0.05 to 0.2 mol equivalents relative to Compound (F-1).

The reaction temperature is 0° C. to the reflux temperature of the solvent, preferably room temperature to 50° C.

The reaction time is 0.1 to 24 hour(s), preferably 0.5 to 12 hour(s).

As the reaction solvent, DMF, THF and the like are exemplified, and it can be used alone or in combination.

(Step 2)

Compound (F-4) can be obtained by treating Compound (F-3) which is obtained in the above step 1 with an acid in a sealed tube.

As the acid, hydrochloric acid, sulfuric acid and the like are exemplified, and it can be used at 1 to 10 mol equivalent(s) relative to Compound (F-3).

The reaction temperature is 0° C. to 120° C., preferably room temperature to 100° C.

The reaction time is 0.1 to 24 hour(s), preferably 0.5 to 12 hour(s).

As the reaction solvent, methanol, ethanol and the like are exemplified, and it can be used alone or in combination.

(Step 3)

Compound (F-5) can be obtained by treating Compound (F-4) which is obtained in the above step 2 in the presence of a catalyst under hydrogen atmosphere.

As the catalyst, palladium-carbon, palladium hydroxide and the like are exemplified, and it can be used at 0.01 to 0.1 mol equivalent relative to Compound (F-4).

The reaction temperature is 0° C. to the reflux temperature of the solvent, preferably room temperature to 80° C.

The reaction time is 0.1 to 24 hour(s), preferably 0.5 to 12 hour(s).

As the reaction solvent, methanol, ethyl acetate, tetrahydrofuran and the like are exemplified, and it can be used alone or in combination.

(Step 4)

Compound (F-6) can be obtained by deprotection of protecting group for carboxyl group of Compound (F-5) which is obtained in the above step 2. For example, the method disclosed in the above literature A can be used.

(Step 5)

Compound (I-F) can be synthesized in accordance with steps 5 and 6 of the above Method A, and Method B, Method C and Method D.

[Chemical Formula 64]

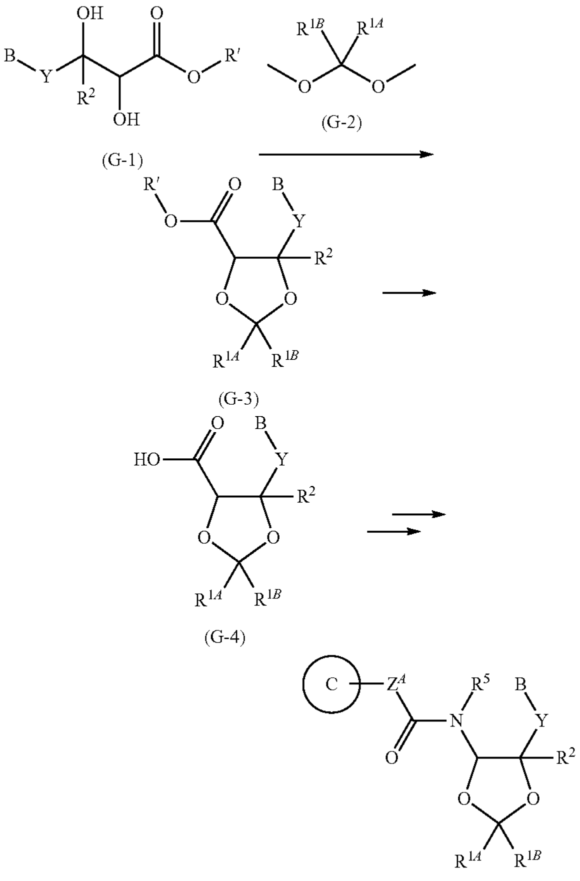

(G-1) (G-2) (G-3) (G-4) (I-G)

wherein each symbol in the formula is the same as above, and R' is C1-C4 alkyl.

(Method G)

(Step 1)

Compound (G-3) can be obtained by reacting Compound (G-1) with Compound (G-2) in the presence of an acid.

Compound (G-1) is commercially available or can be synthesized according to the methods well known in the art.

Compound (G-2) is commercially available or can be synthesized according to the methods well known in the art. It can be used at 1 to 3 mol equivalent(s) relative to Compound (G-1).

As the acid, paratoluenesulfonic acid, hydrochloric acid and the like are exemplified, and it can be used at 0.01 to 0.2 mol equivalent relative to Compound (G-1).

The reaction temperature is 0° C. to the reflux temperature of the solvent, preferably room temperature to 80° C.

The reaction time is 0.1 to 24 hour(s), preferably 0.5 to 12 hour(s).

Examples of the reaction solvent include toluene and dichloroethane are exemplified, and it can be used alone or in combination.

(Step 2)

Compound (G-4) can be obtained by deprotection of protecting group for carboxyl group of Compound (G-3) which is obtained in the above step 1. For example, the method disclosed in the above literature A can be used.

(Step 3)

Compound (I-G) can be synthesized in accordance with steps 5 and 6 of the above Method A, and Method B, Method C and Method D.

[Chemical Formula 65]

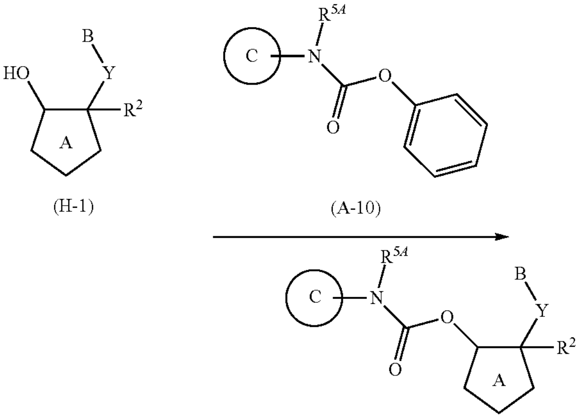

(H-1) (A-10) (I-H)

wherein each symbol in the formula is the same as above, and the ring A is

[Chemical Formula 66]

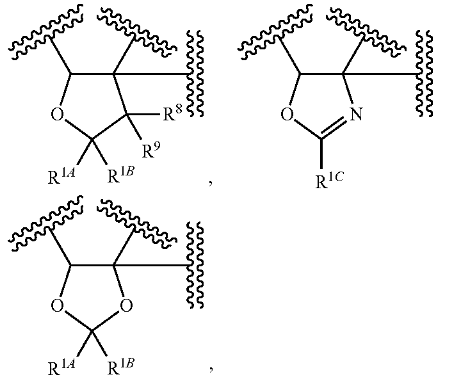

, or , wherein each symbol in the formula is the same as above.

(Method H)

(Step 1)

Compound (I-H) can be obtained in accordance with step 6 of the above Method A.

Compound (H-1) is commercially available or can be synthesized according to the known methods.

Compound (A-10) can be synthesized according to the known methods.

[Chemical Formula 67]

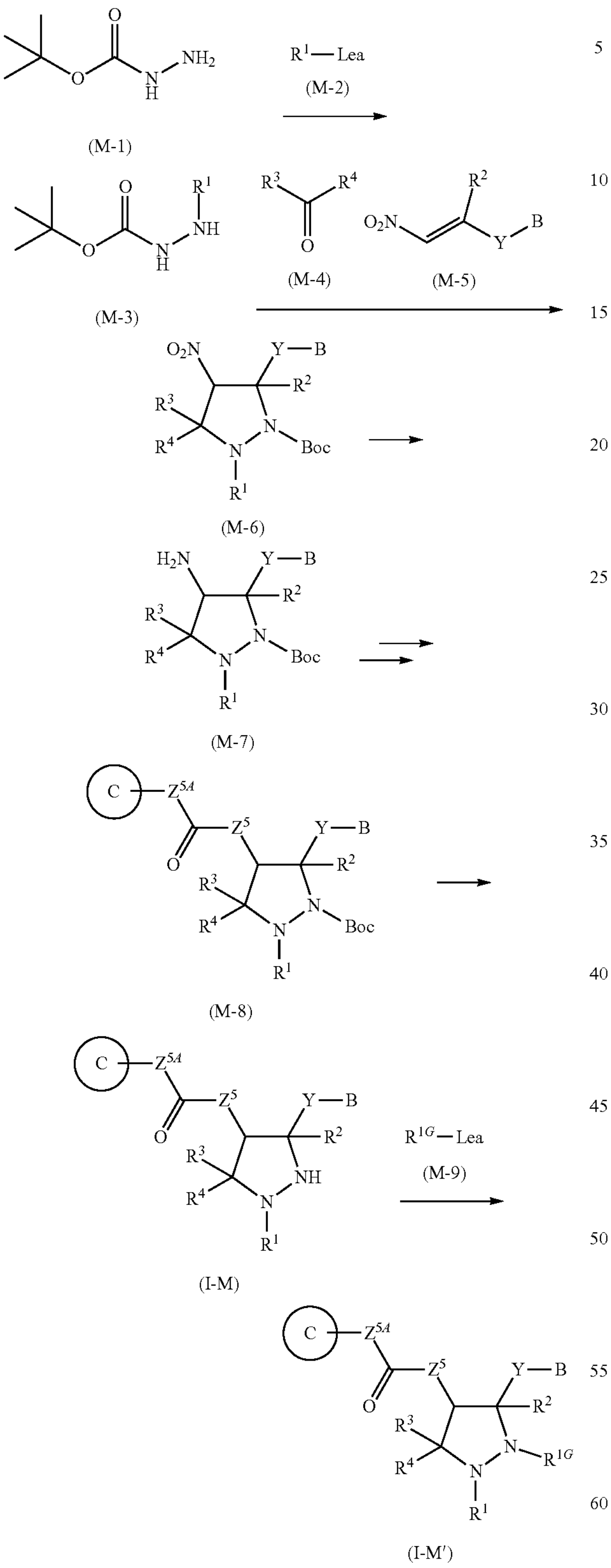

wherein each symbol in the formula is the same as above, and Lea is a leaving group, such as halogen, tosylate, mesylate and the like.

(Method M)

(Step 1)

Compound (M-3) can be obtained by reacting Compound (M-1) with Compound (M-2) in the presence of a base. A catalyst can be also present.

Compound (M-2) is commercially available or can be synthesized according to the known methods. It can be used at 1 to 3 mol equivalent(s) relative to Compound (M-1).

As the base, diisopropyl ethylamine, triethylamine and the like are exemplified, and it can be used at 1 to 1.5 mol equivalent(s) relative to Compound (M-1).

As the catalyst, sodium iodide, potassium iodide and the like are exemplified, and it can be used at 0.05 to 0.2 mol equivalent relative to Compound (M-1).

The reaction temperature is 0° C. to the reflux temperature of the solvent, preferably room temperature to 100° C.

The reaction time is 0.1 to 24 hour(s), preferably 8 to 24 hour(s).

As the reaction solvent, DMF, DMSO and the like are exemplified, and it can be used alone or in combination.

(Step 2)

Compound (M-6) can be obtained by reacting Compound (M-3) which is obtained in the above step 1 with Compound (M-4) and Compound (M-5) in the presence of a desiccant.

Compound (M-4) is commercially available or can be synthesized according to the known methods. It can be used at 1 to 3 mol equivalent(s) relative to Compound (M-3).

Compound (M-5) is commercially available or can be synthesized according to the known methods. It can be used at 1 to 3 mol equivalent(s) relative to Compound (M-3).

As the desiccant, molecular sieve 5 A, magnesium sulfate and the like are exemplified.

The reaction temperature is 0° C. to the reflux temperature of the solvent, preferably room temperature to 100° C.

The reaction time is 0.1 to 24 hour(s), preferably 8 to 24 hour(s).

As the reaction solvent, toluene, xylene and the like are exemplified, and it can be used alone or in combination.

(Step 3)

Compound (M-7) can be obtained by treating Compound (M-6) which is obtained in the above step 2 in the presence of a catalyst under hydrogen atmosphere.

As the catalyst, palladium-carbon, palladium hydroxide and the like are exemplified, and it can be used at 0.01 to 0.1 mol equivalent relative to Compound (M-6).

The reaction temperature is 0° C. to the reflux temperature of the solvent, preferably room temperature to 80° C.

The reaction time is 0.1 to 24 hour(s), preferably 0.5 to 12 hour(s).

As the reaction solvent, methanol, ethyl acetate, tetrahydrofuran and the like are exemplified, and it can be used alone or in combination.

(Step 4)

Compound (M-9) can be obtained by deprotection of the Boc group of Compound (M-8). For example, the method disclosed in the above literature A can be used.

Compound (I-M) can be synthesized in accordance with the above Methods A, B, C, D and E by using Compound (M-7) as the starting material.

(Step 5)

Compound (I-M') can be obtained by reacting Compound (I-M) with Compound (M-9) in the presence of a base. A catalyst can be also present.

Compound (M-9) is commercially available or can be synthesized according to the known methods. It can be used at 1 to 3 mol equivalent(s) relative to Compound (I-M).

As the base, diisopropylethylamine, triethylamine and the like are exemplified, and it can be used at 1 to 1.5 mol equivalent(s) relative to Compound (I-M).

As the catalyst, sodium iodide, potassium iodide and the like are exemplified, and it can be used at 0.05 to 0.2 mol equivalent relative to Compound (I-M).

The reaction temperature is 0° C. to the reflux temperature of the solvent, preferably room temperature to 80° C.

The reaction time is 0.1 to 24 hour(s), preferably 8 to 24 hour(s).

As the reaction solvent, DMF, DMSO and the like are exemplified, and it can be used alone or in combination.

[Chemical Formula 68]

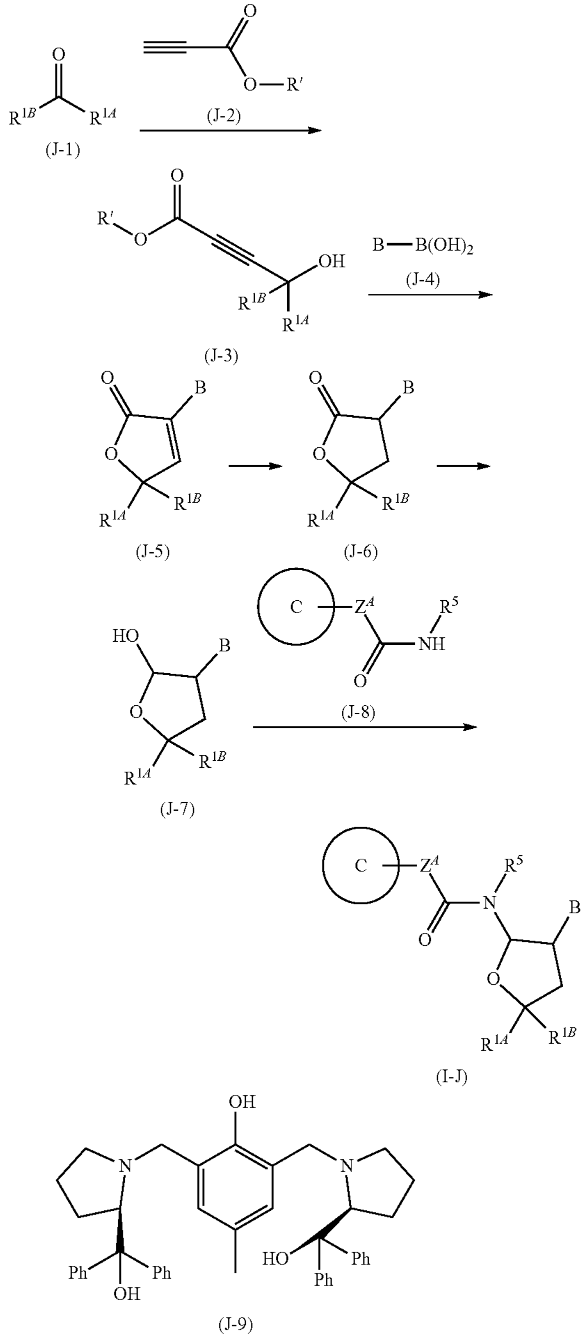

(J-1) (J-2) (J-3) (J-4) (J-5) (J-6) (J-7) (J-8) (I-J) (J-9)

wherein each symbol in the formula is the same as above, and R' is C1-C4 alkyl.

(Method J)

(Step 1)

Compound (J-3) can be obtained by reacting Compound (J-1) with Compound (J-2) in the presence of dimethylzinc. A catalyst can be also present.

Compound (J-1) is commercially available or can be synthesized according to the known methods.

Compound (J-2) is commercially available or can be synthesized according to the known methods. It can be used at 1 to 3 mol equivalent(s) relative to Compound (J-1).

The dimethylzinc can be used at 1 to 5 mol equivalent(s) relative to Compound (J-1).

As the catalyst, Compound (J-9) is exemplified, and it can be used at 0.01 mol to 0.2 mol equivalent.

The reaction temperature is 0° C. to the reflux temperature of the solvent, preferably 0° C. to 50° C.

The reaction time is 0.1 to 100 hour(s), preferably 10 to 50 hours.

As the reaction solvent, xylene, toluene and the like are exemplified, and it can be used alone or in combination.

(Step 2)

Compound (J-5) can be obtained by reacting Compound (J-3) which is obtained in the above step 1 with Compound (J-4) in the presence of palladium acetate, tri-tert-butylphosphine, and acetic acid.

Compound (J-4) is commercially available or can be synthesized according to the known methods. Compound (J-4) means boronic acid of the above substituent B. It can be used at 1 to 5 mol equivalent(s) relative to Compound (J-3).

The palladium acetate can be used at 0.01 to 0.1 mol equivalent relative to Compound (J-3).

The tri-tert-butylphosphine can be used at 0.01 to 0.1 mol equivalent relative to Compound (J-3).

The acetic acid can be used at 0.05 to 0.2 mol equivalent relative to Compound (J-3).

The reaction temperature is room temperature to the reflux temperature of the solvent, preferably 0 to 80° C.

The reaction time is 0.1 to 24 hour(s), preferably 0.5 to 12 hour(s).

As the reaction solvent, tetrahydrofuran, 1,4-dioxane and the like are exemplified, and it can be used alone or in combination.

(Step 3)

Compound (J-6) can be obtained by stirring Compound (J-5) which is obtained in the above step 2 in the presence of a catalyst under hydrogen atmosphere.

As the catalyst, palladium-carbon, palladium hydroxide and the like are exemplified, and it can be used at 0.01 to 0.2 mol equivalent relative to Compound (J-5).

The reaction temperature is room temperature to the reflux temperature of the solvent, preferably 0 to 60° C.

The reaction time is 0.1 to 24 hour(s), preferably 0.5 to 12 hour(s).

As the reaction solvent, ethyl acetate, tetrahydrofuran, methanol and the like are exemplified, and it can be used alone or in combination.

(Step 4)

Compound (J-7) can be obtained by reacting Compound (J-6) which is obtained in the above step 3 with a reducing agent.

As the reducing agent, diisobutyl aluminum hydride, lithium aluminum hydride, sodium borohydride and the like are exemplified, and it can be used at 1 to 3 mol equivalent(s) relative to Compound (J-6).

The reaction temperature is −78° C. to the reflux temperature of the solvent, preferably −78° C. to room temperature.

The reaction time is 0.1 to 24 hour(s), preferably 0.5 to 12 hour(s).

As the reaction solvent, dichloromethane, tetrahydrofuran, methanol and the like are exemplified, and it can be used alone or in combination.

(Step 5)

Compound (I-J) can be obtained by reacting Compound (J-7) which is obtained in the above step 4 with Compound (J-8) in the presence of an acid.

Compound (J-8) is commercially available or can be synthesized according to the known methods. It can be used at 1 to 5 mol equivalent(s) relative to Compound (J-7).

As the acid, paratoluenesulfonic acid and the like are exemplified, and it can be used at 0.01 mol to 2 mol equivalent(s) relative to Compound (J-7).

The reaction temperature is 0° C. to the reflux temperature of the solvent, preferably 50° C. to the reflux temperature of the solvent.

The reaction time is 0.1 to 100 hour(s), preferably 10 to 50 hours.

As the reaction solvent, 1,4-dioxane, toluene and the like are exemplified, and it can be used alone or in combination.

[Chemical Formula 69]

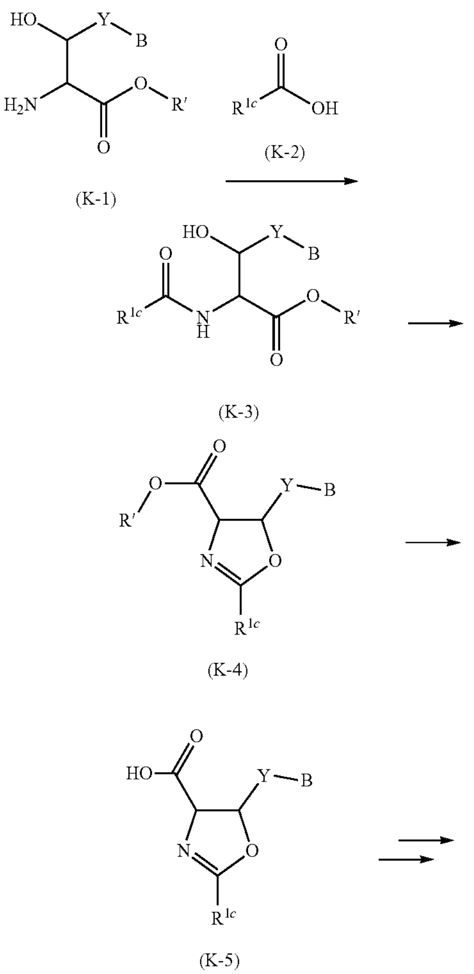

(K-1) (K-2) (K-3) (K-4) (K-5)

-continued

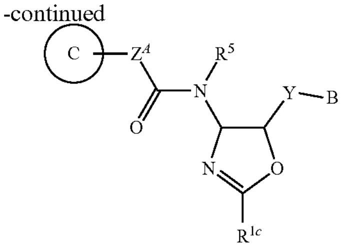

(I-K)

wherein each symbol in the formula is the same as above, and R' is C1-C4 alkyl.

(Method K)

(Step 1)

Compound (K-3) can be obtained by reacting Compound (K-1) with Compound (K-2) in the presence of a condensing agent and a base.

Compound (K-1) is commercially available or can be synthesized according to the known methods.

Compound (K-2) is commercially available or can be synthesized according to the known methods. It can be used at 1 to 3 mol equivalent(s) relative to Compound (K-1).

As the condensing agent, HATU, COMU, EDC and the like are exemplified, and it can be used at 1 to 5 mol equivalent(s) relative to Compound (K-1).

As the base, pyridine, triethylamine, diisopropylethylamine, N-methylmorpholine and the like are exemplified, and it can be used at 1 to 5 mol equivalent(s) relative to Compound (K-1).

The reaction temperature is −20° C. to the reflux temperature of the solvent, preferably −10 to 50° C.

The reaction time is 0.1 to 24 hour(s), preferably 0.5 to 12 hour(s).

As the reaction solvent, dichloromethane, chloroform, THF, toluene, DMF, DMSO, NMP, dioxane and the like are exemplified, and it can be used alone or in combination.

(Step 2)

Compound (K-4) can be obtained by reacting Compound (K-3) which is obtained in the above step 1 with a halogenating agent.

As the halogenating agent, thionyl chloride, N,N-diethylaminosulfur trifluoride and the like are exemplified, and it can be used at 1 mol to 3 mol equivalent(s) relative to Compound (K-3).

The reaction temperature is −78° C. to the reflux temperature of the solvent, preferably −78° C. to 50° C.

The reaction time is 0.1 to 100 hour(s), preferably 0.5 to 12 hour(s).

As the reaction solvent, dichloromethane, chloroform and the like are exemplified, and it can be used alone or in combination.

(Step 3)

Compound (K-5) can be obtained by deprotection of protecting group for carboxyl group of Compound (K-4) which is obtained in the above step 2. For example, the method disclosed in the above literature A can be used.

(Step 4)

Compound (I-K) can be synthesized in accordance with steps 5 and 6 of the above Method A, and Method B, Method C and Method D.

[Chemical Formula 70]

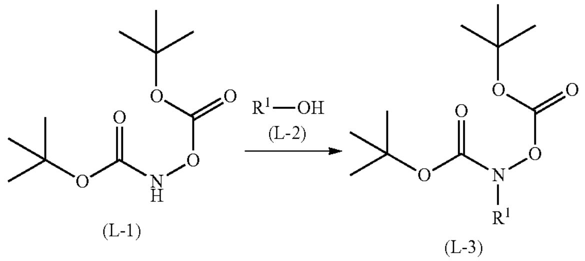

(L-1) (L-3) (L-4)

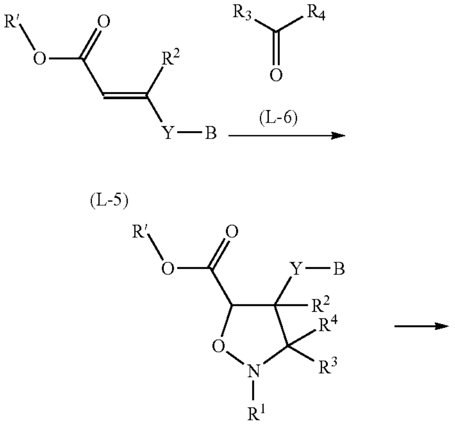

(L-5) (L-7)

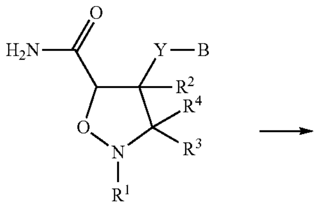

(L-8)

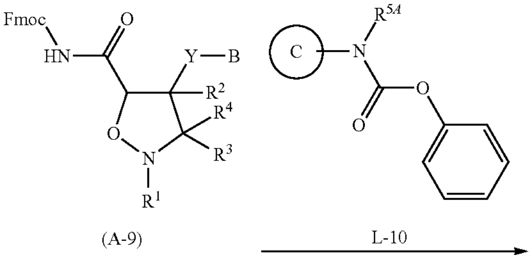

(A-9)

-continued

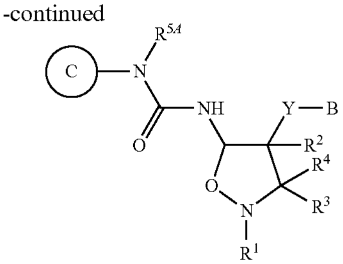

(I-L)

wherein each symbol in the formula is the same as above, R' is C1-C4 alkyl, X' is halogen, and Fmoc is 9-fluorenylmethyloxycarbonyl.

(Method L)

(Steps 1 to 3)

Compound (L-7) can be obtained in accordance with steps 1, 2 and 3 of the above Method A.

(Step 4)

Compound (L-8) can be obtained in accordance with step 1 of Method A'.

(Step 5)

Compound (L-9) can be obtained by reacting Compound (L-8) with (9H-fluoren-9-yl)methanol and iodobenzene diacetate.

(9H-Fluoren-9-yl)methanol can be used at 1 to 10 mol equivalent(s) relative to Compound (L-8).

Iodobenzene diacetate can be used at 1 to 5 mol equivalent(s) relative to Compound (A-8-1).

The reaction temperature is 50° C. to the reflux temperature of the solvent, preferably 60 to 80° C.

The reaction time is 0.1 to 24 hour(s), preferably 0.5 to 12 hour(s).

As the reaction solvent, 1,2-dichloroethane, toluene, xylene and the like are exemplified, and it can be used alone or in combination.

(Step 6)

Compound (I-L) can be obtained by reacting Compound (L-9) with Compound (L-10) in the presence of DMAP.

Compound (L-10) can be synthesized in accordance with the method described in WO2012158413. It can be used at 1 to 1.5 mol equivalent(s) relative to Compound (L-9).

DMAP can be used at 1 to 1.5 mol equivalent(s) relative to Compound (L-9).

The reaction temperature is 0° C. to the reflux temperature of the solvent, preferably room temperature to 50° C.

The reaction time is 0.1 to 24 hour(s), preferably 0.5 to 12 hour(s).

As the reaction solvent, dichloromethane, chloroform, THF, toluene, DMF, DMSO, dioxane and the like are exemplified, and it can be used alone or in combination.

[Chemical Formula 71]

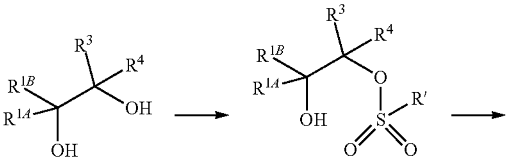

N-1 N-2

-continued

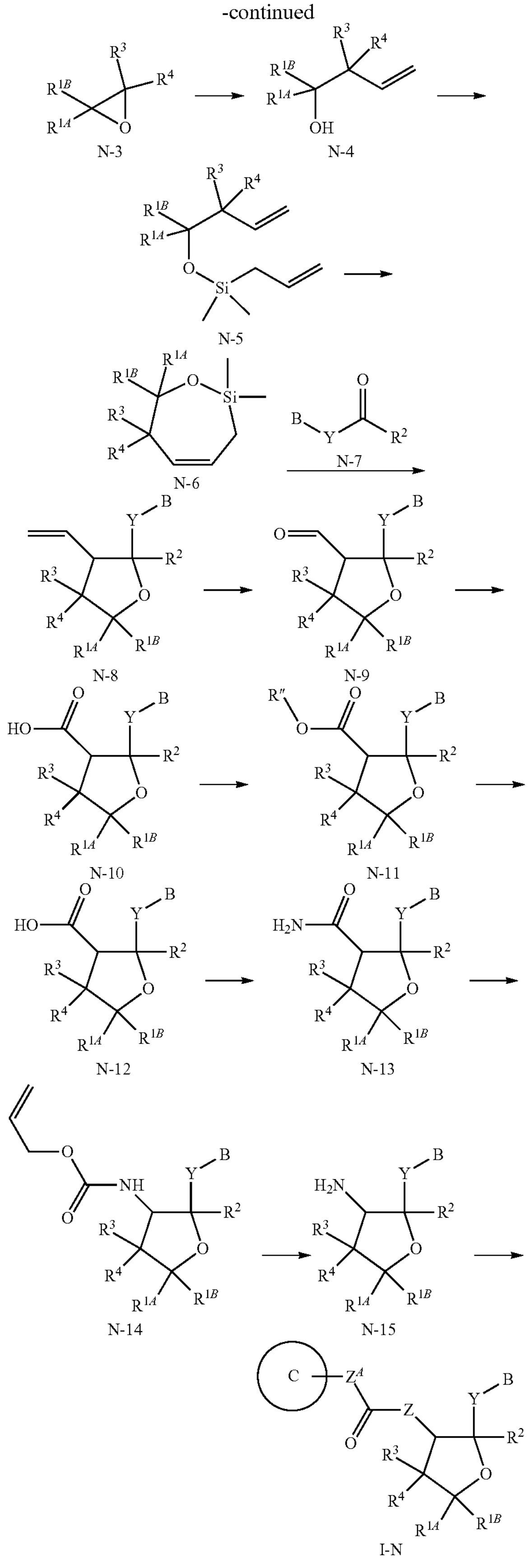

N-3 N-4 N-5 N-6 N-7 N-8 N-9 N-10 N-11 N-12 N-13 N-14 N-15 I-N wherein each symbol in the formula is the same as above, and each of R' and R" is C1-C4 alkyl.

(Method N)

(Step 1)

Compound (N-2) can be obtained by reacting Compound (N-1) which can be synthesized in accordance with the known methods with sulfonyl chloride in the presence of a base and a catalyst.

As the sulfonyl chloride, methanesulfonyl chloride, p-toluenesulfonyl chloride and the like are exemplified, and it can be used at 1 to 1.5 mol equivalent(s) relative to Compound (N-1).

As the base, triethylamine, diisopropylethylamine, pyridine and the like are exemplified, and it can be used at 1 to 1.5 mol equivalent(s) relative to Compound (N-1).

As the catalyst, dibutyltin oxide and the like are exemplified, and it can be used at 0.01 to 0.1 mol equivalent relative to Compound (N-1).

The reaction temperature is 0° C. to the reflux temperature of the solvent, preferably room temperature to 50° C.

The reaction time is 0.1 to 24 hour(s), preferably 0.5 to 12 hour(s).

As the reaction solvent, dichloromethane, chloroform, 1,2-dichloroethane, toluene and the like are exemplified, and it can be used alone or in combination.

(Step 2)

Compound (N-3) can be obtained by treating Compound (N-2) with a base.

As the base, sodium hydride, potassium tert-butoxide, potassium carbonate and the like are exemplified, and it can be used at 1 to 1.5 mol equivalent(s) relative to Compound (N-2).

The reaction temperature is 0° C. to the reflux temperature of the solvent, preferably room temperature to 50° C.

The reaction time is 0.1 to 24 hour(s), preferably 0.5 to 12 hour(s).

As the reaction solvent, THF, DMF, dioxane, methanol, tert-butanol and the like are exemplified, and it can be used alone or in combination.

(Step 3)

Compound (N-4) can be obtained by treating Compound (N-3) with vinyl magnesium bromide in the presence of a catalyst.

The vinyl magnesium bromide can be used at 1 to 1.5 mol equivalent(s) relative to Compound (N-3).

As the catalyst, copper iodide, copper cyanide and the like are exemplified, and it can be used at 0.01 to 0.2 mol equivalent relative to Compound (N-3).

The reaction temperature is −78° C. to the reflux temperature of the solvent, preferably −78° C. to room temperature.

The reaction time is 0.1 to 24 hour(s), preferably 0.5 to 12 hour(s).

As the reaction solvent, THF, diethyl ether and the like are exemplified, and it can be used alone or in combination.

(Step 4)

Compound (N-5) can be obtained by reacting Compound (N-4) with allylchlorodimethylsilane in the presence of a base.

The allylchlorodimethylsilane can be used at 1 to 1.5 mol equivalent(s) relative to Compound (N-4).

As the base, triethylamine, diisopropylethylamine, imidazole and the like are exemplified, and it can be used at 1 to 5 mol equivalent(s) relative to Compound (N-4).

The reaction temperature is −20° C. to 50° C., preferably 0° C. to room temperature.

The reaction time is 0.1 to 24 hour(s), preferably 0.5 to 12 hour(s).

As the reaction solvent, dichloromethane, 1,2-dichloroethane, DMF and the like are exemplified, and it can be used alone or in combination.

(Step 5)

Compound (N-6) can be obtained by reacting Compound (N-5) with a Grubbs catalyst.

As the Grubbs catalyst, first-generation Grubbs catalysts and second-generation Grubbs catalysts and the like are exemplified, and it can be used at 0.01 to 0.05 mol equivalent relative to Compound (N-5).

The reaction temperature is 0° C. to 50° C., preferably room temperature to 40° C.

The reaction time is 0.1 to 24 hour(s), preferably 0.5 to 12 hour(s).

As the reaction solvent, dichloromethane, 1,2-dichloroethane, toluene and the like are exemplified, and it can be used alone or in combination.

(Step 6)

Compound (N-8) can be obtained by reacting Compound (N-6) with Compound (N-7) in the presence of a Lewis acid.

Compound (N-7) is commercially available or can be synthesized according to the known synthetic methods, and it can be used at 1 to 2 mol equivalent(s) relative to Compound (N-6).

As the Lewis acid, a boron trifluoride-diethyl ether complex, trimethylsilyl trifluoromethanesulfonate and the like are exemplified, and it can be used at 1 to 1.5 mol equivalent (s) relative to Compound (N-6).

The reaction temperature is −78° C. to 50° C., preferably −78° C. to room temperature.

The reaction time is 0.1 to 24 hour(s), preferably 0.5 to 12 hour(s).

As the reaction solvent, dichloromethane, 1,2-dichloroethane and the like are exemplified, and it can be used alone or in combination.

(Step 7)

Compound (N-9) can be obtained by subjecting Compound (N-8) to ozone oxidation, followed by treatment with dimethyl sulfide.

Dimethyl sulfide can be used at 10 to 50 mol equivalents relative to Compound (N-8).

The reaction temperature is −100 to −50° C., preferably −78° C. to −60° C.

The reaction time is 0.1 to 24 hour(s), preferably 0.5 to 12 hour(s).

As the reaction solvent, dichloromethane, methanol and the like are exemplified, and it can be used alone or in combination.

(Step 8)

Compound (N-10) can be obtained by reacting Compound (N-9) with sodium chlorite in the presence of 2-methyl-2-butene and sodium dihydrogen phosphate.

Sodium chlorite can be used at 1 to 5 mol equivalent(s) relative to Compound (N-9).

2-Methyl-2-butene can be used at 10 to 20 mol equivalents relative to Compound (N-9).

Sodium dihydrogen phosphate can be used at 3 to 10 mol equivalents relative to Compound (N-9).

The reaction temperature is 0° C. to the reflux temperature of the solvent, preferably room temperature to 50° C.

The reaction time is 0.1 to 24 hour(s), preferably 0.5 to 12 hour(s).

As the reaction solvent, t-BuOH, water and the like are exemplified, and it can be used alone or in combination.

(Step 9)

Compound (N-11) can be obtained by reacting Compound (N-10) with diazoalkane.

As diazoalkane, diazomethane, trimethylsilyldiazomethane and the like are exemplified, and it can be used at 1 to 3 mol equivalent(s) relative to Compound (N-10).

The reaction temperature is −20° C. to 50° C., preferably 0° C. to room temperature.

The reaction time is 0.1 to 24 hour(s), preferably 0.5 to 2 hour(s).

As the reaction solvent, dichloromethane, toluene, ether, methanol and the like are exemplified, and it can be used alone or in combination.

(Step 10)

Compound (N-12) can be obtained by treating Compound (N-11) with a base.

As the base, sodium methoxide, sodium ethoxide and the like are exemplified, and it can be used at 1 to 10 mol equivalent(s) relative to Compound (N-11).

The reaction temperature is −20° C. to 50° C., preferably 0° C. to room temperature.

The reaction time is 0.1 to 24 hour(s), preferably 0.5 to 2 hour(s).

As the reaction solvent, methanol, ethanol and the like are exemplified, and it can be used alone or in combination.

(Step 11)

Compound (N-13) can be obtained by reacting Compound (N-12) with ammonia in the presence of a condensing agent and a base.

As ammonia, an ammonia-dioxane solution, ammonium chloride and the like are exemplified, and it can be used at 1 to 5 mol equivalent(s) relative to Compound (N-12).

Examples of the condensing agent include HATU, COMU, and EDC, and it can be used at 1 to 5 mol equivalent(s) relative to Compound (N-12).

Examples of the base include pyridine, triethylamine, diisopropylethylamine, and N-methylmorpholine, and it can be used at 1 to 5 mol equivalent(s) relative to Compound (N-12).

The reaction temperature is −20° C. to the reflux temperature of the solvent, preferably −10 to 50° C.

The reaction time is 0.1 to 24 hour(s), preferably 0.5 to 12 hour(s).

As the reaction solvent, dichloromethane, chloroform, THF, toluene, DMF, DMSO, NMP, dioxane and the like are exemplified, and it can be used alone or in combination.

(Step 12)

Compound (N-14) can be obtained by reacting Compound (N-13) with allyl alcohol in the presence of iodobenzene diacetate.

Iodobenzene diacetate can be used at 1 to 3 mol equivalent(s) relative to Compound (N-13).

The allyl alcohol can be used at 10 to 50 mol equivalents relative to Compound (N-13).

The reaction temperature is room temperature to the reflux temperature of the solvent, preferably 40° C. to 80° C.

The reaction time is 0.1 to 24 hour(s), preferably 0.5 to 12 hour(s).

As the reaction solvent, 1,2-dichloroethane, toluene and the like are exemplified, and it can be used alone or in combination.

(Step 13)

Compound (N-14) can be deprotected in accordance with the method described in the above literature A to give Compound (N-15).

(Step 14)

Compound (I-N) can be obtained in accordance with step 6 of the above Method A.

The Compounds of Formula (I) of the present invention prepared by the above general synthetic method can be purified by referring to the known methods (e.g., chromatography, and recrystallization).

The compound of the present invention has TrkA inhibitory activity and it can be available for therapeutic agent and/or prophylactic agent for pain associated with osteoarthritis, rheumatoid arthritis, fracture, interstitial cystitis, chronic pancreatitis and prostate inflammation; and nociceptive pain as typified by chronic low back pain, diabetic peripheral neuropathy pain, postoperative pain, pelvic pain and cancer pain; neuropathic pain, acute pain, chronic pain, cancer, inflammatory disease, allergic disease, dermatological disease and the like.

The compound of the present invention has not only TrkA inhibitory activity but also are useful as a medicine and has any or all of the following excellent characteristics:

a) The compound is a weak inhibitor of CYP enzymes (e.g., CYP1A2, CYP2C9, CYP2C19, CYP2D6, and CYP3A4).
b) The compound demonstrates good pharmacokinetics, such as a high bioavailability, and moderate clearance.
c) The compound has a high metabolic stability.
d) The compound has no irreversible inhibitory action against CYP enzymes (e.g., CYP3A4) when the concentration is within the range described in the present description as the measurement conditions.
e) The compound has no mutagenicity.
f) The compound is associated with a low cardiovascular risk.
g) The compound has a high solubility.
h) The compound is highly selective for TrkA receptor.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, and inner ear or vaginal administration.

In the case of oral administration of pharmaceutical composition of the present invention, any forms, which are usually used, such as oral solid formulations (e.g., tablets, powders, granules, capsules, pills, or films), and oral liquid formulations (e.g., suspension, emulsion, elixir, syrup, lemonade, spirit, aromatic water, extract, decoction, or tincture) may prepared according to the usual method and administered. The tablets can be sugar-coated tablets, film-coated tablets, enteric-coating tablets, sustained-release tablets, troche tablets, sublingual tablets, buccal tablets, chewable tablets or orally disintegrating tablets. Powders and granules can be dry syrups. Capsules can be soft capsules, micro capsules or sustained-release capsules.

In the case of parenteral administration of pharmaceutical composition of the present invention, any forms, which are usually used, such as injections, drips, and external preparations (e.g., ophthalmic drops, nasal drops, ear drops, aerosols, inhalations, lotion, infusion, liniment, mouthwash, enema, ointment, plaster, jelly, cream, patch, cataplasm, external powder, or suppository) can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, moistening agents, disintegrants, lubricants, and diluents. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of a compound of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

The compound of the present invention can be used in combination of therapeutic agents for pain, anti-inflammatory agents, anticancer agents, or the like (hereinafter referred to as a co-administered drug) to increase the activity of the compound or reduce the dose of the compound, or the like. In this case, the timing of administration for a compound of the present invention and the co-administered drug is not limited. They can be administered to the subjects to be treated, at a time or at different times. Furthermore, a compound of the present invention and the co-administered drug can be administered as two formulations independently comprising each active ingredient or a single formulation comprising the both active ingredients.

The dose for co-administered drugs may be appropriately selected in reference to the clinical dose. The compounding ratio of the compounds of the present invention and co-administered drugs may be appropriately selected depending on the subject to be treated, administration route, disease to be treated, symptoms, combination of the drugs and the like. For administration in humans, for example, 1 part by weight of the compounds of the present invention may be used in combination with 0.01 to 100 parts by weight of co-administered drugs.

For example, the therapeutic agent for pain includes cyclooxygenase inhibitor (e.g., ketoprofen, celecoxib), neuropathic disorder agent (e.g., pregabalin), antidepressant (e.g., duloxetine, amitriptyline), opioid receptor agonist (e.g., morphine, tramadol), regional anesthetic (e.g., lidocaine), ketamine, and acetaminophen.

For example, the anti-inflammatory agent includes steroid agent (e.g., prednisolone), and antihistamine agent (e.g., loratadine).

For example, the anticancer agent includes molecularly-targeted agent (e.g., lapatinib, rituximab), alkylating agent (e.g., cyclophosphamide), antimetabolite (e.g., methotrexate), alkaloid agent (e.g., paclitaxel), platinum agent (e.g., oxaliplatin), and hormonal agent (e.g., tamoxifen, leuprorelin).

EXAMPLES

The present invention will be described in more detail with reference to, but not limited to, the following Examples, Reference Examples and Test Examples.

In this description, meaning of each abbreviation is as follows:

Boc: tert-butoxycarbonyl
$Boc_2O$: di-tert-butyl dicarbonate

CDCl$_3$: deuterated chloroform
CD$_3$OD: deuterated methanol
CF$_3$: trifluoromethyl
COMU: (1-cyano-2-ethoxy-2-oxoethylidenaminooxy)dimethylaminomorpholinocarbenium hexafluorophosphate
DEAD: diethyl azodicarboxylate
DIEA: N,N-diisopropylethylamine
DMA: N,N-dimethylacetamide
DMAP: 4-dimethylaminopyridine
DMF: N,N-dimethylformamide
DMSO: dimethylsulfoxide
DPPA: diphenylphosphoryl azide
EDC: 1-ethyl-3-(3-dimethylaminopropyl)carbodiimide
Fmoc: 9-fluorenylmethyloxycarbonyl
HATU: O-(7-azabenzotriazol-1-yl)-N,N,N',N'-tetramethyluronium hexafluorophosphate
Fmoc: 9-fluorenylmethyloxycarbonyl
HOBt: 1-hydroxybenzotriazole
Me: methyl
NO$_2$: nitro
PdCl$_2$(dppf): 1,1'-bis(diphenylphosphino)ferrocene-palladium(II) dichloride
t-BuOH: tert-butanol
THF: tetrahydrofuran
TMS: trimethylsilyl
TFA: trifluoroacetic acid NMR analysis of each example was performed by 400 MHz using DMSO-d$_6$ or CDCl$_3$. In the case of indicating NMR data, there are cases in which not all measured peaks are described.

"RT" in the following tables means a retention time of LC/MS: liquid chromatography/mass spectrometry, and the measurement conditions are as follows.

(Method 1)
Column: Shim-pack XR-ODS (2.2 μm, i.d. 50×3.0 mm) (Shimadzu)
Flow rate: 1.6 mL/min
UV detection wavelength: 254 nm
Mobile phase: [A] is 0.1% formic acid in aqueous solution, and [B] is 0.1% formic acid in acetonitrile solution.
Gradient: Linear gradient of 10% to 100% solvent [B] for 3 minutes was performed, and 100% solvent [B] was maintained for 0.5 minute.

(Method 2)
Column: ACQUITY UPLC™ BEH C18 (1.7 μm i.d. 2.1×50 mm) (Waters)
Flow rate: 0.8 mL/min
UV detection wavelength: 254 nm
Mobile phase: [A] is 0.1% formic acid in aqueous solution, and [B] is 0.1% formic acid in acetonitrile solution.
Gradient: Linear gradient of 5% to 100% solvent [B] for 3.5 minutes was performed, and 100% solvent [B] was maintained for 0.5 minute.

(Method 3)
Column: ACQUITY UPLC™ BEH C18 (1.7 μm i.d. 2.1×50 mm) (Waters)
Flow rate: 0.8 mL/min
UV detection wavelength: 254 nm
Mobile phase: [A] is 10 mM ammonium carbonate in aqueous solution, and [B] is acetonitrile.
Gradient: Linear gradient of 5% to 100% solvent [B] for 3.5 minutes was performed, and 100% solvent [B] was maintained for 0.5 minute.

Hereinafter, MS(m/z) indicates the value observed in the mass spectrometry.

(Reference Example 1) Synthesis of Compound W

[Chemical Formula 72]

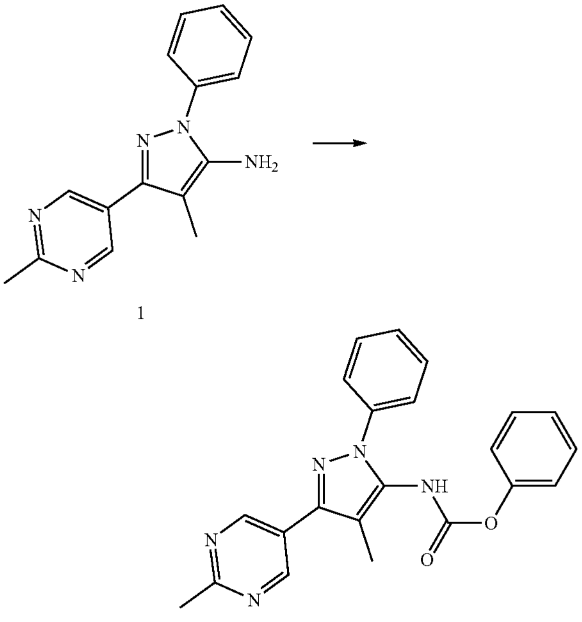

1

W

Step 1

Compound 1 (815 mg, 3.07 mmol) which can be synthesized in accordance with the known method (WO2014/078331) was dissolved in dichloromethane (10 mL) under nitrogen atmosphere, and phenyl chloroformate (0.424 ml, 3.38 mmol) and pyridine (0.298 ml, 3.69 mmol) were added to the solution. The reaction mixture was stirred at room temperature for 1 hour.

Ethyl acetate was added to the mixture. The organic layer was washed with saturated ammonium chloride aqueous solution and subsequently brine and then dried over magnesium sulfate, and then the solvent was distilled off under reduced pressure to give Compound W (1184 mg, Yield 100%).

LC/MS (Method 1) RT=1.79, MS(m/z)=386.20.

(Reference Example 2) Synthesis of Compound Y

[Chemical Formula 73]

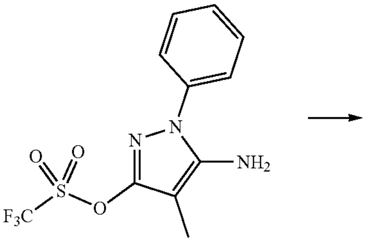

V

-continued

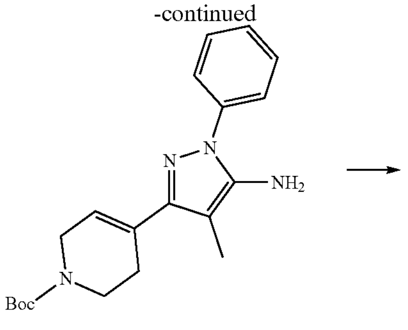

2

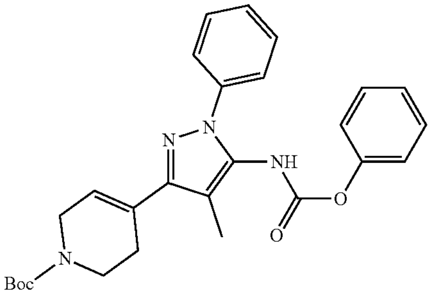

Y

Step 1 Synthesis of Compound 2

To a solution of Compound V (3 g, 9.34 mmol) which can be synthesized in accordance with the known method (WO2012/158413) in 1,4-dioxane (30 mL) were added boronic acid ester (2.89 g, 9.34 mmol), chloro(2-dicyclohexylphosphino-2',4',6'-triisopropyl-1,1'-biphenyl)[2-(2'-amino-1,1'-biphenyl)]palladium(II) (73 mg, 0.093 mmol), potassium phosphate (3.96 g, 18.7 mmol), and water (15 mL) under nitrogen atmosphere, and the reaction mixture was stirred at 90° C. for 12 hours. Brine was added to the mixture, followed by extraction with ethyl acetate twice. Then, the organic layer was dried over sodium sulfate. The solvent was distilled off under reduced pressure, and the residue was purified by silicagel column chromatography (hexane-ethyl acetate) to give Compound 2 (3.17 g, Yield 96%).

$^1$H-NMR ($CDCl_3$) δ: 1.49 (s, 9H), 2.04 (s, 3H), 2.64 (brs, 2H), 3.58-3.62 (m, 4H), 4.09 (brs, 2H), 6.02 (brs, 1H), 7.32 (tt, J=7.6, 1.2 Hz, 1H), 7.64 (t, J=7.6 Hz, 2H), 7.56 (dd. J=8.4, 1.2 Hz, 2H).

Step 2 Synthesis of Compound Y

To a solution of Compound 2 (1.84 g, 5.19 mmol) in DMA (20 mL) were added pyridine (1.68 mL, 20.8 mmol) and phenyl chloroformate (0.684 mL, 5.45 mmol), and the reaction mixture was stirred at room temperature for 12 hours. Water was added to the mixture, followed by extraction with ethyl acetate twice. Then, the organic layer was washed with water and dried over sodium sulfate. The solvent was distilled off under reduced pressure, and the residue was purified by silicagel column chromatography (hexane-ethyl acetate) to give Compound Y (1.47 g, Yield 60%).

$^1$H-NMR ($CDCl_3$) δ: 1.49 (s, 9H), 2.19 (brs, 3H), 2.68 (brs, 2H), 3.62 (t, J=5.2 Hz, 2H), 4.11 (brs, 2H), 6.09 (brs, 1H), 7.12-7.52 (m, 10H).

Example 1

Synthesis of Compound I-7

[Chemical Formula 74]

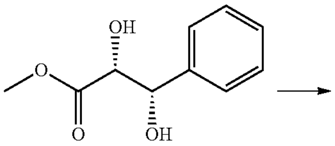

3

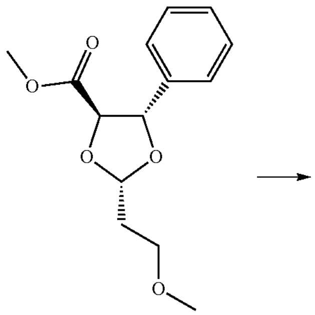

4

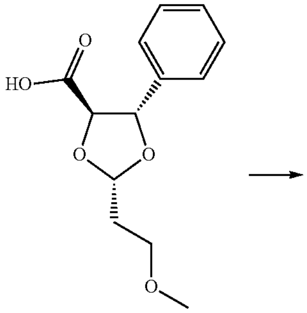

5

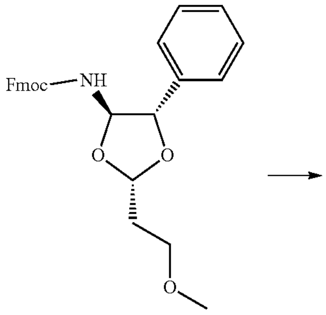

6

-continued

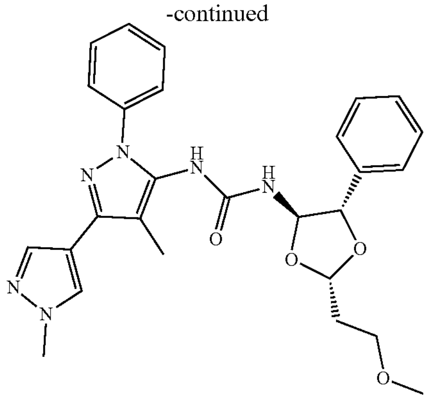

I-7

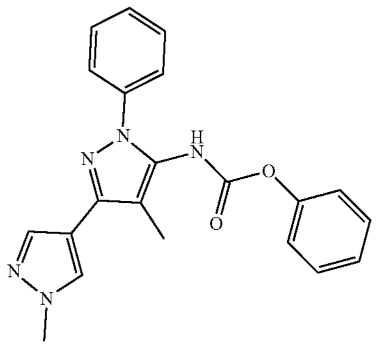

X

Step 1 Synthesis of Compound 4

Commercially available optically active Compound 3 (1.078 g, 5.49 mmol) was dissolved in dichloroethane (10.78 mL), and 1,1,3-trimethoxypropane (1.017 mL, 7.14 mmol) and paratoluenesulfonic acid (0.052 g, 0.275 mmol) were added to the solution. The reaction mixture was refluxed for 1.5 hours. After the mixture was allowed to cool to room temperature, saturated sodium bicarbonate aqueous solution and chloroform were added to the mixture to separate an organic layer. The separated organic layer was washed with water and then dried over anhydrous sodium sulfate, and the solvent was distilled off to give a residue. The obtained residue was purified by silicagel column chromatography (hexane-ethyl acetate) to give Compound 4 (1.096 g, Yield 74.9%) as a colorless oil.

$^1$H-NMR ($CDCl_3$) δ: 2.04-2.26 (m, 2H), 3.37 (s, 3H), 3.63 (t, J=6.4 Hz, 2H), 3.81 (s, 3H), 4.36 (d, J=6.0 Hz, 1H), 5.04 (d, J=6.4 Hz, 1H), 5.40 (t, J=4.4 Hz, 1H), 7.32-7.45 (m, 5H)

Step 2 Synthesis of Compound 5

Compound 4 (1.09 g, 4.09 mmol) was dissolved in methanol (10.9 mL), and 2 mol/L sodium hydroxide aqueous solution (4.09 mL, 8.19 mmol) was added to the solution. The reaction mixture was stirred at room temperature for 30 minutes. After the termination of the reaction was confirmed, 10% citric acid aqueous solution was added to the mixture, followed by extraction with chloroform three times. The organic layer was dried over anhydrous sodium sulfate, and then the solvent was distilled off to give crude Compound 5. The compound was used in the next reaction without further purification.

Step 3 Synthesis of Compound 6

The crude Compound 5 (4.409 mmol) which was obtained in the above step was dissolved in 1,4-dioxane (20.64 mL), and triethylamine (0.624 mL, 4.50 mmol) and DPPA (0.967 mL, 4.50 mmol) were added to the solution. The reaction mixture was stirred at room temperature for 1 hour and 45 minutes. (9H-Fluoren-9-yl)methanol (1.204 g, 6.14 mmol) was added to the mixture, and the reaction mixture was stirred at 80° C. for 1 hour. After the mixture was allowed to cool to room temperature, the reaction was terminated by the addition of water. The product was extracted with ethyl acetate, washed with water, and then dried over anhydrous sodium sulfate, and the solvent was distilled off. The obtained residue was purified by silicagel column chromatography (hexane-ethyl acetate) to give Compound 6 (1.945 g, Yield 106.7% (including fluorenemethanol as an impurity)) as a colorless solid.

$^1$H-NMR ($CDCl_3$) δ: 2.10 (br s, 2H), 3.36 (s, 3H), 3.60 (br t, 2H), 4.04 (d, J=6.0 Hz, 1H), 4.21 (t, J=6.4 Hz, 1H), 4.44 (br s, 2H), 4.67 (br s, 1H), 5.37 (t, J=4.4 Hz, 1H), 5.45 (dd, J=5.6, 9.6 Hz, 1H), 5.59 (d, J=9.6 Hz, 1H), 7.26-7.78 (m, 13H)

Step 4 Synthesis of Compound (I-7)

Compound 6 (280 mg, 0.629 mmol) was dissolved in DMF (4.7 mL), and Compound X (235 mg, 0.629 mmol) which can be synthesized in accordance with the known method (WO2012/158413) was added to the solution, and further DMAP (1.153 g, 9.44 mmol) was added. The reaction mixture was stirred at room temperature for 2 hours and then left standing overnight at room temperature. 10% Citric acid aqueous solution was added to the mixture, followed by extraction with ethyl acetate. The organic layer was washed with water and then dried over anhydrous sodium sulfate, and the solvent was distilled off. The obtained residue was purified by silicagel column chromatography (chloroform-methanol) to give Compound (I-7) (45 mg, Yield 14.2%) as a solid.

$^1$H-NMR ($CDCl_3$) δ: 2.01-2.12 (m, 2H), 2.17 (s, 3H), 3.33 (s, 3H), 3.56 (t, J=6.4 Hz, 2H), 3.97 (s, 3H), 4.54 (d, J=4.4 Hz, 1H), 5.27 (t, J=4.8 Hz, 1H), 5.48-5.51 (m, 2H), 6.34 (s, 1H), 7.23-7.53 (m, 10H), 7.78 (s, 1H), 7.89 (s, 1H).

Example 2

Synthesis of Compound (I-28)

[Chemical Formula 75]

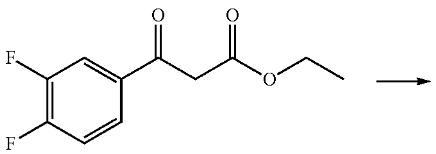

7

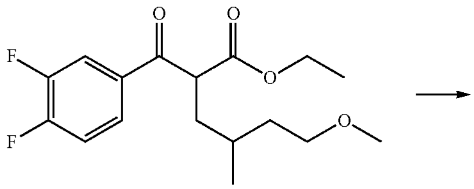

8

-continued

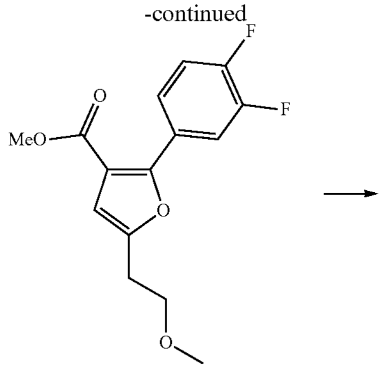

9

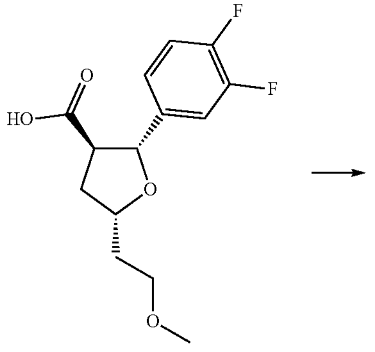

10

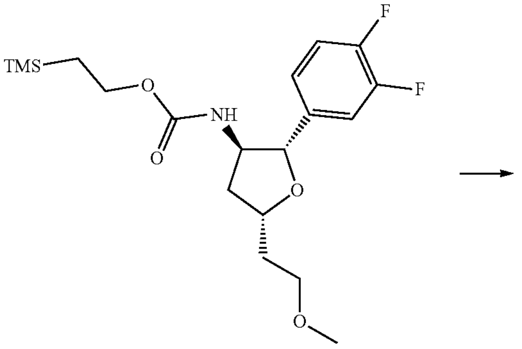

11

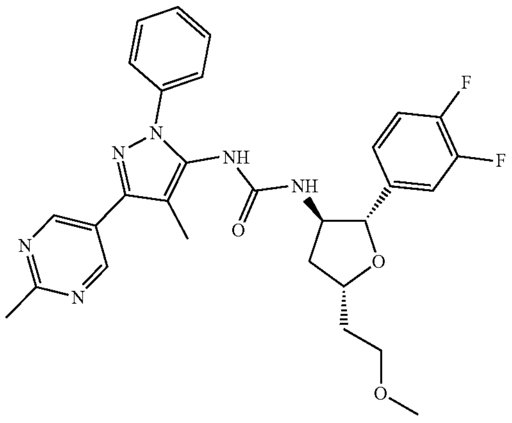

I-28

Step 1 Synthesis of Compound 8

A solution of Compound 7 (1.40 g, 6.14 mmol) which can be synthesized in accordance with the known method (JP201256944A) in tetrahydrofuran (14 mL) was cooled to 1° C. in an ice bath. 60% Sodium hydride (294 mg, 7.36 mmol) was added thereto, and the reaction mixture was stirred at room temperature for 30 minutes. The mixture was cooled to 1° C. again, and sodium iodide (92 mg, 0.614 mmol) and 1-chloro-4-methoxybutan-2-one (1.17 g, 8.59 mmol) were added to the mixture. The reaction mixture was stirred at room temperature for 2.5 hours. Saturated ammonium chloride aqueous solution (50 mL) was added to the mixture, followed by extraction with ethyl acetate (100 mL) twice. The organic layer was washed with brine (30 mL) and then dried over anhydrous sodium sulfate. The solvent was distilled off under reduced pressure, and the obtained residue was purified by silicagel chromatography (hexane-ethyl acetate) to give Compound 8 (1.88 g, Yield 93%) as a pale yellow oil.

1H-NMR (CDCl3) δ: 1.17 (3H, t, J=7.0 Hz), 2.65-2.83 (2H, m), 3.16 (1H, dd, J=18.4, 5.4 Hz), 3.28-3.38 (4H, m), 3.58-3.69 (2H, m), 4.13 (2H, q, J=7.2 Hz), 4.81 (1H, dd, J=8.4, 5.4 Hz), 7.22-7.33 (1H, m), 7.81-7.92 (2H, m).

Step 2 Synthesis of Compound 9

Compound 8 (1.83 g, 5.57 mmol) was dissolved in methanol (18 mL), and concentrated hydrochloric acid (2.79 mL, 33.4 mmol) was added to the solution. The reaction mixture was stirred at 100° C. for 2 hours under microwave irradiation in a sealed tube. The mixture was added to a sodium bicarbonate aqueous solution to be neutralized, followed by extraction with ethyl acetate (100 mL). The organic layer was dried over anhydrous magnesium sulfate and then concentrated under reduced pressure. The obtained residue was purified by silicagel chromatography (hexane-ethyl acetate) to give Compound 9 as a mixture with ethyl ester form (1.11 g, Yield 67%).

Step 3 Synthesis of Compound 10

The mixture of Compound 9 and its ethyl ester form (1.00 g, 3.38 mmol) which were obtained in step 2 was dissolved in ethyl acetate (10 mL), and 10% palladium-carbon (760 mg) was added to the solution. The reaction mixture was stirred for 21 hours under hydrogen atmosphere. The mixture was filtered through celite pad, and the solvent was concentrated under reduced pressure. The residue was purified by silicagel chromatography (hexane-ethyl acetate) to give a colorless oil (891 mg).

The obtained oil (888 mg) was dissolved in methanol (2.6 mL), and 28% sodium methoxide-methanol solution (2.94 mL, 14.8 mmol) was added to the solution. The reaction mixture was stirred at room temperature for 67 hours. Water (1 mL) was added to the mixture, and the reaction mixture was further stirred for 1 hour and then neutralized by the addition of 2 mol/L hydrochloric acid aqueous solution (7.4 mL, 14.8 mmol). The solvent and water were distilled off under reduced pressure, and the obtained residue was purified by silicagel chromatography (chloroform-methanol) to give Compound 10 (racemate, 831 mg, Yield 84%) as a colorless oil.

1H-NMR (CDCl3) δ: 1.88-2.05 (3H, m), 2.42-2.48 (1H, m), 2.93 (1H, ddd, J=11.2, 5.9, 4.1 Hz), 3.36 (3H, s), 3.56 (2H, t, J=6.4 Hz), 4.20-4.27 (1H, m), 5.01 (1H, d, J=7.0 Hz), 7.08-7.17 (2H, m), 7.20-7.25 (1H, m).

Step 4 Synthesis of Compound 11

Compound 10 (750 mg, 2.62 mmol) was dissolved in DMF (7.5 mL), and DPPA (789 L, 3.67 mmol) and triethylamine (908 μL, 6.55 mmol) were added to the solution. The reaction mixture was stirred at room temperature for 30 minutes, then stirred at 80° C. for 1 hour, and allowed to cool. 2-Trimethylsilylethanol (1.13 mL, 7.86 mmol) and triethylamine (1.45 mL, 10.5 mmol) were added thereto, and the reaction mixture was stirred at 80° C. for 7 hours.

Sodium bicarbonate aqueous solution (70 mL) was added to the mixture, followed by extraction with ethyl acetate (100 mL) twice. The obtained organic layer was washed with brine (50 mL) and then dried over anhydrous sodium sulfate. The solvent was distilled off under reduced pressure, and the obtained residue was purified by silicagel chromatography (hexane-ethyl acetate) to give Compound 11 (racemate, 668 mg, Yield 64%) as a colorless oil.

1H-NMR (CDCl3) δ: 0.04 (9H, s), 0.98 (2H, t, J=8.1 Hz), 1.86-2.04 (4H, m), 3.37 (3H, s), 3.50-3.63 (2H, m), 4.06 (1H, br s), 4.11-4.22 (2H, m), 4.27-4.34 (1H, m), 4.75 (1H, br s), 4.88 (1H, br s), 7.07-7.21 (2H, m), 7.22-7.34 (2H, m).

Step 5 Synthesis of Compound (I-28)

To a solution of Compound 11 (40 mg, 0.10 mmol) in dichloromethane (0.4 mL) was added TFA (0.4 mL), and the reaction mixture was stirred at room temperature for 1 hour. The solvent and TFA were distilled off under reduced pressure. The obtained residue was dissolved in dichloromethane (1 mL) again, and DIEA (87 μL, 0.50 mmol) and Compound W (48 mg, 0.13 mmol) were added to the solution. The reaction mixture was stirred at room temperature for 2 days. After concentration under reduced pressure, the obtained residue was purified by amino silicagel chromatography (hexane-ethyl acetate) to give Compound (I-28) (racemate, 42 mg, Yield 77%) as a pale yellow solid.

1H-NMR (CDCl3) δ: 1.74-1.81 (1H, m), 1.83-2.01 (3H, m), 2.24 (3H, s), 2.81 (3H, s), 3.35 (3H, s), 3.47-3.60 (2H, m), 4.11-4.22 (2H, m), 4.54 (1H, d, J=3.8 Hz), 4.85 (1H, d, J=7.5 Hz), 6.11 (1H, s), 7.01-7.12 (2H, m), 7.16 (1H, t, J=8.8 Hz), 7.41 (1H, t, J=7.3 Hz), 7.49 (2H, t, J=7.7 Hz), 7.56 (2H, d, J=7.9 Hz), 9.05 (2H, s).

Example 3

Synthesis of Compound (I-31)

[Chemical Formula 76]

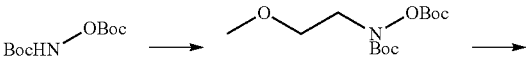

12 13

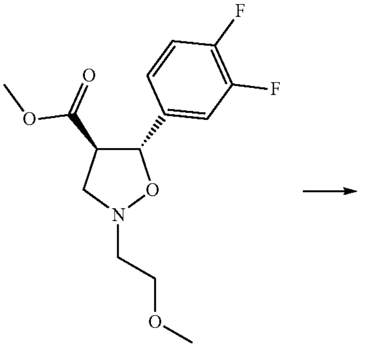

14

-continued

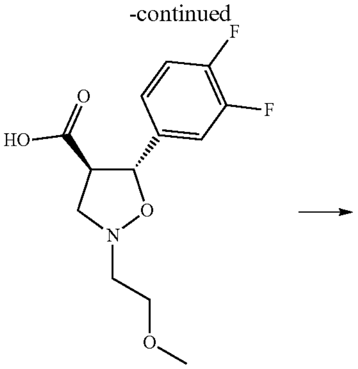

15

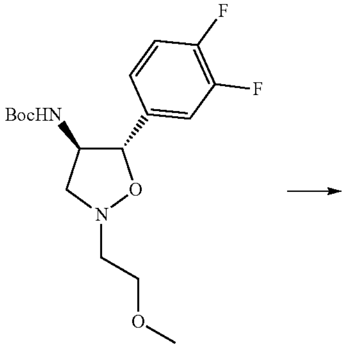

16

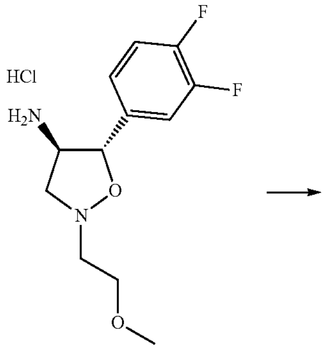

Z

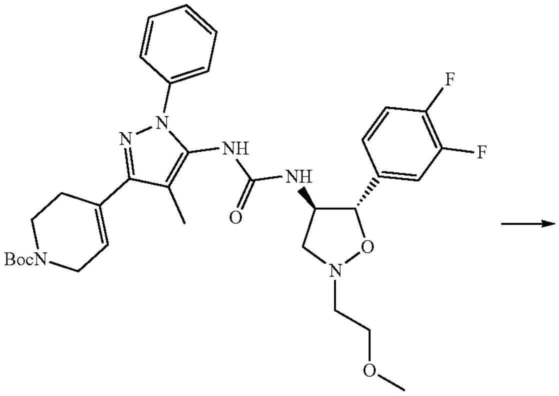

17

-continued

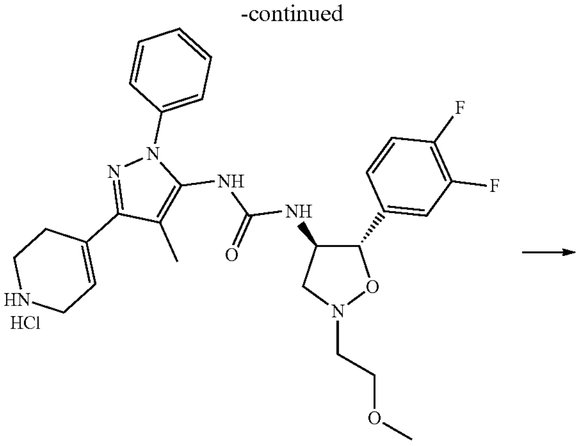

18

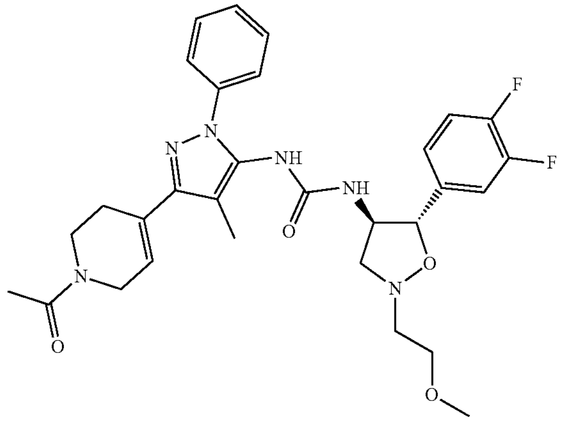

I-31

Step 1 Synthesis of Compound 13

Commercially available Compound 12 (6.7 g, 28.7 mmol), 2-methoxyethanol (2.267 mL, 28.7 mmol) and triphenylphosphine (9 g, 34.5 mmol) were dissolved in tetrahydrofuran (67 mL) under water-cooling bath, and 2.2 mol/L DEAD-toluene solution (15.67 mL, 34.5 mmol) was added dropwise to the solution over 30 minutes. Then, the reaction mixture was stirred at room temperature for 1 hour.

The solvent was distilled off under reduced pressure, and the obtained residue was purified by silicagel column chromatography (hexane-ethyl acetate) to give Compound 13 (8.15 g, Yield 97.4%).

LC/MS (Method 2) RT=2.20, MS (m/z)=292

Step 2 Synthesis of Compound 14

To Compound 13 (1510 mg, 5.2 mmol) was added 4 mol/L hydrochloric acid-dioxane solution (20 mL), and the reaction mixture was stirred at room temperature for 1 hour.

The solvent was distilled off under reduced pressure, then the obtained residue was suspended in toluene (10 mL), and triethylamine (2.16 mL, 15.6 mmol), paraformaldehyde (468 mg, 15.6 mmol), and (E)-methyl 3-(3,4-difluorophenyl) acrylate (1030 mg, 5.2 mmol) were added to the suspension. Then, the reaction mixture was stirred overnight at 70° C.

The solvent was distilled off under reduced pressure, and the obtained residue was purified by silicagel column chromatography (hexane-ethyl acetate) to give Compound 14 (racemate, 1293 mg, 82.6%).

LC/MS (Method 2) RT=1.90, MS (m/z)=302

Step 3 Synthesis of Compound 15

Compound 14 (1290 mg, 4.28 mmol) was dissolved in tetrahydrofuran (5 mL) and methanol (5 mL), and 2 mol/L sodium hydroxide aqueous solution (2.57 mmol) was added to the solution. The reaction mixture was stirred at room temperature for 0.5 hour.

The mixture was neutralized by the addition of 2 mol/L hydrochloric acid (2.57 mL), and then the solvent was distilled off under reduced pressure. Further, water was removed by azeotropy with toluene to give Compound 15 (racemate). The compound was used in the next reaction without further purification.

LC/MS (Method 2) RT=1.66, MS (m/z)=288

Step 4 Synthesis of Compound 16

Compound 15 (100 mg, 0.348 mmol) was dissolved in DMF (2 mL), and triethylamine (0.097 mL, 0.696 mmol) and DPPA (0.090 mL, 0.418 mmol) were added to the solution. The reaction mixture was stirred at room temperature for 0.5 hour.

Water was added to the mixture, followed by extraction with ethyl acetate. Then, the organic layer was washed with water and dried over sodium sulfate. The solvent was distilled off under reduced pressure, and the obtained residue was purified by silicagel column chromatography (hexane-ethyl acetate) to give Compound 16 (racemate, 40 mg, Yield 32.1%).

LC/MS (Method 2) RT=1.99, MS (m/z)=359

Step 5 Synthesis of Compound Z

To Compound 16 (45 mg, 0.126 mmol) was added 4 mol/L hydrochloric acid-dioxane solution (1 mL), and the reaction mixture was stirred at room temperature for 1 hour.

The solvent was distilled off under reduced pressure to give Compound Z (racemate). The compound was used in the next reaction without further purification.

LC/MS (Method 2) RT=1.01, MS (m/z)=259

Step 6 Synthesis of Compound 17

Compound Z (0.126 mmol) was dissolved in tetrahydrofuran (1 mL), and triethylamine (0.087 mL, 0.63 mmol) and Compound Y (71.8 mg, 0.151 mmol) which was synthesized in Reference Example 2 were added to the solution. The reaction mixture was stirred at room temperature for 1 hour.

The solvent was distilled off under reduced pressure, and then the obtained residue was purified by silicagel column chromatography (hexane-ethyl acetate) to give Compound 17 (racemate, 55 mg, Yield 68.3%).

LC/MS (Method 2) RT=2.63, MS (m/z)=639

Step 7 Synthesis of Compound 18

To Compound 17 (50 mg, 0.078 mmol) was added 4 mol/L hydrochloric acid-dioxane solution (1 mL), and the reaction mixture was stirred at room temperature for 1 hour.

The solvent was distilled off under reduced pressure, and then diisopropyl ether was added to the obtained residue for precipitating to give Compound 18 (racemate, 43 mg, Yield 95.5%) as a yellow solid.

LC/MS (Method 2) RT=1.56, MS (m/z)=539

Step 8 Synthesis of Compound (I-31)

Compound 18 (17 mg, 0.03 mmol) was dissolved in dichloromethane (1 mL), and triethylamine (0.041 mL, 0.296 mmol) and acetyl chloride (5.27 μL, 0.074 mmol) were added to the solution. The reaction mixture was left standing overnight. Water was added to the residue, followed by extraction with chloroform. Then, the organic layer was dried over anhydrous sodium sulfate. The solvent was distilled off under reduced pressure, and the obtained residue was purified by silicagel column chromatography (chloroform-methanol) to give Compound (I-31) (racemate, 15 mg, Yield 87.4%).

LC/MS (Method 2) RT=1.95, MS(m/z)=581

$^1$H-NMR (CDCl3) δ: 1.62 (m, 2H), 2.14 (s, 3H), 2.17 (m, 3H), 2.75 (m, 2H), 3.04 (m, 2H), 3.33 (s, 3H), 3.51 (m, 1H), 3.67 (m, 2H), 3.82 (m, 1H), 4.19 (m, 1H), 4.29 (m, 1H), 4.50 (m, 2H), 5.63 (brs, 1H), 6.12 (d, J=11.9 Hz, 1H), 6.34 (brs, 1H), 6.97-7.16 (m, 3H), 7.32 (m, 1H), 7.41 (m, 2H), 7.51 (m, 2H).

Example 4

Synthesis of Compound (I-43)

[Chemical Formula 77]

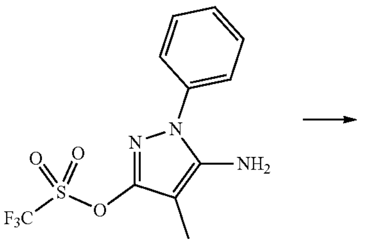

V

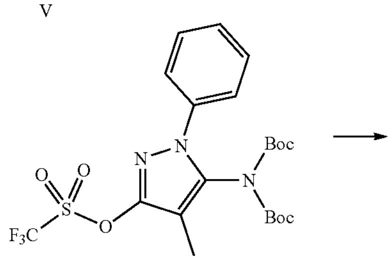

19

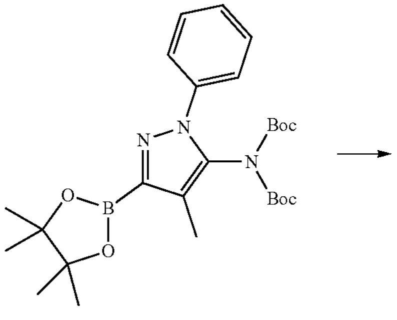

20

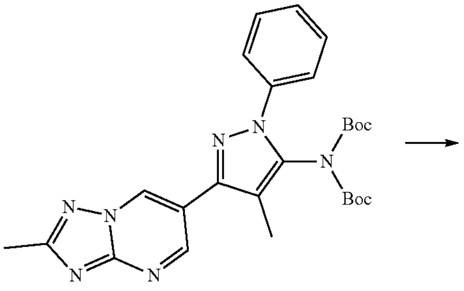

21

-continued

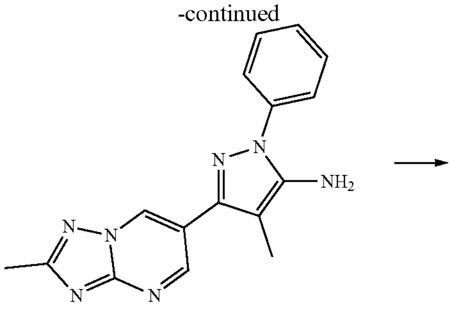

22

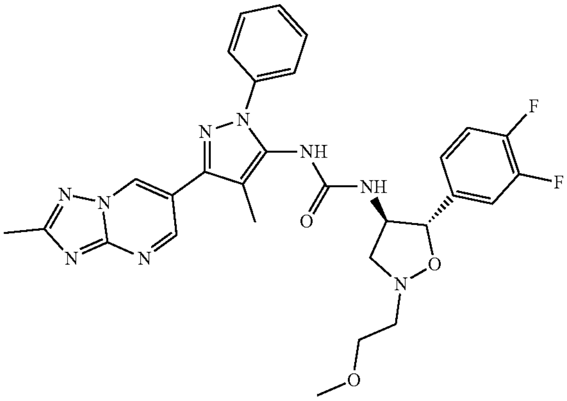

I-43

Step 1 Synthesis of Compound 19

To a solution of Compound V (40 g, 121 mmol) which can be synthesized in accordance with the known method (WO2012/158413) in 1,4-dioxane (150 mL) were added $Boc_2O$ (85 mL, 364 mmol), triethylamine (50.5 mL, 364 mmol) and DMAP (0.3 g, 2.4 mmol), and the reaction mixture was stirred at room temperature for 24 hours. The solvent was distilled off under reduced pressure, and the residue was purified by silicagel column chromatography (hexane-ethyl acetate) to give Compound 19 (33 g, Yield 78%).

$^1$H-NMR ($CDCl_3$) δ: 1.31 (s, 18H), 2.00 (s, 3H), 7.37-7.48 (m, 5H).

Step 2 Synthesis of Compound 20

To a solution of Compound 19 (31 g, 59 mmol) in 1,4-dioxane (230 mL) were added bis(pinacolato)diboron (18.1 g, 71.3 mmol), a dichloromethane adduct of $PdCl_2$ (dppf) (4.85 g, 5.94 mmol), and potassium acetate (17.5 g, 178 mmol) under nitrogen atmosphere, and the reaction mixture was stirred at 95° C. for 7 hours. The solvent was distilled off under reduced pressure until the amount of the solvent became one-third. Ethyl acetate (300 mL) was added to the residue. The organic layer was washed with water (100 mL) and brine (100 mL×2) and dried over sodium sulfate. The solvent was distilled off under reduced pressure, and the residue was purified by silicagel column chromatography (hexane-ethyl acetate) to give Compound 20 (26.5 g, Yield 90%).

$^1$H-NMR (DMSO-$d_6$) δ: 1.26-1.31 (m, 30H), 2.01 (s, 3H), 7.38 (d, J=7.6 Hz, 2H), 7.45 (t, J=7.6 Hz, 1H), 7.55 (t, J=7.6 Hz, 2H).

Step 3 Synthesis of Compound 21

To a solution of Compound 20 (542 mg, 1.08 mmol) in 1,4-dioxane (25 mL) were added 6-bromo-2-methyl[1,2,4]triazolo[1,5-a]pyrimidine (231 mg, 1.08 mmol) which can be synthesized in accordance with the known method (J.

Heterocyclic Chem. 2014, 51, E68), chloro(2-dicyclohexylphosphino-2',4',6'-triisopropyl-1,1'-biphenyl)[2-(2'-amino-1,1'-biphenyl)]palladium(II) (85 mg, 0.11 mmol), and cesium carbonate (707 mg, 2.17 mmol) under nitrogen atmosphere, and the reaction mixture was stirred at 90° C. for 7 hours. Brine was added to the mixture, followed by extraction with ethyl acetate twice. Then, the organic layer was dried over sodium sulfate. The solvent was distilled off under reduced pressure, and the residue was purified by silicagel column chromatography (hexane-ethyl acetate) to give Compound 21 (446 mg, Yield 81%).

$^1$H-NMR ($CDCl_3$) δ: 1.35 (s, 18H), 2.22 (s, 3H), 2.67 (s, 3H), 7.39-7.52 (m, 5H), 9.08 (d, J=2.4 Hz, 1H), 9.27 (d, J=2.4 Hz, 1H).

Step 4 Synthesis of Compound 22

To a solution of Compound 21 (445 mg, 0.88 mmol) in dichloromethane (2 mL) was added trifluoroacetic acid (2 mL), and the reaction mixture was stirred at room temperature for 3 hours. The solvent was distilled off under reduced pressure, and saturated sodium hydrogen carbonate aqueous solution was added to the residue, followed by extraction with chloroform twice. Then, the organic layer was dried over sodium sulfate. The solvent was distilled off under reduced pressure to give Compound 22 (269 mg, Yield 100%).

$^1$H-NMR ($CDCl_3$) δ: 2.17 (s, 3H), 2.59 (s, 3H), 7.44 (t, J=7.6 Hz, 1H), 7.55 (t, J=7.6 Hz, 2H), 7.63 (d, J=7.6 Hz, 2H), 9.15 (d, J=2.4 Hz, 1H), 9.26 (d, J=2.4 Hz, 1H).

Step 4 Synthesis of Compound (I-43)

To a solution of Compound 22 (28.6 mg, 0.094 mmol) in DMA (2 mL) were added pyridine (0.030 mL, 0.375 mmol) and phenyl chloroformate (0.013 mL, 0.103 mmol), and the reaction mixture was stirred at room temperature for 12 hours. Compound Z (27.5 mg, 0.094 mmol) which was synthesized in step 5 of Example 3 and triethylamine (0.065 mL, 0.468 mmol) were added to the mixture, and the reaction mixture was stirred at room temperature for 4 hours. Water was added to the mixture, followed by extraction with ethyl acetate twice. Then, the organic layer was washed with water and dried over sodium sulfate. The solvent was distilled off under reduced pressure, and the residue was purified by amino silicagel column chromatography (ethyl acetate-methanol) to give Compound (I-43) (racemate, 29.0 mg, Yield 56%).

$^1$H-NMR ($CDCl_3$) δ: 2.29 (s, 3H), 2.68 (s, 3H), 2.884-3.13 (m, 4H), 3.35 (s, 3H), 3.94-3.52 (m, 1H), 3.68 (brs, 1H), 4.54-4.59 (m, 2H), 7.00-7.14 (m, 3H), 7.41 (t, J=7.6 Hz, 1H), 7.49 (d, J=7.6 Hz, 2H), 7.58 (d, J=7.6 Hz, 2H), 9.09 (d, J=2.4 Hz, 1H), 9.25 (d, J=2.4 Hz, 1H).

Example 5

Synthesis of Compound (I-36)

[Chemical Formula 78]

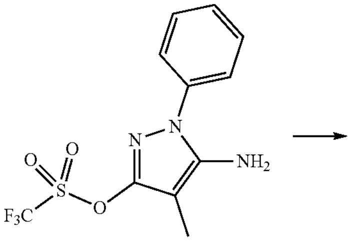

V

-continued

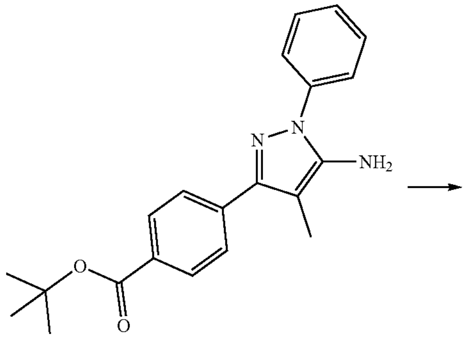

23

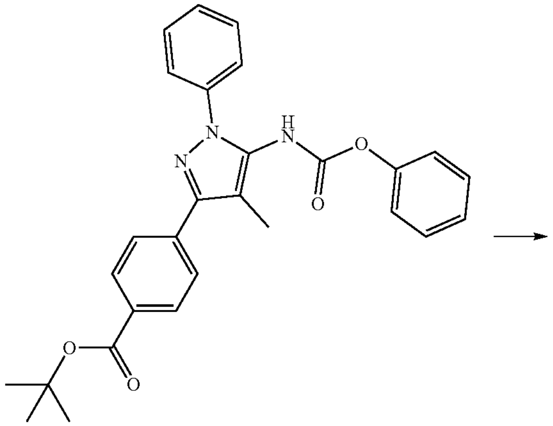

24

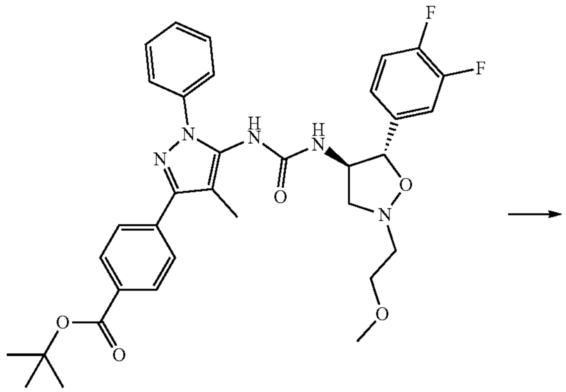

25

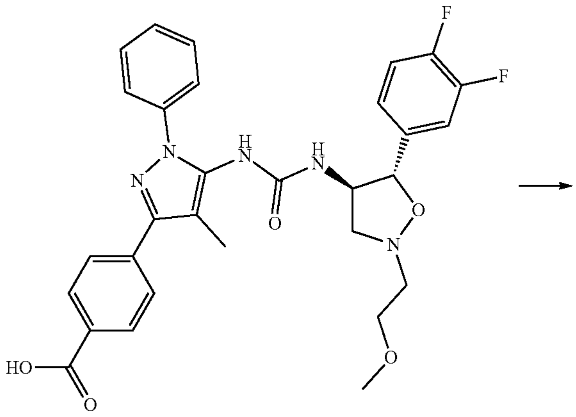

26

-continued

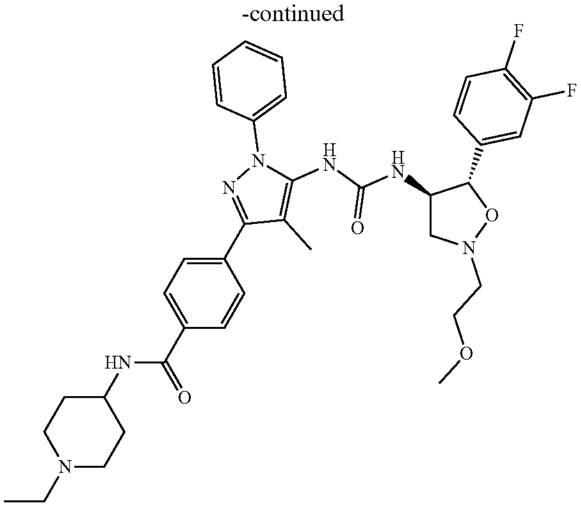

I-36

Step 1 Synthesis of Compound 23

To a solution of Compound V (1.34 g, 4.17 mmol) which can be synthesized in accordance with the known method (WO2012/158413) in 1,4-dioxane (15 mL) were added (4-(tert-butoxycarbonyl)phenyl)boronic acid (1.11 g, 5.00 mmol), potassium phosphate (1.77 g, 8.34 mmol), chloro (2-dicyclohexylphosphino-2',4',6'-triisopropyl-1,1'-biphenyl)[2-(2'-amino-1,1'-biphenyl)]palladium(II) (0.033 g, 0.042 mmol), and water (7.5 mL), and the reaction mixture was stirred at 90° C. for 6 hours. Brine was added to the mixture, followed by extraction with ethyl acetate twice. Then, the organic layer was dried over sodium sulfate. The solvent was distilled off under reduced pressure, and the residue was purified by silicagel column chromatography (hexane-ethyl acetate) to give Compound 23 (1.21 g, Yield 83%).

$^1$H-NMR ($CDCl_3$) δ: 1.61 (s, 9H), 2.14 (s, 3H), 3.67 (s, 2H), 7.37 (t, J=7.6 Hz, 1H), 7.50 (t, J=7.6 Hz, 2H), 7.64 (d, J=7.6 Hz, 2H), 7.79 (d, J=8.4 Hz, 2H), 8.03 (d, J=8.4 Hz, 2H).

Step 2 Synthesis of Compound 24

To a solution of Compound 23 (268 mg, 0.766 mmol) in ethyl acetate (3 mL) were added 2 mol/L sodium hydroxide aqueous solution (1.92 mL, 3.83 mmol) and phenyl chloroformate (0.288 mL, 2.30 mmol), and the reaction mixture was stirred at room temperature for 12 hours. Water was added to the mixture, followed by extraction with ethyl acetate twice. Then, the organic layer was dried over sodium sulfate. The solvent was distilled off under reduced pressure, and the residue was purified by silicagel column chromatography (hexane-ethyl acetate) to give Compound 24 (320 mg, Yield 89%).

$^1$H-NMR ($CDCl_3$) δ: 1.62 (s, 9H), 2.29 (brs, 3H), 7.14-7.37 (brm, 5H), 7.43 (t, J=7.6 Hz, 1H), 7.52 (t, J=7.6 Hz, 2H), 7.60 (d, J=6.4 Hz, 2H), 7.83 (d, J=8.4 Hz, 2H), 8.06 (d, J=8.4 Hz, 2H).

Step 3 Synthesis of Compound 25

Compound Z (113 mg, 0.383 mmol) which was synthesized in step 5 of Example 3, Compound 24 (180 mg, 0.383 mmol) and N,N-diisopropylethylamine (334 μL, 1.91 mmol) were dissolved in tetrahydrofuran (1.9 mL), and the solution was stirred overnight at room temperature. Sodium hydrogen carbonate aqueous solution was added to the mixture, followed by extraction with ethyl acetate. The organic layer was washed with brine and then dried over anhydrous sodium sulfate. The solvent was distilled off under reduced pressure, and the obtained residue was purified by silicagel column chromatography (hexane-ethyl acetate) to give Compound 25 (racemate, 117 mg, Yield 48%).

LC/MS (Method 1) RT=2.57, MS (m/z)=634.25

Step 4 Synthesis of Compound 26

To Compound 25 (107 mg, 0.169 mmol) was added 4 mol/L hydrogen chloride-dioxane solution (2.00 ml, 8.00 mmol), and the reaction mixture was stirred at room temperature for 2 hours. Next, the mixture was stirred at 40° C. for 2 hours. After the mixture was allowed to cool, the solvent was distilled off under reduced pressure. The residue was solidified by the addition of diethyl ether to give Compound 26 (racemate, 113 mg, Yield 115%).

LC/MS (Method 1) RT=1.87, MS (m/z)=578.20

Step 5 Synthesis of Compound (I-36)

Compound 26 (59.9 mg, 0.104 mmol) was dissolved in DMF (1 ml). N,N-Diisopropylethylamine (65 μL, 0.373 mmol), 1-ethylpiperidin-4-amine (18 μL, 0.124 mmol) and COMU (53.3 mg, 0.124 mmol) were added to the solution, and the reaction mixture was stirred overnight at room temperature. Sodium hydrogen carbonate aqueous solution was added to the mixture, followed by extraction with ethyl acetate. The organic layer was washed with water and brine, successively and then dried over anhydrous sodium sulfate. The solvent was distilled off under reduced pressure, and the obtained residue was purified by silicagel column chromatography (ethyl acetate-methanol) to give Compound (I-36) (racemate, 49.8 mg, Yield 70%).

LC/MS (Method 1) RT=1.34, MS (m/z)=688.30

$^1$H-NMR ($CDCl_3$) δ: 0.84 (m, 1H), 1.11 (t, J=7.2 Hz, 3H), 1.64 (m, 1H), 2.05-2.20 (m, 4H), 2.24 (s, 3H), 2.45 (q, J=7.3 Hz, 2H), 2.85-3.15 (m, 5H), 3.33 (s, 3H), 3.51 (m, 1H), 3.65 (m, 1H), 4.05 (m, 1H), 4.54 (br s, 2H), 5.56 (br, 1H), 6.02 (d, J=7.9 Hz, 1H), 6.15 (br, 1H), 6.98-7.20 (m, 3H), 7.37 (t, J=7.4 Hz, 1H), 7.46 (t, J=7.8 Hz, 2H), 7.59 (d, J=8.0 Hz, 2H), 7.85 (dd, J=15.1, 8.6 Hz, 4H).

Example 6

Synthesis of Compound (I-10)

[Chemical Formula 79]

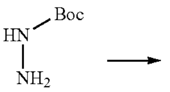

27

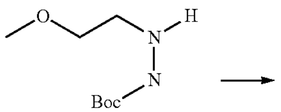

28

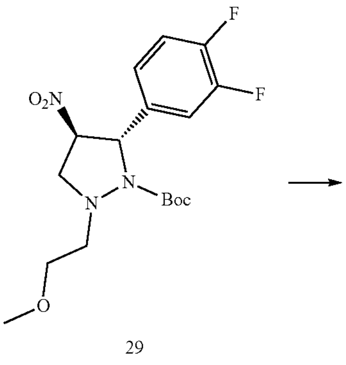

29

-continued

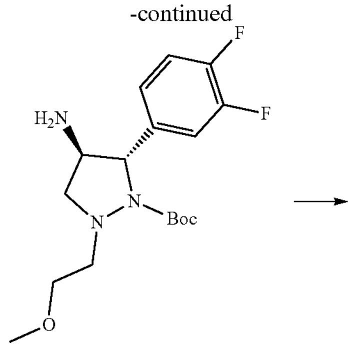

30

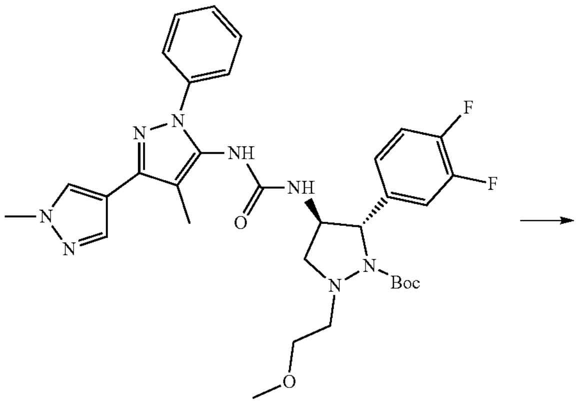

31

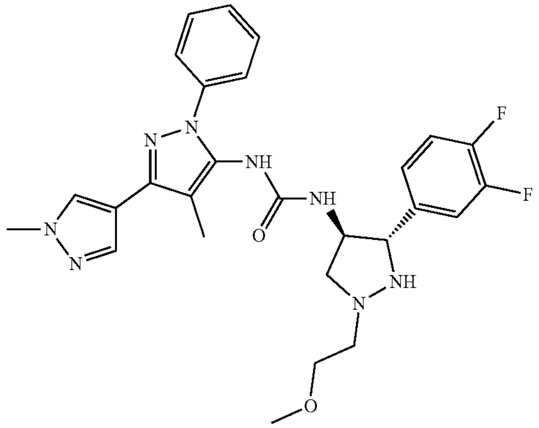

I-10

Step 1 Synthesis of Compound 28

1-Bromo-2-methoxyethane (2 g, 14.4 mmol) was dissolved in DMSO (10 mL), and NaI (216 mg, 1.44 mmol), diisopropylethylamine (2.51 ml, 14.4 mmol) and commercially available tert-butyl carbazate (1.9 g, 1.44 mmol) were added to the solution. The reaction mixture was heated at 90° C. for 20 hours. After the mixture was allowed to cool, water was added to the mixture, followed by extraction with ethyl acetate. The organic layer was washed with brine and then dried over anhydrous magnesium sulfate. The solvent was distilled off under reduced pressure, and the obtained residue was purified by silicagel column chromatography (hexane-ethyl acetate) to give Compound 28 (340 mg, 1.79 mmol, Yield 12%).

$^1$H-NMR ($CDCl_3$) δ: 1.46 (s, 11H), 3.04 (t, J=5.1 Hz, 2H), 3.37 (s, 3H), 3.49 (t, J=5.1 Hz, 2H), 6.23 (s, 1H).

Step 2 Synthesis of Compound 29

To Compound 28 (100 mg, 0.53 mmol) were added toluene (3 mL), formaldehyde (0.080 mL, 1.05 mmol), (E)-1,2-difluoro-4-(2-nitrovinyl)benzene (146 mg, 0.79 mmol) and molecular sieve 5 A (100 mg), and the reaction mixture was stirred overnight at 90° C. Saturated ammonium chloride aqueous solution was added to the mixture, followed by extraction with ethyl acetate. The organic layer was dried over anhydrous magnesium sulfate, and then the solvent was distilled off under reduced pressure. The residue was purified by silicagel column chromatography (hexane-ethyl acetate) to give Compound 29 (racemate, 28 mg, 0.072 mmol, Yield 13.8%).

$^1$H-NMR (DMSO-$d_6$) 1H-NMR ($CDCl_3$) δ: 1.40 (s, 7H), 1.49 (s, 2H), 2.97 (dq, J=12.6, 3.9 Hz, 1H), 3.09-3.18 (m, 1H), 3.35 (s, 3H), 3.56-3.65 (m, 2H), 3.79 (dd, J=7.3, 4.5 Hz, 1H), 5.20 (q, J=7.1 Hz, 1H), 5.63 (d, J=6.1 Hz, 1H), 7.05-7.10 (m, 1H), 7.14-7.24 (m, 2H).

LC/MS (Method 1) RT=2.20, MS (m/z)=332.05

Step 3 Synthesis of Compound 30

To Compound 29 (28 mg, 0.072 mmol) were added methanol (3 mL), tetrahydrofuran (1 ml), and palladium-carbon (16 mg), and the reaction mixture was stirred at room temperature under hydrogen atmosphere. The mixture was filtered through celite pad, and then the solvent was distilled off under reduced pressure to give Compound 30 (racemate, 26 mg, 0.072 mmol, Yield 100%, crude product).

LC/MS (Method 1) RT=1.23, MS (m/z)=358.20

Step 4 Synthesis of Compound 31

To a solution of Compound 30 (26 mg, 0.072 mmol) in dichloromethane (1 mL) were added Compound X (25 mg, 0.070 mmol) which can be synthesized in accordance with the known method (WO2012/158413) and triethylamine (0.019 mL, 0.140 mmol) under nitrogen atmosphere, and the reaction mixture was stirred at room temperature. Saturated ammonium chloride aqueous solution was added to the mixture, followed by extraction with ethyl acetate. The organic layer was dried over anhydrous magnesium sulfate, and then the solvent was distilled off under reduced pressure. The residue was purified by amino silicagel column chromatography (chloroform-methanol) to give Compound 31 (racemate, 4.4 mg, 6.9 μmol, Yield 11%) as a crude product.

LC/MS (Method 1) RT=1.95, MS (m/z)=637.30

Step 5 Synthesis of Compound (I-10)

To a solution of Compound 31 (4.4 mg, 6.9 μmol) in dichloromethane (1 mL) was added TFA (0.2 mL, 2.6 mmol) under nitrogen atmosphere, and the reaction mixture was stirred at room temperature for 1 hour. After the mixture was concentrated, dichloromethane (1 mL) was added to the mixture. The organic layer was washed with saturated sodium hydrogen carbonate aqueous solution. The organic layer was dried over anhydrous magnesium sulfate, and then the solvent was distilled off under reduced pressure. The residue was purified by amino silicagel column chromatography (chloroform-methanol), and the obtained crude product was further purified by reverse-phase chromatography (HP20SS, acetonitrile-water) to give Compound (I-10) (racemate, 2.6 mg, 4.9 μmol, Yield 70%).

$^1$H-NMR ($CD_3OD$) δ: 2.06 (s, 3H), 3.15-3.23 (m, 1H), 3.26-3.34 (m, 4H), 3.35-3.41 (m, 1H), 3.38 (s, 1H), 3.60-3.68 (m, 1H), 3.68-3.75 (m, 1H), 3.94 (s, 3H), 5.45 (t, J=6.3 Hz, 1H), 7.18-7.27 (m, 1H), 7.33-7.48 (m, 6H), 7.52-7.61 (m, 1H), 7.83 (s, 1H), 7.95 (s, 1H).

LC/MS (Method 1) RT=1.28, MS (m/z)=537.25

Example 7
Synthesis of Compound (I-235)
[Chemical Formula 80]
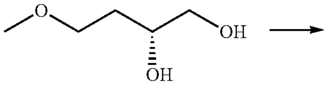
32
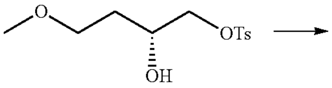
33
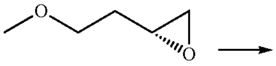
34
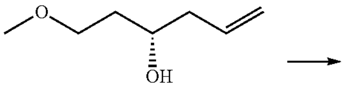
35
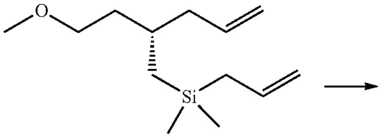
36
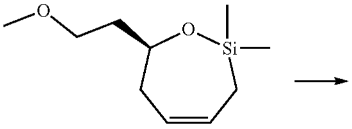
37
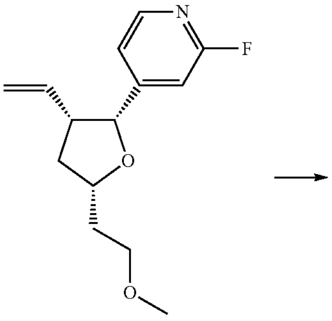
38
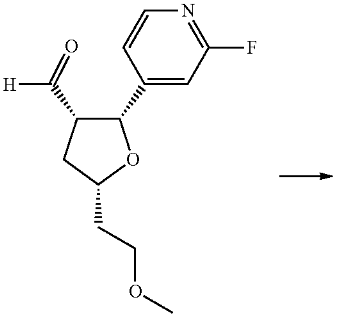
39
-continued
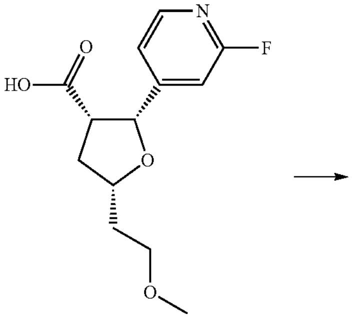
40
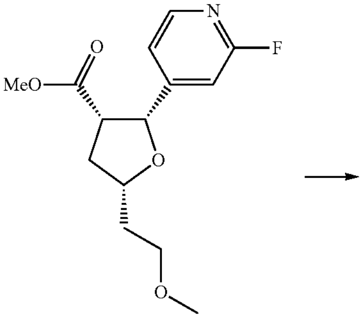
41
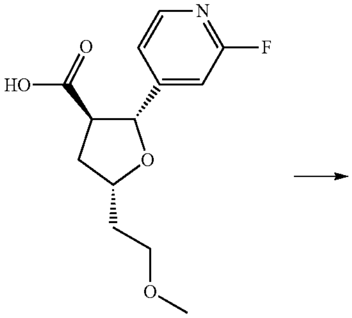
42
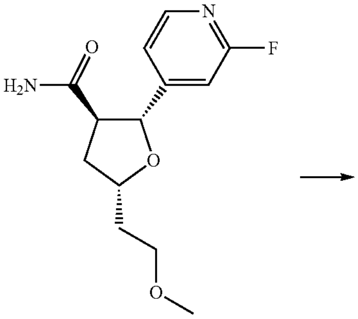
43

-continued

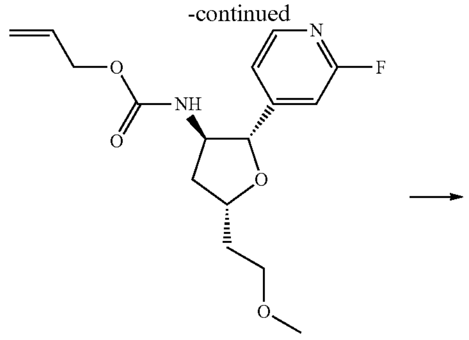

44

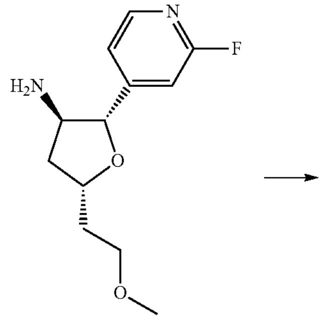

45

[Chemical Formula 81]

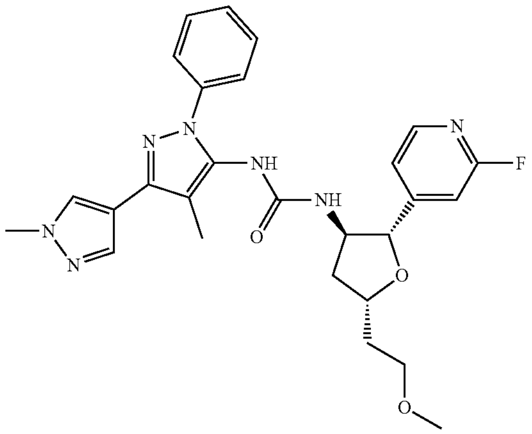

I-235

Step 1 Synthesis of Compound 33

To Compound 32 (12.15 g, 101 mmol) which can be synthesized in accordance with the method described in Synthetic Communications 1992, 22, 83-95 was added dichloromethane (97 mL), and triethylamine (14.7 mL, 106 mmol), dibutyltin oxide (503 mg, 2.02 mmol), and p-toluenesulfonyl chloride (20.24 g, 106 mmol) were subsequently added thereto. The reaction mixture was stirred at room temperature for 2 hours, and then water was added to the mixture, followed by extraction with chloroform. The organic layer was washed with brine, then dried over anhydrous sodium sulfate, and filtered, and the organic solvent was distilled off under reduced pressure. The obtained crude product (38.88 g) was purified by silicagel column chromatography (hexane-ethyl acetate) to give Compound 33 (25.0 g, Yield 90%) as a colorless oil.

Compound 33 LC/MS (Method 1) RT=1.47, MS (m/z)=275.15

$^1$H-NMR ($CDCl_3$) δ: 1.69-1.78 (2H, m), 2.45 (3H, s), 3.32 (3H, s), 3.48-3.55 (1H, m), 3.55-3.62 (1H, m), 3.92-4.07 (3H, m), 7.35 (2H, d, J=8.0 Hz), 7.80 (2H, d, J=8.3 Hz).

Step 2 Synthesis of Compound 34

Compound 33 (25.0 g, 91.0 mmol) was dissolved in THF (100 mL). After the solution was cooled in an ice bath, sodium hydride (60% in oil, 3.86 g, 97.0 mmol) was added to the solution. The reaction mixture was stirred at room temperature for 14 hours. Further, sodium hydride (971 mg, 24.3 mmol) was added to the mixture, and the reaction mixture was stirred at room temperature for 3 hours. Saturated ammonium chloride aqueous solution was added to the mixture, followed by extraction with diethyl ether twice. The organic layer was washed with brine. The organic layer was dried over anhydrous magnesium sulfate, and then the organic solvent was distilled off under reduced pressure to give Compound 34 (49.4 g, 12.5% purity, 66% yield).

Step 3 Synthesis of Compound 35

Compound 34 (49.4 g, 12.5% purity, 60.5 mmol) was dissolved in THF (50 mL), and copper(I) cyanide (542 mg, 6.05 mmol) was added to the solution. Then, the reaction mixture was cooled to −78° C. in a dry ice-acetone bath. Vinyl magnesium bromide solution (1 mol/L THF solution, 79 mL, 79 mmol) was added dropwise thereto, and then the reaction mixture was allowed to warm up gradually to room temperature. The mixture was left standing overnight at room temperature, and saturated ammonium chloride aqueous solution was added to the mixture, followed by extraction with ethyl acetate. The organic layer was washed with brine and then dried over anhydrous sodium sulfate. The solvent was distilled off under reduced pressure, and the obtained crude product (18.0 g) was purified by silicagel column chromatography (hexane-ethyl acetate) to give Compound 35 (12.1 g, <65% purity) as a yellow liquid.

$^1$H-NMR ($CDCl_3$) δ: 1.69-1.97 (2H, m), 2.25 (2H, t, J=6.5 Hz), 2.80-2.91 (1H, m), 3.32-3.50 (4H, m), 3.52-3.75 (1H, m), 3.82-3.94 (1H, m), 5.07-5.22 (2H, m), 5.78-5.97 (1H, m).

Step 4 Synthesis of Compound 36

Compound 35 (12.1 g, <65% purity, 60.3 mmol) was dissolved in dichloromethane (60 mL), and the mixture was cooled in an ice bath. Allylchlorodimethylsilane (8.53 g, 63.3 mmol) and triethylamine (17.6 mL, 127 mmol) were added thereto, and the reaction mixture was stirred at room temperature for 90 minutes. Then, saturated sodium bicarbonate aqueous solution was added to the mixture, followed by extraction with dichloromethane. The solvent in the organic layer was distilled off under reduced pressure, and the obtained crude product (25.4 g) was purified by silicagel column chromatography (hexane-ethyl acetate) to give Compound 36 (17.6 g, 42% purity, Yield 54%) as a colorless liquid.

$^1$H-NMR ($CDCl_3$) δ: 0.13 (6H, s), 1.59-1.69 (4H, m), 1.71-1.80 (1H, m), 2.23 (2H, t, J=6.5 Hz), 3.32 (3H, s), 3.35-3.50 (2H, m), 3.86-3.93 (1H, m), 4.83-4.95 (2H, m), 5.04 (1H, s), 5.07 (1H, d, J=4.4 Hz), 5.74-5.87 (2H, m).

Step 5 and Step 6 Synthesis of Compound 38

Compound 36 (17.6 g, 42% purity, 32.4 mmol) was dissolved in dichloromethane (882 mL), and a second-generation Grubbs catalyst (413 mg, 0.487 mmol) was added to the solution. The reaction mixture was stirred at room temperature for 1 week. After conversion to Compound 37 was confirmed by NMR, the volume of the organic solvent was concentrated into approximately one-tenth. The residue was cooled in a dry ice-acetone bath. A boron trifluoride-diethyl ether complex (4.11 mL, 32.4 mmol) was added thereto, and the reaction mixture was stirred at −78°

C. for 5 minutes. Then, 2-fluoro-4-pyridinecarboxaldehyde (10.1 g, 40% purity, 32.4 mmol) was added to the mixture, and the reaction mixture was stirred at −78° C. for 30 minutes. The mixture was allowed to warm up gradually to room temperature and stirred for 21 hours. Brine was added to the mixture, followed by extraction with chloroform. The organic layer was dried over anhydrous magnesium sulfate. The solvent was distilled off under reduced pressure, and the obtained residue (20.7 g) was purified by silicagel column chromatography (hexane-ethyl acetate) to give Compound 38 (3.68 g, Yield 45%) as a yellow oil.

1H-NMR ($CDCl_3$) δ: 1.49-1.58 (1H, m), 1.95-2.10 (2H, m), 2.25-2.31 (1H, m), 3.20-3.28 (1H, m), 3.38 (3H, s), 3.58 (2H, t, J=6.4 Hz), 4.13-4.22 (1H, m), 4.84 (1H, dd, J=10.0, 1.7 Hz), 4.96 (1H, dd, J=17.1, 1.6 Hz), 5.02 (1H, d, J=8.2 Hz), 5.12 (1H, dt, J=18.3, 8.5 Hz), 6.84 (1H, s), 7.00 (1H, d, J=5.1 Hz), 8.12 (1H, d, J=5.1 Hz).

Compound 38 LC/MS (Method 1) RT=1.82, MS (m/z)=252.25

Step 7 and Step 8 Synthesis of Compound 40

Compound 38 (3.68 g, 14.6 mmol) was dissolved in dichloromethane (74 mL), and the solution was treated with ozone at −78° C. for 4 hours. Then, dimethyl sulfide (10.8 mL, 146 mmol) was added to the solution, and the reaction mixture was stirred at room temperature for 21 hours. The mixture was concentrated under reduced pressure to give a crude product of Compound 39 (5.75 g) as a brown oil.

To the obtained crude product were added t-BuOH (45 mL) and water (22 mL), and 2-methyl-2-butene (15.5 mL, 146 mmol), sodium dihydrogen phosphate (8.79 g, 73.2 mmol) and sodium chlorite (3.97 g, 43.9 mmol) were added successively thereto. The reaction mixture was stirred at room temperature for 1 hour. Then, citric acid monohydrate was added to the mixture, and the solvent was distilled off under reduced pressure. The obtained residue was purified by silicagel column chromatography (chloroform-methanol) to give Compound 40 (2.19 g, Yield 56% over two steps) as a yellow oil.

Compound 40 LC/MS (Method 1) RT=1.13, MS (m/z)=270.15

Step 9 Synthesis of Compound 41

To Compound 40 (2.19 g, 8.13 mmol) were added dichloromethane (10 mL) and methanol (22 mL), and the reaction mixture was cooled in an ice bath. Trimethylsilyldiazomethane-hexane solution (11.1 mL, 22.2 mmol) was added dropwise thereto, and the reaction mixture was stirred at room temperature for 30 minutes. Acetic acid was added to the mixture until the yellow mixture became colorless. Then, the reaction mixture was concentrated under reduced pressure, and the obtained residue (2.53 g) was purified by silicagel column chromatography (hexane-ethyl acetate) to give Compound 41 (1.05 g, Yield 46%) as a pale yellow oil.

$^1$H-NMR ($CDCl_3$) δ: 1.98-2.19 (3H, m), 2.30 (1H, ddd, J=13.6, 7.5, 5.3 Hz), 3.27 (3H, s), 3.37 (3H, s), 3.50 (1H, q, J=8.2 Hz), 3.55-3.62 (2H, m), 4.12-4.22 (1H, m), 5.10 (1H, d, J=8.5 Hz), 6.91 (1H, s), 7.10 (1H, d, J=5.1 Hz), 8.14 (1H, d, J=5.3 Hz).

Compound 41 LC/MS (Method 1) RT=1.47, MS (m/z)=284.20

Step 10 Synthesis of Compound 42

Compound 41 (1.05 g, 3.71 mmol) was dissolved in methanol (10.5 mL), and sodium methoxide (28% methanol solution, 3.58 g, 18.5 mmol) was added to the solution. The reaction mixture was stirred at room temperature for 2 hours. Water (1.0 mL) was added to the mixture, and the reaction mixture was stirred at room temperature for 30 minutes. Then, 2 mol/L hydrochloric acid aqueous solution (9 mL) was added to the mixture, followed by extraction with chloroform. The organic layer was washed with brine, dried over anhydrous sodium sulfate, and concentrated under reduced pressure to give Compound 42 (982 mg, 3.65 mmol) as a yellow oil.

Compound 42 LC/MS (Method 1) RT=1.24, MS (m/z)=270.20

Step 11 Synthesis of Compound 43

Compound 42 (982 mg, 3.65 mmol) was dissolved in DMF (20 mL), and HATU (2.77 g, 7.29 mmol) and DIEA (2.55 mL, 14.6 mmol) were added to the solution. The reaction mixture was stirred at room temperature for 1 minute. Ammonia-dioxane solution (0.5 mol/L, 21.9 mL, 10.9 mmol) was added to the mixture, and the reaction mixture was stirred at room temperature for 3 hours. Saturated sodium bicarbonate aqueous solution was added to the mixture, followed by extraction with ethyl acetate twice. The organic layer was washed with 3% citric acid aqueous solution and brine and dried over anhydrous sodium sulfate, and the solvent was distilled off under reduced pressure to give a crude product (1.90 g). The crude product was purified by amino silicagel column chromatography (hexane-10% methanol/ethyl acetate) to give Compound 43 (542 mg, Yield 55%) as a white solid.

1H-NMR ($CDCl_3$) δ: 1.86-2.07 (3H, m), 2.42-2.48 (1H, m), 2.65 (1H, dt, J=13.0, 4.9 Hz), 3.36 (3H, s), 3.56 (2H, dt, J=16.2, 4.5 Hz), 4.35 (1H, dt, J=13.9, 6.4 Hz), 5.10 (1H, d, J=7.8 Hz), 5.42 (2H, br s), 6.99 (1H, s), 7.18 (1H, d, J=5.1 Hz), 8.17 (1H, d, J=5.1 Hz).

Compound 43 LC/MS (Method 1) RT=0.99, MS (m/z)=269.20

Step 12 Synthesis of Compound 44

Compound 43 (540 mg, 2.01 mmol) was dissolved in 1,2-dichloroethane (11 mL), and allyl alcohol (2.74 mL, 40.3 mmol) and iodobenzene diacetate (1.30 g, 4.03 mmol) were added to the solution. The reaction mixture was stirred at 80° C. for 1 hour. Saturated sodium bicarbonate aqueous solution was added to the mixture, followed by extraction with ethyl acetate twice. Then, the organic layer was washed with brine and dried over anhydrous sodium sulfate. The solvent was distilled off, and the obtained residue (1.89 g) was purified by silicagel column chromatography (hexane-ethyl acetate) to give Compound 44 (542 mg, Yield 83%) as a clear colorless oil.

1H-NMR ($CDCl_3$) δ: 1.80-2.08 (4H, m), 3.37 (3H, s), 3.54-3.60 (2H, m), 4.11 (1H, t, J=7.0 Hz), 4.36 (1H, dt, J=15.9, 6.3 Hz), 4.60 (2H, d, J=5.6 Hz), 4.88 (1H, s), 5.00-5.12 (1H, m), 5.25 (1H, d, J=10.4 Hz), 5.33 (1H, d, J=17.2 Hz), 5.83-6.01 (1H, m), 7.05 (1H, s), 7.29-7.37 (1H, m), 8.17 (1H, d, J=5.1 Hz).

Compound 44 LC/MS (Method 1) RT=1.59, MS (m/z)=325.20

Step 13 Synthesis of Compound 45

Compound 44 (542 mg, 1.67 mmol) was dissolved in THF (5.42 mL), and diethylamine (0.524 mL, 5.01 mmol) and tetrakis(triphenylphosphine)palladium(0) (193 mg, 0.167 mmol) were added to the solution. The reaction mixture was stirred at room temperature for 1 hour, and then the solvent was distilled off under reduced pressure. 2 mol/L hydrochloric acid aqueous solution (5 mL) was added to the residue. The reaction mixture was washed with ether, and 2 mol/L sodium hydroxide aqueous solution (5 mL) and saturated sodium bicarbonate aqueous solution were added to the aqueous layer, followed by extraction with 10% methanol-chloroform five times. The organic layer was dried over anhydrous sodium sulfate, and the solvent was distilled off under reduced pressure to give Compound 45 (362 mg, Yield 90%) as a pale yellow oil.

Compound 45 LC/MS (Method 1) RT=0.62, MS (m/z)=241.20

Step 14 Synthesis of Compound (I-235)

Compound (I-235) (32 mg, Yield 98%) was obtained as a colorless foam in the same manner as described in the step 4 of Example 6 by using Compound 45 (15 mg, 0.062 mmol) as the starting material.

1H-NMR ($CDCl_3$) δ: 1.71-1.99 (4H, m), 2.20 (3H, s), 3.35 (3H, s), 3.53 (2H, dt, J=16.4, 5.1 Hz), 3.99 (3H, s), 4.16 (2H, tt, J=12.7, 4.5 Hz), 4.58 (1H, d, J=3.3 Hz), 4.87 (1H, d, J=7.3 Hz), 6.15 (1H, s), 6.92 (1H, s), 7.16 (1H, d, J=5.1 Hz), 7.37 (1H, t, J=7.4 Hz), 7.47 (2H, t, J=7.8 Hz), 7.56 (2H, d, J=7.7 Hz), 7.79 (1H, s), 7.90 (1H, s), 8.11 (1H, d, J=5.3 Hz).

Compound (I-235) LC/MS (Method 1) RT=1.53, MS (m/z)=520.30

The following Compounds were obtained in accordance with the general synthetic methods and Examples. The chemical structures and the physical properties(LC/MS data) of Compounds are described below.

In the following tables, Compound with "HCl" in the chemical structure means that Compound forms "HCl" salt. Compound with plural "HCl" in the chemical structure means that Compound forms plural "HCl salt".

In addition, "wedged bond" and "hashed wedged bond" in the chemical structure means configuration. Specifically Compound with "racemate" in item of "configuration" means racemic compound whose relative configuration was determined. Compound with "trans" in item of "configuration" means compound whose relative configuration between the group of —Z-L-$Z^A$-(ring C) and the group of —Y—B was trans, and other configuration were not determined. Compound with "diastereo mixture" in item of "configuration" means compound whose relative configuration between the group of —Z-L-$Z^A$-(ring C) and the group of —Y—B was trans, and other absolute configuration were as described in the chemical structure. Compound whose item of "configuration" is blank means Compound in which absolute configurations at the carbon atom binding to the group of —Z-L-$Z^A$-(ring C) and the carbon atom binding to the group of —Y—B were as described in the chemical structure. Compound with "single isomer" is a single isomer compound.

Moreover, the bond which binds to the asymmetric carbon is indicated as solid line when their configurations were not determined.

TABLE 1

| No. | Structure | LCMS method No | RT | MS (m/z) | configuration |
|---|---|---|---|---|---|
| I-1 | 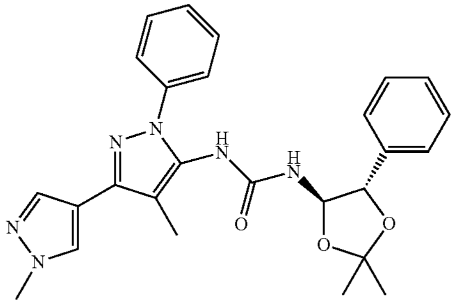 [SMILES: Cc1c(-c2cnn(C)c2)nn(-c2ccccc2)c1NC(=O)N[C@@H]1OC(C)(C)O[C@H]1c1ccccc1] | 2 | 1.84 | 473 | racemate |
| I-2 | 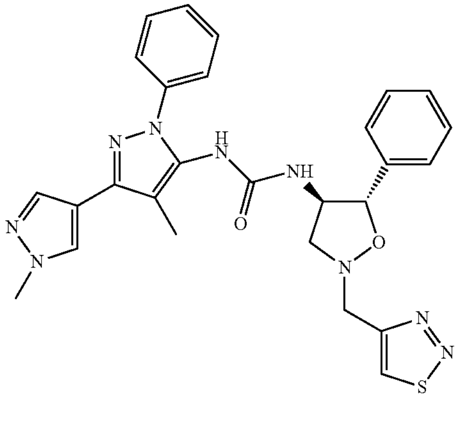 [SMILES: Cc1c(-c2cnn(C)c2)nn(-c2ccccc2)c1NC(=O)N[C@@H]1CN(Cc2csnn2)O[C@H]1c1ccccc1] | 1 | 1.61 | 542.2 | racemate |

TABLE 1-continued
| No. | Structure | LCMS method No | RT | MS (m/z) | configuration |
|---|---|---|---|---|---|
| I-3 | 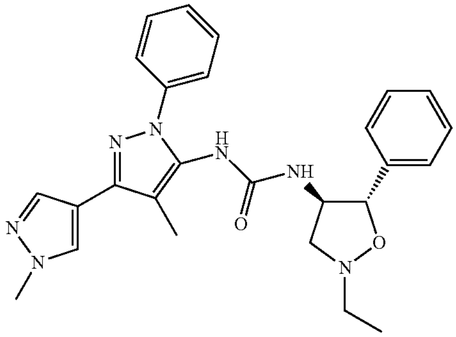 [SMILES: CCN1C[C@@H](NC(=O)Nc2c(C)c(-c3cnn(C)c3)nn2-c2ccccc2)[C@H](c2ccccc2)O1] | 1 | 1.48 | 472.2 | racemate |
| I-4 | 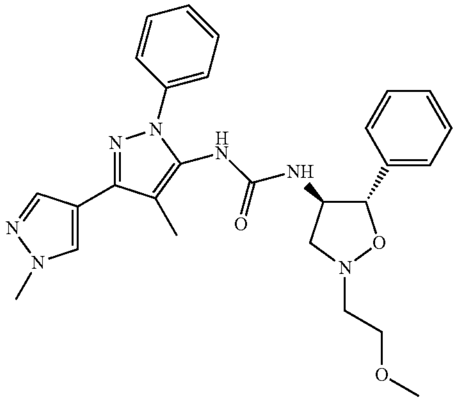 [SMILES: COCCN1C[C@@H](NC(=O)Nc2c(C)c(-c3cnn(C)c3)nn2-c2ccccc2)[C@H](c2ccccc2)O1] | 1 | 1.56 | 502.25 | racemate |
| I-5 | 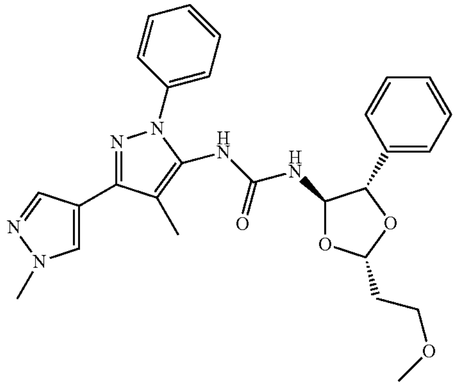 [SMILES: COCC[C@@H]1O[C@@H](NC(=O)Nc2c(C)c(-c3cnn(C)c3)nn2-c2ccccc2)[C@H](c2ccccc2)O1] | 2 | 1.78 | 503 | racemate |

TABLE 2
| No. | Structure | LCMS method No | RT | MS (m/z) | configuration |
|---|---|---|---|---|---|
| I-6 | 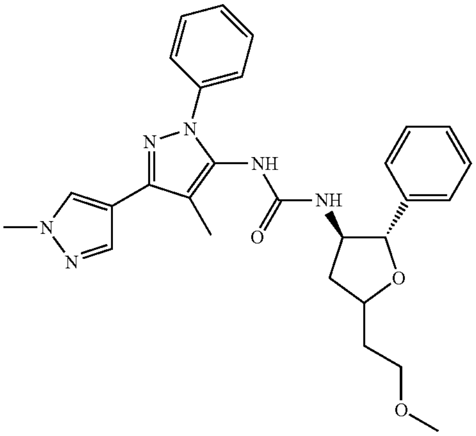 [SMILES: COCCC1C[C@@H](NC(=O)Nc2c(C)c(-c3cnn(C)c3)nn2-c2ccccc2)[C@H](c2ccccc2)O1] | 1 | 1.68 | 501 | trans |
| I-7 | 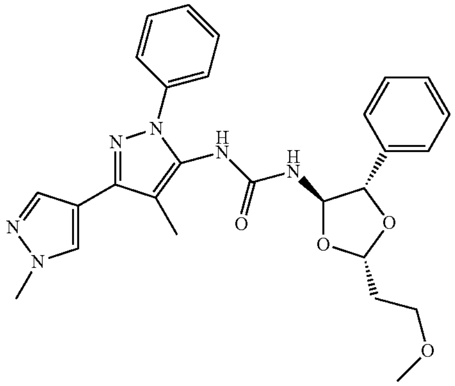 [SMILES: COCC[C@@H]1O[C@@H](NC(=O)Nc2c(C)c(-c3cnn(C)c3)nn2-c2ccccc2)[C@H](c2ccccc2)O1] | 2 | 1.78 | 503 | |
| I-8 | 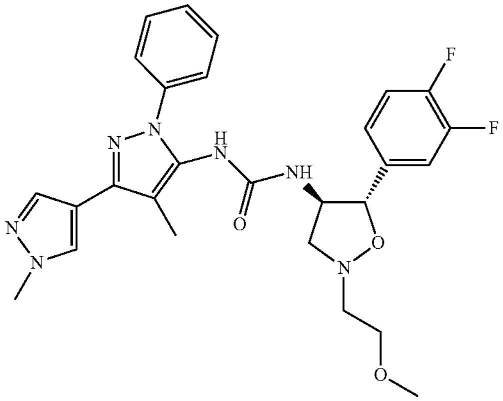 [SMILES: COCCN1C[C@@H](NC(=O)Nc2c(C)c(-c3cnn(C)c3)nn2-c2ccccc2)[C@H](c2ccc(F)c(F)c2)O1] | 1 | 1.7 | 538.25 | racemate |

TABLE 2-continued
| No. | Structure | LCMS method No | RT | MS (m/z) | configuration |
|---|---|---|---|---|---|
| I-9 | 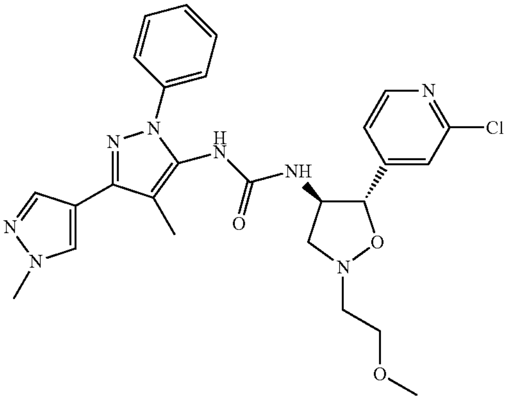 [SMILES: COCCN1C[C@@H](NC(=O)Nc2c(C)c(-c3cnn(C)c3)nn2-c2ccccc2)[C@H](c2ccnc(Cl)c2)O1] | 1 | 1.6 | 537.3 | racemate |
TABLE 3
| No. | Structure | LCMS method No | RT | MS (m/z) | configuration |
|---|---|---|---|---|---|
| 1-10 | 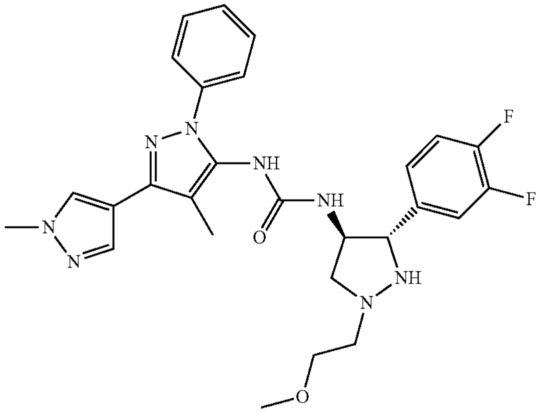 [SMILES: COCCN1C[C@@H](NC(=O)Nc2c(C)c(-c3cnn(C)c3)nn2-c2ccccc2)[C@H](c2ccc(F)c(F)c2)N1] | 1 | 1.28 | 537.25 | racemate |
| 1-11 | 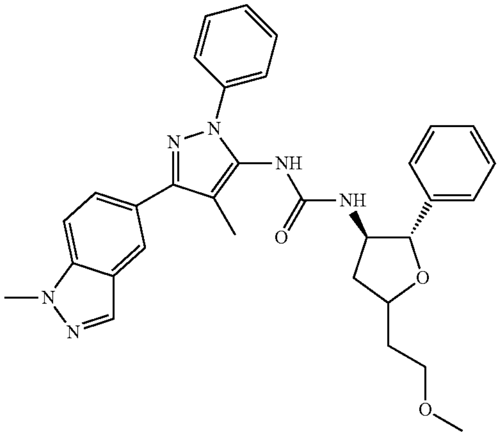 [SMILES: COCCC1C[C@@H](NC(=O)Nc2c(C)c(-c3ccc4c(cnn4C)c3)nn2-c2ccccc2)[C@H](c2ccccc2)O1] | 1 | 1.96 | 551 | trans |

TABLE 3-continued
| No. | Structure | LCMS method No | RT | MS (m/z) | configuration |
|---|---|---|---|---|---|
| 1-12 | 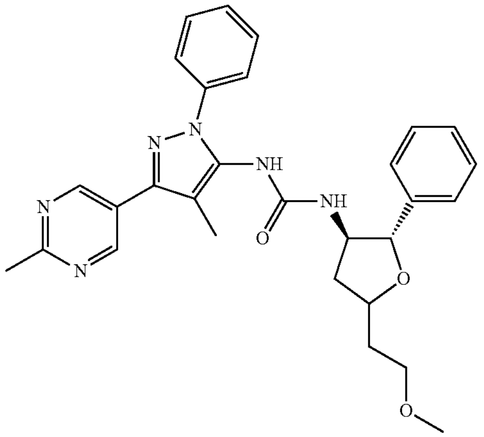 [SMILES: COCCC1C[C@@H](NC(=O)Nc2c(C)c(-c3cnc(C)nc3)nn2-c2ccccc2)[C@H](c2ccccc2)O1] | 1 | 1.71 | 513 | trans |
| 1-13 | 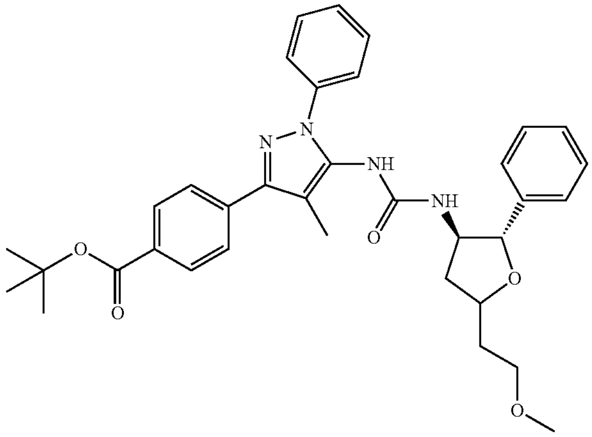 [SMILES: COCCC1C[C@@H](NC(=O)Nc2c(C)c(-c3ccc(C(=O)OC(C)(C)C)cc3)nn2-c2ccccc2)[C@H](c2ccccc2)O1] | 1 | 2.54 | 597 | trans |

TABLE 4
| No. | Structure | LCMS method No | RT | MS (m/z) | configuration |
|---|---|---|---|---|---|
| 1-14 | 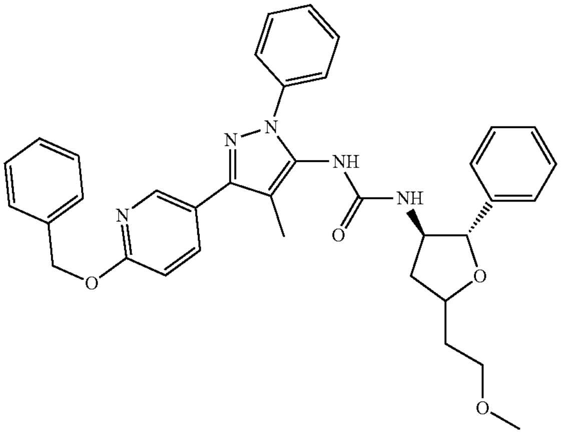 [SMILES: COCCC1C[C@@H](NC(=O)Nc2c(C)c(-c3ccc(OCc4ccccc4)nc3)nn2-c2ccccc2)[C@H](c2ccccc2)O1] | 1 | 2.43 | 604 | trans |
| 1-15 | 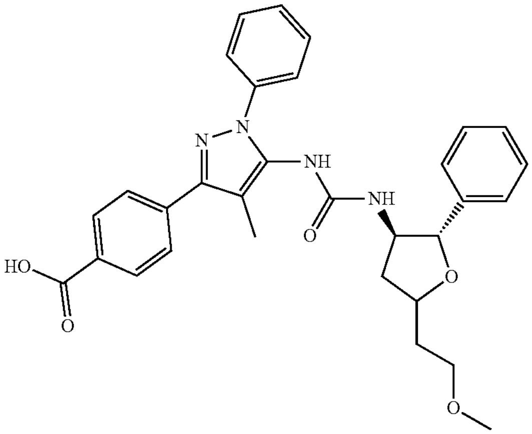 [SMILES: COCCC1C[C@@H](NC(=O)Nc2c(C)c(-c3ccc(C(=O)O)cc3)nn2-c2ccccc2)[C@H](c2ccccc2)O1] | 1 | 1.83 | 541 | trans |
| 1-16 | 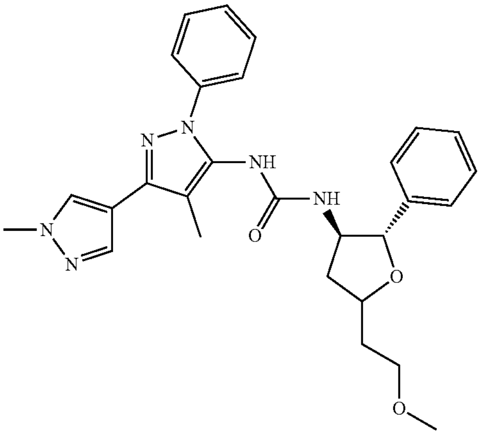 [SMILES: COCCC1C[C@@H](NC(=O)Nc2c(C)c(-c3cnn(C)c3)nn2-c2ccccc2)[C@H](c2ccccc2)O1] | 1 | 1.67 | 501 | trans |

TABLE 4-continued
| No. | Structure | LCMS method No | RT | MS (m/z) | configuration |
|---|---|---|---|---|---|
| 1-17 | 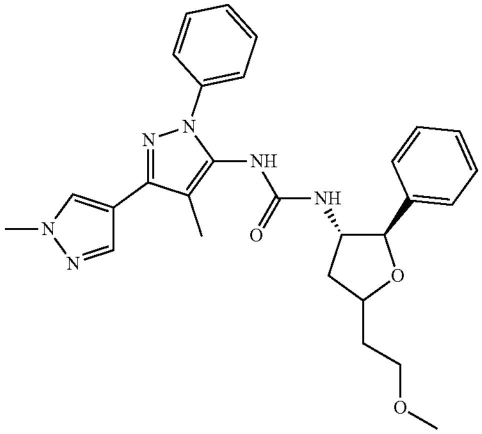 [SMILES: COCCC1C[C@H](NC(=O)Nc2c(C)c(-c3cnn(C)c3)nn2-c2ccccc2)[C@@H](c2ccccc2)O1] | 1 | 1.67 | 501 | trans |
TABLE 5
| No. | Structure | LCMS method No | RT | MS (m/z) | configuration |
|---|---|---|---|---|---|
| 1-18 | 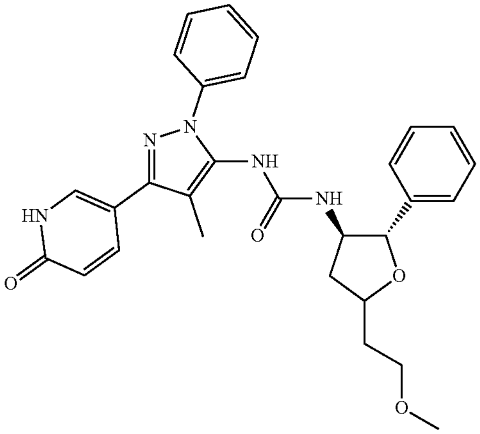 [SMILES: COCCC1C[C@@H](NC(=O)Nc2c(C)c(-c3ccc(=O)[nH]c3)nn2-c2ccccc2)[C@H](c2ccccc2)O1] | 1 | 1.52 | 514 | trans |
| 1-19 | 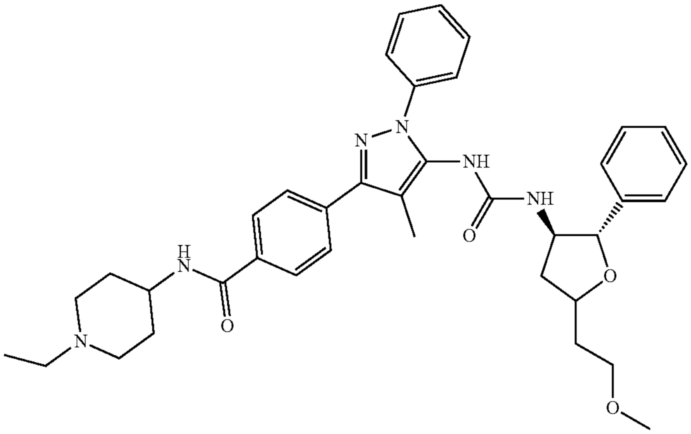 [SMILES: CCN1CCC(NC(=O)c2ccc(-c3nn(-c4ccccc4)c(NC(=O)N[C@@H]4CC(CCOC)O[C@H]4c4ccccc4)c3C)cc2)CC1] | 1 | 1.4 | 651 | trans |

TABLE 5-continued
| No. | Structure | LCMS method No | RT | MS (m/z) | configuration |
|---|---|---|---|---|---|
| 1-20 | 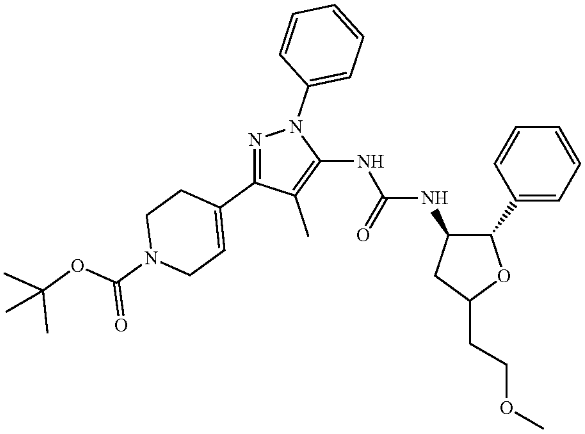 [SMILES: COCCC1C[C@@H](NC(=O)Nc2c(C)c(C3=CCN(C(=O)OC(C)(C)C)CC3)nn2-c2ccccc2)[C@H](c2ccccc2)O1] | 1 | 2.32 | 602 | trans |
| 1-21 | 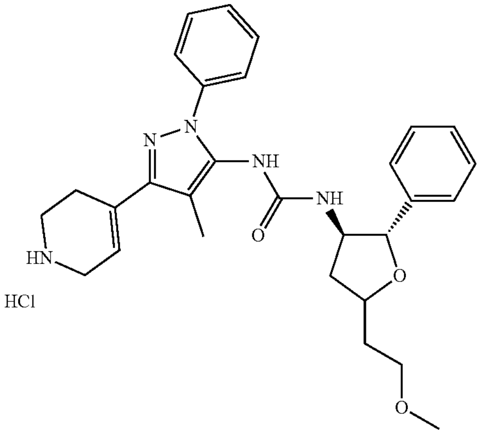 [SMILES: Cl ; COCCC1C[C@@H](NC(=O)Nc2c(C)c(C3=CCNCC3)nn2-c2ccccc2)[C@H](c2ccccc2)O1] | 1 | 1.26 | 502 | trans |
TABLE 6
| No. | Structure | LCMS method No | RT | MS (m/z) | configuration |
|---|---|---|---|---|---|
| 1-22 | 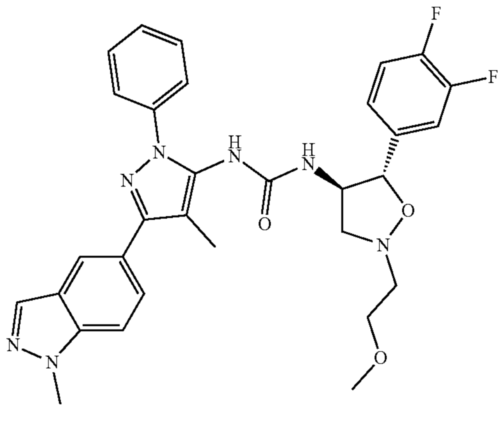 [SMILES: COCCN1C[C@@H](NC(=O)Nc2c(C)c(-c3ccc4c(cnn4C)c3)nn2-c2ccccc2)[C@H](c2ccc(F)c(F)c2)O1] | 1 | 1.98 | 588.2 | racemate |

TABLE 6-continued
| No. | Structure | LCMS method No | RT | MS (m/z) | configuration |
| --- | --- | --- | --- | --- | --- |
| 1-23 | 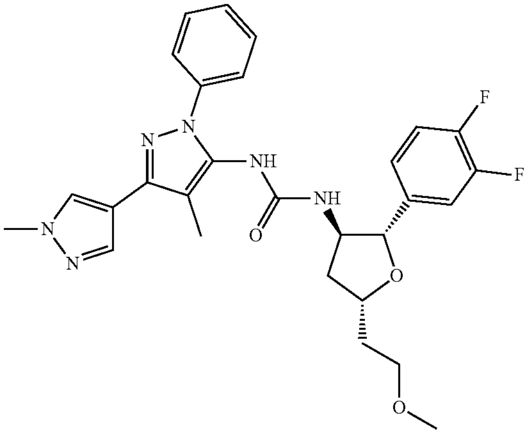 [SMILES: COCC[C@@H]1C[C@@H](NC(=O)Nc2c(C)c(-c3cnn(C)c3)nn2-c2ccccc2)[C@H](c2ccc(F)c(F)c2)O1] | 1 | 1.81 | 537 | racemate |
| 1-24 | 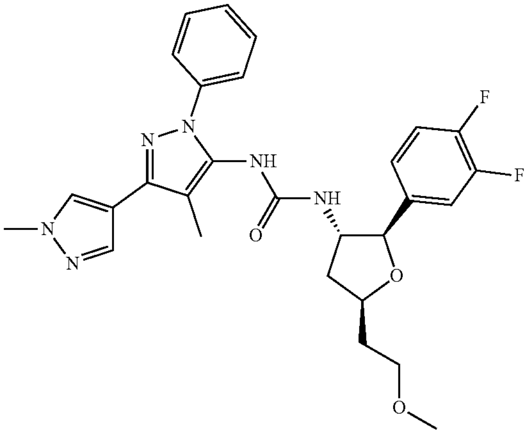 [SMILES: COCC[C@H]1C[C@H](NC(=O)Nc2c(C)c(-c3cnn(C)c3)nn2-c2ccccc2)[C@@H](c2ccc(F)c(F)c2)O1] | 1 | 1.81 | 537 | |
| 1-25 | 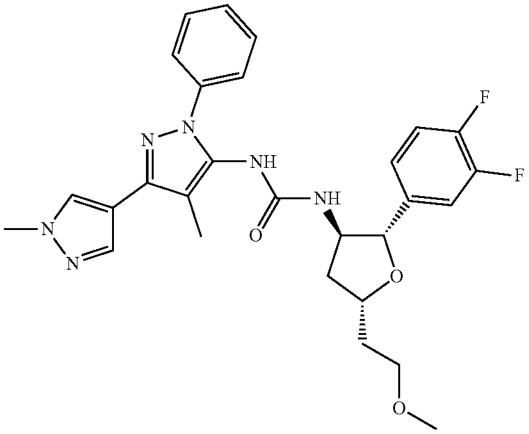 [SMILES: COCC[C@@H]1C[C@@H](NC(=O)Nc2c(C)c(-c3cnn(C)c3)nn2-c2ccccc2)[C@H](c2ccc(F)c(F)c2)O1] | 1 | 1.81 | 537 | |

TABLE 7
| No. | Structure | LCMS method No | RT | MS (m/z) | configuration |
| --- | --- | --- | --- | --- | --- |
| 1-26 | 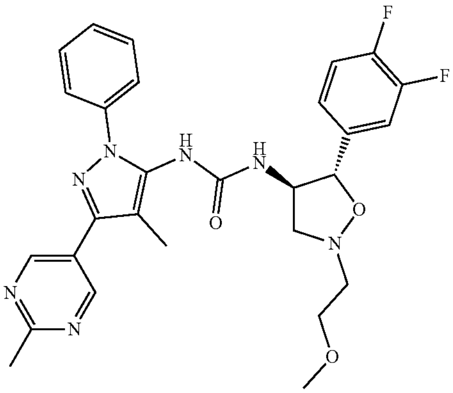 [SMILES: COCCN1C[C@@H](NC(=O)Nc2c(C)c(-c3cnc(C)nc3)nn2-c2ccccc2)[C@H](c2ccc(F)c(F)c2)O1] | 1 | 1.76 | 550.2 | racemate |
| 1-27 | 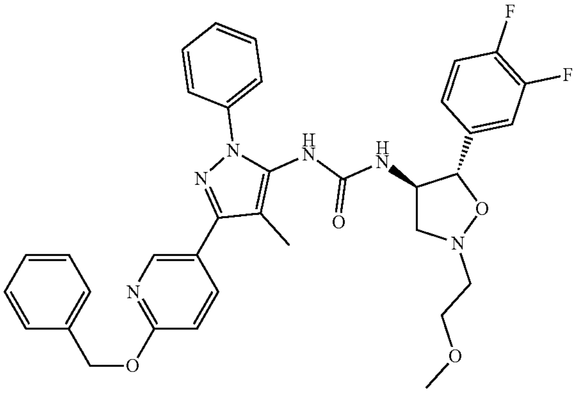 [SMILES: COCCN1C[C@@H](NC(=O)Nc2c(C)c(-c3ccc(OCc4ccccc4)nc3)nn2-c2ccccc2)[C@H](c2ccc(F)c(F)c2)O1] | 1 | 2.44 | 641.25 | racemate |
| 1-28 | 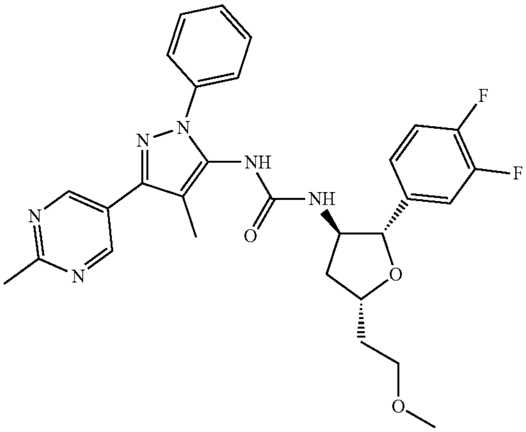 [SMILES: COCC[C@@H]1C[C@@H](NC(=O)Nc2c(C)c(-c3cnc(C)nc3)nn2-c2ccccc2)[C@H](c2ccc(F)c(F)c2)O1] | 1 | 1.85 | 549 | racemate |

TABLE 7-continued
| No. | Structure | LCMS method No | RT | MS (m/z) | configuration |
|---|---|---|---|---|---|
| 1-29 | 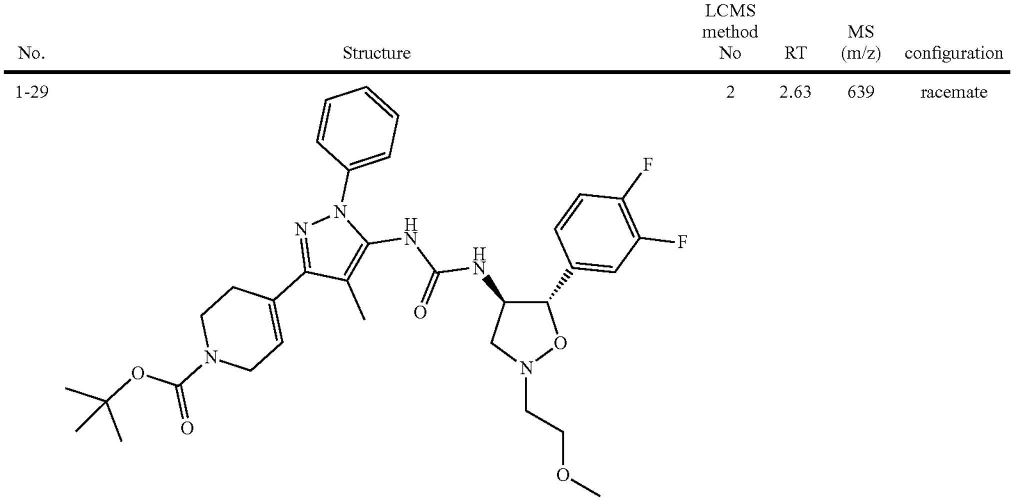 | 2 | 2.63 | 639 | racemate |
TABLE 8
| No. | Structure | LCMS method No | RT | MS (m/z) | configuration |
|---|---|---|---|---|---|
| 1-30 | 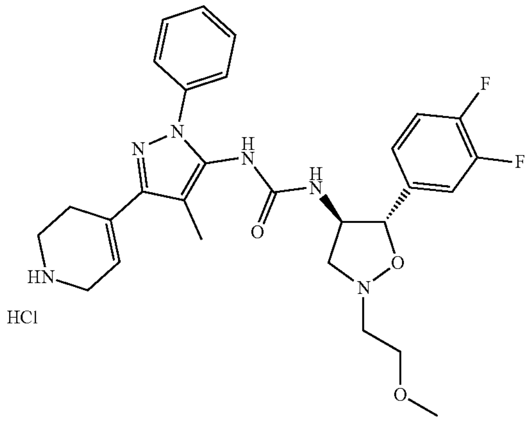 [SMILES: Cl ; COCCN1C[C@@H](NC(=O)Nc2c(C)c(C3=CCNCC3)nn2-c2ccccc2)[C@H](c2ccc(F)c(F)c2)O1] | 2 | 1.57 | 539 | racemate |
| 1-31 | 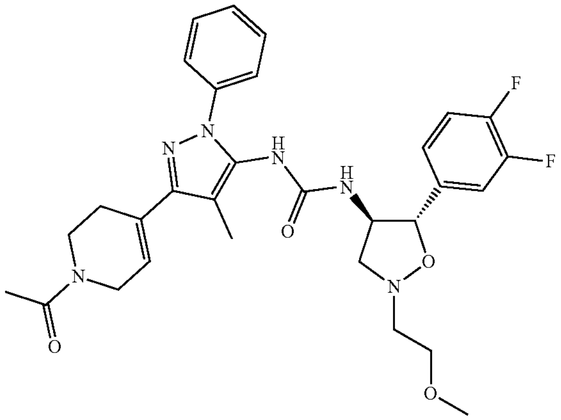 [SMILES: COCCN1C[C@@H](NC(=O)Nc2c(C)c(C3=CCN(C(C)=O)CC3)nn2-c2ccccc2)[C@H](c2ccc(F)c(F)c2)O1] | 2 | 1.95 | 581 | racemate |

TABLE 8-continued
| No. | Structure | LCMS method No | RT | MS (m/z) | configuration |
|---|---|---|---|---|---|
| 1-32 | 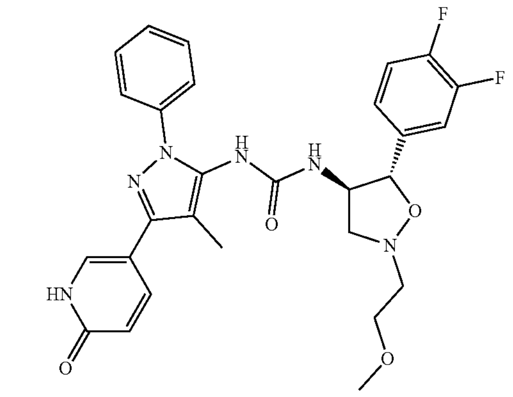 [SMILES: COCCN1C[C@@H](NC(=O)Nc2c(C)c(-c3ccc(=O)[nH]c3)nn2-c2ccccc2)[C@H](c2ccc(F)c(F)c2)O1] | 1 | 1.57 | 551.2 | racemate |
| 1-33 | 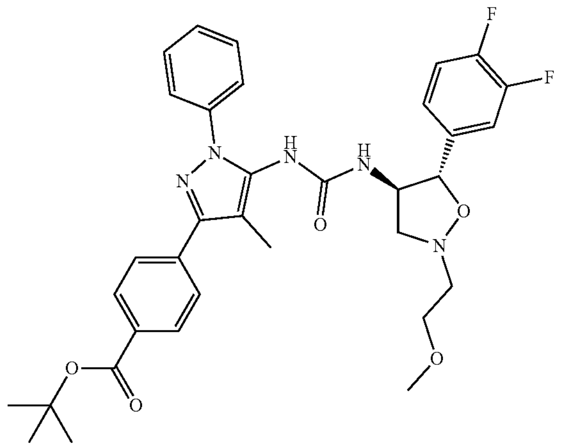 [SMILES: COCCN1C[C@@H](NC(=O)Nc2c(C)c(-c3ccc(C(=O)OC(C)(C)C)cc3)nn2-c2ccccc2)[C@H](c2ccc(F)c(F)c2)O1] | 1 | 2.57 | 634.25 | racemate |
TABLE 9
| No. | Structure | LCMS method No | RT | MS (m/z) | configuration |
|---|---|---|---|---|---|
| 1-34 | 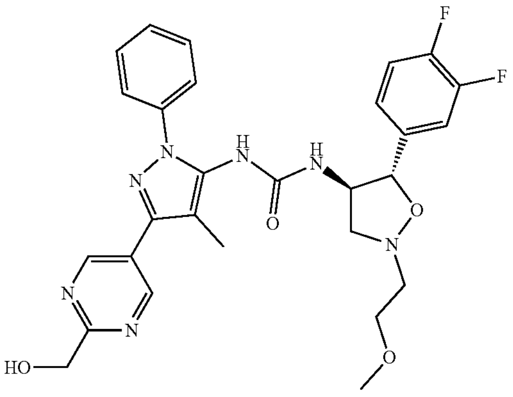 [SMILES: COCCN1C[C@@H](NC(=O)Nc2c(C)c(-c3cnc(CO)nc3)nn2-c2ccccc2)[C@H](c2ccc(F)c(F)c2)O1] | 1 | 1.64 | 566.4 | racemate |

TABLE 9-continued
| No. | Structure | LCMS method No | RT | MS (m/z) | configuration |
|---|---|---|---|---|---|
| 1-35 | 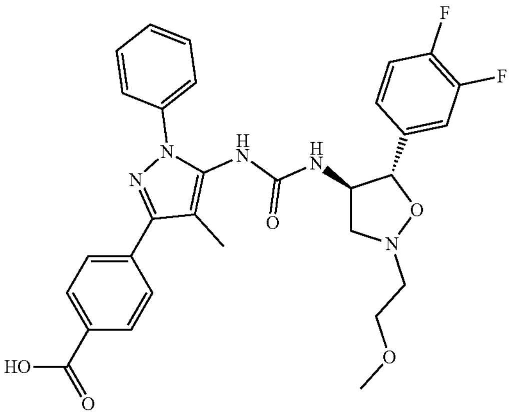 [SMILES: COCCN1C[C@@H](NC(=O)Nc2c(C)c(-c3ccc(C(=O)O)cc3)nn2-c2ccccc2)[C@H](c2ccc(F)c(F)c2)O1] | 1 | 1.87 | 578.2 | racemate |
| 1-36 | 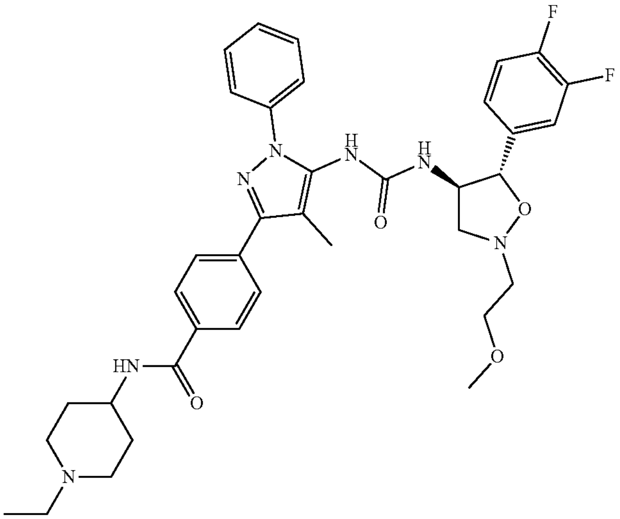 [SMILES: CCN1CCC(NC(=O)c2ccc(-c3nn(-c4ccccc4)c(NC(=O)N[C@@H]4CN(CCOC)O[C@H]4c4ccc(F)c(F)c4)c3C)cc2)CC1] | 1 | 1.34 | 688.3 | racemate |

TABLE 10
| No. | Structure | LCMS method No | RT | MS (m/z) | configuration |
|---|---|---|---|---|---|
| 1-38 | 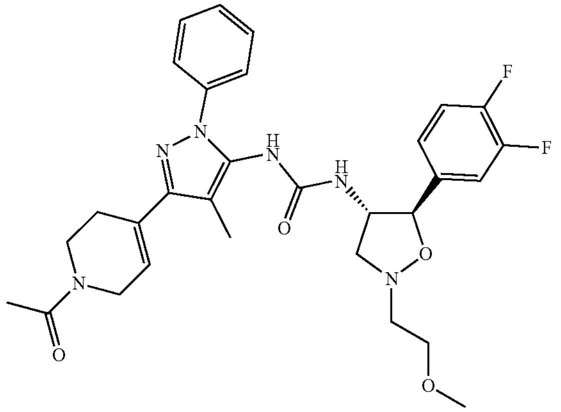 [SMILES: COCCN1C[C@H](NC(=O)Nc2c(C)c(C3=CCN(C(C)=O)CC3)nn2-c2ccccc2)[C@@H](c2ccc(F)c(F)c2)O1] | 2 | 1.61 | 581 | |
| 1-39 | 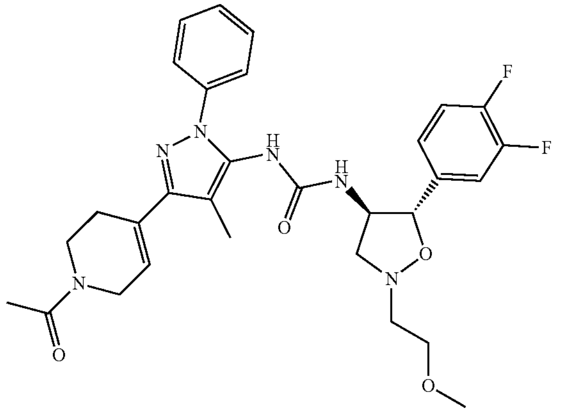 [SMILES: COCCN1C[C@@H](NC(=O)Nc2c(C)c(C3=CCN(C(C)=O)CC3)nn2-c2ccccc2)[C@H](c2ccc(F)c(F)c2)O1] | 2 | 1.61 | 581 | |
| 1-40 | 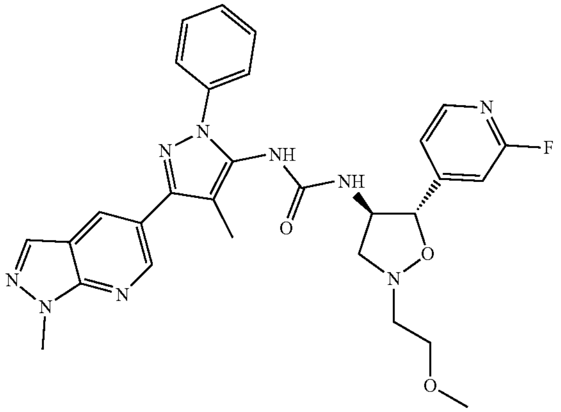 [SMILES: COCCN1C[C@@H](NC(=O)Nc2c(C)c(-c3cnc4c(cnn4C)c3)nn2-c2ccccc2)[C@H](c2ccnc(F)c2)O1] | 2 | 1.59 | 572 | racemate |

TABLE 10-continued
| No. | Structure | LCMS method No | RT | MS (m/z) | configuration |
|---|---|---|---|---|---|
| 1-41 | 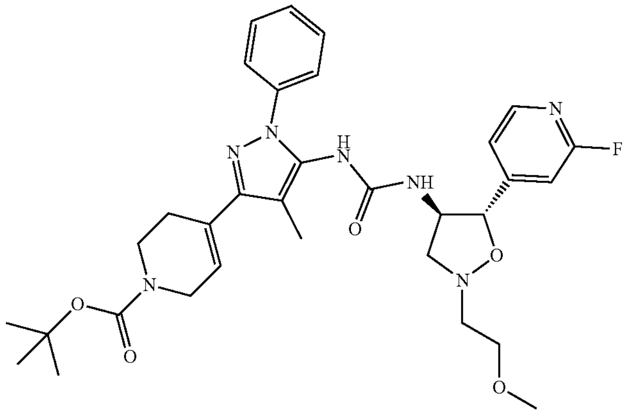 [SMILES: COCCN1C[C@@H](NC(=O)Nc2c(C)c(C3=CCN(C(=O)OC(C)(C)C)CC3)nn2-c2ccccc2)[C@H](c2ccnc(F)c2)O1] | 2 | 2.06 | 622 | racemate |
TABLE 11
| No. | Structure | LCMS method No | RT | MS (m/z) | configuration |
|---|---|---|---|---|---|
| 1-42 | 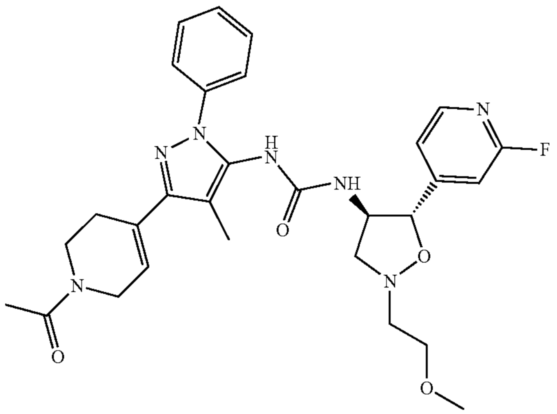 [SMILES: COCCN1C[C@@H](NC(=O)Nc2c(C)c(C3=CCN(C(C)=O)CC3)nn2-c2ccccc2)[C@H](c2ccnc(F)c2)O1] | 2 | 1.46 | 564 | racemate |
| 1-43 | 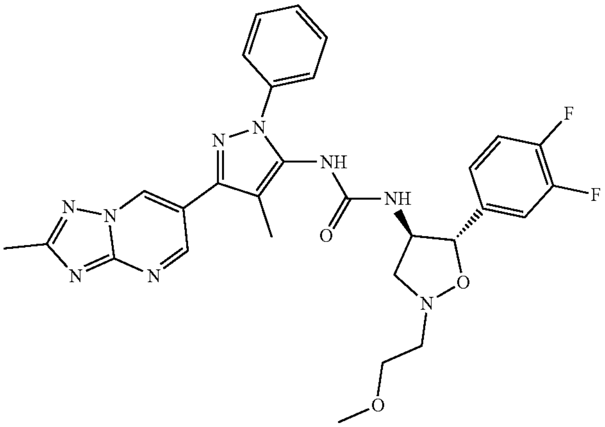 [SMILES: COCCN1C[C@@H](NC(=O)Nc2c(C)c(-c3cnc4nc(C)nn4c3)nn2-c2ccccc2)[C@H](c2ccc(F)c(F)c2)O1] | 1 | 1.73 | 590.2 | racemate |

TABLE 11-continued
| No. | Structure | LCMS method No | RT | MS (m/z) | configuration |
|---|---|---|---|---|---|
| 1-44 | 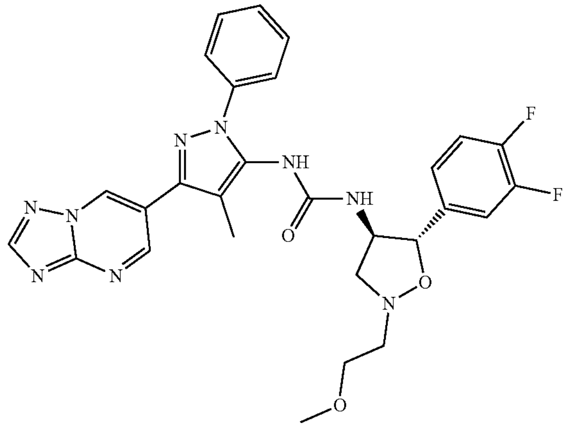 [SMILES: COCCN1C[C@@H](NC(=O)Nc2c(C)c(-c3cnc4ncnn4c3)nn2-c2ccccc2)[C@H](c2ccc(F)c(F)c2)O1] | 1 | 1.7 | 576.2 | racemate |
TABLE 12
| No. | Structure | LCMS method No | RT | MS (m/z) | configuration |
|---|---|---|---|---|---|
| 1-45 | 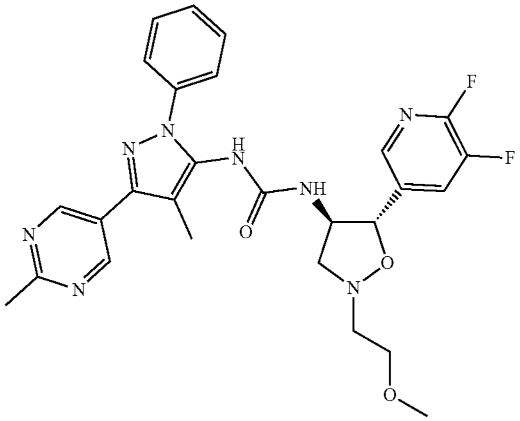 [SMILES: COCCN1C[C@@H](NC(=O)Nc2c(C)c(-c3cnc(C)nc3)nn2-c2ccccc2)[C@H](c2cnc(F)c(F)c2)O1] | 2 | 1.63 | 551 | racemate |
| 1-46 | 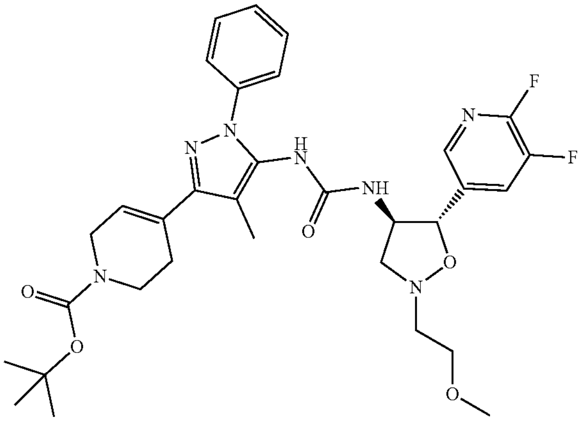 [SMILES: COCCN1C[C@@H](NC(=O)Nc2c(C)c(C3=CCN(C(=O)OC(C)(C)C)CC3)nn2-c2ccccc2)[C@H](c2cnc(F)c(F)c2)O1] | 2 | 2.35 | 640 | racemate |

TABLE 12-continued
| No. | Structure | LCMS method No | RT | MS (m/z) | configuration |
|---|---|---|---|---|---|
| 1-47 | 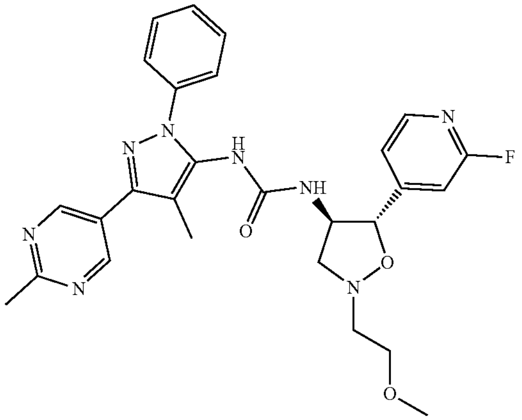 [SMILES: COCCN1C[C@@H](NC(=O)Nc2c(C)c(-c3cnc(C)nc3)nn2-c2ccccc2)[C@H](c2ccnc(F)c2)O1] | 2 | 1.47 | 533 | racemate |
| 1-48 | 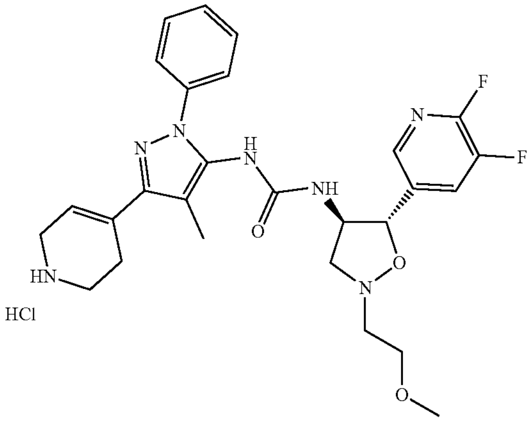 [SMILES: Cl ; COCCN1C[C@@H](NC(=O)Nc2c(C)c(C3=CCNCC3)nn2-c2ccccc2)[C@H](c2cnc(F)c(F)c2)O1] | 2 | 1.36 | 540 | racemate |
| 1-49 | 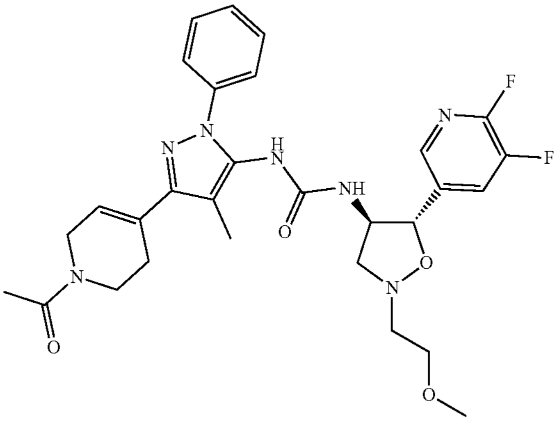 [SMILES: COCCN1C[C@@H](NC(=O)Nc2c(C)c(C3=CCN(C(C)=O)CC3)nn2-c2ccccc2)[C@H](c2cnc(F)c(F)c2)O1] | 2 | 1.66 | 582 | racemate |

TABLE 11
| No. | Structure | LCMS method No | RT | MS (m/z) | configuration |
|---|---|---|---|---|---|
| 1-50 | 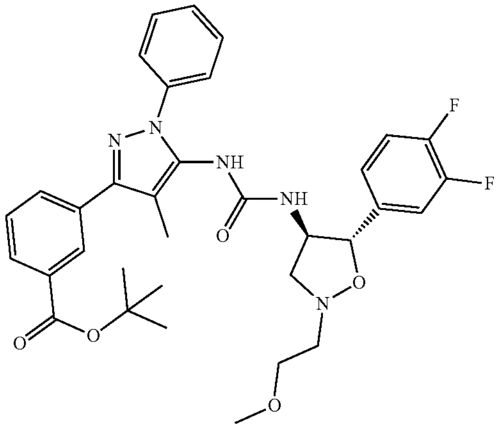 [SMILES: COCCN1C[C@@H](NC(=O)Nc2c(C)c(-c3cccc(C(=O)OC(C)(C)C)c3)nn2-c2ccccc2)[C@H](c2ccc(F)c(F)c2)O1] | 1 | 2.54 | 634.25 | racemate |
| 1-51 | 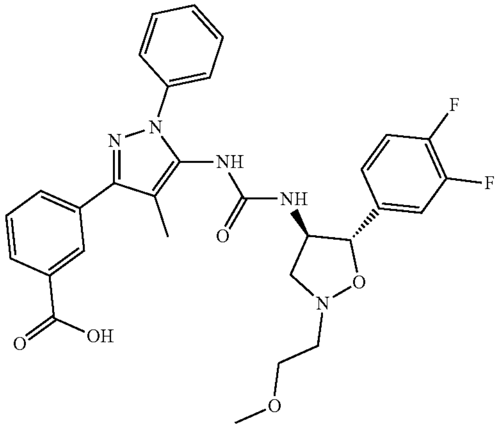 [SMILES: COCCN1C[C@@H](NC(=O)Nc2c(C)c(-c3cccc(C(=O)O)c3)nn2-c2ccccc2)[C@H](c2ccc(F)c(F)c2)O1] | 1 | 1.89 | 578.2 | racemate |
| 1-52 | 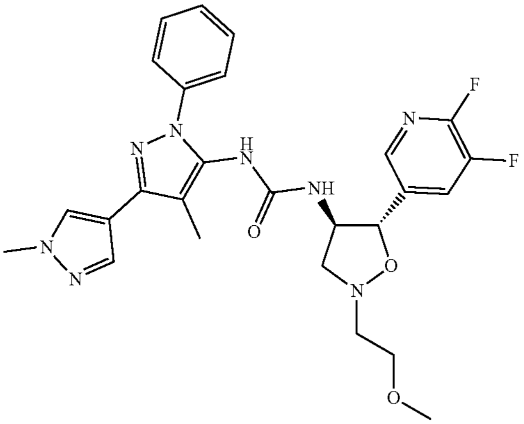 [SMILES: COCCN1C[C@@H](NC(=O)Nc2c(C)c(-c3cnn(C)c3)nn2-c2ccccc2)[C@H](c2cnc(F)c(F)c2)O1] | 2 | 1.61 | 539 | racemate |

TABLE 11-continued
| No. | Structure | LCMS method No | RT | MS (m/z) | configuration |
|---|---|---|---|---|---|
| 1-53 | 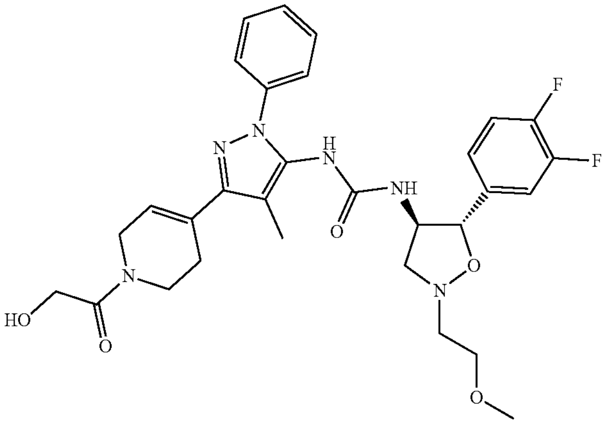 [SMILES: COCCN1C[C@@H](NC(=O)Nc2c(C)c(C3=CCN(C(=O)CO)CC3)nn2-c2ccccc2)[C@H](c2ccc(F)c(F)c2)O1] | 2 | 1.73 | 597 | racemate |
| 1-54 | 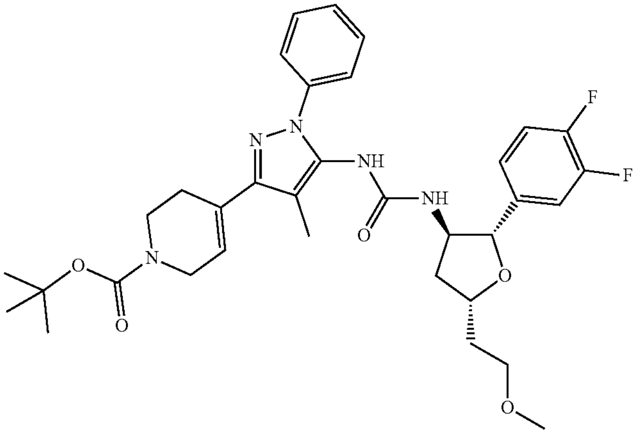 [SMILES: COCC[C@@H]1C[C@@H](NC(=O)Nc2c(C)c(C3=CCN(C(=O)OC(C)(C)C)CC3)nn2-c2ccccc2)[C@H](c2ccc(F)c(F)c2)O1] | 1 | 2.43 | 638 | racemate |
TABLE 12
| No. | Structure | LCMS method No | RT | MS (m/z) | configuration |
|---|---|---|---|---|---|
| 1-55 | 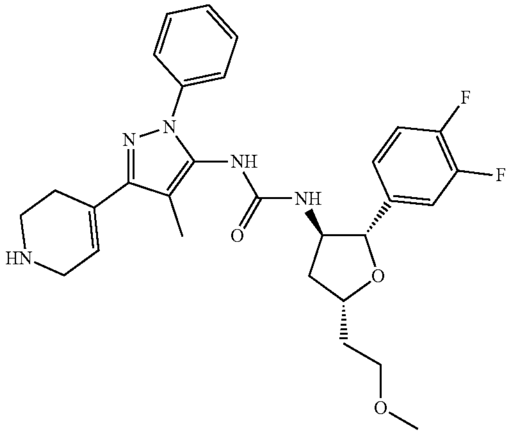 [SMILES: COCC[C@@H]1C[C@@H](NC(=O)Nc2c(C)c(C3=CCNCC3)nn2-c2ccccc2)[C@H](c2ccc(F)c(F)c2)O1] | 1 | 1.28 | 538 | racemate |

TABLE 12-continued
| No. | Structure | LCMS method No | RT | MS (m/z) | configuration |
|---|---|---|---|---|---|
| 1-56 | 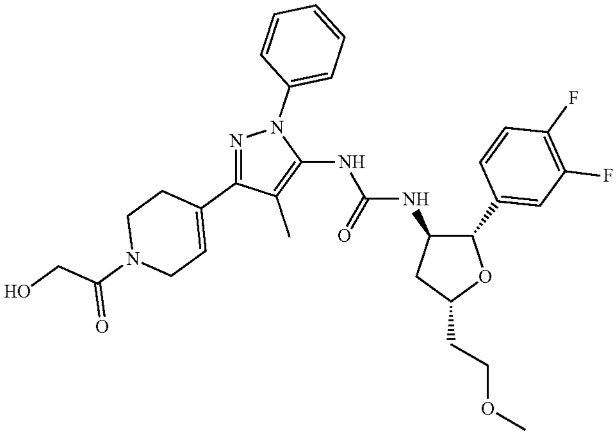 [SMILES: COCC[C@@H]1C[C@@H](NC(=O)Nc2c(C)c(C3=CCN(C(=O)CO)CC3)nn2-c2ccccc2)[C@H](c2ccc(F)c(F)c2)O1] | 1 | 1.77 | 596 | racemate |
| 1-57 | 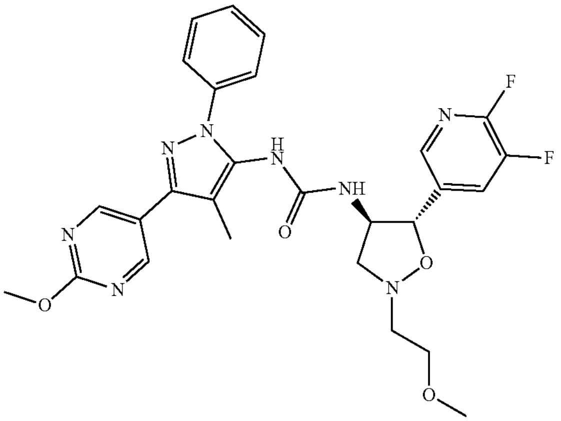 [SMILES: COCCN1C[C@@H](NC(=O)Nc2c(C)c(-c3cnc(OC)nc3)nn2-c2ccccc2)[C@H](c2cnc(F)c(F)c2)O1] | 2 | 1.77 | 567 | racemate |
| 1-58 | 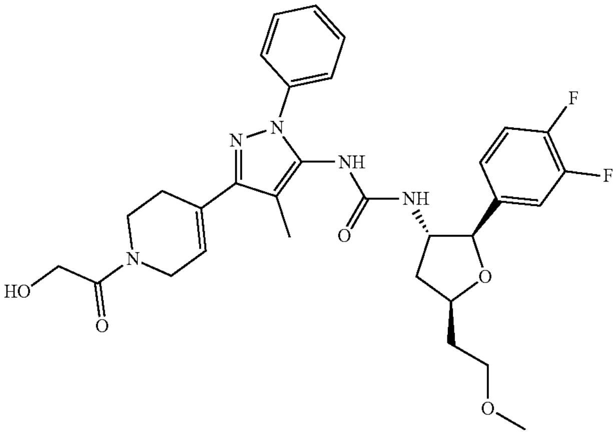 [SMILES: COCC[C@H]1C[C@H](NC(=O)Nc2c(C)c(C3=CCN(C(=O)CO)CC3)nn2-c2ccccc2)[C@@H](c2ccc(F)c(F)c2)O1] | 1 | 1.78 | 596 | |

TABLE 12-continued
| No. | Structure | LCMS method No | RT | MS (m/z) | configuration |
|---|---|---|---|---|---|
| 1-59 | 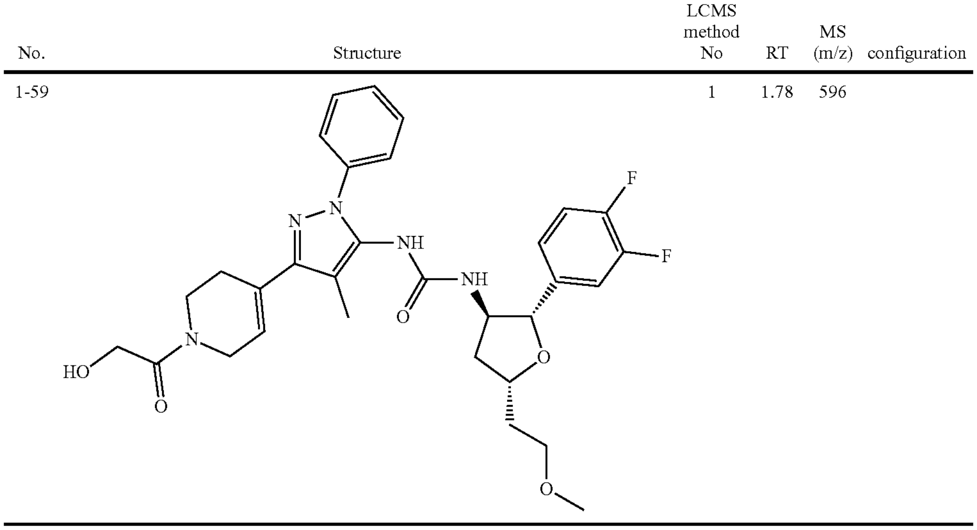 | 1 | 1.78 | 596 | |
TABLE 13
| No. | Structure | LCMS method No | RT | MS (m/z) | configuration |
|---|---|---|---|---|---|
| 1-60 | 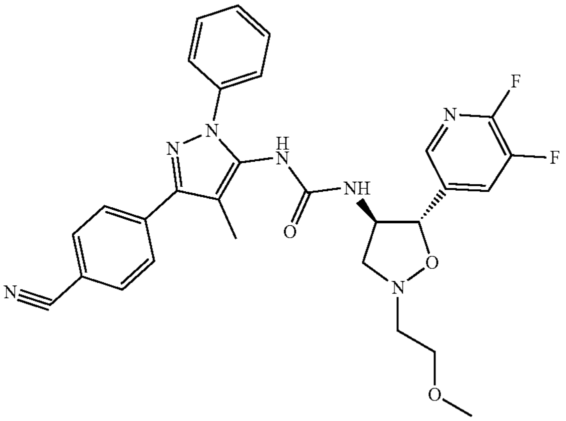 [SMILES: COCCN1C[C@@H](NC(=O)Nc2c(C)c(-c3ccc(C#N)cc3)nn2-c2ccccc2)[C@H](c2cnc(F)c(F)c2)O1] | 2 | 2.11 | 560 | racemate |
| 1-61 | 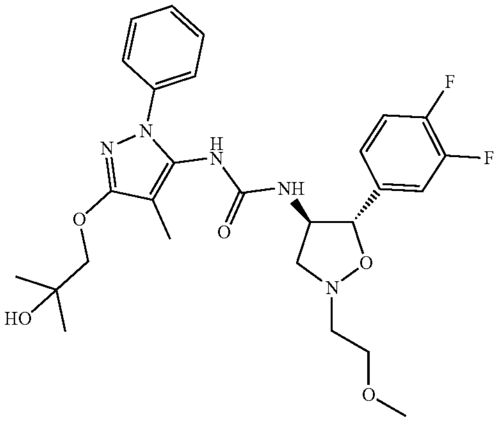 [SMILES: COCCN1C[C@@H](NC(=O)Nc2c(C)c(OCC(C)(C)O)nn2-c2ccccc2)[C@H](c2ccc(F)c(F)c2)O1] | 2 | 1.9 | 546 | racemate |

TABLE 13-continued
| No. | Structure | LCMS method No | RT | MS (m/z) | configuration |
|---|---|---|---|---|---|
| 1-62 | 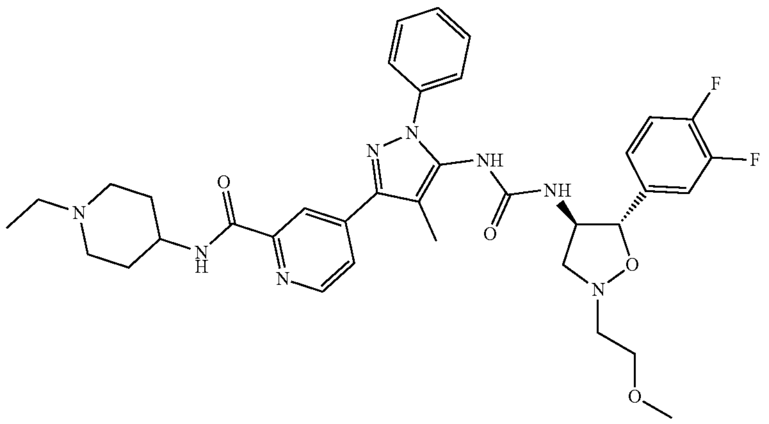 [SMILES: CCN1CCC(NC(=O)c2cc(-c3nn(-c4ccccc4)c(NC(=O)N[C@@H]4CN(CCOC)O[C@H]4c4ccc(F)c(F)c4)c3C)ccn2)CC1] | 2 | 1.75 | 689 | racemate |
| 1-63 | 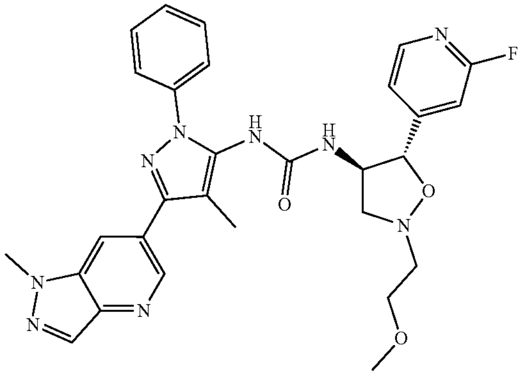 [SMILES: COCCN1C[C@@H](NC(=O)Nc2c(C)c(-c3cnc4cnn(C)c4c3)nn2-c2ccccc2)[C@H](c2ccnc(F)c2)O1] | 2 | 1.57 | 572 | racemate |
| 1-64 | 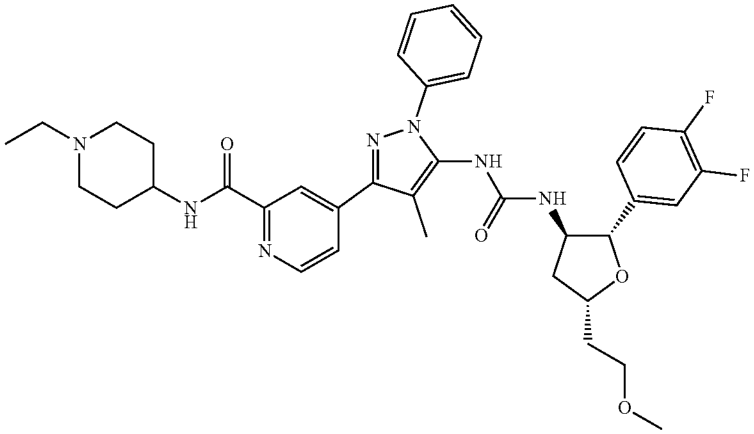 [SMILES: CCN1CCC(NC(=O)c2cc(-c3nn(-c4ccccc4)c(NC(=O)N[C@@H]4C[C@@H](CCOC)O[C@H]4c4ccc(F)c(F)c4)c3C)ccn2)CC1] | 1 | 1.37 | 688 | racemate |

TABLE 14
| No. | Structure | LCMS method No | RT | MS (m/z) | configuration |
|---|---|---|---|---|---|
| 1-65 | 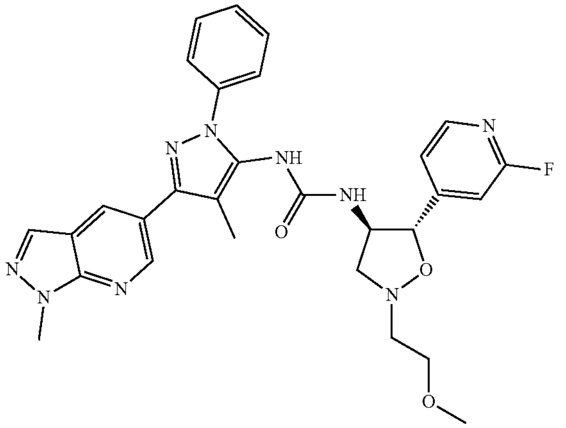 [SMILES: COCCN1C[C@@H](NC(=O)Nc2c(C)c(-c3cnc4c(cnn4C)c3)nn2-c2ccccc2)[C@H](c2ccnc(F)c2)O1] | 2 | 1.68 | 572 | |
| 1-66 | 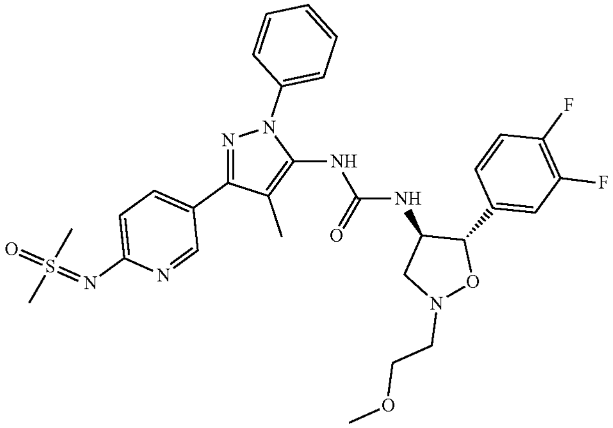 [SMILES: COCCN1C[C@@H](NC(=O)Nc2c(C)c(-c3ccc(N=S(C)(C)=O)nc3)nn2-c2ccccc2)[C@H](c2ccc(F)c(F)c2)O1] | 1 | 1.38 | 626.2 | racemate |
| 1-67 | 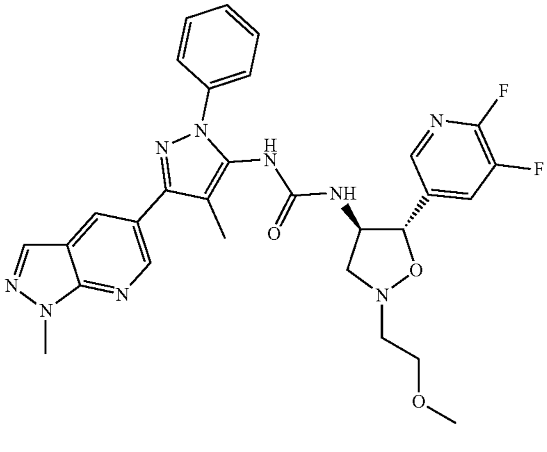 [SMILES: COCCN1C[C@@H](NC(=O)Nc2c(C)c(-c3cnc4c(cnn4C)c3)nn2-c2ccccc2)[C@H](c2cnc(F)c(F)c2)O1] | 2 | 1.81 | 590 | racemate |

TABLE 14-continued
| No. | Structure | LCMS method No | RT | MS (m/z) | configuration |
|---|---|---|---|---|---|
| 1-68 | 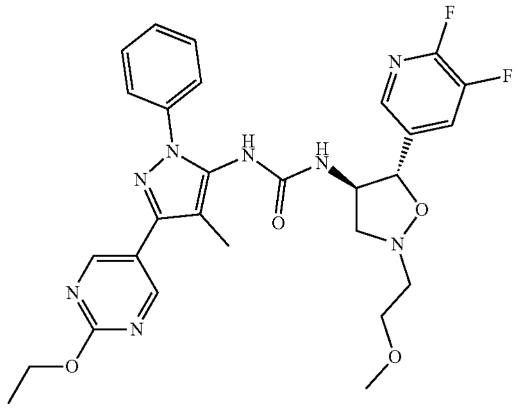 [SMILES: CCOc1ncc(-c2nn(-c3ccccc3)c(NC(=O)N[C@@H]3CN(CCOC)O[C@H]3c3cnc(F)c(F)c3)c2C)cn1] | 2 | 1.92 | 581 | racemate |
| 1-69 | 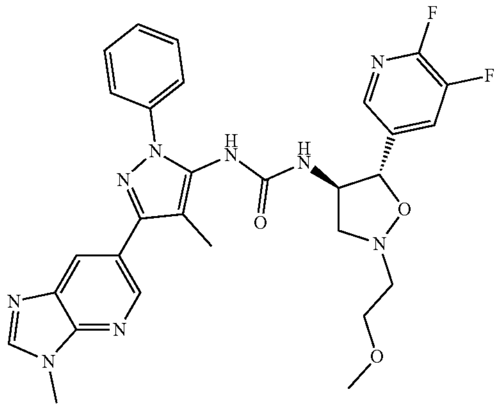 [SMILES: COCCN1C[C@@H](NC(=O)Nc2c(C)c(-c3cnc4c(c3)ncn4C)nn2-c2ccccc2)[C@H](c2cnc(F)c(F)c2)O1] | 2 | 1.5 | 590 | racemate |
TABLE 15
| No. | Structure | LCMS method No | RT | MS (m/z) | configuration |
|---|---|---|---|---|---|
| 1-70 | 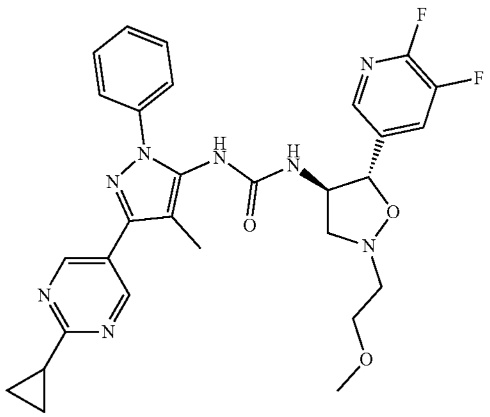 [SMILES: COCCN1C[C@@H](NC(=O)Nc2c(C)c(-c3cnc(C4CC4)nc3)nn2-c2ccccc2)[C@H](c2cnc(F)c(F)c2)O1] | 2 | 1.93 | 577 | racemate |

TABLE 15-continued
| No. | Structure | LCMS method No | RT | MS (m/z) | configuration |
|---|---|---|---|---|---|
| 1-71 | 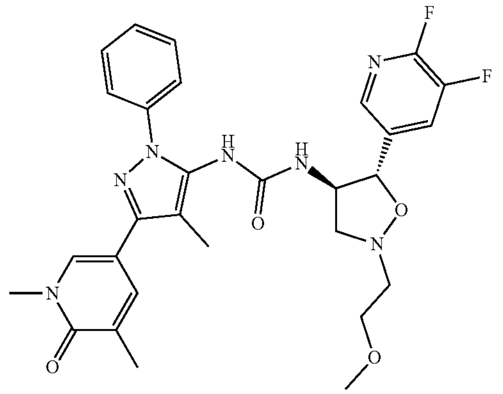 [SMILES: COCCN1C[C@@H](NC(=O)Nc2c(C)c(-c3cc(C)c(=O)n(C)c3)nn2-c2ccccc2)[C@H](c2cnc(F)c(F)c2)O1] | 2 | 1.66 | 580 | racemate |
| 1-72 | 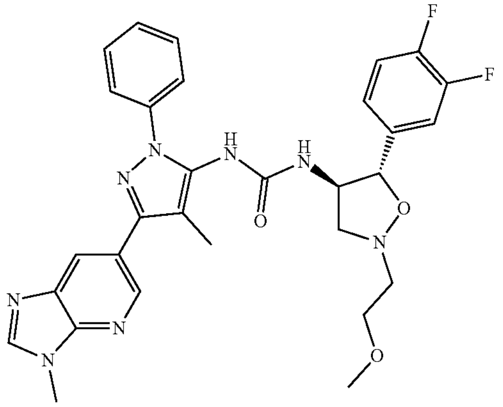 | 2 | 1.69 | 589 | racemate |
| 1-73 | 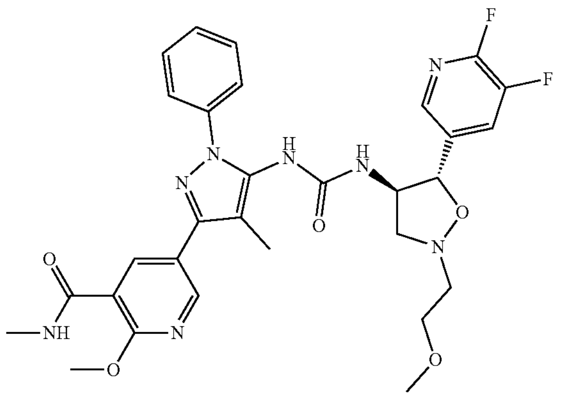 [SMILES: CNC(=O)c1cc(-c2nn(-c3ccccc3)c(NC(=O)N[C@@H]3CN(CCOC)O[C@H]3c3cnc(F)c(F)c3)c2C)cnc1OC] | 2 | 1.78 | 623 | racemate |

TABLE 15-continued
| No. | Structure | LCMS method No | RT | MS (m/z) | configuration |
|---|---|---|---|---|---|
| 1-74 | 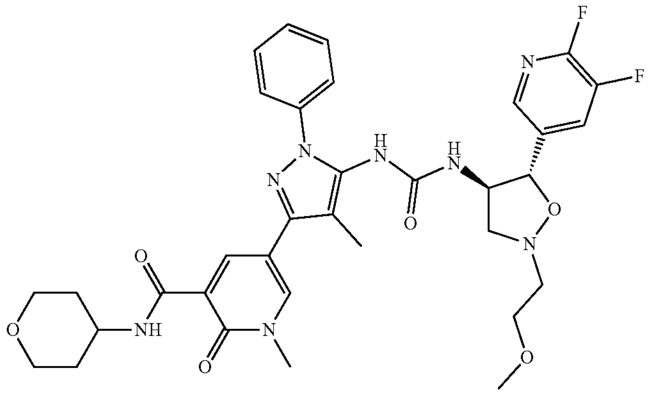 [SMILES: COCCN1C[C@@H](NC(=O)Nc2c(C)c(-c3cc(C(=O)NC4CCOCC4)c(=O)n(C)c3)nn2-c2ccccc2)[C@H](c2cnc(F)c(F)c2)O1] | 2 | 1.7 | 693 | racemate |
TABLE 16
| No. | Structure | LCMS method No | RT | MS (m/z) | configuration |
|---|---|---|---|---|---|
| 1-75 | 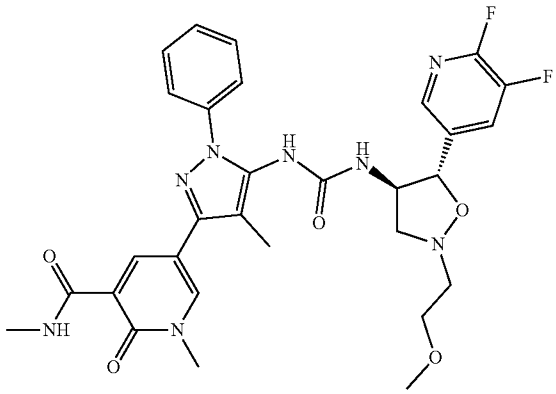 [SMILES: CNC(=O)c1cc(-c2nn(-c3ccccc3)c(NC(=O)N[C@@H]3CN(CCOC)O[C@H]3c3cnc(F)c(F)c3)c2C)cn(C)c1=O] | 2 | 1.61 | 623 | racemate |
| 1-76 | 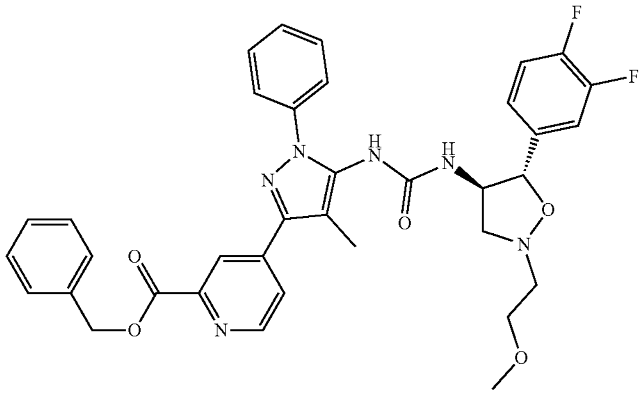 [SMILES: COCCN1C[C@@H](NC(=O)Nc2c(C)c(-c3ccnc(C(=O)OCc4ccccc4)c3)nn2-c2ccccc2)[C@H](c2ccc(F)c(F)c2)O1] | 1 | 2.24 | 669.25 | racemate |

TABLE 16-continued
| No. | Structure | LCMS method No | RT | MS (m/z) | configuration |
|---|---|---|---|---|---|
| 1-77 | 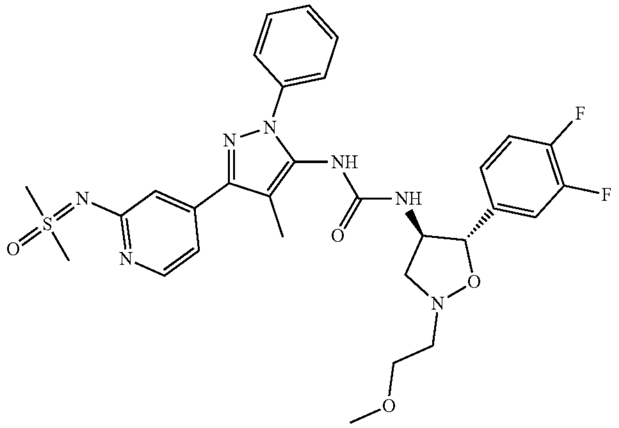 [SMILES: COCCN1C[C@@H](NC(=O)Nc2c(C)c(-c3ccnc(N=S(C)(C)=O)c3)nn2-c2ccccc2)[C@H](c2ccc(F)c(F)c2)O1] | 1 | 1.33 | 626.2 | racemate |
| 1-78 | 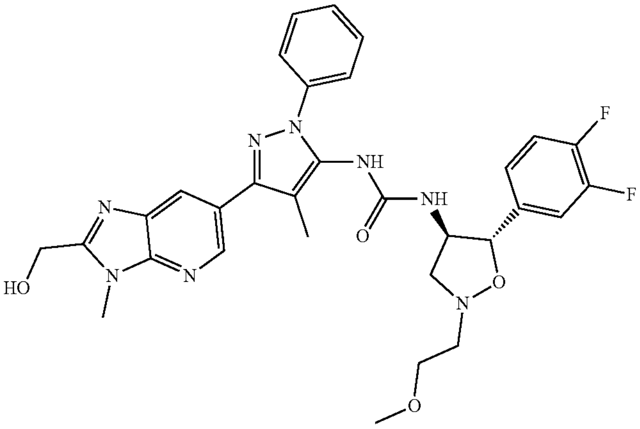 [SMILES: COCCN1C[C@@H](NC(=O)Nc2c(C)c(-c3cnc4c(c3)nc(CO)n4C)nn2-c2ccccc2)[C@H](c2ccc(F)c(F)c2)O1] | 1 | 1.49 | 619.25 | racemate |
| 1-79 | 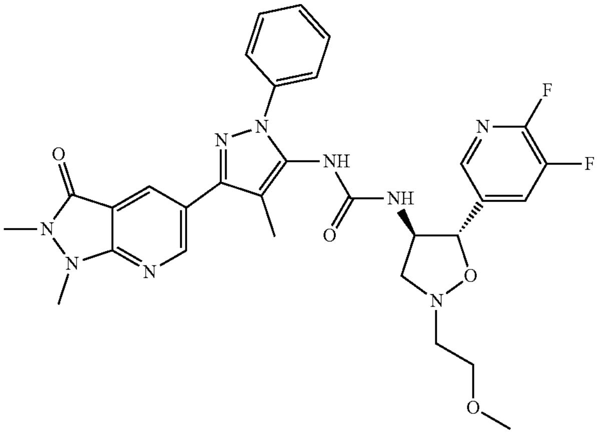 [SMILES: COCCN1C[C@@H](NC(=O)Nc2c(C)c(-c3cnc4c(c3)c(=O)n(C)n4C)nn2-c2ccccc2)[C@H](c2cnc(F)c(F)c2)O1] | 1 | 1.59 | 620 | racemate |

TABLE 17
| No. | Structure | LCMS method No | RT | MS (m/z) | configuration |
|---|---|---|---|---|---|
| I-80 | 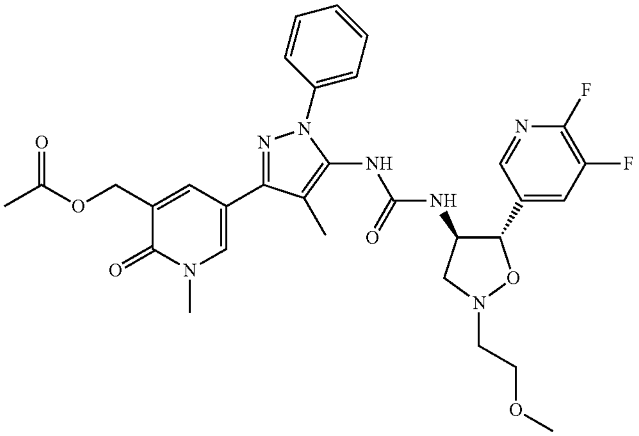 [SMILES: COCCN1C[C@@H](NC(=O)Nc2c(C)c(-c3cc(COC(C)=O)c(=O)n(C)c3)nn2-c2ccccc2)[C@H](c2cnc(F)c(F)c2)O1] | 1 | 1.65 | 638 | racemate |
| I-81 | 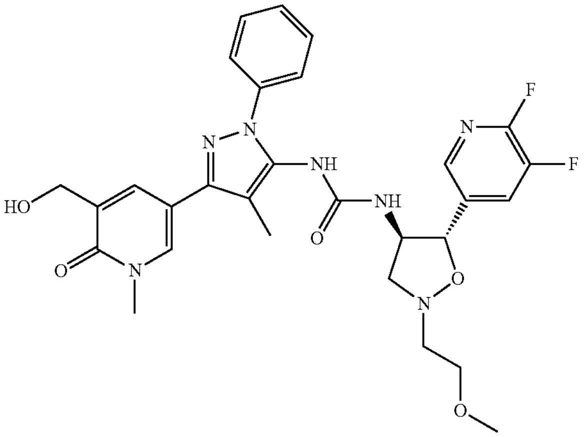 [SMILES: COCCN1C[C@@H](NC(=O)Nc2c(C)c(-c3cc(CO)c(=O)n(C)c3)nn2-c2ccccc2)[C@H](c2cnc(F)c(F)c2)O1] | 1 | 1.45 | 596 | racemate |
| I-82 | 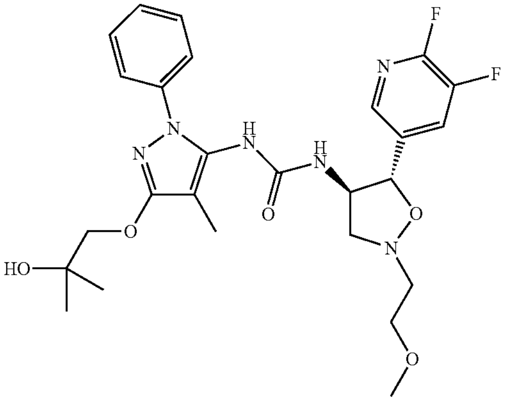 [SMILES: COCCN1C[C@@H](NC(=O)Nc2c(C)c(OCC(C)(C)O)nn2-c2ccccc2)[C@H](c2cnc(F)c(F)c2)O1] | 2 | 1.73 | 547 | |

TABLE 17-continued
| No. | Structure | LCMS method No | RT | MS (m/z) | configuration |
|---|---|---|---|---|---|
| I-83 | 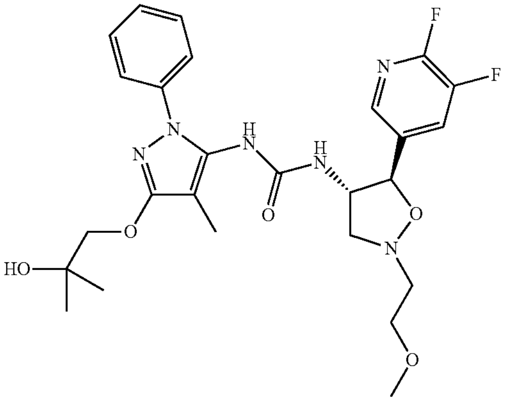 [SMILES: COCCN1C[C@H](NC(=O)Nc2c(C)c(OCC(C)(C)O)nn2-c2ccccc2)[C@@H](c2cnc(F)c(F)c2)O1] | 2 | 1.73 | 547 | |
| I-84 | 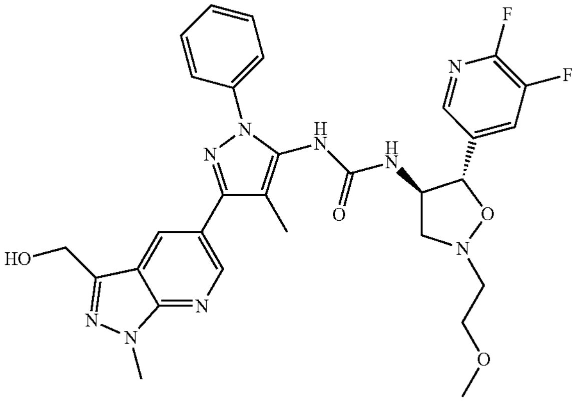 [SMILES: COCCN1C[C@@H](NC(=O)Nc2c(C)c(-c3cnc4c(c3)c(CO)nn4C)nn2-c2ccccc2)[C@H](c2cnc(F)c(F)c2)O1] | 2 | 1.61 | 620 | racemate |
TABLE 18
| No. | Structure | LCMS method No | RT | MS (m/z) | configuration |
|---|---|---|---|---|---|
| I-85 | 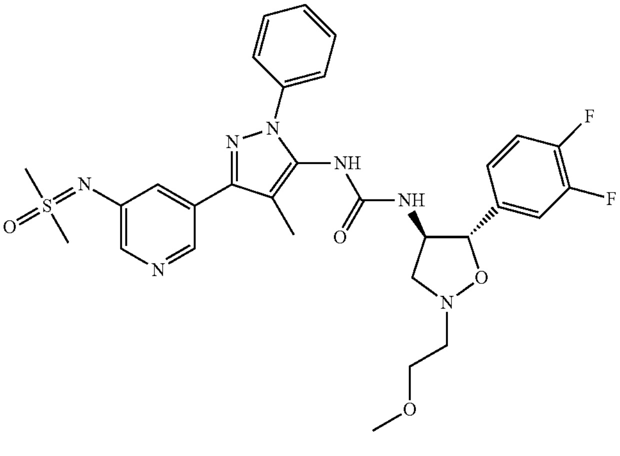 [SMILES: COCCN1C[C@@H](NC(=O)Nc2c(C)c(-c3cncc(N=S(C)(C)=O)c3)nn2-c2ccccc2)[C@H](c2ccc(F)c(F)c2)O1] | 1 | 1.35 | 626.2 | racemate |

TABLE 18-continued
| No. | Structure | LCMS method No | RT | MS (m/z) | configuration |
|---|---|---|---|---|---|
| I-86 | 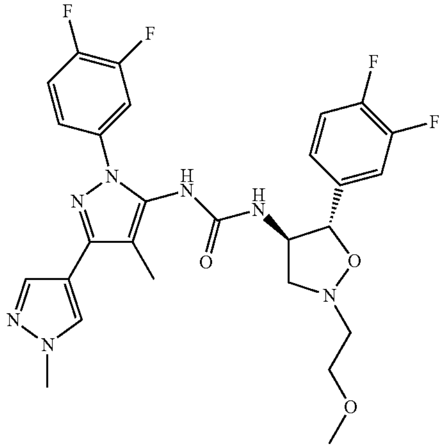 [SMILES: COCCN1C[C@@H](NC(=O)Nc2c(C)c(-c3cnn(C)c3)nn2-c2ccc(F)c(F)c2)[C@H](c2ccc(F)c(F)c2)O1] | 2 | 1.91 | 574 | racemate |
| I-87 | 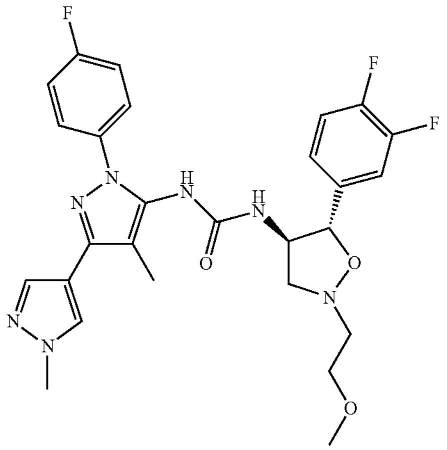 [SMILES: COCCN1C[C@@H](NC(=O)Nc2c(C)c(-c3cnn(C)c3)nn2-c2ccc(F)cc2)[C@H](c2ccc(F)c(F)c2)O1] | 2 | 1.82 | 556 | racemate |
| I-88 | 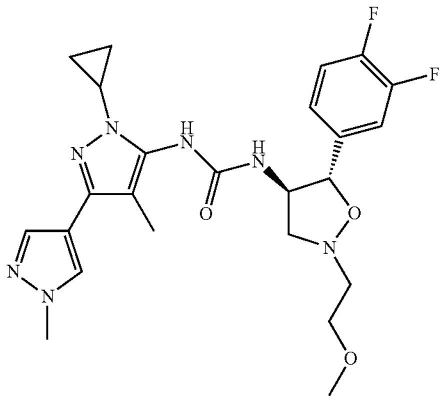 [SMILES: COCCN1C[C@@H](NC(=O)Nc2c(C)c(-c3cnn(C)c3)nn2C2CC2)[C@H](c2ccc(F)c(F)c2)O1] | 2 | 1.57 | 502 | racemate |

TABLE 18-continued
| No. | Structure | LCMS method No | RT | MS (m/z) | configuration |
|---|---|---|---|---|---|
| I-89 | 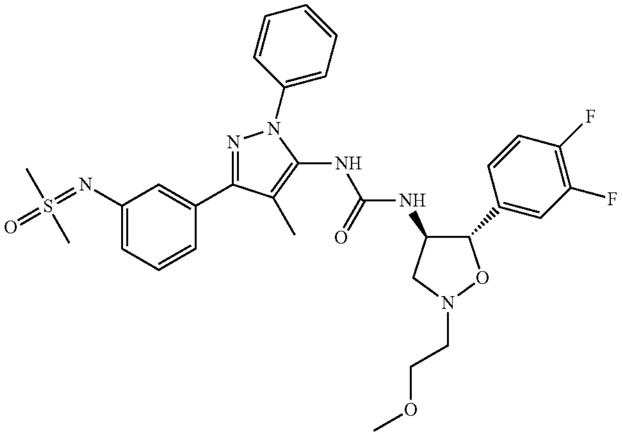 [SMILES: COCCN1C[C@@H](NC(=O)Nc2c(C)c(-c3cccc(N=S(C)(C)=O)c3)nn2-c2ccccc2)[C@H](c2ccc(F)c(F)c2)O1] | 1 | 1.78 | 625.2 | racemate |
TABLE 19
| No. | Structure | LCMS method No | RT | MS (m/z) | configuration |
|---|---|---|---|---|---|
| I-90 | 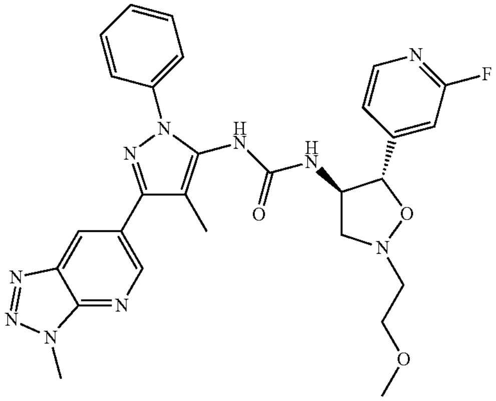 [SMILES: COCCN1C[C@@H](NC(=O)Nc2c(C)c(-c3cnc4c(c3)nnn4C)nn2-c2ccccc2)[C@H](c2ccnc(F)c2)O1] | 1 | 1.58 | 573.2 | racemate |
| I-91 | 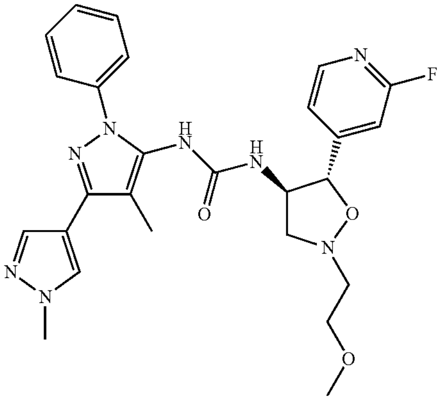 [SMILES: COCCN1C[C@@H](NC(=O)Nc2c(C)c(-c3cnn(C)c3)nn2-c2ccccc2)[C@H](c2ccnc(F)c2)O1] | 1 | 1.42 | 521.25 | racemate |

TABLE 19-continued
| No. | Structure | LCMS method No | RT | MS (m/z) | configuration |
| --- | --- | --- | --- | --- | --- |
| I-92 | 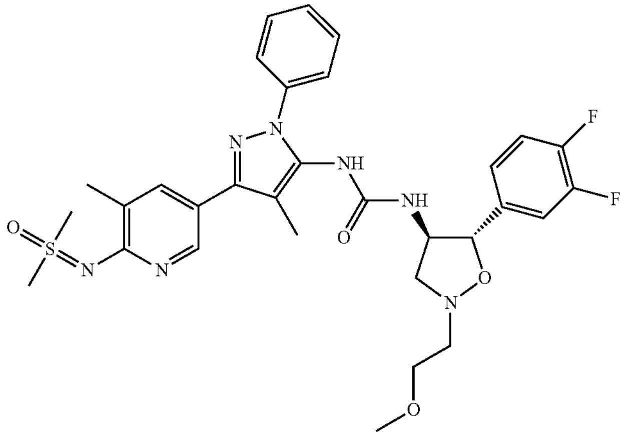 [SMILES: COCCN1C[C@@H](NC(=O)Nc2c(C)c(-c3cnc(N=S(C)(C)=O)c(C)c3)nn2-c2ccccc2)[C@H](c2ccc(F)c(F)c2)O1] | 1 | 1.62 | 640.2 | racemate |
| I-93 | 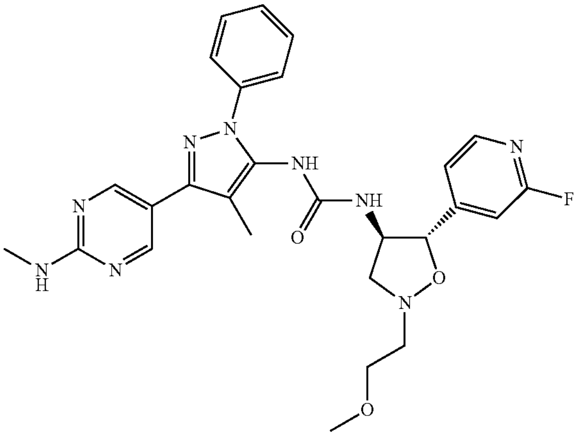 [SMILES: CNc1ncc(-c2nn(-c3ccccc3)c(NC(=O)N[C@@H]3CN(CCOC)O[C@H]3c3ccnc(F)c3)c2C)cn1] | 1 | 1.4 | 548.25 | racemate |
| I-94 | 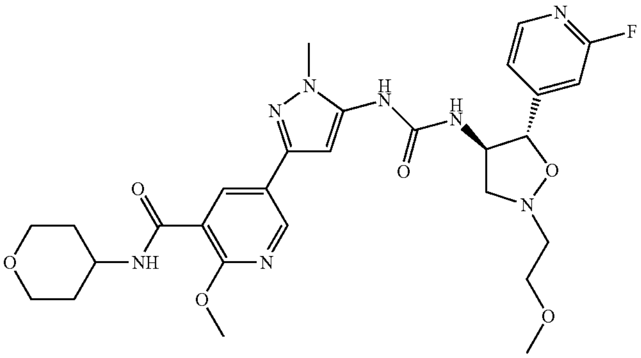 [SMILES: COCCN1C[C@@H](NC(=O)Nc2cc(-c3cnc(OC)c(C(=O)NC4CCOCC4)c3)nn2C)[C@H](c2ccnc(F)c2)O1] | 2 | 1.45 | 599 | racemate |

TABLE 20
| No. | Structure | LCMS method No | RT | MS (m/z) | configuration |
|---|---|---|---|---|---|
| I-95 | 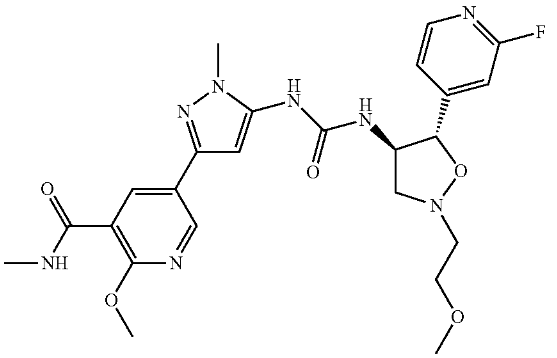 [SMILES: CNC(=O)c1cc(-c2cc(NC(=O)N[C@@H]3CN(CCOC)O[C@H]3c3ccnc(F)c3)n(C)n2)cnc1OC] | 2 | 1.33 | 529 | racemate |
| I-96 | 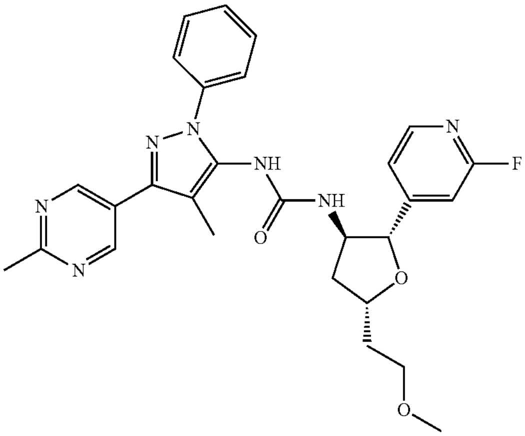 [SMILES: COCC[C@@H]1C[C@@H](NC(=O)Nc2c(C)c(-c3cnc(C)nc3)nn2-c2ccccc2)[C@H](c2ccnc(F)c2)O1] | 1 | 1.55 | 532.25 | racemate |
| I-97 | 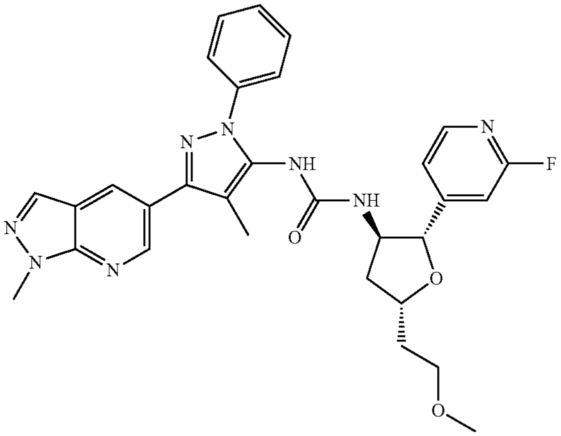 [SMILES: COCC[C@@H]1C[C@@H](NC(=O)Nc2c(C)c(-c3cnc4c(cnn4C)c3)nn2-c2ccccc2)[C@H](c2ccnc(F)c2)O1] | 1 | 1.71 | 571.2 | racemate |

TABLE 20-continued
| No. | Structure | LCMS method No | RT | MS (m/z) | configuration |
|---|---|---|---|---|---|
| I-98 | 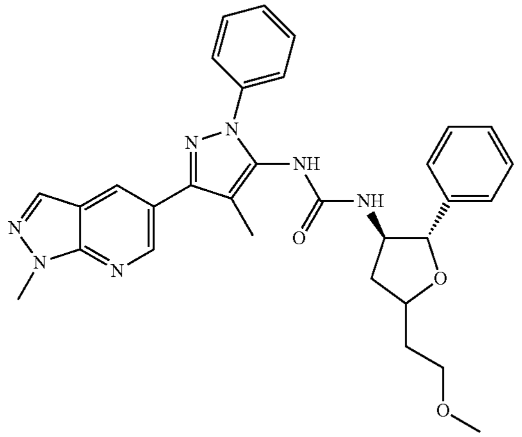 [SMILES: COCCC1C[C@@H](NC(=O)Nc2c(C)c(-c3cnc4c(cnn4C)c3)nn2-c2ccccc2)[C@H](c2ccccc2)O1] | 1 | 1.87 | 552.25 | trans |
| I-99 | 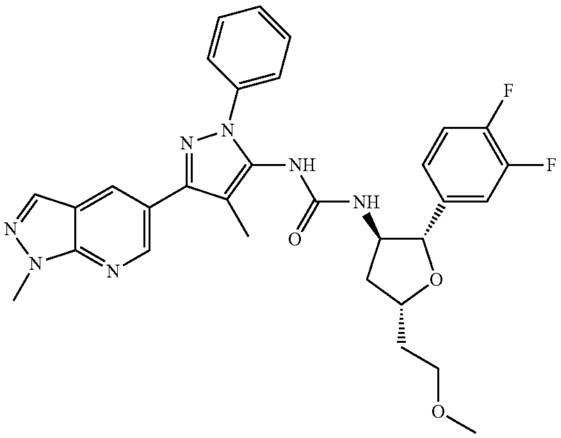 [SMILES: COCC[C@@H]1C[C@@H](NC(=O)Nc2c(C)c(-c3cnc4c(cnn4C)c3)nn2-c2ccccc2)[C@H](c2ccc(F)c(F)c2)O1] | 1 | 2.01 | 588.2 | racemate |
TABLE 21
| No. | Structure | LCMS method No | RT | MS (m/z) | configuration |
|---|---|---|---|---|---|
| I-100 | 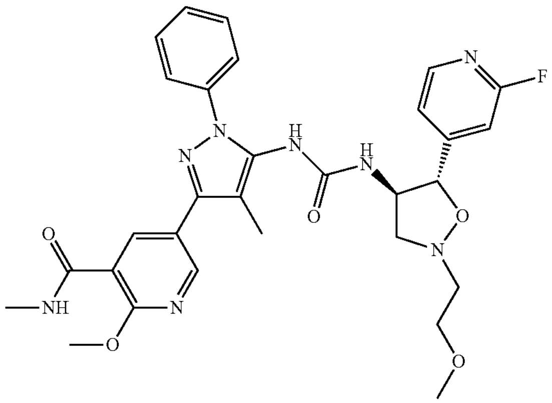 [SMILES: CNC(=O)c1cc(-c2nn(-c3ccccc3)c(NC(=O)N[C@@H]3CN(CCOC)O[C@H]3c3ccnc(F)c3)c2C)cnc1OC] | 2 | 1.63 | 605 | racemate |

TABLE 21-continued
| No. | Structure | LCMS method No | RT | MS (m/z) | configuration |
|---|---|---|---|---|---|
| I-101 | 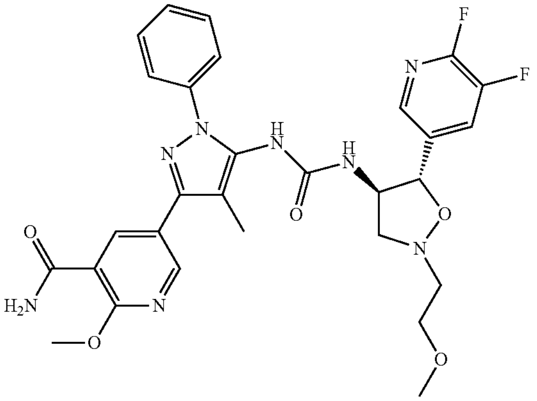 [SMILES: COCCN1C[C@@H](NC(=O)Nc2c(C)c(-c3cnc(OC)c(C(N)=O)c3)nn2-c2ccccc2)[C@H](c2cnc(F)c(F)c2)O1] | 2 | 1.71 | 609 | racemate |
| I-102 | 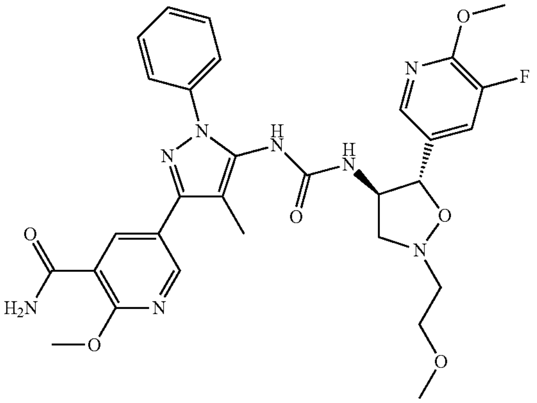 [SMILES: COCCN1C[C@@H](NC(=O)Nc2c(C)c(-c3cnc(OC)c(C(N)=O)c3)nn2-c2ccccc2)[C@H](c2cnc(OC)c(F)c2)O1] | 2 | 1.68 | 621 | racemate |
| I-103 | 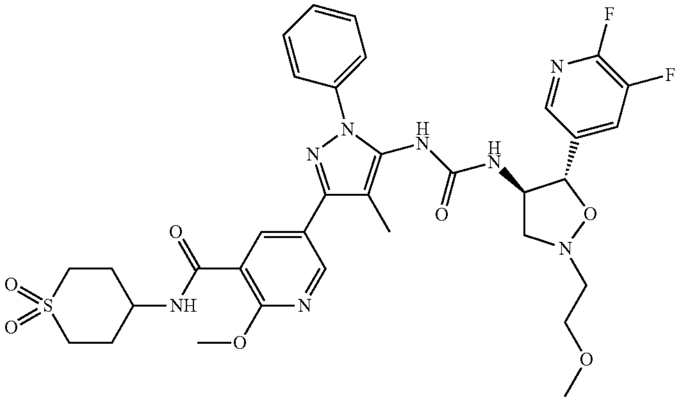 [SMILES: COCCN1C[C@@H](NC(=O)Nc2c(C)c(-c3cnc(OC)c(C(=O)NC4CCS(=O)(=O)CC4)c3)nn2-c2ccccc2)[C@H](c2cnc(F)c(F)c2)O1] | 2 | 1.8 | 741 | racemate |

TABLE 21-continued
| No. | Structure | LCMS method No | RT | MS (m/z) | configuration |
|---|---|---|---|---|---|
| I-104 | 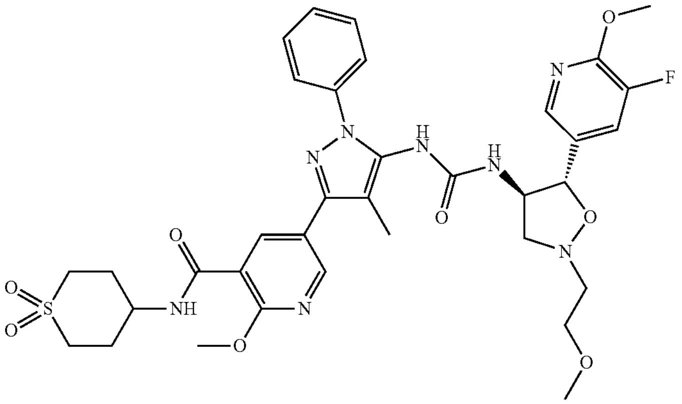 [SMILES: COCCN1C[C@@H](NC(=O)Nc2c(C)c(-c3cnc(OC)c(C(=O)NC4CCS(=O)(=O)CC4)c3)nn2-c2ccccc2)[C@H](c2cnc(OC)c(F)c2)O1] | 2 | 1.77 | 753 | racemate |
TABLE 22
| No. | Structure | LCMS method No | RT | MS (m/z) | configuration |
|---|---|---|---|---|---|
| I-105 | 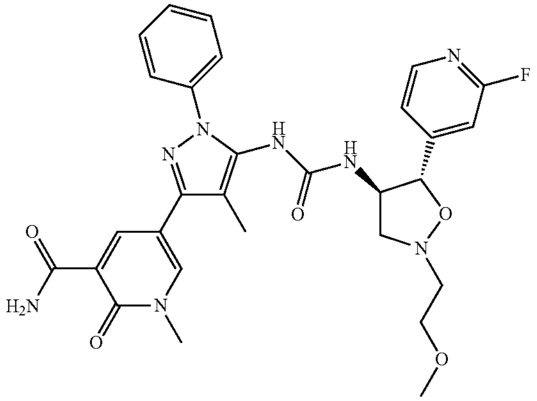 [SMILES: COCCN1C[C@@H](NC(=O)Nc2c(C)c(-c3cc(C(N)=O)c(=O)n(C)c3)nn2-c2ccccc2)[C@H](c2ccnc(F)c2)O1] | 2 | 1.37 | 591 | racemate |
| I-106 | 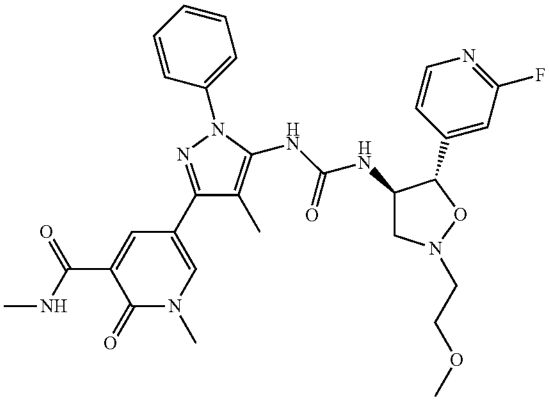 [SMILES: CNC(=O)c1cc(-c2nn(-c3ccccc3)c(NC(=O)N[C@@H]3CN(CCOC)O[C@H]3c3ccnc(F)c3)c2C)cn(C)c1=O] | 2 | 1.46 | 605 | racemate |

TABLE 22-continued
| No. | Structure | LCMS method No | RT | MS (m/z) | configuration |
|---|---|---|---|---|---|
| I-107 | 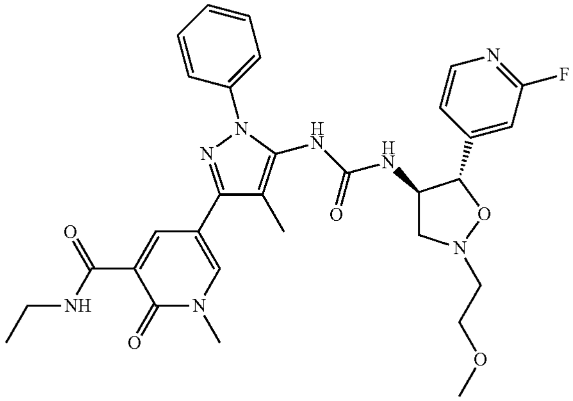 [SMILES: CCNC(=O)c1cc(-c2nn(-c3ccccc3)c(NC(=O)N[C@@H]3CN(CCOC)O[C@H]3c3ccnc(F)c3)c2C)cn(C)c1=O] | 2 | 1.59 | 619 | racemate |
| I-108 | 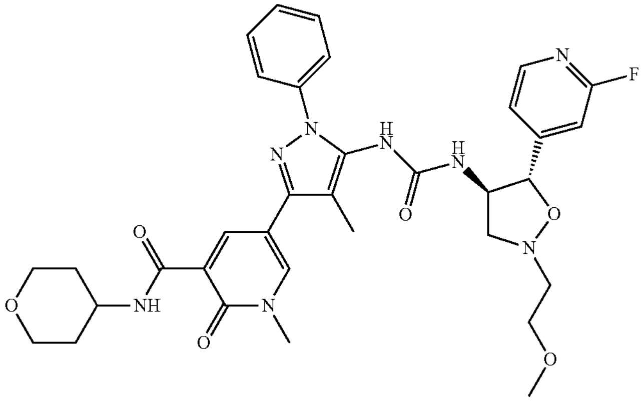 [SMILES: COCCN1C[C@@H](NC(=O)Nc2c(C)c(-c3cc(C(=O)NC4CCOCC4)c(=O)n(C)c3)nn2-c2ccccc2)[C@H](c2ccnc(F)c2)O1] | 2 | 1.55 | 675 | racemate |
| I-109 | 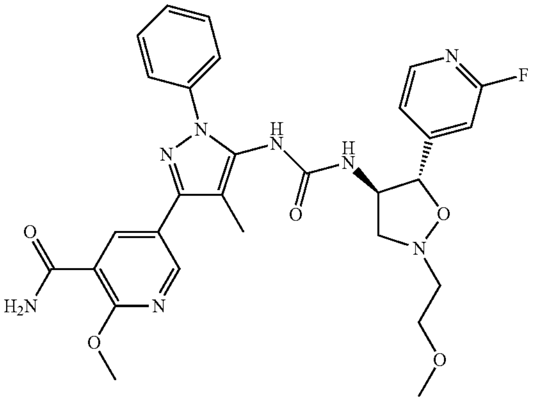 [SMILES: COCCN1C[C@@H](NC(=O)Nc2c(C)c(-c3cnc(OC)c(C(N)=O)c3)nn2-c2ccccc2)[C@H](c2ccnc(F)c2)O1] | 2 | 1.54 | 591 | racemate |

TABLE 23
| No. | Structure | LCMS method No | RT | MS (m/z) | configuration |
|---|---|---|---|---|---|
| I-110 | 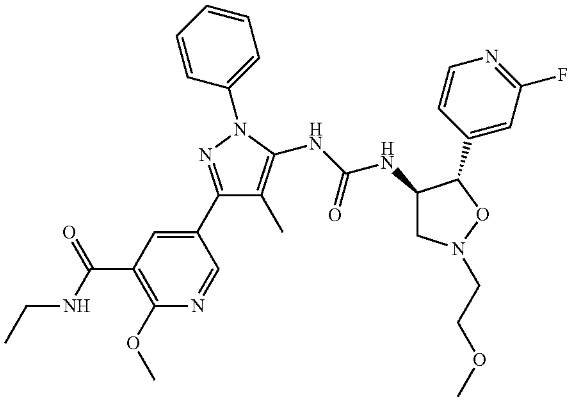 [SMILES: CCNC(=O)c1cc(-c2nn(-c3ccccc3)c(NC(=O)N[C@@H]3CN(CCOC)O[C@H]3c3ccnc(F)c3)c2C)cnc1OC] | 2 | 1.78 | 619 | racemate |
| I-111 | 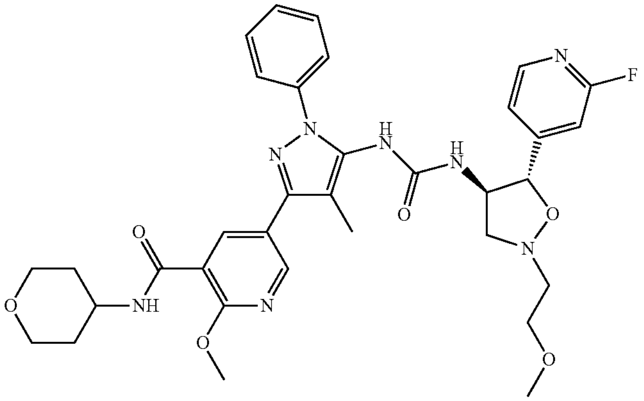 [SMILES: COCCN1C[C@@H](NC(=O)Nc2c(C)c(-c3cnc(OC)c(C(=O)NC4CCOCC4)c3)nn2-c2ccccc2)[C@H](c2ccnc(F)c2)O1] | 2 | 1.72 | 675 | racemate |
| I-112 | 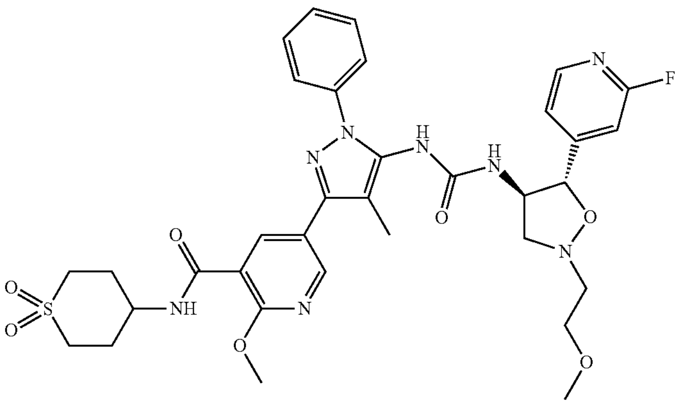 [SMILES: COCCN1C[C@@H](NC(=O)Nc2c(C)c(-c3cnc(OC)c(C(=O)NC4CCS(=O)(=O)CC4)c3)nn2-c2ccccc2)[C@H](c2ccnc(F)c2)O1] | 2 | 1.65 | 723 | racemate |

TABLE 23-continued
| No. | Structure | LCMS method No | RT | MS (m/z) | configuration |
|---|---|---|---|---|---|
| I-113 | 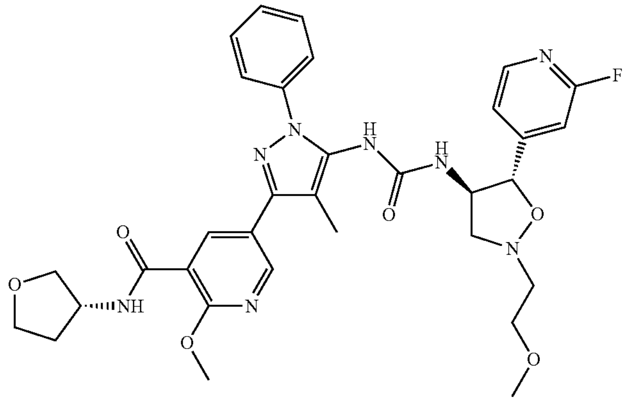 [SMILES: COCCN1C[C@@H](NC(=O)Nc2c(C)c(-c3cnc(OC)c(C(=O)N[C@@H]4CCOC4)c3)nn2-c2ccccc2)[C@H](c2ccnc(F)c2)O1] | 2 | 1.68 | 661 | Diastereo mixture |
| I-114 | 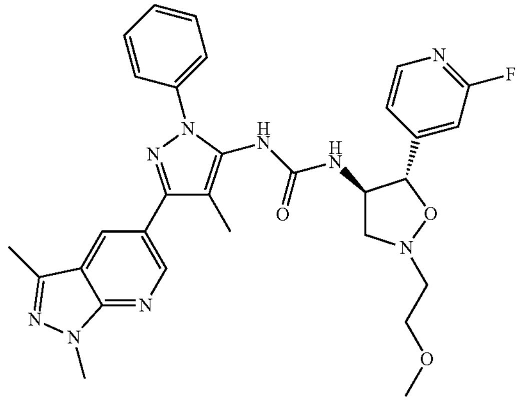 [SMILES: COCCN1C[C@@H](NC(=O)Nc2c(C)c(-c3cnc4c(c3)c(C)nn4C)nn2-c2ccccc2)[C@H](c2ccnc(F)c2)O1] | 1 | 1.68 | 586.2 | racemate |
TABLE 24
| No. | Structure | LCMS method No | RT | MS (m/z) | configuration |
|---|---|---|---|---|---|
| I-115 | 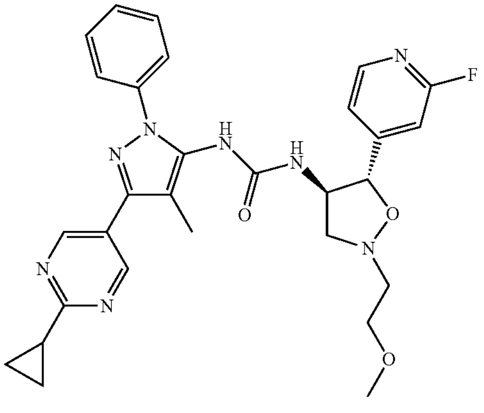 [SMILES: COCCN1C[C@@H](NC(=O)Nc2c(C)c(-c3cnc(C4CC4)nc3)nn2-c2ccccc2)[C@H](c2ccnc(F)c2)O1] | 1 | 1.75 | 559.2 | racemate |

TABLE 24-continued
| No. | Structure | LCMS method No | RT | MS (m/z) | configuration |
|---|---|---|---|---|---|
| I-116 | 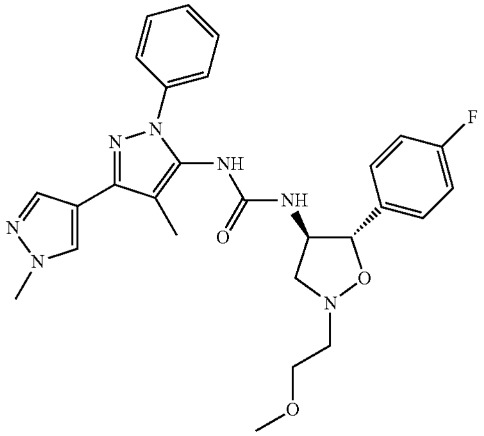 [SMILES: COCCN1C[C@@H](NC(=O)Nc2c(C)c(-c3cnn(C)c3)nn2-c2ccccc2)[C@H](c2ccc(F)cc2)O1] | 1 | 1.6 | 520.25 | racemate |
| I-117 | 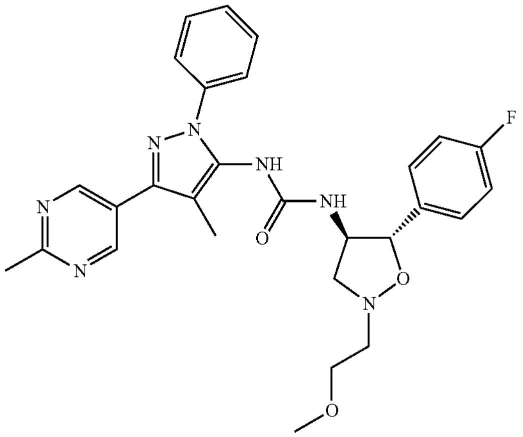 [SMILES: COCCN1C[C@@H](NC(=O)Nc2c(C)c(-c3cnc(C)nc3)nn2-c2ccccc2)[C@H](c2ccc(F)cc2)O1] | 1 | 1.65 | 532.2 | racemate |
| I-118 | 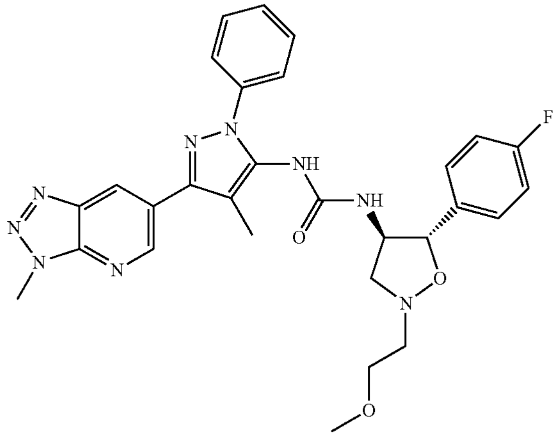 [SMILES: COCCN1C[C@@H](NC(=O)Nc2c(C)c(-c3cnc4c(c3)nnn4C)nn2-c2ccccc2)[C@H](c2ccc(F)cc2)O1] | 1 | 1.76 | 572.2 | racemate |

TABLE 24-continued
| No. | Structure | LCMS method No | RT | MS (m/z) | configuration |
|---|---|---|---|---|---|
| I-119 | 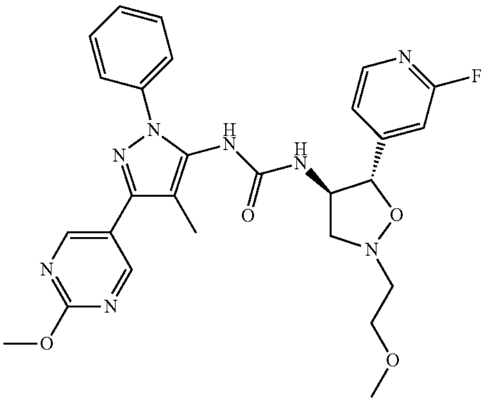 [SMILES: COCCN1C[C@@H](NC(=O)Nc2c(C)c(-c3cnc(OC)nc3)nn2-c2ccccc2)[C@H](c2ccnc(F)c2)O1] | 1 | 1.58 | 549.2 | racemate |
TABLE 25
| No. | Structure | LCMS method No | RT | MS (m/z) | configuration |
|---|---|---|---|---|---|
| I-120 | 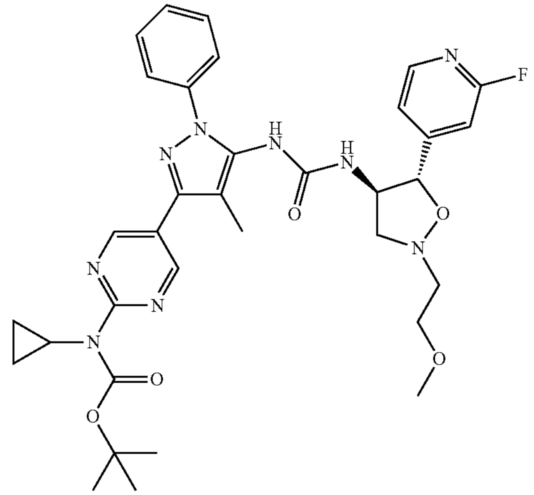 [SMILES: COCCN1C[C@@H](NC(=O)Nc2c(C)c(-c3cnc(N(C(=O)OC(C)(C)C)C4CC4)nc3)nn2-c2ccccc2)[C@H](c2ccnc(F)c2)O1] | 1 | 2.01 | 674.25 | racemate |
| I-121 | 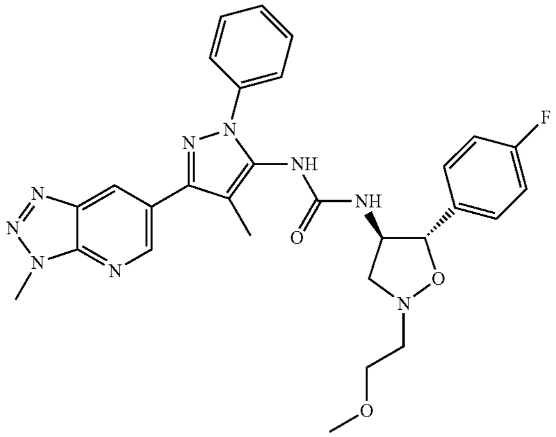 [SMILES: COCCN1C[C@@H](NC(=O)Nc2c(C)c(-c3cnc4c(c3)nnn4C)nn2-c2ccccc2)[C@H](c2ccc(F)cc2)O1] | 1 | 1.5 | 571.2 | racemate |

TABLE 25-continued
| No. | Structure | LCMS method No | RT | MS (m/z) | configuration |
|---|---|---|---|---|---|
| I-122 | 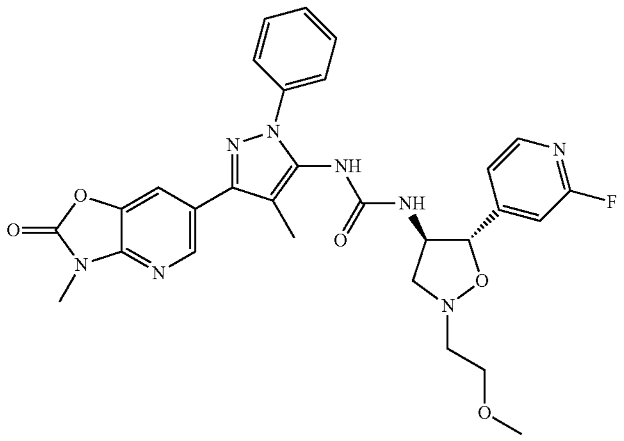 [SMILES: COCCN1C[C@@H](NC(=O)Nc2c(C)c(-c3cnc4c(c3)oc(=O)n4C)nn2-c2ccccc2)[C@H](c2ccnc(F)c2)O1] | 1 | 1.65 | 589.2 | racemate |
| I-123 | 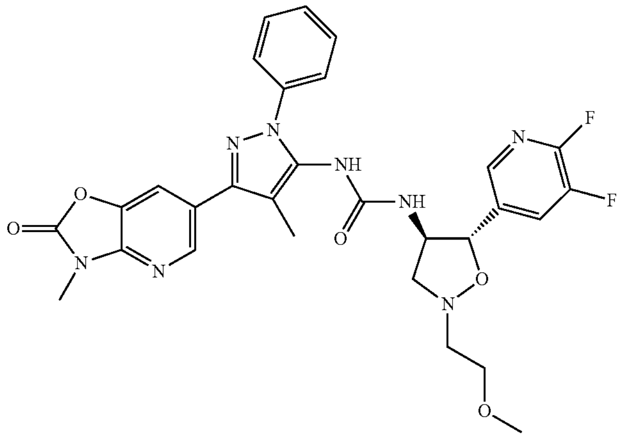 [SMILES: COCCN1C[C@@H](NC(=O)Nc2c(C)c(-c3cnc4c(c3)oc(=O)n4C)nn2-c2ccccc2)[C@H](c2cnc(F)c(F)c2)O1] | 1 | 1.81 | 607.2 | racemate |

TABLE 26
| No. | Structure | LCMS method No | RT | MS (m/z) | configuration |
|---|---|---|---|---|---|
| I-124 | 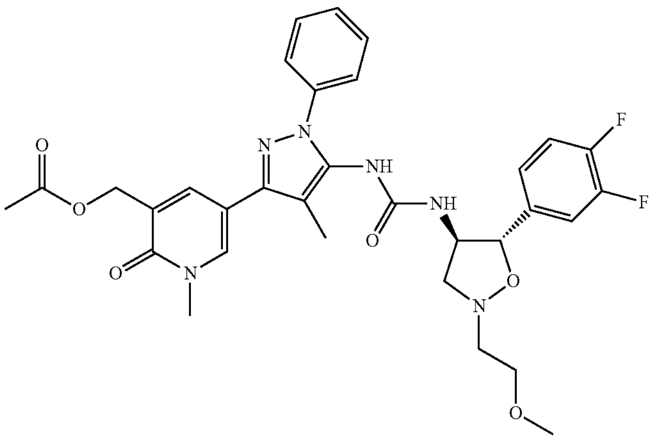 [SMILES: COCCN1C[C@@H](NC(=O)Nc2c(C)c(-c3cc(COC(C)=O)c(=O)n(C)c3)nn2-c2ccccc2)[C@H](c2ccc(F)c(F)c2)O1] | 1 | 1.78 | 637.3 | racemate |
| I-125 | 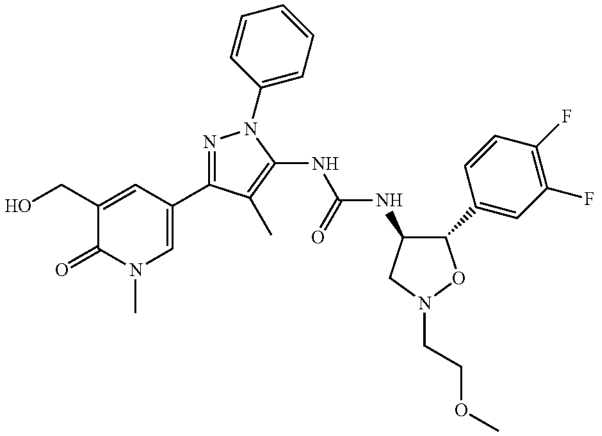 [SMILES: COCCN1C[C@@H](NC(=O)Nc2c(C)c(-c3cc(CO)c(=O)n(C)c3)nn2-c2ccccc2)[C@H](c2ccc(F)c(F)c2)O1] | 1 | 1.58 | 595.25 | racemate |
| I-126 | 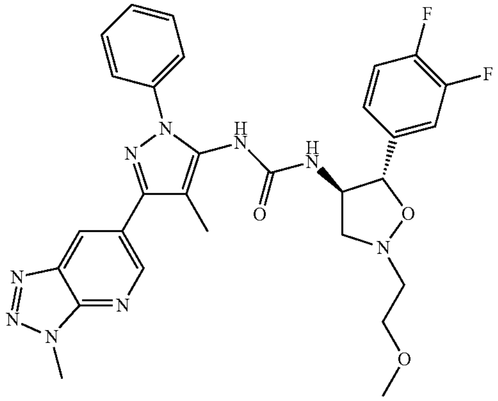 | 2 | 1.94 | 590 | racemate |

TABLE 26-continued
| No. | Structure | LCMS method No | RT | MS (m/z) | configuration |
|---|---|---|---|---|---|
| I-127 | 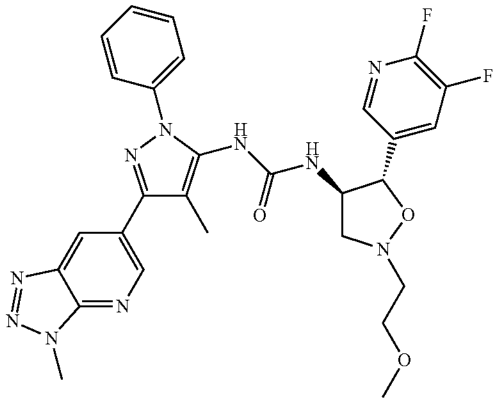 [SMILES: COCCN1C[C@@H](NC(=O)Nc2c(C)c(-c3cnc4c(c3)nnn4C)nn2-c2ccccc2)[C@H](c2cnc(F)c(F)c2)O1] | 2 | 1.79 | 591 | racemate |
| I-128 | 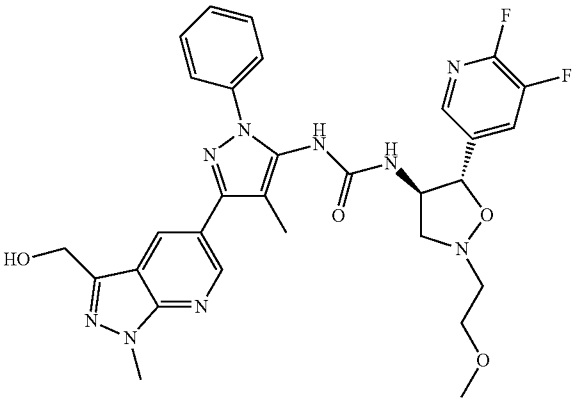 [SMILES: COCCN1C[C@@H](NC(=O)Nc2c(C)c(-c3cnc4c(c3)c(CO)nn4C)nn2-c2ccccc2)[C@H](c2cnc(F)c(F)c2)O1] | 2 | 1.6 | 620 | |
40
TABLE 27
| No. | Structure | LCMS method No | RT | MS (m/z) | configuration |
|---|---|---|---|---|---|
| I-129 | 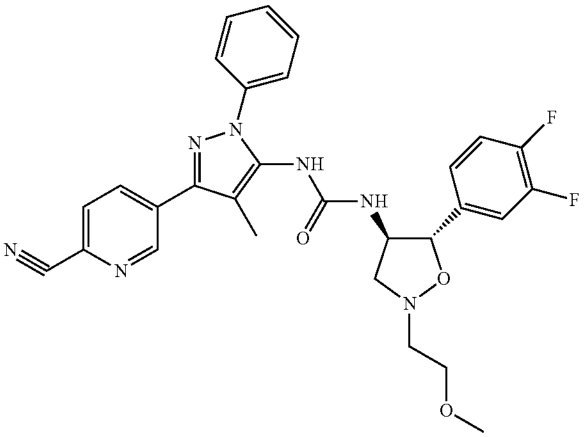 [SMILES: COCCN1C[C@@H](NC(=O)Nc2c(C)c(-c3ccc(C#N)nc3)nn2-c2ccccc2)[C@H](c2ccc(F)c(F)c2)O1] | 1 | 2.02 | 560 | racemate |

TABLE 27-continued
| No. | Structure | LCMS method No | RT | MS (m/z) | configuration |
|---|---|---|---|---|---|
| I-130 | 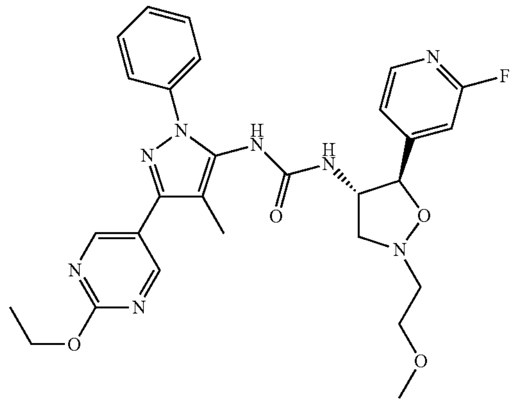 [SMILES: CCOc1ncc(-c2nn(-c3ccccc3)c(NC(=O)N[C@H]3CN(CCOC)O[C@@H]3c3ccnc(F)c3)c2C)cn1] | 1 | 1.73 | 563.2 | |
| I-131 | 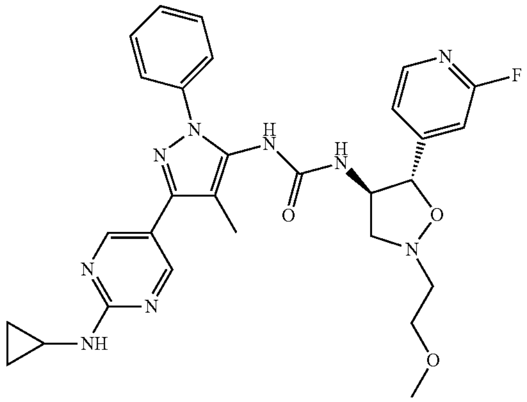 [SMILES: COCCN1C[C@@H](NC(=O)Nc2c(C)c(-c3cnc(NC4CC4)nc3)nn2-c2ccccc2)[C@H](c2ccnc(F)c2)O1] | 1 | 1.52 | 574.25 | racemate |
| I-132 | 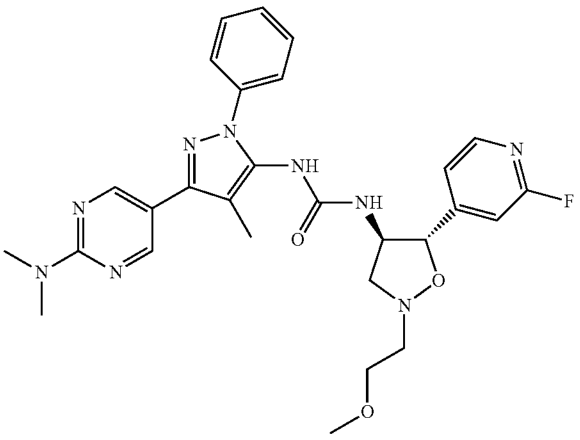 [SMILES: COCCN1C[C@@H](NC(=O)Nc2c(C)c(-c3cnc(N(C)C)nc3)nn2-c2ccccc2)[C@H](c2ccnc(F)c2)O1] | 1 | 1.72 | 562.45 | racemate |

TABLE 27-continued
| No. | Structure | LCMS method No | RT | MS (m/z) | configuration |
|---|---|---|---|---|---|
| I-133 | 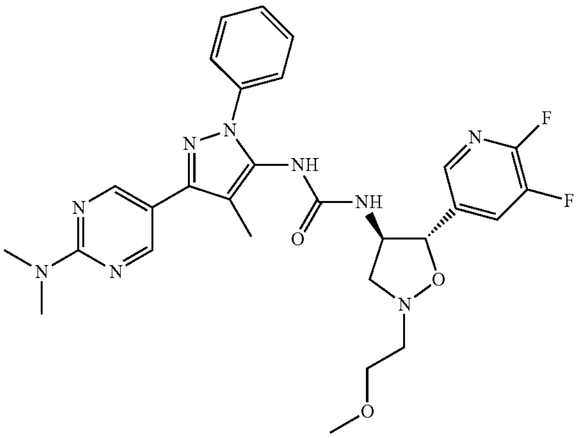 | 1 | 1.87 | 580.45 | |
TABLE 28
| No. | Structure | LCMS method No | RT | MS (m/z) | configuration |
|---|---|---|---|---|---|
| I-134 | 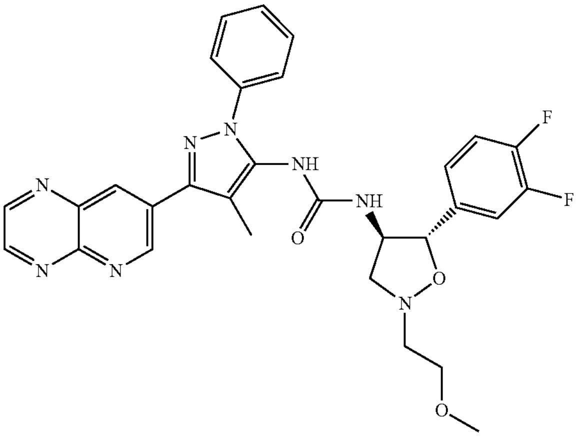 [SMILES: COCCN1C[C@@H](NC(=O)Nc2c(C)c(-c3cnc4nccnc4c3)nn2-c2ccccc2)[C@H](c2ccc(F)c(F)c2)O1] | 1 | 1.74 | 587 | racemate |
| I-135 | 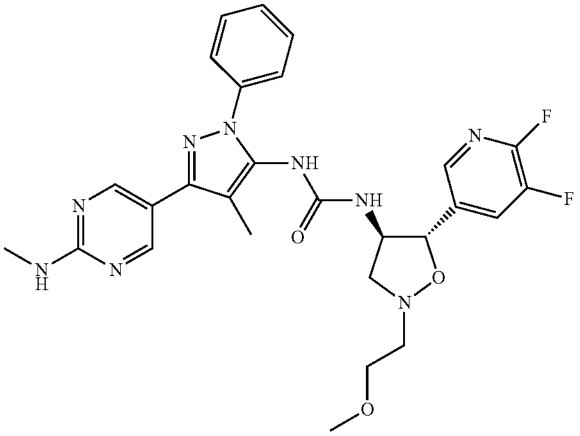 [SMILES: CNc1ncc(-c2nn(-c3ccccc3)c(NC(=O)N[C@@H]3CN(CCOC)O[C@H]3c3cnc(F)c(F)c3)c2C)cn1] | 1 | 1.56 | 566.2 | |

TABLE 28-continued
| No. | Structure | LCMS method No | RT | MS (m/z) | configuration |
|---|---|---|---|---|---|
| I-136 | 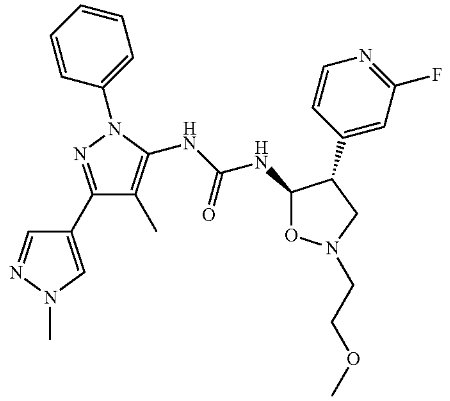 [SMILES: COCCN1C[C@@H](c2ccnc(F)c2)[C@H](NC(=O)Nc2c(C)c(-c3cnn(C)c3)nn2-c2ccccc2)O1] | 1 | 1.33 | 521.25 | racemate |
| I-137 | 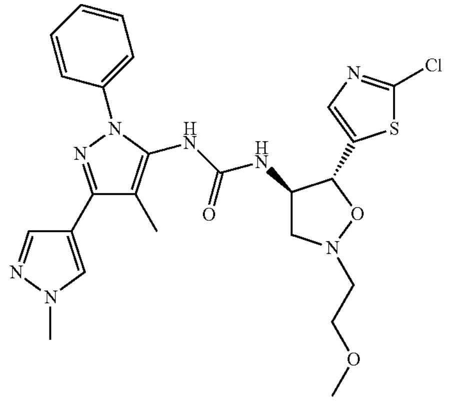 [SMILES: COCCN1C[C@@H](NC(=O)Nc2c(C)c(-c3cnn(C)c3)nn2-c2ccccc2)[C@H](c2cnc(Cl)s2)O1] | 1 | 1.57 | 543.15 | racemate |
| I-138 | 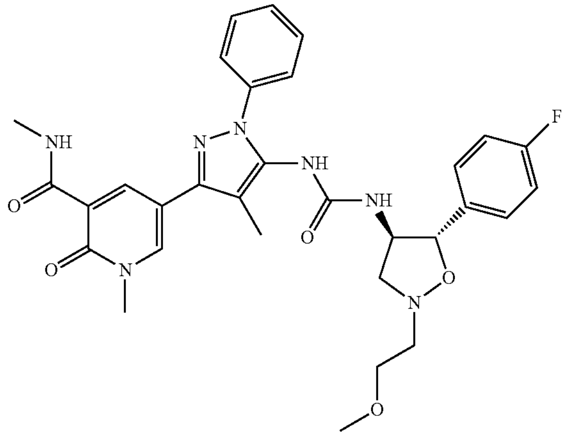 [SMILES: CNC(=O)c1cc(-c2nn(-c3ccccc3)c(NC(=O)N[C@@H]3CN(CCOC)O[C@H]3c3ccc(F)cc3)c2C)cn(C)c1=O] | 1 | 1.61 | 604.25 | racemate |

TABLE 29
| No. | Structure | LCMS method No | RT | MS (m/z) | configuration |
|---|---|---|---|---|---|
| 1-139 | 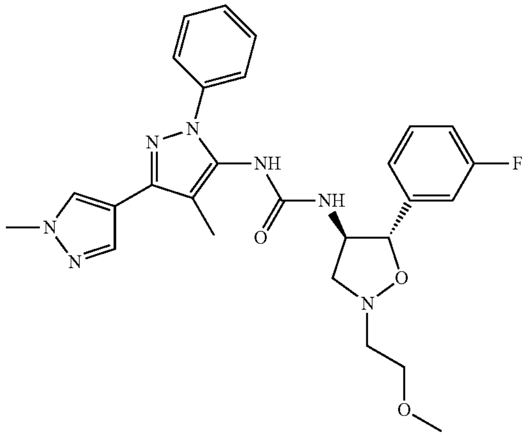 [SMILES: COCCN1C[C@@H](NC(=O)Nc2c(C)c(-c3cnn(C)c3)nn2-c2ccccc2)[C@H](c2cccc(F)c2)O1] | 1 | 1.64 | 520.25 | racemate |
| 1-140 | 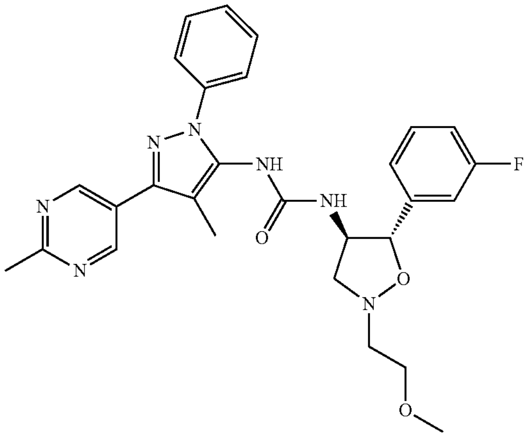 [SMILES: COCCN1C[C@@H](NC(=O)Nc2c(C)c(-c3cnc(C)nc3)nn2-c2ccccc2)[C@H](c2cccc(F)c2)O1] | 1 | 1.68 | 532.25 | racemate |
| 1-141 | 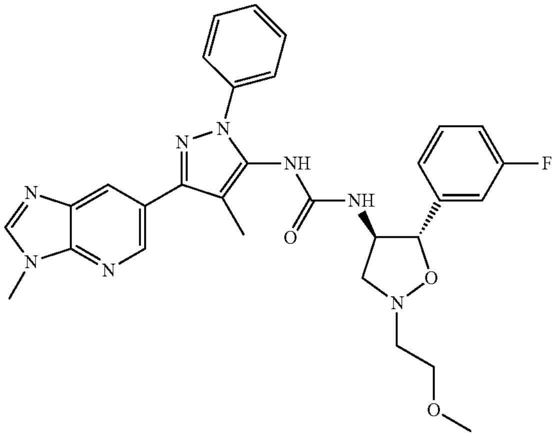 [SMILES: COCCN1C[C@@H](NC(=O)Nc2c(C)c(-c3cnc4c(c3)ncn4C)nn2-c2ccccc2)[C@H](c2cccc(F)c2)O1] | 1 | 1.53 | 571.25 | racemate |

TABLE 29-continued
| No. | Structure | LCMS method No | RT | MS (m/z) | configuration |
|---|---|---|---|---|---|
| 1-142 | 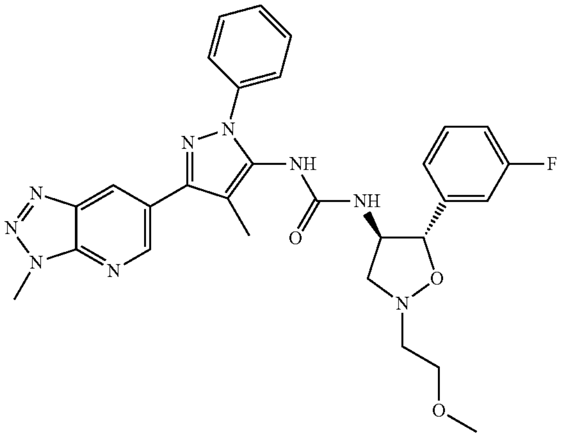 [SMILES: COCCN1C[C@@H](NC(=O)Nc2c(C)c(-c3cnc4c(c3)nnn4C)nn2-c2ccccc2)[C@H](c2cccc(F)c2)O1] | 1 | 1.79 | 572.25 | racemate |
| 1-143 | 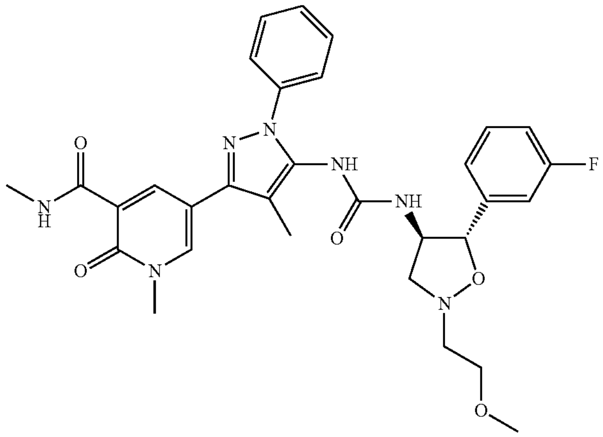 [SMILES: CNC(=O)c1cc(-c2nn(-c3ccccc3)c(NC(=O)N[C@@H]3CN(CCOC)O[C@H]3c3cccc(F)c3)c2C)cn(C)c1=O] | 1 | 1.65 | 604.2 | racemate |
TABLE 30
| No. | Structure | LCMS method No | RT | MS (m/z) | configuration |
|---|---|---|---|---|---|
| I-144 | 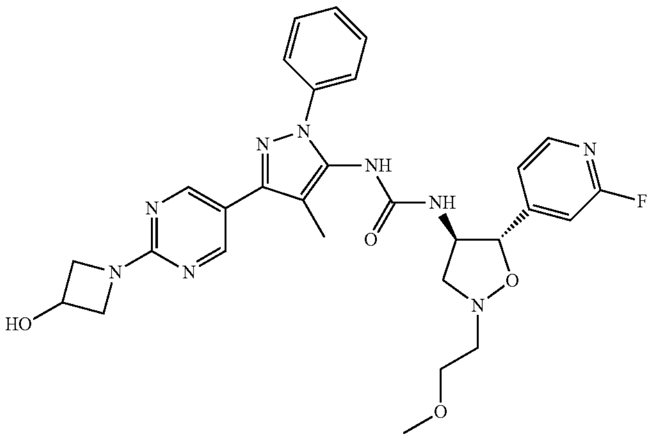 [SMILES: COCCN1C[C@@H](NC(=O)Nc2c(C)c(-c3cnc(N4CC(O)C4)nc3)nn2-c2ccccc2)[C@H](c2ccnc(F)c2)O1] | 1 | 1.32 | 590.25 | racemate |

TABLE 30-continued
| No. | Structure | LCMS method No | RT | MS (m/z) | configuration |
|---|---|---|---|---|---|
| I-145 | 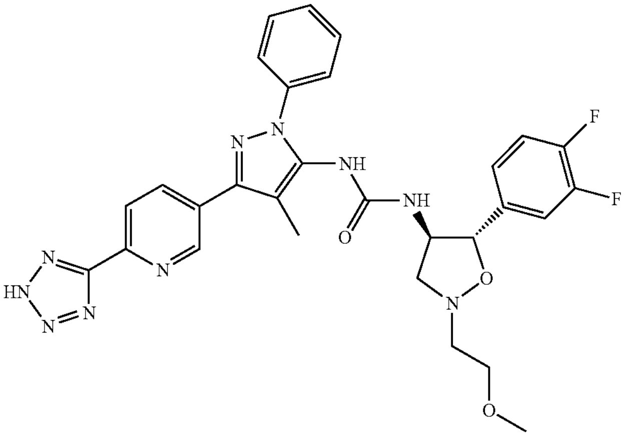 [SMILES: COCCN1C[C@@H](NC(=O)Nc2c(C)c(-c3ccc(-c4nn[nH]n4)nc3)nn2-c2ccccc2)[C@H](c2ccc(F)c(F)c2)O1] | 2 | 1.85 | 603 | racemate |
| I-146 | 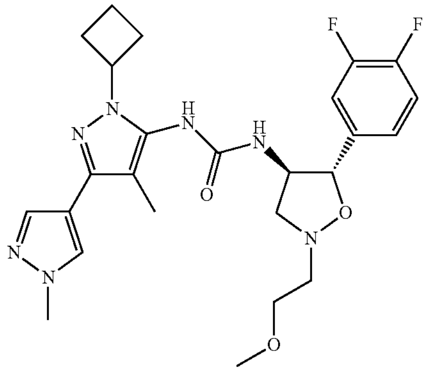 [SMILES: COCCN1C[C@@H](NC(=O)Nc2c(C)c(-c3cnn(C)c3)nn2C2CCC2)[C@H](c2ccc(F)c(F)c2)O1] | 2 | 1.72 | 516 | racemate |
| I-147 | 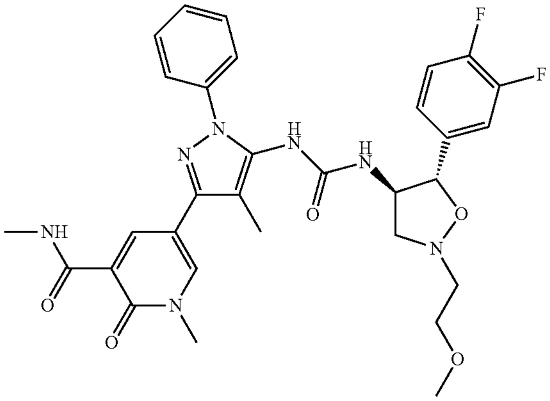 [SMILES: CNC(=O)c1cc(-c2nn(-c3ccccc3)c(NC(=O)N[C@@H]3CN(CCOC)O[C@H]3c3ccc(F)c(F)c3)c2C)cn(C)c1=O] | 2 | 1.77 | 622 | racemate |

TABLE 30-continued
| No. | Structure | LCMS method No | RT | MS (m/z) | configuration |
|---|---|---|---|---|---|
| I-148 | 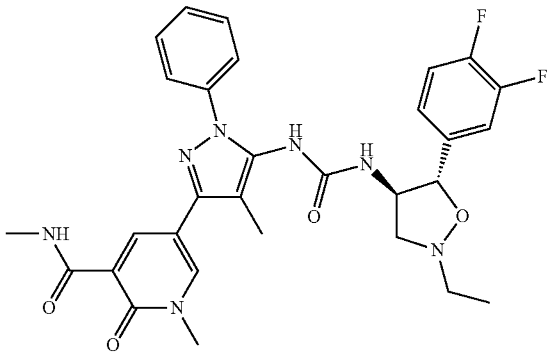 [SMILES: CCN1C[C@@H](NC(=O)Nc2c(C)c(-c3cc(C(=O)NC)c(=O)n(C)c3)nn2-c2ccccc2)[C@H](c2ccc(F)c(F)c2)O1] | 2 | 1.75 | 592 | racemate |
TABLE 31
| No. | Structure | LCMS method No | RT | MS (m/z) | configuration |
|---|---|---|---|---|---|
| I-149 | 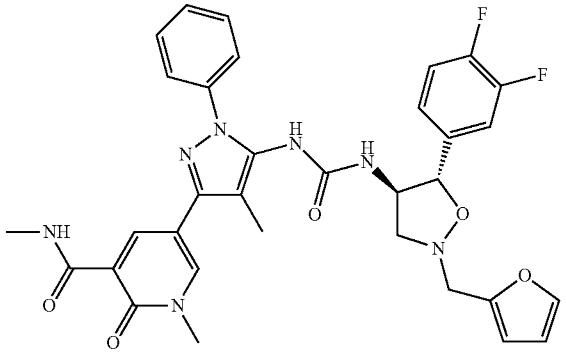 [SMILES: CNC(=O)c1cc(-c2nn(-c3ccccc3)c(NC(=O)N[C@@H]3CN(Cc4ccco4)O[C@H]3c3ccc(F)c(F)c3)c2C)cn(C)c1=O] | 2 | 2 | 644 | racemate |
| I-150 | 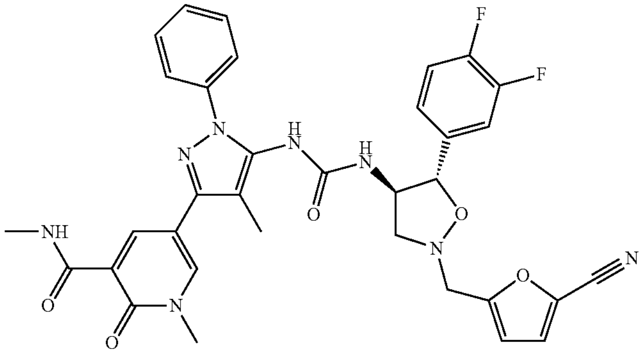 [SMILES: CNC(=O)c1cc(-c2nn(-c3ccccc3)c(NC(=O)N[C@@H]3CN(Cc4ccc(C#N)o4)O[C@H]3c3ccc(F)c(F)c3)c2C)cn(C)c1=O] | 2 | 2.01 | 669 | racemate |

TABLE 31-continued
| No. | Structure | LCMS method No | RT | MS (m/z) | configuration |
|---|---|---|---|---|---|
| I-151 | 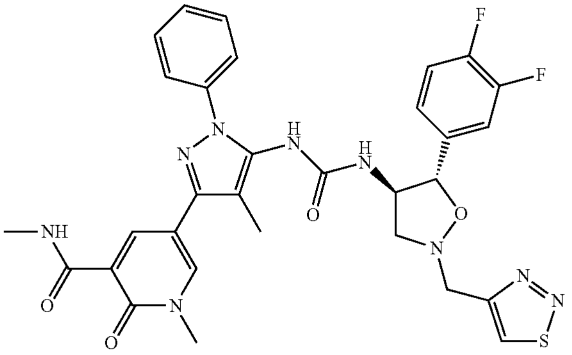 [SMILES: CNC(=O)c1cc(-c2nn(-c3ccccc3)c(NC(=O)N[C@@H]3CN(Cc4csnn4)O[C@H]3c3ccc(F)c(F)c3)c2C)cn(C)c1=O] | 2 | 1.8 | 662 | racemate |
| I-152 | 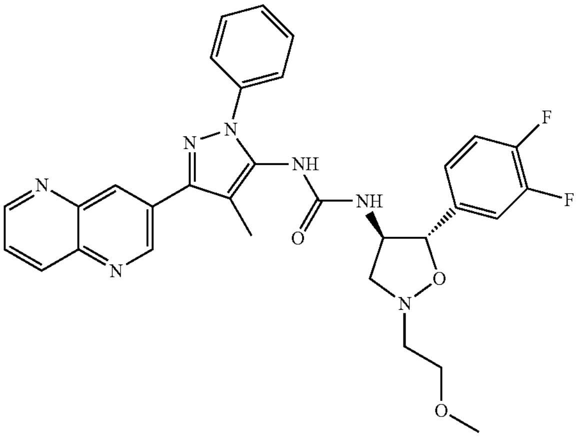 [SMILES: COCCN1C[C@@H](NC(=O)Nc2c(C)c(-c3cnc4cccnc4c3)nn2-c2ccccc2)[C@H](c2ccc(F)c(F)c2)O1] | 1 | 1.81 | 586 | racemate |
| I-153 | 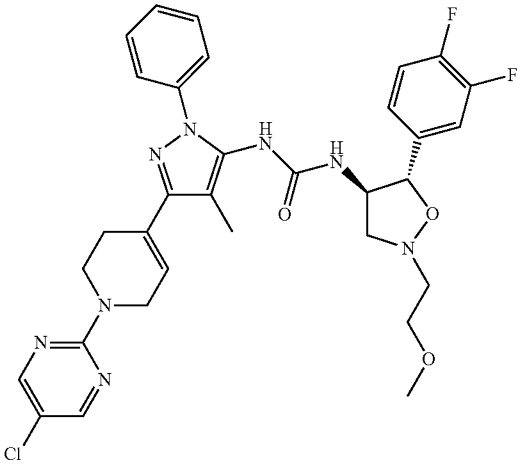 [SMILES: COCCN1C[C@@H](NC(=O)Nc2c(C)c(C3=CCN(c4ncc(Cl)cn4)CC3)nn2-c2ccccc2)[C@H](c2ccc(F)c(F)c2)O1] | 1 | 2.52 | 651.25 | racemate |

TABLE 32
| No. | Structure | LCMS method No | RT | MS (m/z) | configuration |
|---|---|---|---|---|---|
| I-154 | 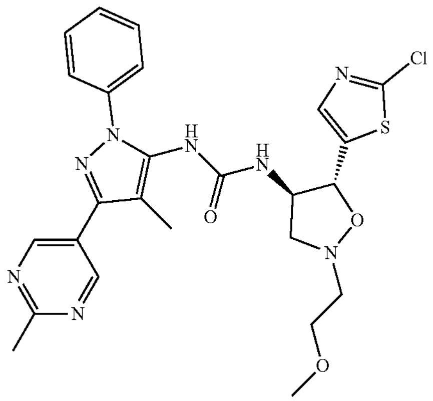 [SMILES: COCCN1C[C@@H](NC(=O)Nc2c(C)c(-c3cnc(C)nc3)nn2-c2ccccc2)[C@H](c2cnc(Cl)s2)O1] | 1 | 1.6 | 555.15 | racemate |
| I-155 | 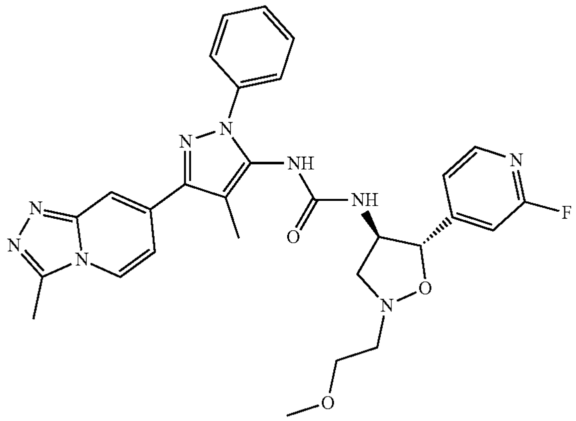 [SMILES: COCCN1C[C@@H](NC(=O)Nc2c(C)c(-c3ccn4c(C)nnc4c3)nn2-c2ccccc2)[C@H](c2ccnc(F)c2)O1] | 1 | 1.28 | 572.2 | racemate |
| I-156 | 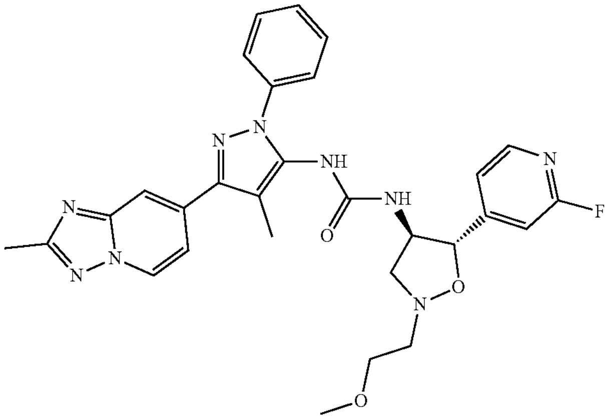 [SMILES: COCCN1C[C@@H](NC(=O)Nc2c(C)c(-c3ccn4nc(C)nc4c3)nn2-c2ccccc2)[C@H](c2ccnc(F)c2)O1] | 1 | 1.49 | 572.2 | racemate |

TABLE 32-continued
| No. | Structure | LCMS method No | RT | MS (m/z) | configuration |
|---|---|---|---|---|---|
| I-157 | 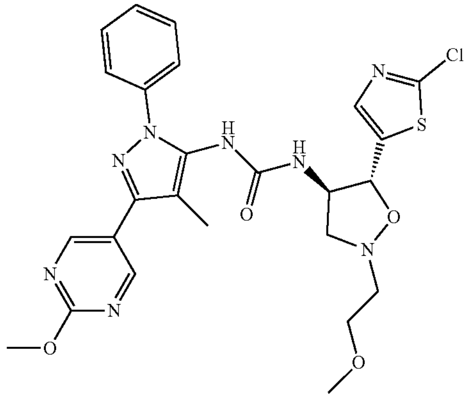 [SMILES: COCCN1C[C@@H](NC(=O)Nc2c(C)c(-c3cnc(OC)nc3)nn2-c2ccccc2)[C@H](c2cnc(Cl)s2)O1] | 1 | 1.73 | 571.15 | racemate |
| I-158 | 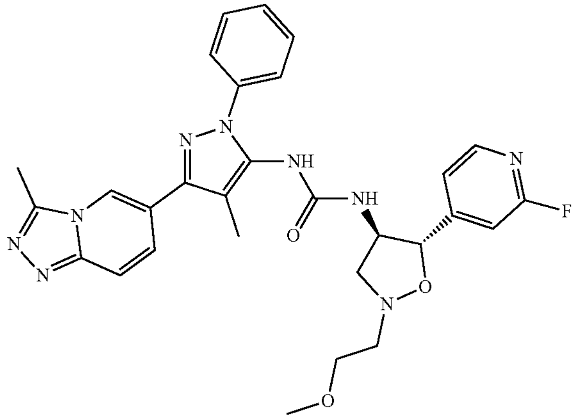 [SMILES: COCCN1C[C@@H](NC(=O)Nc2c(C)c(-c3ccc4nnc(C)n4c3)nn2-c2ccccc2)[C@H](c2ccnc(F)c2)O1] | 1 | 1.31 | 572.2 | racemate |
TABLE 33
| No. | Structure | LCMS method No | RT | MS (m/z) | configuration |
|---|---|---|---|---|---|
| I-159 | 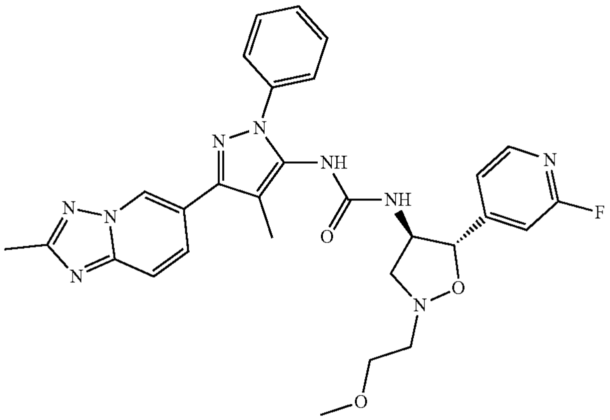 [SMILES: COCCN1C[C@@H](NC(=O)Nc2c(C)c(-c3ccc4nc(C)nn4c3)nn2-c2ccccc2)[C@H](c2ccnc(F)c2)O1] | 1 | 1.5 | 572.2 | racemate |

TABLE 33-continued
| No. | Structure | LCMS method No | RT | MS (m/z) | configuration |
|---|---|---|---|---|---|
| I-160 | 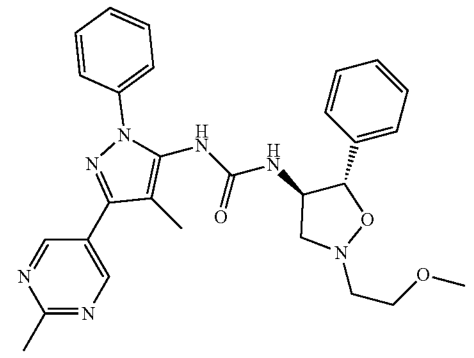 [SMILES: COCCN1C[C@@H](NC(=O)Nc2c(C)c(-c3cnc(C)nc3)nn2-c2ccccc2)[C@H](c2ccccc2)O1] | 2 | 1.75 | 514 | racemate |
| 1-161 | 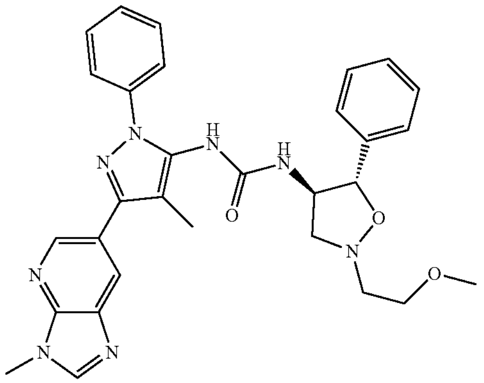 | 2 | 1.54 | 553 | racemate |
| I-162 | 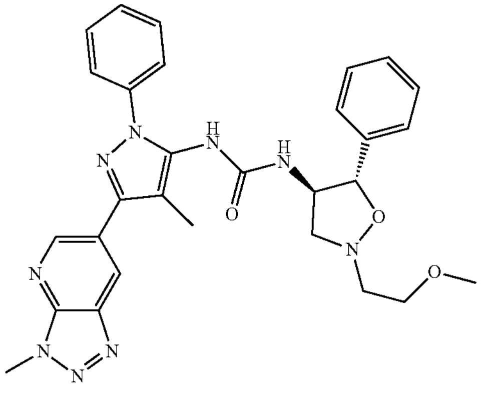 | 2 | 1.77 | 554 | racemate |

TABLE 33-continued
| No. | Structure | LCMS method No | RT | MS (m/z) | configuration |
|---|---|---|---|---|---|
| I-163 | 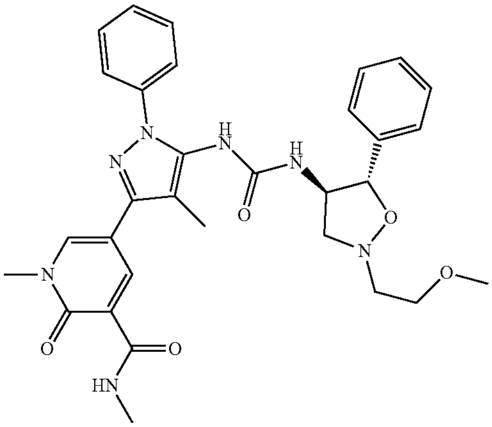 | 2 | 1.59 | 586 | racemate |
TABLE 34
| No. | Structure | LCMS method No | RT | MS (m/z) | configuration |
|---|---|---|---|---|---|
| I-164 | 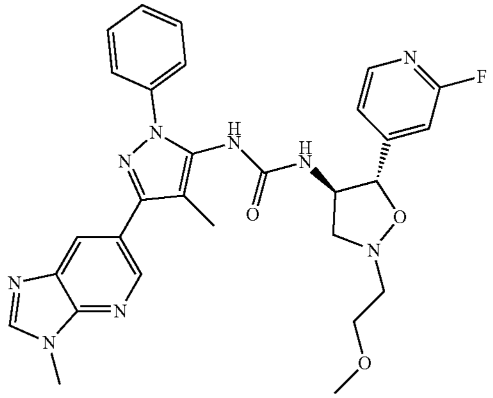 [SMILES: COCCN1C[C@@H](NC(=O)Nc2c(C)c(-c3cnc4c(c3)ncn4C)nn2-c2ccccc2)[C@H](c2ccnc(F)c2)O1] | 1 | 1.31 | 572.2 | racemate |
| I-165 | 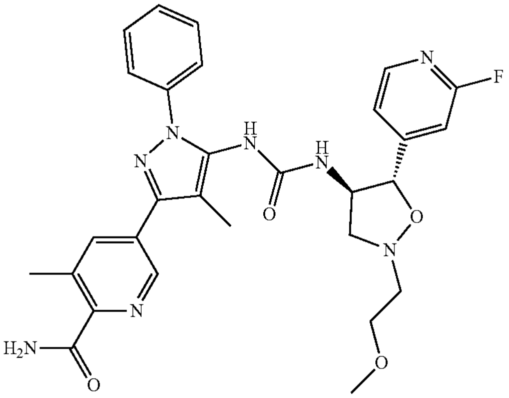 [SMILES: COCCN1C[C@@H](NC(=O)Nc2c(C)c(-c3cnc(C(N)=O)c(C)c3)nn2-c2ccccc2)[C@H](c2ccnc(F)c2)O1] | 2 | 1.77 | 575 | racemate |

TABLE 34-continued
| No. | Structure | LCMS method No | RT | MS (m/z) | configuration |
|---|---|---|---|---|---|
| I-166 | 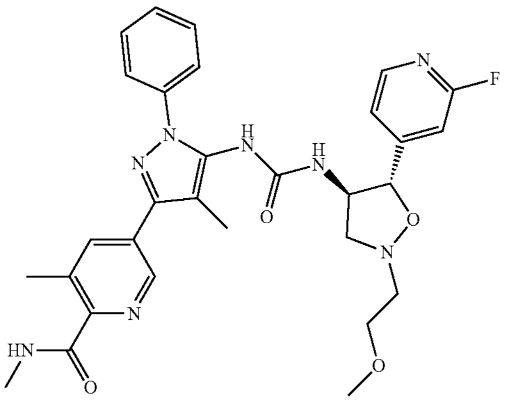 [SMILES: CNC(=O)c1ncc(-c2nn(-c3ccccc3)c(NC(=O)N[C@@H]3CN(CCOC)O[C@H]3c3ccnc(F)c3)c2C)cc1C] | 2 | 1.88 | 589 | racemate |
| I-167 | 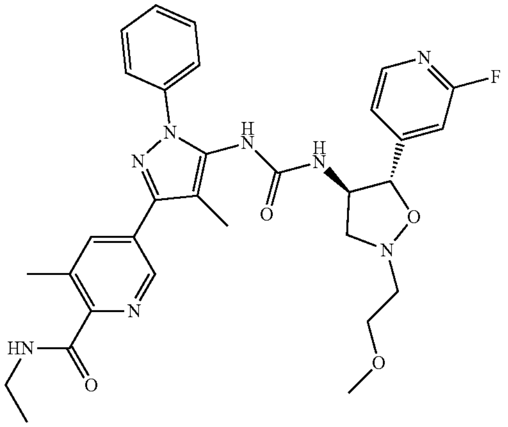 [SMILES: CCNC(=O)c1ncc(-c2nn(-c3ccccc3)c(NC(=O)N[C@@H]3CN(CCOC)O[C@H]3c3ccnc(F)c3)c2C)cc1C] | 2 | 2.03 | 603 | racemate |
| I-168 | 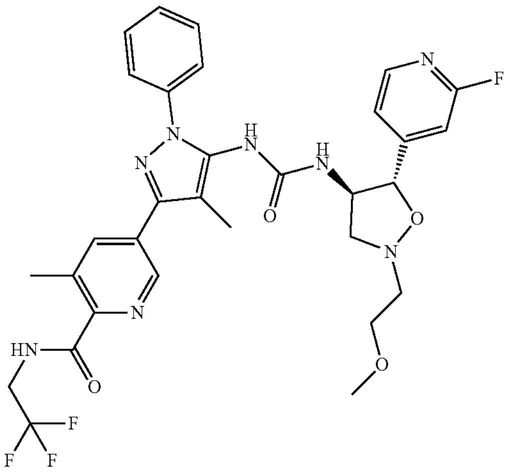 [SMILES: COCCN1C[C@@H](NC(=O)Nc2c(C)c(-c3cnc(C(=O)NCC(F)(F)F)c(C)c3)nn2-c2ccccc2)[C@H](c2ccnc(F)c2)O1] | 2 | 2.37 | 657 | racemate |

TABLE 35
| No. | Structure | LCMS method No | RT | MS (m/z) | configuration |
|---|---|---|---|---|---|
| I-169 | 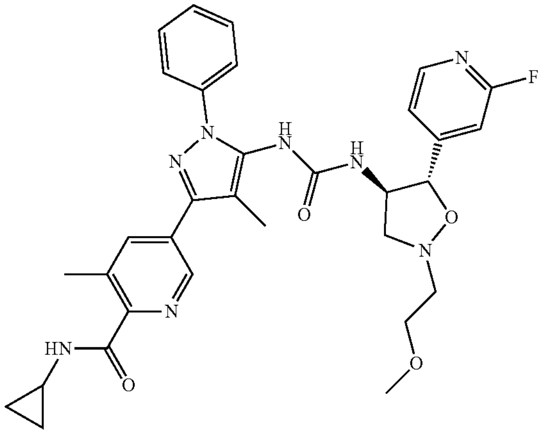 [SMILES: COCCN1C[C@@H](NC(=O)Nc2c(C)c(-c3cnc(C(=O)NC4CC4)c(C)c3)nn2-c2ccccc2)[C@H](c2ccnc(F)c2)O1] | 2 | 2.06 | 615 | racemate |
| I-170 | 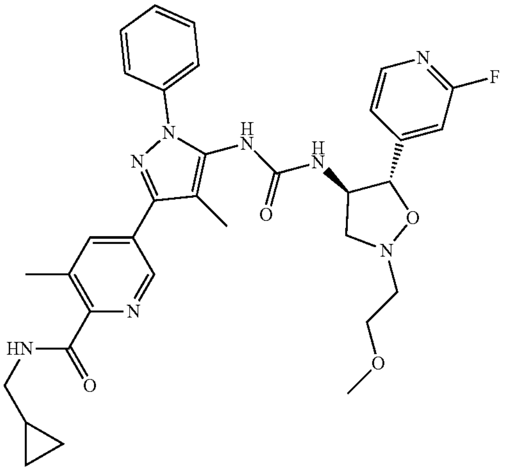 [SMILES: COCCN1C[C@@H](NC(=O)Nc2c(C)c(-c3cnc(C(=O)NCC4CC4)c(C)c3)nn2-c2ccccc2)[C@H](c2ccnc(F)c2)O1] | 2 | 2.28 | 629 | racemate |
| I-171 | 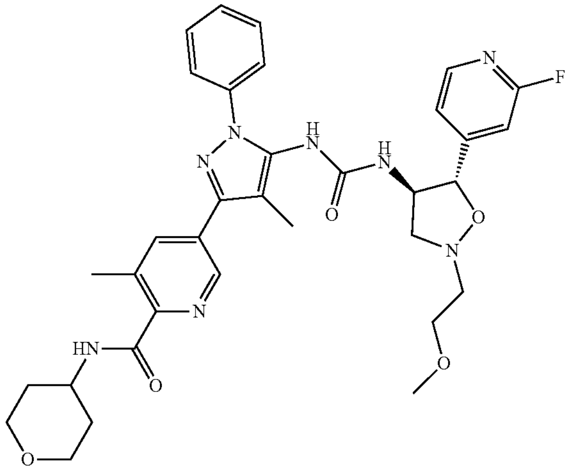 [SMILES: COCCN1C[C@@H](NC(=O)Nc2c(C)c(-c3cnc(C(=O)NC4CCOCC4)c(C)c3)nn2-c2ccccc2)[C@H](c2ccnc(F)c2)O1] | 2 | 1.97 | 659 | racemate |

TABLE 35-continued
| No. | Structure | LCMS method No | RT | MS (m/z) | configuration |
|---|---|---|---|---|---|
| I-172 | 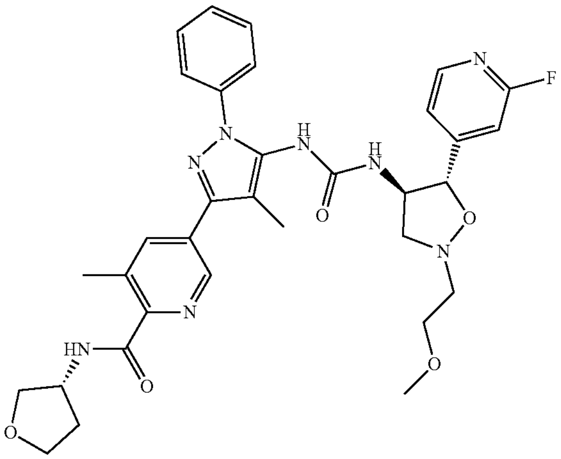 [SMILES: COCCN1C[C@@H](NC(=O)Nc2c(C)c(-c3cnc(C(=O)N[C@@H]4CCOC4)c(C)c3)nn2-c2ccccc2)[C@H](c2ccnc(F)c2)O1] | 2 | 1.93 | 645 | Diastereo mixture |
TABLE 36
| No. | Structure | LCMS method No | RT | MS (m/z) | configuration |
|---|---|---|---|---|---|
| I-173 | 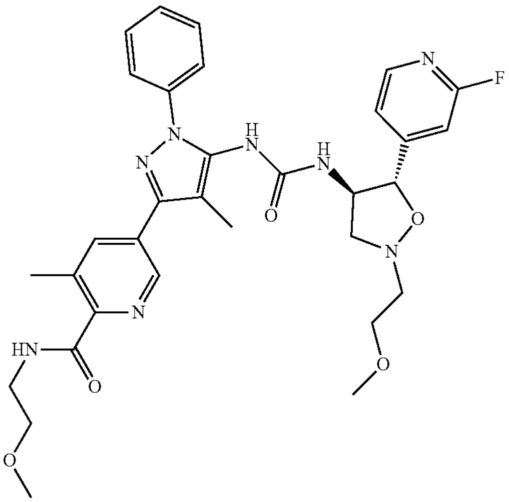 [SMILES: COCCNC(=O)c1ncc(-c2nn(-c3ccccc3)c(NC(=O)N[C@@H]3CN(CCOC)O[C@H]3c3ccnc(F)c3)c2C)cc1C] | 2 | 1.99 | 633 | racemate |
| I-174 | 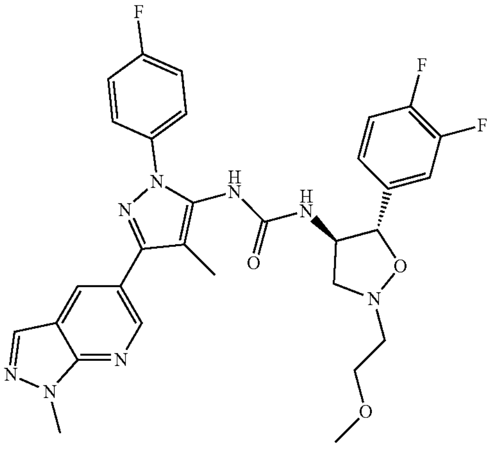 [SMILES: COCCN1C[C@@H](NC(=O)Nc2c(C)c(-c3cnc4c(cnn4C)c3)nn2-c2ccc(F)cc2)[C@H](c2ccc(F)c(F)c2)O1] | 2 | 2.34 | 607 | racemate |

TABLE 36-continued
| No. | Structure | LCMS method No | RT | MS (m/z) | configuration |
|---|---|---|---|---|---|
| I-175 | 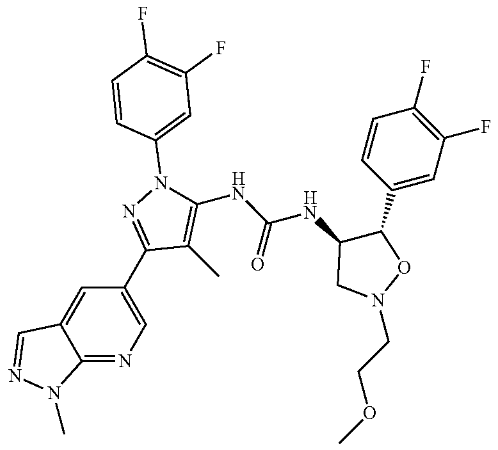 [SMILES: COCCN1C[C@@H](NC(=O)Nc2c(C)c(-c3cnc4c(cnn4C)c3)nn2-c2ccc(F)c(F)c2)[C@H](c2ccc(F)c(F)c2)O1] | 2 | 2.46 | 625 | racemate |
| I-176 | 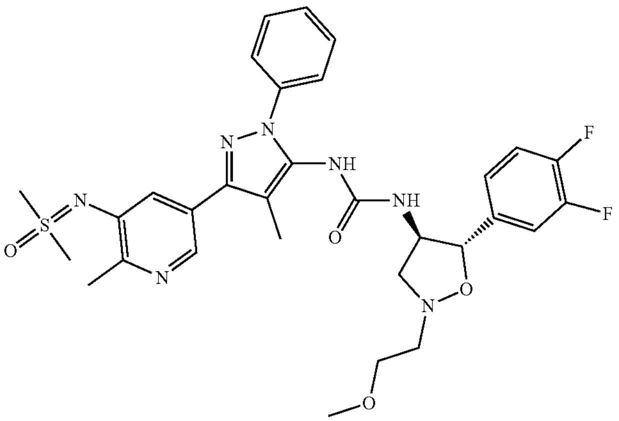 [SMILES: COCCN1C[C@@H](NC(=O)Nc2c(C)c(-c3cnc(C)c(N=S(C)(C)=O)c3)nn2-c2ccccc2)[C@H](c2ccc(F)c(F)c2)O1] | 1 | 1.31 | 640.2 | racemate |
| I-177 | 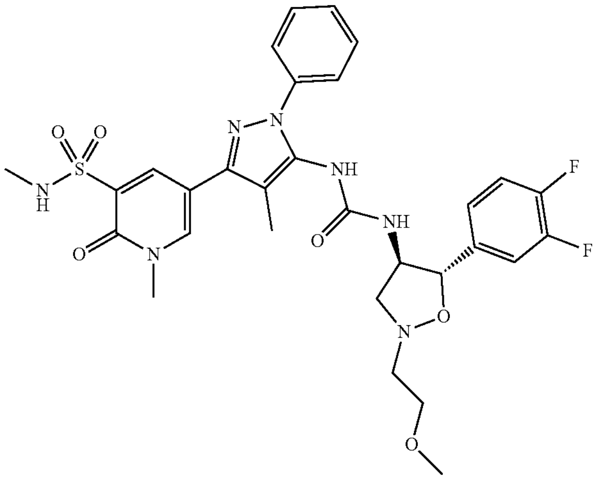 [SMILES: CNS(=O)(=O)c1cc(-c2nn(-c3ccccc3)c(NC(=O)N[C@@H]3CN(CCOC)O[C@H]3c3ccc(F)c(F)c3)c2C)cn(C)c1=O] | 2 | 2.13 | 658 | racemate |

TABLE 37
| No. | Structure | LCMS method No | RT | MS (m/z) | configuration |
|---|---|---|---|---|---|
| I-178 | 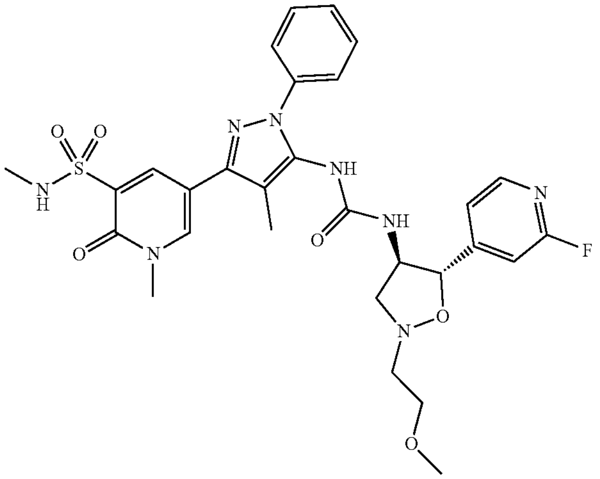 [SMILES: CNS(=O)(=O)c1cc(-c2nn(-c3ccccc3)c(NC(=O)N[C@@H]3CN(CCOC)O[C@H]3c3ccnc(F)c3)c2C)cn(C)c1=O] | 2 | 1.81 | 641 | racemate |
| I-179 | 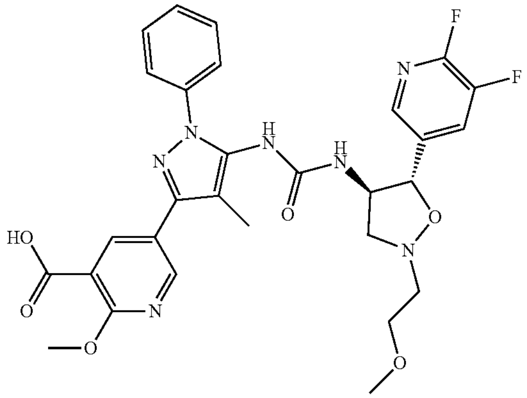 [SMILES: COCCN1C[C@@H](NC(=O)Nc2c(C)c(-c3cnc(OC)c(C(=O)O)c3)nn2-c2ccccc2)[C@H](c2cnc(F)c(F)c2)O1] | 2 | 1.73 | 610 | racemate |
| I-180 | 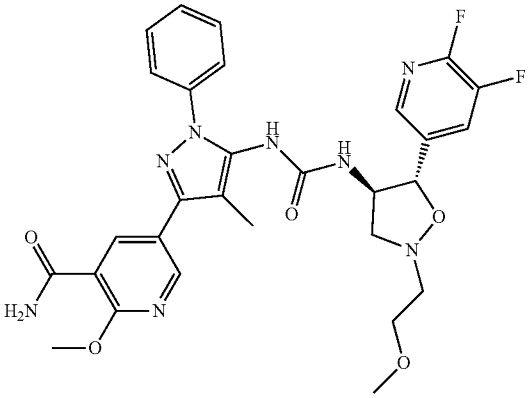 [SMILES: COCCN1C[C@@H](NC(=O)Nc2c(C)c(-c3cnc(OC)c(C(N)=O)c3)nn2-c2ccccc2)[C@H](c2cnc(F)c(F)c2)O1] | 2 | 1.69 | 609 | |

TABLE 37-continued
| No. | Structure | LCMS method No | RT | MS (m/z) | configuration |
|---|---|---|---|---|---|
| I-181 | 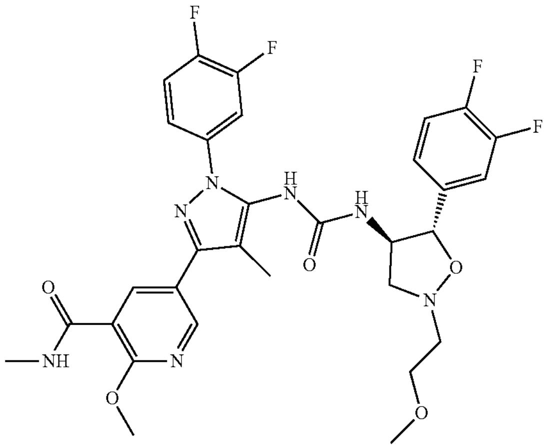 [SMILES: CNC(=O)c1cc(-c2nn(-c3ccc(F)c(F)c3)c(NC(=O)N[C@@H]3CN(CCOC)O[C@H]3c3ccc(F)c(F)c3)c2C)cnc1OC] | 2 | 2.06 | 658 | racemate |
| I-182 | 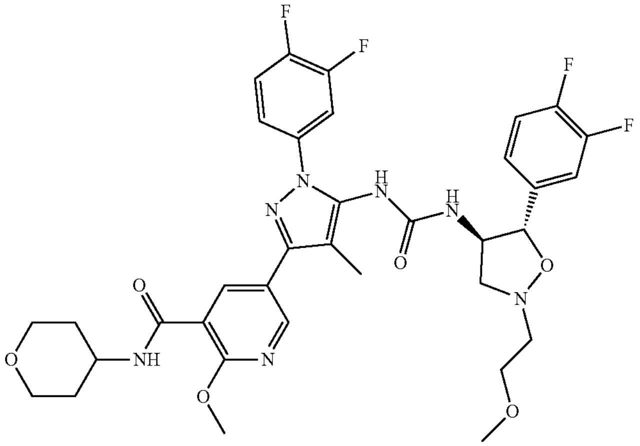 [SMILES: COCCN1C[C@@H](NC(=O)Nc2c(C)c(-c3cnc(OC)c(C(=O)NC4CCOCC4)c3)nn2-c2ccc(F)c(F)c2)[C@H](c2ccc(F)c(F)c2)O1] | 2 | 2.14 | 728 | racemate |
TABLE 38
| No. | Structure | LCMS method No | RT | MS (m/z) | configuration |
|---|---|---|---|---|---|
| I-183 | 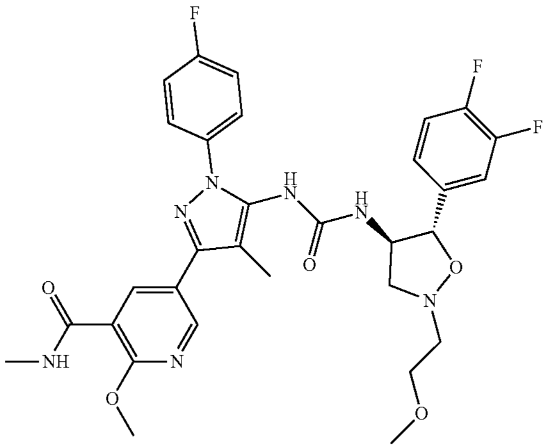 [SMILES: CNC(=O)c1cc(-c2nn(-c3ccc(F)cc3)c(NC(=O)N[C@@H]3CN(CCOC)O[C@H]3c3ccc(F)c(F)c3)c2C)cnc1OC] | 2 | 1.98 | 640 | racemate |

TABLE 38-continued
| No. | Structure | LCMS method No | RT | MS (m/z) | configuration |
|---|---|---|---|---|---|
| I-184 | 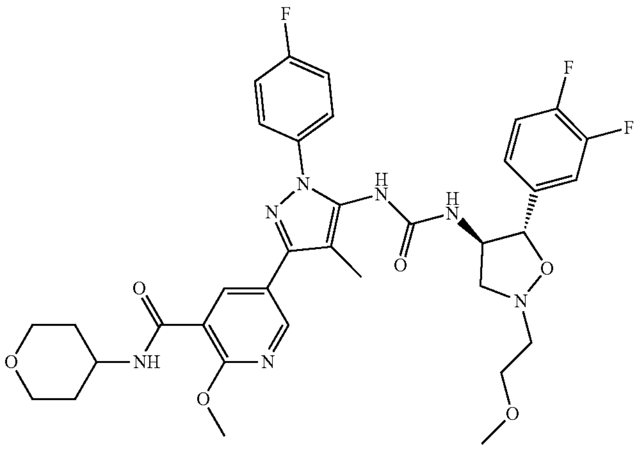 [SMILES: COCCN1C[C@@H](NC(=O)Nc2c(C)c(-c3cnc(OC)c(C(=O)NC4CCOCC4)c3)nn2-c2ccc(F)cc2)[C@H](c2ccc(F)c(F)c2)O1] | 2 | 2.05 | 710 | racemate |
| I-185 | 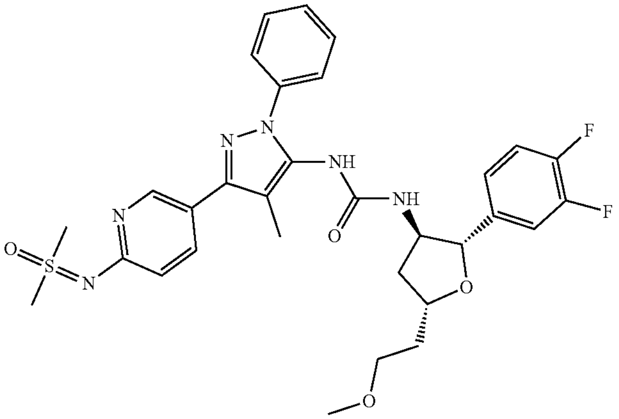 [SMILES: COCC[C@@H]1C[C@@H](NC(=O)Nc2c(C)c(-c3ccc(N=S(C)(C)=O)nc3)nn2-c2ccccc2)[C@H](c2ccc(F)c(F)c2)O1] | 1 | 1.49 | 625.25 | racemate |
| I-186 | 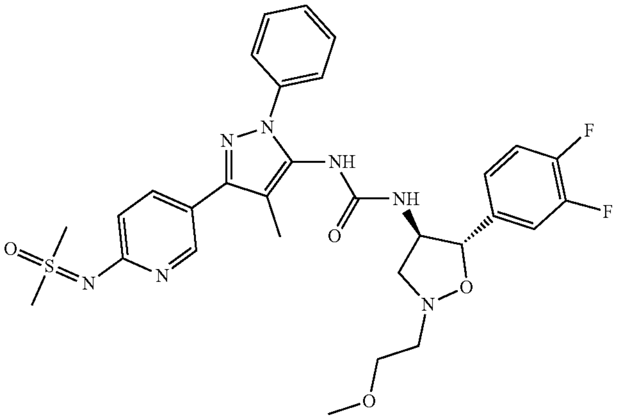 [SMILES: COCCN1C[C@@H](NC(=O)Nc2c(C)c(-c3ccc(N=S(C)(C)=O)nc3)nn2-c2ccccc2)[C@H](c2ccc(F)c(F)c2)O1] | 1 | 1.41 | 626.2 | |

TABLE 38-continued
| No. | Structure | LCMS method No | RT | MS (m/z) | configuration |
|---|---|---|---|---|---|
| I-187 | 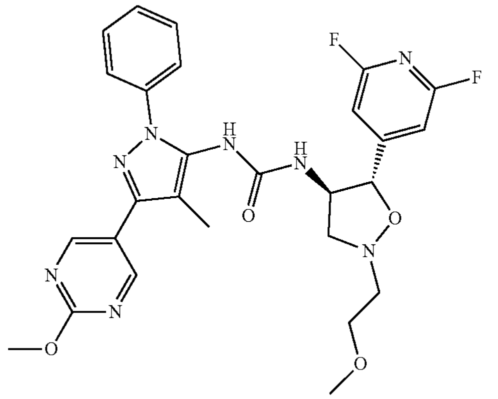 [SMILES: COCCN1C[C@@H](NC(=O)Nc2c(C)c(-c3cnc(OC)nc3)nn2-c2ccccc2)[C@H](c2cc(F)nc(F)c2)O1] | 1 | 1.82 | 567.25 | racemate |
TABLE 39
| No. | Structure | LCMS method No | RT | MS (m/z) | configuration |
|---|---|---|---|---|---|
| I-188 | 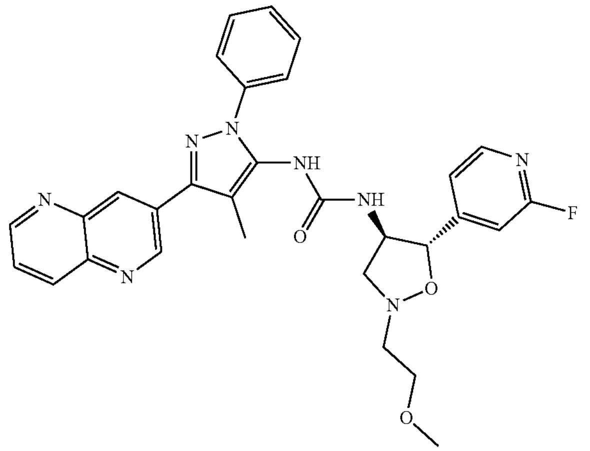 [SMILES: COCCN1C[C@@H](NC(=O)Nc2c(C)c(-c3cnc4cccnc4c3)nn2-c2ccccc2)[C@H](c2ccnc(F)c2)O1] | 2 | 1.92 | 569 | racemate |
| I-189 | 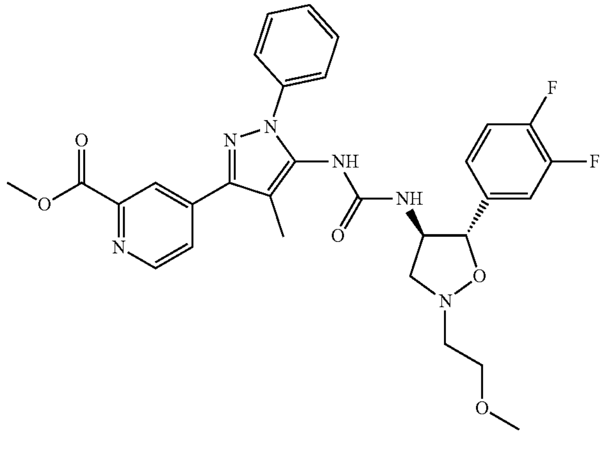 [SMILES: COCCN1C[C@@H](NC(=O)Nc2c(C)c(-c3ccnc(C(=O)OC)c3)nn2-c2ccccc2)[C@H](c2ccc(F)c(F)c2)O1] | 1 | 1.87 | 593.2 | racemate |

TABLE 39-continued
| No. | Structure | LCMS method No | RT | MS (m/z) | configuration |
|---|---|---|---|---|---|
| I-190 | 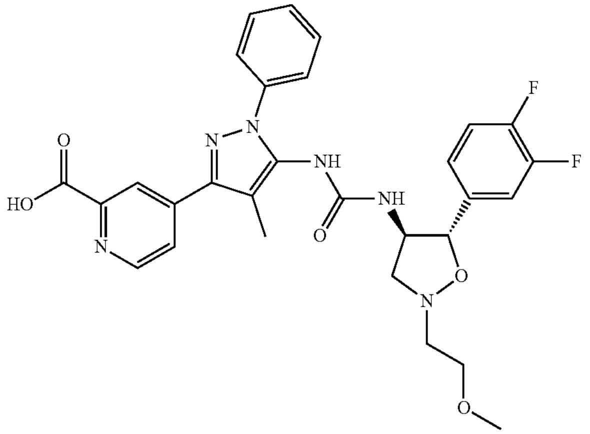 [SMILES: COCCN1C[C@@H](NC(=O)Nc2c(C)c(-c3ccnc(C(=O)O)c3)nn2-c2ccccc2)[C@H](c2ccc(F)c(F)c2)O1] | 1 | 1.49 | 579.2 | racemate |
| I-191 | 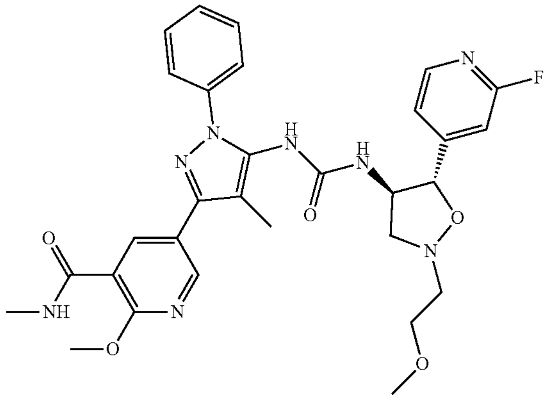 [SMILES: CNC(=O)c1cc(-c2nn(-c3ccccc3)c(NC(=O)N[C@@H]3CN(CCOC)O[C@H]3c3ccnc(F)c3)c2C)cnc1OC] | 2 | 1.61 | 605 | |
| I-192 | 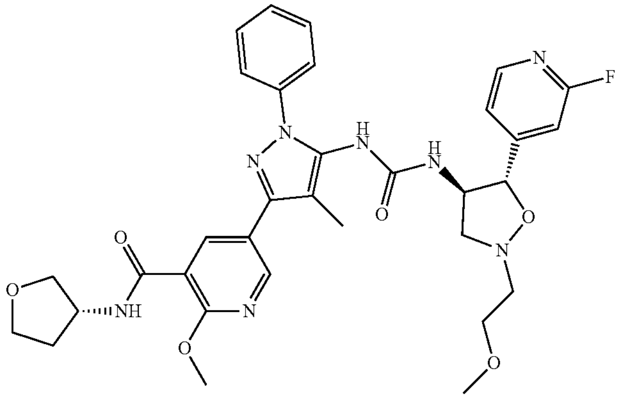 [SMILES: COCCN1C[C@@H](NC(=O)Nc2c(C)c(-c3cnc(OC)c(C(=O)N[C@@H]4CCOC4)c3)nn2-c2ccccc2)[C@H](c2ccnc(F)c2)O1] | 2 | 1.66 | 661 | |

TABLE 40
| No. | Structure | LCMS method No | RT | MS (m/z) | configuration |
| --- | --- | --- | --- | --- | --- |
| I-193 | 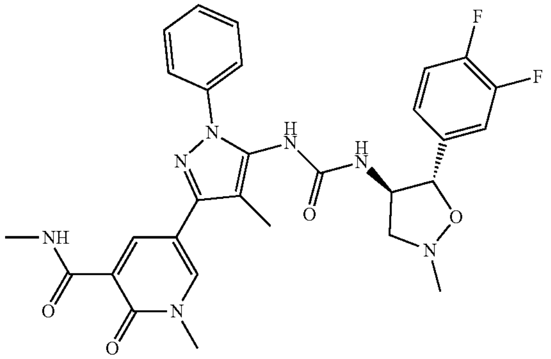 [SMILES: CNC(=O)c1cc(-c2nn(-c3ccccc3)c(NC(=O)N[C@@H]3CN(C)O[C@H]3c3ccc(F)c(F)c3)c2C)cn(C)c1=O] | 2 | 1.66 | 578 | racemate |
| I-194 | 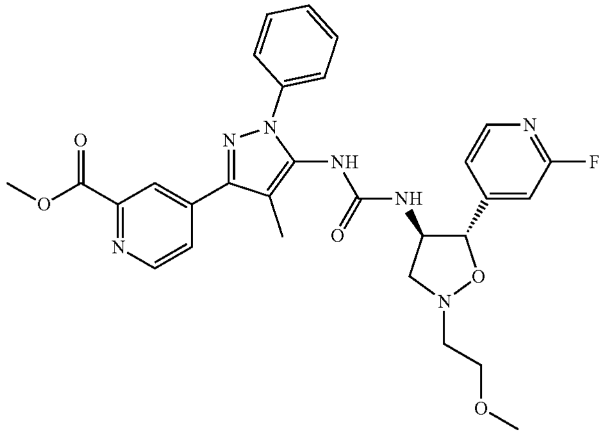 [SMILES: COCCN1C[C@@H](NC(=O)Nc2c(C)c(-c3ccnc(C(=O)OC)c3)nn2-c2ccccc2)[C@H](c2ccnc(F)c2)O1] | 1 | 1.58 | 576.25 | racemate |
| I-195 | 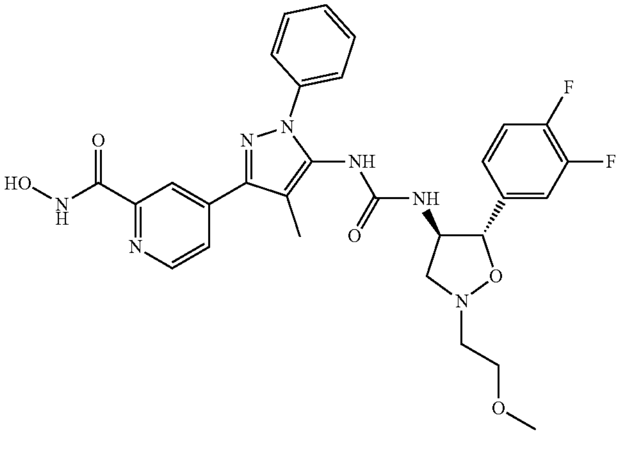 [SMILES: COCCN1C[C@@H](NC(=O)Nc2c(C)c(-c3ccnc(C(=O)NO)c3)nn2-c2ccccc2)[C@H](c2ccc(F)c(F)c2)O1] | 1 | 1.64 | 594.2 | racemate |

TABLE 40-continued
| No. | Structure | LCMS method No | RT | MS (m/z) | configuration |
|---|---|---|---|---|---|
| I-196 | 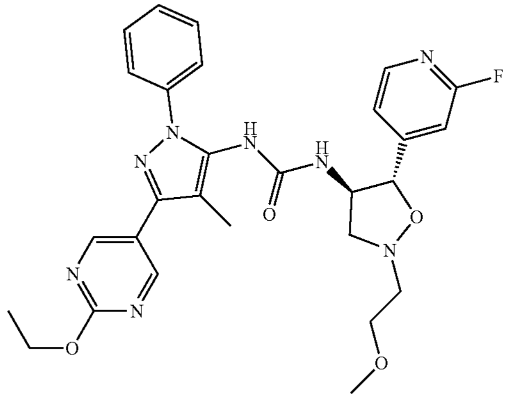 [SMILES: CCOc1ncc(-c2nn(-c3ccccc3)c(NC(=O)N[C@@H]3CN(CCOC)O[C@H]3c3ccnc(F)c3)c2C)cn1] | 1 | 1.73 | 563.2 | racemate |
| I-197 | 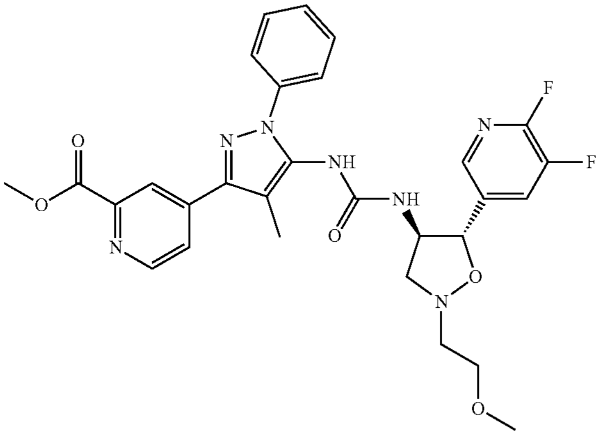 [SMILES: COCCN1C[C@@H](NC(=O)Nc2c(C)c(-c3ccnc(C(=O)OC)c3)nn2-c2ccccc2)[C@H](c2cnc(F)c(F)c2)O1] | 1 | 1.73 | 594.2 | |
40
TABLE 41
| No. | Structure | LCMS method No | RT | MS (m/z) | configuration |
|---|---|---|---|---|---|
| I-198 | 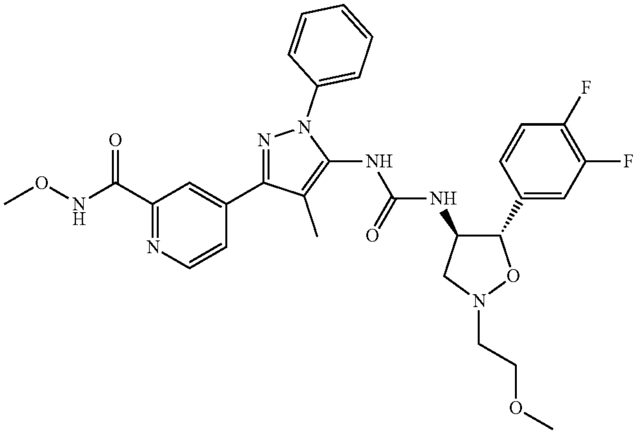 [SMILES: COCCN1C[C@@H](NC(=O)Nc2c(C)c(-c3ccnc(C(=O)NOC)c3)nn2-c2ccccc2)[C@H](c2ccc(F)c(F)c2)O1] | 1 | 1.79 | 608.25 | racemate |

TABLE 41-continued
| No. | Structure | LCMS method No | RT | MS (m/z) | configuration |
|---|---|---|---|---|---|
| I-199 | 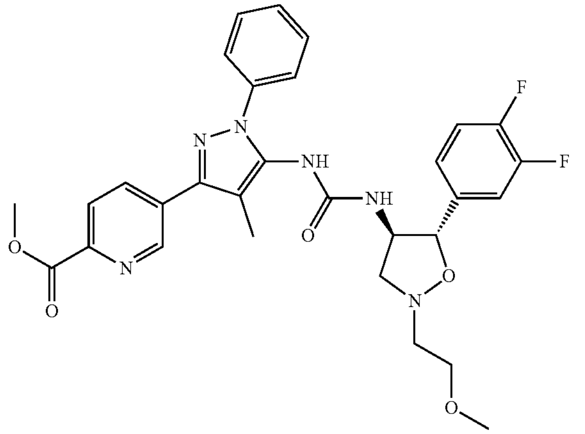 [SMILES: COCCN1C[C@@H](NC(=O)Nc2c(C)c(-c3ccc(C(=O)OC)nc3)nn2-c2ccccc2)[C@H](c2ccc(F)c(F)c2)O1] | 1 | 1.88 | 593.25 | racemate |
| I-200 | 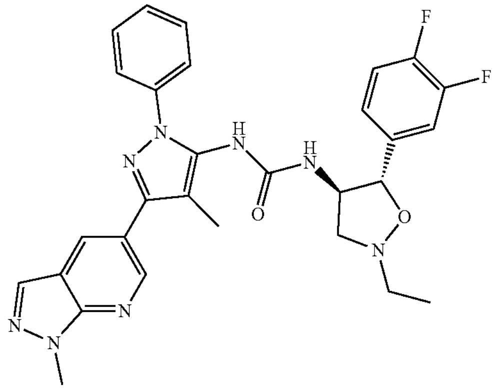 [SMILES: CCN1C[C@@H](NC(=O)Nc2c(C)c(-c3cnc4c(cnn4C)c3)nn2-c2ccccc2)[C@H](c2ccc(F)c(F)c2)O1] | 1 | 2.02 | 559 | racemate |
| I-201 | 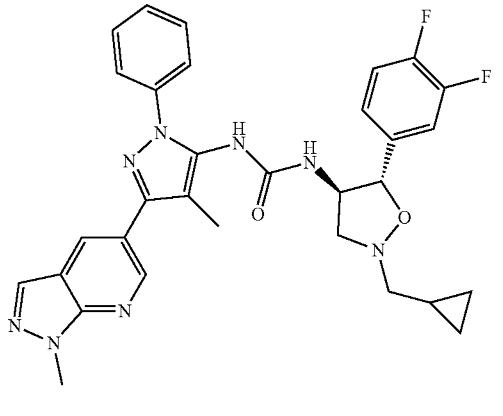 [SMILES: Cc1c(-c2cnc3c(cnn3C)c2)nn(-c2ccccc2)c1NC(=O)N[C@@H]1CN(CC2CC2)O[C@H]1c1ccc(F)c(F)c1] | 1 | 2.2 | 585 | racemate |

TABLE 41-continued
| No. | Structure | LCMS method No | RT | MS (m/z) | configuration |
| --- | --- | --- | --- | --- | --- |
| I-202 | 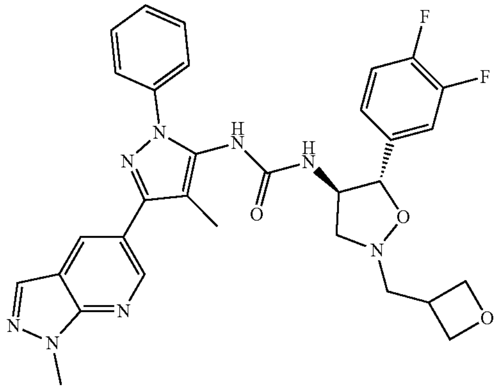 [SMILES: Cc1c(-c2cnc3c(cnn3C)c2)nn(-c2ccccc2)c1NC(=O)N[C@@H]1CN(CC2COC2)O[C@H]1c1ccc(F)c(F)c1] | 1 | 1.95 | 601 | racemate |
TABLE 42
| No. | Structure | LCMS method No | RT | MS (m/z) | configuration |
| --- | --- | --- | --- | --- | --- |
| I-203 | 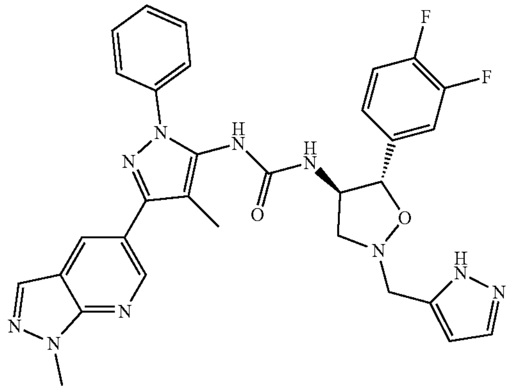 [SMILES: Cc1c(-c2cnc3c(cnn3C)c2)nn(-c2ccccc2)c1NC(=O)N[C@@H]1CN(Cc2ccn[nH]2)O[C@H]1c1ccc(F)c(F)c1] | 1 | 1.9 | 611 | racemate |
| I-204 | 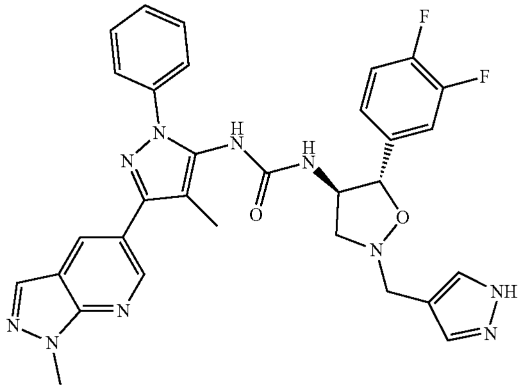 [SMILES: Cc1c(-c2cnc3c(cnn3C)c2)nn(-c2ccccc2)c1NC(=O)N[C@@H]1CN(Cc2cn[nH]c2)O[C@H]1c1ccc(F)c(F)c1] | 1 | 1.82 | 611 | racemate |

TABLE 42-continued
| No. | Structure | LCMS method No | RT | MS (m/z) | configuration |
|---|---|---|---|---|---|
| I-205 | 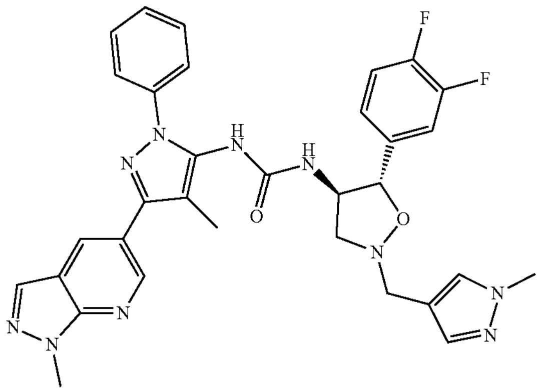 [SMILES: Cc1c(-c2cnc3c(cnn3C)c2)nn(-c2ccccc2)c1NC(=O)N[C@@H]1CN(Cc2cnn(C)c2)O[C@H]1c1ccc(F)c(F)c1] | 1 | 1.92 | 625 | racemate |
| I-206 | 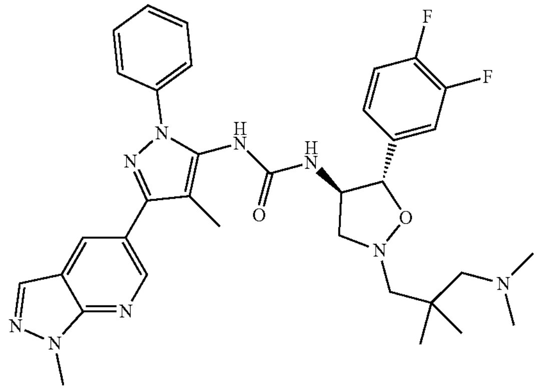 [SMILES: Cc1c(-c2cnc3c(cnn3C)c2)nn(-c2ccccc2)c1NC(=O)N[C@@H]1CN(CC(C)(C)CN(C)C)O[C@H]1c1ccc(F)c(F)c1] | 1 | 1.7 | 644 | racemate |
| I-207 | 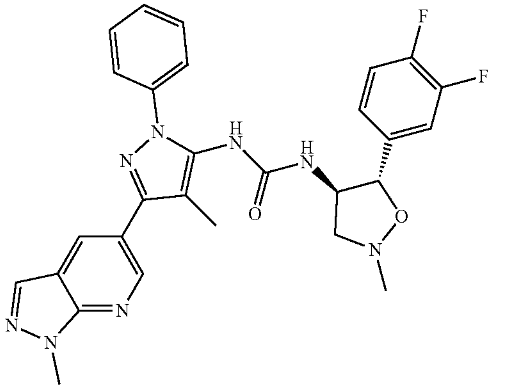 [SMILES: Cc1c(-c2cnc3c(cnn3C)c2)nn(-c2ccccc2)c1NC(=O)N[C@@H]1CN(C)O[C@H]1c1ccc(F)c(F)c1] | 2 | 1.87 | 545 | racemate |

TABLE 43
| No. | Structure | LCMS method No | RT | MS (m/z) | configuration |
|---|---|---|---|---|---|
| I-208 | 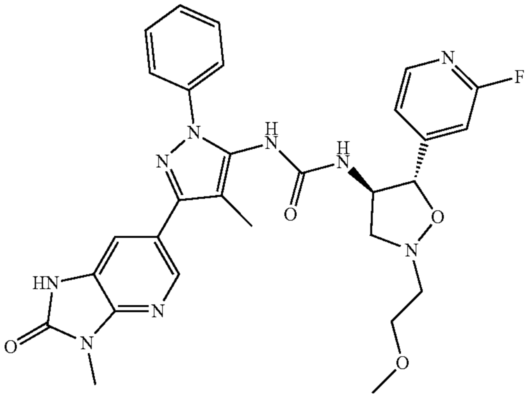 [SMILES: COCCN1C[C@@H](NC(=O)Nc2c(C)c(-c3cnc4c(c3)[nH]c(=O)n4C)nn2-c2ccccc2)[C@H](c2ccnc(F)c2)O1] | 2 | 1.4 | 588 | racemate |
| I-209 | 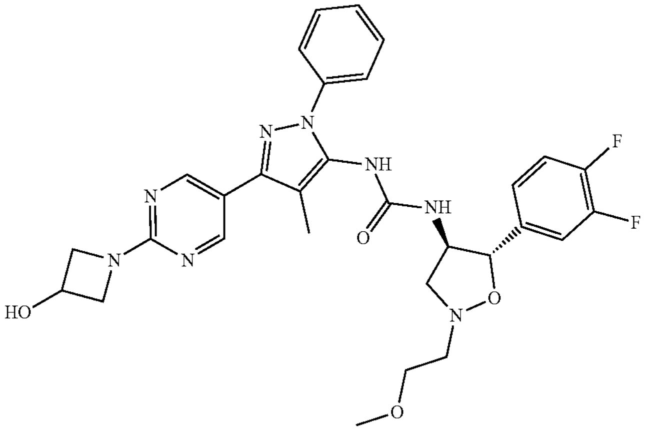 [SMILES: COCCN1C[C@@H](NC(=O)Nc2c(C)c(-c3cnc(N4CC(O)C4)nc3)nn2-c2ccccc2)[C@H](c2ccc(F)c(F)c2)O1] | 1 | 1.59 | 607.25 | |
| I-210 | 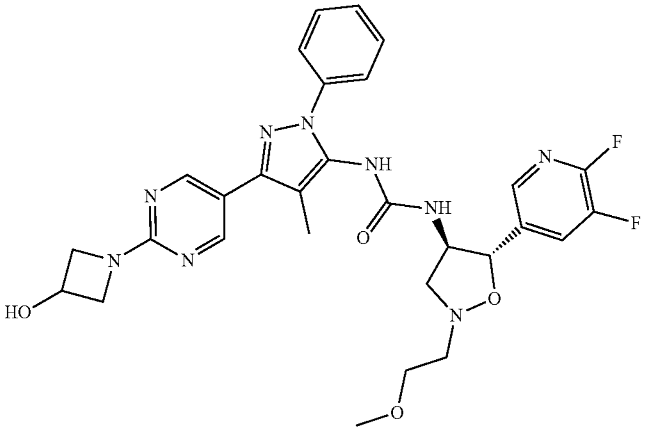 [SMILES: COCCN1C[C@@H](NC(=O)Nc2c(C)c(-c3cnc(N4CC(O)C4)nc3)nn2-c2ccccc2)[C@H](c2cnc(F)c(F)c2)O1] | 1 | 1.47 | 608.25 | |

TABLE 43-continued
| No. | Structure | LCMS method No | RT | MS (m/z) | configuration |
|---|---|---|---|---|---|
| I-211 | 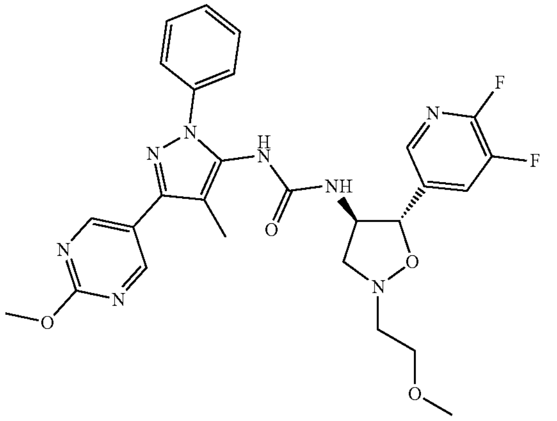 [SMILES: COCCN1C[C@@H](NC(=O)Nc2c(C)c(-c3cnc(OC)nc3)nn2-c2ccccc2)[C@H](c2cnc(F)c(F)c2)O1] | 1 | 1.76 | 567 | |
| I-212 | 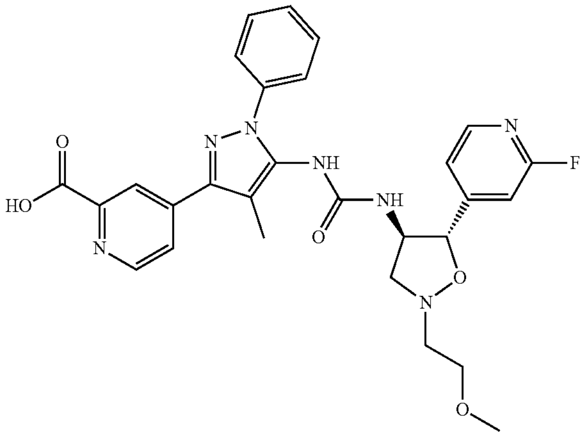 [SMILES: COCCN1C[C@@H](NC(=O)Nc2c(C)c(-c3ccnc(C(=O)O)c3)nn2-c2ccccc2)[C@H](c2ccnc(F)c2)O1] | 1 | 1.21 | 562.2 | racemate |
TABLE 44
| No. | Structure | LCMS method No | RT | MS (m/z) | configuration |
|---|---|---|---|---|---|
| I-213 | 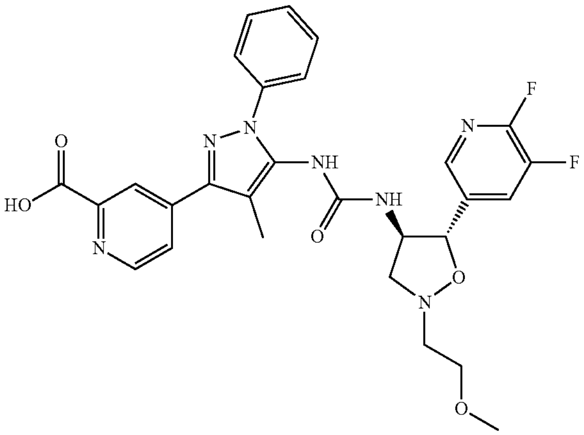 [SMILES: COCCN1C[C@@H](NC(=O)Nc2c(C)c(-c3ccnc(C(=O)O)c3)nn2-c2ccccc2)[C@H](c2cnc(F)c(F)c2)O1] | 1 | 1.36 | 580.2 | |

TABLE 44-continued
| No. | Structure | LCMS method No | RT | MS (m/z) | configuration |
|---|---|---|---|---|---|
| I-214 | 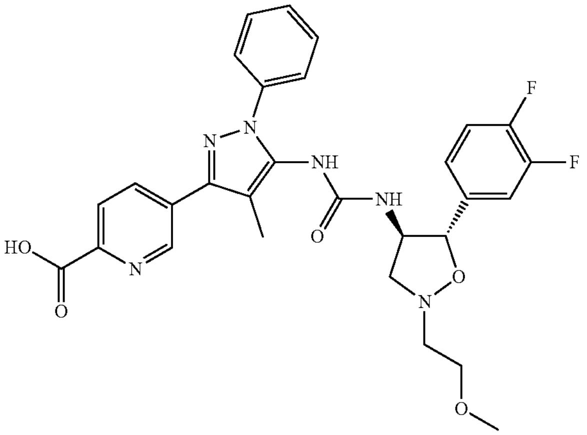 [SMILES: COCCN1C[C@@H](NC(=O)Nc2c(C)c(-c3ccc(C(=O)O)nc3)nn2-c2ccccc2)[C@H](c2ccc(F)c(F)c2)O1] | 1 | 1.6 | 579.2 | racemate |
| I-215 | 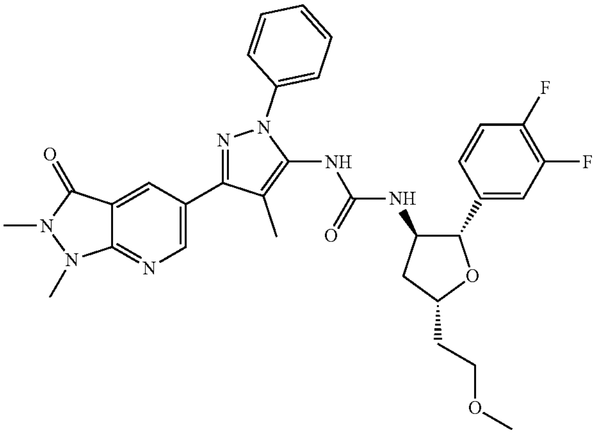 [SMILES: COCC[C@@H]1C[C@@H](NC(=O)Nc2c(C)c(-c3cnc4c(c3)c(=O)n(C)n4C)nn2-c2ccccc2)[C@H](c2ccc(F)c(F)c2)O1] | 1 | 1.81 | 618.25 | racemate |
| I-216 | 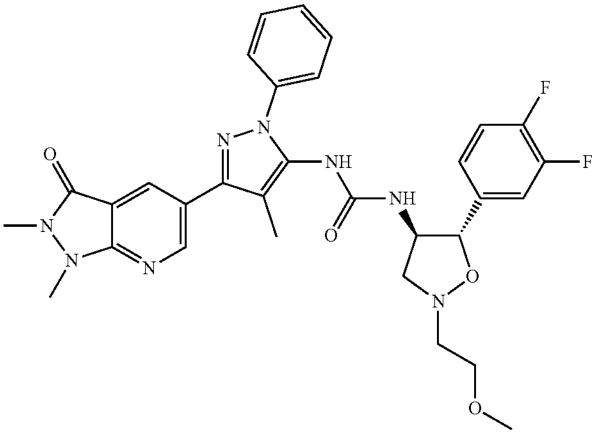 [SMILES: COCCN1C[C@@H](NC(=O)Nc2c(C)c(-c3cnc4c(c3)c(=O)n(C)n4C)nn2-c2ccccc2)[C@H](c2ccc(F)c(F)c2)O1] | 1 | 1.71 | 619.25 | |

TABLE 44-continued
| No. | Structure | LCMS method No | RT | MS (m/z) | configuration |
| --- | --- | --- | --- | --- | --- |
| I-217 | 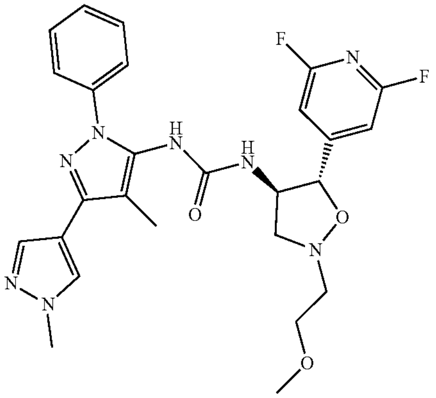 [SMILES: COCCN1C[C@@H](NC(=O)Nc2c(C)c(-c3cnn(C)c3)nn2-c2ccccc2)[C@H](c2cc(F)nc(F)c2)O1] | 1 | 1.66 | 539.25 | racemate |
TABLE 45
| No. | Structure | LCMS method No | RT | MS (m/z) | configuration |
| --- | --- | --- | --- | --- | --- |
| I-218 | 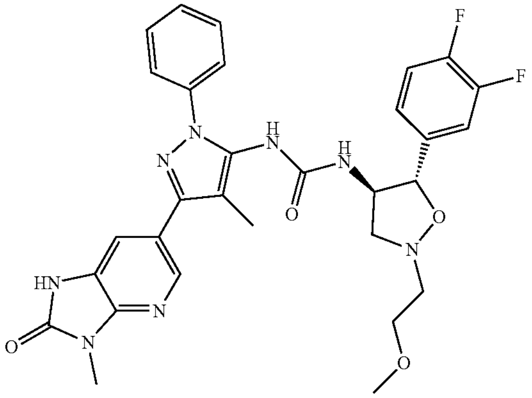 [SMILES: COCCN1C[C@@H](NC(=O)Nc2c(C)c(-c3cnc4c(c3)[nH]c(=O)n4C)nn2-c2ccccc2)[C@H](c2ccc(F)c(F)c2)O1] | 2 | 1.72 | 605 | |
| I-219 | 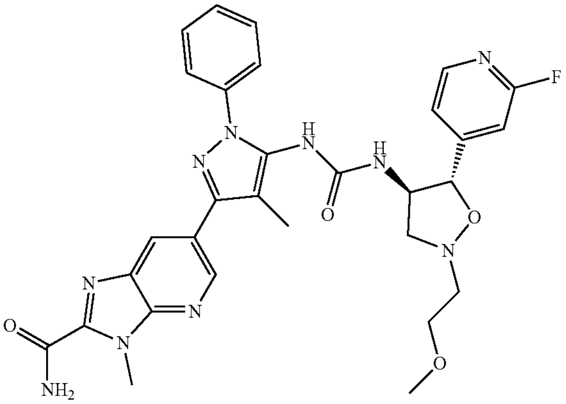 [SMILES: COCCN1C[C@@H](NC(=O)Nc2c(C)c(-c3cnc4c(c3)nc(C(N)=O)n4C)nn2-c2ccccc2)[C@H](c2ccnc(F)c2)O1] | 2 | 1.49 | 615 | racemate |

TABLE 45-continued
| No. | Structure | LCMS method No | RT | MS (m/z) | configuration |
|---|---|---|---|---|---|
| I-220 | 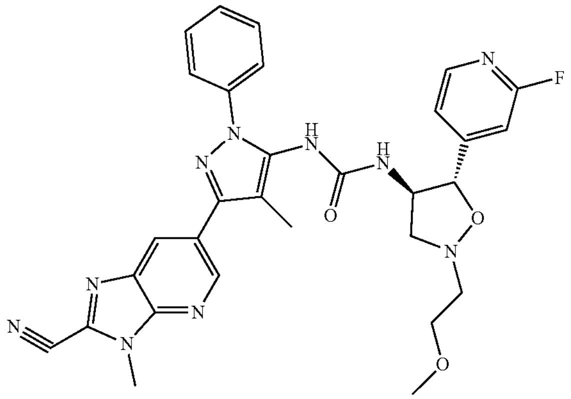 [SMILES: COCCN1C[C@@H](NC(=O)Nc2c(C)c(-c3cnc4c(c3)nc(C#N)n4C)nn2-c2ccccc2)[C@H](c2ccnc(F)c2)O1] | 2 | 1.75 | 597 | racemate |
| I-221 | 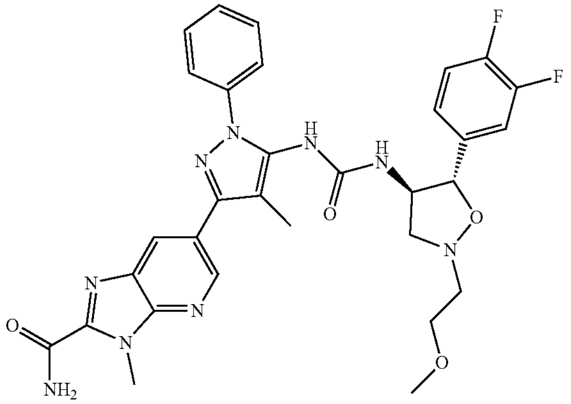 [SMILES: COCCN1C[C@@H](NC(=O)Nc2c(C)c(-c3cnc4c(c3)nc(C(N)=O)n4C)nn2-c2ccccc2)[C@H](c2ccc(F)c(F)c2)O1] | 2 | 1.79 | 632 | |
| I-222 | 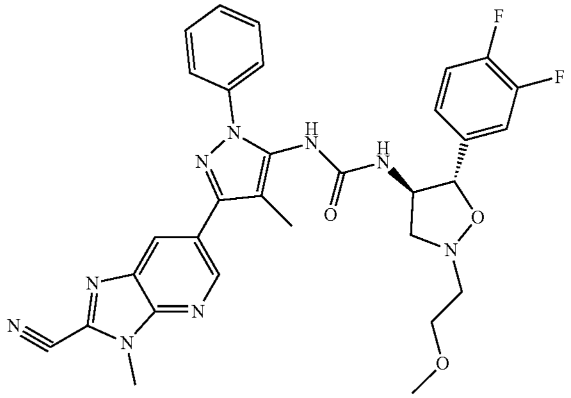 [SMILES: COCCN1C[C@@H](NC(=O)Nc2c(C)c(-c3cnc4c(c3)nc(C#N)n4C)nn2-c2ccccc2)[C@H](c2ccc(F)c(F)c2)O1] | 2 | 2.06 | 614 | |

TABLE 46
| No. | Structure | LCMS method No | RT | MS (m/z) | configuration |
|---|---|---|---|---|---|
| I-223 | 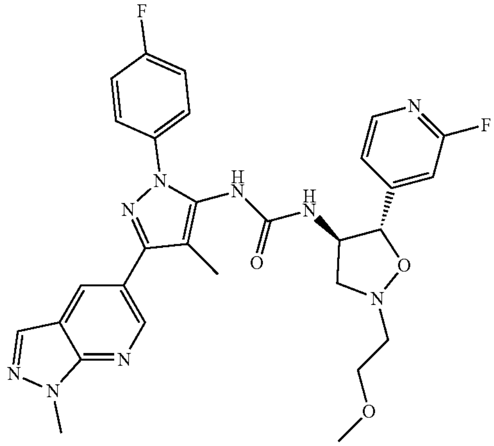 [SMILES: COCCN1C[C@@H](NC(=O)Nc2c(C)c(-c3cnc4c(cnn4C)c3)nn2-c2ccc(F)cc2)[C@H](c2ccnc(F)c2)O1] | 2 | 1.68 | 590 | racemate |
| I-224 | 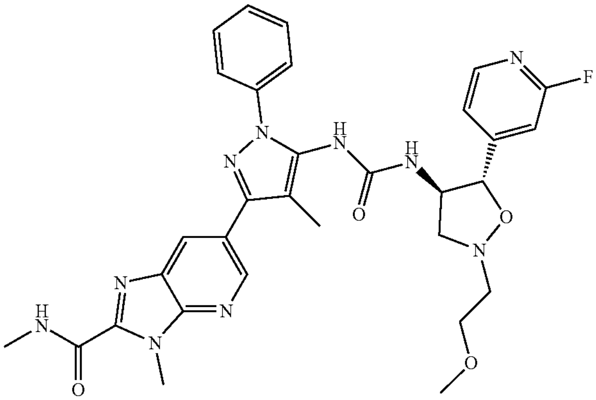 [SMILES: CNC(=O)c1nc2cc(-c3nn(-c4ccccc4)c(NC(=O)N[C@@H]4CN(CCOC)O[C@H]4c4ccnc(F)c4)c3C)cnc2n1C] | 2 | 1.59 | 629 | racemate |
| I-225 | 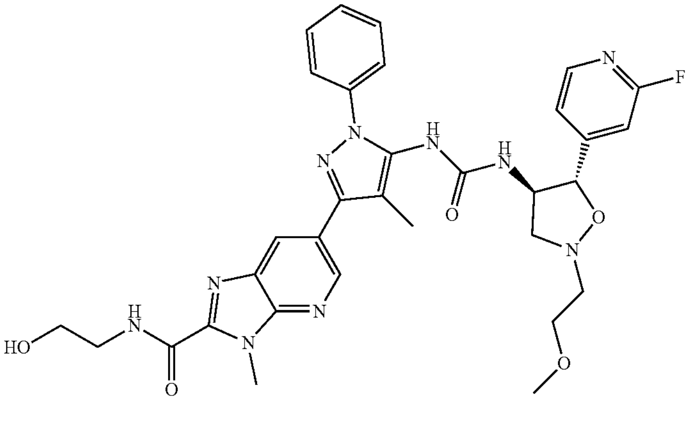 [SMILES: COCCN1C[C@@H](NC(=O)Nc2c(C)c(-c3cnc4c(c3)nc(C(=O)NCCO)n4C)nn2-c2ccccc2)[C@H](c2ccnc(F)c2)O1] | 2 | 1.45 | 659 | racemate |

TABLE 46-continued
| No. | Structure | LCMS method No | RT | MS (m/z) | configuration |
|---|---|---|---|---|---|
| I-226 | 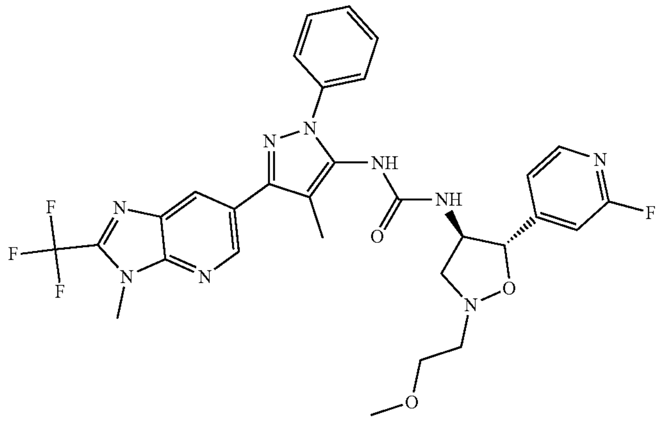 [SMILES: COCCN1C[C@@H](NC(=O)Nc2c(C)c(-c3cnc4c(c3)nc(C(F)(F)F)n4C)nn2-c2ccccc2)[C@H](c2ccnc(F)c2)O1] | 1 | 1.91 | 640.25 | racemate |
| I-227 | 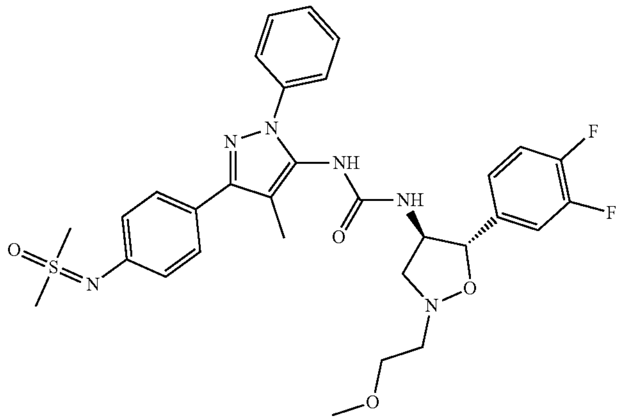 [SMILES: COCCN1C[C@@H](NC(=O)Nc2c(C)c(-c3ccc(N=S(C)(C)=O)cc3)nn2-c2ccccc2)[C@H](c2ccc(F)c(F)c2)O1] | 1 | 1.76 | 625.25 | |
TABLE 47
| No. | Structure | LCMS method No | RT | MS (m/z) | configuration |
|---|---|---|---|---|---|
| I-228 | 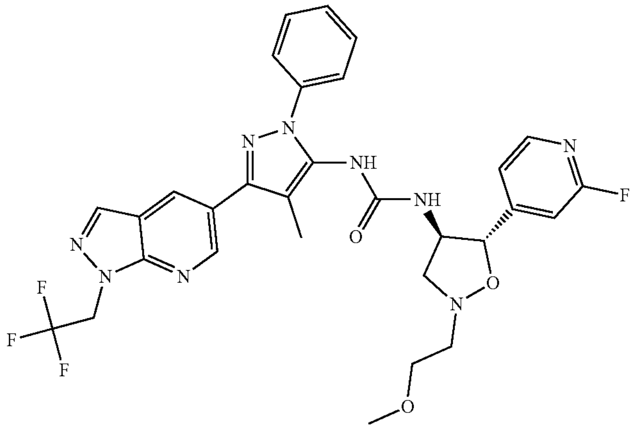 [SMILES: COCCN1C[C@@H](NC(=O)Nc2c(C)c(-c3cnc4c(cnn4CC(F)(F)F)c3)nn2-c2ccccc2)[C@H](c2ccnc(F)c2)O1] | 1 | 1.9 | 640.2 | racemate |

TABLE 47-continued
| No. | Structure | LCMS method No | RT | MS (m/z) | configuration |
|---|---|---|---|---|---|
| I-229 | 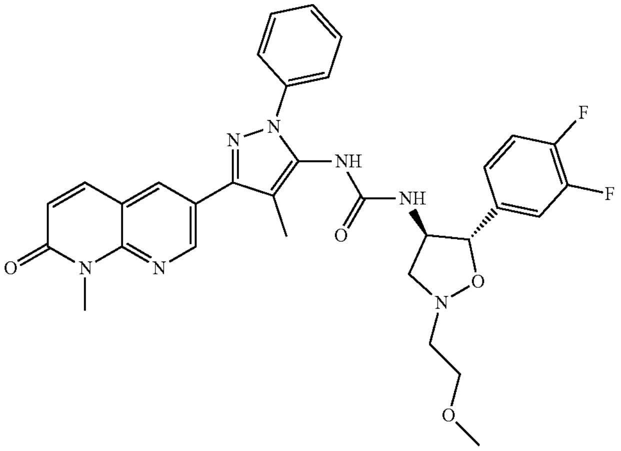 [SMILES: COCCN1C[C@@H](NC(=O)Nc2c(C)c(-c3cnc4c(ccc(=O)n4C)c3)nn2-c2ccccc2)[C@H](c2ccc(F)c(F)c2)O1] | 1 | 1.89 | 616 | |
| I-230 | 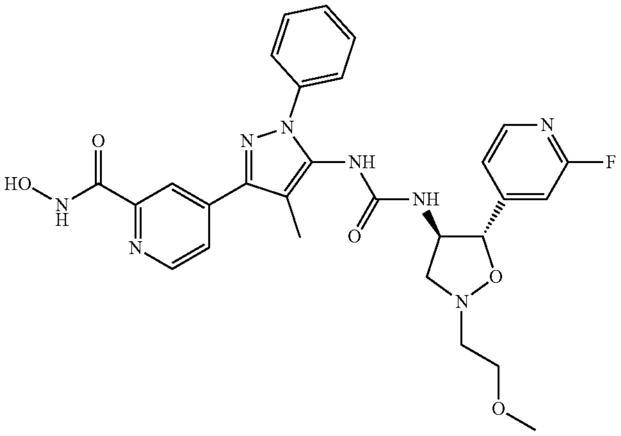 [SMILES: COCCN1C[C@@H](NC(=O)Nc2c(C)c(-c3ccnc(C(=O)NO)c3)nn2-c2ccccc2)[C@H](c2ccnc(F)c2)O1] | 1 | 1.37 | 577.25 | racemate |
| I-231 | 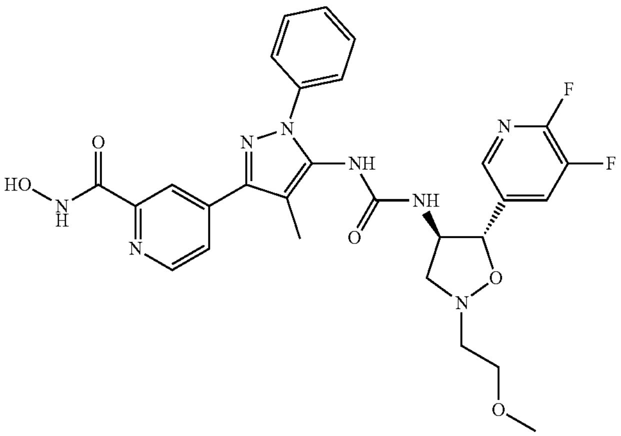 [SMILES: COCCN1C[C@@H](NC(=O)Nc2c(C)c(-c3ccnc(C(=O)NO)c3)nn2-c2ccccc2)[C@H](c2cnc(F)c(F)c2)O1] | 1 | 1.53 | 595.3 | |

TABLE 47-continued
| No. | Structure | LCMS method No | RT | MS (m/z) | configuration |
|---|---|---|---|---|---|
| I-232 | 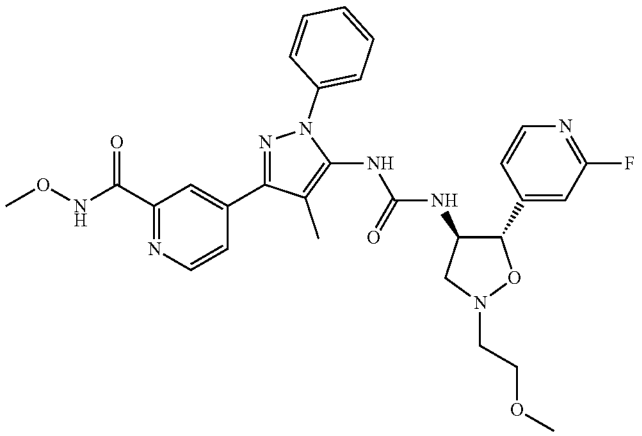 [SMILES: COCCN1C[C@@H](NC(=O)Nc2c(C)c(-c3ccnc(C(=O)NOC)c3)nn2-c2ccccc2)[C@H](c2ccnc(F)c2)O1] | 1 | 1.52 | 591.3 | racemate |
TABLE 48
| No. | Structure | LCMS method No | RT | MS (m/z) | configuration |
|---|---|---|---|---|---|
| I-233 | 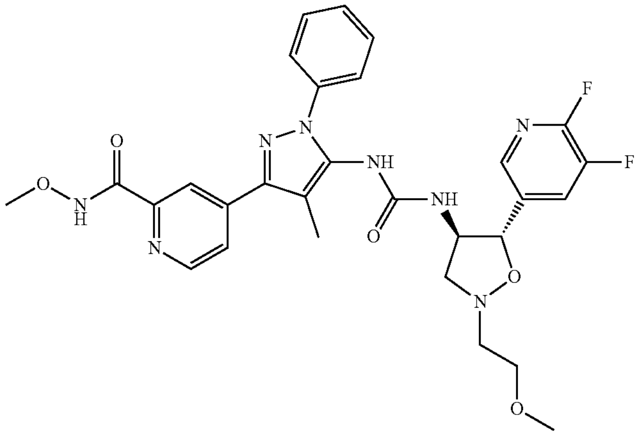 | 1 | 1.68 | 609.3 | |
| I-234 | 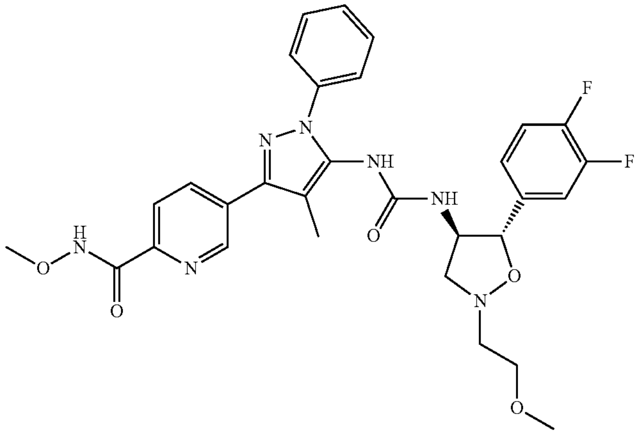 [SMILES: COCCN1C[C@@H](NC(=O)Nc2c(C)c(-c3ccc(C(=O)NOC)nc3)nn2-c2ccccc2)[C@H](c2ccc(F)c(F)c2)O1] | 1 | 1.78 | 608.3 | racemate |

TABLE 48-continued
| No. | Structure | LCMS method No | RT | MS (m/z) | configuration |
|---|---|---|---|---|---|
| I-235 | 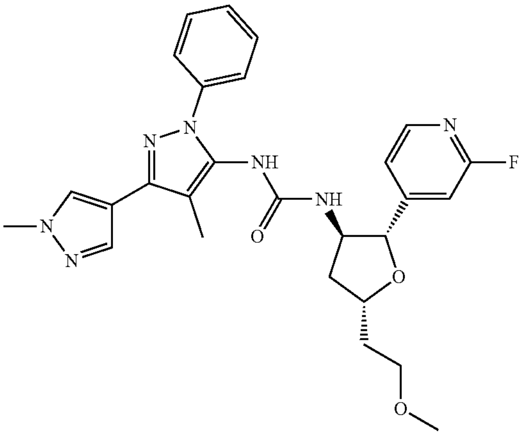 [SMILES: COCC[C@@H]1C[C@@H](NC(=O)Nc2c(C)c(-c3cnn(C)c3)nn2-c2ccccc2)[C@H](c2ccnc(F)c2)O1] | 1 | 1.53 | 520.3 | |
| I-236 | 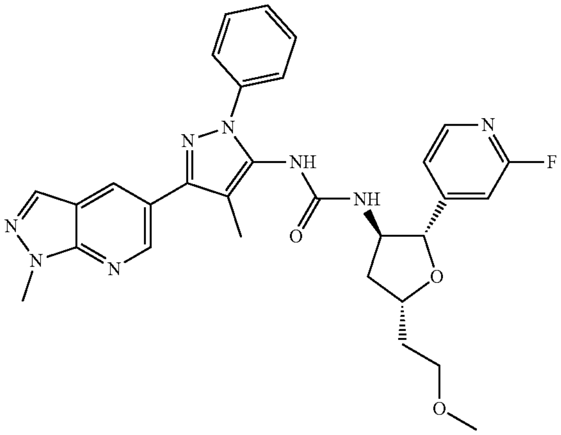 [SMILES: COCC[C@@H]1C[C@@H](NC(=O)Nc2c(C)c(-c3cnc4c(cnn4C)c3)nn2-c2ccccc2)[C@H](c2ccnc(F)c2)O1] | 1 | 1.71 | 571.25 | |
| I-237 | 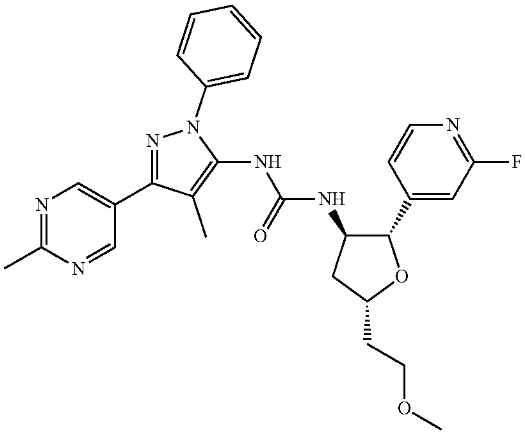 [SMILES: COCC[C@@H]1C[C@@H](NC(=O)Nc2c(C)c(-c3cnc(C)nc3)nn2-c2ccccc2)[C@H](c2ccnc(F)c2)O1] | 1 | 1.56 | 532.25 | |

TABLE 49
| No. | Structure | LCMS method No | RT | MS (m/z) | configuration |
|---|---|---|---|---|---|
| I-238 | 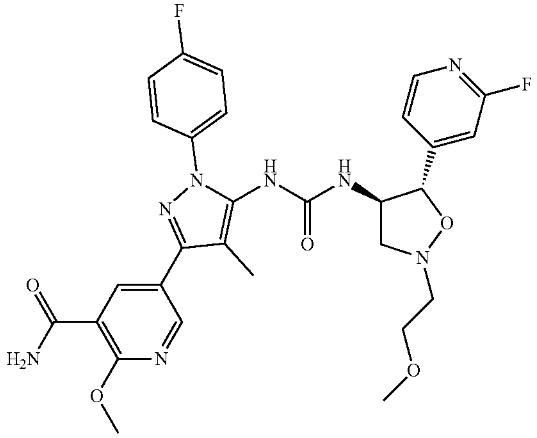 [SMILES: COCCN1C[C@@H](NC(=O)Nc2c(C)c(-c3cnc(OC)c(C(N)=O)c3)nn2-c2ccc(F)cc2)[C@H](c2ccnc(F)c2)O1] | 2 | 1.62 | 609 | racemate |
| I-239 | 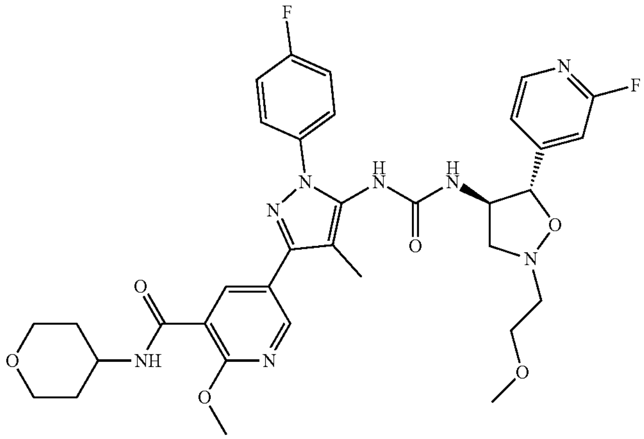 [SMILES: COCCN1C[C@@H](NC(=O)Nc2c(C)c(-c3cnc(OC)c(C(=O)NC4CCOCC4)c3)nn2-c2ccc(F)cc2)[C@H](c2ccnc(F)c2)O1] | 2 | 1.77 | 693 | racemate |
| I-240 | 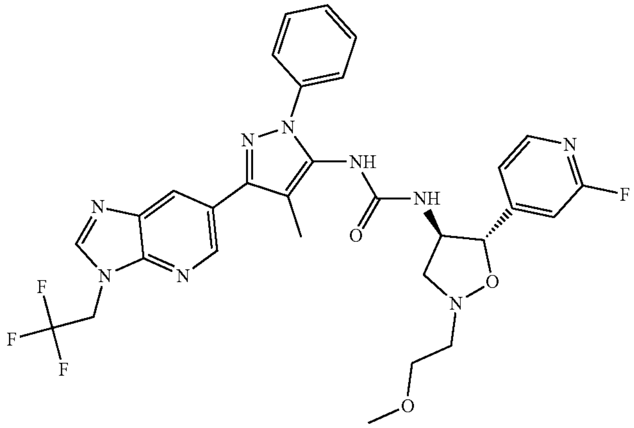 [SMILES: COCCN1C[C@@H](NC(=O)Nc2c(C)c(-c3cnc4c(c3)ncn4CC(F)(F)F)nn2-c2ccccc2)[C@H](c2ccnc(F)c2)O1] | 1 | 1.68 | 640.2 | racemate |

TABLE 49-continued
| No. | Structure | LCMS method No | RT | MS (m/z) | configuration |
|---|---|---|---|---|---|
| I-241 | 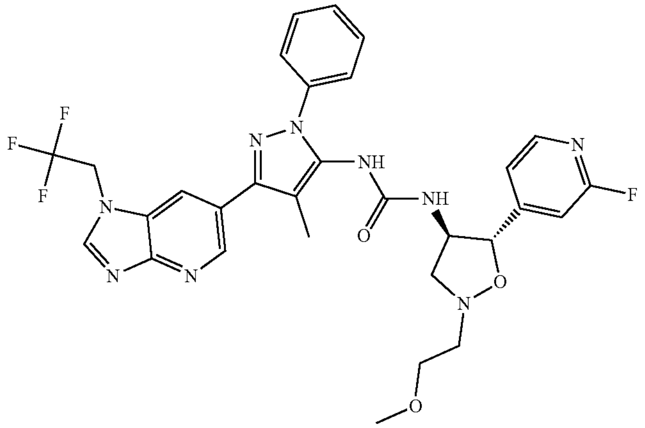 [SMILES: COCCN1C[C@@H](NC(=O)Nc2c(C)c(-c3cnc4ncn(CC(F)(F)F)c4c3)nn2-c2ccccc2)[C@H](c2ccnc(F)c2)O1] | 1 | 1.56 | 640.2 | racemate |
| I-242 | 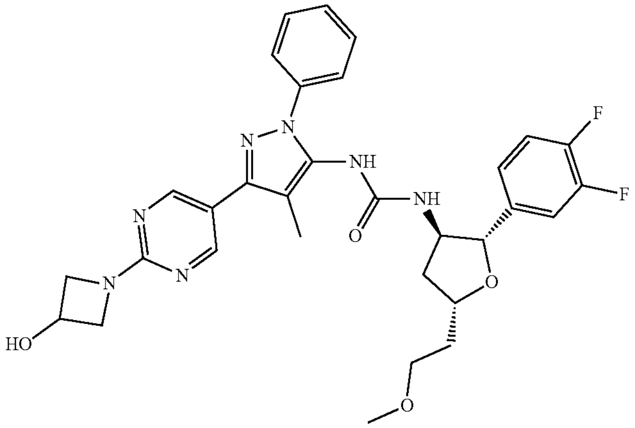 [SMILES: COCC[C@@H]1C[C@@H](NC(=O)Nc2c(C)c(-c3cnc(N4CC(O)C4)nc3)nn2-c2ccccc2)[C@H](c2ccc(F)c(F)c2)O1] | 1 | 1.69 | 606.25 | racemate |
TABLE 50
| No. | Structure | LCMS method No | RT | MS (m/z) | configuration |
|---|---|---|---|---|---|
| I-243 | 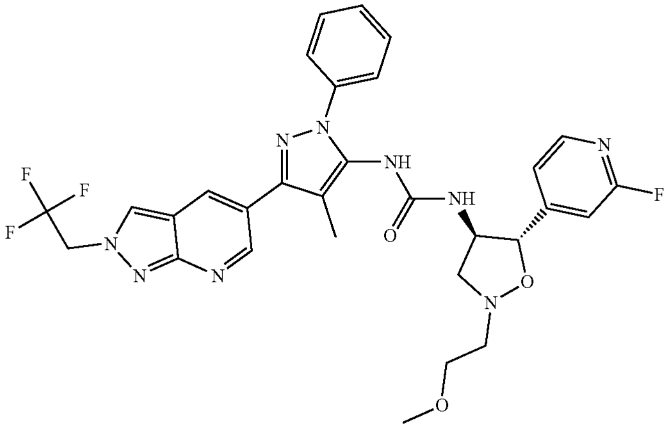 [SMILES: COCCN1C[C@@H](NC(=O)Nc2c(C)c(-c3cnc4nn(CC(F)(F)F)cc4c3)nn2-c2ccccc2)[C@H](c2ccnc(F)c2)O1] | 1 | 1.64 | 640.25 | racemate |

TABLE 50-continued
| No. | Structure | LCMS method No | RT | MS (m/z) | configuration |
|---|---|---|---|---|---|
| I-244 | 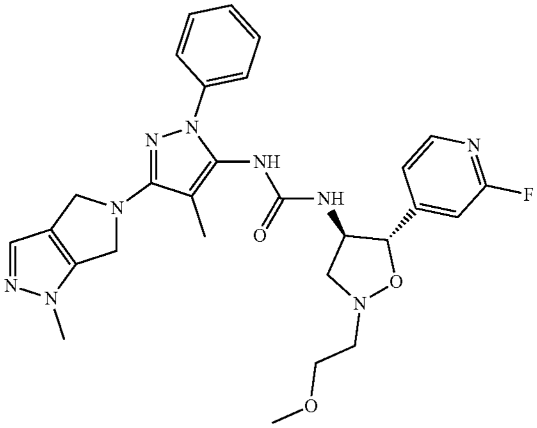 [SMILES: COCCN1C[C@@H](NC(=O)Nc2c(C)c(N3Cc4cnn(C)c4C3)nn2-c2ccccc2)[C@H](c2ccnc(F)c2)O1] | 1 | 1.51 | 562.25 | racemate |
| I-245 | 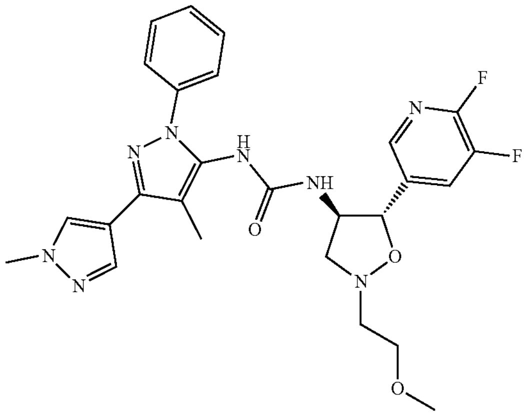 [SMILES: COCCN1C[C@@H](NC(=O)Nc2c(C)c(-c3cnn(C)c3)nn2-c2ccccc2)[C@H](c2cnc(F)c(F)c2)O1] | 2 | 1.59 | 539 | |
| I-246 | 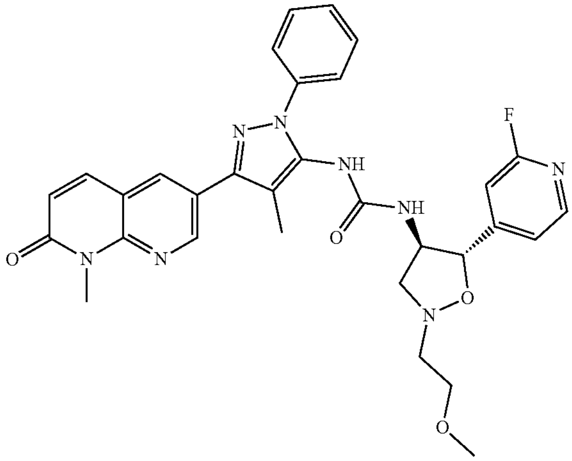 [SMILES: COCCN1C[C@@H](NC(=O)Nc2c(C)c(-c3cnc4c(ccc(=O)n4C)c3)nn2-c2ccccc2)[C@H](c2ccnc(F)c2)O1] | 2 | 1.64 | 599 | racemate |

TABLE 50-continued
| No. | Structure | LCMS method No | RT | MS (m/z) | configuration |
|---|---|---|---|---|---|
| I-247 | 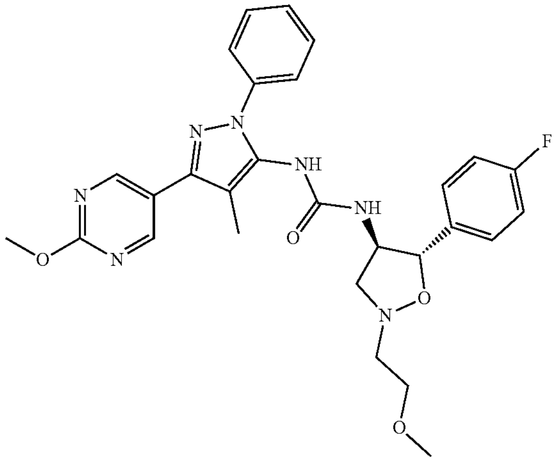 [SMILES: COCCN1C[C@@H](NC(=O)Nc2c(C)c(-c3cnc(OC)nc3)nn2-c2ccccc2)[C@H](c2ccc(F)cc2)O1] | 1 | 1.77 | 548 | racemate |
TABLE 51
| No. | Structure | LCMS method No | RT | MS (m/z) | configuration |
|---|---|---|---|---|---|
| I-248 | 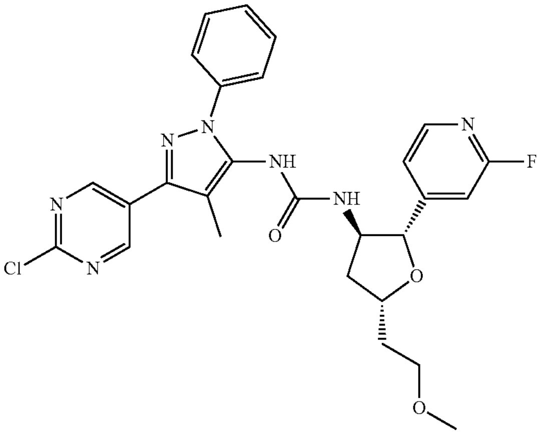 [SMILES: COCC[C@@H]1C[C@@H](NC(=O)Nc2c(C)c(-c3cnc(Cl)nc3)nn2-c2ccccc2)[C@H](c2ccnc(F)c2)O1] | 1 | 1.86 | 552.25 | |
| I-249 | 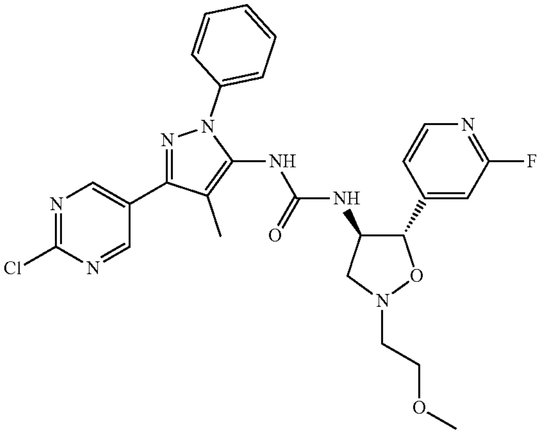 [SMILES: COCCN1C[C@@H](NC(=O)Nc2c(C)c(-c3cnc(Cl)nc3)nn2-c2ccccc2)[C@H](c2ccnc(F)c2)O1] | 1 | 1.77 | 553.2 | racemate |

TABLE 51-continued
| No. | Structure | LCMS method No | RT | MS (m/z) | configuration |
| --- | --- | --- | --- | --- | --- |
| I-250 | 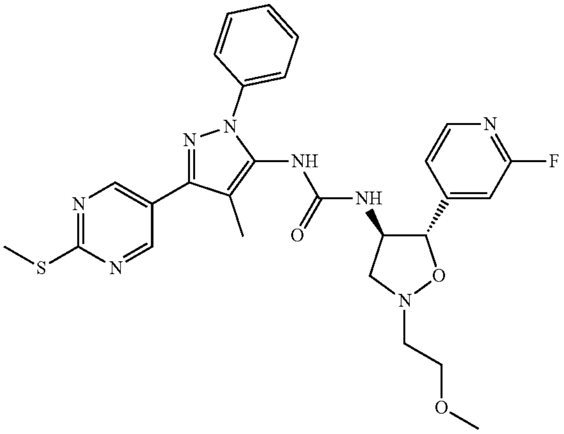 | 1 | 1.84 | 565.25 | racemate |
| I-251 | 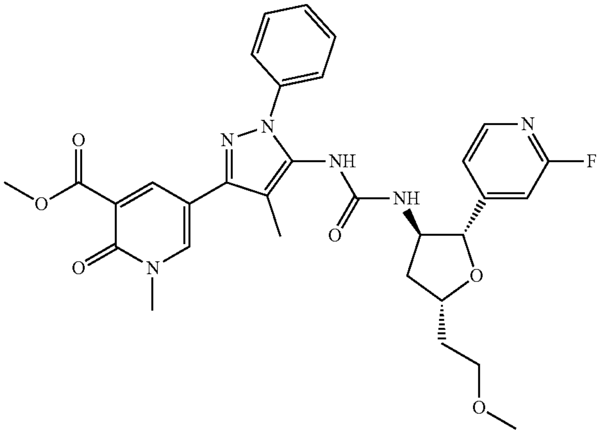 [SMILES: COCC[C@@H]1C[C@@H](NC(=O)Nc2c(C)c(-c3cc(C(=O)OC)c(=O)n(C)c3)nn2-c2ccccc2)[C@H](c2ccnc(F)c2)O1] | 1 | 1.53 | 605.25 | |
| I-252 | 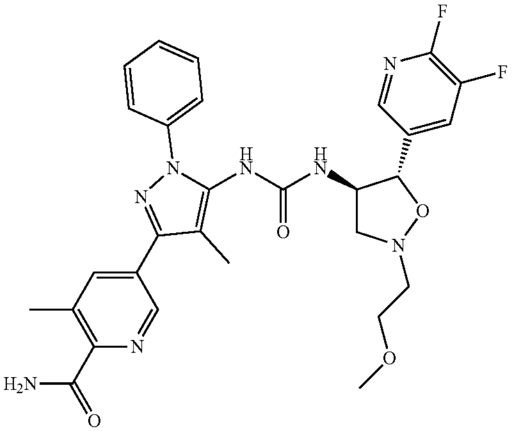 [SMILES: COCCN1C[C@@H](NC(=O)Nc2c(C)c(-c3cnc(C(N)=O)c(C)c3)nn2-c2ccccc2)[C@H](c2cnc(F)c(F)c2)O1] | 2 | 1.66 | 593 | |

TABLE 52
| No. | Structure | LCMS method No | RT | MS (m/z) | configuration |
|---|---|---|---|---|---|
| I-253 | 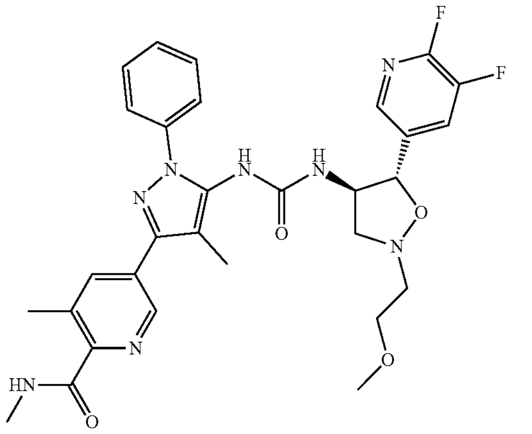 [SMILES: CNC(=O)c1ncc(-c2nn(-c3ccccc3)c(NC(=O)N[C@@H]3CN(CCOC)O[C@H]3c3cnc(F)c(F)c3)c2C)cc1C] | 2 | 1.76 | 607 | |
| I-254 | 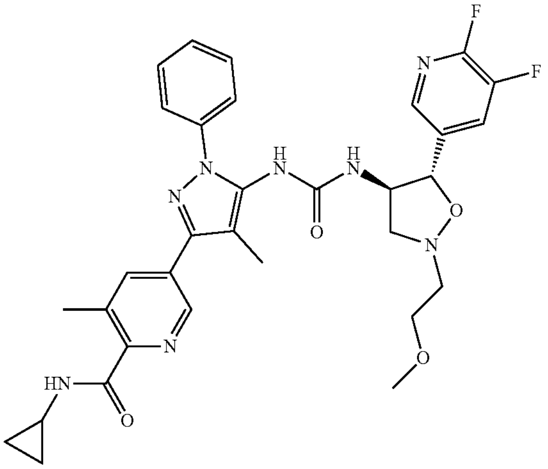 [SMILES: COCCN1C[C@@H](NC(=O)Nc2c(C)c(-c3cnc(C(=O)NC4CC4)c(C)c3)nn2-c2ccccc2)[C@H](c2cnc(F)c(F)c2)O1] | 2 | 1.91 | 633 | |
| I-255 | 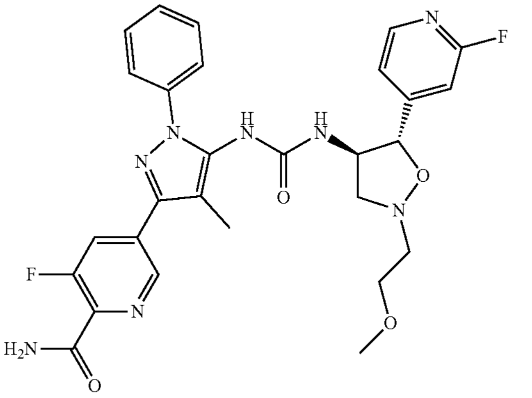 [SMILES: COCCN1C[C@@H](NC(=O)Nc2c(C)c(-c3cnc(C(N)=O)c(F)c3)nn2-c2ccccc2)[C@H](c2ccnc(F)c2)O1] | 1 | 1.61 | 579 | racemate |

TABLE 52-continued
| No. | Structure | LCMS method No | RT | MS (m/z) | configuration |
| --- | --- | --- | --- | --- | --- |
| I-256 | 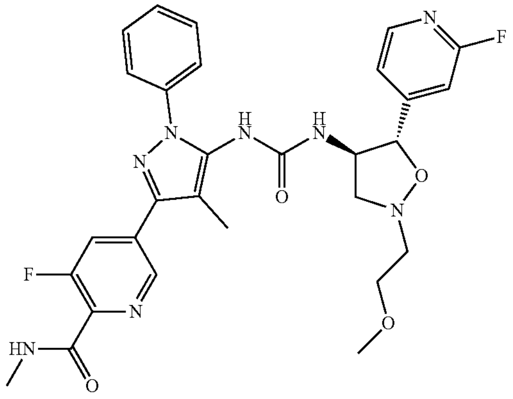 [SMILES: CNC(=O)c1ncc(-c2nn(-c3ccccc3)c(NC(=O)N[C@@H]3CN(CCOC)O[C@H]3c3ccnc(F)c3)c2C)cc1F] | 1 | 1.68 | 593 | racemate |
| I-257 | 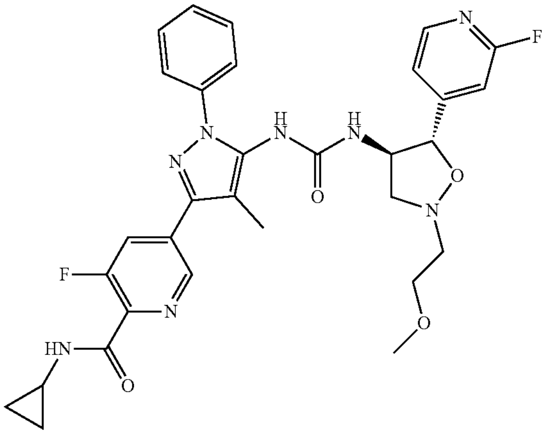 [SMILES: COCCN1C[C@@H](NC(=O)Nc2c(C)c(-c3cnc(C(=O)NC4CC4)c(F)c3)nn2-c2ccccc2)[C@H](c2ccnc(F)c2)O1] | 1 | 1.83 | 619 | racemate |
TABLE 53
| No. | Structure | LCMS method No | RT | MS (m/z) | configuration |
| --- | --- | --- | --- | --- | --- |
| I-258 | 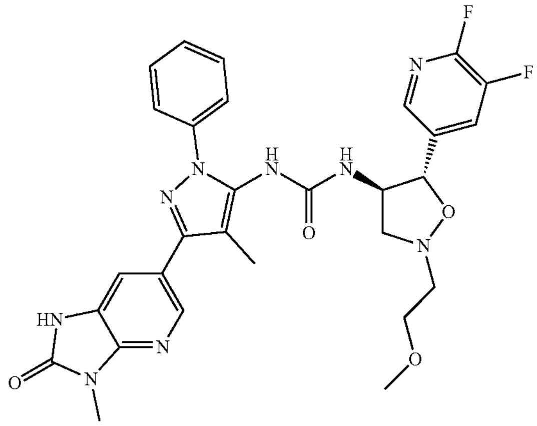 [SMILES: COCCN1C[C@@H](NC(=O)Nc2c(C)c(-c3cnc4c(c3)[nH]c(=O)n4C)nn2-c2ccccc2)[C@H](c2cnc(F)c(F)c2)O1] | 2 | 1.56 | 606 | |

TABLE 53-continued
| No. | Structure | LCMS method No | RT | MS (m/z) | configuration |
| --- | --- | --- | --- | --- | --- |
| I-259 | 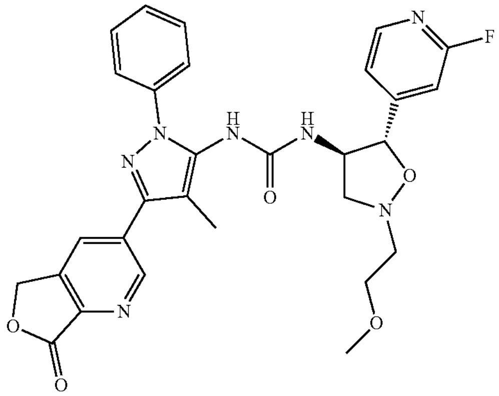 [SMILES: COCCN1C[C@@H](NC(=O)Nc2c(C)c(-c3cnc4c(c3)COC4=O)nn2-c2ccccc2)[C@H](c2ccnc(F)c2)O1] | 2 | 1.52 | 574 | racemate |
| I-260 | 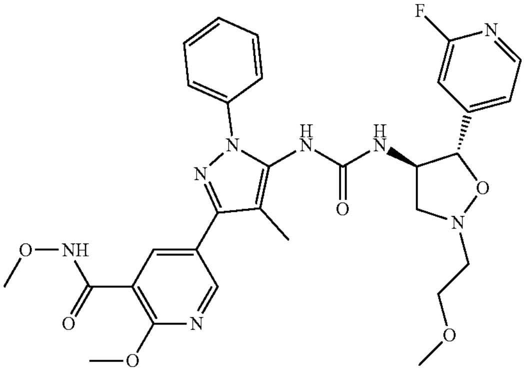 [SMILES: COCCN1C[C@@H](NC(=O)Nc2c(C)c(-c3cnc(OC)c(C(=O)NOC)c3)nn2-c2ccccc2)[C@H](c2ccnc(F)c2)O1] | 2 | 1.58 | 621 | racemate |
| I-261 | 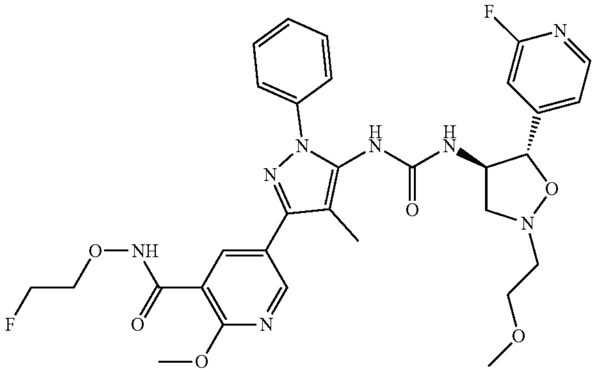 [SMILES: COCCN1C[C@@H](NC(=O)Nc2c(C)c(-c3cnc(OC)c(C(=O)NOCCF)c3)nn2-c2ccccc2)[C@H](c2ccnc(F)c2)O1] | 2 | 1.67 | 653 | racemate |
| I-262 | 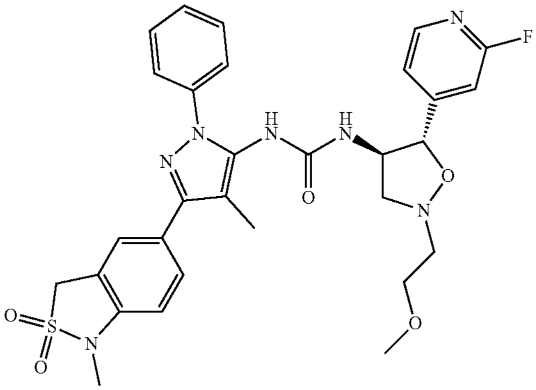 [SMILES: COCCN1C[C@@H](NC(=O)Nc2c(C)c(-c3ccc4c(c3)CS(=O)(=O)N4C)nn2-c2ccccc2)[C@H](c2ccnc(F)c2)O1] | 1 | 1.74 | 622.25 | racemate |

TABLE 54
| No. | Structure | LCMS method No | RT | MS (m/z) | configuration |
|---|---|---|---|---|---|
| I-263 | 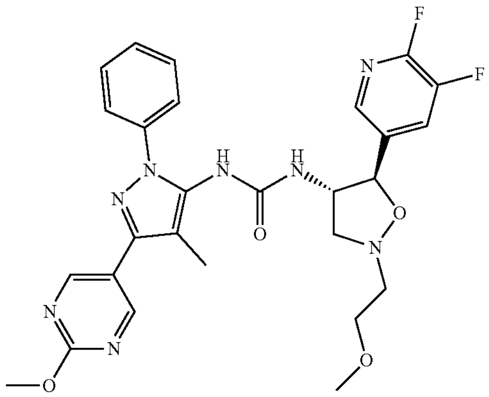 [SMILES: COCCN1C[C@H](NC(=O)Nc2c(C)c(-c3cnc(OC)nc3)nn2-c2ccccc2)[C@@H](c2cnc(F)c(F)c2)O1] | 1 | 1.75 | 567.2 | |
| I-264 | 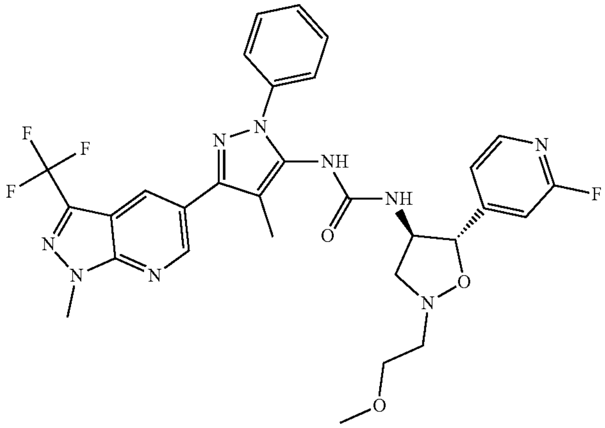 [SMILES: COCCN1C[C@@H](NC(=O)Nc2c(C)c(-c3cnc4c(c3)c(C(F)(F)F)nn4C)nn2-c2ccccc2)[C@H](c2ccnc(F)c2)O1] | 1 | 2.1 | 640.2 | racemate |
| I-265 | 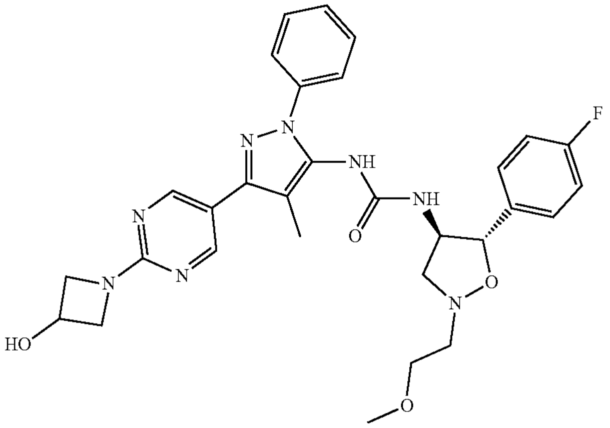 [SMILES: COCCN1C[C@@H](NC(=O)Nc2c(C)c(-c3cnc(N4CC(O)C4)nc3)nn2-c2ccccc2)[C@H](c2ccc(F)cc2)O1] | 1 | 1.5 | 589.25 | racemate |

TABLE 54-continued
| No. | Structure | LCMS method No | RT | MS (m/z) | configuration |
|---|---|---|---|---|---|
| I-266 | 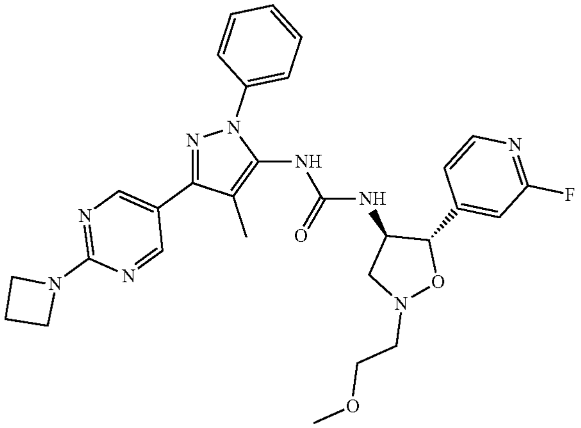 [SMILES: COCCN1C[C@@H](NC(=O)Nc2c(C)c(-c3cnc(N4CCC4)nc3)nn2-c2ccccc2)[C@H](c2ccnc(F)c2)O1] | 1 | 1.55 | 574.25 | racemate |
| I-267 | 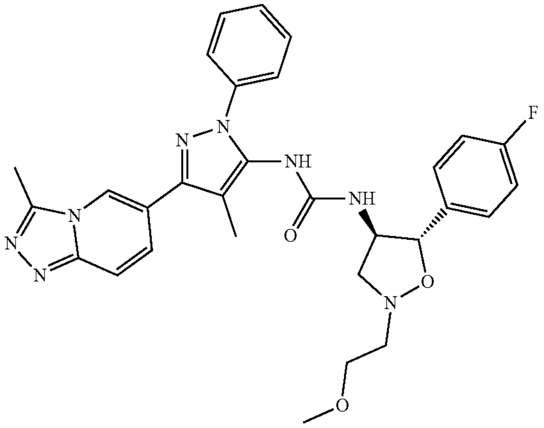 [SMILES: COCCN1C[C@@H](NC(=O)Nc2c(C)c(-c3ccc4nnc(C)n4c3)nn2-c2ccccc2)[C@H](c2ccc(F)cc2)O1] | 1 | 1.5 | 571.25 | racemate |
TABLE 55
| No. | Structure | LCMS method No | RT | MS (m/z) | configuration |
|---|---|---|---|---|---|
| I-268 | 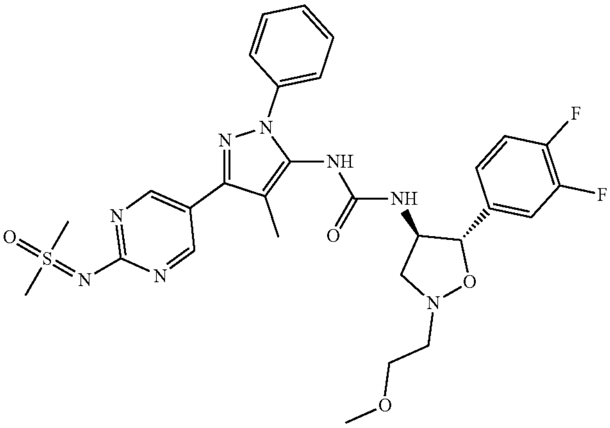 [SMILES: COCCN1C[C@@H](NC(=O)Nc2c(C)c(-c3cnc(N=S(C)(C)=O)nc3)nn2-c2ccccc2)[C@H](c2ccc(F)c(F)c2)O1] | 1 | 1.56 | 627.2 | |

TABLE 55-continued
| No. | Structure | LCMS method No | RT | MS (m/z) | configuration |
|---|---|---|---|---|---|
| I-269 | 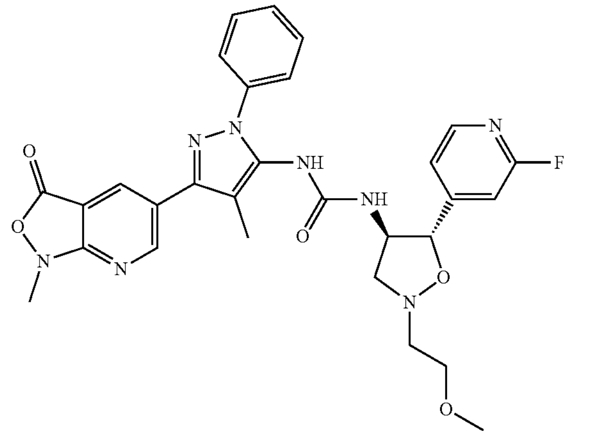 [SMILES: COCCN1C[C@@H](NC(=O)Nc2c(C)c(-c3cnc4c(c3)c(=O)on4C)nn2-c2ccccc2)[C@H](c2ccnc(F)c2)O1] | 1 | 1.74 | 589.2 | racemate |
| I-270 | 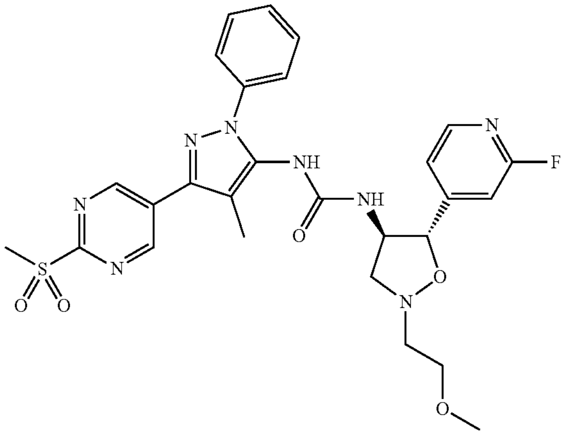 [SMILES: COCCN1C[C@@H](NC(=O)Nc2c(C)c(-c3cnc(S(C)(=O)=O)nc3)nn2-c2ccccc2)[C@H](c2ccnc(F)c2)O1] | 1 | 1.53 | 597.2 | racemate |
| I-271 | 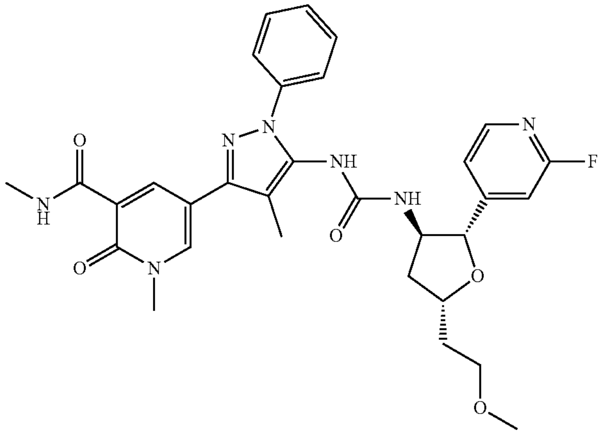 [SMILES: CNC(=O)c1cc(-c2nn(-c3ccccc3)c(NC(=O)N[C@@H]3C[C@@H](CCOC)O[C@H]3c3ccnc(F)c3)c2C)cn(C)c1=O] | 1 | 1.53 | 604.25 | |

TABLE 55-continued
| No. | Structure | LCMS method No | RT | MS (m/z) | configuration |
|---|---|---|---|---|---|
| I-272 | 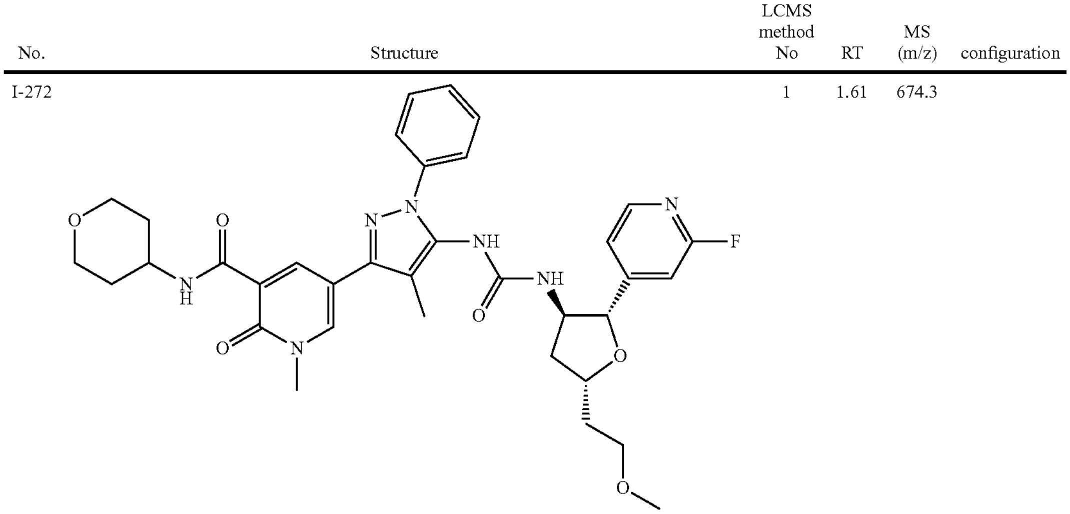 | 1 | 1.61 | 674.3 | |
TABLE 56
| No. | Structure | LCMS method No | RT | MS (m/z) | configuration |
|---|---|---|---|---|---|
| I-273 | 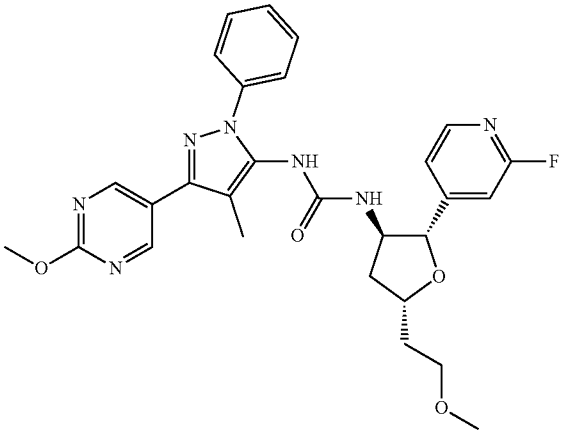 [SMILES: COCC[C@@H]1C[C@@H](NC(=O)Nc2c(C)c(-c3cnc(OC)nc3)nn2-c2ccccc2)[C@H](c2ccnc(F)c2)O1] | 1 | 1.68 | 548.25 | |
| I-274 | 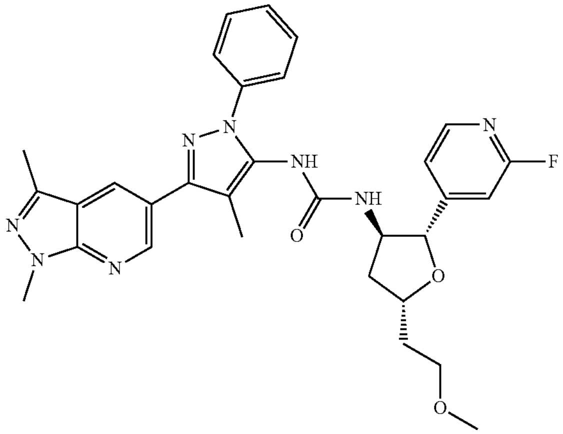 [SMILES: COCC[C@@H]1C[C@@H](NC(=O)Nc2c(C)c(-c3cnc4c(c3)c(C)nn4C)nn2-c2ccccc2)[C@H](c2ccnc(F)c2)O1] | 1 | 1.78 | 585.25 | |

TABLE 56-continued
| No. | Structure | LCMS method No | RT | MS (m/z) | configuration |
|---|---|---|---|---|---|
| I-275 | 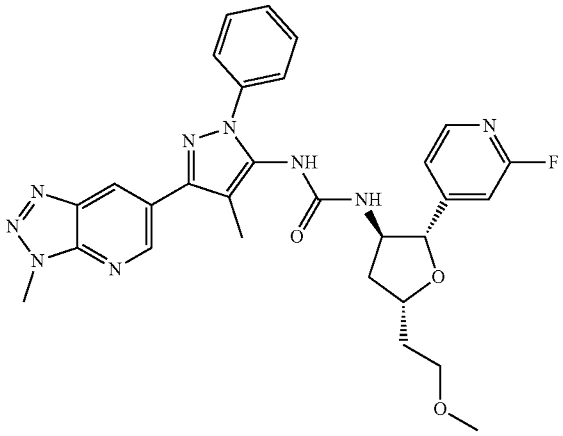 | 1 | 1.67 | 572.2 | |
| I-276 | 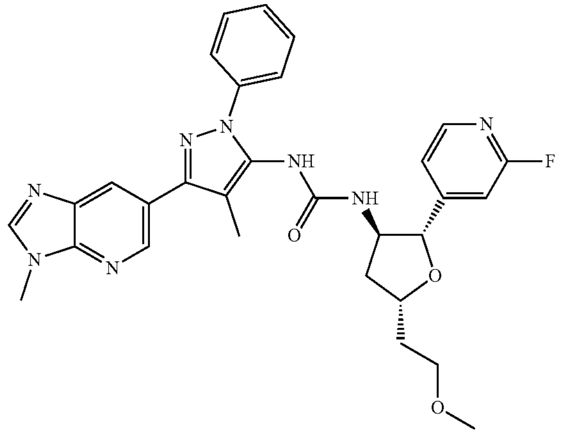 [SMILES: COCC[C@@H]1C[C@@H](NC(=O)Nc2c(C)c(-c3cnc4c(c3)ncn4C)nn2-c2ccccc2)[C@H](c2ccnc(F)c2)O1] | 1 | 1.4 | 571.25 | |

TABLE 57
| No. | Structure | LCMS method No | RT | MS (m/z) | configuration |
|---|---|---|---|---|---|
| I-277 | 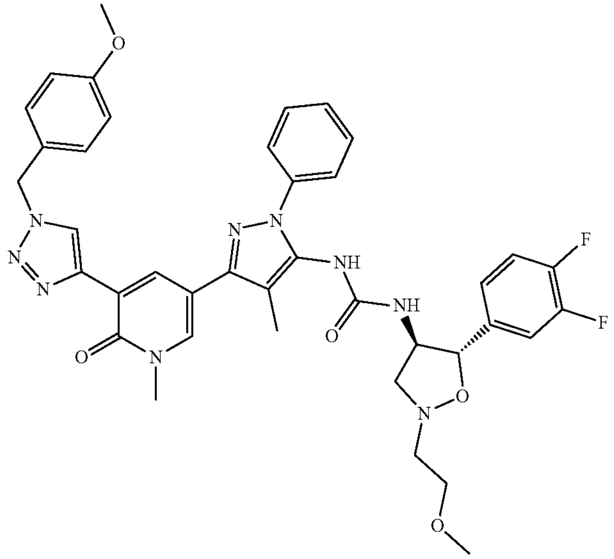 [SMILES: COCCN1C[C@@H](NC(=O)Nc2c(C)c(-c3cc(-c4cn(Cc5ccc(OC)cc5)nn4)c(=O)n(C)c3)nn2-c2ccccc2)[C@H](c2ccc(F)c(F)c2)O1] | 2 | 2.14 | 752 | |
| I-278 | 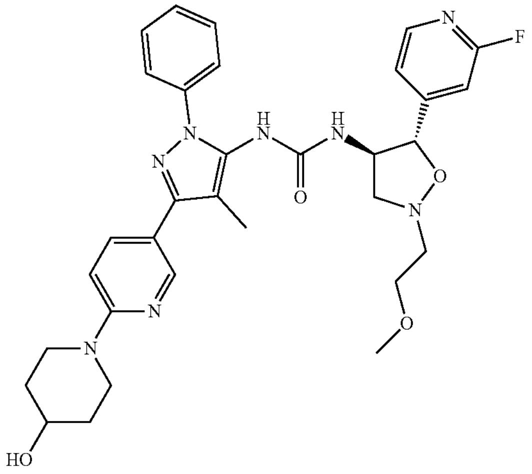 [SMILES: COCCN1C[C@@H](NC(=O)Nc2c(C)c(-c3ccc(N4CCC(O)CC4)nc3)nn2-c2ccccc2)[C@H](c2ccnc(F)c2)O1] | 2 | 1.26 | 617 | racemate |
| I-279 | 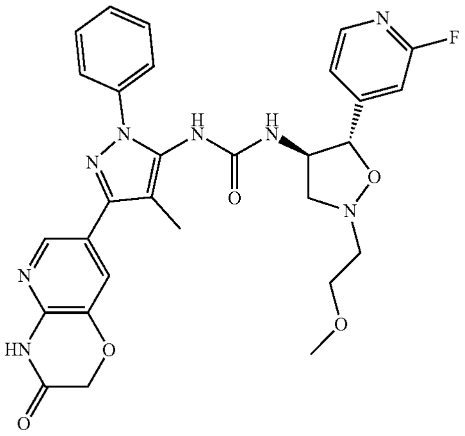 [SMILES: COCCN1C[C@@H](NC(=O)Nc2c(C)c(-c3cnc4c(c3)OCC(=O)N4)nn2-c2ccccc2)[C@H](c2ccnc(F)c2)O1] | 2 | 1.51 | 589 | racemate |

TABLE 57-continued
| No. | Structure | LCMS method No | RT | MS (m/z) | configuration |
|---|---|---|---|---|---|
| I-280 | 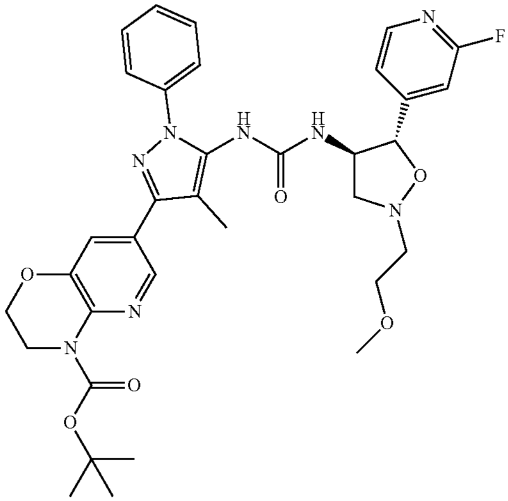 [SMILES: COCCN1C[C@@H](NC(=O)Nc2c(C)c(-c3cnc4c(c3)OCCN4C(=O)OC(C)(C)C)nn2-c2ccccc2)[C@H](c2ccnc(F)c2)O1] | 2 | 1.91 | 675 | racemate |
TABLE 58
| No. | Structure | LCMS method No | RT | MS (m/z) | configuration |
|---|---|---|---|---|---|
| I-281 | 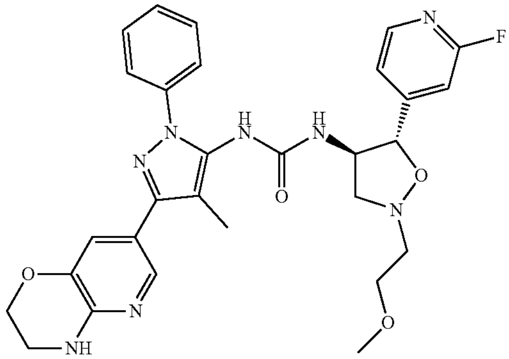 [SMILES: COCCN1C[C@@H](NC(=O)Nc2c(C)c(-c3cnc4c(c3)OCCN4)nn2-c2ccccc2)[C@H](c2ccnc(F)c2)O1] | 2 | 1.38 | 575 | racemate |
| I-282 | 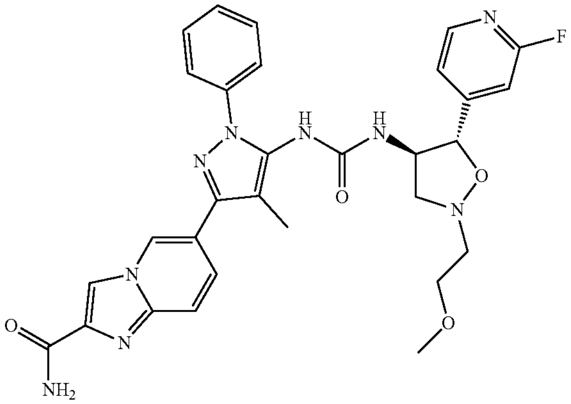 [SMILES: COCCN1C[C@@H](NC(=O)Nc2c(C)c(-c3ccc4nc(C(N)=O)cn4c3)nn2-c2ccccc2)[C@H](c2ccnc(F)c2)O1] | 2 | 1.36 | 600 | racemate |

TABLE 58-continued
| No. | Structure | LCMS method No | RT | MS (m/z) | configuration |
|---|---|---|---|---|---|
| I-283 | 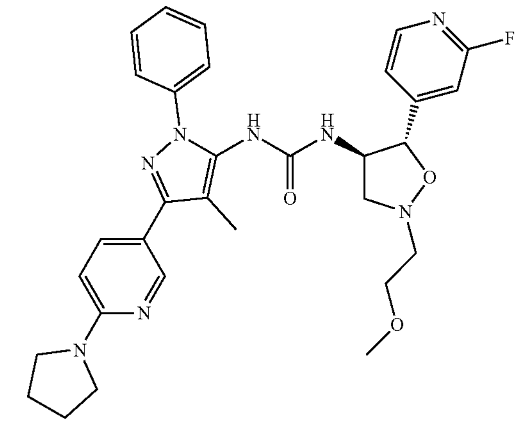 [SMILES: COCCN1C[C@@H](NC(=O)Nc2c(C)c(-c3ccc(N4CCCC4)nc3)nn2-c2ccccc2)[C@H](c2ccnc(F)c2)O1] | 2 | 1.42 | 587 | racemate |
| I-284 | 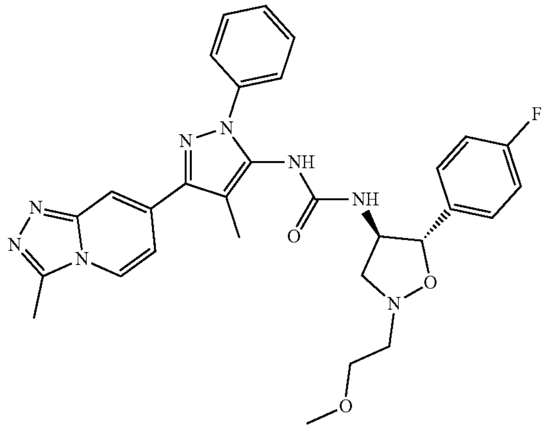 [SMILES: COCCN1C[C@@H](NC(=O)Nc2c(C)c(-c3ccn4c(C)nnc4c3)nn2-c2ccccc2)[C@H](c2ccc(F)cc2)O1] | 1 | 1.47 | 571.25 | racemate |
| I-285 | 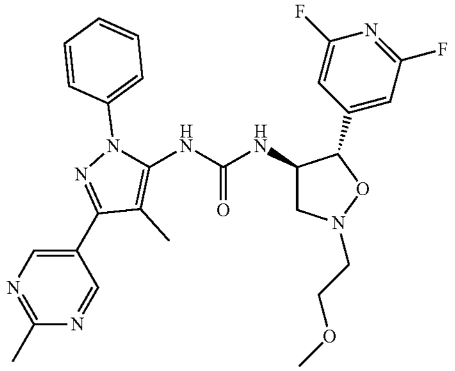 [SMILES: COCCN1C[C@@H](NC(=O)Nc2c(C)c(-c3cnc(C)nc3)nn2-c2ccccc2)[C@H](c2cc(F)nc(F)c2)O1] | 1 | 1.7 | 551.25 | racemate |

TABLE 59
| No. | Structure | LCMS method No | RT | MS (m/z) | configuration |
|---|---|---|---|---|---|
| I-286 | 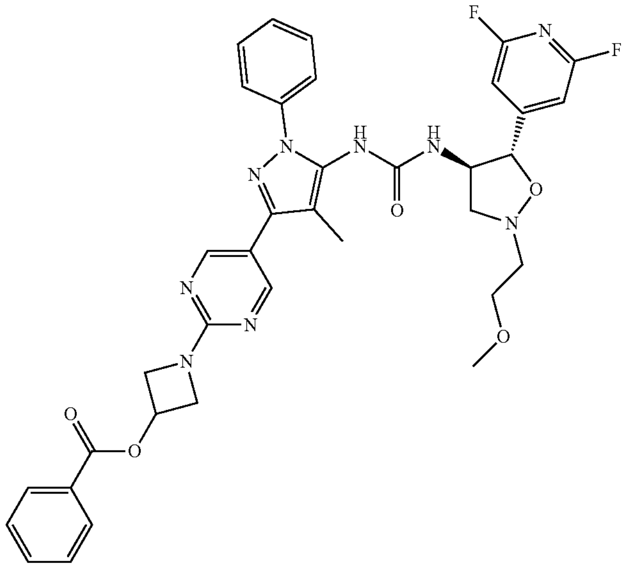 [SMILES: COCCN1C[C@@H](NC(=O)Nc2c(C)c(-c3cnc(N4CC(OC(=O)c5ccccc5)C4)nc3)nn2-c2ccccc2)[C@H](c2cc(F)nc(F)c2)O1] | 1 | 2.22 | 712.25 | racemate |
| I-287 | 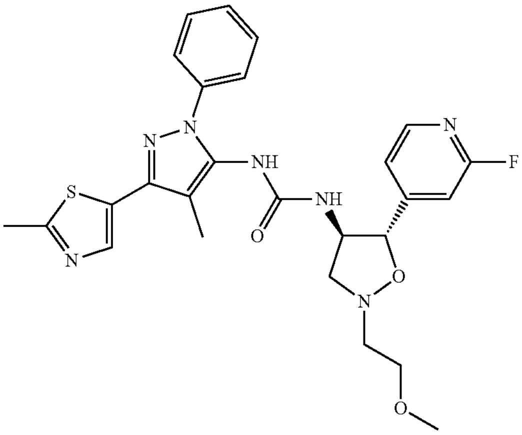 [SMILES: COCCN1C[C@@H](NC(=O)Nc2c(C)c(-c3cnc(C)s3)nn2-c2ccccc2)[C@H](c2ccnc(F)c2)O1] | 1 | 1.64 | 538.2 | racemate |
| I-288 | 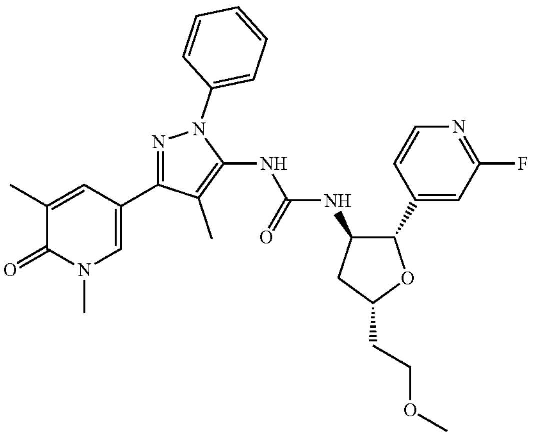 [SMILES: COCC[C@@H]1C[C@@H](NC(=O)Nc2c(C)c(-c3cc(C)c(=O)n(C)c3)nn2-c2ccccc2)[C@H](c2ccnc(F)c2)O1] | 1 | 1.57 | 561.25 | |

TABLE 59-continued
| No. | Structure | LCMS method No | RT | MS (m/z) | configuration |
|---|---|---|---|---|---|
| I-289 | 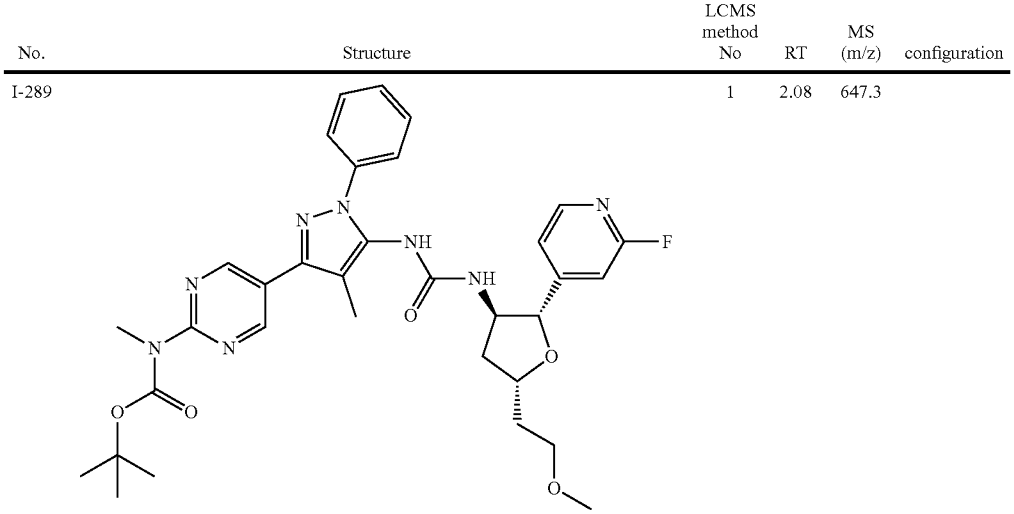 | 1 | 2.08 | 647.3 | |
TABLE 60
| No. | Structure | LCMS method No | RT | MS (m/z) | configuration |
|---|---|---|---|---|---|
| I-290 | 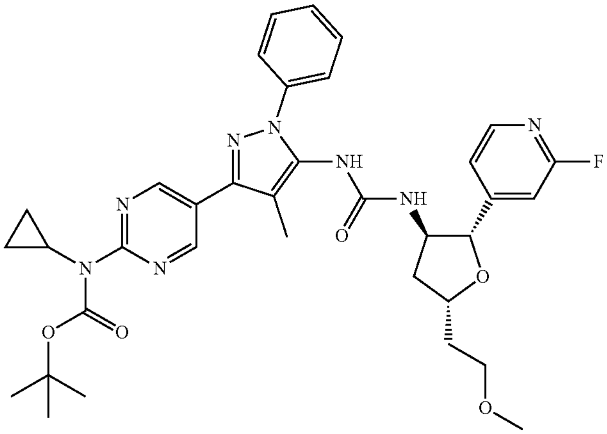 [SMILES: COCC[C@@H]1C[C@@H](NC(=O)Nc2c(C)c(-c3cnc(N(C(=O)OC(C)(C)C)C4CC4)nc3)nn2-c2ccccc2)[C@H](c2ccnc(F)c2)O1] | 1 | 2.09 | 673.3 | |
| I-291 | 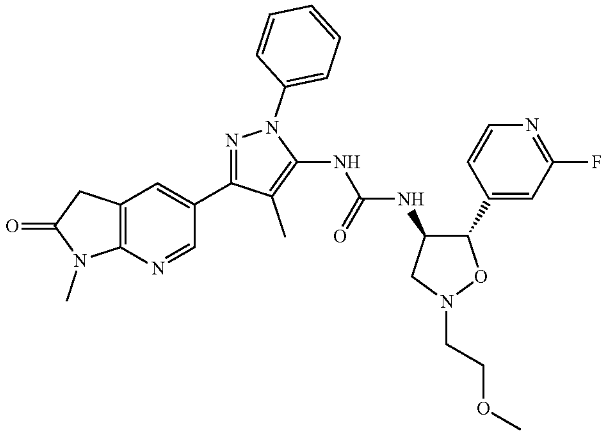 [SMILES: COCCN1C[C@@H](NC(=O)Nc2c(C)c(-c3cnc4c(c3)CC(=O)N4C)nn2-c2ccccc2)[C@H](c2ccnc(F)c2)O1] | 1 | 1.5 | 587.25 | racemate |

TABLE 60-continued
| No. | Structure | LCMS method No | RT | MS (m/z) | configuration |
|---|---|---|---|---|---|
| I-292 | 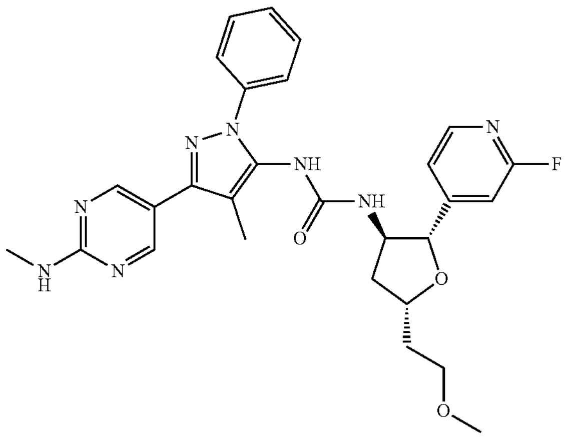 [SMILES: CNc1ncc(-c2nn(-c3ccccc3)c(NC(=O)N[C@@H]3C[C@@H](CCOC)O[C@H]3c3ccnc(F)c3)c2C)cn1] | 1 | 1.5 | 547.25 | |
| I-293 | 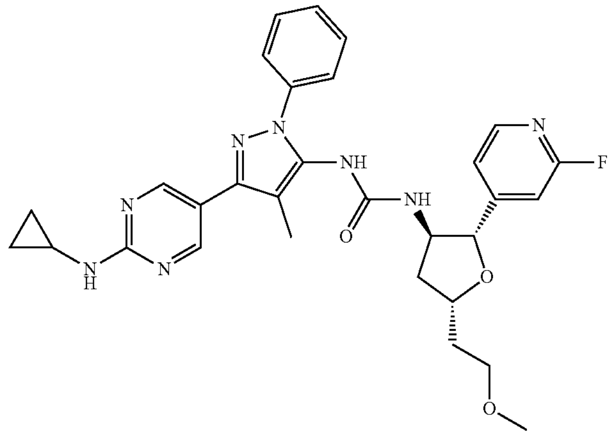 [SMILES: COCC[C@@H]1C[C@@H](NC(=O)Nc2c(C)c(-c3cnc(NC4CC4)nc3)nn2-c2ccccc2)[C@H](c2ccnc(F)c2)O1] | 1 | 1.6 | 573.25 | |
| I-294 | 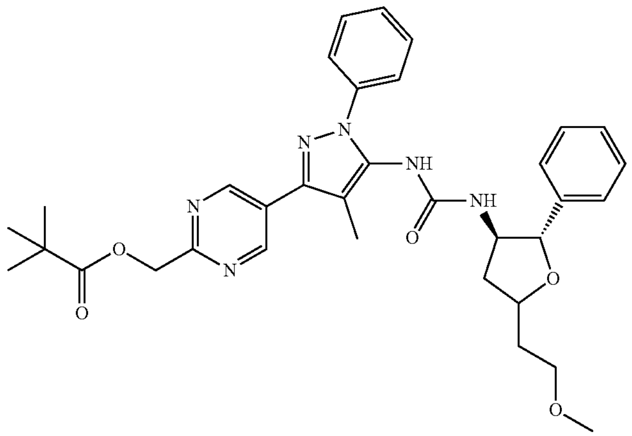 [SMILES: COCCC1C[C@@H](NC(=O)Nc2c(C)c(-c3cnc(COC(=O)C(C)(C)C)nc3)nn2-c2ccccc2)[C@H](c2ccccc2)O1] | 1 | 2.27 | 613.3 | trans |

TABLE 61
| No. | Structure | LCMS method No | RT | MS (m/z) | configuration |
|---|---|---|---|---|---|
| I-295 | 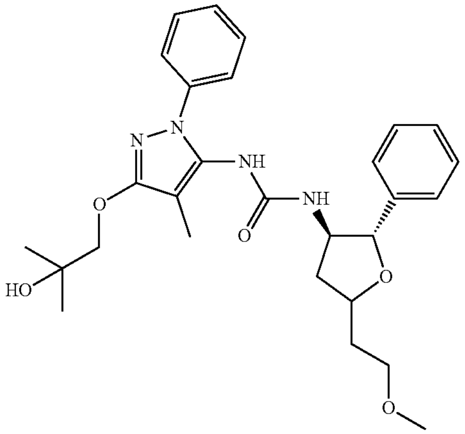 [SMILES: COCCC1C[C@@H](NC(=O)Nc2c(C)c(OCC(C)(C)O)nn2-c2ccccc2)[C@H](c2ccccc2)O1] | 1 | 1.83 | 509.3 | trans |
| I-296 | 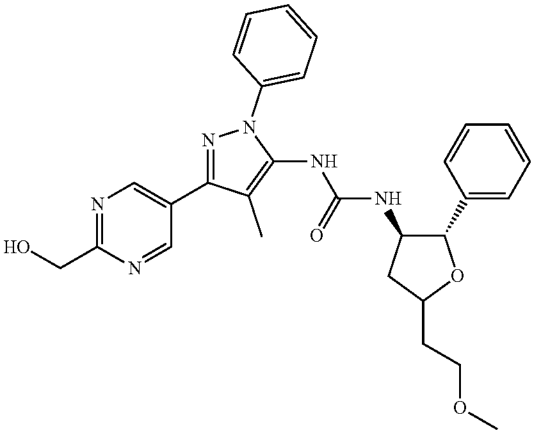 [SMILES: COCCC1C[C@@H](NC(=O)Nc2c(C)c(-c3cnc(CO)nc3)nn2-c2ccccc2)[C@H](c2ccccc2)O1] | 1 | 1.55 | 529.25 | trans |
| I-297 | 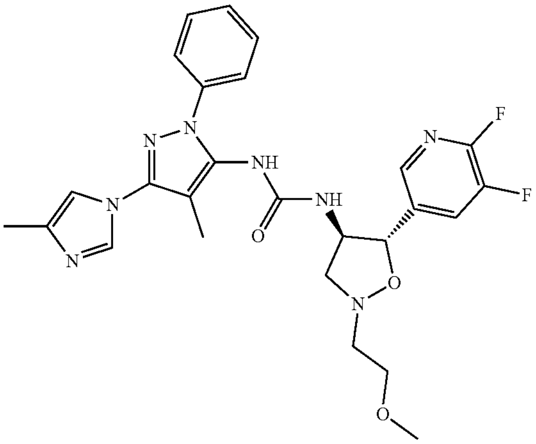 [SMILES: COCCN1C[C@@H](NC(=O)Nc2c(C)c(-n3cnc(C)c3)nn2-c2ccccc2)[C@H](c2cnc(F)c(F)c2)O1] | 1 | 1.22 | 539 | racemate |

TABLE 61-continued
| No. | Structure | LCMS method No | RT | MS (m/z) | configuration |
|---|---|---|---|---|---|
| I-298 | 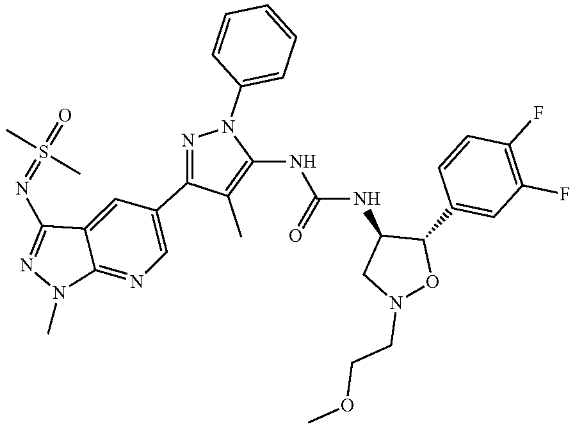 [SMILES: COCCN1C[C@@H](NC(=O)Nc2c(C)c(-c3cnc4c(c3)c(N=S(C)(C)=O)nn4C)nn2-c2ccccc2)[C@H](c2ccc(F)c(F)c2)O1] | 1 | 1.69 | 680.25 | |
| I-299 | 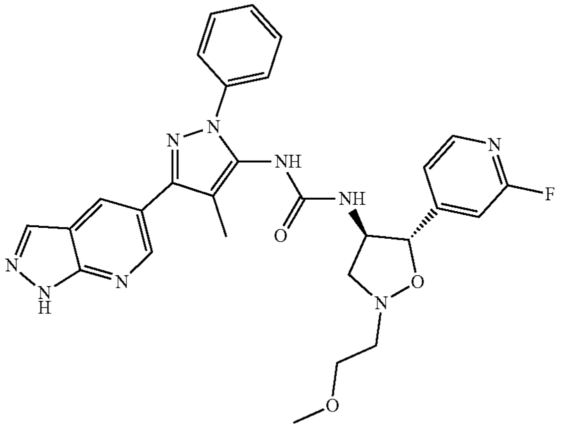 [SMILES: COCCN1C[C@@H](NC(=O)Nc2c(C)c(-c3cnc4[nH]ncc4c3)nn2-c2ccccc2)[C@H](c2ccnc(F)c2)O1] | 1 | 1.44 | 558.2 | racemate |
TABLE 62
| No. | Structure | LCMS method No | RT | MS (m/z) | configuration |
|---|---|---|---|---|---|
| I-300 | 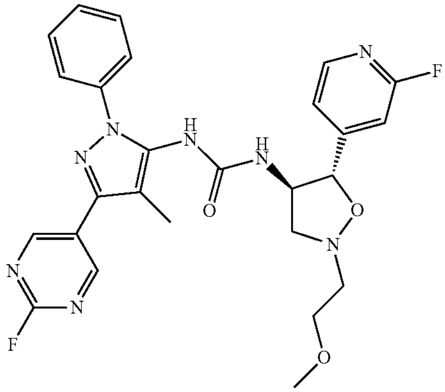 [SMILES: COCCN1C[C@@H](NC(=O)Nc2c(C)c(-c3cnc(F)nc3)nn2-c2ccccc2)[C@H](c2ccnc(F)c2)O1] | 1 | 1.69 | 537.25 | racemate |

TABLE 62-continued
| No. | Structure | LCMS method No | RT | MS (m/z) | configuration |
| --- | --- | --- | --- | --- | --- |
| I-301 | 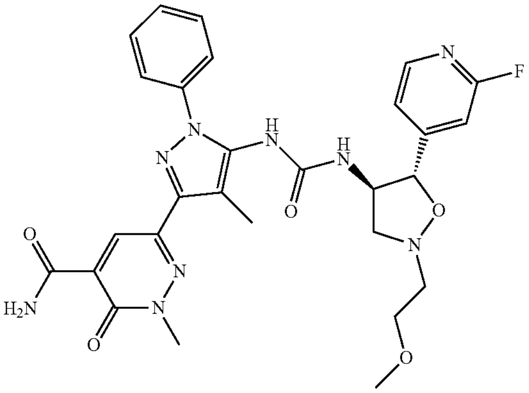 [SMILES: COCCN1C[C@@H](NC(=O)Nc2c(C)c(-c3cc(C(N)=O)c(=O)n(C)n3)nn2-c2ccccc2)[C@H](c2ccnc(F)c2)O1] | 1 | 1.47 | 592.25 | racemate |
| I-302 | 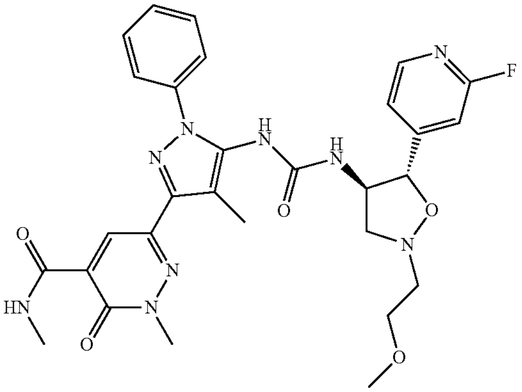 [SMILES: CNC(=O)c1cc(-c2nn(-c3ccccc3)c(NC(=O)N[C@@H]3CN(CCOC)O[C@H]3c3ccnc(F)c3)c2C)nn(C)c1=O] | 1 | 1.59 | 606.25 | racemate |
| I-303 | 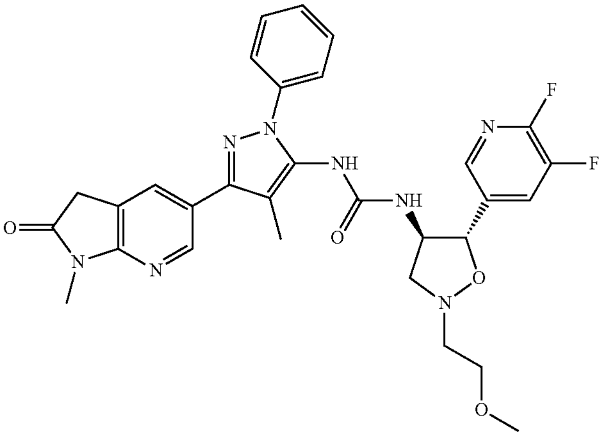 [SMILES: COCCN1C[C@@H](NC(=O)Nc2c(C)c(-c3cnc4c(c3)CC(=O)N4C)nn2-c2ccccc2)[C@H](c2cnc(F)c(F)c2)O1] | 1 | 1.65 | 605.25 | racemate |

TABLE 62-continued
| No. | Structure | LCMS method No | RT | MS (m/z) | configuration |
|---|---|---|---|---|---|
| I-304 | 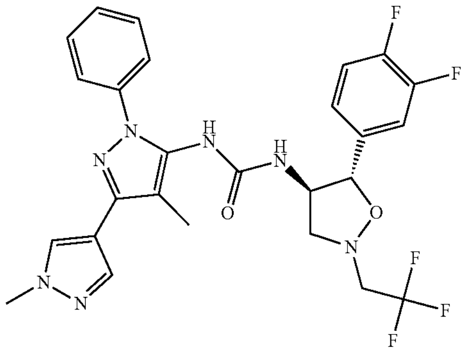 [SMILES: Cc1c(-c2cnn(C)c2)nn(-c2ccccc2)c1NC(=O)N[C@@H]1CN(CC(F)(F)F)O[C@H]1c1ccc(F)c(F)c1] | 1 | 2.17 | 562 | racemate |
TABLE 63
| No. | Structure | LCMS method No | RT | MS (m/z) | configuration |
|---|---|---|---|---|---|
| I-305 | 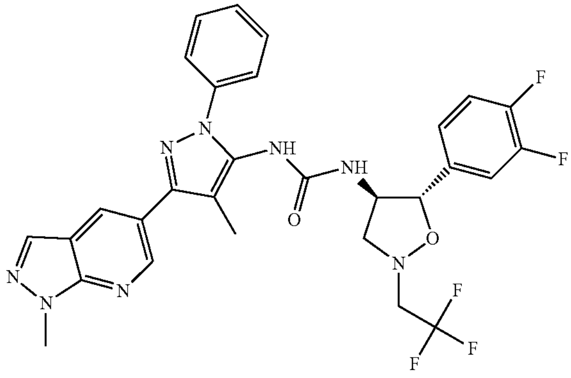 [SMILES: Cc1c(-c2cnc3c(cnn3C)c2)nn(-c2ccccc2)c1NC(=O)N[C@@H]1CN(CC(F)(F)F)O[C@H]1c1ccc(F)c(F)c1] | 1 | 2.34 | 613 | racemate |
| I-306 | 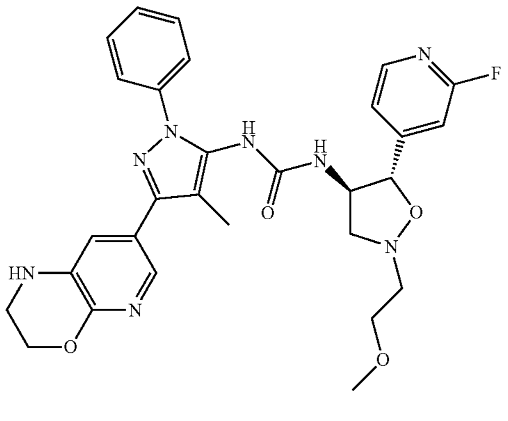 [SMILES: COCCN1C[C@@H](NC(=O)Nc2c(C)c(-c3cnc4c(c3)NCCO4)nn2-c2ccccc2)[C@H](c2ccnc(F)c2)O1] | 1 | 1.47 | 575 | racemate |

TABLE 63-continued
| No. | Structure | LCMS method No | RT | MS (m/z) | configuration |
|---|---|---|---|---|---|
| I-307 | 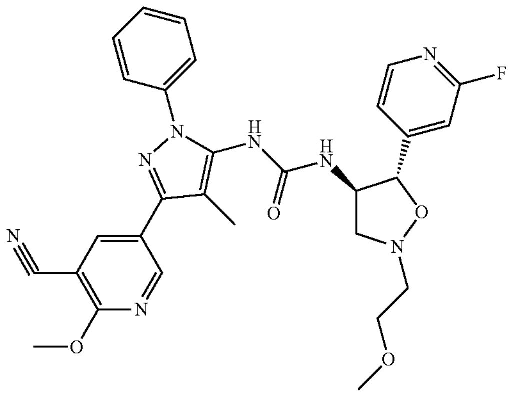 [SMILES: COCCN1C[C@@H](NC(=O)Nc2c(C)c(-c3cnc(OC)c(C#N)c3)nn2-c2ccccc2)[C@H](c2ccnc(F)c2)O1] | 2 | 1.93 | 573 | racemate |
| I-308 | 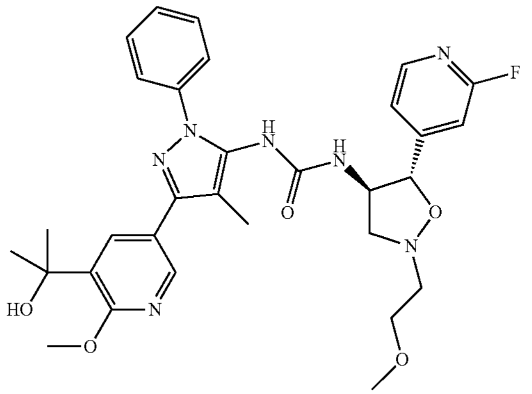 [SMILES: COCCN1C[C@@H](NC(=O)Nc2c(C)c(-c3cnc(OC)c(C(C)(C)O)c3)nn2-c2ccccc2)[C@H](c2ccnc(F)c2)O1] | 2 | 1.8 | 606 | racemate |
| I-309 | 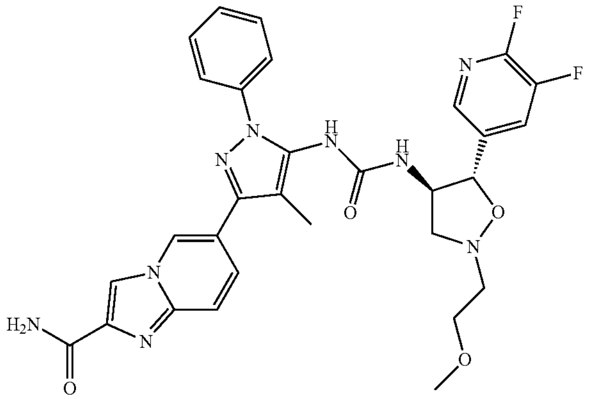 [SMILES: COCCN1C[C@@H](NC(=O)Nc2c(C)c(-c3ccc4nc(C(N)=O)cn4c3)nn2-c2ccccc2)[C@H](c2cnc(F)c(F)c2)O1] | 2 | 1.53 | 618 | racemate |

TABLE 64
| No. | Structure | LCMS method No | RT | MS (m/z) | configuration |
|---|---|---|---|---|---|
| I-310 | 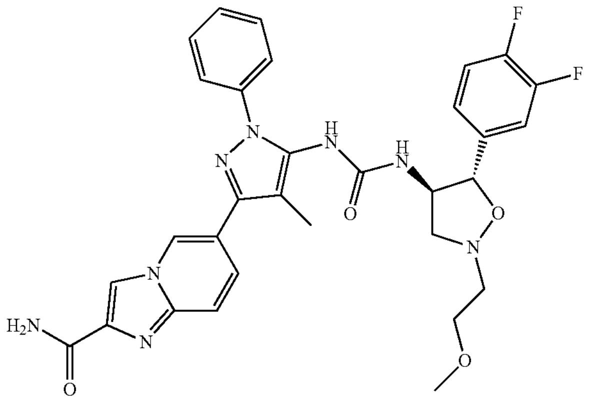 [SMILES: COCCN1C[C@@H](NC(=O)Nc2c(C)c(-c3ccc4nc(C(N)=O)cn4c3)nn2-c2ccccc2)[C@H](c2ccc(F)c(F)c2)O1] | 2 | 1.68 | 617 | |
| I-311 | 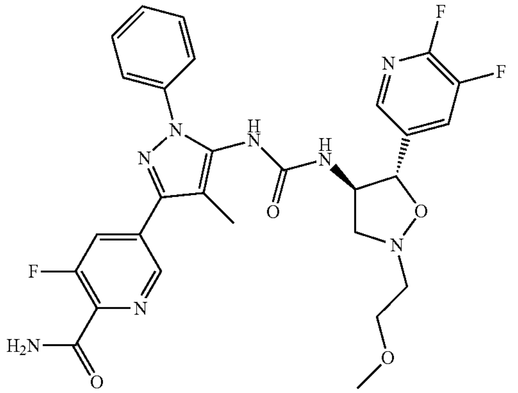 | 2 | 1.62 | 597 | racemate |
| I-312 | 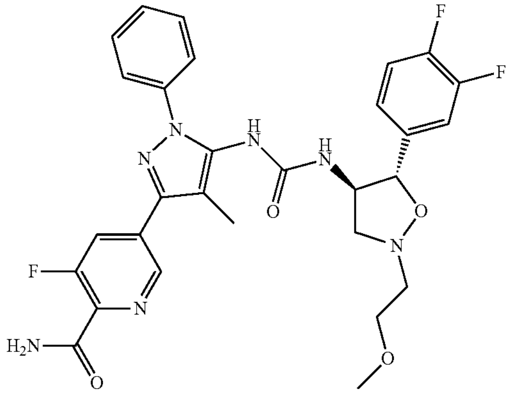 [SMILES: COCCN1C[C@@H](NC(=O)Nc2c(C)c(-c3cnc(C(N)=O)c(F)c3)nn2-c2ccccc2)[C@H](c2ccc(F)c(F)c2)O1] | 2 | 1.77 | 596 | |

TABLE 64-continued
| No. | Structure | LCMS method No | RT | MS (m/z) | configuration |
|---|---|---|---|---|---|
| I-313 | 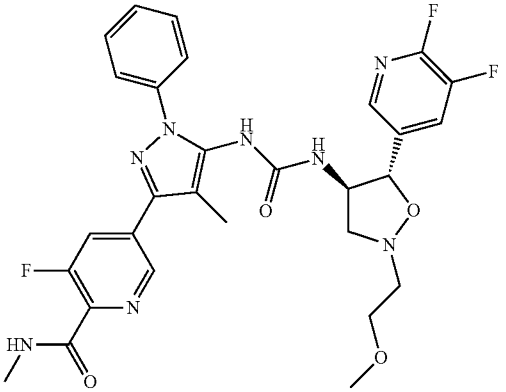 [SMILES: CNC(=O)c1ncc(-c2nn(-c3ccccc3)c(NC(=O)N[C@@H]3CN(CCOC)O[C@H]3c3ccc(F)c(F)c3)c2C)cc1F] | 2 | 1.71 | 611 | racemate |
| I-314 | 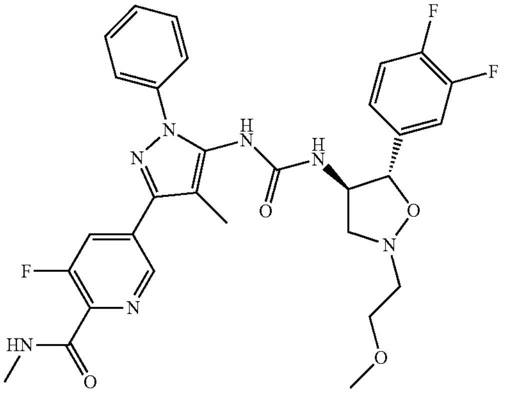 | 2 | 1.87 | 610 | |
TABLE 65
| No. | Structure | LCMS method No | RT | MS (m/z) | configuration |
|---|---|---|---|---|---|
| I-315 | 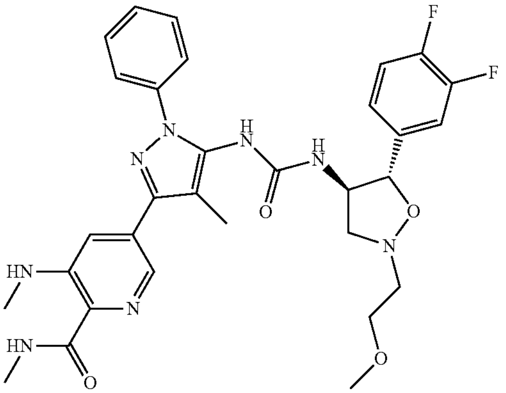 [SMILES: CNC(=O)c1ncc(-c2nn(-c3ccccc3)c(NC(=O)N[C@@H]3CN(CCOC)O[C@H]3c3ccc(F)c(F)c3)c2C)cc1NC] | 2 | 2.09 | 621 | |

TABLE 65-continued
| No. | Structure | LCMS method No | RT | MS (m/z) | configuration |
|---|---|---|---|---|---|
| I-316 | 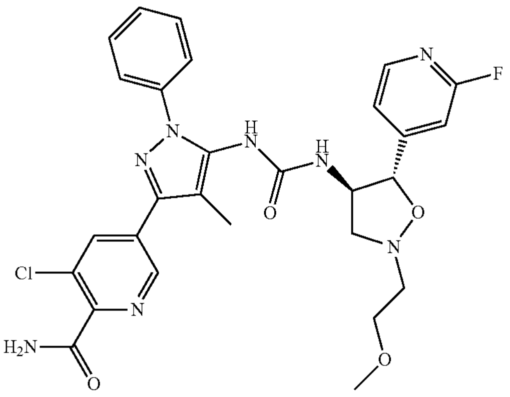 [SMILES: COCCN1C[C@@H](NC(=O)Nc2c(C)c(-c3cnc(C(N)=O)c(Cl)c3)nn2-c2ccccc2)[C@H](c2ccnc(F)c2)O1] | 2 | 1.53 | 595 | racemate |
| I-317 | 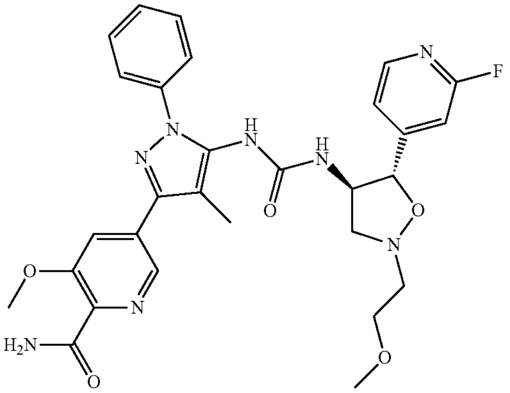 [SMILES: COCCN1C[C@@H](NC(=O)Nc2c(C)c(-c3cnc(C(N)=O)c(OC)c3)nn2-c2ccccc2)[C@H](c2ccnc(F)c2)O1] | 2 | 1.37 | 591 | racemate |
| I-318 | 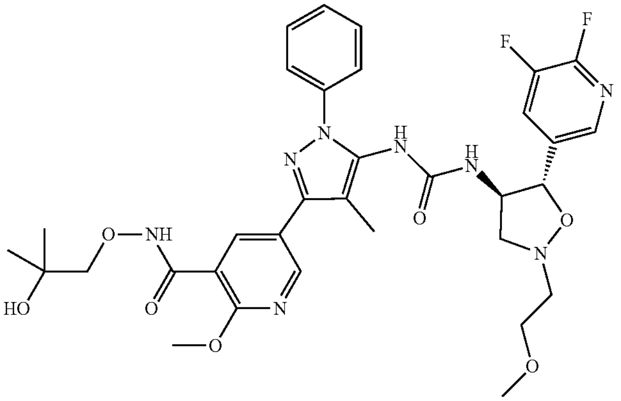 [SMILES: COCCN1C[C@@H](NC(=O)Nc2c(C)c(-c3cnc(OC)c(C(=O)NOCC(C)(C)O)c3)nn2-c2ccccc2)[C@H](c2cnc(F)c(F)c2)O1] | 2 | 1.8 | 697 | racemate |

TABLE 66
| No. | Structure | LCMS method No. | RT | MS (m/z) | configuration |
|---|---|---|---|---|---|
| I-319 | 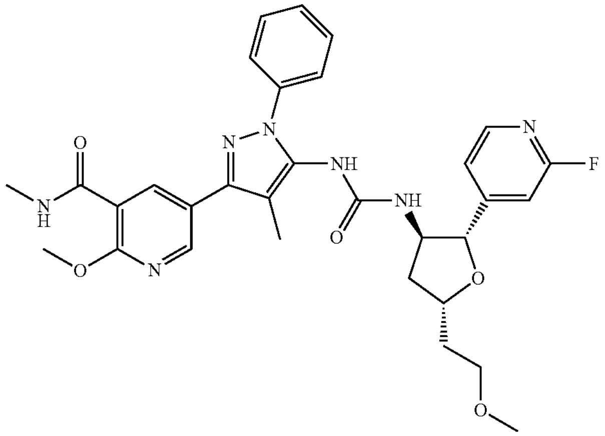 [SMILES: CNC(=O)c1cc(-c2nn(-c3ccccc3)c(NC(=O)N[C@@H]3C[C@@H](CCOC)O[C@H]3c3ccnc(F)c3)c2C)cnc1OC] | 1 | 1.7 | 604.25 | |
| I-320 | 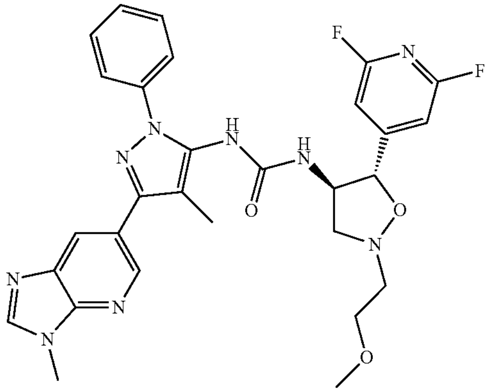 [SMILES: COCCN1C[C@@H](NC(=O)Nc2c(C)c(-c3cnc4c(c3)ncn4C)nn2-c2ccccc2)[C@H](c2cc(F)nc(F)c2)O1] | 1 | 1.53 | 590.2 | racemate |
| I-321 | 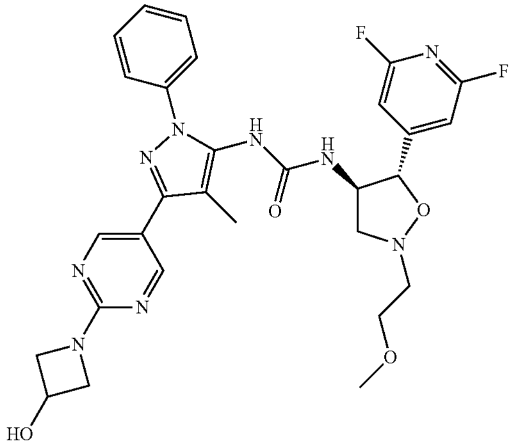 [SMILES: COCCN1C[C@@H](NC(=O)Nc2c(C)c(-c3cnc(N4CC(O)C4)nc3)nn2-c2ccccc2)[C@H](c2cc(F)nc(F)c2)O1] | 1 | 1.53 | 608.3 | racemate |

TABLE 66-continued
| No. | Structure | LCMS method No. | RT | MS (m/z) | configuration |
|---|---|---|---|---|---|
| I-322 | 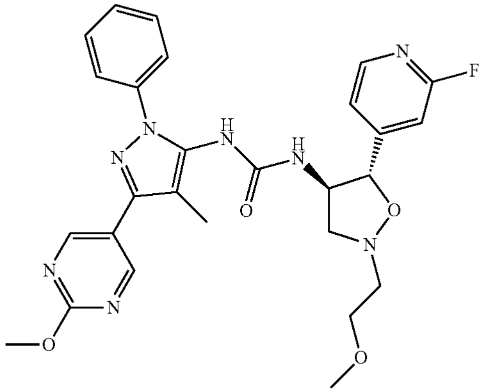 [SMILES: COCCN1C[C@@H](NC(=O)Nc2c(C)c(-c3cnc(OC)nc3)nn2-c2ccccc2)[C@H](c2ccnc(F)c2)O1] | 2 | 1.61 | 549 | |
TABLE 67
| No. | Structure | LCMS method No. | RT | MS (m/z) | configuration |
|---|---|---|---|---|---|
| I-323 | 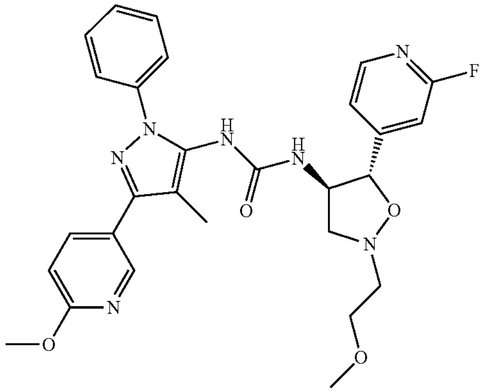 [SMILES: COCCN1C[C@@H](NC(=O)Nc2c(C)c(-c3ccc(OC)nc3)nn2-c2ccccc2)[C@H](c2ccnc(F)c2)O1] | 1 | 1.77 | 548.3 | racemate |
| I-324 | 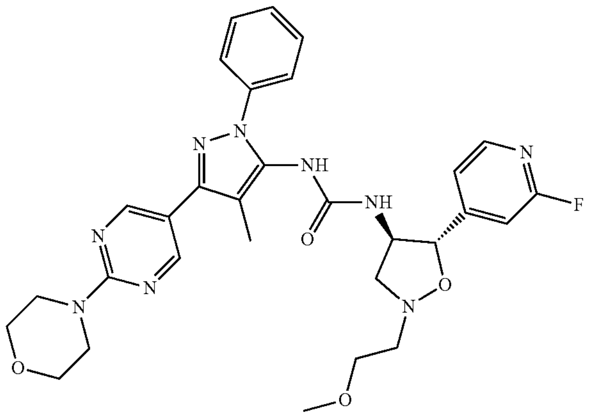 [SMILES: COCCN1C[C@@H](NC(=O)Nc2c(C)c(-c3cnc(N4CCOCC4)nc3)nn2-c2ccccc2)[C@H](c2ccnc(F)c2)O1] | 1 | 1.69 | 604.3 | racemate |

TABLE 67-continued
| No. | Structure | LCMS method No. | RT | MS (m/z) | configuration |
|---|---|---|---|---|---|
| I-325 | 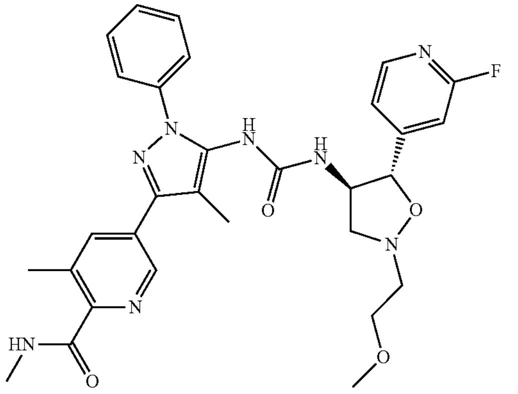 [SMILES: CNC(=O)c1ncc(-c2nn(-c3ccccc3)c(NC(=O)N[C@@H]3CN(CCOC)O[C@H]3c3ccnc(F)c3)c2C)cc1C] | 2 | 1.9 | 589 | |
| I-326 | 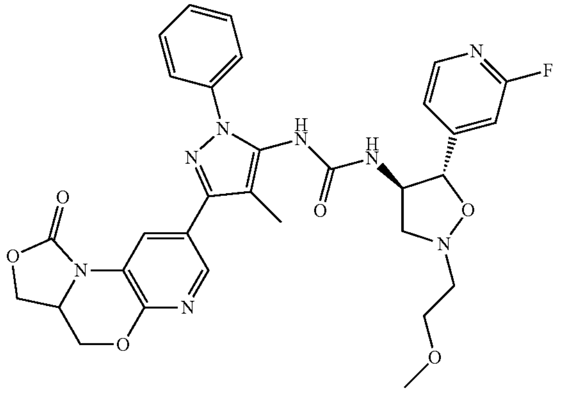 [SMILES: COCCN1C[C@@H](NC(=O)Nc2c(C)c(-c3cnc4c(c3)N3C(=O)OCC3CO4)nn2-c2ccccc2)[C@H](c2ccnc(F)c2)O1] | 2 | 1.55 | 631 | racemate |
TABLE 68
| No. | Structure | LCMS method No. | RT | MS (m/z) | configuration |
|---|---|---|---|---|---|
| I-327 | 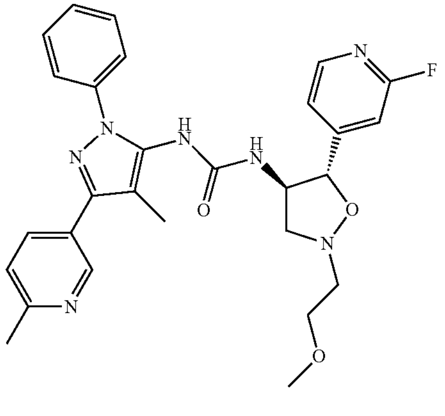 [SMILES: COCCN1C[C@@H](NC(=O)Nc2c(C)c(-c3ccc(C)nc3)nn2-c2ccccc2)[C@H](c2ccnc(F)c2)O1] | 1 | 1.14 | 532.3 | racemate |

TABLE 68-continued
| No. | Structure | LCMS method No. | RT | MS (m/z) | configuration |
|---|---|---|---|---|---|
| I-328 | 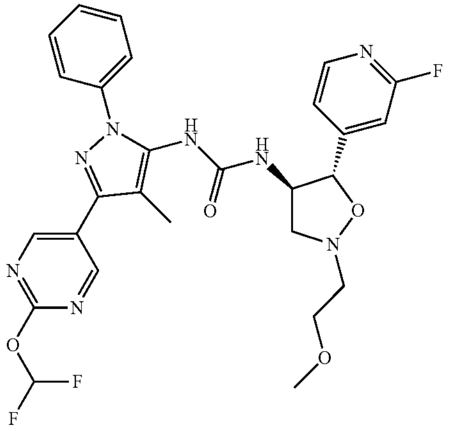 [SMILES: COCCN1C[C@@H](NC(=O)Nc2c(C)c(-c3cnc(OC(F)F)nc3)nn2-c2ccccc2)[C@H](c2ccnc(F)c2)O1] | 1 | 1.87 | 585.2 | racemate |
| I-329 | 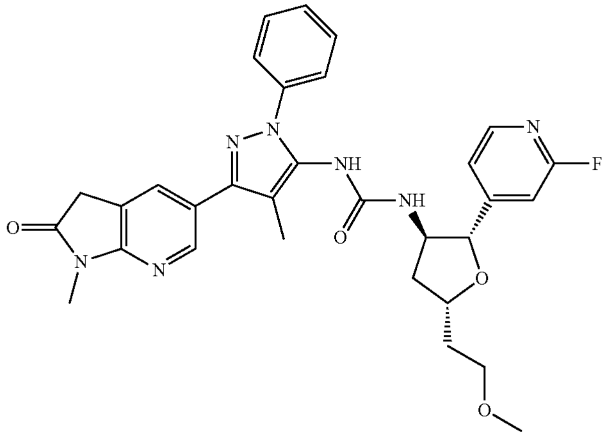 [SMILES: COCC[C@@H]1C[C@@H](NC(=O)Nc2c(C)c(-c3cnc4c(c3)CC(=O)N4C)nn2-c2ccccc2)[C@H](c2ccnc(F)c2)O1] | 1 | 1.59 | 586.3 | |
| I-330 | 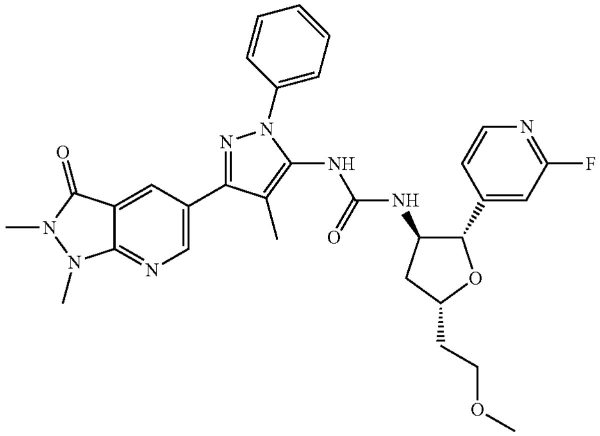 [SMILES: COCC[C@@H]1C[C@@H](NC(=O)Nc2c(C)c(-c3cnc4c(c3)c(=O)n(C)n4C)nn2-c2ccccc2)[C@H](c2ccnc(F)c2)O1] | 1 | 1.53 | 601.3 | |

TABLE 69
| No. | Structure | LCMS method No. | RT | MS (m/z) | configuration |
| --- | --- | --- | --- | --- | --- |
| I-331 | 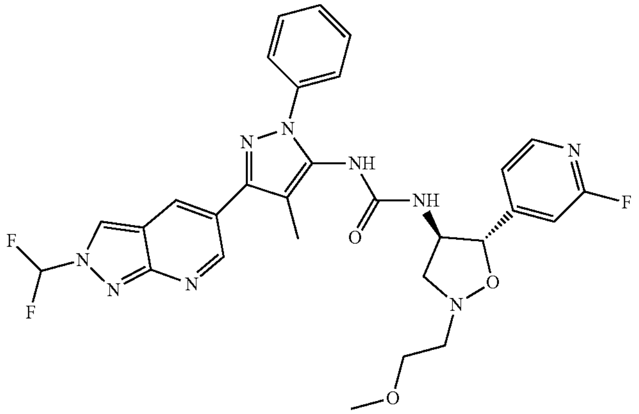 [SMILES: COCCN1C[C@@H](NC(=O)Nc2c(C)c(-c3cnc4nn(C(F)F)cc4c3)nn2-c2ccccc2)[C@H](c2ccnc(F)c2)O1] | 1 | 1.61 | 608.25 | racemate |
| I-332 | 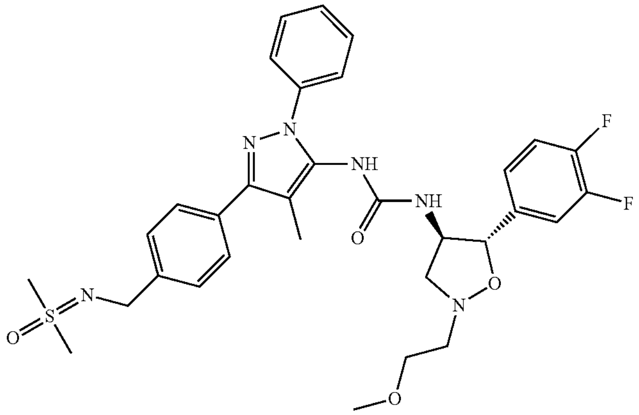 [SMILES: COCCN1C[C@@H](NC(=O)Nc2c(C)c(-c3ccc(CN=S(C)(C)=O)cc3)nn2-c2ccccc2)[C@H](c2ccc(F)c(F)c2)O1] | 1 | 1.56 | 639.3 | |
| I-333 | 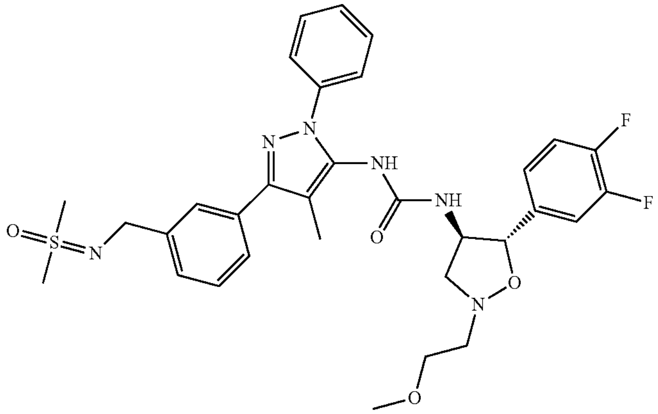 [SMILES: COCCN1C[C@@H](NC(=O)Nc2c(C)c(-c3cccc(CN=S(C)(C)=O)c3)nn2-c2ccccc2)[C@H](c2ccc(F)c(F)c2)O1] | 1 | 1.59 | 639.3 | |

TABLE 69-continued
| No. | Structure | LCMS method No. | RT | MS (m/z) | configuration |
|---|---|---|---|---|---|
| I-334 | 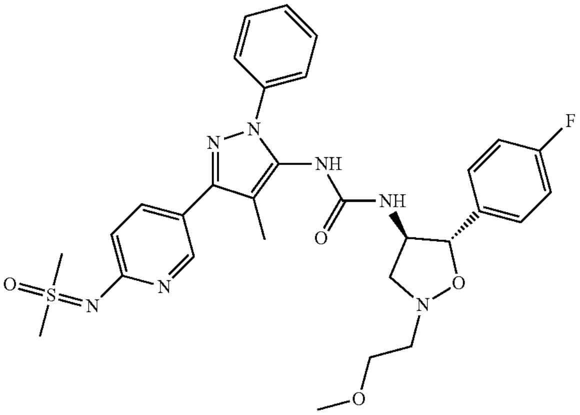 [SMILES: COCCN1C[C@@H](NC(=O)Nc2c(C)c(-c3ccc(N=S(C)(C)=O)nc3)nn2-c2ccccc2)[C@H](c2ccc(F)cc2)O1] | 1 | 1.32 | 608.25 | |
TABLE 70
| No. | Structure | LCMS method No. | RT | MS (m/z) | configuration |
|---|---|---|---|---|---|
| I-335 | 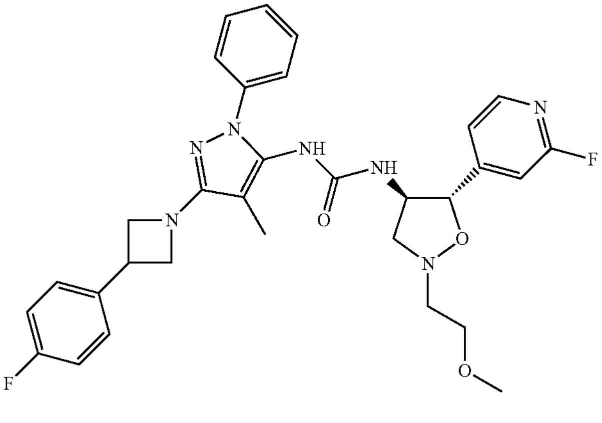 [SMILES: COCCN1C[C@@H](NC(=O)Nc2c(C)c(N3CC(c4ccc(F)cc4)C3)nn2-c2ccccc2)[C@H](c2ccnc(F)c2)O1] | 2 | 2.09 | 590 | racemate |
| I-336 | 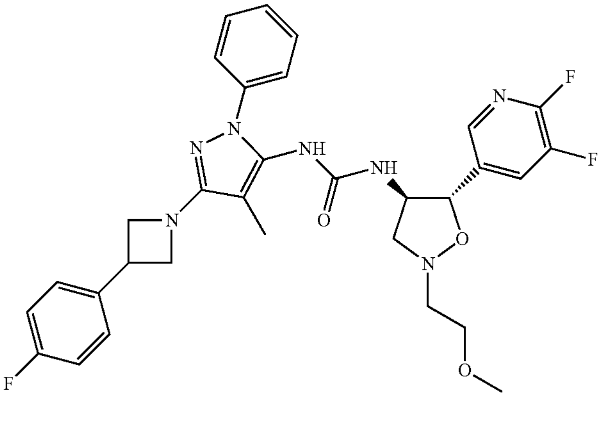 [SMILES: COCCN1C[C@@H](NC(=O)Nc2c(C)c(N3CC(c4ccc(F)cc4)C3)nn2-c2ccccc2)[C@H](c2cnc(F)c(F)c2)O1] | 2 | 2.25 | 608 | racemate |

TABLE 70-continued
| No. | Structure | LCMS method No. | RT | MS (m/z) | configuration |
|---|---|---|---|---|---|
| I-337 | 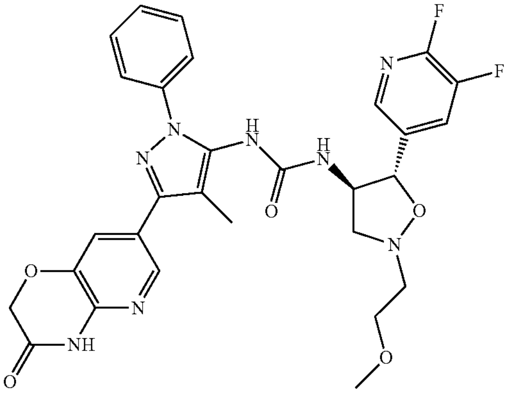 [SMILES: COCCN1C[C@@H](NC(=O)Nc2c(C)c(-c3cnc4c(c3)OCC(=O)N4)nn2-c2ccccc2)[C@H](c2cnc(F)c(F)c2)O1] | 1 | 1.81 | 607 | racemate |
| I-338 | 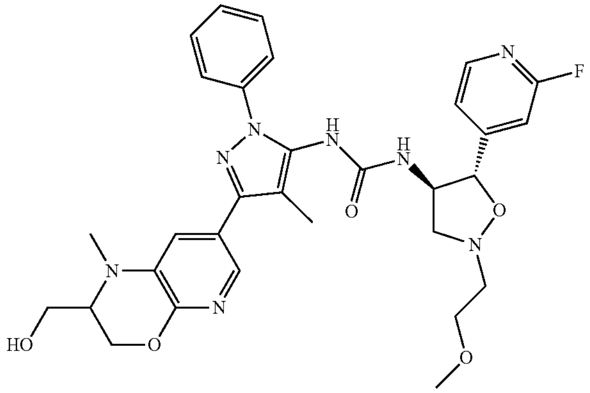 [SMILES: COCCN1C[C@@H](NC(=O)Nc2c(C)c(-c3cnc4c(c3)N(C)C(CO)CO4)nn2-c2ccccc2)[C@H](c2ccnc(F)c2)O1] | 2 | 1.37 | 619 | racemate |
TABLE 71
| No. | Structure | LCMS method No. | RT | MS (m/z) | configuration |
|---|---|---|---|---|---|
| I-339 | 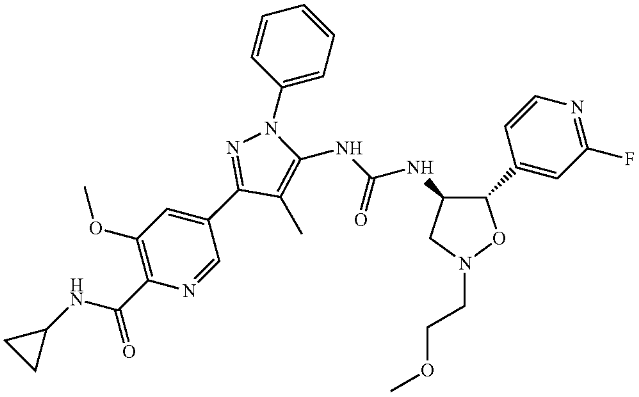 [SMILES: COCCN1C[C@@H](NC(=O)Nc2c(C)c(-c3cnc(C(=O)NC4CC4)c(OC)c3)nn2-c2ccccc2)[C@H](c2ccnc(F)c2)O1] | 2 | 1.55 | 631 | racemate |

TABLE 71-continued
| No. | Structure | LCMS method No. | RT | MS (m/z) | configuration |
|---|---|---|---|---|---|
| I-340 | 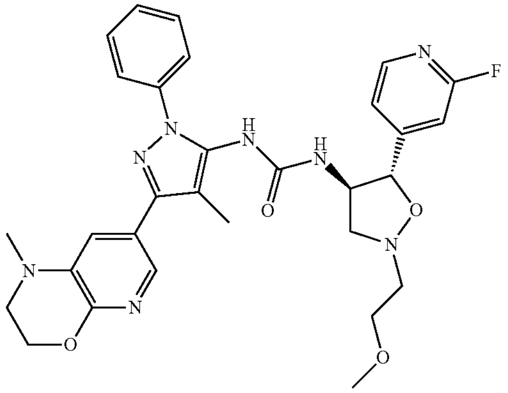 [SMILES: COCCN1C[C@@H](NC(=O)Nc2c(C)c(-c3cnc4c(c3)N(C)CCO4)nn2-c2ccccc2)[C@H](c2ccnc(F)c2)O1] | 2 | 1.52 | 589 | racemate |
| I-341 | 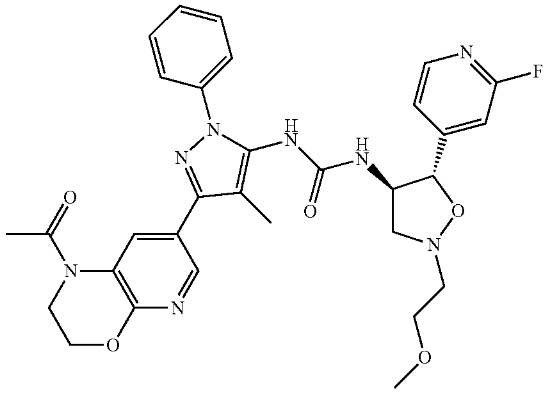 [SMILES: COCCN1C[C@@H](NC(=O)Nc2c(C)c(-c3cnc4c(c3)N(C(C)=O)CCO4)nn2-c2ccccc2)[C@H](c2ccnc(F)c2)O1] | 2 | 1.46 | 617 | racemate |
| I-342 | 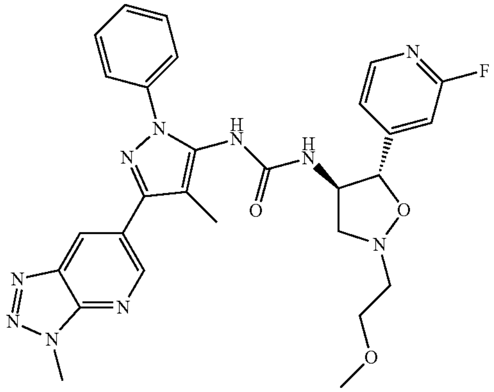 [SMILES: COCCN1C[C@@H](NC(=O)Nc2c(C)c(-c3cnc4c(c3)nnn4C)nn2-c2ccccc2)[C@H](c2ccnc(F)c2)O1] | 1 | 1.58 | 573.25 | |

TABLE 72
| No. | Structure | LCMS method No. | RT | MS (m/z) | configuration |
|---|---|---|---|---|---|
| I-343 | 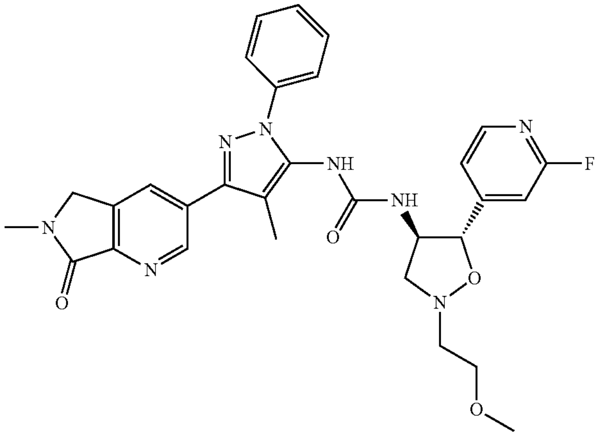 [SMILES: COCCN1C[C@@H](NC(=O)Nc2c(C)c(-c3cnc4c(c3)CN(C)C4=O)nn2-c2ccccc2)[C@H](c2ccnc(F)c2)O1] | 1 | 1.39 | 587.25 | racemate |
| I-344 | 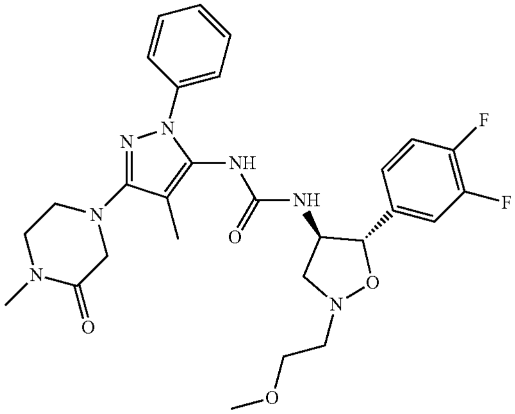 [SMILES: COCCN1C[C@@H](NC(=O)Nc2c(C)c(N3CCN(C)C(=O)C3)nn2-c2ccccc2)[C@H](c2ccc(F)c(F)c2)O1] | 1 | 1.65 | 570.25 | |
| I-345 | 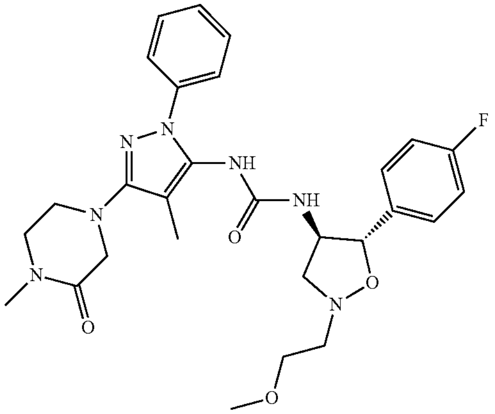 [SMILES: COCCN1C[C@@H](NC(=O)Nc2c(C)c(N3CCN(C)C(=O)C3)nn2-c2ccccc2)[C@H](c2ccc(F)cc2)O1] | 1 | 1.55 | 552.3 | |

TABLE 72-continued
| No. | Structure | LCMS method No. | RT | MS (m/z) | configuration |
|---|---|---|---|---|---|
| I-346 | 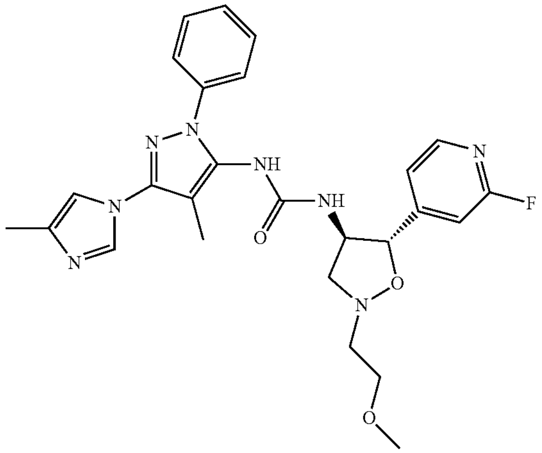 [SMILES: COCCN1C[C@@H](NC(=O)Nc2c(C)c(-n3cnc(C)c3)nn2-c2ccccc2)[C@H](c2ccnc(F)c2)O1] | 2 | 1.04 | 521 | racemate |
TABLE 73
| No. | Structure | LCMS method No. | RT | MS (m/z) | configuration |
|---|---|---|---|---|---|
| I-347 | 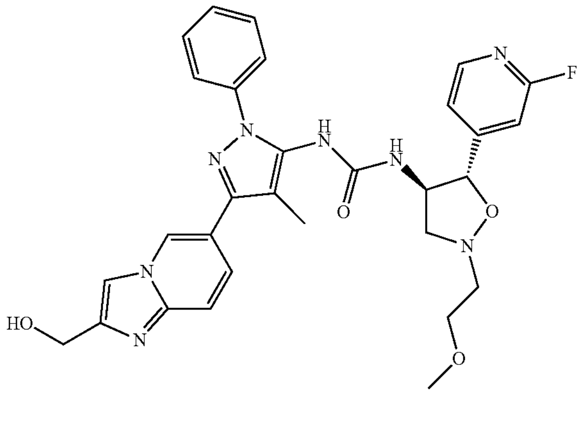 [SMILES: COCCN1C[C@@H](NC(=O)Nc2c(C)c(-c3ccc4nc(CO)cn4c3)nn2-c2ccccc2)[C@H](c2ccnc(F)c2)O1] | 1 | 1.31 | 587 | racemate |
| I-348 | 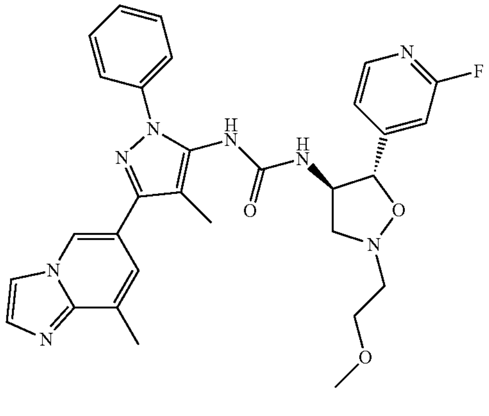 [SMILES: COCCN1C[C@@H](NC(=O)Nc2c(C)c(-c3cc(C)c4nccn4c3)nn2-c2ccccc2)[C@H](c2ccnc(F)c2)O1] | 1 | 1.37 | 571 | racemate |

TABLE 73-continued
| No. | Structure | LCMS method No. | RT | MS (m/z) | configuration |
|---|---|---|---|---|---|
| I-349 | 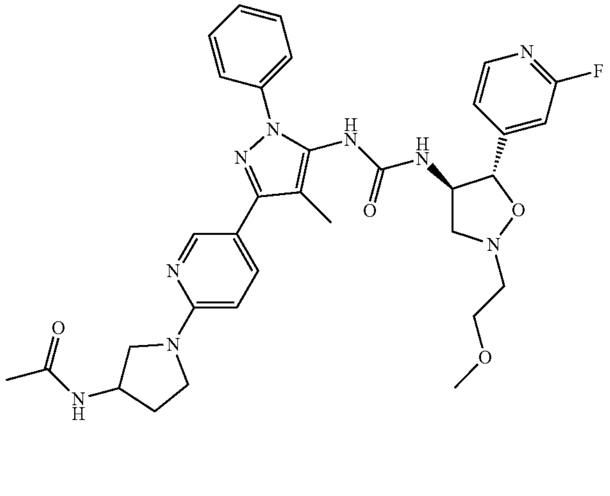 [SMILES: COCCN1C[C@@H](NC(=O)Nc2c(C)c(-c3ccc(N4CCC(NC(C)=O)C4)nc3)nn2-c2ccccc2)[C@H](c2ccnc(F)c2)O1] | 1 | 1.32 | 644 | diastereo mixture |
| I-350 | 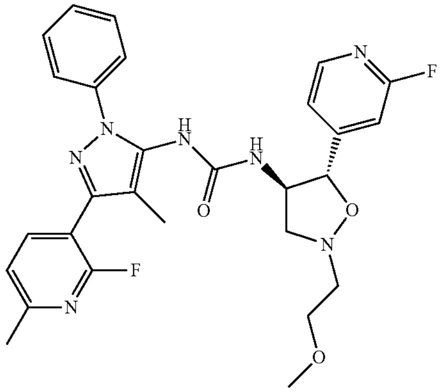 [SMILES: COCCN1C[C@@H](NC(=O)Nc2c(C)c(-c3ccc(C)nc3F)nn2-c2ccccc2)[C@H](c2ccnc(F)c2)O1] | 1 | 1.9 | 550 | racemate |
TABLE 74
| No. | Structure | LCMS method No. | RT | MS (m/z) | configuration |
|---|---|---|---|---|---|
| I-351 | 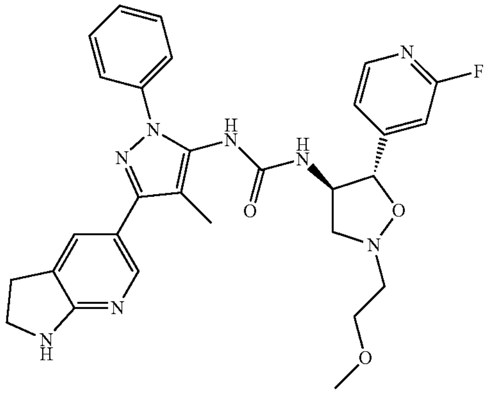 [SMILES: COCCN1C[C@@H](NC(=O)Nc2c(C)c(-c3cnc4c(c3)CCN4)nn2-c2ccccc2)[C@H](c2ccnc(F)c2)O1] | 1 | 1.37 | 559.2 | racemate |

TABLE 74-continued
| No. | Structure | LCMS method No. | RT | MS (m/z) | configuration |
|---|---|---|---|---|---|
| I-352 | 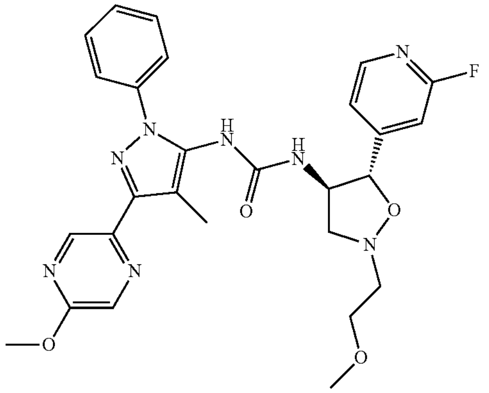 [SMILES: COCCN1C[C@@H](NC(=O)Nc2c(C)c(-c3cnc(OC)cn3)nn2-c2ccccc2)[C@H](c2ccnc(F)c2)O1] | 1 | 1.93 | 549.2 | racemate |
| I-353 | 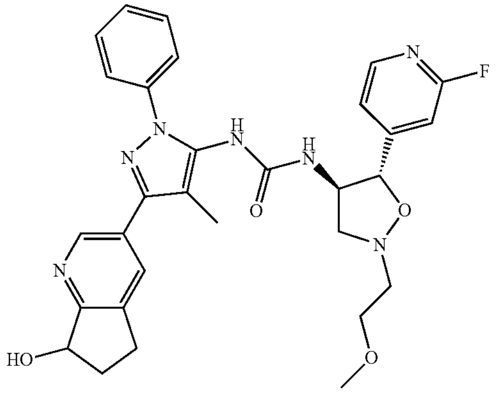 [SMILES: COCCN1C[C@@H](NC(=O)Nc2c(C)c(-c3cnc4c(c3)CCC4O)nn2-c2ccccc2)[C@H](c2ccnc(F)c2)O1] | 1 | 1.43 | 574 | diastereo mixture |
| I-354 | 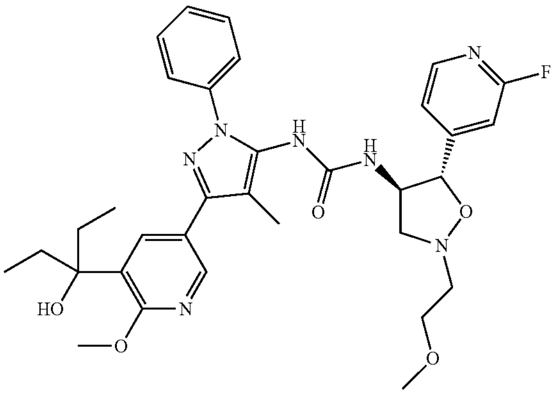 [SMILES: CCC(O)(CC)c1cc(-c2nn(-c3ccccc3)c(NC(=O)N[C@@H]3CN(CCOC)O[C@H]3c3ccnc(F)c3)c2C)cnc1OC] | 2 | 2.08 | 634 | racemate |

TABLE 75
| No. | Structure | LCMS method No. | RT | MS (m/z) | configuration |
|---|---|---|---|---|---|
| I-355 | 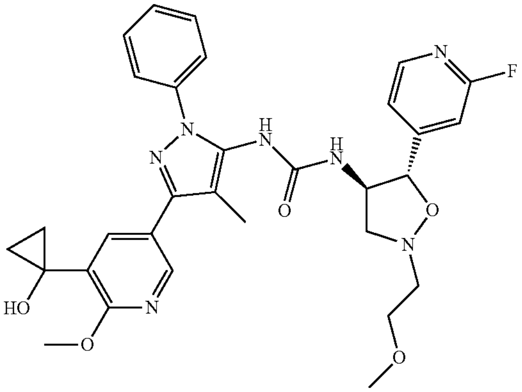 [SMILES: COCCN1C[C@@H](NC(=O)Nc2c(C)c(-c3cnc(OC)c(C4(O)CC4)c3)nn2-c2ccccc2)[C@H](c2ccnc(F)c2)O1] | 2 | 2.05 | 604 | racemate |
| I-356 | 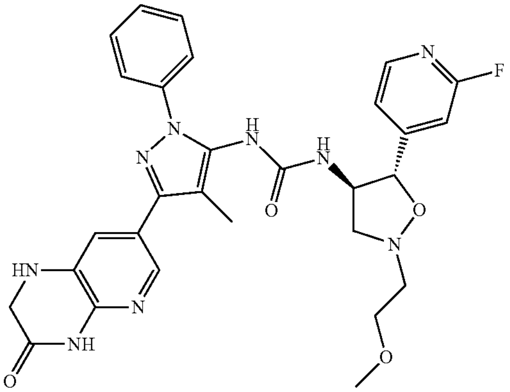 [SMILES: COCCN1C[C@@H](NC(=O)Nc2c(C)c(-c3cnc4c(c3)NCC(=O)N4)nn2-c2ccccc2)[C@H](c2ccnc(F)c2)O1] | 2 | 1.18 | 588 | racemate |
| I-357 | 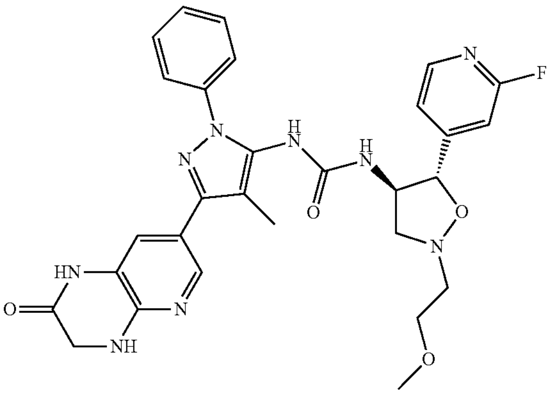 [SMILES: COCCN1C[C@@H](NC(=O)Nc2c(C)c(-c3cnc4c(c3)NC(=O)CN4)nn2-c2ccccc2)[C@H](c2ccnc(F)c2)O1] | 2 | 1.39 | 588 | racemate |

TABLE 75-continued
| No. | Structure | LCMS method No. | RT | MS (m/z) | configuration |
|---|---|---|---|---|---|
| I-358 | 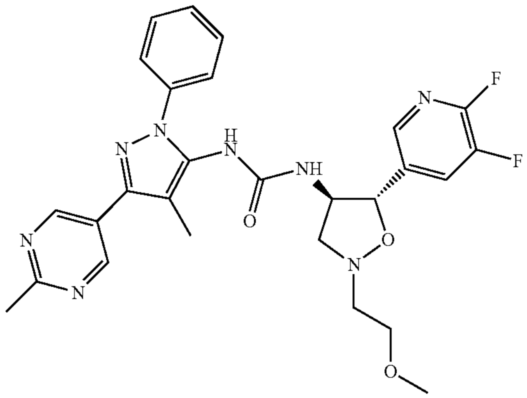 [SMILES: COCCN1C[C@@H](NC(=O)Nc2c(C)c(-c3cnc(C)nc3)nn2-c2ccccc2)[C@H](c2cnc(F)c(F)c2)O1] | 1 | 1.63 | 551.25 | |
TABLE 76
| No. | Structure | LCMS method No. | RT | MS (m/z) | configuration |
|---|---|---|---|---|---|
| I-359 | 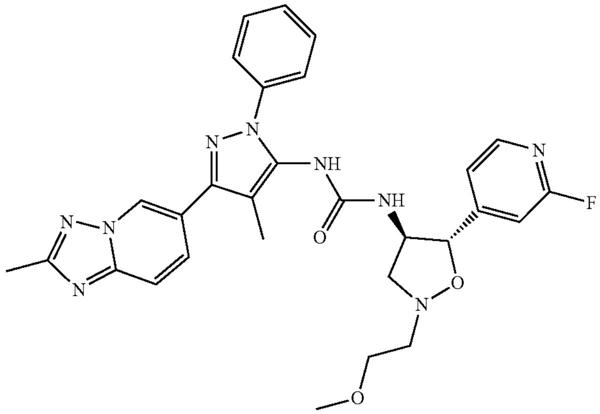 [SMILES: COCCN1C[C@@H](NC(=O)Nc2c(C)c(-c3ccc4nc(C)nn4c3)nn2-c2ccccc2)[C@H](c2ccnc(F)c2)O1] | 1 | 1.51 | 572 | |
| I-360 | 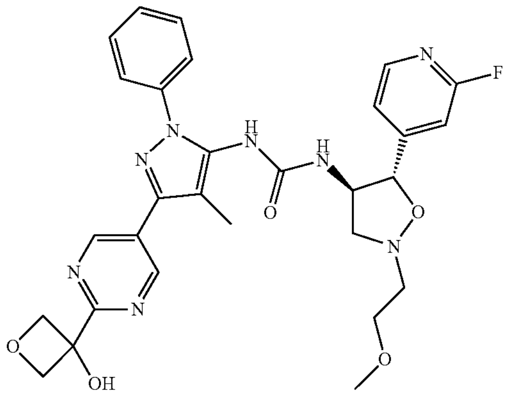 [SMILES: COCCN1C[C@@H](NC(=O)Nc2c(C)c(-c3cnc(C4(O)COC4)nc3)nn2-c2ccccc2)[C@H](c2ccnc(F)c2)O1] | 1 | 1.39 | 591.25 | racemate |

TABLE 76-continued
| No. | Structure | LCMS method No. | RT | MS (m/z) | configuration |
|---|---|---|---|---|---|
| I-361 | 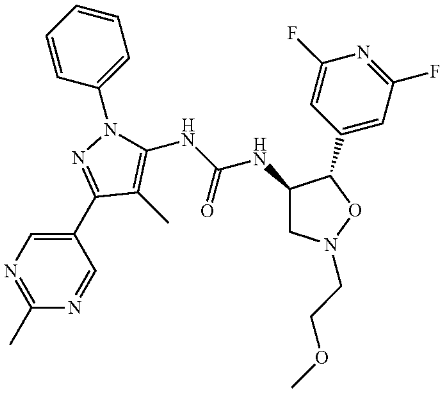 [SMILES: COCCN1C[C@@H](NC(=O)Nc2c(C)c(-c3cnc(C)nc3)nn2-c2ccccc2)[C@H](c2cc(F)nc(F)c2)O1] | 1 | 1.7 | 551.25 | |
| I-362 | 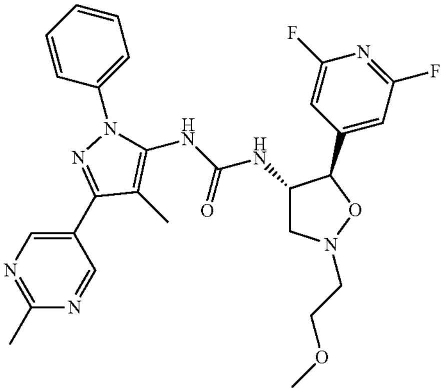 [SMILES: COCCN1C[C@H](NC(=O)Nc2c(C)c(-c3cnc(C)nc3)nn2-c2ccccc2)[C@@H](c2cc(F)nc(F)c2)O1] | 1 | 1.7 | 551.25 | |
TABLE 77
| No. | Structure | LCMS method No. | RT | MS (m/z) | configuration |
|---|---|---|---|---|---|
| I-363 | 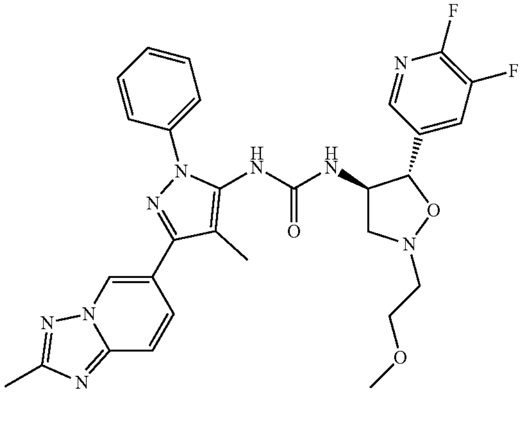 [SMILES: COCCN1C[C@@H](NC(=O)Nc2c(C)c(-c3ccc4nc(C)nn4c3)nn2-c2ccccc2)[C@H](c2cnc(F)c(F)c2)O1] | 1 | 1.66 | 590 | |

TABLE 77-continued
| No. | Structure | LCMS method No. | RT | MS (m/z) | configuration |
|---|---|---|---|---|---|
| I-364 | 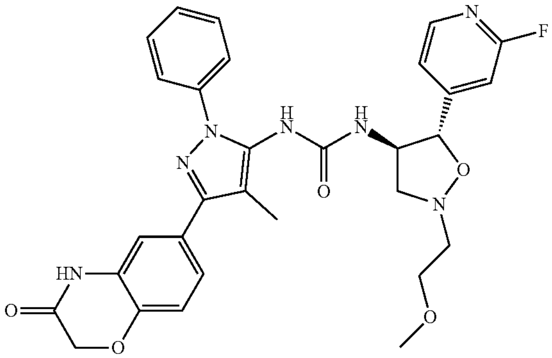 [SMILES: COCCN1C[C@@H](NC(=O)Nc2c(C)c(-c3ccc4c(c3)NC(=O)CO4)nn2-c2ccccc2)[C@H](c2ccnc(F)c2)O1] | 1 | 1.71 | 588 | racemate |
| I-365 | 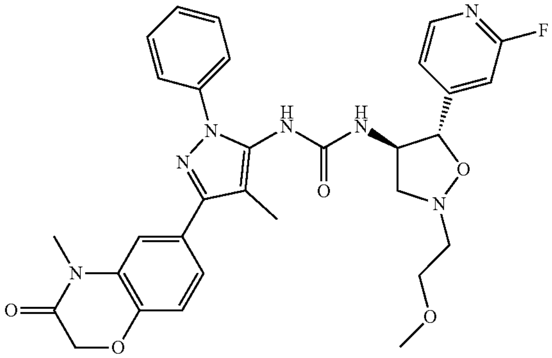 [SMILES: COCCN1C[C@@H](NC(=O)Nc2c(C)c(-c3ccc4c(c3)N(C)C(=O)CO4)nn2-c2ccccc2)[C@H](c2ccnc(F)c2)O1] | 1 | 1.83 | 602 | racemate |
| I-366 | 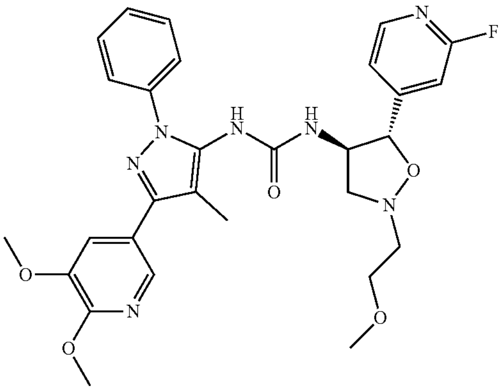 [SMILES: COCCN1C[C@@H](NC(=O)Nc2c(C)c(-c3cnc(OC)c(OC)c3)nn2-c2ccccc2)[C@H](c2ccnc(F)c2)O1] | 1 | 1.8 | 578 | racemate |

TABLE 78
| No. | Structure | LCMS method No. | RT | MS (m/z) | config-uration |
|---|---|---|---|---|---|
| I-367 | 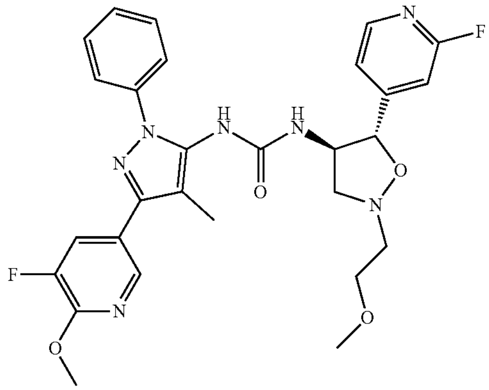 [SMILES: COCCN1C[C@@H](NC(=O)Nc2c(C)c(-c3cnc(OC)c(F)c3)nn2-c2ccccc2)[C@H](c2ccnc(F)c2)O1] | 1 | 2.02 | 566 | racemate |
| I-368 | 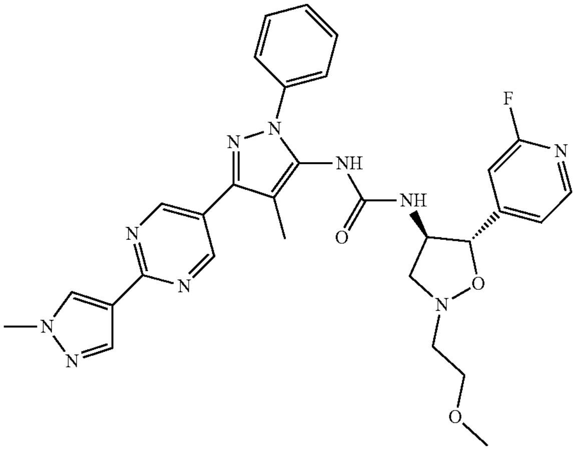 [SMILES: COCCN1C[C@@H](NC(=O)Nc2c(C)c(-c3cnc(-c4cnn(C)c4)nc3)nn2-c2ccccc2)[C@H](c2ccnc(F)c2)O1] | 1 | 1.66 | 599 | racemate |

TABLE 78-continued
| No. | Structure | LCMS method No. | RT | MS (m/z) | config-uration |
|---|---|---|---|---|---|
| I-369 | 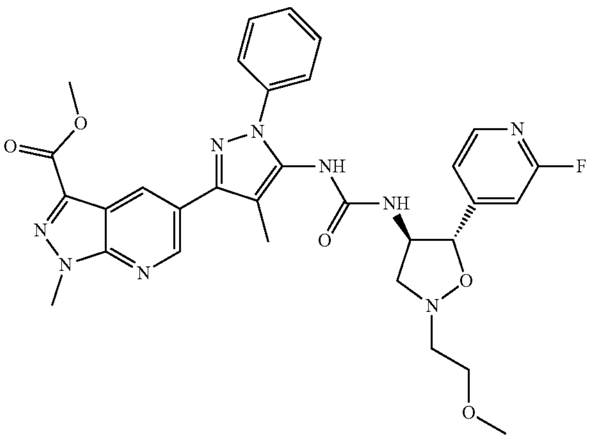 [SMILES: COCCN1C[C@@H](NC(=O)Nc2c(C)c(-c3cnc4c(c3)c(C(=O)OC)nn4C)nn2-c2ccccc2)[C@H](c2ccnc(F)c2)O1] | 1 | 1.74 | 630.3 | racemate |
| I-370 | 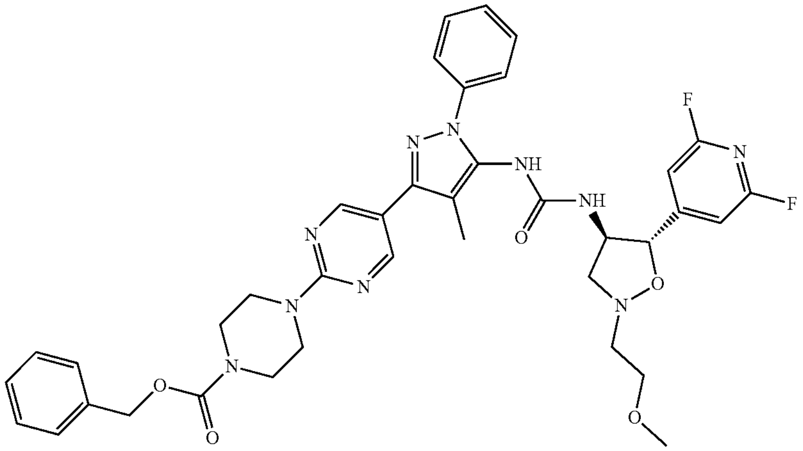 [SMILES: COCCN1C[C@@H](NC(=O)Nc2c(C)c(-c3cnc(N4CCN(C(=O)OCc5ccccc5)CC4)nc3)nn2-c2ccccc2)[C@H](c2cc(F)nc(F)c2)O1] | 1 | 2.35 | 755 | racemate |
TABLE 79
| No. | Structure | LCMS method No. | RT | MS (m/z) | config-uration |
|---|---|---|---|---|---|
| I-371 | 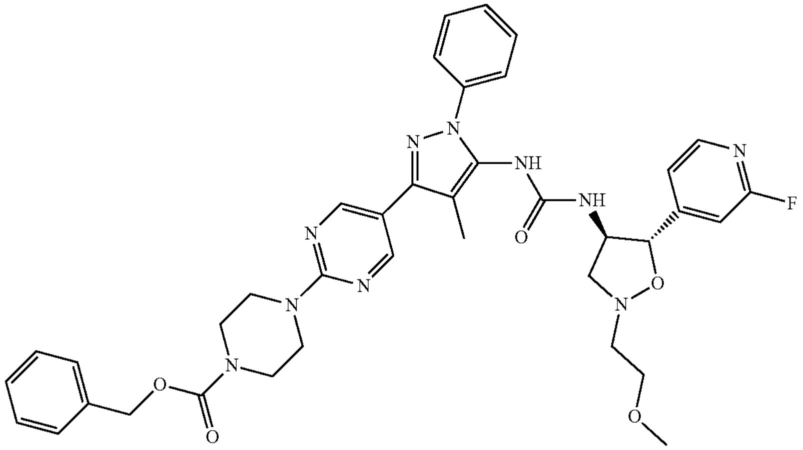 [SMILES: COCCN1C[C@@H](NC(=O)Nc2c(C)c(-c3cnc(N4CCN(C(=O)OCc5ccccc5)CC4)nc3)nn2-c2ccccc2)[C@H](c2ccnc(F)c2)O1] | 1 | 2.32 | 737 | racemate |

TABLE 79-continued
| No. | Structure | LCMS method No. | RT | MS (m/z) | config-uration |
|---|---|---|---|---|---|
| I-372 | 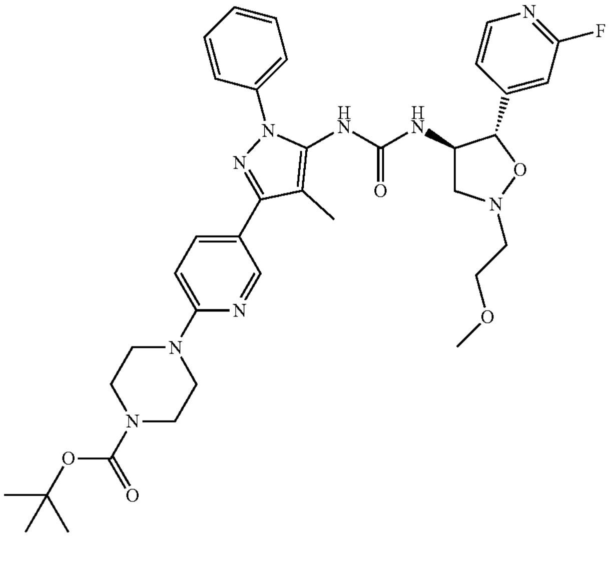 [SMILES: COCCN1C[C@@H](NC(=O)Nc2c(C)c(-c3ccc(N4CCN(C(=O)OC(C)(C)C)CC4)nc3)nn2-c2ccccc2)[C@H](c2ccnc(F)c2)O1] | 1 | 1.76 | 702.35 | racemate |
| I-373 | 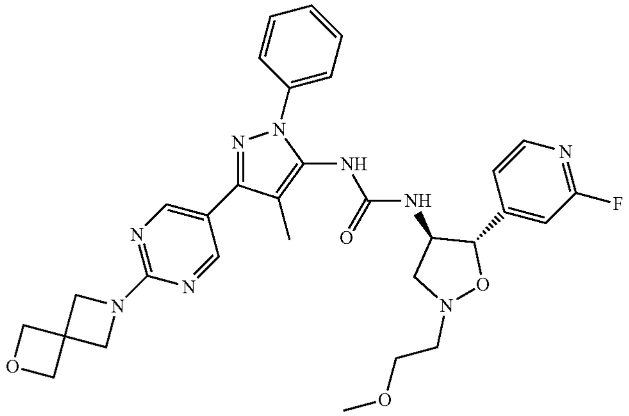 [SMILES: COCCN1C[C@@H](NC(=O)Nc2c(C)c(-c3cnc(N4CC5(COC5)C4)nc3)nn2-c2ccccc2)[C@H](c2ccnc(F)c2)O1] | 1 | 1.45 | 616.3 | racemate |
| I-374 | 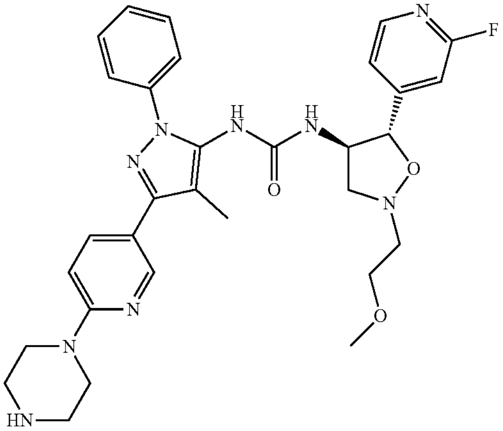 [SMILES: COCCN1C[C@@H](NC(=O)Nc2c(C)c(-c3ccc(N4CCNCC4)nc3)nn2-c2ccccc2)[C@H](c2ccnc(F)c2)O1] | 1 | 1.06 | 602.3 | racemate |

TABLE 80
| No. | Structure | LCMS method No. | RT | MS (m/z) | configuration |
|---|---|---|---|---|---|
| I-375 | 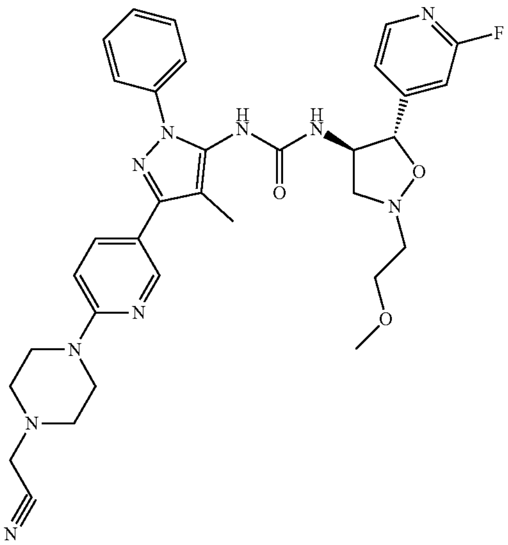 [SMILES: COCCN1C[C@@H](NC(=O)Nc2c(C)c(-c3ccc(N4CCN(CC#N)CC4)nc3)nn2-c2ccccc2)[C@H](c2ccnc(F)c2)O1] | 1 | 1.34 | 641.3 | racemate |
| I-376 | 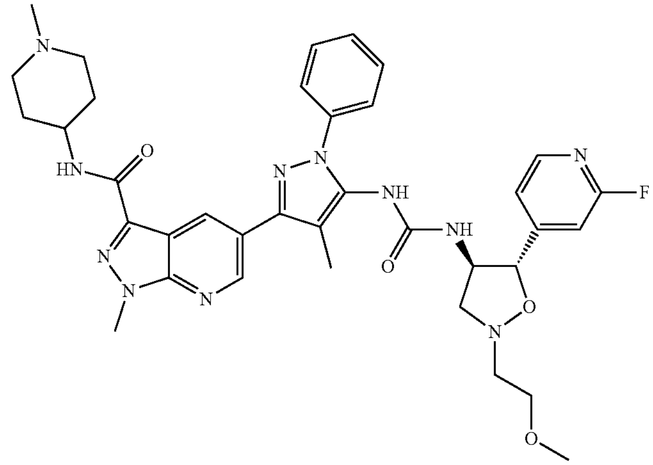 [SMILES: COCCN1C[C@@H](NC(=O)Nc2c(C)c(-c3cnc4c(c3)c(C(=O)NC3CCN(C)CC3)nn4C)nn2-c2ccccc2)[C@H](c2ccnc(F)c2)O1] | 1 | 1.21 | 712.45 | racemate |
| I-377 | 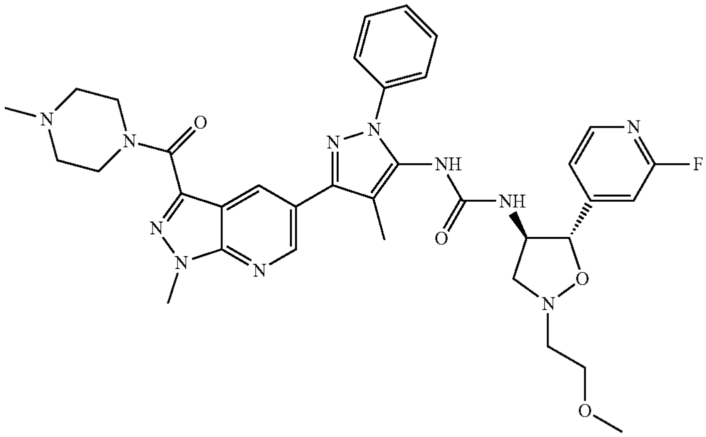 [SMILES: COCCN1C[C@@H](NC(=O)Nc2c(C)c(-c3cnc4c(c3)c(C(=O)N3CCN(C)CC3)nn4C)nn2-c2ccccc2)[C@H](c2ccnc(F)c2)O1] | 1 | 1.18 | 698.35 | racemate |

TABLE 80-continued
| No. | Structure | LCMS method No. | RT | MS (m/z) | configuration |
|---|---|---|---|---|---|
| I-378 | 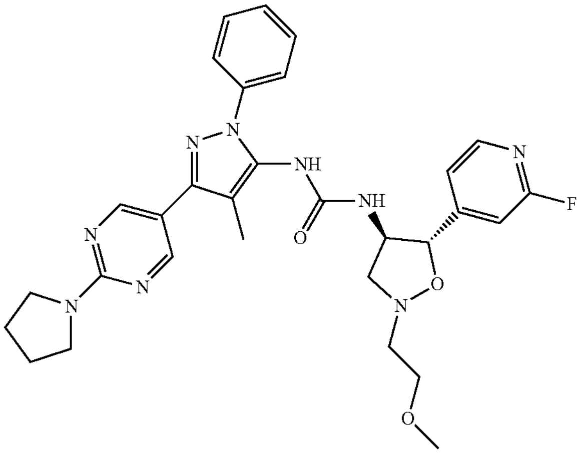 [SMILES: COCCN1C[C@@H](NC(=O)Nc2c(C)c(-c3cnc(N4CCCC4)nc3)nn2-c2ccccc2)[C@H](c2ccnc(F)c2)O1] | 1 | 1.69 | 588 | racemate |
TABLE 81
| No. | Structure | LCMS method No. | RT | MS (m/z) | configuration |
|---|---|---|---|---|---|
| I-379 | 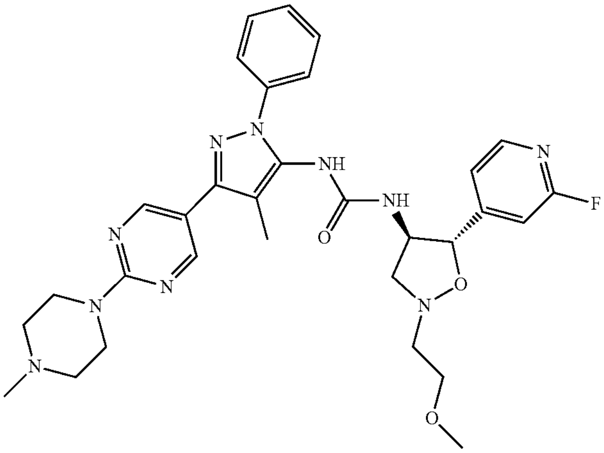 [SMILES: COCCN1C[C@@H](NC(=O)Nc2c(C)c(-c3cnc(N4CCN(C)CC4)nc3)nn2-c2ccccc2)[C@H](c2ccnc(F)c2)O1] | 1 | 1.12 | 617 | racemate |
| I-380 | 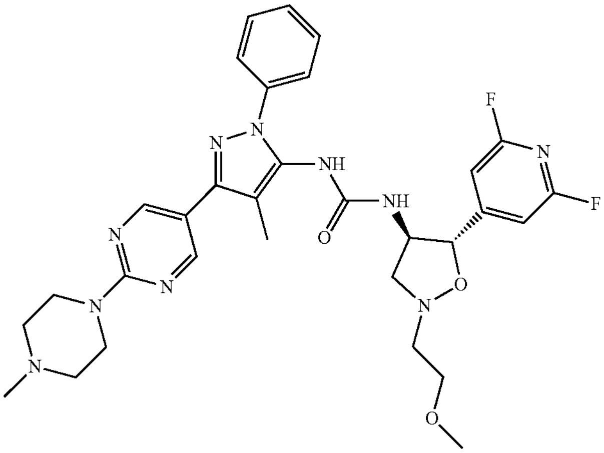 [SMILES: COCCN1C[C@@H](NC(=O)Nc2c(C)c(-c3cnc(N4CCN(C)CC4)nc3)nn2-c2ccccc2)[C@H](c2cc(F)nc(F)c2)O1] | 1 | 1.29 | 635 | racemate |

TABLE 81-continued
| No. | Structure | LCMS method No. | RT | MS (m/z) | configuration |
|---|---|---|---|---|---|
| I-381 | 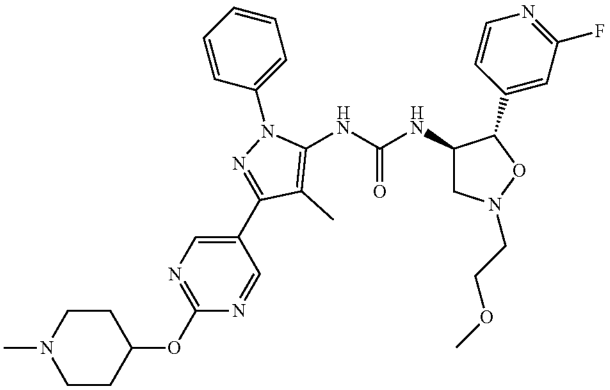 [SMILES: COCCN1C[C@@H](NC(=O)Nc2c(C)c(-c3cnc(OC4CCN(C)CC4)nc3)nn2-c2ccccc2)[C@H](c2ccnc(F)c2)O1] | 1 | 1.16 | 632.35 | racemate |
| I-382 | 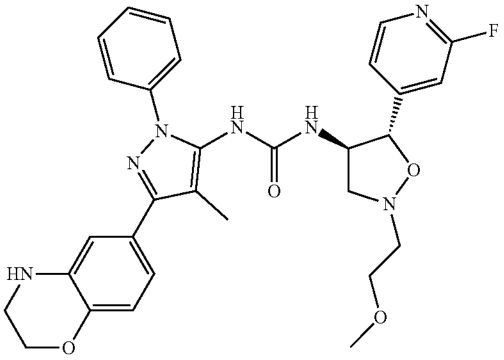 [SMILES: COCCN1C[C@@H](NC(=O)Nc2c(C)c(-c3ccc4c(c3)NCCO4)nn2-c2ccccc2)[C@H](c2ccnc(F)c2)O1] | 1 | 1.83 | 574 | racemate |
TABLE 82
| No. | Structure | LCMS method No. | RT | MS (m/z) | configuration |
|---|---|---|---|---|---|
| I-383 | 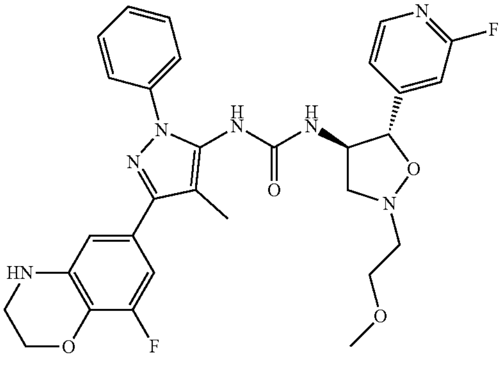 [SMILES: COCCN1C[C@@H](NC(=O)Nc2c(C)c(-c3cc(F)c4c(c3)NCCO4)nn2-c2ccccc2)[C@H](c2ccnc(F)c2)O1] | 1 | 1.97 | 592 | racemate |

TABLE 82-continued
| No. | Structure | LCMS method No. | RT | MS (m/z) | configuration |
|---|---|---|---|---|---|
| I-384 | 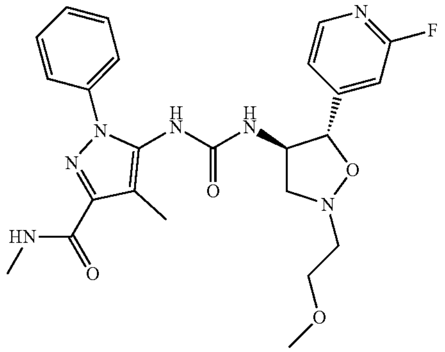 [SMILES: CNC(=O)c1nn(-c2ccccc2)c(NC(=O)N[C@@H]2CN(CCOC)O[C@H]2c2ccnc(F)c2)c1C] | 1 | 1.46 | 498 | racemate |
| I-385 | 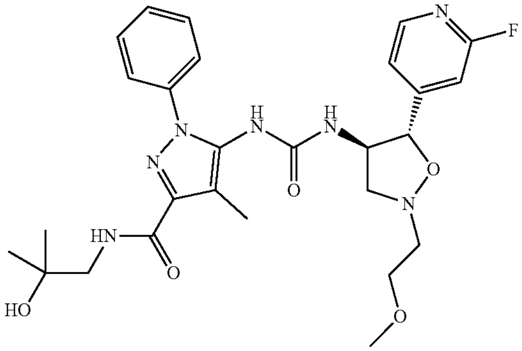 [SMILES: COCCN1C[C@@H](NC(=O)Nc2c(C)c(C(=O)NCC(C)(C)O)nn2-c2ccccc2)[C@H](c2ccnc(F)c2)O1] | 1 | 1.46 | 556 | racemate |
| I-386 | 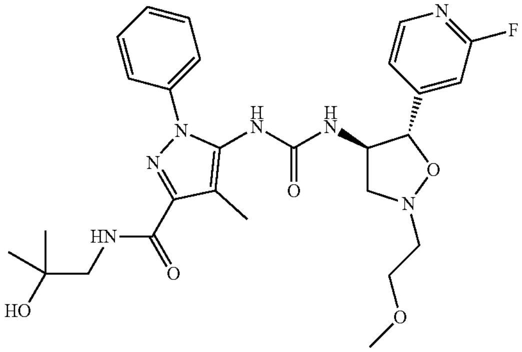 [SMILES: COCCN1C[C@@H](NC(=O)Nc2c(C)c(C(=O)NCC(C)(C)O)nn2-c2ccccc2)[C@H](c2ccnc(F)c2)O1] | 1 | 1.43 | 542 | racemate |
| I-387 | 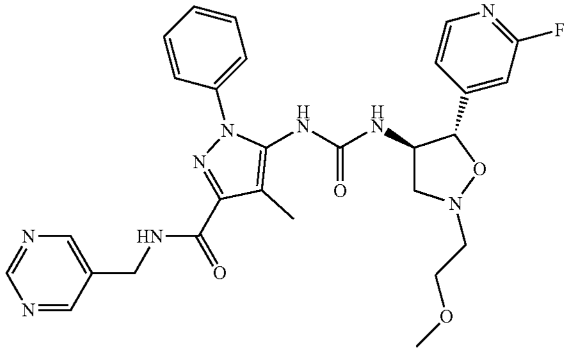 [SMILES: COCCN1C[C@@H](NC(=O)Nc2c(C)c(C(=O)NCc3cncnc3)nn2-c2ccccc2)[C@H](c2ccnc(F)c2)O1] | 1 | 1.39 | 562 | racemate |

TABLE 83
| No. | Structure | LCMS method No. | RT | MS (m/z) | configuration |
|---|---|---|---|---|---|
| I-388 | 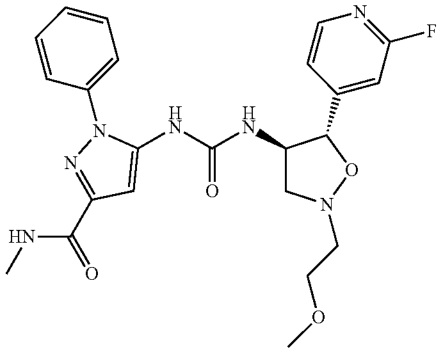 [SMILES: CNC(=O)c1cc(NC(=O)N[C@@H]2CN(CCOC)O[C@H]2c2ccnc(F)c2)n(-c2ccccc2)n1] | 1 | 1.43 | 484 | racemate |
| I-389 | 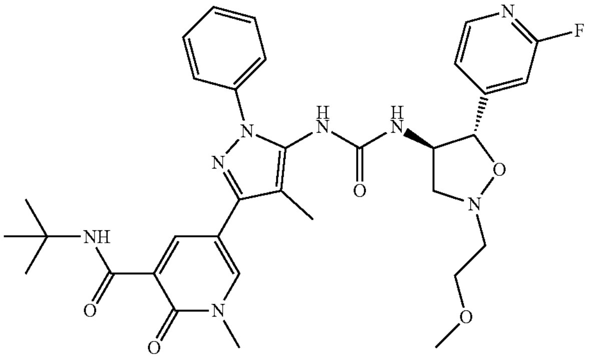 [SMILES: COCCN1C[C@@H](NC(=O)Nc2c(C)c(-c3cc(C(=O)NC(C)(C)C)c(=O)n(C)c3)nn2-c2ccccc2)[C@H](c2ccnc(F)c2)O1] | 1 | 1.98 | 647 | racemate |
| I-390 | 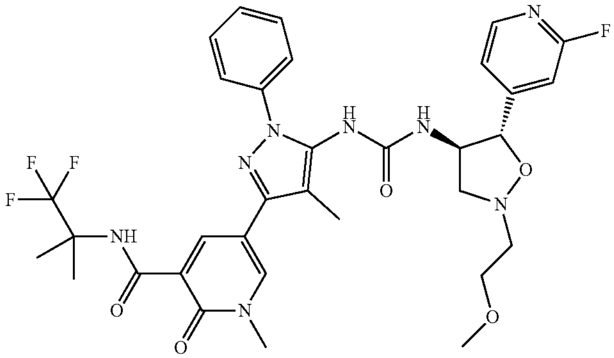 [SMILES: COCCN1C[C@@H](NC(=O)Nc2c(C)c(-c3cc(C(=O)NC(C)(C)C(F)(F)F)c(=O)n(C)c3)nn2-c2ccccc2)[C@H](c2ccnc(F)c2)O1] | 1 | 2.17 | 701 | racemate |
| I-391 | 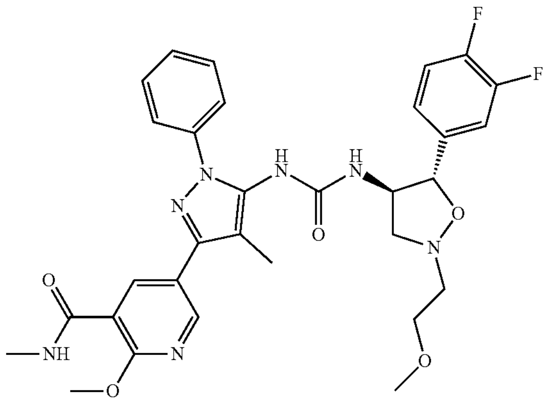 [SMILES: CNC(=O)c1cc(-c2nn(-c3ccccc3)c(NC(=O)N[C@@H]3CN(CCOC)O[C@H]3c3ccc(F)c(F)c3)c2C)cnc1OC] | 2 | 1.95 | 622 | |

TABLE 84
| No. | Structure | LCMS method No. | RT | MS (m/z) | configuration |
|---|---|---|---|---|---|
| I-392 | 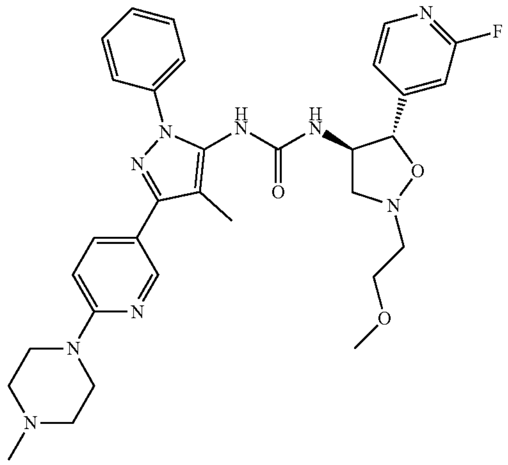 [SMILES: COCCN1C[C@@H](NC(=O)Nc2c(C)c(-c3ccc(N4CCN(C)CC4)nc3)nn2-c2ccccc2)[C@H](c2ccnc(F)c2)O1] | 1 | 1.15 | 616.35 | racemate |
| I-393 | 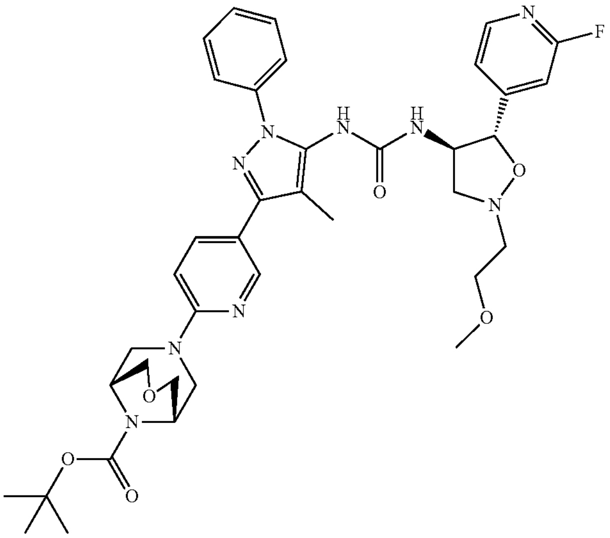 [SMILES: COCCN1C[C@@H](NC(=O)Nc2c(C)c(-c3ccc(N4C[C@H]5COC[C@@H](C4)N5C(=O)OC(C)(C)C)nc3)nn2-c2ccccc2)[C@H](c2ccnc(F)c2)O1] | 1 | 1.63 | 744.35 | racemate |
| I-394 | 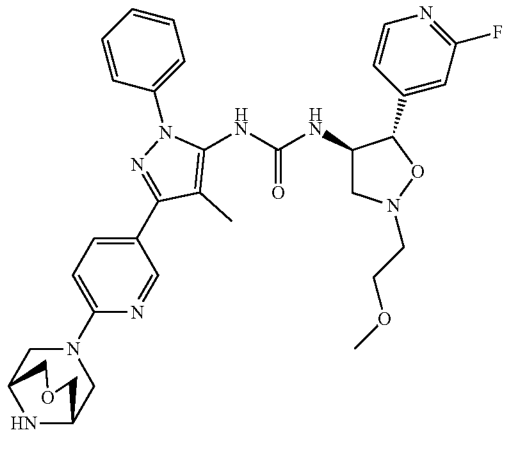 [SMILES: COCCN1C[C@@H](NC(=O)Nc2c(C)c(-c3ccc(N4C[C@H]5COC[C@@H](C4)N5)nc3)nn2-c2ccccc2)[C@H](c2ccnc(F)c2)O1] | 1 | 1.09 | 644.3 | racemate |

TABLE 84-continued
| No. | Structure | LCMS method No. | RT | MS (m/z) | configuration |
|---|---|---|---|---|---|
| I-395 | 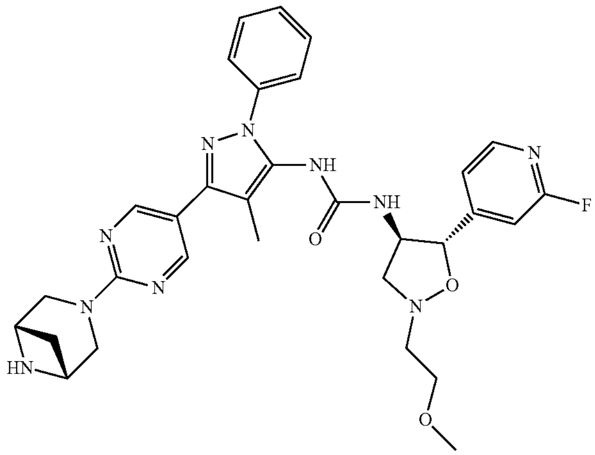 [SMILES: COCCN1C[C@@H](NC(=O)Nc2c(C)c(-c3cnc(N4C[C@H]5C[C@@H](C4)N5)nc3)nn2-c2ccccc2)[C@H](c2ccnc(F)c2)O1] | 1 | 1.15 | 629 | racemate |
TABLE 85
| No. | Structure | LCMS method No. | RT | MS (m/z) | configuration |
|---|---|---|---|---|---|
| I-396 | 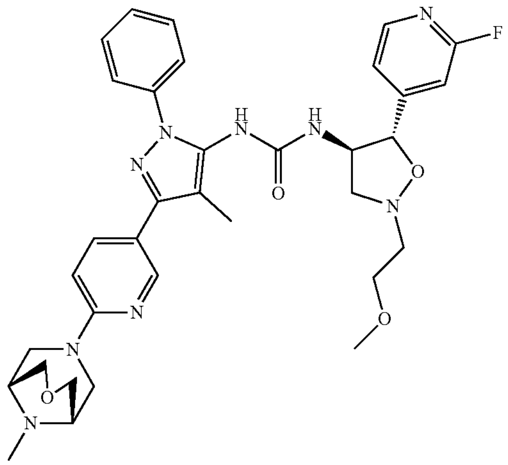 [SMILES: COCCN1C[C@@H](NC(=O)Nc2c(C)c(-c3ccc(N4C[C@H]5COC[C@@H](C4)N5C)nc3)nn2-c2ccccc2)[C@H](c2ccnc(F)c2)O1] | 1 | 1.12 | 658.35 | racemate |
| I-397 | 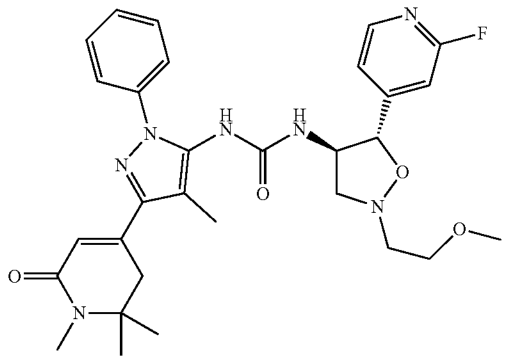 [SMILES: COCCN1C[C@@H](NC(=O)Nc2c(C)c(C3=CC(=O)N(C)C(C)(C)C3)nn2-c2ccccc2)[C@H](c2ccnc(F)c2)O1] | 2 | 1.78 | 578 | racemate |

TABLE 85-continued
| No. | Structure | LCMS method No. | RT | MS (m/z) | configuration |
|---|---|---|---|---|---|
| I-398 | 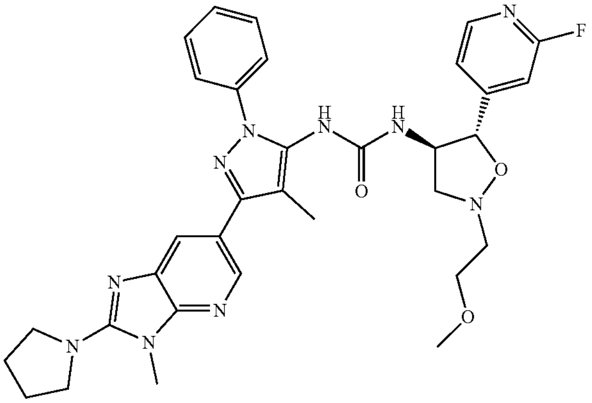 [SMILES: COCCN1C[C@@H](NC(=O)Nc2c(C)c(-c3cnc4c(c3)nc(N3CCCC3)n4C)nn2-c2ccccc2)[C@H](c2ccnc(F)c2)O1] | 1 | 1.43 | 641.3 | racemate |
| I-399 | 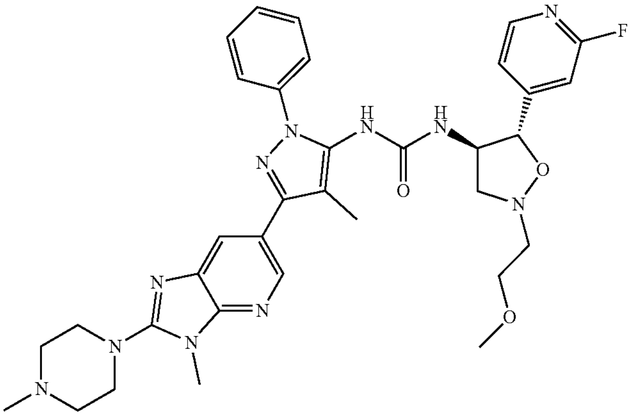 [SMILES: COCCN1C[C@@H](NC(=O)Nc2c(C)c(-c3cnc4c(c3)nc(N3CCN(C)CC3)n4C)nn2-c2ccccc2)[C@H](c2ccnc(F)c2)O1] | 1 | 1.31 | 670.3 | racemate |
TABLE 86
| No. | Structure | LCMS method No. | RT | MS (m/z) | configuration |
|---|---|---|---|---|---|
| I-400 | 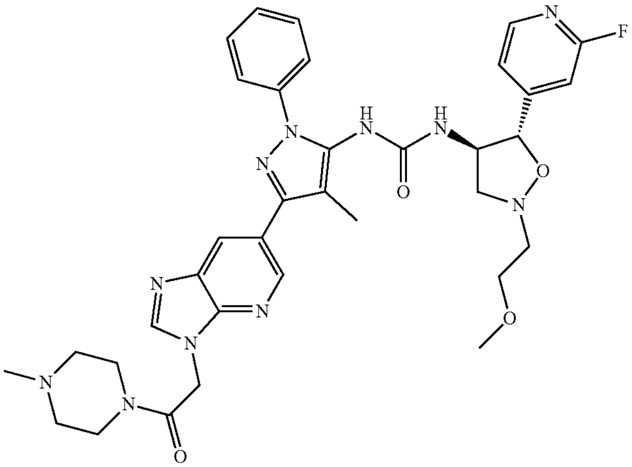 [SMILES: COCCN1C[C@@H](NC(=O)Nc2c(C)c(-c3cnc4c(c3)ncn4CC(=O)N3CCN(C)CC3)nn2-c2ccccc2)[C@H](c2ccnc(F)c2)O1] | 1 | 1.27 | 698.3 | racemate |

TABLE 86-continued
| No. | Structure | LCMS method No. | RT | MS (m/z) | configuration |
|---|---|---|---|---|---|
| I-401 | 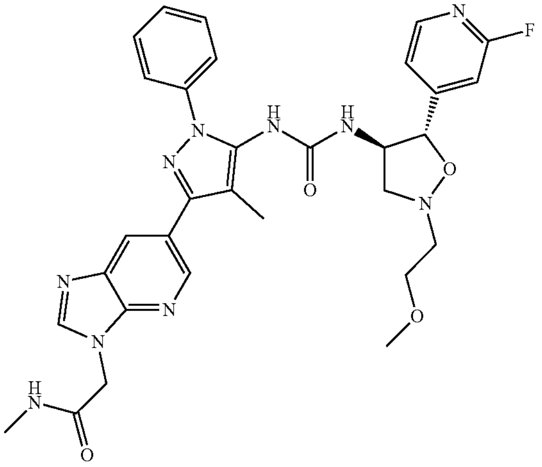 [SMILES: CNC(=O)Cn1cnc2cc(-c3nn(-c4ccccc4)c(NC(=O)N[C@@H]4CN(CCOC)O[C@H]4c4ccnc(F)c4)c3C)cnc21] | 1 | 1.44 | 629.3 | racemate |
| I-402 | 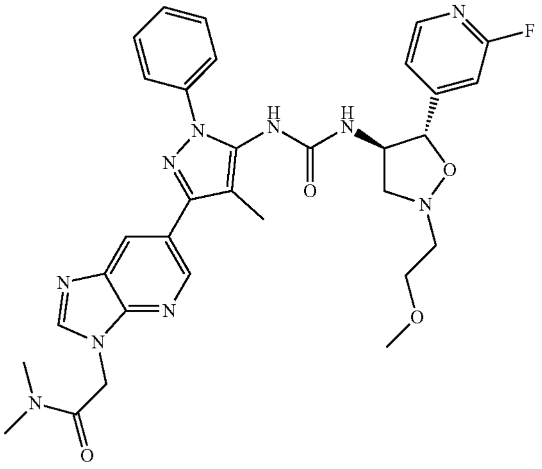 [SMILES: COCCN1C[C@@H](NC(=O)Nc2c(C)c(-c3cnc4c(c3)ncn4CC(=O)N(C)C)nn2-c2ccccc2)[C@H](c2ccnc(F)c2)O1] | 1 | 1.49 | 643.2 | racemate |
| I-403 | 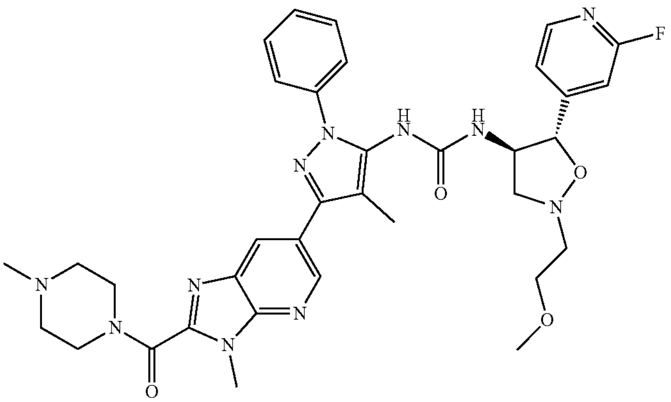 [SMILES: COCCN1C[C@@H](NC(=O)Nc2c(C)c(-c3cnc4c(c3)nc(C(=O)N3CCN(C)CC3)n4C)nn2-c2ccccc2)[C@H](c2ccnc(F)c2)O1] | 1 | 1.35 | 698.3 | racemate |

TABLE 87
| No. | Structure | LCMS method No. | RT | MS (m/z) | configuration |
|---|---|---|---|---|---|
| I-404 | 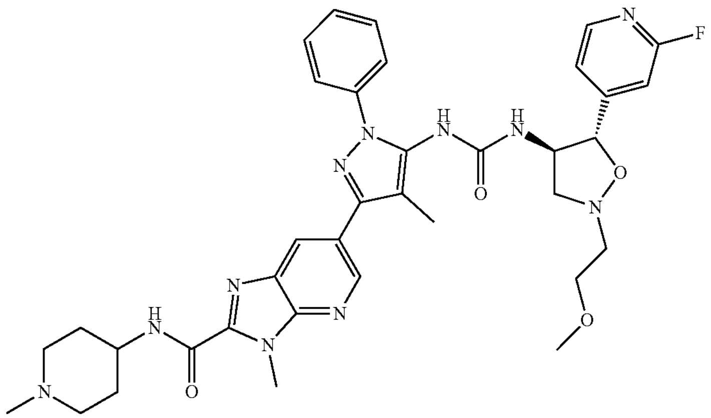 [SMILES: COCCN1C[C@@H](NC(=O)Nc2c(C)c(-c3cnc4c(c3)nc(C(=O)NC3CCN(C)CC3)n4C)nn2-c2ccccc2)[C@H](c2ccnc(F)c2)O1] | 1 | 1.39 | 712.3 | racemate |
| I-405 | 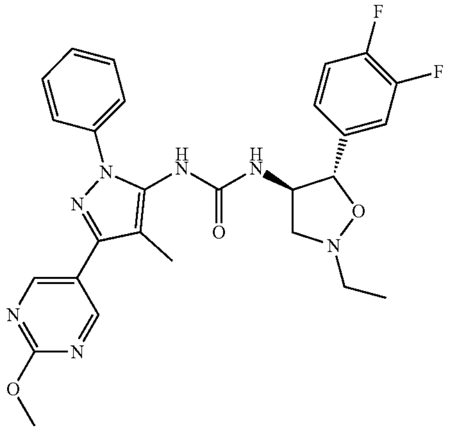 [SMILES: CCN1C[C@@H](NC(=O)Nc2c(C)c(-c3cnc(OC)nc3)nn2-c2ccccc2)[C@H](c2ccc(F)c(F)c2)O1] | 1 | 1.99 | 536.1 | racemate |
| I-406 | 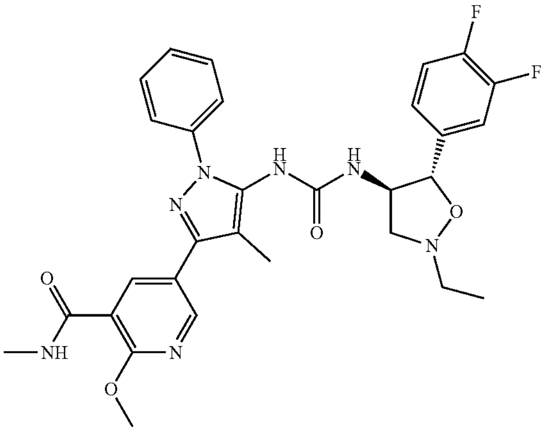 [SMILES: CCN1C[C@@H](NC(=O)Nc2c(C)c(-c3cnc(OC)c(C(=O)NC)c3)nn2-c2ccccc2)[C@H](c2ccc(F)c(F)c2)O1] | 1 | 1.99 | 592.2 | racemate |

TABLE 87-continued
| No. | Structure | LCMS method No. | RT | MS (m/z) | configuration |
|---|---|---|---|---|---|
| I-407 | 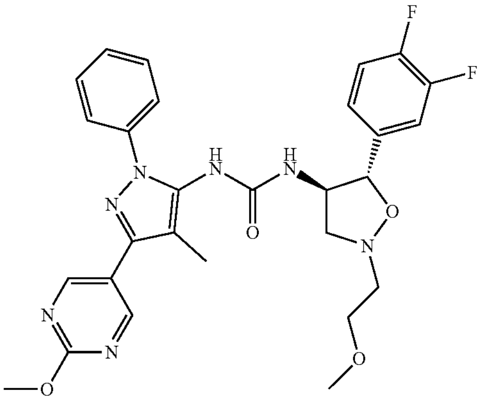 [SMILES: COCCN1C[C@@H](NC(=O)Nc2c(C)c(-c3cnc(OC)nc3)nn2-c2ccccc2)[C@H](c2ccc(F)c(F)c2)O1] | 2 | 1.94 | 566 | |
TABLE 88
| No. | Structure | LCMS method No. | RT | MS (m/z) | configuration |
|---|---|---|---|---|---|
| I-408 | 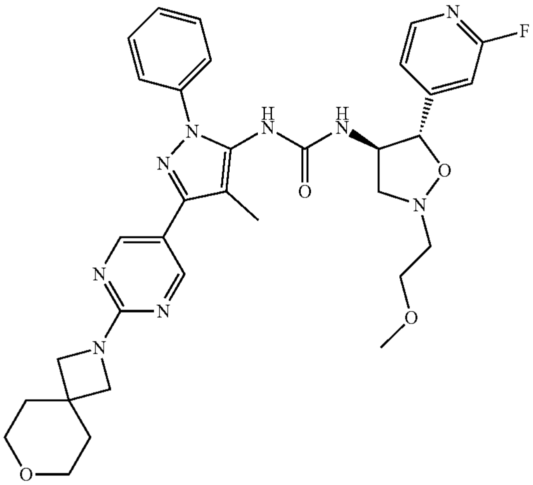 [SMILES: COCCN1C[C@@H](NC(=O)Nc2c(C)c(-c3cnc(N4CC5(CCOCC5)C4)nc3)nn2-c2ccccc2)[C@H](c2ccnc(F)c2)O1] | 2 | 1.63 | 644 | racemate |
| I-409 | 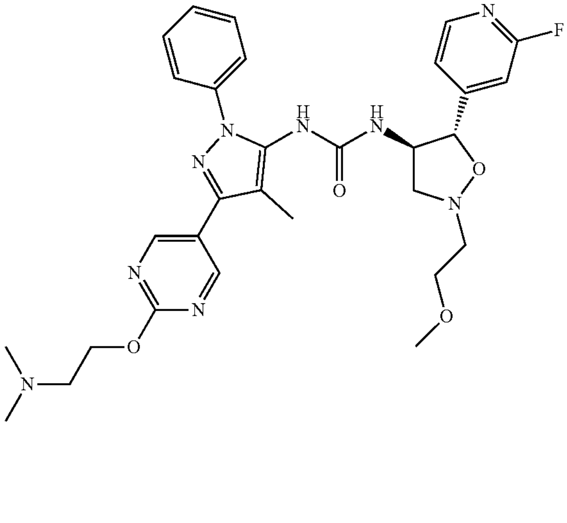 [SMILES: COCCN1C[C@@H](NC(=O)Nc2c(C)c(-c3cnc(OCCN(C)C)nc3)nn2-c2ccccc2)[C@H](c2ccnc(F)c2)O1] | 1 | 1.11 | 606.3 | racemate |

TABLE 88-continued
| No. | Structure | LCMS method No. | RT | MS (m/z) | configuration |
|---|---|---|---|---|---|
| I-410 | 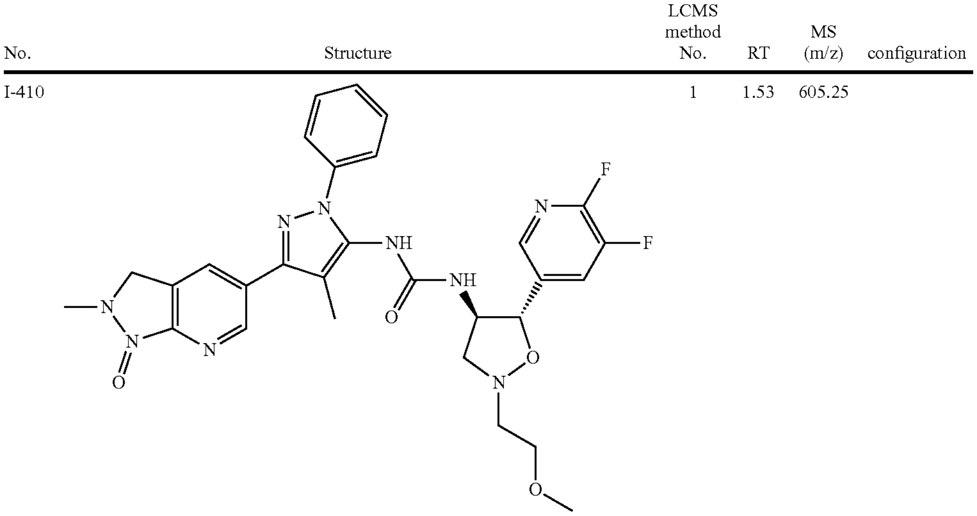 | 1 | 1.53 | 605.25 | |
| I-411 | 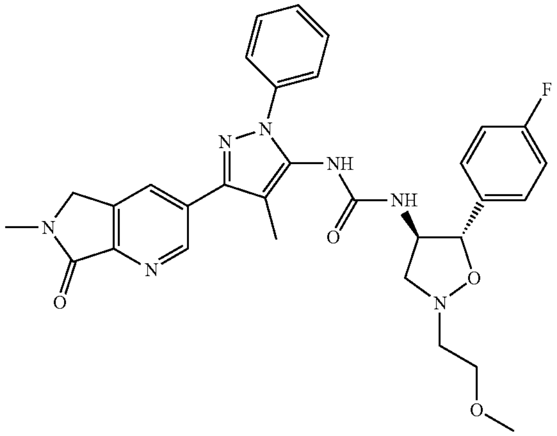 [SMILES: COCCN1C[C@@H](NC(=O)Nc2c(C)c(-c3cnc4c(c3)CN(C)C4=O)nn2-c2ccccc2)[C@H](c2ccc(F)cc2)O1] | 1 | 1.56 | 586.3 | |
TABLE 89
| No. | Structure | LCMS method No. | RT | MS (m/z) | configuration |
|---|---|---|---|---|---|
| I-412 | 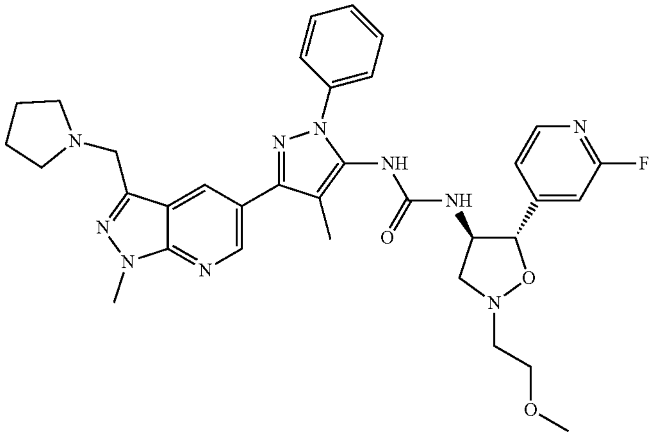 [SMILES: COCCN1C[C@@H](NC(=O)Nc2c(C)c(-c3cnc4c(c3)c(CN3CCCC3)nn4C)nn2-c2ccccc2)[C@H](c2ccnc(F)c2)O1] | 1 | 1.24 | 655.35 | racemate |

TABLE 89-continued
| No. | Structure | LCMS method No. | RT | MS (m/z) | configuration |
|---|---|---|---|---|---|
| I-413 | 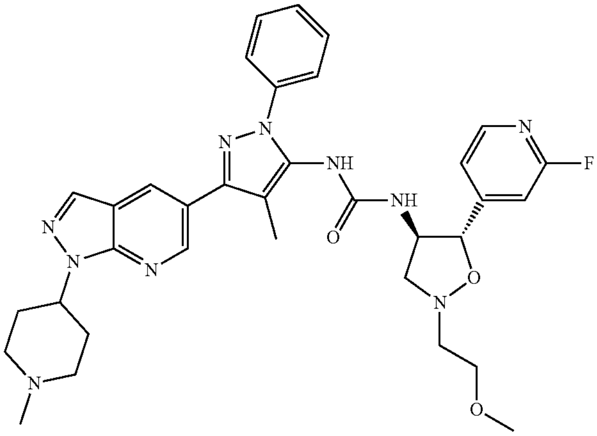 [SMILES: COCCN1C[C@@H](NC(=O)Nc2c(C)c(-c3cnc4c(cnn4C4CCN(C)CC4)c3)nn2-c2ccccc2)[C@H](c2ccnc(F)c2)O1] | 1 | 1.21 | 655.35 | racemate |
| I-414 | 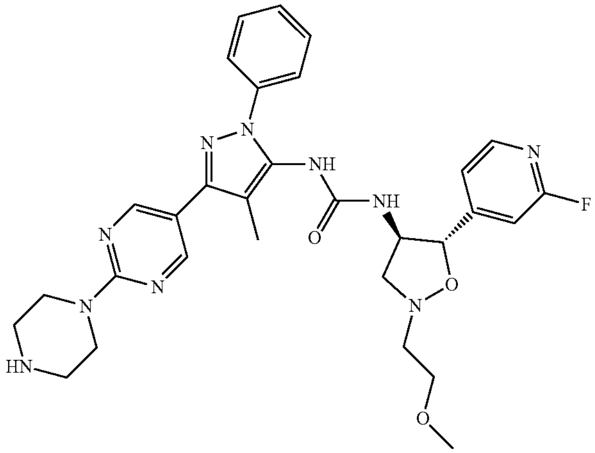 [SMILES: COCCN1C[C@@H](NC(=O)Nc2c(C)c(-c3cnc(N4CCNCC4)nc3)nn2-c2ccccc2)[C@H](c2ccnc(F)c2)O1] | 1 | 1.1 | 603 | racemate |
| I-415 | 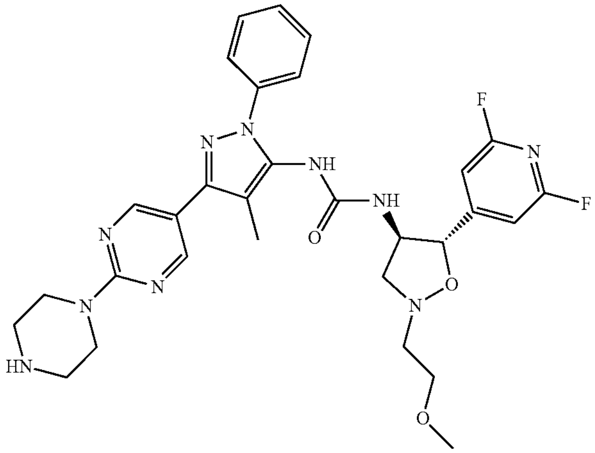 [SMILES: COCCN1C[C@@H](NC(=O)Nc2c(C)c(-c3cnc(N4CCNCC4)nc3)nn2-c2ccccc2)[C@H](c2cc(F)nc(F)c2)O1] | 1 | 1.28 | 621 | racemate |

TABLE 90
| No. | Structure | LCMS method No. | RT | MS (m/z) | configuration |
| --- | --- | --- | --- | --- | --- |
| I-416 | 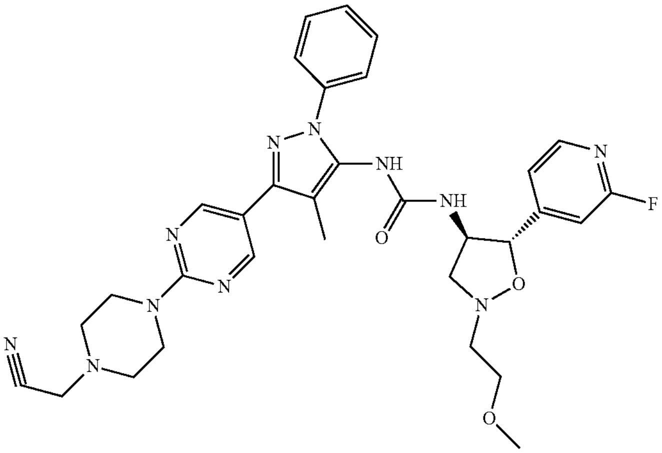 [SMILES: COCCN1C[C@@H](NC(=O)Nc2c(C)c(-c3cnc(N4CCN(CC#N)CC4)nc3)nn2-c2ccccc2)[C@H](c2ccnc(F)c2)O1] | 1 | 1.65 | 642 | racemate |
| I-417 | 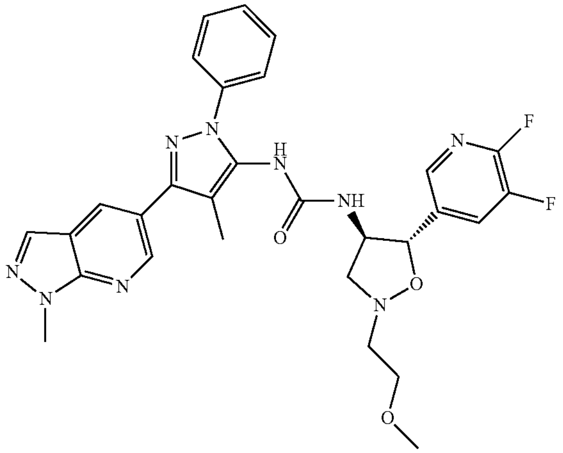 [SMILES: COCCN1C[C@@H](NC(=O)Nc2c(C)c(-c3cnc4c(cnn4C)c3)nn2-c2ccccc2)[C@H](c2cnc(F)c(F)c2)O1] | 1 | 1.78 | 590.25 | |
| I-418 | 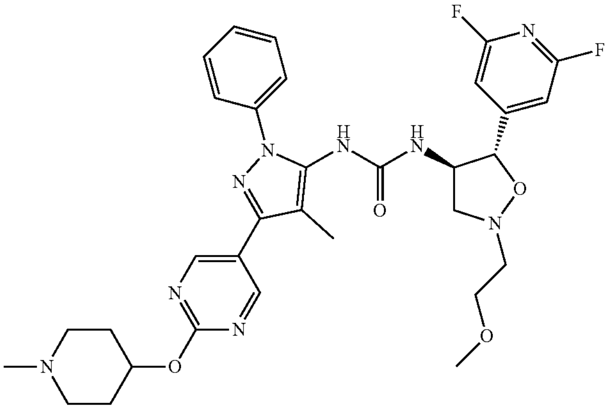 [SMILES: COCCN1C[C@@H](NC(=O)Nc2c(C)c(-c3cnc(OC4CCN(C)CC4)nc3)nn2-c2ccccc2)[C@H](c2cc(F)nc(F)c2)O1] | 1 | 1.38 | 650.3 | racemate |

TABLE 90-continued
| No. | Structure | LCMS method No. | RT | MS (m/z) | configuration |
|---|---|---|---|---|---|
| I-419 | 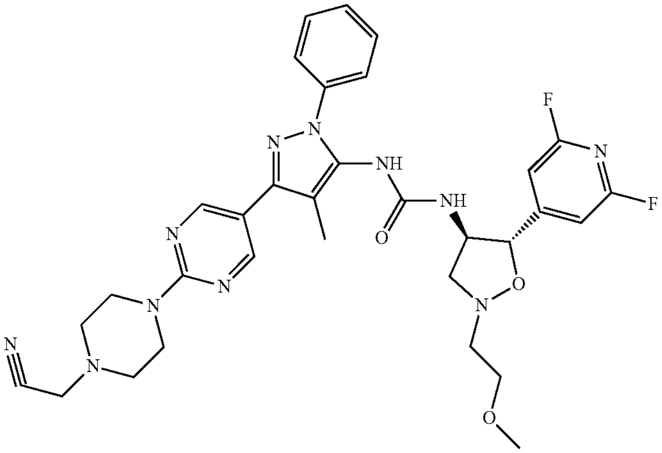 [SMILES: COCCN1C[C@@H](NC(=O)Nc2c(C)c(-c3cnc(N4CCN(CC#N)CC4)nc3)nn2-c2ccccc2)[C@H](c2cc(F)nc(F)c2)O1] | 1 | 1.88 | 660 | racemate |
TABLE 91
| No. | Structure | LCMS method No. | RT | MS (m/z) | configuration |
|---|---|---|---|---|---|
| I-420 | 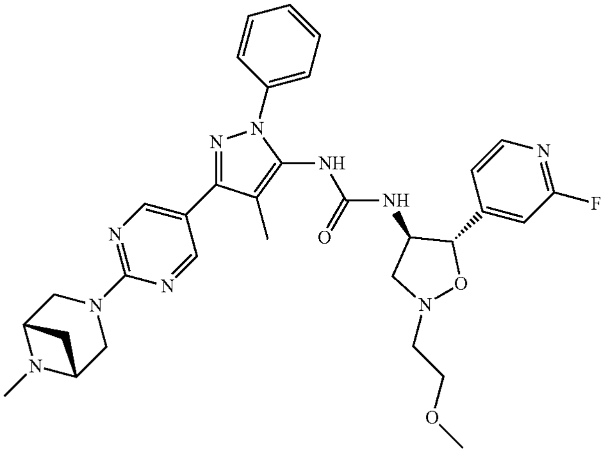 [SMILES: COCCN1C[C@@H](NC(=O)Nc2c(C)c(-c3cnc(N4C[C@H]5C[C@@H](C4)N5C)nc3)nn2-c2ccccc2)[C@H](c2ccnc(F)c2)O1] | 1 | 1.17 | 643 | racemate |
| I-421 | 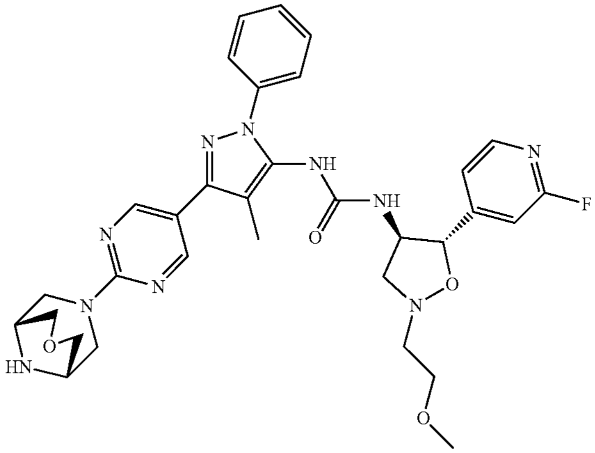 [SMILES: COCCN1C[C@@H](NC(=O)Nc2c(C)c(-c3cnc(N4C[C@H]5COC[C@@H](C4)N5)nc3)nn2-c2ccccc2)[C@H](c2ccnc(F)c2)O1] | 1 | 1.1 | 645 | racemate |

TABLE 91-continued
| No. | Structure | LCMS method No. | RT | MS (m/z) | configuration |
|---|---|---|---|---|---|
| I-422 | 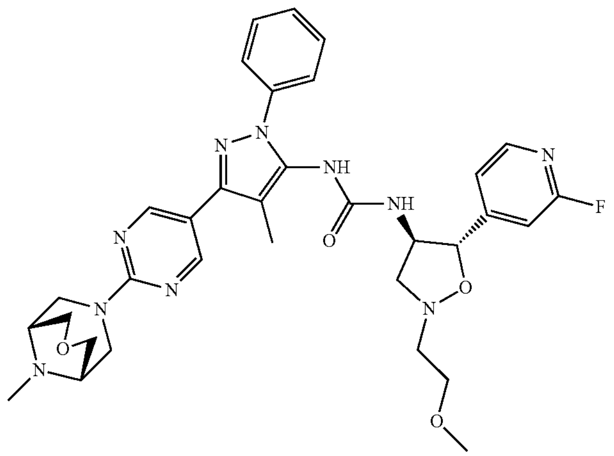 [SMILES: COCCN1C[C@@H](NC(=O)Nc2c(C)c(-c3cnc(N4C[C@H]5COC[C@@H](C4)N5C)nc3)nn2-c2ccccc2)[C@H](c2ccnc(F)c2)O1] | 1 | 1.18 | 659 | racemate |
| I-423 | 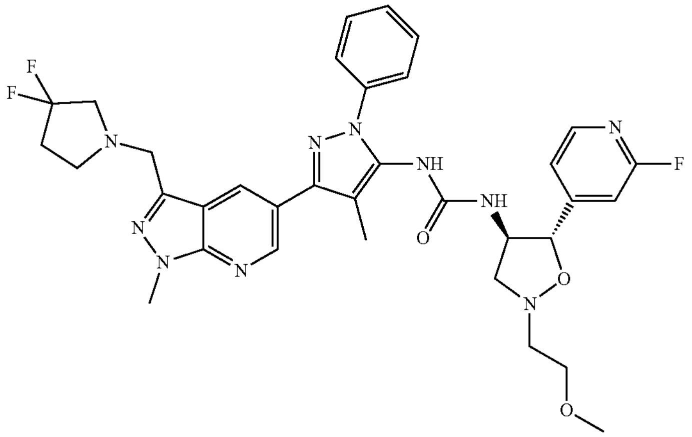 [SMILES: COCCN1C[C@@H](NC(=O)Nc2c(C)c(-c3cnc4c(c3)c(CN3CCC(F)(F)C3)nn4C)nn2-c2ccccc2)[C@H](c2ccnc(F)c2)O1] | 1 | 1.51 | 691.3 | racemate |
TABLE 92
| No. | Structure | LCMS method No. | RT | MS (m/z) | configuration |
|---|---|---|---|---|---|
| I-424 | 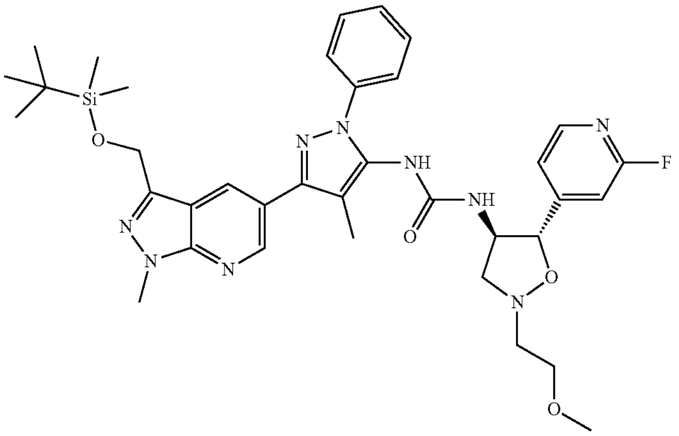 [SMILES: COCCN1C[C@@H](NC(=O)Nc2c(C)c(-c3cnc4c(c3)c(CO[Si](C)(C)C(C)(C)C)nn4C)nn2-c2ccccc2)[C@H](c2ccnc(F)c2)O1] | 1 | 2.56 | 716.35 | racemate |

TABLE 92-continued
| No. | Structure | LCMS method No. | RT | MS (m/z) | configuration |
|---|---|---|---|---|---|
| I-425 | 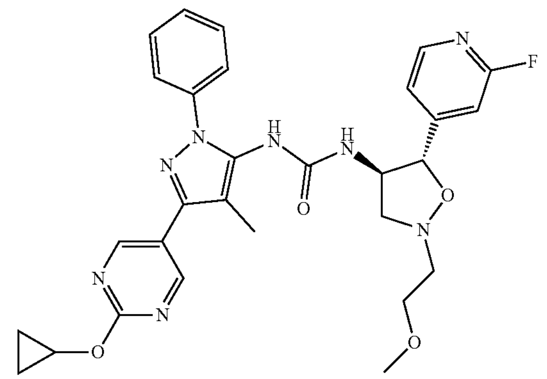 [SMILES: COCCN1C[C@@H](NC(=O)Nc2c(C)c(-c3cnc(OC4CC4)nc3)nn2-c2ccccc2)[C@H](c2ccnc(F)c2)O1] | 1 | 1.74 | 575.25 | racemate |
| I-426 | 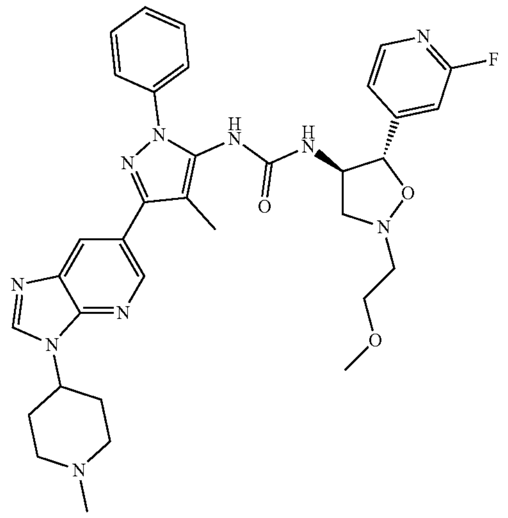 [SMILES: COCCN1C[C@@H](NC(=O)Nc2c(C)c(-c3cnc4c(c3)ncn4C3CCN(C)CC3)nn2-c2ccccc2)[C@H](c2ccnc(F)c2)O1] | 1 | 1.28 | 655 | racemate |
| I-427 | 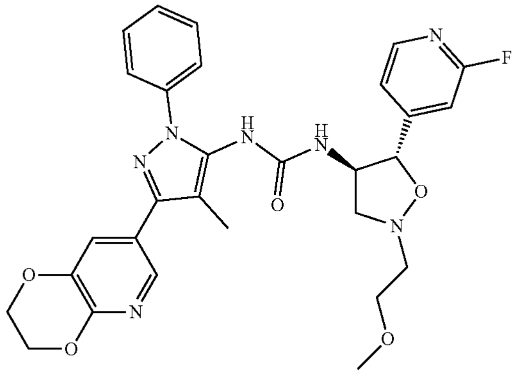 [SMILES: COCCN1C[C@@H](NC(=O)Nc2c(C)c(-c3cnc4c(c3)OCCO4)nn2-c2ccccc2)[C@H](c2ccnc(F)c2)O1] | 2 | 1.59 | 576 | racemate |

TABLE 93
| No. | Structure | LCMS method No. | RT | MS (m/z) | configuration |
|---|---|---|---|---|---|
| I-428 | 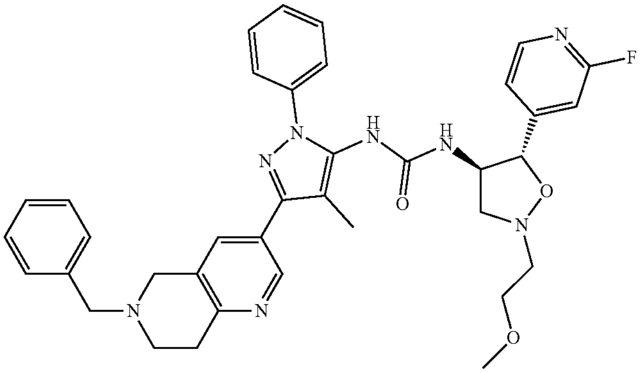 [SMILES: COCCN1C[C@@H](NC(=O)Nc2c(C)c(-c3cnc4c(c3)CN(Cc3ccccc3)CC4)nn2-c2ccccc2)[C@H](c2ccnc(F)c2)O1] | 2 | 1.44 | 663 | racemate |
| I-429 | 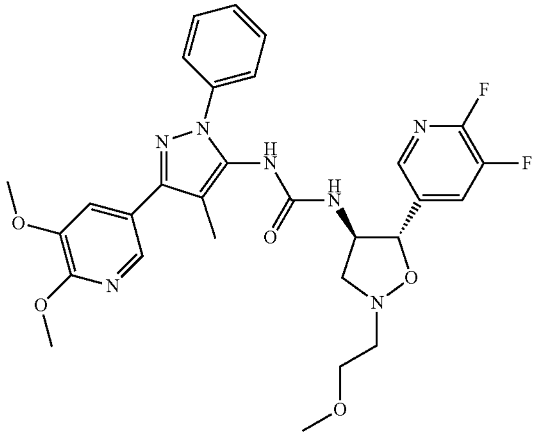 [SMILES: COCCN1C[C@@H](NC(=O)Nc2c(C)c(-c3cnc(OC)c(OC)c3)nn2-c2ccccc2)[C@H](c2cnc(F)c(F)c2)O1] | 2 | 1.89 | 596 | racemate |
| I-430 | 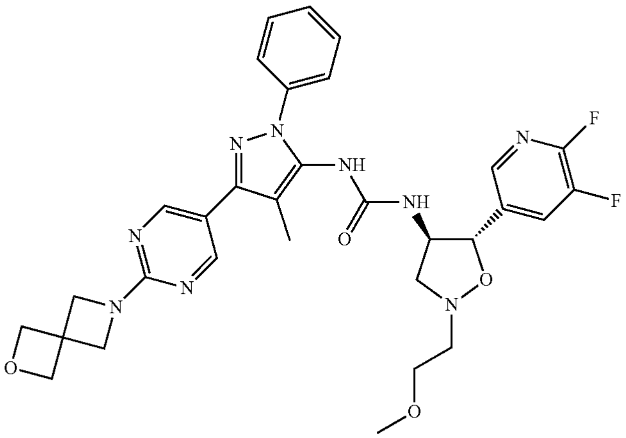 [SMILES: COCCN1C[C@@H](NC(=O)Nc2c(C)c(-c3cnc(N4CC5(COC5)C4)nc3)nn2-c2ccccc2)[C@H](c2cnc(F)c(F)c2)O1] | 1 | 1.59 | 634.3 | |

TABLE 93-continued
| No. | Structure | LCMS method No. | RT | MS (m/z) | configuration |
|---|---|---|---|---|---|
| I-431 | 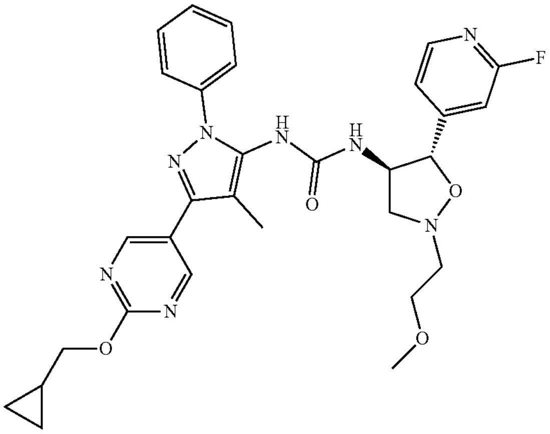 [SMILES: COCCN1C[C@@H](NC(=O)Nc2c(C)c(-c3cnc(OCC4CC4)nc3)nn2-c2ccccc2)[C@H](c2ccnc(F)c2)O1] | 1 | 1.91 | 589.25 | racemate |
TABLE 94
| No. | Structure | LCMS method No. | RT | MS (m/z) | configuration |
|---|---|---|---|---|---|
| I-432 | 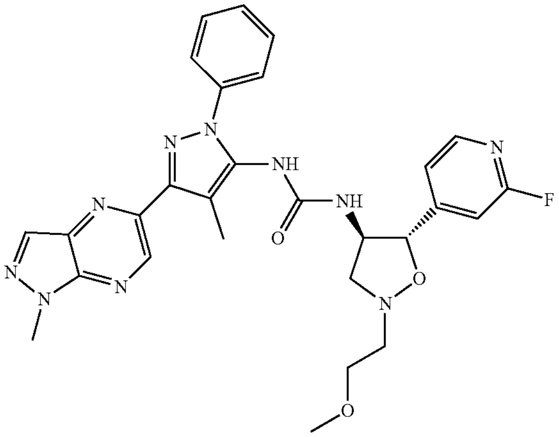 [SMILES: COCCN1C[C@@H](NC(=O)Nc2c(C)c(-c3cnc4c(cnn4C)n3)nn2-c2ccccc2)[C@H](c2ccnc(F)c2)O1] | 1 | 1.72 | 573.25 | racemate |
| I-433 | 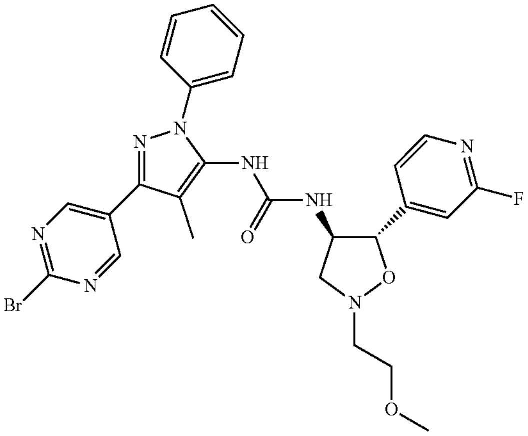 [SMILES: COCCN1C[C@@H](NC(=O)Nc2c(C)c(-c3cnc(Br)nc3)nn2-c2ccccc2)[C@H](c2ccnc(F)c2)O1] | 1 | 1.8 | 597.15 | racemate |

TABLE 94-continued
| No. | Structure | LCMS method No. | RT | MS (m/z) | configuration |
|---|---|---|---|---|---|
| I-434 | 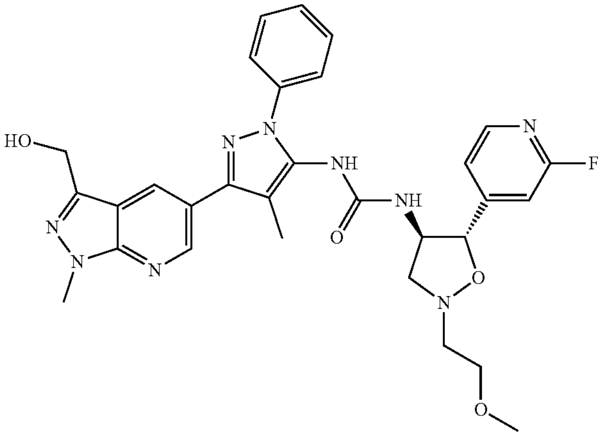 [SMILES: COCCN1C[C@@H](NC(=O)Nc2c(C)c(-c3cnc4c(c3)c(CO)nn4C)nn2-c2ccccc2)[C@H](c2ccnc(F)c2)O1] | 1 | 1.43 | 602.25 | racemate |
| I-435 | 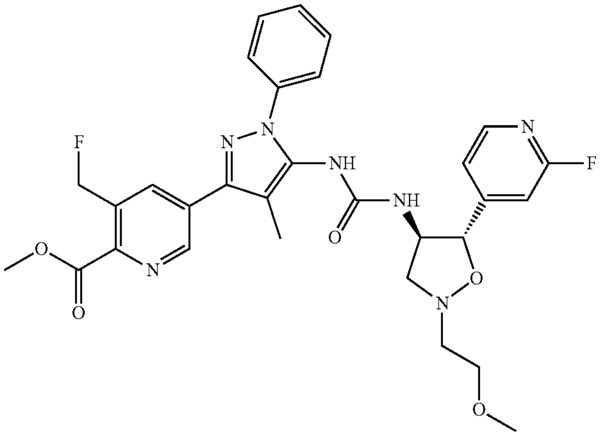 [SMILES: COCCN1C[C@@H](NC(=O)Nc2c(C)c(-c3cnc(C(=O)OC)c(CF)c3)nn2-c2ccccc2)[C@H](c2ccnc(F)c2)O1] | 1 | 1.75 | 608.25 | racemate |
TABLE 95
| No. | Structure | LCMS method No. | RT | MS (m/z) | configuration |
|---|---|---|---|---|---|
| I-436 | 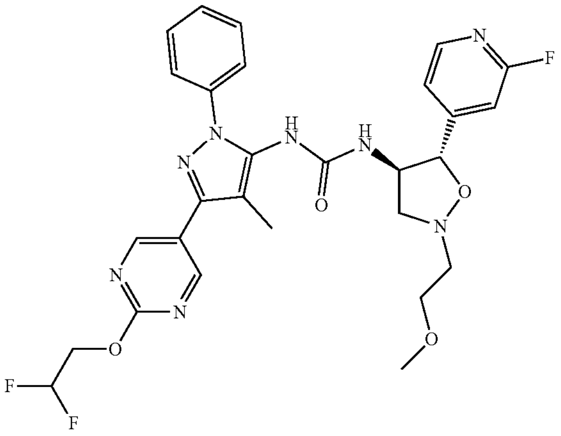 [SMILES: COCCN1C[C@@H](NC(=O)Nc2c(C)c(-c3cnc(OCC(F)F)nc3)nn2-c2ccccc2)[C@H](c2ccnc(F)c2)O1] | 1 | 1.79 | 599.25 | racemate |

TABLE 95-continued
| No. | Structure | LCMS method No. | RT | MS (m/z) | configuration |
| --- | --- | --- | --- | --- | --- |
| I-437 | 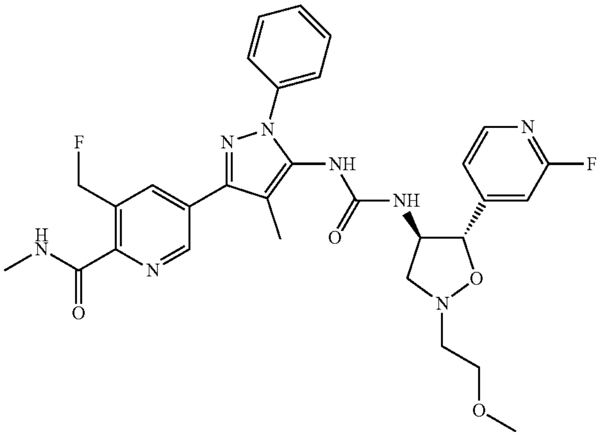 [SMILES: CNC(=O)c1ncc(-c2nn(-c3ccccc3)c(NC(=O)N[C@@H]3CN(CCOC)O[C@H]3c3ccnc(F)c3)c2C)cc1CF] | 1 | 1.73 | 607.25 | racemate |
| I-438 | 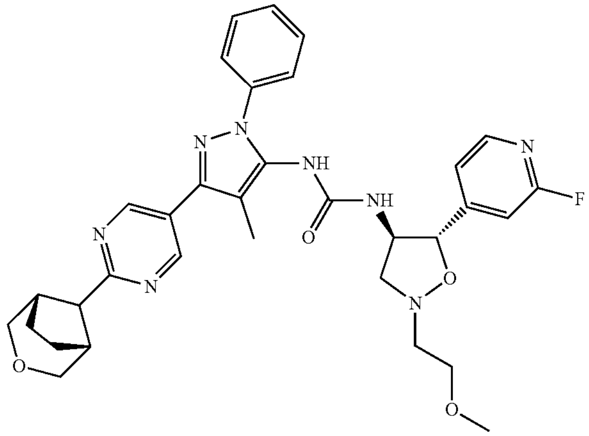 [SMILES: COCCN1C[C@@H](NC(=O)Nc2c(C)c(-c3cnc(C4[C@@H]5CC[C@H]4COC5)nc3)nn2-c2ccccc2)[C@H](c2ccnc(F)c2)O1] | 1 | 1.75 | 630 | racemate |
| I-439 | 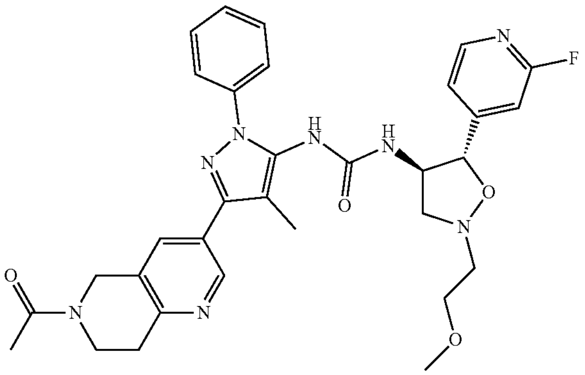 [SMILES: COCCN1C[C@@H](NC(=O)Nc2c(C)c(-c3cnc4c(c3)CN(C(C)=O)CC4)nn2-c2ccccc2)[C@H](c2ccnc(F)c2)O1] | 2 | 1.29 | 615 | racemate |

TABLE 96
| No. | Structure | LCMS method No. | RT | MS (m/z) | configuration |
|---|---|---|---|---|---|
| I-440 | 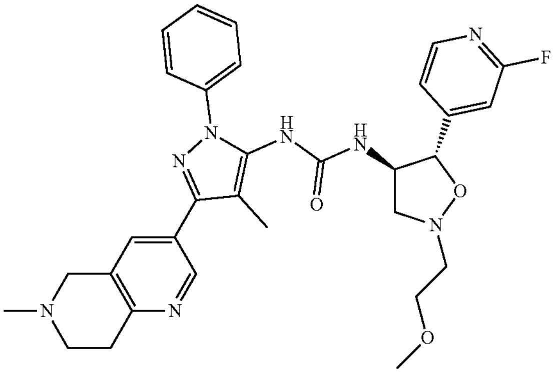 [SMILES: COCCN1C[C@@H](NC(=O)Nc2c(C)c(-c3cnc4c(c3)CN(C)CC4)nn2-c2ccccc2)[C@H](c2ccnc(F)c2)O1] | 2 | 1.19 | 587 | racemate |
| I-441 | 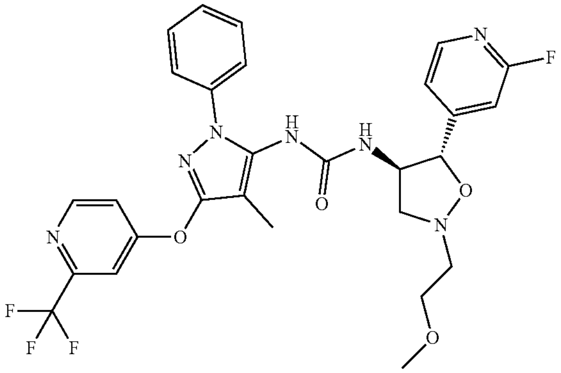 [SMILES: COCCN1C[C@@H](NC(=O)Nc2c(C)c(Oc3ccnc(C(F)(F)F)c3)nn2-c2ccccc2)[C@H](c2ccnc(F)c2)O1] | 2 | 2.08 | 602 | racemate |
| I-442 | 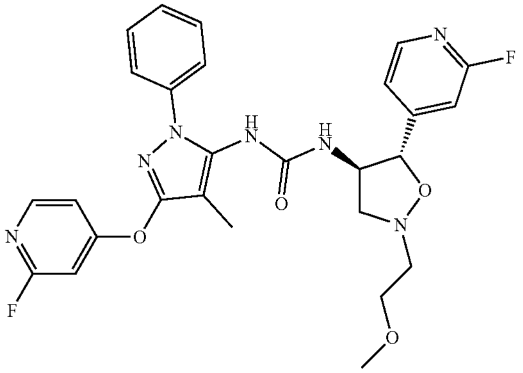 [SMILES: COCCN1C[C@@H](NC(=O)Nc2c(C)c(Oc3ccnc(F)c3)nn2-c2ccccc2)[C@H](c2ccnc(F)c2)O1] | 2 | 1.85 | 552 | racemate |
| I-443 | 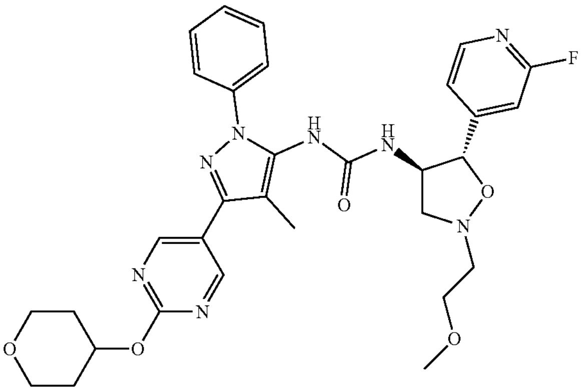 [SMILES: COCCN1C[C@@H](NC(=O)Nc2c(C)c(-c3cnc(OC4CCOCC4)nc3)nn2-c2ccccc2)[C@H](c2ccnc(F)c2)O1] | 1 | 1.66 | 619.3 | racemate |

TABLE 96-continued
| No. | Structure | LCMS method No. | RT | MS (m/z) | configuration |
|---|---|---|---|---|---|
| I-444 | 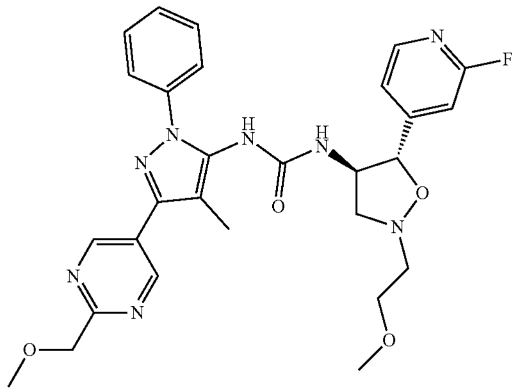 [SMILES: COCCN1C[C@@H](NC(=O)Nc2c(C)c(-c3cnc(COC)nc3)nn2-c2ccccc2)[C@H](c2ccnc(F)c2)O1] | 1 | 1.46 | 563.25 | racemate |
TABLE 97
| No. | Structure | LCMS method No. | RT | MS (m/z) | configuration |
|---|---|---|---|---|---|
| I-445 | 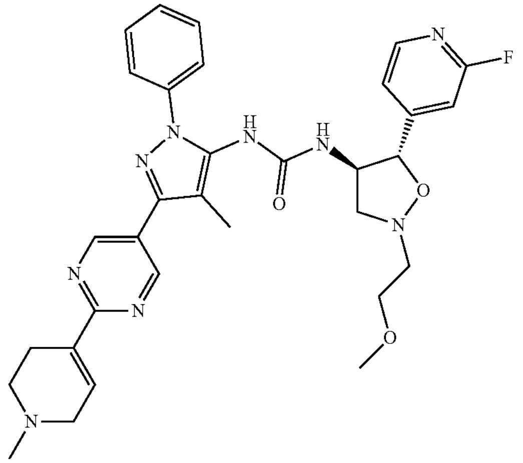 [SMILES: COCCN1C[C@@H](NC(=O)Nc2c(C)c(-c3cnc(C4=CCN(C)CC4)nc3)nn2-c2ccccc2)[C@H](c2ccnc(F)c2)O1] | 1 | 1.16 | 614.25 | racemate |
| I-446 | 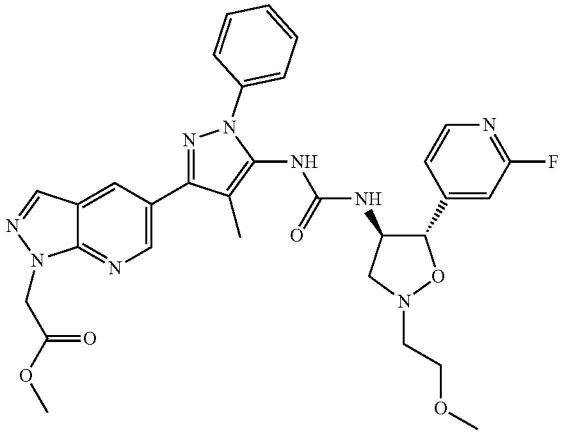 [SMILES: COCCN1C[C@@H](NC(=O)Nc2c(C)c(-c3cnc4c(cnn4CC(=O)OC)c3)nn2-c2ccccc2)[C@H](c2ccnc(F)c2)O1] | 1 | 1.66 | 630.25 | racemate |

TABLE 97-continued
| No. | Structure | LCMS method No. | RT | MS (m/z) | configuration |
|---|---|---|---|---|---|
| I-447 | 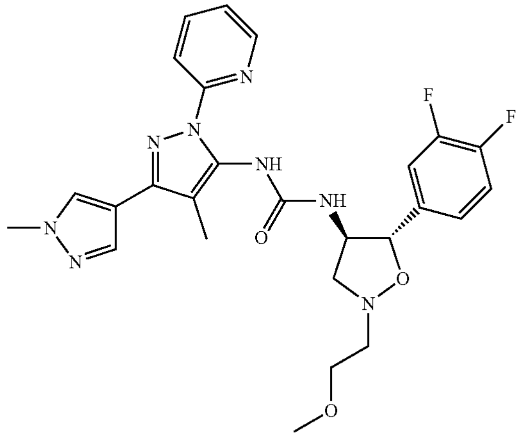 [SMILES: COCCN1C[C@@H](NC(=O)Nc2c(C)c(-c3cnn(C)c3)nn2-c2ccccn2)[C@H](c2ccc(F)c(F)c2)O1] | 1 | 1.71 | 539.25 | |
| I-448 | 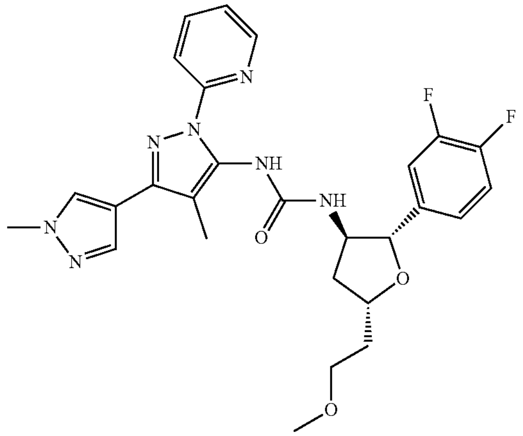 [SMILES: COCC[C@@H]1C[C@@H](NC(=O)Nc2c(C)c(-c3cnn(C)c3)nn2-c2ccccn2)[C@H](c2ccc(F)c(F)c2)O1] | 1 | 1.84 | 538.3 | racemate |
TABLE 98
| No. | Structure | LCMS method No. | RT | MS (m/z) | configuration |
|---|---|---|---|---|---|
| I-449 | 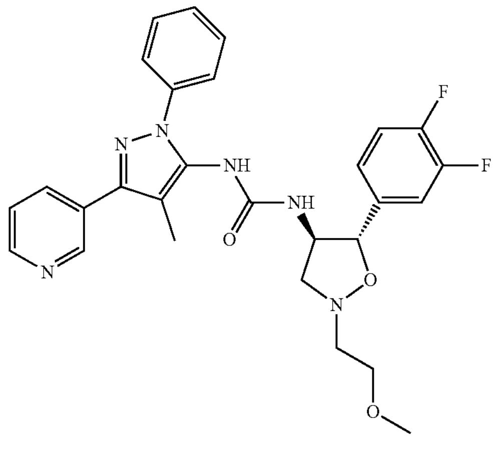 [SMILES: COCCN1C[C@@H](NC(=O)Nc2c(C)c(-c3cccnc3)nn2-c2ccccc2)[C@H](c2ccc(F)c(F)c2)O1] | 1 | 1.49 | 535.3 | |

TABLE 98-continued
| No. | Structure | LCMS method No. | RT | MS (m/z) | configuration |
|---|---|---|---|---|---|
| I-450 | 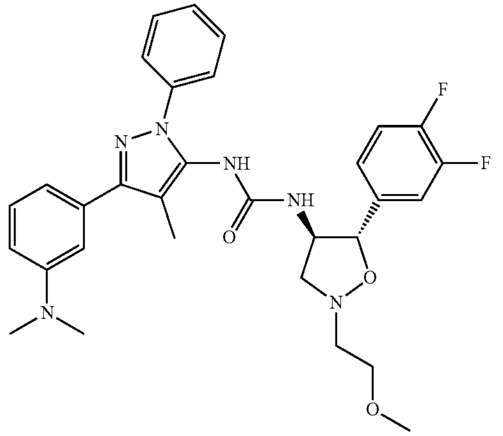 [SMILES: COCCN1C[C@@H](NC(=O)Nc2c(C)c(-c3cccc(N(C)C)c3)nn2-c2ccccc2)[C@H](c2ccc(F)c(F)c2)O1] | 1 | 1.91 | 577.25 | |
| I-451 | 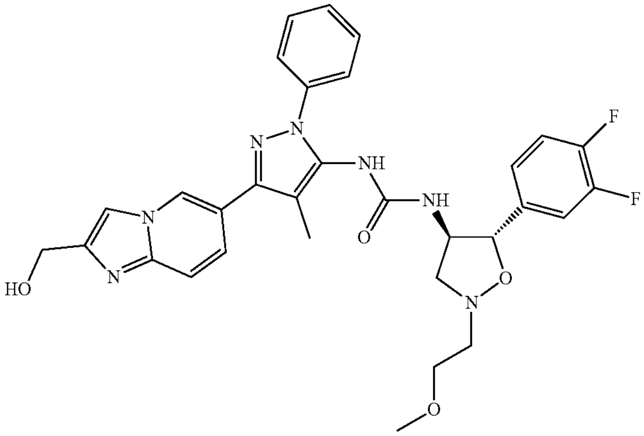 [SMILES: COCCN1C[C@@H](NC(=O)Nc2c(C)c(-c3ccc4nc(CO)cn4c3)nn2-c2ccccc2)[C@H](c2ccc(F)c(F)c2)O1] | 2 | 1.6 | 604 | |
| I-452 | 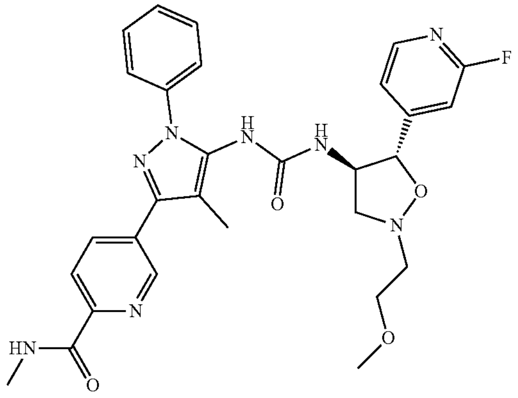 [SMILES: CNC(=O)c1ccc(-c2nn(-c3ccccc3)c(NC(=O)N[C@@H]3CN(CCOC)O[C@H]3c3ccnc(F)c3)c2C)cn1] | 2 | 1.43 | 575 | racemate |

TABLE 99
| No. | Structure | LCMS method No. | RT | MS (m/z) | configuration |
|---|---|---|---|---|---|
| I-453 | 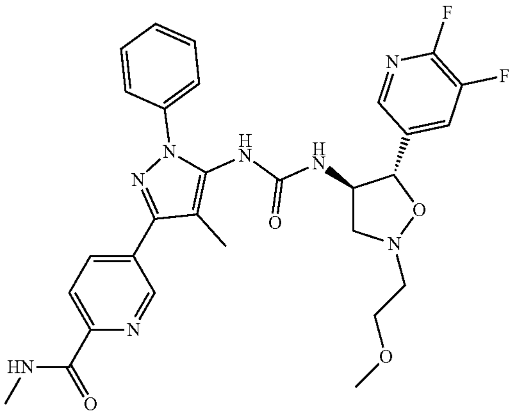 [SMILES: CNC(=O)c1ccc(-c2nn(-c3ccccc3)c(NC(=O)N[C@@H]3CN(CCOC)O[C@H]3c3cnc(F)c(F)c3)c2C)cn1] | 2 | 1.61 | 593 | racemate |
| I-454 | 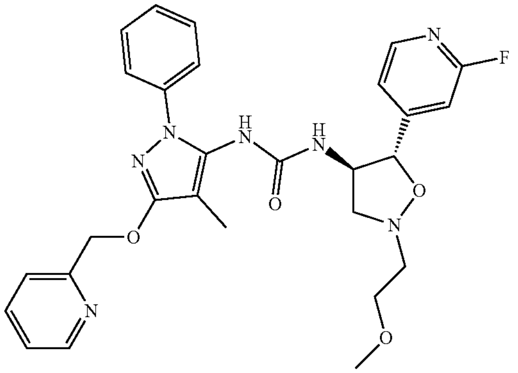 [SMILES: COCCN1C[C@@H](NC(=O)Nc2c(C)c(OCc3ccccn3)nn2-c2ccccc2)[C@H](c2ccnc(F)c2)O1] | 2 | 1.28 | 548 | racemate |
| I-455 | 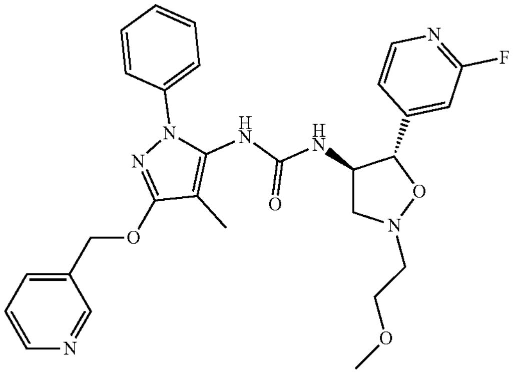 [SMILES: COCCN1C[C@@H](NC(=O)Nc2c(C)c(OCc3cccnc3)nn2-c2ccccc2)[C@H](c2ccnc(F)c2)O1] | 2 | 1.13 | 548 | racemate |
| I-456 | 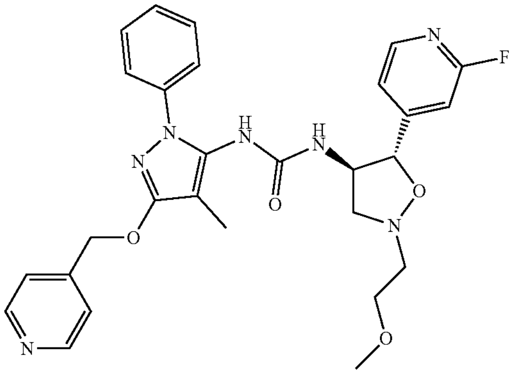 [SMILES: COCCN1C[C@@H](NC(=O)Nc2c(C)c(OCc3ccncc3)nn2-c2ccccc2)[C@H](c2ccnc(F)c2)O1] | 2 | 1.79 | 548 | racemate |

TABLE 99-continued
| No. | Structure | LCMS method No. | RT | MS (m/z) | configuration |
|---|---|---|---|---|---|
| I-457 | 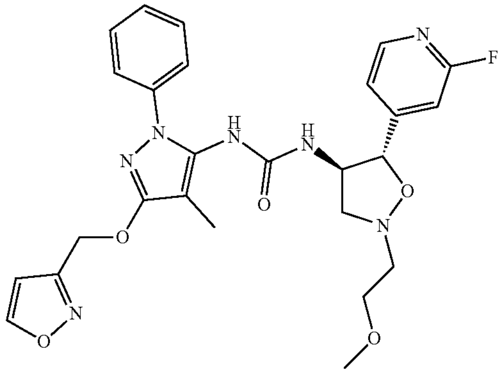 [SMILES: COCCN1C[C@@H](NC(=O)Nc2c(C)c(OCc3ccon3)nn2-c2ccccc2)[C@H](c2ccnc(F)c2)O1] | 2 | 1.68 | 538 | racemate |
TABLE 100
| No. | Structure | LCMS method No. | RT | MS (m/z) | configuration |
|---|---|---|---|---|---|
| I-458 | 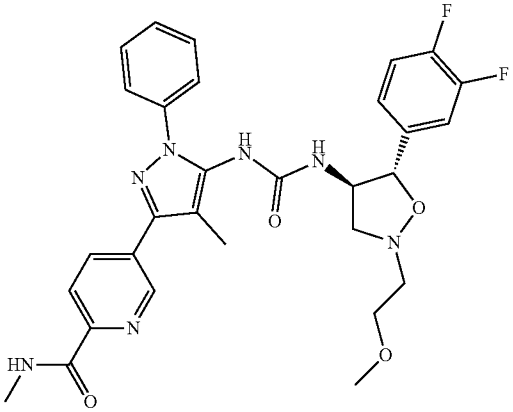 [SMILES: CNC(=O)c1ccc(-c2nn(-c3ccccc3)c(NC(=O)N[C@@H]3CN(CCOC)O[C@H]3c3ccc(F)c(F)c3)c2C)cn1] | 2 | 1.76 | 592 | |
| I-459 | 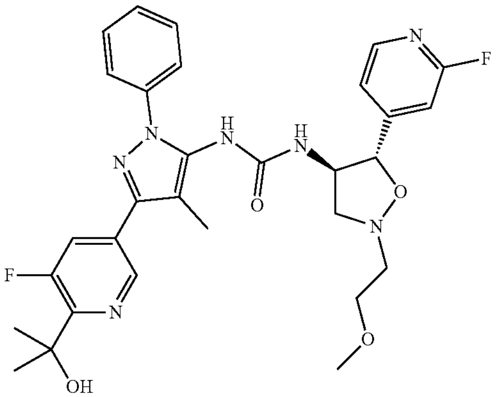 [SMILES: COCCN1C[C@@H](NC(=O)Nc2c(C)c(-c3cnc(C(C)(C)O)c(F)c3)nn2-c2ccccc2)[C@H](c2ccnc(F)c2)O1] | 2 | 1.73 | 594 | racemate |

TABLE 100-continued
| No. | Structure | LCMS method No. | RT | MS (m/z) | configuration |
|---|---|---|---|---|---|
| I-460 | 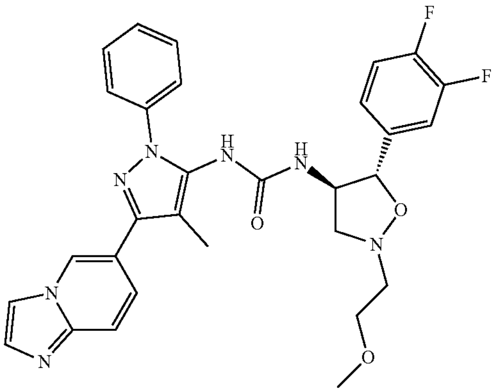 [SMILES: COCCN1C[C@@H](NC(=O)Nc2c(C)c(-c3ccc4nccn4c3)nn2-c2ccccc2)[C@H](c2ccc(F)c(F)c2)O1] | 2 | 1.45 | 574 | |
| I-461 | 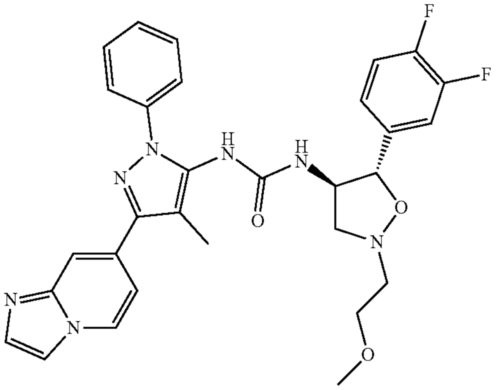 [SMILES: COCCN1C[C@@H](NC(=O)Nc2c(C)c(-c3ccn4ccnc4c3)nn2-c2ccccc2)[C@H](c2ccc(F)c(F)c2)O1] | 2 | 1.42 | 574 | |
TABLE 101
| No. | Structure | LCMS method No. | RT | MS (m/z) | configuration |
|---|---|---|---|---|---|
| I-462 | 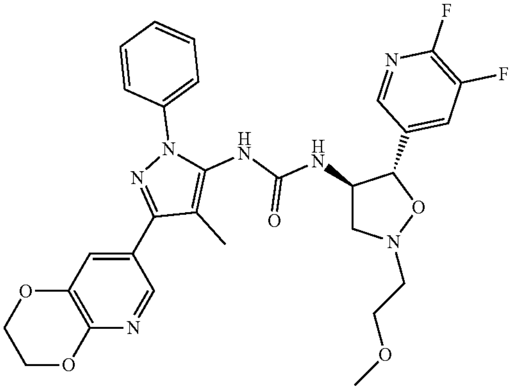 [SMILES: COCCN1C[C@@H](NC(=O)Nc2c(C)c(-c3cnc4c(c3)OCCO4)nn2-c2ccccc2)[C@H](c2cnc(F)c(F)c2)O1] | 2 | 1.65 | 594 | racemate |

TABLE 101-continued
| No. | Structure | LCMS method No. | RT | MS (m/z) | configuration |
|---|---|---|---|---|---|
| I-463 | 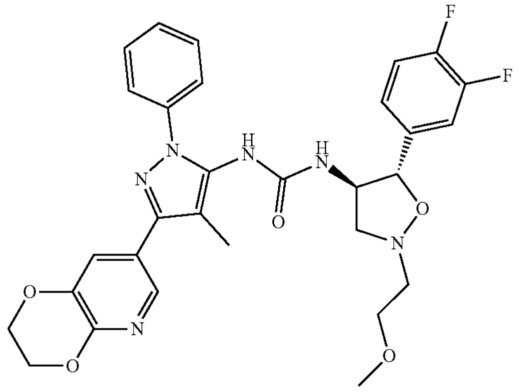 [SMILES: COCCN1C[C@@H](NC(=O)Nc2c(C)c(-c3cnc4c(c3)OCCO4)nn2-c2ccccc2)[C@H](c2ccc(F)c(F)c2)O1] | 2 | 1.8 | 593 | |
| I-464 | 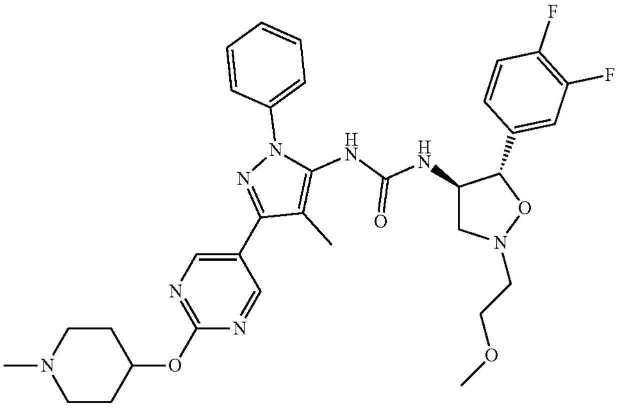 [SMILES: COCCN1C[C@@H](NC(=O)Nc2c(C)c(-c3cnc(OC4CCN(C)CC4)nc3)nn2-c2ccccc2)[C@H](c2ccc(F)c(F)c2)O1] | 1 | 1.4 | 649.35 | |
| I-465 | 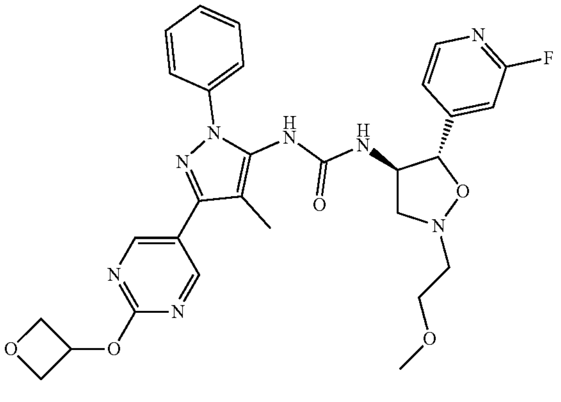 [SMILES: COCCN1C[C@@H](NC(=O)Nc2c(C)c(-c3cnc(OC4COC4)nc3)nn2-c2ccccc2)[C@H](c2ccnc(F)c2)O1] | 1 | 1.55 | 591.25 | racemate |

TABLE 102
| No. | Structure | LCMS method No. | RT | MS (m/z) | configuration |
| --- | --- | --- | --- | --- | --- |
| I-466 | 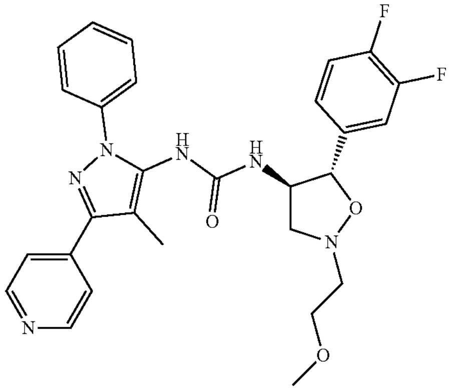 [SMILES: COCCN1C[C@@H](NC(=O)Nc2c(C)c(-c3ccncc3)nn2-c2ccccc2)[C@H](c2ccc(F)c(F)c2)O1] | 1 | 1.44 | 535.25 | |
| I-467 | 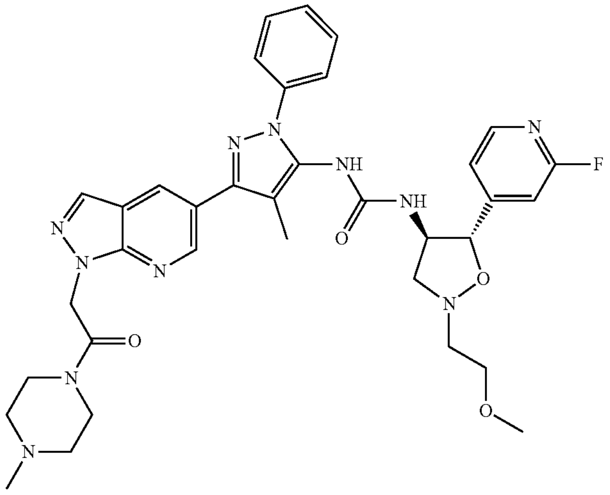 [SMILES: COCCN1C[C@@H](NC(=O)Nc2c(C)c(-c3cnc4c(cnn4CC(=O)N4CCN(C)CC4)c3)nn2-c2ccccc2)[C@H](c2ccnc(F)c2)O1] | 1 | 1.14 | 698.3 | racemate |
| I-468 | 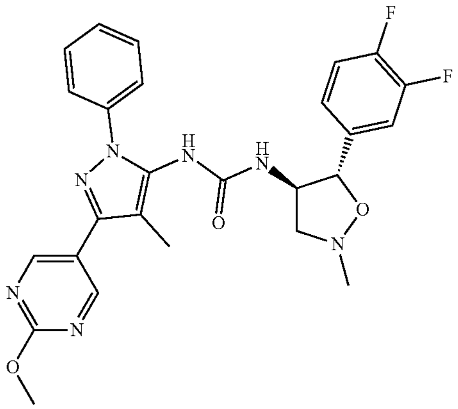 [SMILES: COc1ncc(-c2nn(-c3ccccc3)c(NC(=O)N[C@@H]3CN(C)O[C@H]3c3ccc(F)c(F)c3)c2C)cn1] | 2 | 1.85 | 522 | racemate |

TABLE 102-continued
| No. | Structure | LCMS method No. | RT | MS (m/z) | configuration |
| --- | --- | --- | --- | --- | --- |
| I-469 | 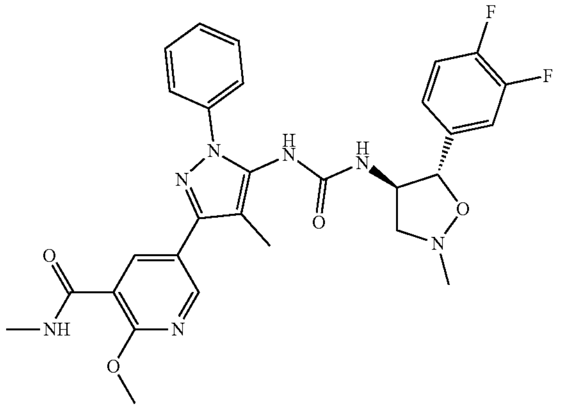 [SMILES: CNC(=O)c1cc(-c2nn(-c3ccccc3)c(NC(=O)N[C@@H]3CN(C)O[C@H]3c3ccc(F)c(F)c3)c2C)cnc1OC] | 2 | 1.84 | 578 | racemate |
TABLE 103
| No. | Structure | LCMS method No. | RT | MS (m/z) | configuration |
| --- | --- | --- | --- | --- | --- |
| I-470 | 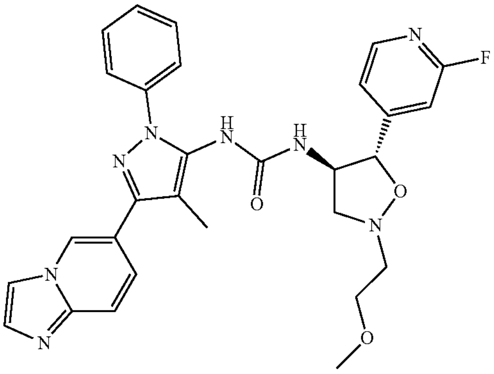 [SMILES: COCCN1C[C@@H](NC(=O)Nc2c(C)c(-c3ccc4nccn4c3)nn2-c2ccccc2)[C@H](c2ccnc(F)c2)O1] | 1 | 1.23 | 557 | racemate |
| I-471 | 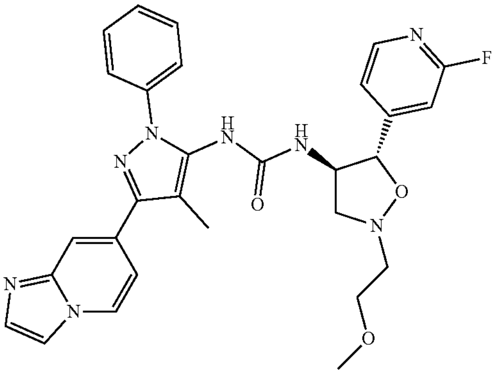 [SMILES: COCCN1C[C@@H](NC(=O)Nc2c(C)c(-c3ccn4ccnc4c3)nn2-c2ccccc2)[C@H](c2ccnc(F)c2)O1] | 1 | 1.26 | 557 | racemate |

TABLE 103-continued
| No. | Structure | LCMS method No. | RT | MS (m/z) | configuration |
|---|---|---|---|---|---|
| I-472 | 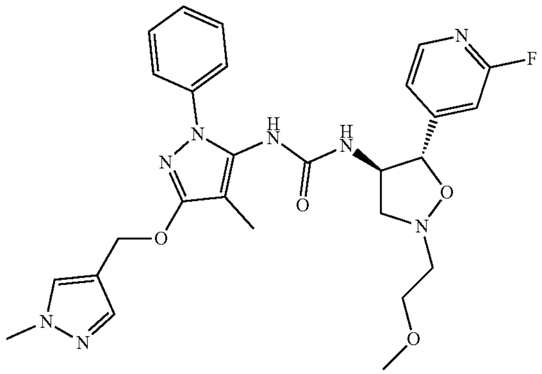 [SMILES: COCCN1C[C@@H](NC(=O)Nc2c(C)c(OCc3cnn(C)c3)nn2-c2ccccc2)[C@H](c2ccnc(F)c2)O1] | 1 | 1.64 | 551 | racemate |
| I-473 | 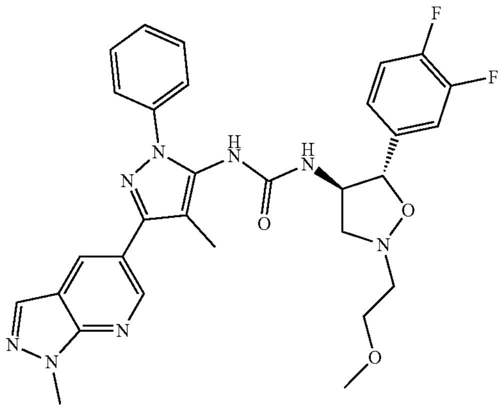 [SMILES: COCCN1C[C@@H](NC(=O)Nc2c(C)c(-c3cnc4c(cnn4C)c3)nn2-c2ccccc2)[C@H](c2ccc(F)c(F)c2)O1] | 1 | 1.96 | 589 | |
TABLE 104
| No. | Structure | LCMS method No. | RT | MS (m/z) | configuration |
|---|---|---|---|---|---|
| I-474 | 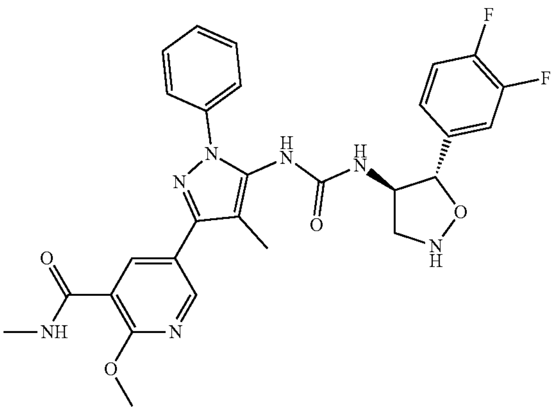 [SMILES: CNC(=O)c1cc(-c2nn(-c3ccccc3)c(NC(=O)N[C@@H]3CNO[C@H]3c3ccc(F)c(F)c3)c2C)cnc1OC] | 2 | 1.68 | 564 | racemate |

TABLE 104-continued
| No. | Structure | LCMS method No. | RT | MS (m/z) | configuration |
|---|---|---|---|---|---|
| I-475 | 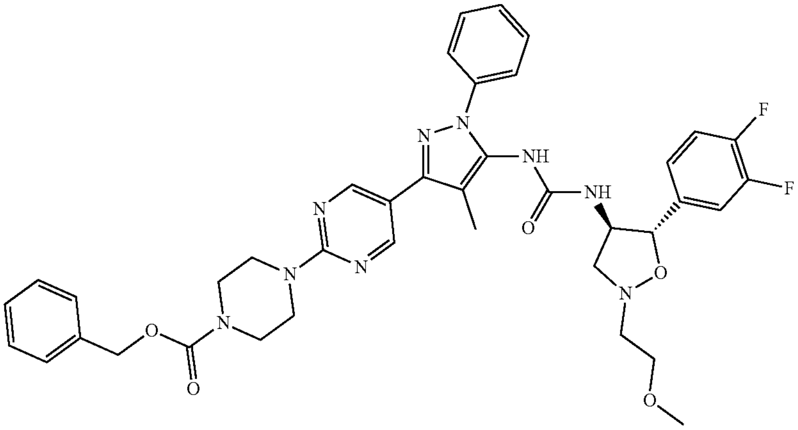 [SMILES: COCCN1C[C@@H](NC(=O)Nc2c(C)c(-c3cnc(N4CCN(C(=O)OCc5ccccc5)CC4)nc3)nn2-c2ccccc2)[C@H](c2ccc(F)c(F)c2)O1] | 1 | 2.39 | 754 | |
| I-476 | 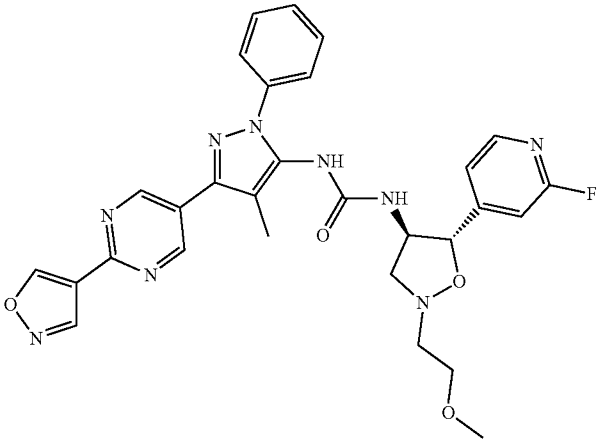 [SMILES: COCCN1C[C@@H](NC(=O)Nc2c(C)c(-c3cnc(-c4cnoc4)nc3)nn2-c2ccccc2)[C@H](c2ccnc(F)c2)O1] | 1 | 1.57 | 586 | racemate |
| I-477 | 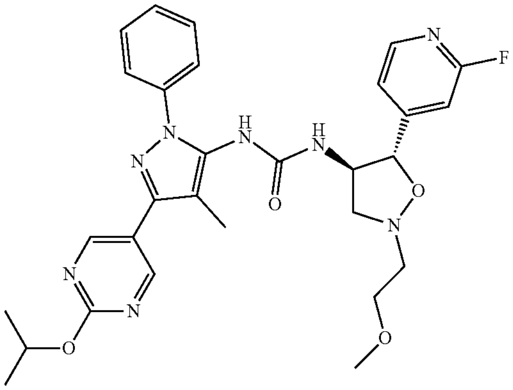 [SMILES: COCCN1C[C@@H](NC(=O)Nc2c(C)c(-c3cnc(OC(C)C)nc3)nn2-c2ccccc2)[C@H](c2ccnc(F)c2)O1] | 1 | 1.87 | 577.3 | racemate |

TABLE 105
| No. | Structure | LCMS method No. | RT | MS (m/z) | configuration |
| --- | --- | --- | --- | --- | --- |
| I-478 | 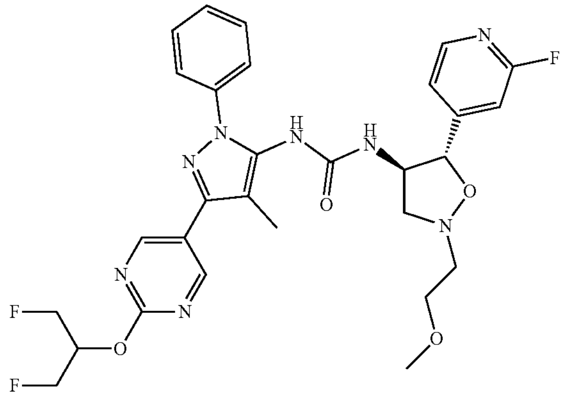 [SMILES: COCCN1C[C@@H](NC(=O)Nc2c(C)c(-c3cnc(OC(CF)CF)nc3)nn2-c2ccccc2)[C@H](c2ccnc(F)c2)O1] | 1 | 1.81 | 613.4 | racemate |
| I-479 | 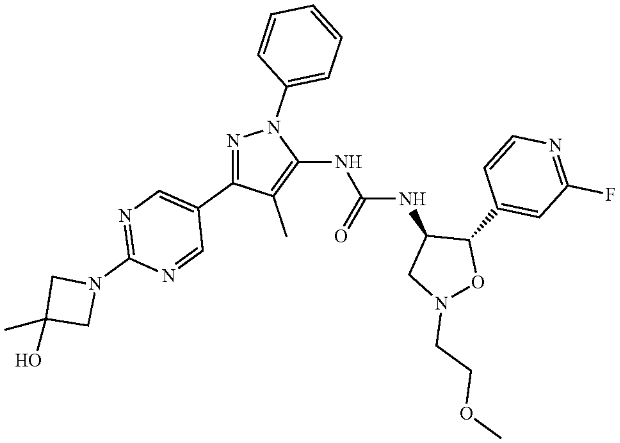 [SMILES: COCCN1C[C@@H](NC(=O)Nc2c(C)c(-c3cnc(N4CC(C)(O)C4)nc3)nn2-c2ccccc2)[C@H](c2ccnc(F)c2)O1] | 1 | 1.51 | 604.15 | racemate |
| I-480 | 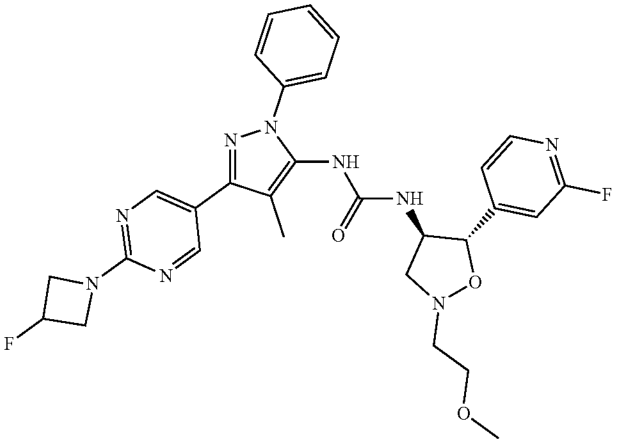 [SMILES: COCCN1C[C@@H](NC(=O)Nc2c(C)c(-c3cnc(N4CC(F)C4)nc3)nn2-c2ccccc2)[C@H](c2ccnc(F)c2)O1] | 1 | 1.71 | 592.2 | racemate |

TABLE 105-continued
| No. | Structure | LCMS method No. | RT | MS (m/z) | configuration |
|---|---|---|---|---|---|
| I-481 | 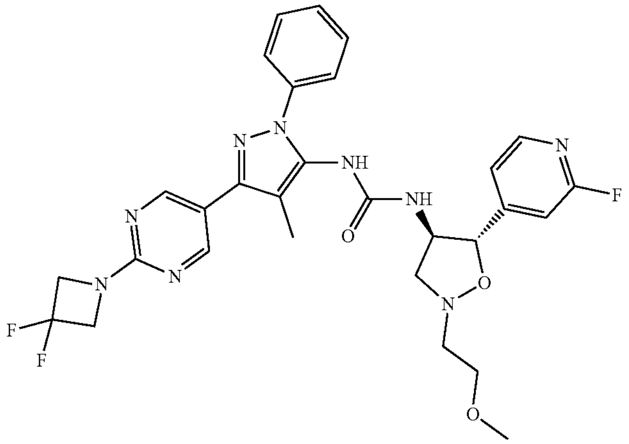 [SMILES: COCCN1C[C@@H](NC(=O)Nc2c(C)c(-c3cnc(N4CC(F)(F)C4)nc3)nn2-c2ccccc2)[C@H](c2ccnc(F)c2)O1] | 1 | 1.89 | 610.15 | racemate |
TABLE 106
| No. | Structure | LCMS method No. | RT | MS (m/z) | configuration |
|---|---|---|---|---|---|
| I-482 | 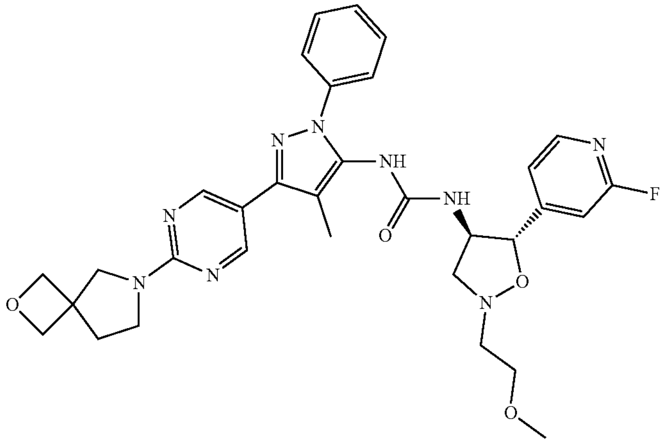 [SMILES: COCCN1C[C@@H](NC(=O)Nc2c(C)c(-c3cnc(N4CCC5(COC5)C4)nc3)nn2-c2ccccc2)[C@H](c2ccnc(F)c2)O1] | 1 | 1.62 | 630.25 | racemate |
| I-483 | 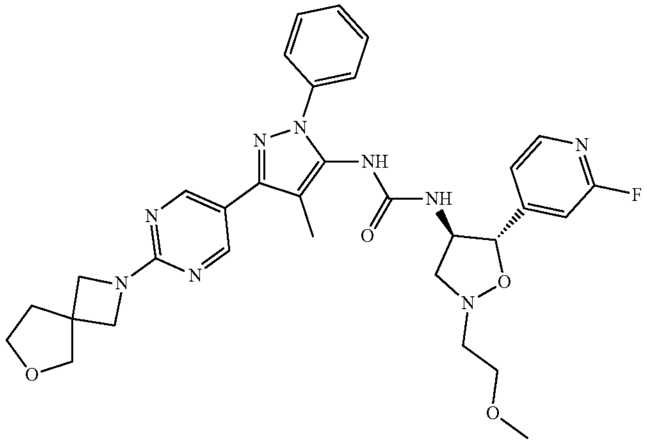 [SMILES: COCCN1C[C@@H](NC(=O)Nc2c(C)c(-c3cnc(N4CC5(CCOC5)C4)nc3)nn2-c2ccccc2)[C@H](c2ccnc(F)c2)O1] | 1 | 1.63 | 630.2 | racemate |

TABLE 106-continued
| No. | Structure | LCMS method No. | RT | MS (m/z) | configuration |
|---|---|---|---|---|---|
| I-484 | 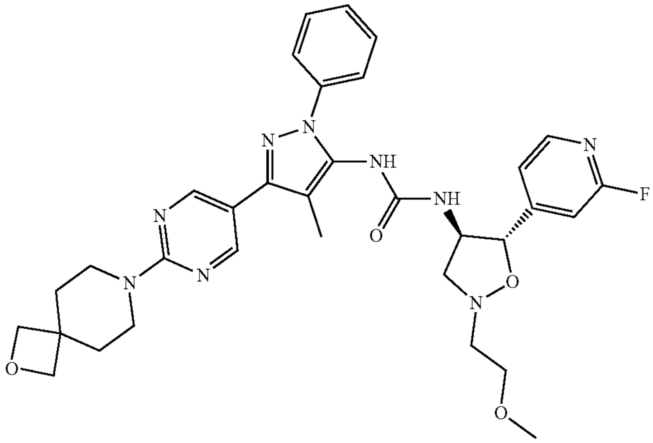 [SMILES: COCCN1C[C@@H](NC(=O)Nc2c(C)c(-c3cnc(N4CCC5(CC4)COC5)nc3)nn2-c2ccccc2)[C@H](c2ccnc(F)c2)O1] | 1 | 1.83 | 644.25 | racemate |
| I-485 | 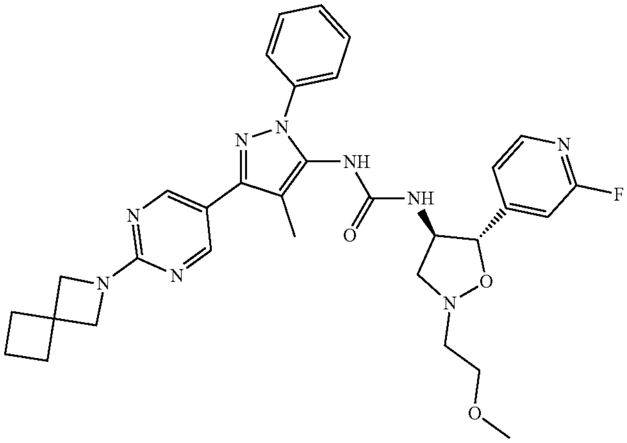 [SMILES: COCCN1C[C@@H](NC(=O)Nc2c(C)c(-c3cnc(N4CC5(CCC5)C4)nc3)nn2-c2ccccc2)[C@H](c2ccnc(F)c2)O1] | 1 | 2.02 | 614.2 | racemate |
TABLE 107
| No. | Structure | LCMS method No. | RT | MS (m/z) | configuration |
|---|---|---|---|---|---|
| I-486 | 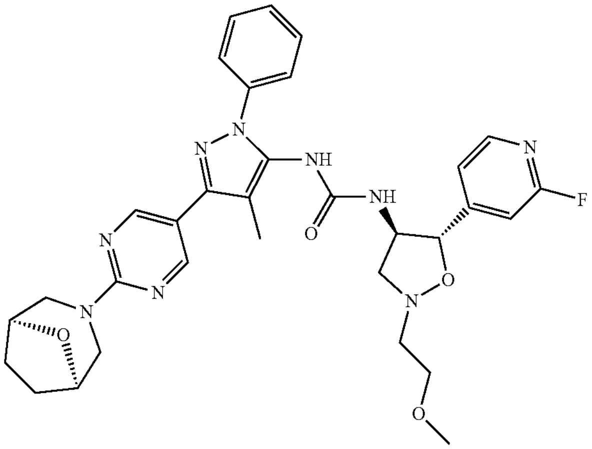 [SMILES: COCCN1C[C@@H](NC(=O)Nc2c(C)c(-c3cnc(N4C[C@H]5CC[C@@H](C4)O5)nc3)nn2-c2ccccc2)[C@H](c2ccnc(F)c2)O1] | 1 | 1.86 | 630.3 | racemate |

TABLE 107-continued
| No. | Structure | LCMS method No. | RT | MS (m/z) | configuration |
|---|---|---|---|---|---|
| I-487 | 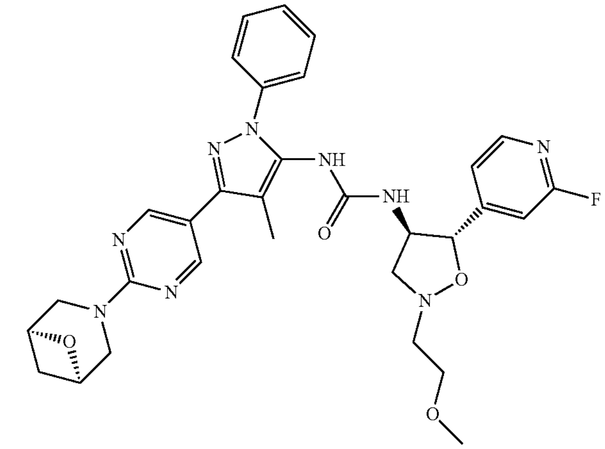 [SMILES: COCCN1C[C@@H](NC(=O)Nc2c(C)c(-c3cnc(N4C[C@H]5C[C@@H](C4)O5)nc3)nn2-c2ccccc2)[C@H](c2ccnc(F)c2)O1] | 1 | 1.64 | 616.2 | racemate |
| I-488 | 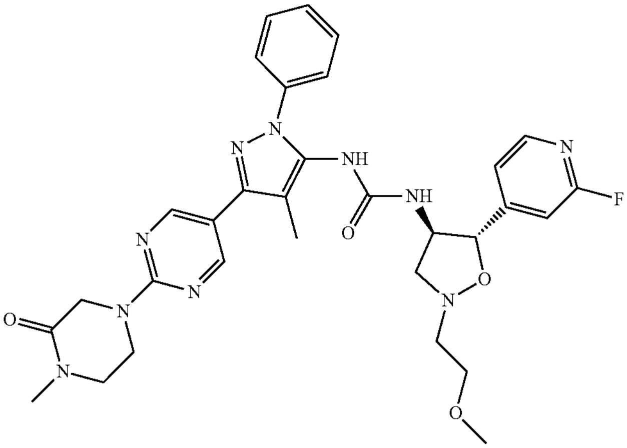 [SMILES: COCCN1C[C@@H](NC(=O)Nc2c(C)c(-c3cnc(N4CCN(C)C(=O)C4)nc3)nn2-c2ccccc2)[C@H](c2ccnc(F)c2)O1] | 1 | 1.61 | 631.2 | racemate |
| I-489 | 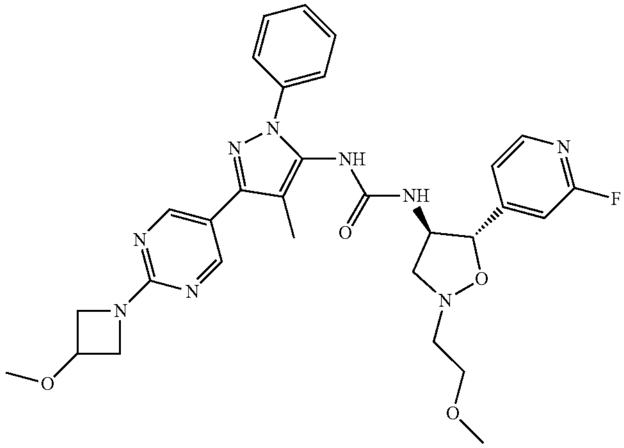 [SMILES: COCCN1C[C@@H](NC(=O)Nc2c(C)c(-c3cnc(N4CC(OC)C4)nc3)nn2-c2ccccc2)[C@H](c2ccnc(F)c2)O1] | 1 | 1.65 | 604.15 | racemate |

TABLE 108
| No. | Structure | LCMS method No. | RT | MS (m/z) | configuration |
|---|---|---|---|---|---|
| I-490 | 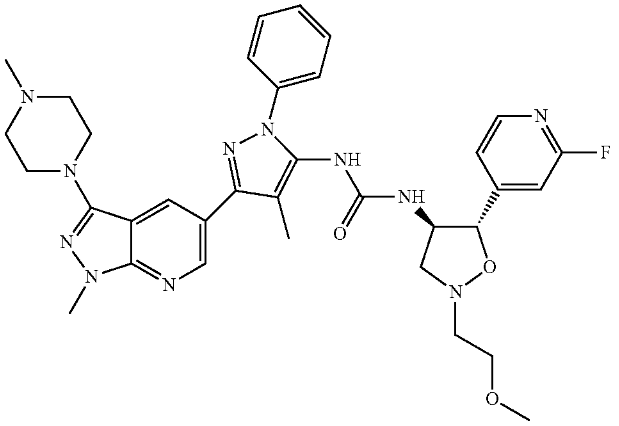 [SMILES: COCCN1C[C@@H](NC(=O)Nc2c(C)c(-c3cnc4c(c3)c(N3CCN(C)CC3)nn4C)nn2-c2ccccc2)[C@H](c2ccnc(F)c2)O1] | 1 | 1.15 | 670.7 | racemate |
| I-491 | 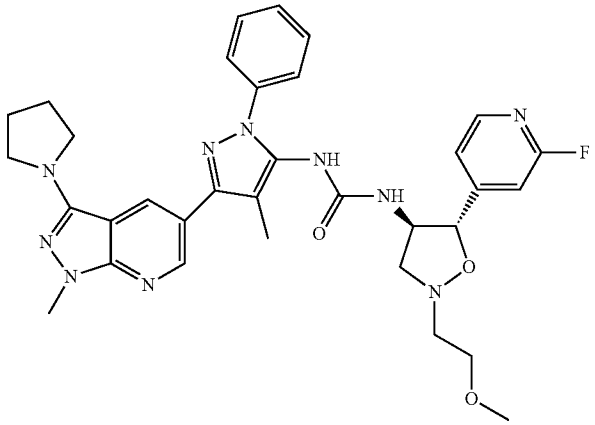 [SMILES: COCCN1C[C@@H](NC(=O)Nc2c(C)c(-c3cnc4c(c3)c(N3CCCC3)nn4C)nn2-c2ccccc2)[C@H](c2ccnc(F)c2)O1] | 1 | 1.87 | 641.45 | racemate |
| I-492 | 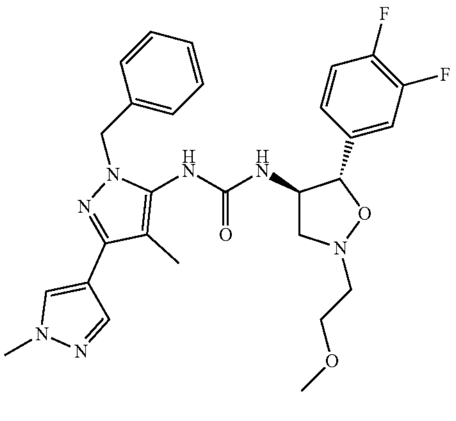 [SMILES: COCCN1C[C@@H](NC(=O)Nc2c(C)c(-c3cnn(C)c3)nn2Cc2ccccc2)[C@H](c2ccc(F)c(F)c2)O1] | 1 | 1.9 | 552.2 | |

TABLE 108-continued
| No. | Structure | LCMS method No. | RT | MS (m/z) | configuration |
|---|---|---|---|---|---|
| I-493 | 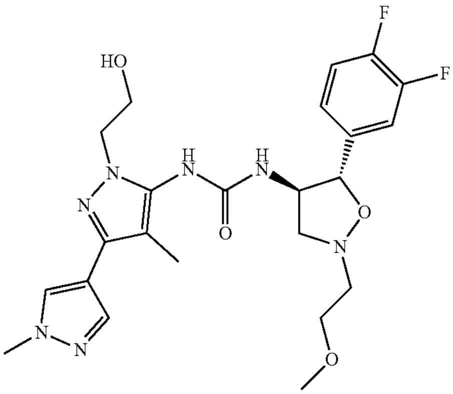 [SMILES: COCCN1C[C@@H](NC(=O)Nc2c(C)c(-c3cnn(C)c3)nn2CCO)[C@H](c2ccc(F)c(F)c2)O1] | 1 | 1.55 | 506.1 | |
TABLE 109
| No. | Structure | LCMS method No. | RT | MS (m/z) | configuration |
|---|---|---|---|---|---|
| I-494 | 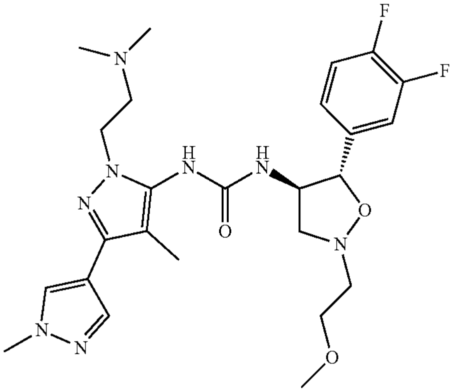 [SMILES: COCCN1C[C@@H](NC(=O)Nc2c(C)c(-c3cnn(C)c3)nn2CCN(C)C)[C@H](c2ccc(F)c(F)c2)O1] | 1 | 1.37 | 533.3 | |
| I-495 | 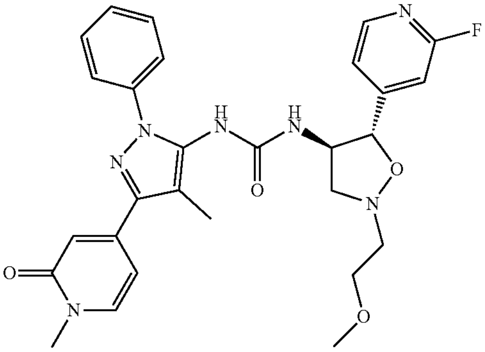 [SMILES: COCCN1C[C@@H](NC(=O)Nc2c(C)c(-c3ccn(C)c(=O)c3)nn2-c2ccccc2)[C@H](c2ccnc(F)c2)O1] | 2 | 1.34 | 548 | racemate |

TABLE 109-continued
| No. | Structure | LCMS method No. | RT | MS (m/z) | configuration |
|---|---|---|---|---|---|
| I-496 | 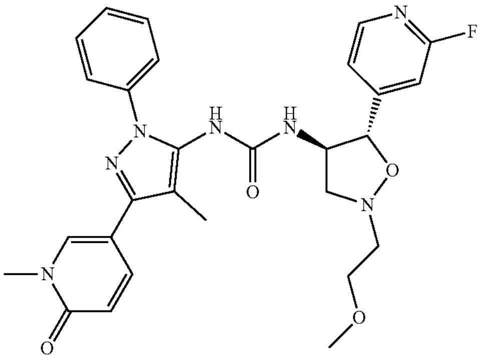 [SMILES: COCCN1C[C@@H](NC(=O)Nc2c(C)c(-c3ccc(=O)n(C)c3)nn2-c2ccccc2)[C@H](c2ccnc(F)c2)O1] | 2 | 1.31 | 548 | racemate |
| I-497 | 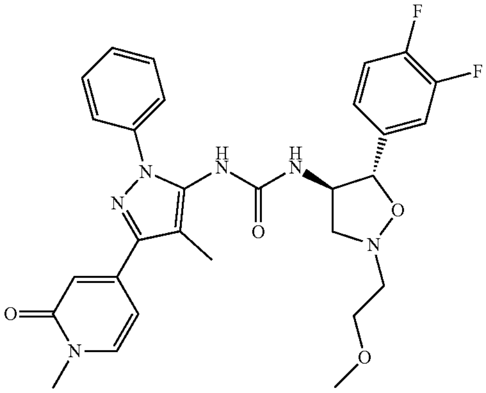 [SMILES: COCCN1C[C@@H](NC(=O)Nc2c(C)c(-c3ccn(C)c(=O)c3)nn2-c2ccccc2)[C@H](c2ccc(F)c(F)c2)O1] | 2 | 1.66 | 565 | |
| I-498 | 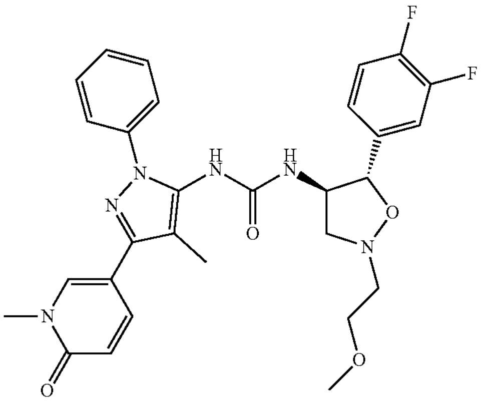 [SMILES: COCCN1C[C@@H](NC(=O)Nc2c(C)c(-c3ccc(=O)n(C)c3)nn2-c2ccccc2)[C@H](c2ccc(F)c(F)c2)O1] | 2 | 1.64 | 565 | |

TABLE 110
| No. | Structure | LCMS method No. | RT | MS (m/z) | configuration |
|---|---|---|---|---|---|
| I-499 | 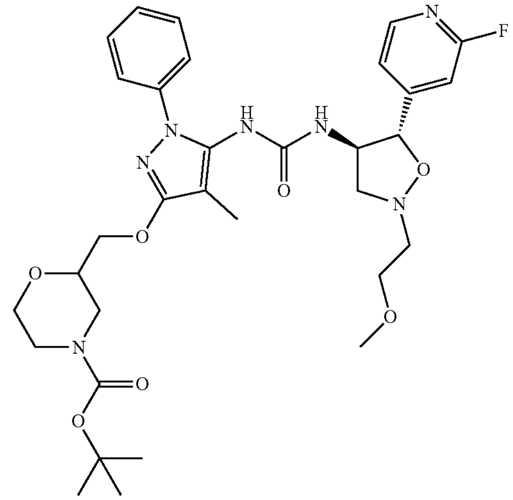 [SMILES: COCCN1C[C@@H](NC(=O)Nc2c(C)c(OCC3CN(C(=O)OC(C)(C)C)CCO3)nn2-c2ccccc2)[C@H](c2ccnc(F)c2)O1] | 2 | 2.14 | 656 | diastereo mixture |
| I-500 | 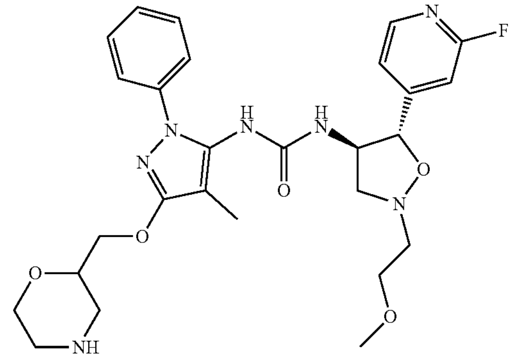 [SMILES: COCCN1C[C@@H](NC(=O)Nc2c(C)c(OCC3CNCCO3)nn2-c2ccccc2)[C@H](c2ccnc(F)c2)O1] | 2 | 1.23 | 556 | diastereo mixture |
| I-501 | 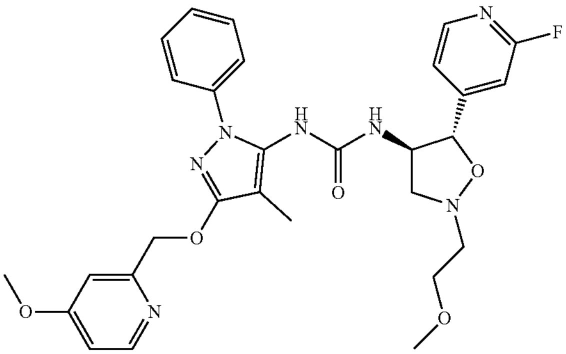 [SMILES: COCCN1C[C@@H](NC(=O)Nc2c(C)c(OCc3cc(OC)ccn3)nn2-c2ccccc2)[C@H](c2ccnc(F)c2)O1] | 2 | 1.38 | 578 | racemate |

TABLE 110-continued
| No. | Structure | LCMS method No. | RT | MS (m/z) | configuration |
|---|---|---|---|---|---|
| I-502 | 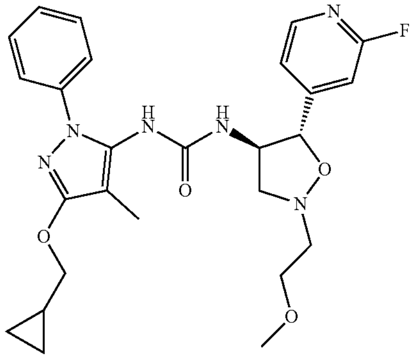 [SMILES: COCCN1C[C@@H](NC(=O)Nc2c(C)c(OCC3CC3)nn2-c2ccccc2)[C@H](c2ccnc(F)c2)O1] | 2 | 2.04 | 511 | racemate |
TABLE 111
| No. | Structure | LCMS method No. | RT | MS (m/z) | configuration |
|---|---|---|---|---|---|
| I-503 | 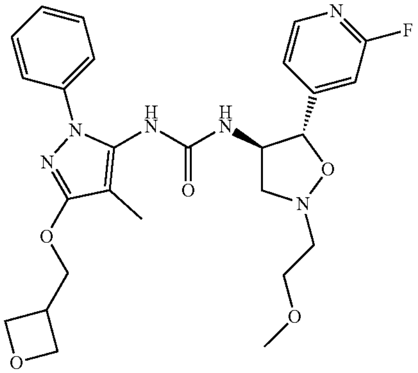 [SMILES: COCCN1C[C@@H](NC(=O)Nc2c(C)c(OCC3COC3)nn2-c2ccccc2)[C@H](c2ccnc(F)c2)O1] | 2 | 1.58 | 527 | racemate |
| I-504 | 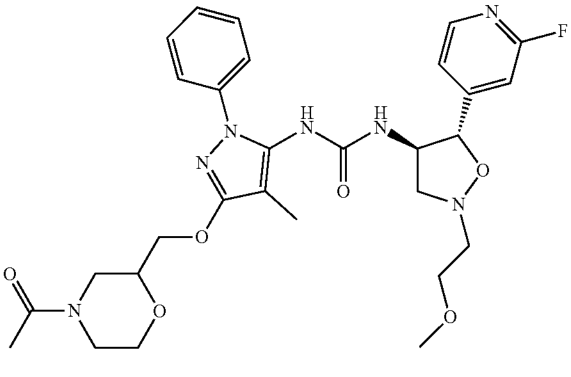 [SMILES: COCCN1C[C@@H](NC(=O)Nc2c(C)c(OCC3CN(C(C)=O)CCO3)nn2-c2ccccc2)[C@H](c2ccnc(F)c2)O1] | 2 | 1.44 | 598 | diastereo mixture |

TABLE 111-continued
| No. | Structure | LCMS method No. | RT | MS (m/z) | configuration |
|---|---|---|---|---|---|
| I-505 | 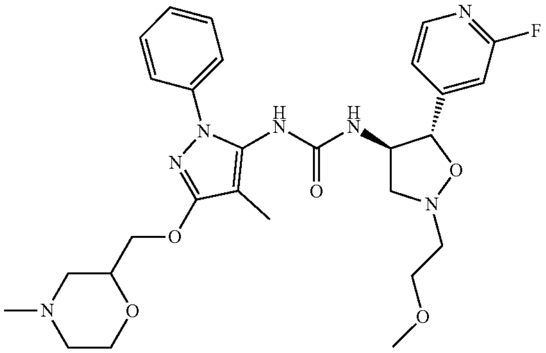 [SMILES: COCCN1C[C@@H](NC(=O)Nc2c(C)c(OCC3CN(C)CCO3)nn2-c2ccccc2)[C@H](c2ccnc(F)c2)O1] | 2 | 1.26 | 570 | diastereo mixture |
| I-506 | 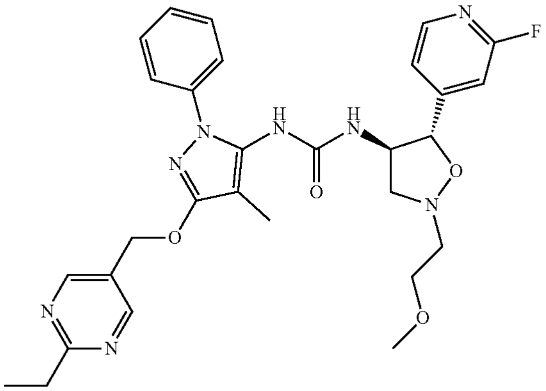 [SMILES: CCc1ncc(COc2nn(-c3ccccc3)c(NC(=O)N[C@@H]3CN(CCOC)O[C@H]3c3ccnc(F)c3)c2C)cn1] | 1 | 1.66 | 547.4 | racemate |
TABLE 112
| No. | Structure | LCMS method No. | RT | MS (m/z) | configuration |
|---|---|---|---|---|---|
| I-507 | 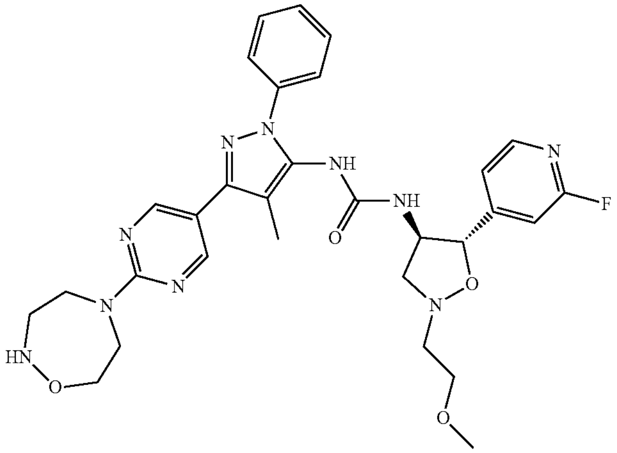 [SMILES: COCCN1C[C@@H](NC(=O)Nc2c(C)c(-c3cnc(N4CCNOCC4)nc3)nn2-c2ccccc2)[C@H](c2ccnc(F)c2)O1] | 1 | 1.55 | 619.5 | racemate |

TABLE 112-continued
| No. | Structure | LCMS method No. | RT | MS (m/z) | configuration |
|---|---|---|---|---|---|
| I-508 | 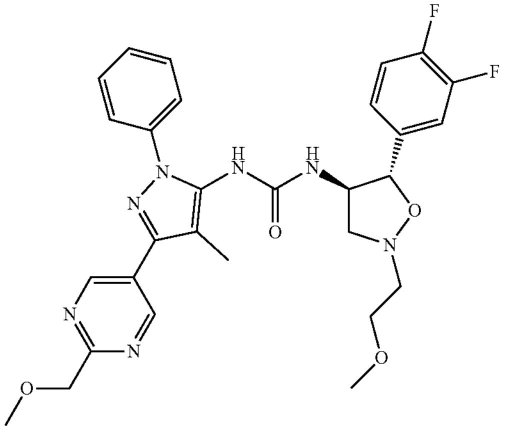 [SMILES: COCCN1C[C@@H](NC(=O)Nc2c(C)c(-c3cnc(COC)nc3)nn2-c2ccccc2)[C@H](c2ccc(F)c(F)c2)O1] | 1 | 1.81 | 580.3 | |
| I-509 | 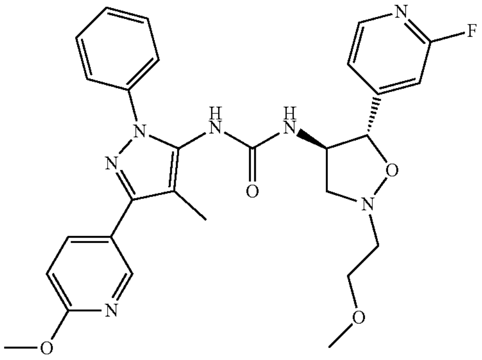 [SMILES: COCCN1C[C@@H](NC(=O)Nc2c(C)c(-c3ccc(OC)nc3)nn2-c2ccccc2)[C@H](c2ccnc(F)c2)O1] | 1 | 1.84 | 548.3 | |
| I-510 | 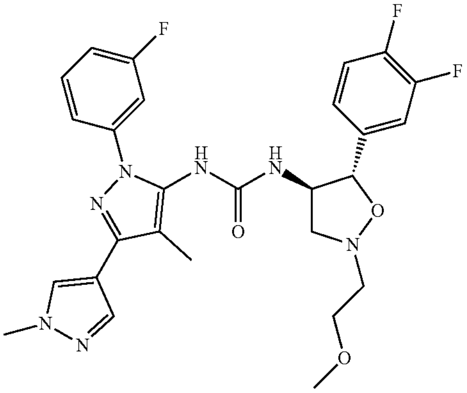 [SMILES: COCCN1C[C@@H](NC(=O)Nc2c(C)c(-c3cnn(C)c3)nn2-c2cccc(F)c2)[C@H](c2ccc(F)c(F)c2)O1] | 2 | 2.16 | 556 | |

TABLE 113
| No. | Structure | LCMS method No. | RT | MS (m/z) | configuration |
|---|---|---|---|---|---|
| I-511 | 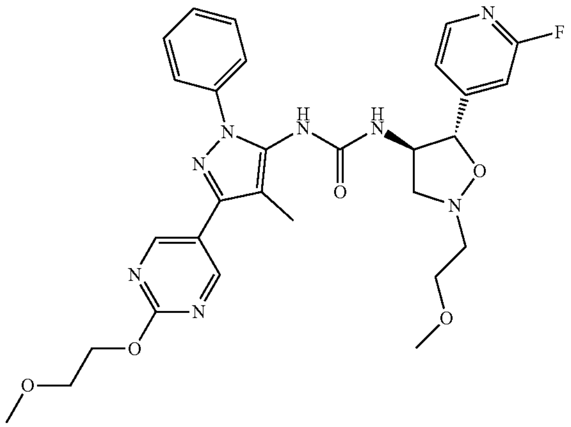 [SMILES: COCCOc1ncc(-c2nn(-c3ccccc3)c(NC(=O)N[C@@H]3CN(CCOC)O[C@H]3c3ccnc(F)c3)c2C)cn1] | 1 | 1.67 | 593.3 | racemate |
| I-512 | 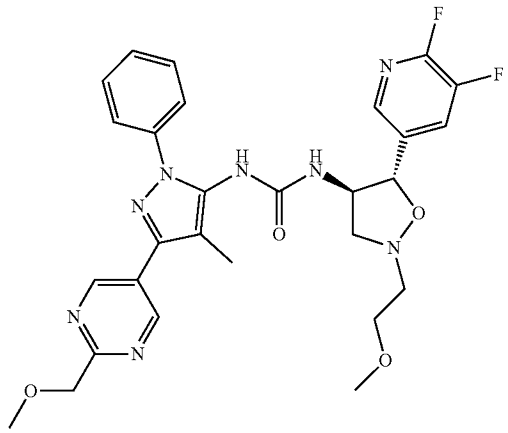 [SMILES: COCCN1C[C@@H](NC(=O)Nc2c(C)c(-c3cnc(COC)nc3)nn2-c2ccccc2)[C@H](c2cnc(F)c(F)c2)O1] | 1 | 1.68 | 581.3 | |
| I-513 | 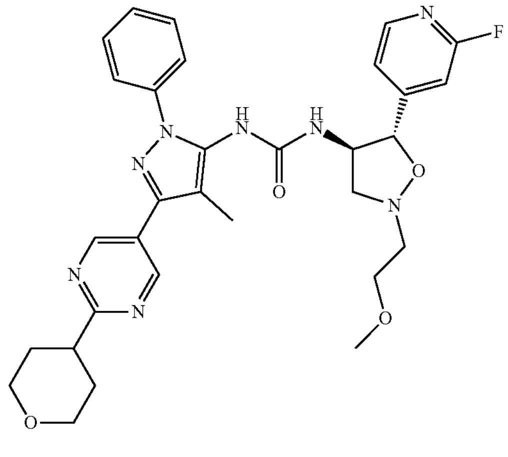 [SMILES: COCCN1C[C@@H](NC(=O)Nc2c(C)c(-c3cnc(C4CCOCC4)nc3)nn2-c2ccccc2)[C@H](c2ccnc(F)c2)O1] | 1 | 1.67 | 603.3 | racemate |

TABLE 113-continued
| No. | Structure | LCMS method No. | RT | MS (m/z) | configuration |
|---|---|---|---|---|---|
| I-514 | 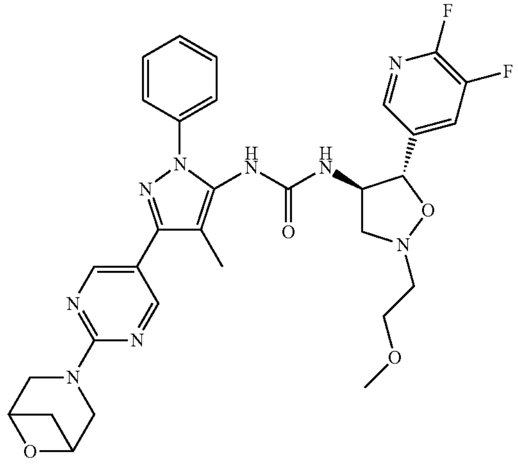 [SMILES: COCCN1C[C@@H](NC(=O)Nc2c(C)c(-c3cnc(N4CC5CC(C4)O5)nc3)nn2-c2ccccc2)[C@H](c2cnc(F)c(F)c2)O1] | 1 | 1.76 | 634.35 | |
TABLE 114
| No. | Structure | LCMS method No. | RT | MS (m/z) | configuration |
|---|---|---|---|---|---|
| I-515 | 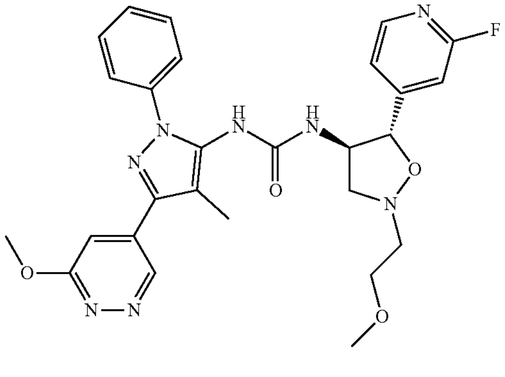 [SMILES: COCCN1C[C@@H](NC(=O)Nc2c(C)c(-c3cnnc(OC)c3)nn2-c2ccccc2)[C@H](c2ccnc(F)c2)O1] | 1 | 1.8 | 548.3 | racemate |
| I-516 | 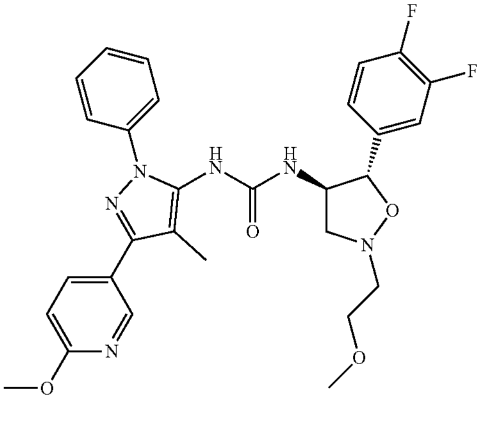 | 1 | 2.13 | 565.3 | |

TABLE 114-continued
| No. | Structure | LCMS method No. | RT | MS (m/z) | configuration |
|---|---|---|---|---|---|
| I-517 | 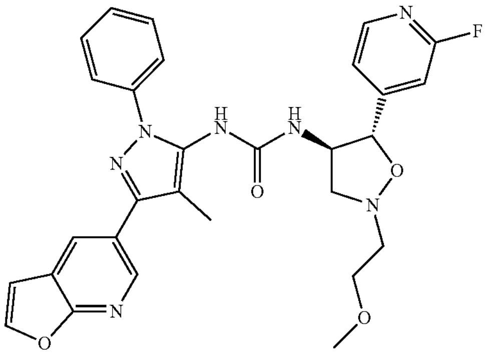 [SMILES: COCCN1C[C@@H](NC(=O)Nc2c(C)c(-c3cnc4occc4c3)nn2-c2ccccc2)[C@H](c2ccnc(F)c2)O1] | 1 | 1.79 | 558.25 | racemate |
| I-518 | 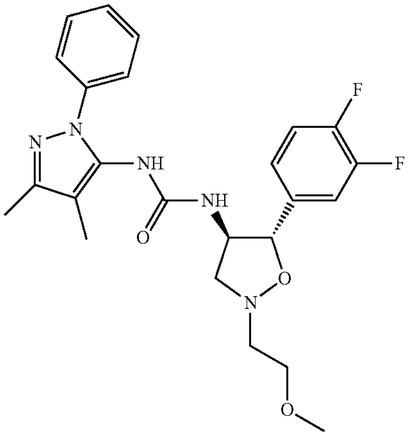 [SMILES: COCCN1C[C@@H](NC(=O)Nc2c(C)c(C)nn2-c2ccccc2)[C@H](c2ccc(F)c(F)c2)O1] | 1 | 1.87 | 472.25 | |
TABLE 115
| No. | Structure | LCMS method No. | RT | MS (m/z) | configuration |
|---|---|---|---|---|---|
| I-519 | 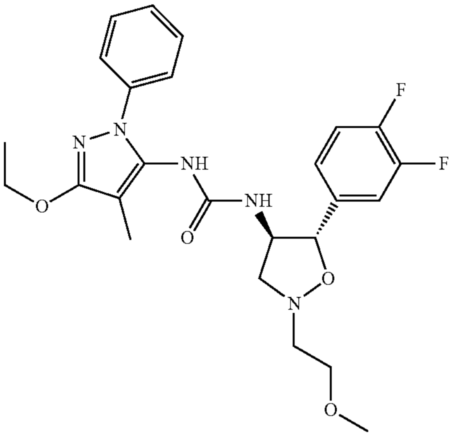 [SMILES: CCOc1nn(-c2ccccc2)c(NC(=O)N[C@@H]2CN(CCOC)O[C@H]2c2ccc(F)c(F)c2)c1C] | 1 | 2.15 | 502.3 | |

TABLE 115-continued
| No. | Structure | LCMS method No. | RT | MS (m/z) | configuration |
| --- | --- | --- | --- | --- | --- |
| I-520 | 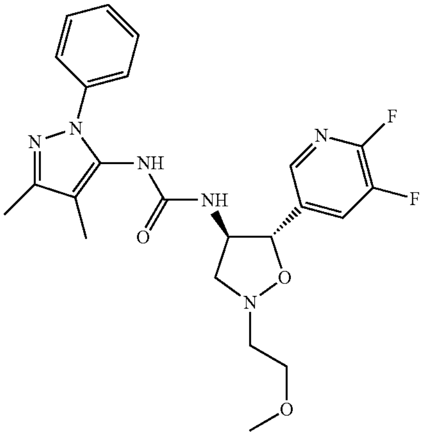 [SMILES: COCCN1C[C@@H](NC(=O)Nc2c(C)c(C)nn2-c2ccccc2)[C@H](c2cnc(F)c(F)c2)O1] | 1 | 1.78 | 473.15 | |
| I-521 | 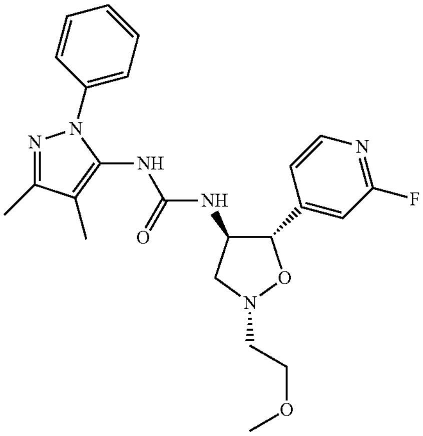 | 1 | 1.72 | 454.15 | |
| I-522 | 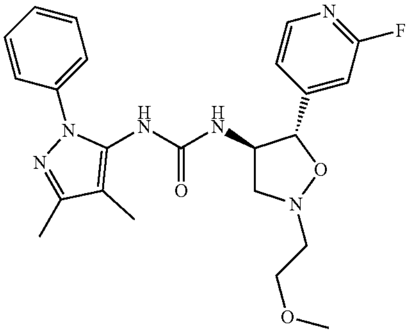 [SMILES: COCCN1C[C@@H](NC(=O)Nc2c(C)c(C)nn2-c2ccccc2)[C@H](c2ccnc(F)c2)O1] | 1 | 1.61 | 455.15 | racemate |

TABLE 116
| No. | Structure | LCMS method No. | RT | MS (m/z) | configuration |
|---|---|---|---|---|---|
| I-523 | 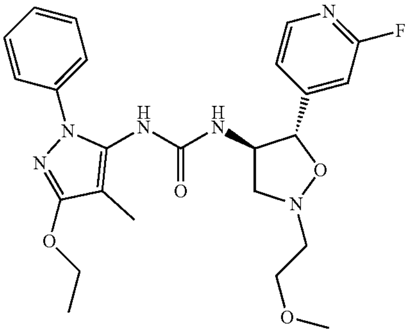 [SMILES: CCOc1nn(-c2ccccc2)c(NC(=O)N[C@@H]2CN(CCOC)O[C@H]2c2ccnc(F)c2)c1C] | 1 | 1.91 | 485.15 | racemate |
| I-524 | 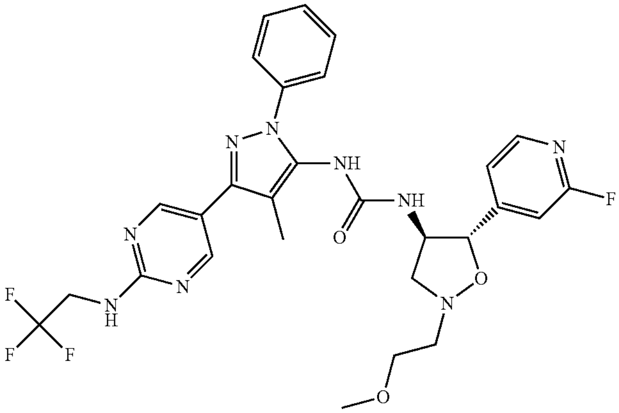 [SMILES: COCCN1C[C@@H](NC(=O)Nc2c(C)c(-c3cnc(NCC(F)(F)F)nc3)nn2-c2ccccc2)[C@H](c2ccnc(F)c2)O1] | 1 | 1.87 | 616.3 | racemate |
| I-525 | 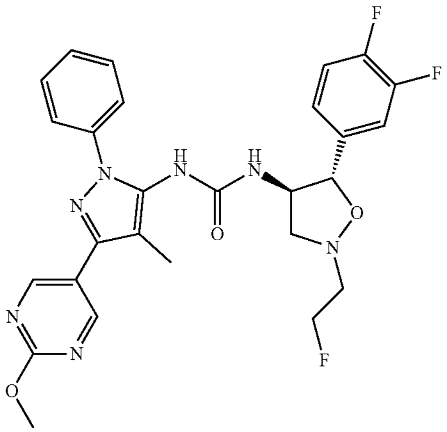 [SMILES: COc1ncc(-c2nn(-c3ccccc3)c(NC(=O)N[C@@H]3CN(CCF)O[C@H]3c3ccc(F)c(F)c3)c2C)cn1] | 2 | 1.94 | 554 | racemate |

TABLE 116-continued
| No. | Structure | LCMS method No. | RT | MS (m/z) | configuration |
|---|---|---|---|---|---|
| I-526 | 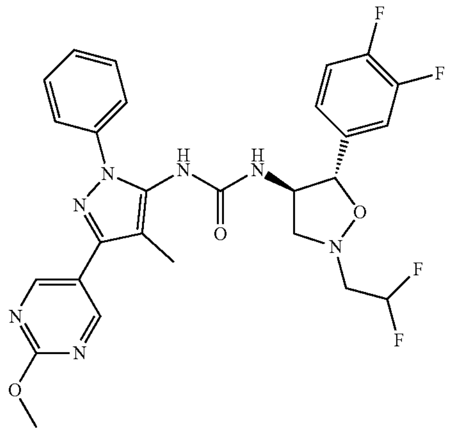 [SMILES: COc1ncc(-c2nn(-c3ccccc3)c(NC(=O)N[C@@H]3CN(CC(F)F)O[C@H]3c3ccc(F)c(F)c3)c2C)cn1] | 2 | 2.07 | 572 | racemate |
TABLE 117
| No. | Structure | LCMS method No. | RT | MS (m/z) | configuration |
|---|---|---|---|---|---|
| I-527 | 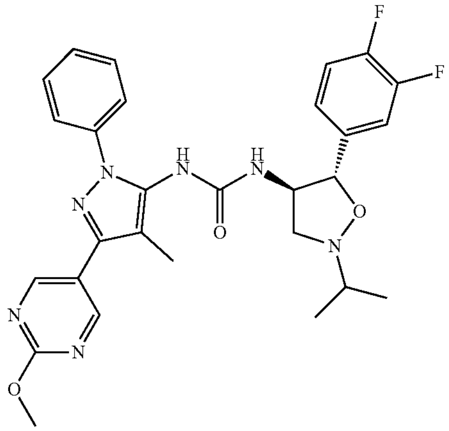 [SMILES: COc1ncc(-c2nn(-c3ccccc3)c(NC(=O)N[C@@H]3CN(C(C)C)O[C@H]3c3ccc(F)c(F)c3)c2C)cn1] | 2 | 2.08 | 550 | racemate |
| I-528 | 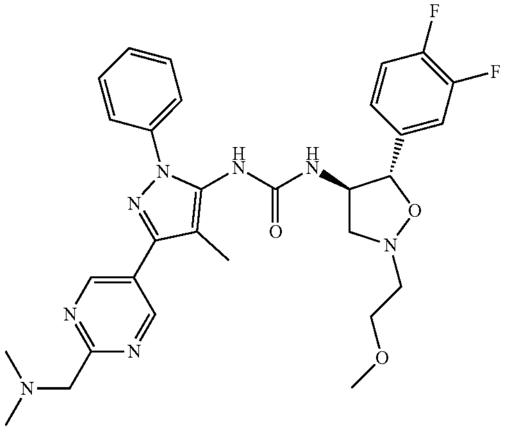 [SMILES: COCCN1C[C@@H](NC(=O)Nc2c(C)c(-c3cnc(CN(C)C)nc3)nn2-c2ccccc2)[C@H](c2ccc(F)c(F)c2)O1] | 1 | 1.41 | 593.35 | racemate |

TABLE 117-continued
| No. | Structure | LCMS method No. | RT | MS (m/z) | configuration |
|---|---|---|---|---|---|
| I-529 | 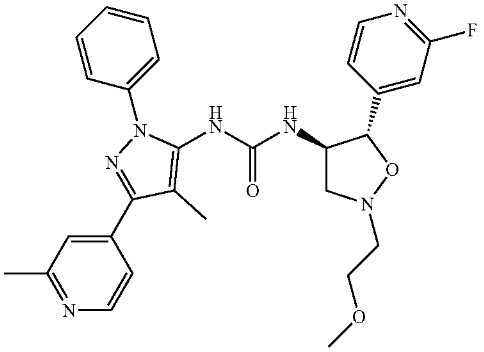 [SMILES: COCCN1C[C@@H](NC(=O)Nc2c(C)c(-c3ccnc(C)c3)nn2-c2ccccc2)[C@H](c2ccnc(F)c2)O1] | 1 | 1.23 | 532.3 | racemate |
| I-530 | 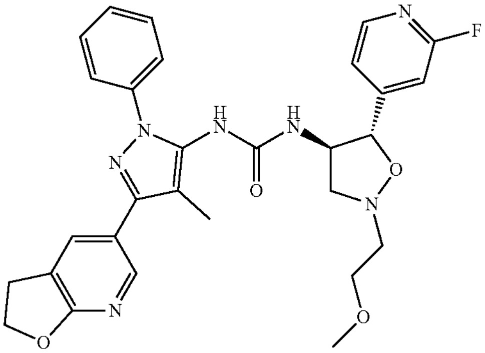 [SMILES: COCCN1C[C@@H](NC(=O)Nc2c(C)c(-c3cnc4c(c3)CCO4)nn2-c2ccccc2)[C@H](c2ccnc(F)c2)O1] | 1 | 1.63 | 560.25 | racemate |
TABLE 118
| No. | Structure | LCMS method No. | RT | MS (m/z) | configuration |
|---|---|---|---|---|---|
| I-531 | 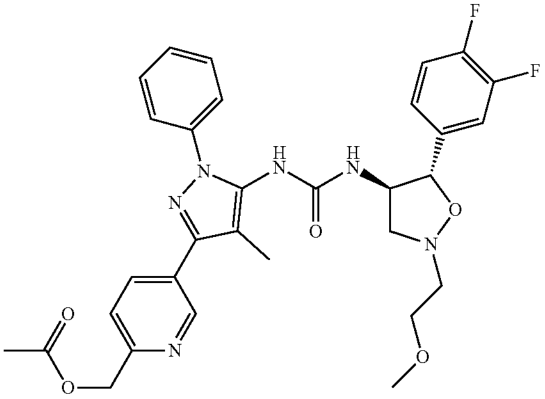 [SMILES: COCCN1C[C@@H](NC(=O)Nc2c(C)c(-c3ccc(COC(C)=O)nc3)nn2-c2ccccc2)[C@H](c2ccc(F)c(F)c2)O1] | 1 | 1.88 | 607.3 | |

TABLE 118-continued
| No. | Structure | LCMS method No. | RT | MS (m/z) | configuration |
|---|---|---|---|---|---|
| I-532 | 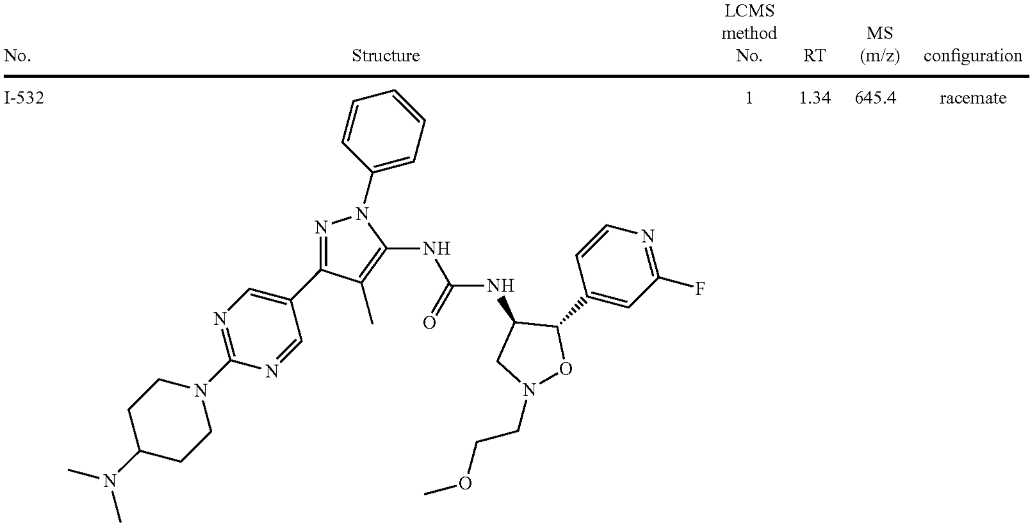 | 1 | 1.34 | 645.4 | racemate |
| I-533 | 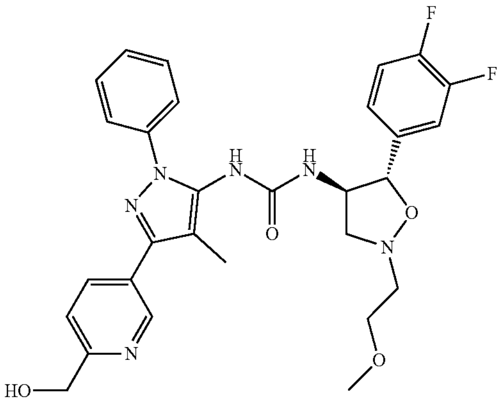 [SMILES: COCCN1C[C@@H](NC(=O)Nc2c(C)c(-c3ccc(CO)nc3)nn2-c2ccccc2)[C@H](c2ccc(F)c(F)c2)O1] | 1 | 1.47 | 565.3 | |
| I-534 | 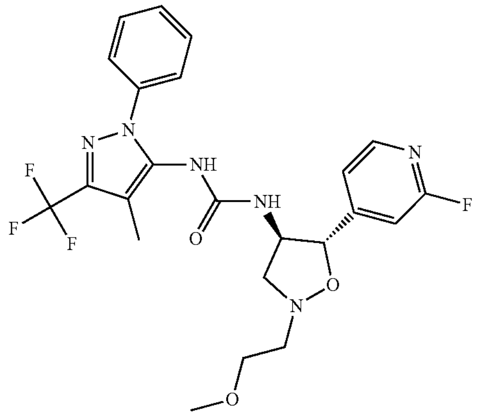 [SMILES: COCCN1C[C@@H](NC(=O)Nc2c(C)c(C(F)(F)F)nn2-c2ccccc2)[C@H](c2ccnc(F)c2)O1] | 1 | 1.91 | 509.25 | racemate |

TABLE 119
| No. | Structure | LCMS method No. | RT | MS (m/z) | configuration |
|---|---|---|---|---|---|
| I-535 | 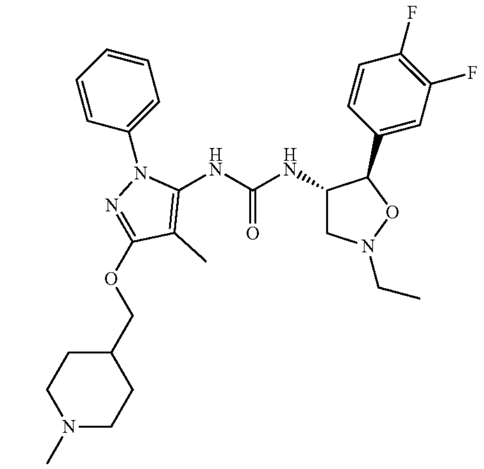 [SMILES: CCN1C[C@H](NC(=O)Nc2c(C)c(OCC3CCN(C)CC3)nn2-c2ccccc2)[C@@H](c2ccc(F)c(F)c2)O1] | 2 | 1.84 | 555 | |
| I-536 | 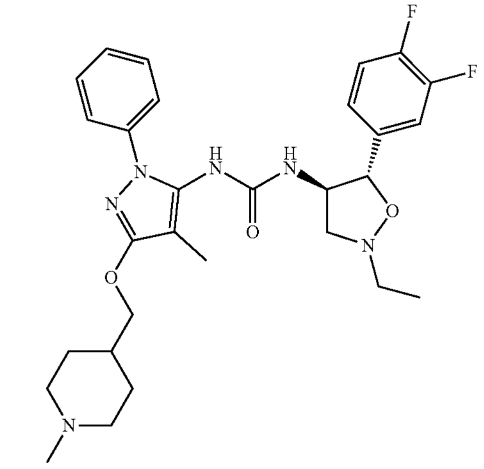 [SMILES: CCN1C[C@@H](NC(=O)Nc2c(C)c(OCC3CCN(C)CC3)nn2-c2ccccc2)[C@H](c2ccc(F)c(F)c2)O1] | 2 | 1.84 | 555 | |
| I-537 | 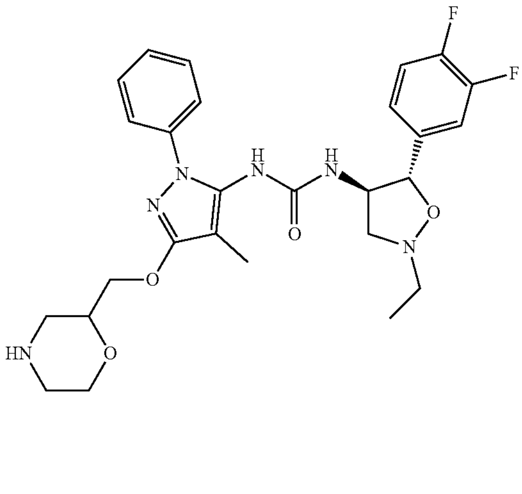 [SMILES: CCN1C[C@@H](NC(=O)Nc2c(C)c(OCC3CNCCO3)nn2-c2ccccc2)[C@H](c2ccc(F)c(F)c2)O1] | 2 | 1.59 | 543 | diastereo mixture |

TABLE 119-continued
| No. | Structure | LCMS method No. | RT | MS (m/z) | configuration |
|---|---|---|---|---|---|
| I-538 | 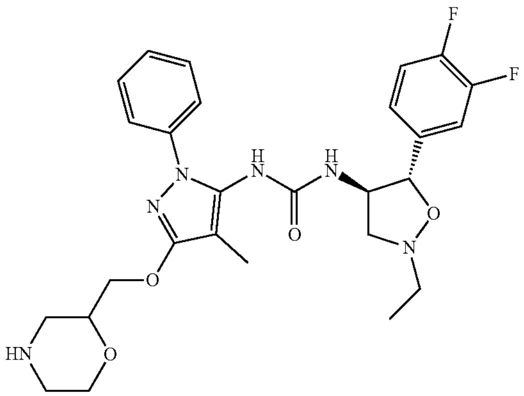 [SMILES: CCN1C[C@@H](NC(=O)Nc2c(C)c(OCC3CNCCO3)nn2-c2ccccc2)[C@H](c2ccc(F)c(F)c2)O1] | 2 | 1.61 | 543 | diastereo mixture |
TABLE 120
| No. | Structure | LCMS method No. | RT | MS (m/z) | configuration |
|---|---|---|---|---|---|
| I-539 | 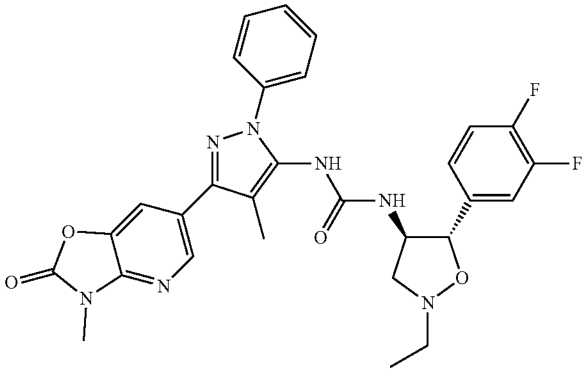 [SMILES: CCN1C[C@@H](NC(=O)Nc2c(C)c(-c3cnc4c(c3)oc(=O)n4C)nn2-c2ccccc2)[C@H](c2ccc(F)c(F)c2)O1] | 1 | 2.02 | 576 | racemate |
| I-540 | 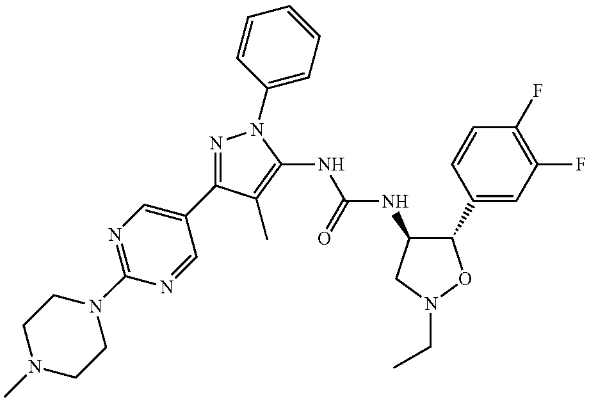 [SMILES: CCN1C[C@@H](NC(=O)Nc2c(C)c(-c3cnc(N4CCN(C)CC4)nc3)nn2-c2ccccc2)[C@H](c2ccc(F)c(F)c2)O1] | 1 | 1.51 | 604 | racemate |

TABLE 120-continued
| No. | Structure | LCMS method No. | RT | MS (m/z) | configuration |
|---|---|---|---|---|---|
| I-541 | 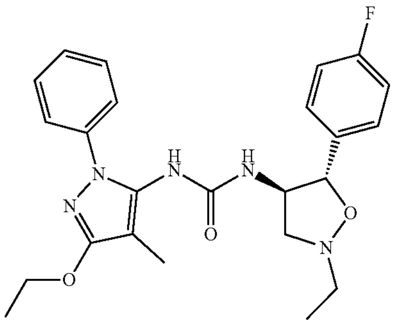 [SMILES: CCOc1nn(-c2ccccc2)c(NC(=O)N[C@@H]2CN(CC)O[C@H]2c2ccc(F)cc2)c1C] | 1 | 1.96 | 454 | racemate |
| I-542 | 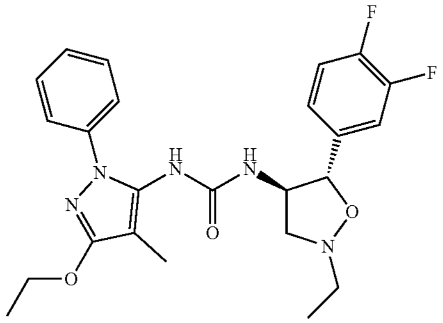 [SMILES: CCOc1nn(-c2ccccc2)c(NC(=O)N[C@@H]2CN(CC)O[C@H]2c2ccc(F)c(F)c2)c1C] | 1 | 2.14 | 472 | racemate |
| I-543 | 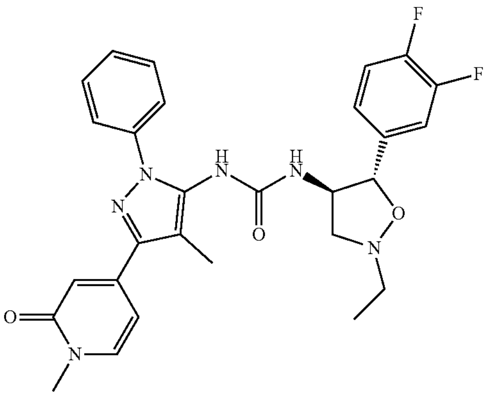 [SMILES: CCN1C[C@@H](NC(=O)Nc2c(C)c(-c3ccn(C)c(=O)c3)nn2-c2ccccc2)[C@H](c2ccc(F)c(F)c2)O1] | 1 | 1.7 | 535 | racemate |

TABLE 121
| No. | Structure | LCMS method No. | RT | MS (m/z) | configuration |
|---|---|---|---|---|---|
| I-544 | 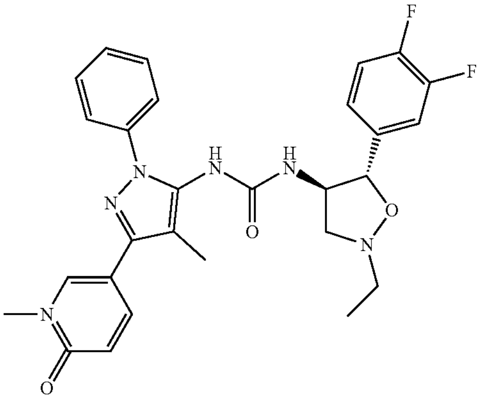 | 1 | 1.71 | 535 | racemate |
| I-545 | 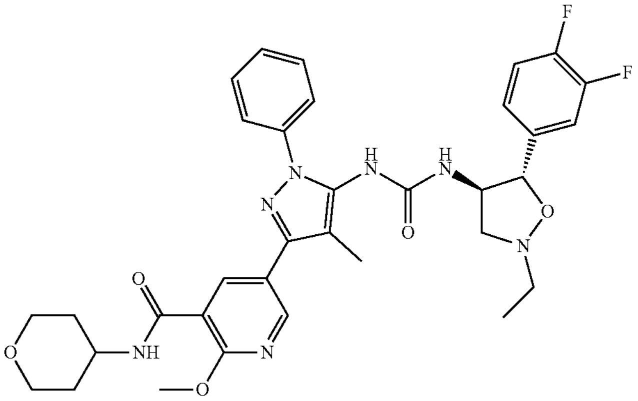 [SMILES: CCN1C[C@@H](NC(=O)Nc2c(C)c(-c3cnc(OC)c(C(=O)NC4CCOCC4)c3)nn2-c2ccccc2)[C@H](c2ccc(F)c(F)c2)O1] | 2 | 2.11 | 662 | racemate |
| I-546 | 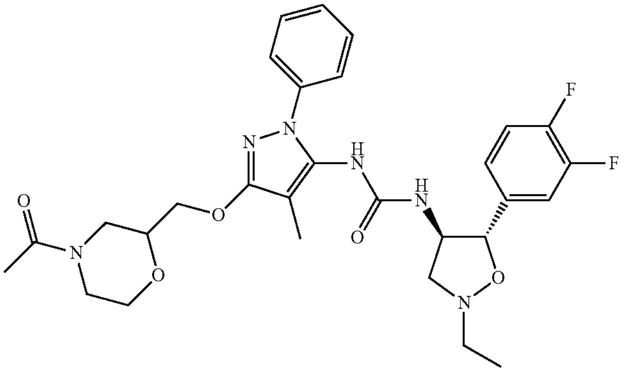 [SMILES: CCN1C[C@@H](NC(=O)Nc2c(C)c(OCC3CN(C(C)=O)CCO3)nn2-c2ccccc2)[C@H](c2ccc(F)c(F)c2)O1] | 2 | 1.83 | 585 | diastereo mixture |
| I-547 | 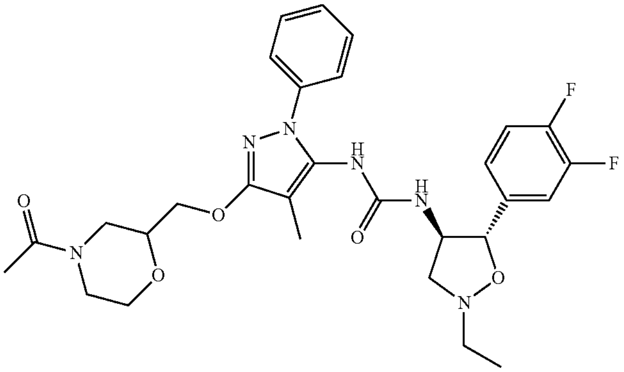 [SMILES: CCN1C[C@@H](NC(=O)Nc2c(C)c(OCC3CN(C(C)=O)CCO3)nn2-c2ccccc2)[C@H](c2ccc(F)c(F)c2)O1] | 2 | 1.83 | 585 | diastereo mixture |

TABLE 121-continued
| No. | Structure | LCMS method No. | RT | MS (m/z) | configuration |
| --- | --- | --- | --- | --- | --- |
| I-548 | 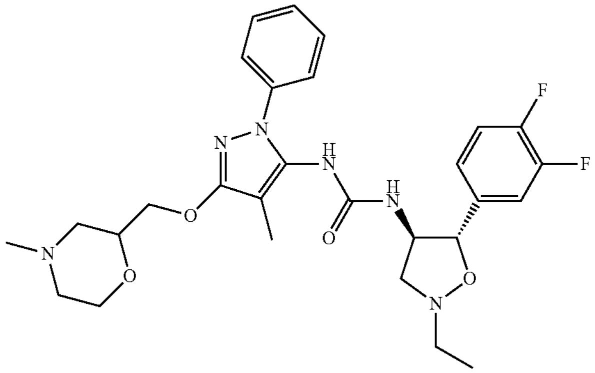 [SMILES: CCN1C[C@@H](NC(=O)Nc2c(C)c(OCC3CN(C)CCO3)nn2-c2ccccc2)[C@H](c2ccc(F)c(F)c2)O1] | 2 | 1.94 | 557 | diastereo mixture |
TABLE 122
| No. | Structure | LCMS method No. | RT | MS (m/z) | configu-ration |
| --- | --- | --- | --- | --- | --- |
| I-549 | 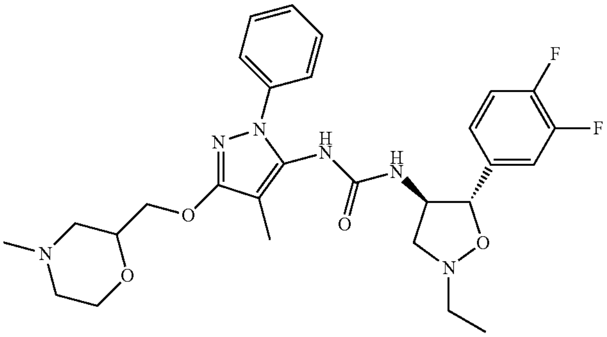 [SMILES: CCN1C[C@@H](NC(=O)Nc2c(C)c(OCC3CN(C)CCO3)nn2-c2ccccc2)[C@H](c2ccc(F)c(F)c2)O1] | 2 | 1.92 | 557 | diastereo mixture |
| I-550 | 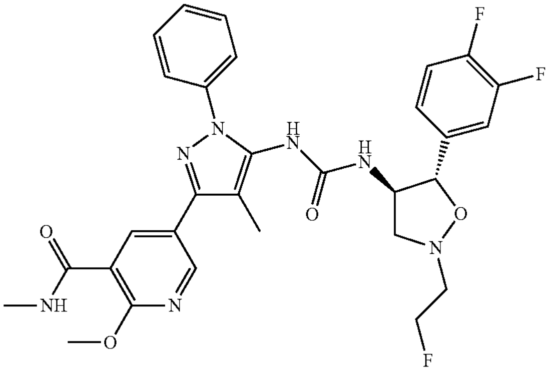 [SMILES: CNC(=O)c1cc(-c2nn(-c3ccccc3)c(NC(=O)N[C@@H]3CN(CCF)O[C@H]3c3ccc(F)c(F)c3)c2C)cnc1OC] | 2 | 2.01 | 610 | racemate |

TABLE 122-continued
| No. | Structure | LCMS method No. | RT | MS (m/z) | configu-ration |
|---|---|---|---|---|---|
| I-551 | 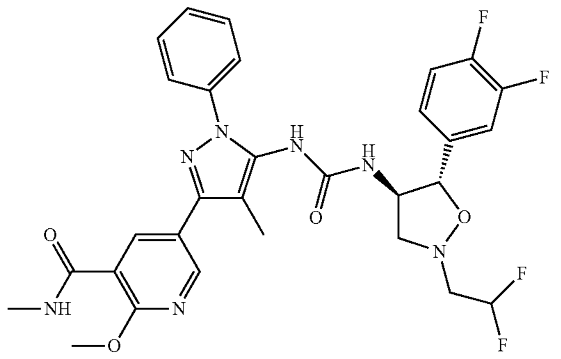 [SMILES: CNC(=O)c1cc(-c2nn(-c3ccccc3)c(NC(=O)N[C@@H]3CN(CC(F)F)O[C@H]3c3ccc(F)c(F)c3)c2C)cnc1OC] | 2 | 2.14 | 628 | racemate |
| I-552 | 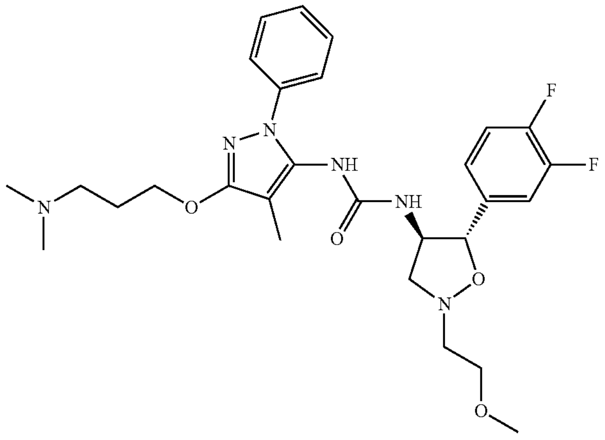 [SMILES: COCCN1C[C@@H](NC(=O)Nc2c(C)c(OCCCN(C)C)nn2-c2ccccc2)[C@H](c2ccc(F)c(F)c2)O1] | 1 | 1.38 | 559.35 | |
| I-553 | 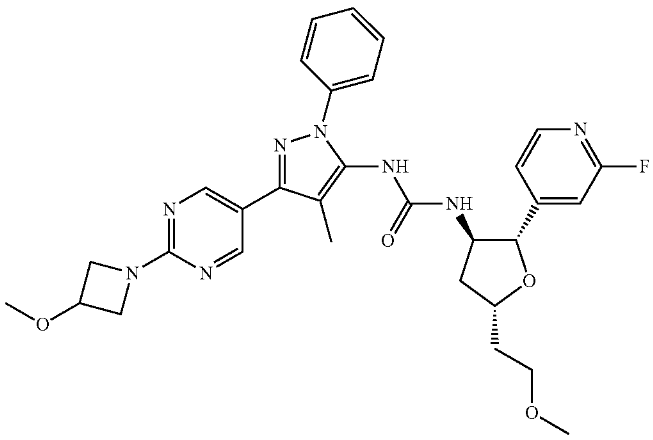 [SMILES: COCC[C@@H]1C[C@@H](NC(=O)Nc2c(C)c(-c3cnc(N4CC(OC)C4)nc3)nn2-c2ccccc2)[C@H](c2ccnc(F)c2)O1] | 1 | 1.65 | 603.35 | |

TABLE 123
| No. | Structure | LCMS method No. | RT | MS (m/z) | configu-ration |
|---|---|---|---|---|---|
| I-554 | 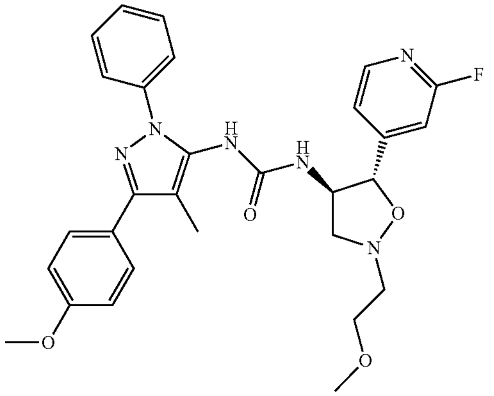 [SMILES: COCCN1C[C@@H](NC(=O)Nc2c(C)c(-c3ccc(OC)cc3)nn2-c2ccccc2)[C@H](c2ccnc(F)c2)O1] | 1 | 1.92 | 547.3 | racemate |
| I-555 | 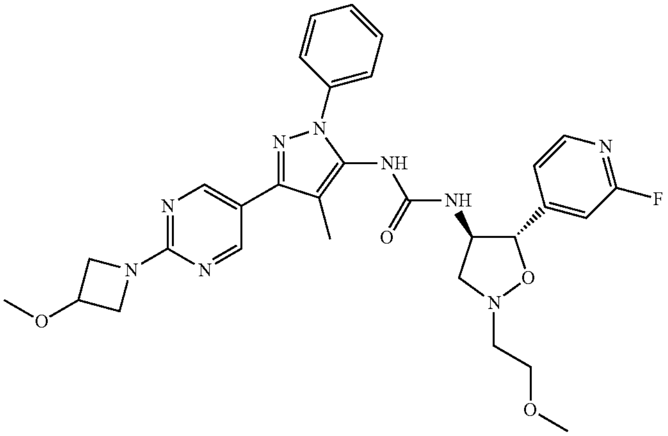 [SMILES: COCCN1C[C@@H](NC(=O)Nc2c(C)c(-c3cnc(N4CC(OC)C4)nc3)nn2-c2ccccc2)[C@H](c2ccnc(F)c2)O1] | 1 | 1.55 | 604.3 | |
| I-556 | 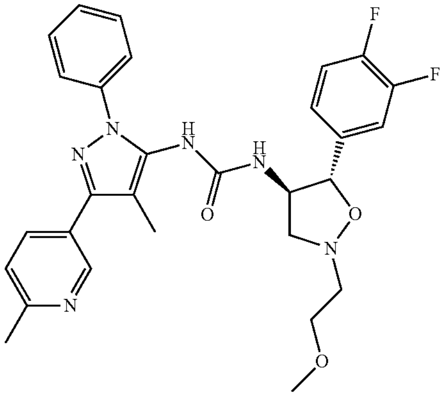 [SMILES: COCCN1C[C@@H](NC(=O)Nc2c(C)c(-c3ccc(C)nc3)nn2-c2ccccc2)[C@H](c2ccc(F)c(F)c2)O1] | 1 | 1.46 | 549.3 | |

TABLE 123-continued
| No. | Structure | LCMS method No. | RT | MS (m/z) | configu-ration |
|---|---|---|---|---|---|
| I-557 | 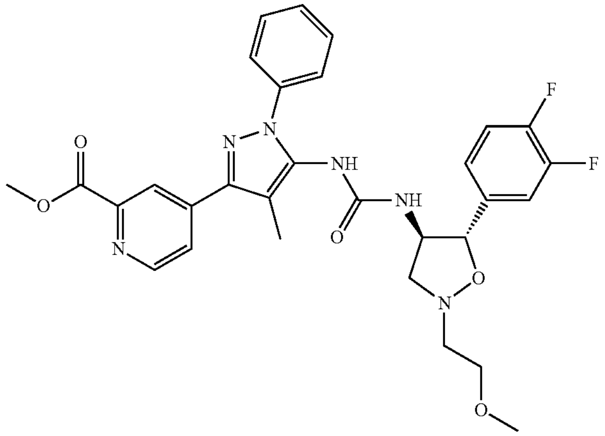 [SMILES: COCCN1C[C@@H](NC(=O)Nc2c(C)c(-c3ccnc(C(=O)OC)c3)nn2-c2ccccc2)[C@H](c2ccc(F)c(F)c2)O1] | 1 | 1.87 | 593.3 | |
TABLE 124
| No. | Structure | LCMS method No. | RT | MS (m/z) | configuration |
|---|---|---|---|---|---|
| I-558 | 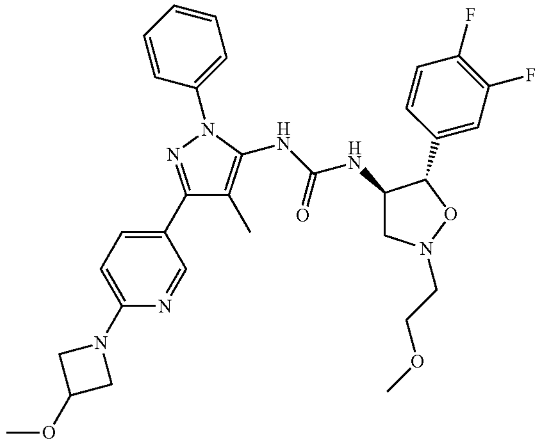 [SMILES: COCCN1C[C@@H](NC(=O)Nc2c(C)c(-c3ccc(N4CC(OC)C4)nc3)nn2-c2ccccc2)[C@H](c2ccc(F)c(F)c2)O1] | 1 | 1.51 | 620.35 | |
| I-559 | 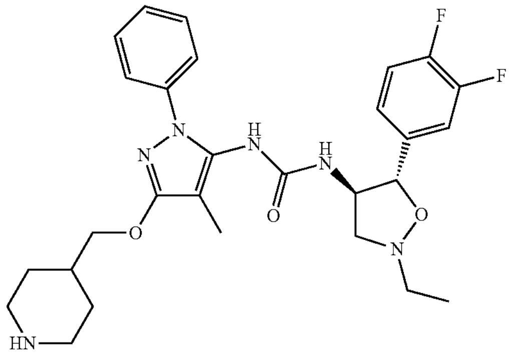 [SMILES: CCN1C[C@@H](NC(=O)Nc2c(C)c(OCC3CCNCC3)nn2-c2ccccc2)[C@H](c2ccc(F)c(F)c2)O1] | 2 | 1.62 | 541 | racemate |

TABLE 124-continued
| No. | Structure | LCMS method No. | RT | MS (m/z) | configuration |
|---|---|---|---|---|---|
| I-560 | 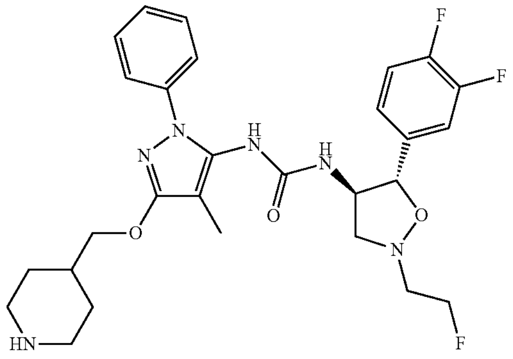 [SMILES: Cc1c(OCC2CCNCC2)nn(-c2ccccc2)c1NC(=O)N[C@@H]1CN(CCF)O[C@H]1c1ccc(F)c(F)c1] | 2 | 1.66 | 559 | racemate |
| I-561 | 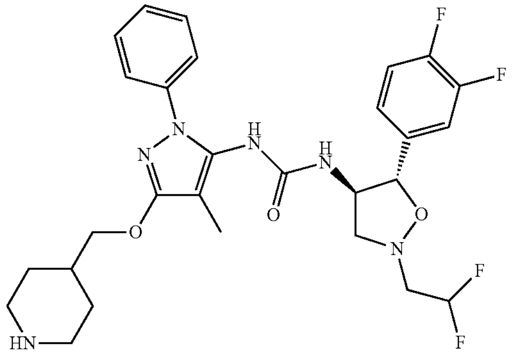 [SMILES: Cc1c(OCC2CCNCC2)nn(-c2ccccc2)c1NC(=O)N[C@@H]1CN(CC(F)F)O[C@H]1c1ccc(F)c(F)c1] | 2 | 1.74 | 577 | racemate |
45
TABLE 125
| No. | Structure | LCMS method No. | RT | MS (m/z) | configu-ration |
|---|---|---|---|---|---|
| I-562 | 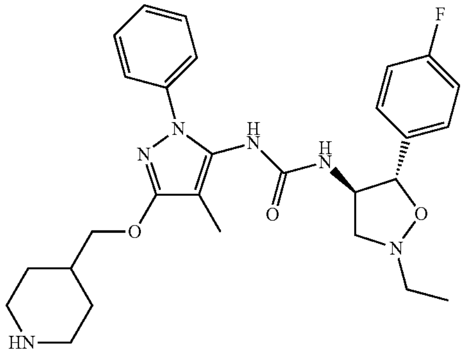 [SMILES: CCN1C[C@@H](NC(=O)Nc2c(C)c(OCC3CCNCC3)nn2-c2ccccc2)[C@H](c2ccc(F)cc2)O1] | 2 | 1.54 | 523 | racemate |

TABLE 125-continued
| No. | Structure | LCMS method No. | RT | MS (m/z) | configu-ration |
|---|---|---|---|---|---|
| I-563 | 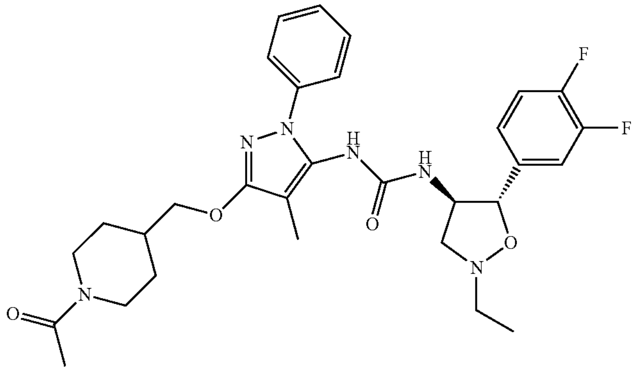 [SMILES: CCN1C[C@@H](NC(=O)Nc2c(C)c(OCC3CCN(C(C)=O)CC3)nn2-c2ccccc2)[C@H](c2ccc(F)c(F)c2)O1] | 2 | 1.96 | 583 | racemate |
| I-564 | 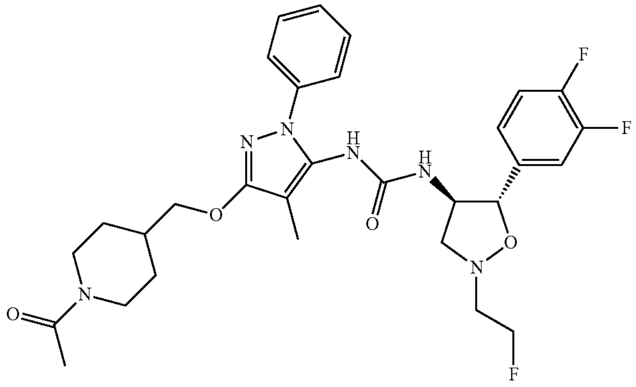 [SMILES: CC(=O)N1CCC(COc2nn(-c3ccccc3)c(NC(=O)N[C@@H]3CN(CCF)O[C@H]3c3ccc(F)c(F)c3)c2C)CC1] | 2 | 1.99 | 601 | racemate |
| I-565 | 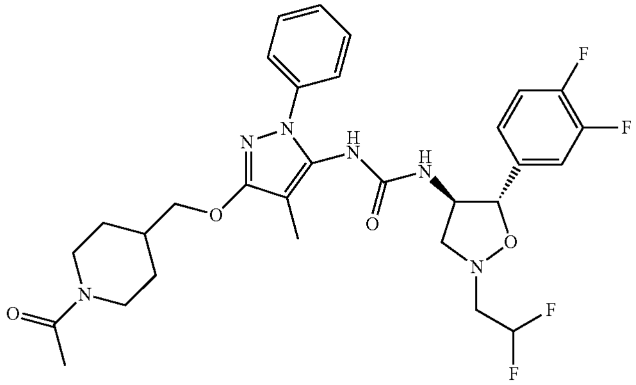 [SMILES: CC(=O)N1CCC(COc2nn(-c3ccccc3)c(NC(=O)N[C@@H]3CN(CC(F)F)O[C@H]3c3ccc(F)c(F)c3)c2C)CC1] | 2 | 2.12 | 619 | racemate |
| I-566 | 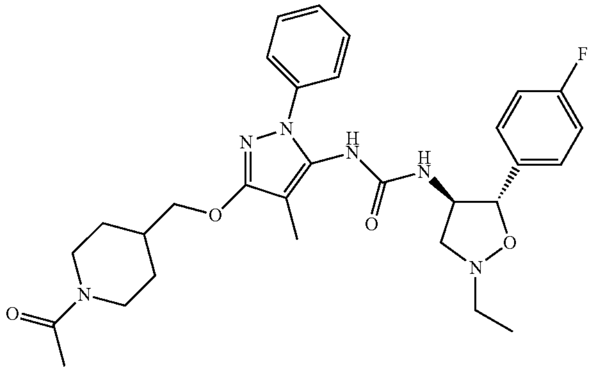 [SMILES: CCN1C[C@@H](NC(=O)Nc2c(C)c(OCC3CCN(C(C)=O)CC3)nn2-c2ccccc2)[C@H](c2ccc(F)cc2)O1] | 2 | 1.85 | 565 | racemate |

TABLE 126
| No. | Structure | LCMS method No. | RT | MS (m/z) | configuration |
|---|---|---|---|---|---|
| I-567 | 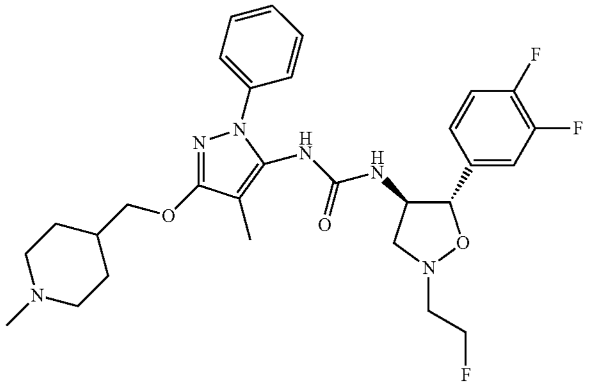 [SMILES: Cc1c(OCC2CCN(C)CC2)nn(-c2ccccc2)c1NC(=O)N[C@@H]1CN(CCF)O[C@H]1c1ccc(F)c(F)c1] | 2 | 1.69 | 573 | racemate |
| I-568 | 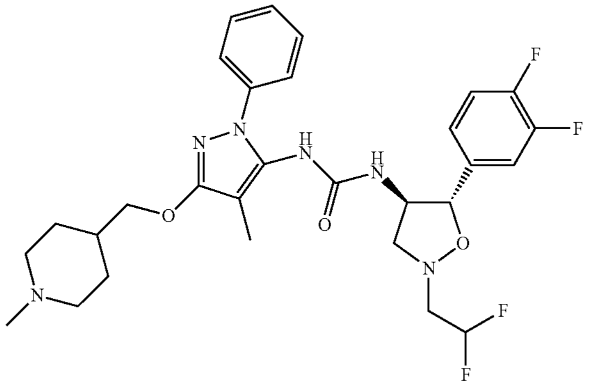 [SMILES: Cc1c(OCC2CCN(C)CC2)nn(-c2ccccc2)c1NC(=O)N[C@@H]1CN(CC(F)F)O[C@H]1c1ccc(F)c(F)c1] | 2 | 1.87 | 591 | racemate |
| I-569 | 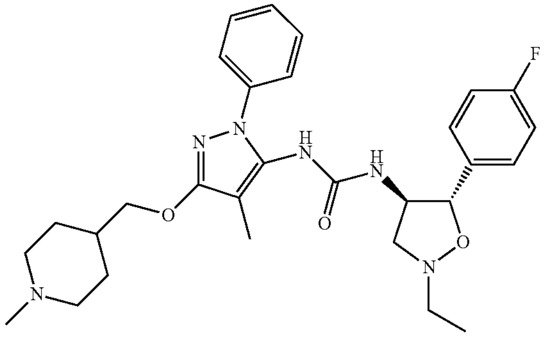 [SMILES: CCN1C[C@@H](NC(=O)Nc2c(C)c(OCC3CCN(C)CC3)nn2-c2ccccc2)[C@H](c2ccc(F)cc2)O1] | 2 | 1.57 | 537 | racemate |
| I-570 | 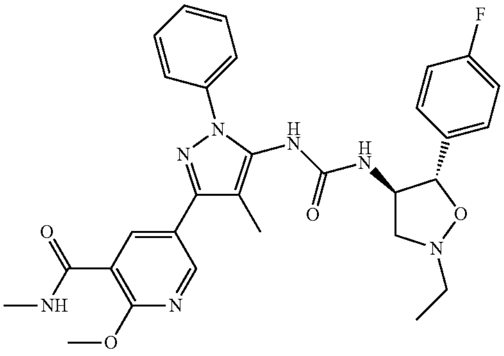 [SMILES: CCN1C[C@@H](NC(=O)Nc2c(C)c(-c3cnc(OC)c(C(=O)NC)c3)nn2-c2ccccc2)[C@H](c2ccc(F)cc2)O1] | 2 | 1.84 | 574 | racemate |

TABLE 126-continued
| No. | Structure | LCMS method No. | RT | MS (m/z) | configuration |
|---|---|---|---|---|---|
| I-571 | 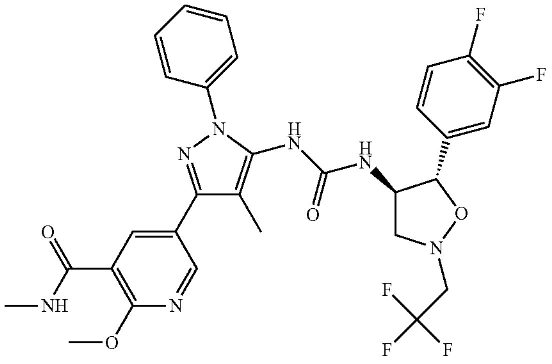 [SMILES: CNC(=O)c1cc(-c2nn(-c3ccccc3)c(NC(=O)N[C@@H]3CN(CC(F)(F)F)O[C@H]3c3ccc(F)c(F)c3)c2C)cnc1OC] | 2 | 2.24 | 646 | racemate |
TABLE 127
| No. | Structure | LCMS method No. | RT | MS (m/z) | configuration |
|---|---|---|---|---|---|
| I-572 | 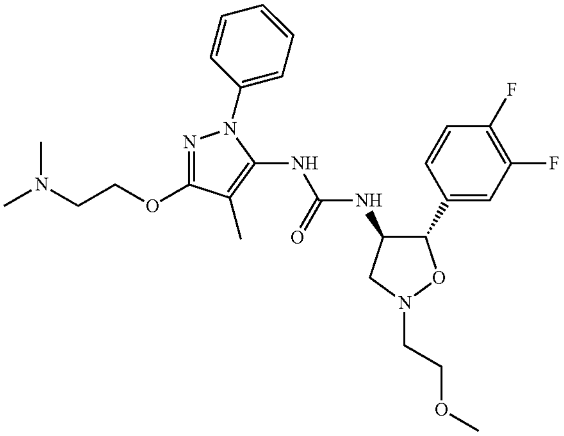 [SMILES: COCCN1C[C@@H](NC(=O)Nc2c(C)c(OCCN(C)C)nn2-c2ccccc2)[C@H](c2ccc(F)c(F)c2)O1] | 1 | 1.34 | 545.35 | |
| I-573 | 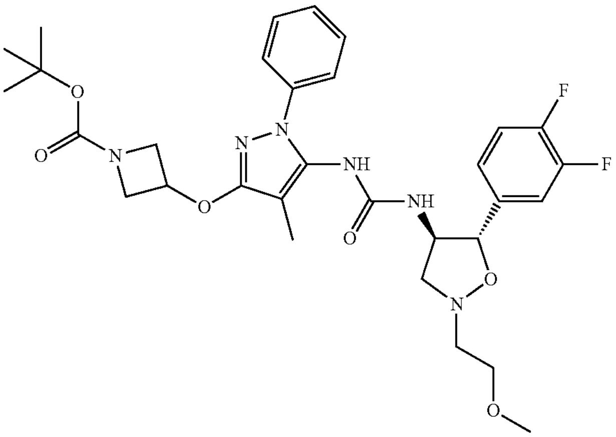 [SMILES: COCCN1C[C@@H](NC(=O)Nc2c(C)c(OC3CN(C(=O)OC(C)(C)C)C3)nn2-c2ccccc2)[C@H](c2ccc(F)c(F)c2)O1] | 1 | 2.32 | 629.35 | |

TABLE 127-continued
| No. | Structure | LCMS method No. | RT | MS (m/z) | configuration |
|---|---|---|---|---|---|
| I-574 | 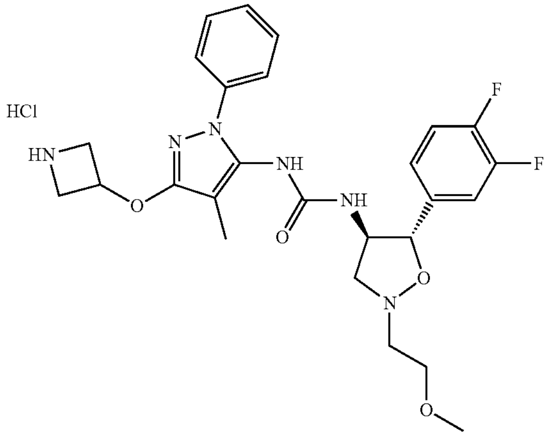 [SMILES: Cl ; COCCN1C[C@@H](NC(=O)Nc2c(C)c(OC3CNC3)nn2-c2ccccc2)[C@H](c2ccc(F)c(F)c2)O1] | 1 | 1.31 | 529.3 | |
| I-575 | 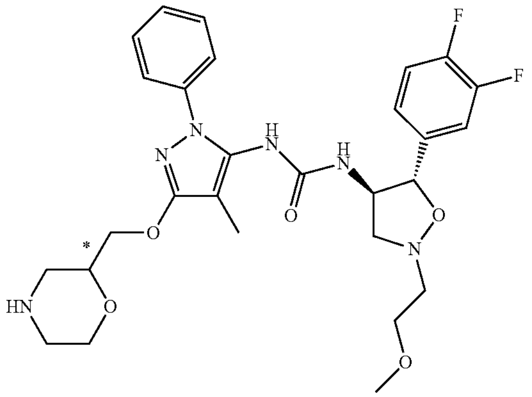 [SMILES: COCCN1C[C@@H](NC(=O)Nc2c(C)c(OCC3CNCCO3)nn2-c2ccccc2)[C@H](c2ccc(F)c(F)c2)O1] | 2 | 1.54 | 573 | single isomer, configuration of assymmetric carbon with * is unknown |
TABLE 128
| No. | Structure | LCMS method No. | RT | MS (m/z) | configuration |
|---|---|---|---|---|---|
| I-576 | 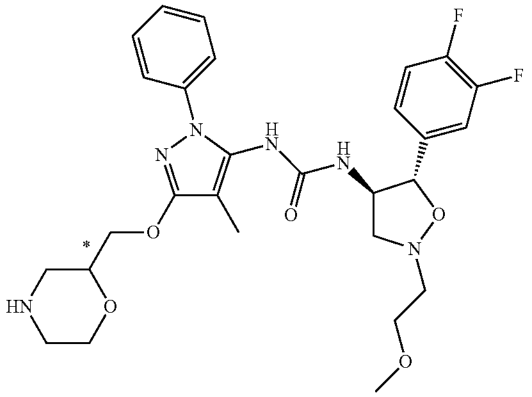 [SMILES: COCCN1C[C@@H](NC(=O)Nc2c(C)c(OCC3CNCCO3)nn2-c2ccccc2)[C@H](c2ccc(F)c(F)c2)O1] | 2 | 1.6 | 573 | single isomer, configuration of assymmetric carbon with * is unknown |

TABLE 128-continued
| No. | Structure | LCMS method No. | RT | MS (m/z) | configuration |
|---|---|---|---|---|---|
| I-577 | 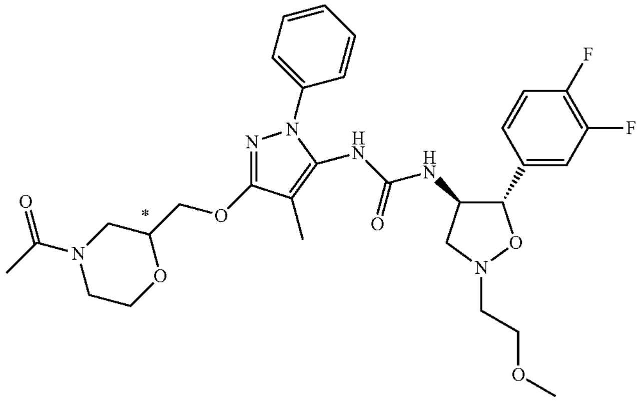 [SMILES: COCCN1C[C@@H](NC(=O)Nc2c(C)c(OCC3CN(C(C)=O)CCO3)nn2-c2ccccc2)[C@H](c2ccc(F)c(F)c2)O1] | 2 | 1.81 | 615 | single isomer, configuration of assymmetric carbon with * is unknown |
| I-578 | 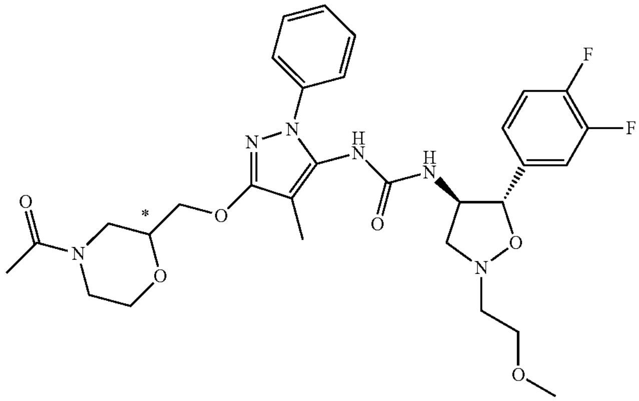 [SMILES: COCCN1C[C@@H](NC(=O)Nc2c(C)c(OCC3CN(C(C)=O)CCO3)nn2-c2ccccc2)[C@H](c2ccc(F)c(F)c2)O1] | 2 | 1.82 | 615 | single isomer, 「*」マークの不斉炭素の立体は不明 |
| I-579 | 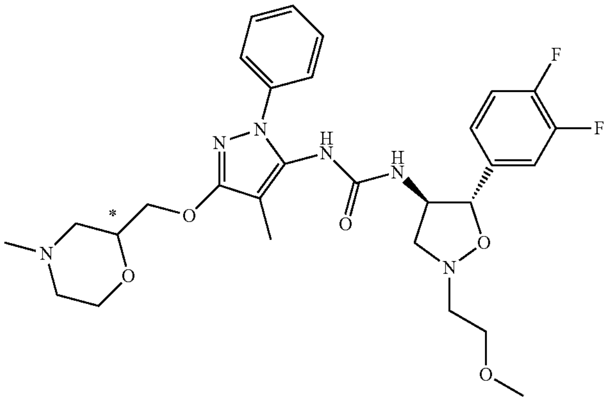 [SMILES: COCCN1C[C@@H](NC(=O)Nc2c(C)c(OCC3CN(C)CCO3)nn2-c2ccccc2)[C@H](c2ccc(F)c(F)c2)O1] | 2 | 1.66 | 587 | single isomer, configuration of assymmetric carbon with * is unknown |

TABLE 129
| No. | Structure | LCMS method No. | RT | MS (m/z) | configuration |
|---|---|---|---|---|---|
| I-580 | 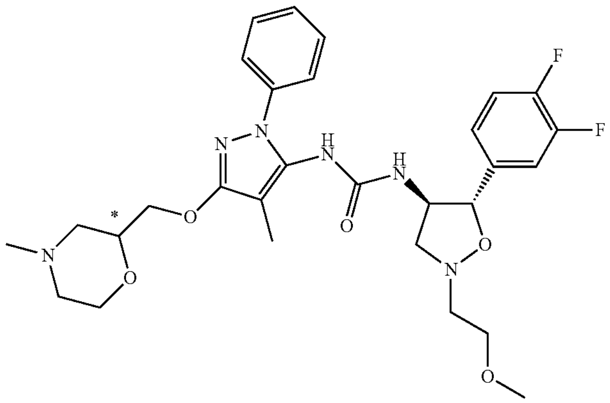 [SMILES: COCCN1C[C@@H](NC(=O)Nc2c(C)c(OCC3CN(C)CCO3)nn2-c2ccccc2)[C@H](c2ccc(F)c(F)c2)O1] | 2 | 1.65 | 587 | single isomer, configuration of assymmetric carbon with * is unknown |
TABLE 130
| No. | Structure | LCMS method No. | RT | MS (m/z) | configu-ration |
|---|---|---|---|---|---|
| I-581 | 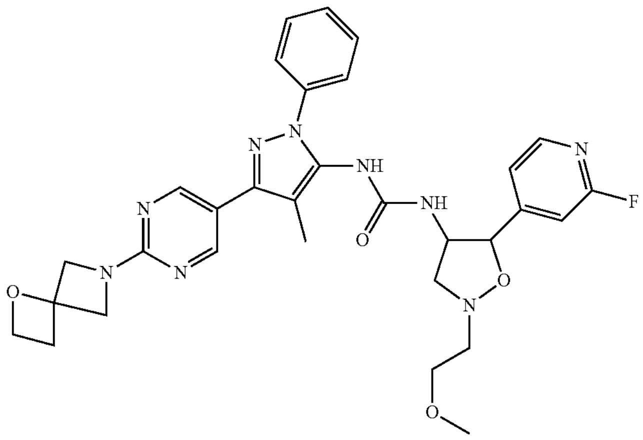 [SMILES: COCCN1CC(NC(=O)Nc2c(C)c(-c3cnc(N4CC5(CCO5)C4)nc3)nn2-c2ccccc2)C(c2ccnc(F)c2)O1] | 1 | 1.6 | 616.3 | racemate |
| I-582 | 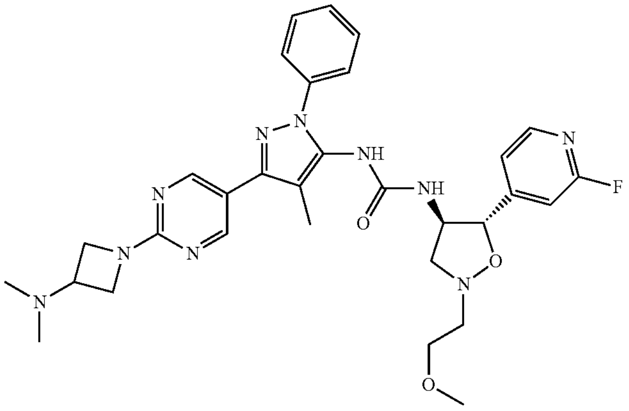 [SMILES: COCCN1C[C@@H](NC(=O)Nc2c(C)c(-c3cnc(N4CC(N(C)C)C4)nc3)nn2-c2ccccc2)[C@H](c2ccnc(F)c2)O1] | 1 | 1.56 | 617.35 | racemate |

TABLE 130-continued
| No. | Structure | LCMS method No. | RT | MS (m/z) | configu-ration |
|---|---|---|---|---|---|
| I-583 | 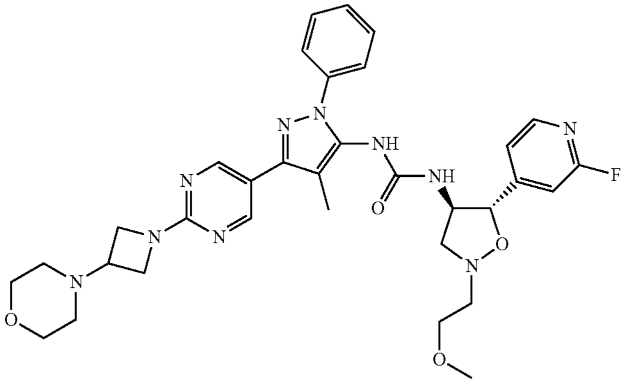 [SMILES: COCCN1C[C@@H](NC(=O)Nc2c(C)c(-c3cnc(N4CC(N5CCOCC5)C4)nc3)nn2-c2ccccc2)[C@H](c2ccnc(F)c2)O1] | 1 | 1.53 | 659.35 | racemate |
| I-584 | 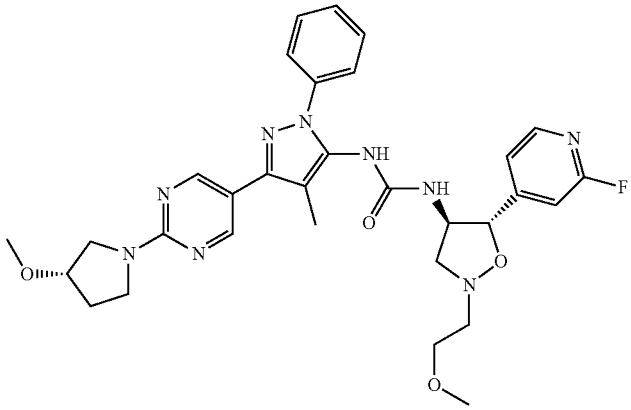 [SMILES: COCCN1C[C@@H](NC(=O)Nc2c(C)c(-c3cnc(N4CC[C@H](OC)C4)nc3)nn2-c2ccccc2)[C@H](c2ccnc(F)c2)O1] | 1 | 1.72 | 618.3 | diastereo mixture |
TABLE 131
| No. | Structure | LCMS method No. | RT | MS (m/z) | configu-ration |
|---|---|---|---|---|---|
| I-585 | 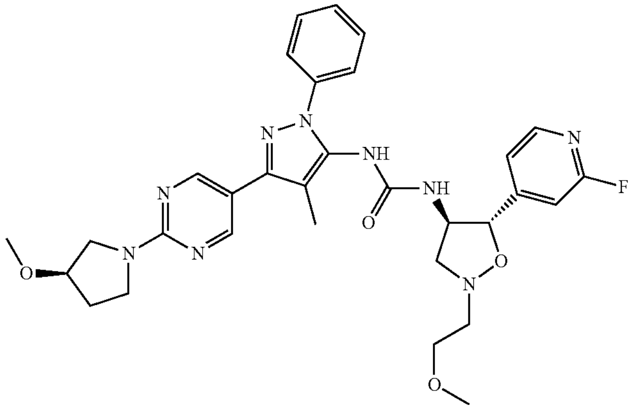 [SMILES: COCCN1C[C@@H](NC(=O)Nc2c(C)c(-c3cnc(N4CC[C@@H](OC)C4)nc3)nn2-c2ccccc2)[C@H](c2ccnc(F)c2)O1] | 1 | 1.72 | 618.3 | diastereo mixture |

TABLE 131-continued
| No. | Structure | LCMS method No. | RT | MS (m/z) | configu-ration |
|---|---|---|---|---|---|
| I-586 | 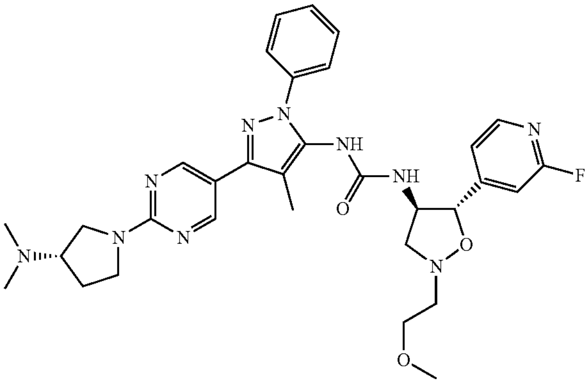 [SMILES: COCCN1C[C@@H](NC(=O)Nc2c(C)c(-c3cnc(N4CC[C@H](N(C)C)C4)nc3)nn2-c2ccccc2)[C@H](c2ccnc(F)c2)O1] | 1 | 1.64 | 631.35 | diastereo mixture |
| I-587 | 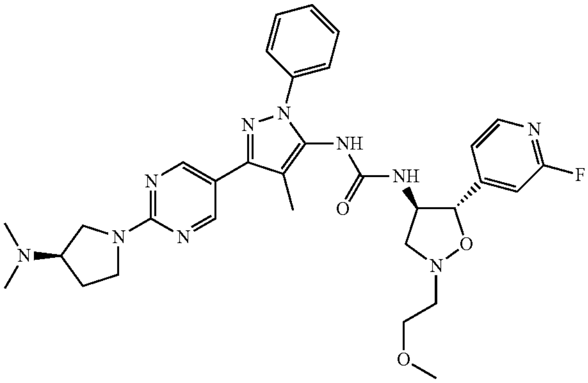 [SMILES: COCCN1C[C@@H](NC(=O)Nc2c(C)c(-c3cnc(N4CC[C@@H](N(C)C)C4)nc3)nn2-c2ccccc2)[C@H](c2ccnc(F)c2)O1] | 1 | 1.64 | 631.35 | diastereo mixture |
| I-588 | 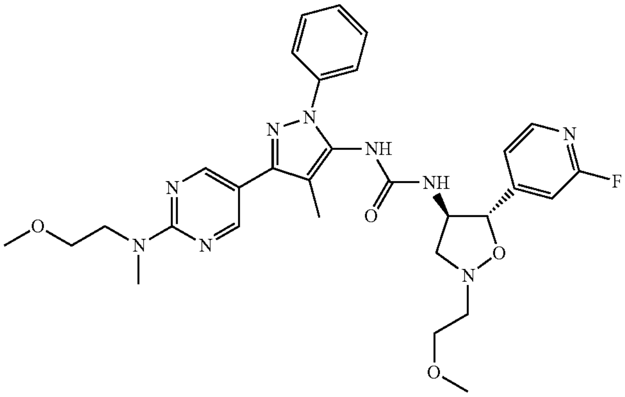 [SMILES: COCCN1C[C@@H](NC(=O)Nc2c(C)c(-c3cnc(N(C)CCOC)nc3)nn2-c2ccccc2)[C@H](c2ccnc(F)c2)O1] | 1 | 1.83 | 606.3 | racemate |

TABLE 132
| No. | Structure | LCMS method No. | RT | MS (m/z) | configu-ration |
|---|---|---|---|---|---|
| I-589 | 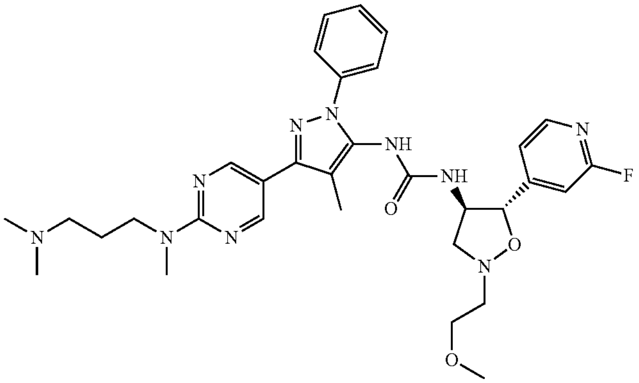 [SMILES: COCCN1C[C@@H](NC(=O)Nc2c(C)c(-c3cnc(N(C)CCCN(C)C)nc3)nn2-c2ccccc2)[C@H](c2ccnc(F)c2)O1] | 1 | 1.62 | 633.35 | racemate |
| I-590 | 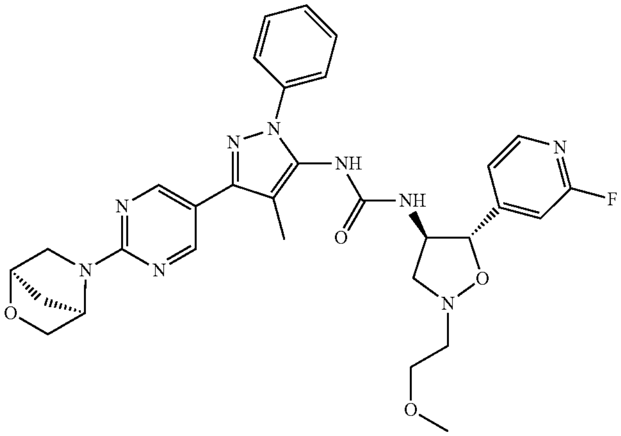 [SMILES: COCCN1C[C@@H](NC(=O)Nc2c(C)c(-c3cnc(N4C[C@H]5C[C@@H]4CO5)nc3)nn2-c2ccccc2)[C@H](c2ccnc(F)c2)O1] | 1 | 1.62 | 616.3 | diastereo mixture |
| I-591 | 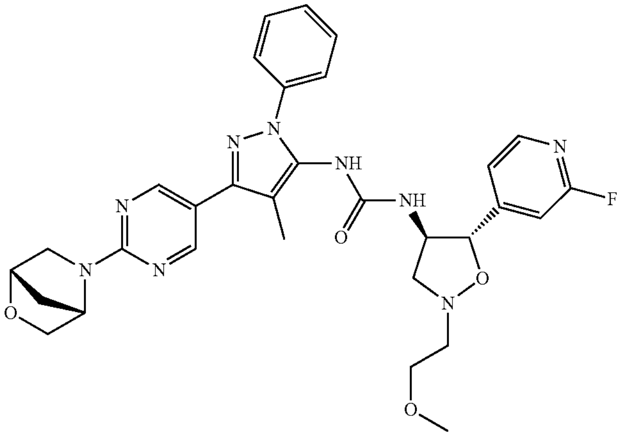 [SMILES: COCCN1C[C@@H](NC(=O)Nc2c(C)c(-c3cnc(N4C[C@@H]5C[C@H]4CO5)nc3)nn2-c2ccccc2)[C@H](c2ccnc(F)c2)O1] | 1 | 1.62 | 616.3 | diastereo mixture |

TABLE 132-continued
| No. | Structure | LCMS method No. | RT | MS (m/z) | configu-ration |
|---|---|---|---|---|---|
| I-592 | 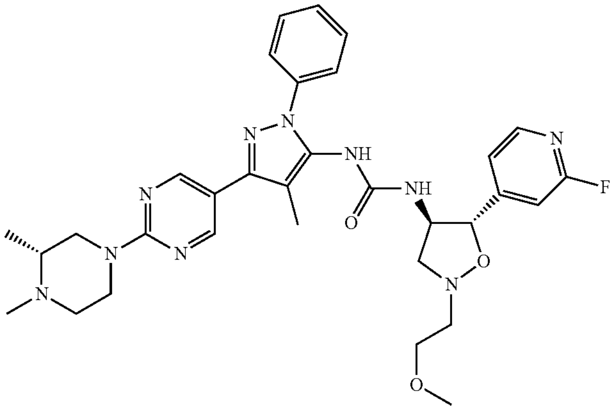 [SMILES: COCCN1C[C@@H](NC(=O)Nc2c(C)c(-c3cnc(N4CCN(C)[C@H](C)C4)nc3)nn2-c2ccccc2)[C@H](c2ccnc(F)c2)O1] | 1 | 1.78 | 631.4 | diastereo mixture |
TABLE 133
| No. | Structure | LCMS method No. | RT | MS (m/z) | configu-ration |
|---|---|---|---|---|---|
| I-593 | 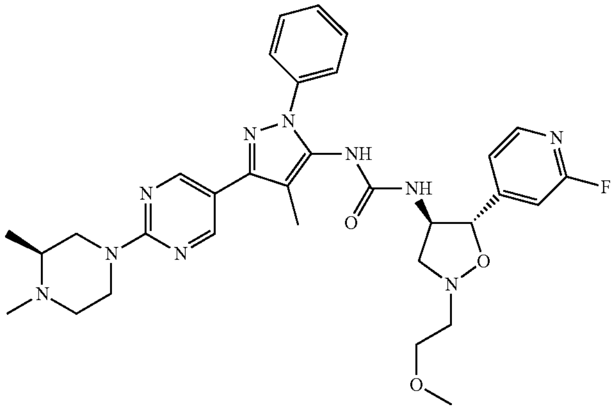 [SMILES: COCCN1C[C@@H](NC(=O)Nc2c(C)c(-c3cnc(N4CCN(C)[C@@H](C)C4)nc3)nn2-c2ccccc2)[C@H](c2ccnc(F)c2)O1] | 1 | 1.77 | 631.35 | diastereo mixture |
| I-594 | 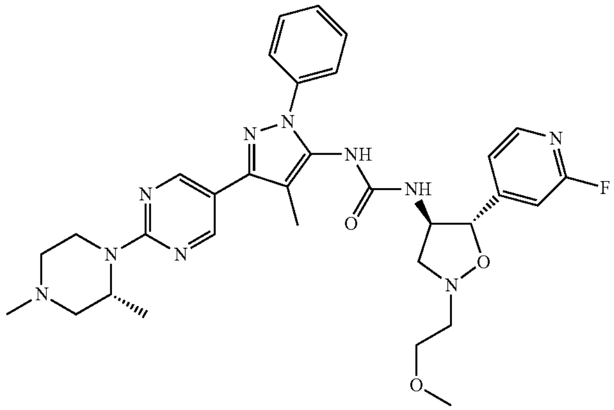 [SMILES: COCCN1C[C@@H](NC(=O)Nc2c(C)c(-c3cnc(N4CCN(C)C[C@H]4C)nc3)nn2-c2ccccc2)[C@H](c2ccnc(F)c2)O1] | 1 | 1.83 | 631.4 | diastereo mixture |

TABLE 133-continued
| No. | Structure | LCMS method No. | RT | MS (m/z) | configu-ration |
|---|---|---|---|---|---|
| I-595 | 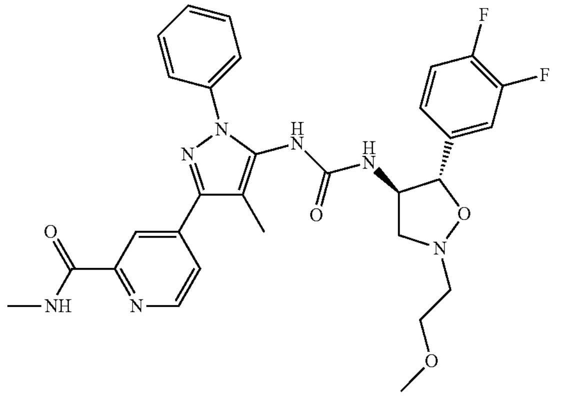 [SMILES: CNC(=O)c1cc(-c2nn(-c3ccccc3)c(NC(=O)N[C@@H]3CN(CCOC)O[C@H]3c3ccc(F)c(F)c3)c2C)ccn1] | 1 | 1.86 | 592.3 | |
| I-596 | 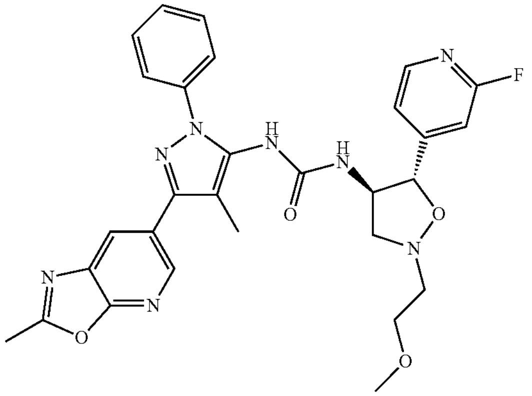 [SMILES: COCCN1C[C@@H](NC(=O)Nc2c(C)c(-c3cnc4oc(C)nc4c3)nn2-c2ccccc2)[C@H](c2ccnc(F)c2)O1] | 1 | 1.64 | 573.3 | racemate |
TABLE 134
| No. | Structure | LCMS method No. | RT | MS (m/z) | configu-ration |
|---|---|---|---|---|---|
| I-597 | 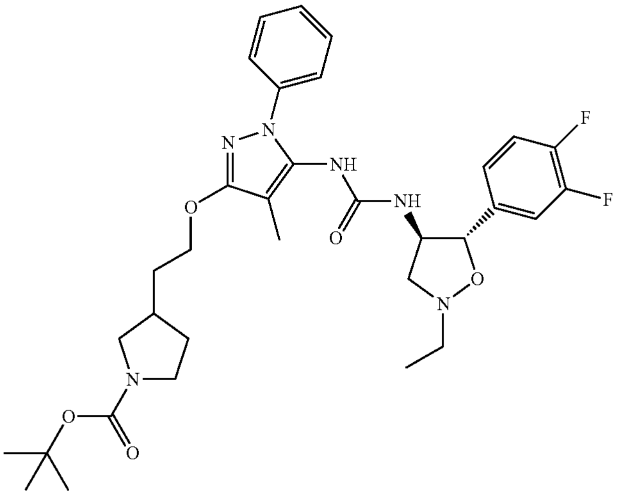 [SMILES: CCN1C[C@@H](NC(=O)Nc2c(C)c(OCCC3CCN(C(=O)OC(C)(C)C)C3)nn2-c2ccccc2)[C@H](c2ccc(F)c(F)c2)O1] | 1 | 2.48 | 641.4 | diastereo mixture |

TABLE 134-continued
| No. | Structure | LCMS method No. | RT | MS (m/z) | configu-ration |
|---|---|---|---|---|---|
| I-598 | 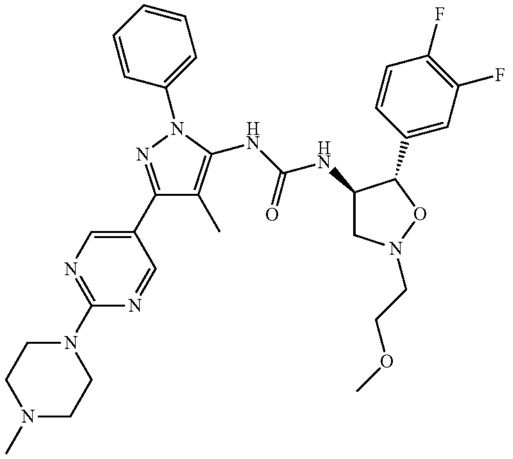 [SMILES: COCCN1C[C@@H](NC(=O)Nc2c(C)c(-c3cnc(N4CCN(C)CC4)nc3)nn2-c2ccccc2)[C@H](c2ccc(F)c(F)c2)O1] | 1 | 1.4 | 634.4 | |
| I-599 | 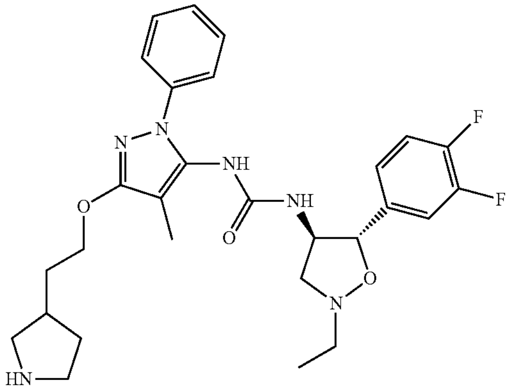 [SMILES: CCN1C[C@@H](NC(=O)Nc2c(C)c(OCCC3CCNC3)nn2-c2ccccc2)[C@H](c2ccc(F)c(F)c2)O1] | 1 | 1.4 | 541.35 | diastereo mixture |
| I-600 | 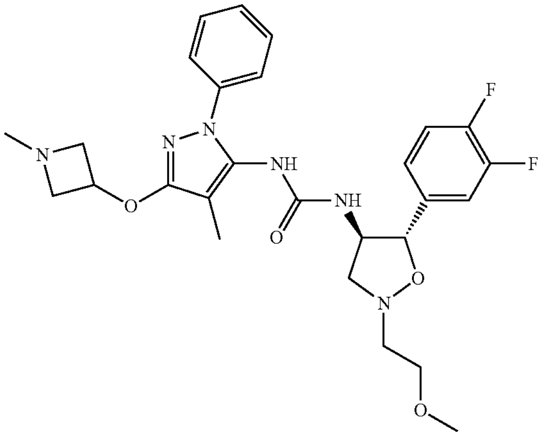 [SMILES: COCCN1C[C@@H](NC(=O)Nc2c(C)c(OC3CN(C)C3)nn2-c2ccccc2)[C@H](c2ccc(F)c(F)c2)O1] | 1 | 1.33 | 543.3 | |

TABLE 135
| No. | Structure | LCMS method No. | RT | MS (m/z) | configu-ration |
|---|---|---|---|---|---|
| I-601 | 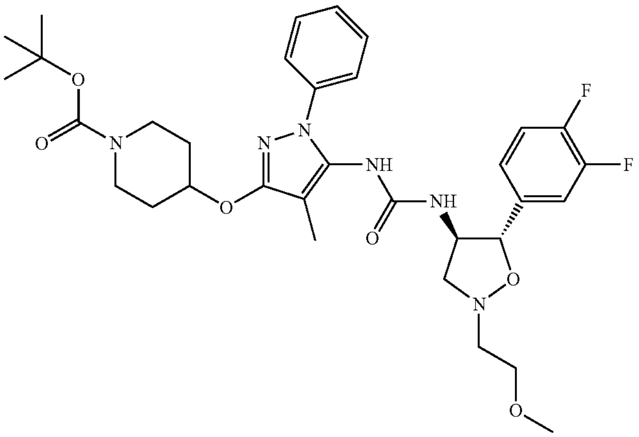 [SMILES: COCCN1C[C@@H](NC(=O)Nc2c(C)c(OC3CCN(C(=O)OC(C)(C)C)CC3)nn2-c2ccccc2)[C@H](c2ccc(F)c(F)c2)O1] | 1 | 2.42 | 657.4 | |
| I-602 | 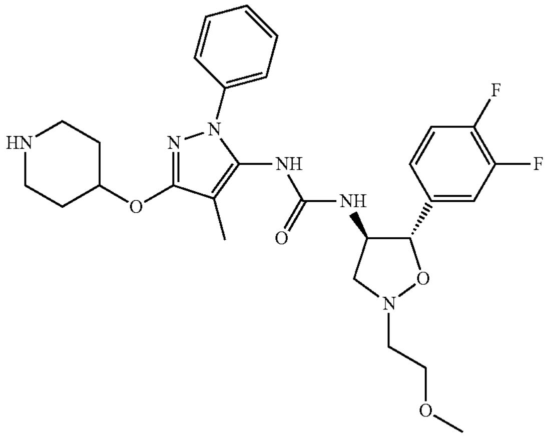 [SMILES: COCCN1C[C@@H](NC(=O)Nc2c(C)c(OC3CCNCC3)nn2-c2ccccc2)[C@H](c2ccc(F)c(F)c2)O1] | 1 | 1.34 | 557.35 | |
| I-603 | 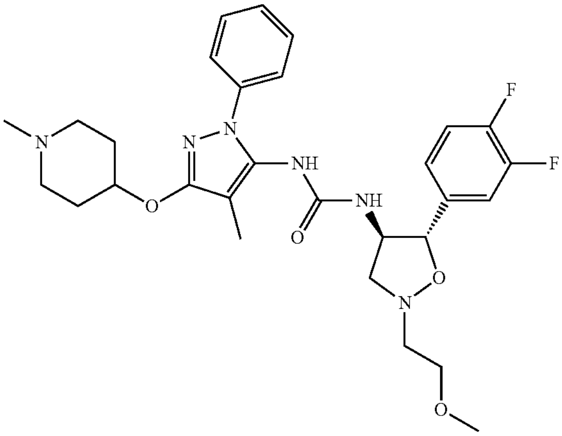 [SMILES: COCCN1C[C@@H](NC(=O)Nc2c(C)c(OC3CCN(C)CC3)nn2-c2ccccc2)[C@H](c2ccc(F)c(F)c2)O1] | 1 | 1.36 | 571.35 | |

TABLE 135-continued
| No. | Structure | LCMS method No. | RT | MS (m/z) | configu-ration |
|---|---|---|---|---|---|
| I-604 | 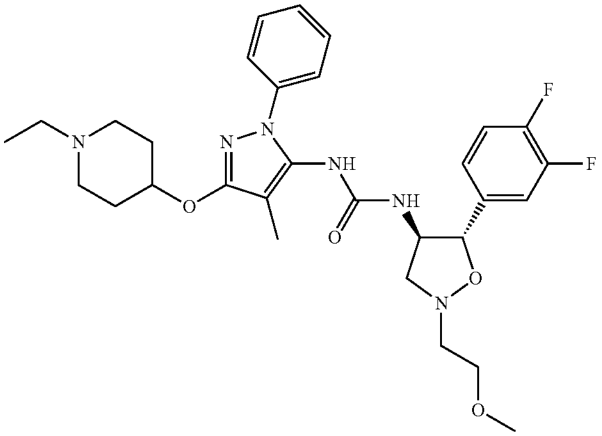 [SMILES: CCN1CCC(Oc2nn(-c3ccccc3)c(NC(=O)N[C@@H]3CN(CCOC)O[C@H]3c3ccc(F)c(F)c3)c2C)CC1] | 1 | 1.4 | 585.35 | |
TABLE 136
| No. | Structure | LCMS method No. | RT | MS (m/z) | configu-ration |
|---|---|---|---|---|---|
| I-605 | 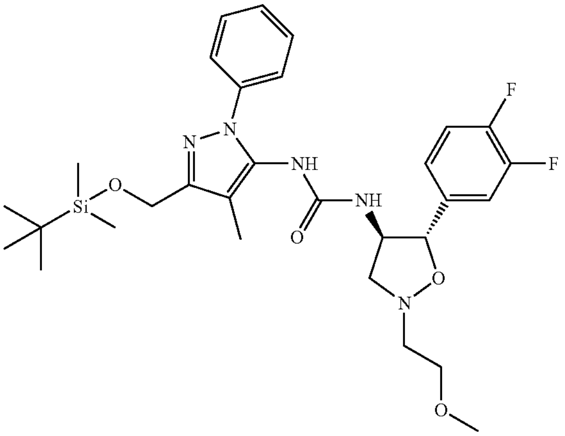 [SMILES: COCCN1C[C@@H](NC(=O)Nc2c(C)c(CO[Si](C)(C)C(C)(C)C)nn2-c2ccccc2)[C@H](c2ccc(F)c(F)c2)O1] | 1 | 2.68 | 602.35 | |
| I-606 | 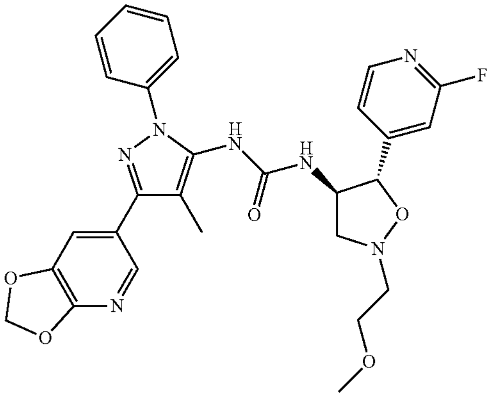 [SMILES: COCCN1C[C@@H](NC(=O)Nc2c(C)c(-c3cnc4c(c3)OCO4)nn2-c2ccccc2)[C@H](c2ccnc(F)c2)O1] | 1 | 1.64 | 562.3 | racemate |

TABLE 136-continued
| No. | Structure | LCMS method No. | RT | MS (m/z) | configu-ration |
|---|---|---|---|---|---|
| I-607 | 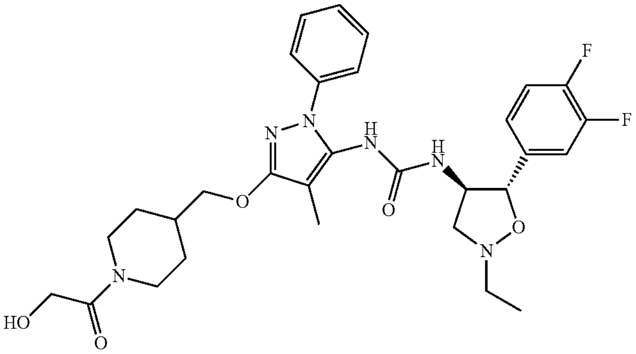 [SMILES: CCN1C[C@@H](NC(=O)Nc2c(C)c(OCC3CCN(C(=O)CO)CC3)nn2-c2ccccc2)[C@H](c2ccc(F)c(F)c2)O1] | 1 | 1.84 | 599 | racemate |
| I-608 | 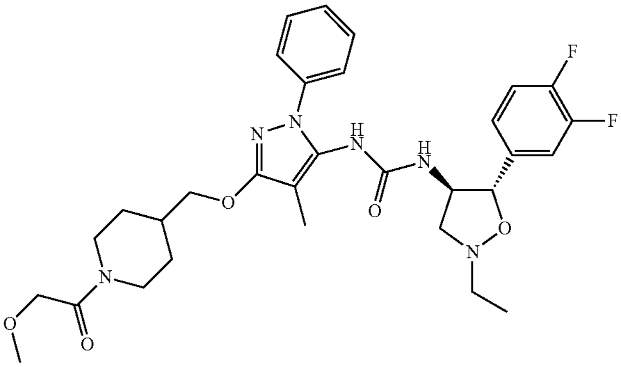 [SMILES: CCN1C[C@@H](NC(=O)Nc2c(C)c(OCC3CCN(C(=O)COC)CC3)nn2-c2ccccc2)[C@H](c2ccc(F)c(F)c2)O1] | 1 | 1.91 | 613 | racemate |
| I-609 | 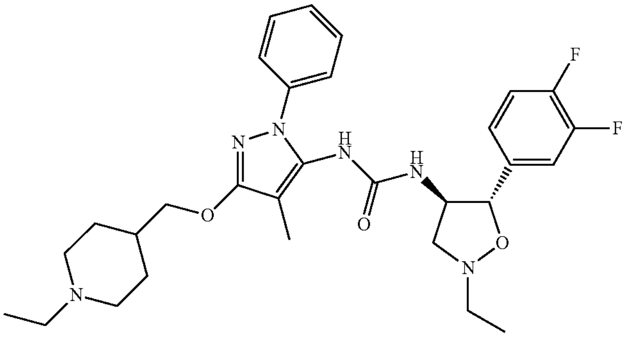 [SMILES: CCN1CCC(COc2nn(-c3ccccc3)c(NC(=O)N[C@@H]3CN(CC)O[C@H]3c3ccc(F)c(F)c3)c2C)CC1] | 1 | 1.55 | 569 | racemate |

TABLE 137
| No. | Structure | LCMS method No. | RT | MS (m/z) | configuration |
|---|---|---|---|---|---|
| I-610 | 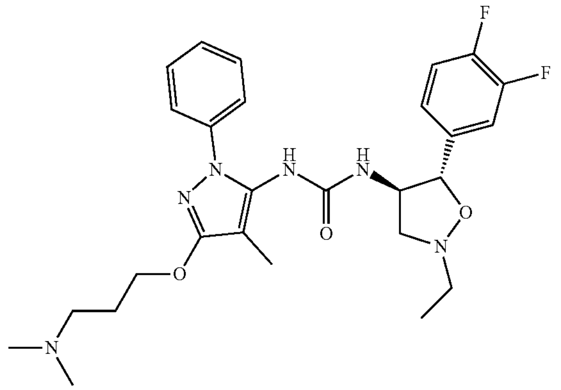 [SMILES: CCN1C[C@@H](NC(=O)Nc2c(C)c(OCCCN(C)C)nn2-c2ccccc2)[C@H](c2ccc(F)c(F)c2)O1] | 1 | 1.5 | 529.2 | racemate |
| I-611 | 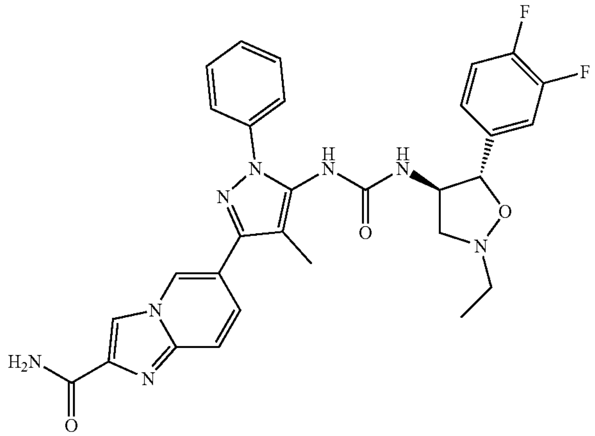 [SMILES: CCN1C[C@@H](NC(=O)Nc2c(C)c(-c3ccc4nc(C(N)=O)cn4c3)nn2-c2ccccc2)[C@H](c2ccc(F)c(F)c2)O1] | 1 | 1.72 | 587 | racemate |
| I-612 | 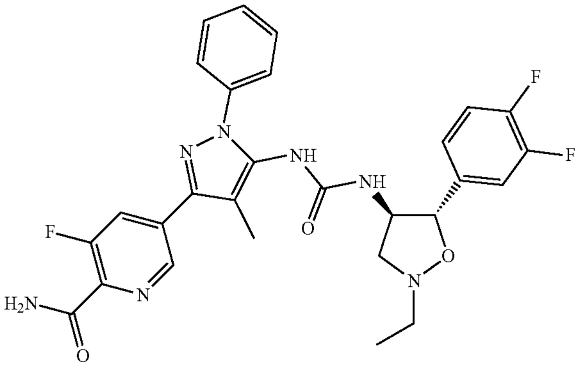 [SMILES: CCN1C[C@@H](NC(=O)Nc2c(C)c(-c3cnc(C(N)=O)c(F)c3)nn2-c2ccccc2)[C@H](c2ccc(F)c(F)c2)O1] | 2 | 1.87 | 566 | racemate |
| I-613 | 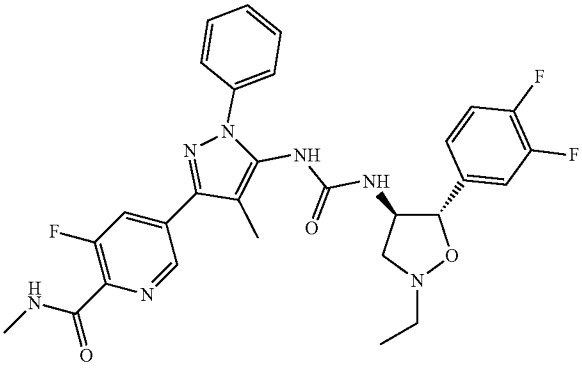 [SMILES: CCN1C[C@@H](NC(=O)Nc2c(C)c(-c3cnc(C(=O)NC)c(F)c3)nn2-c2ccccc2)[C@H](c2ccc(F)c(F)c2)O1] | 2 | 1.96 | 580 | racemate |

TABLE 137-continued
| No. | Structure | LCMS method No. | RT | MS (m/z) | configuration |
|---|---|---|---|---|---|
| I-614 | 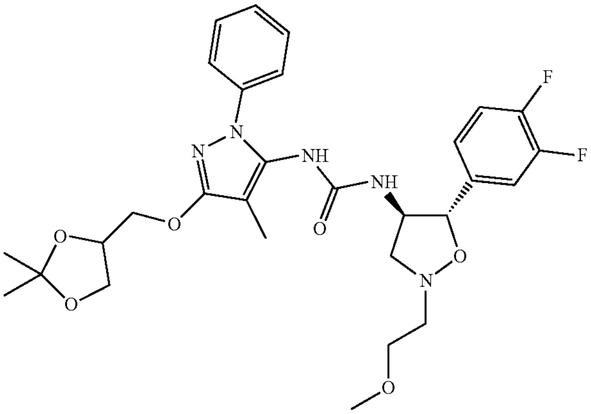 [SMILES: COCCN1C[C@@H](NC(=O)Nc2c(C)c(OCC3COC(C)(C)O3)nn2-c2ccccc2)[C@H](c2ccc(F)c(F)c2)O1] | 2 | 2.21 | 588 | |
TABLE 138
| No. | Structure | LCMS method No. | RT | MS (m/z) | configuration |
|---|---|---|---|---|---|
| I-615 | 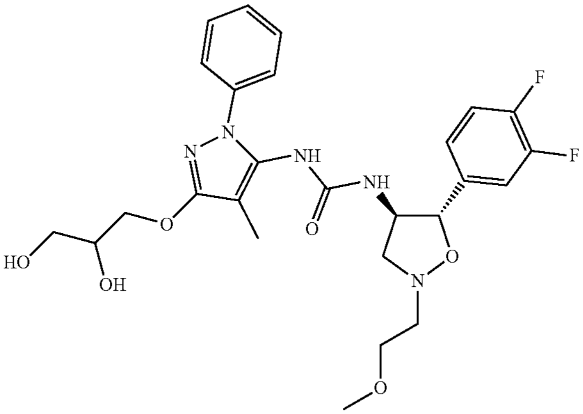 [SMILES: COCCN1C[C@@H](NC(=O)Nc2c(C)c(OCC(O)CO)nn2-c2ccccc2)[C@H](c2ccc(F)c(F)c2)O1] | 2 | 1.62 | 548 | |
| I-616 | 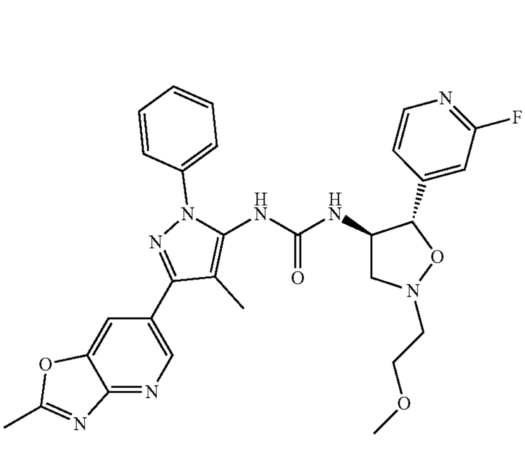 [SMILES: COCCN1C[C@@H](NC(=O)Nc2c(C)c(-c3cnc4nc(C)oc4c3)nn2-c2ccccc2)[C@H](c2ccnc(F)c2)O1] | 1 | 1.57 | 573.3 | racemate |

TABLE 138-continued
| No. | Structure | LCMS method No. | RT | MS (m/z) | configuration |
|---|---|---|---|---|---|
| I-617 | 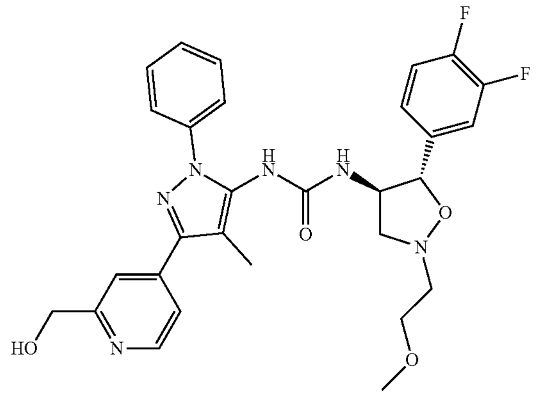 [SMILES: COCCN1C[C@@H](NC(=O)Nc2c(C)c(-c3ccnc(CO)c3)nn2-c2ccccc2)[C@H](c2ccc(F)c(F)c2)O1] | 1 | 1.38 | 565.3 | |
| I-618 | 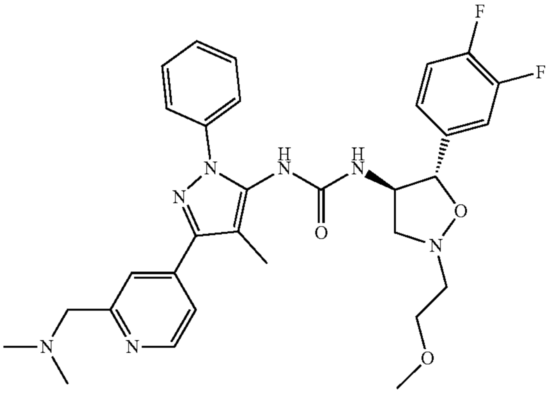 [SMILES: COCCN1C[C@@H](NC(=O)Nc2c(C)c(-c3ccnc(CN(C)C)c3)nn2-c2ccccc2)[C@H](c2ccc(F)c(F)c2)O1] | 1 | 1.38 | 592.4 | |
| I-619 | 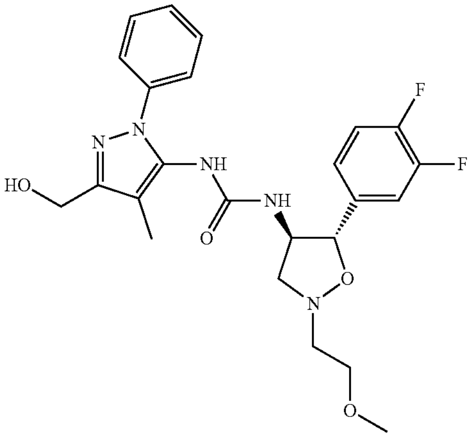 [SMILES: COCCN1C[C@@H](NC(=O)Nc2c(C)c(CO)nn2-c2ccccc2)[C@H](c2ccc(F)c(F)c2)O1] | 1 | 1.54 | 488.3 | |

TABLE 139
| No. | Structure | LCMS method No. | RT | MS (m/z) | configuration |
|---|---|---|---|---|---|
| I-620 | 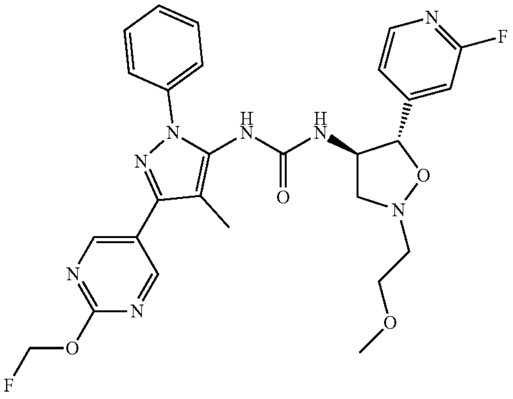 [SMILES: COCCN1C[C@@H](NC(=O)Nc2c(C)c(-c3cnc(OCF)nc3)nn2-c2ccccc2)[C@H](c2ccnc(F)c2)O1] | 1 | 1.67 | 567.3 | racemate |
| I-621 | 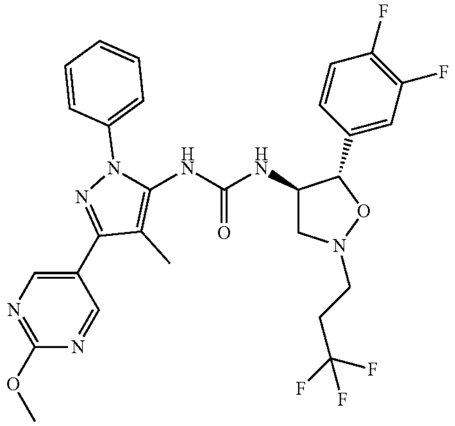 [SMILES: COc1ncc(-c2nn(-c3ccccc3)c(NC(=O)N[C@@H]3CN(CCC(F)(F)F)O[C@H]3c3ccc(F)c(F)c3)c2C)cn1] | 1 | 2.37 | 604.1 | racemate |
| I-622 | 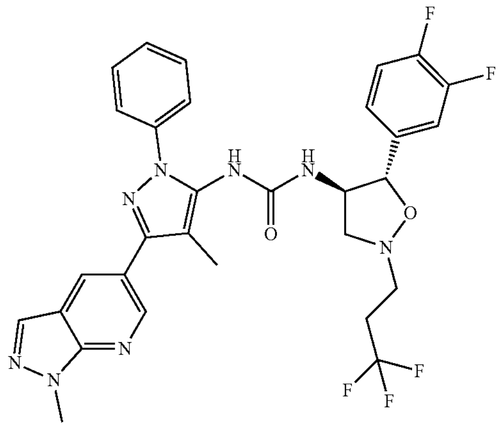 [SMILES: Cc1c(-c2cnc3c(cnn3C)c2)nn(-c2ccccc2)c1NC(=O)N[C@@H]1CN(CCC(F)(F)F)O[C@H]1c1ccc(F)c(F)c1] | 1 | 2.38 | 627.1 | racemate |

TABLE 139-continued
| No. | Structure | LCMS method No. | RT | MS (m/z) | configuration |
|---|---|---|---|---|---|
| I-623 | 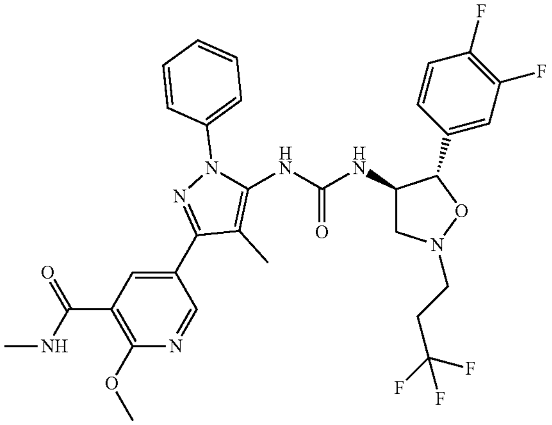 [SMILES: CNC(=O)c1cc(-c2nn(-c3ccccc3)c(NC(=O)N[C@@H]3CN(CCC(F)(F)F)O[C@H]3c3ccc(F)c(F)c3)c2C)cnc1OC] | 1 | 2.35 | 660.1 | racemate |
| I-624 | 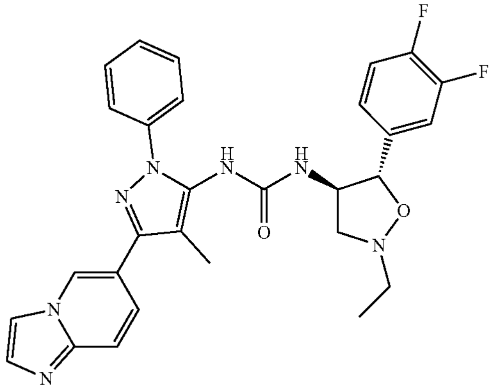 [SMILES: CCN1C[C@@H](NC(=O)Nc2c(C)c(-c3ccc4nccn4c3)nn2-c2ccccc2)[C@H](c2ccc(F)c(F)c2)O1] | 1 | 1.5 | 544 | racemate |
TABLE 140
| No. | Structure | LCMS method No. | RT | MS (m/z) | configuration |
|---|---|---|---|---|---|
| I-625 | 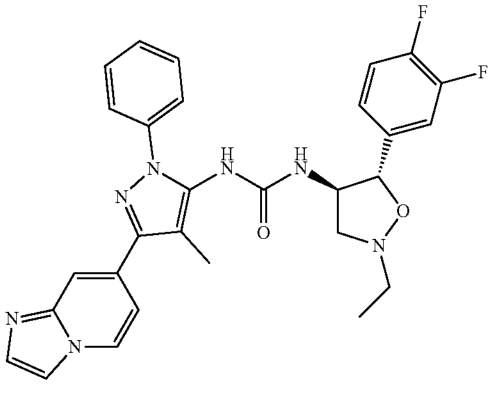 [SMILES: CCN1C[C@@H](NC(=O)Nc2c(C)c(-c3ccn4ccnc4c3)nn2-c2ccccc2)[C@H](c2ccc(F)c(F)c2)O1] | 1 | 1.53 | 544 | racemate |

TABLE 140-continued
| No. | Structure | LCMS method No. | RT | MS (m/z) | configuration |
| --- | --- | --- | --- | --- | --- |
| I-626 | 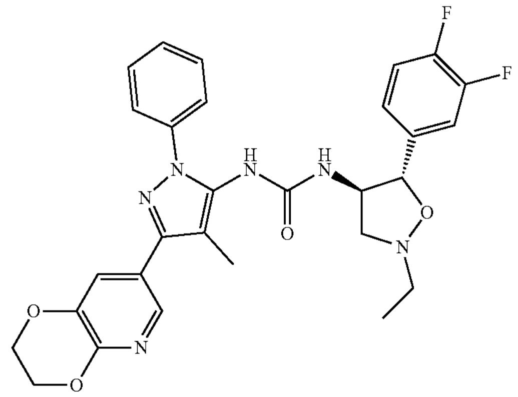 [SMILES: CCN1C[C@@H](NC(=O)Nc2c(C)c(-c3cnc4c(c3)OCCO4)nn2-c2ccccc2)[C@H](c2ccc(F)c(F)c2)O1] | 1 | 1.93 | 563 | racemate |
| I-627 | 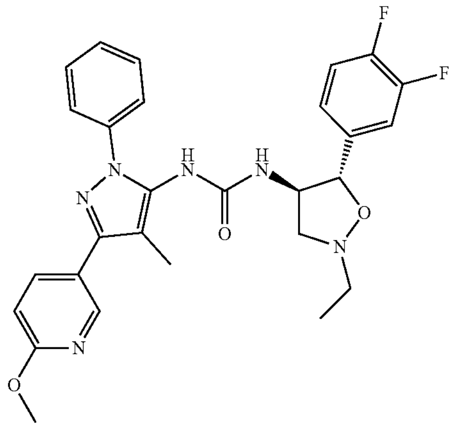 [SMILES: CCN1C[C@@H](NC(=O)Nc2c(C)c(-c3ccc(OC)nc3)nn2-c2ccccc2)[C@H](c2ccc(F)c(F)c2)O1] | 1 | 2.13 | 535 | racemate |
| I-628 | 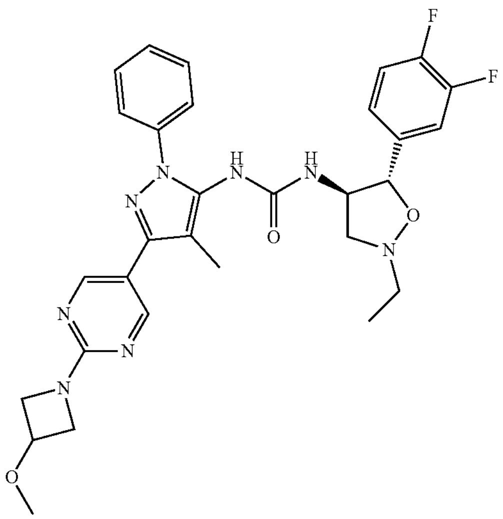 [SMILES: CCN1C[C@@H](NC(=O)Nc2c(C)c(-c3cnc(N4CC(OC)C4)nc3)nn2-c2ccccc2)[C@H](c2ccc(F)c(F)c2)O1] | 1 | 1.87 | 591 | racemate |

TABLE 140-continued
| No. | Structure | LCMS method No. | RT | MS (m/z) | configuration |
|---|---|---|---|---|---|
| I-629 | 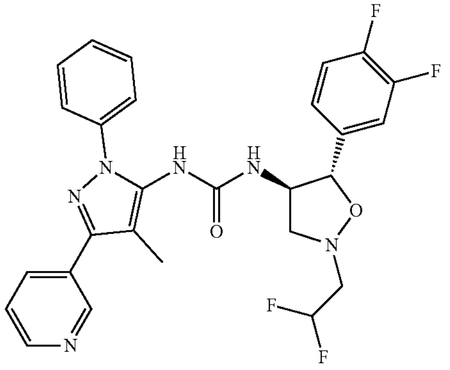 [SMILES: Cc1c(-c2cccnc2)nn(-c2ccccc2)c1NC(=O)N[C@@H]1CN(CC(F)F)O[C@H]1c1ccc(F)c(F)c1] | 1 | 1.75 | 541 | racemate |
TABLE 141
| No. | Structure | LCMS method No. | RT | MS (m/z) | configuration |
|---|---|---|---|---|---|
| I-630 | 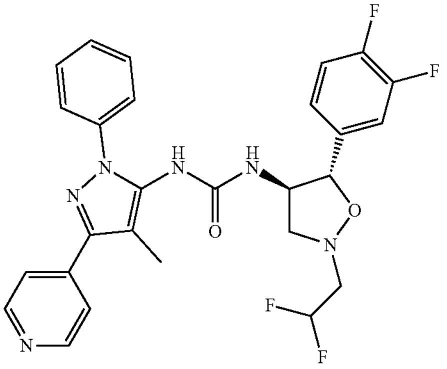 [SMILES: Cc1c(-c2ccncc2)nn(-c2ccccc2)c1NC(=O)N[C@@H]1CN(CC(F)F)O[C@H]1c1ccc(F)c(F)c1] | 1 | 1.67 | 541 | racemate |
| I-631 | 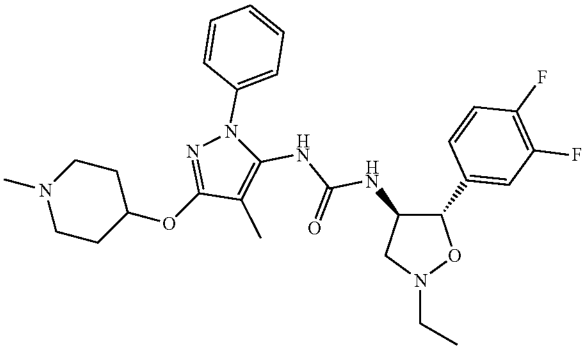 [SMILES: CCN1C[C@@H](NC(=O)Nc2c(C)c(OC3CCN(C)CC3)nn2-c2ccccc2)[C@H](c2ccc(F)c(F)c2)O1] | 3 | 1.68 | 541 | racemate |

TABLE 141-continued
| No. | Structure | LCMS method No. | RT | MS (m/z) | configuration |
|---|---|---|---|---|---|
| I-632 | 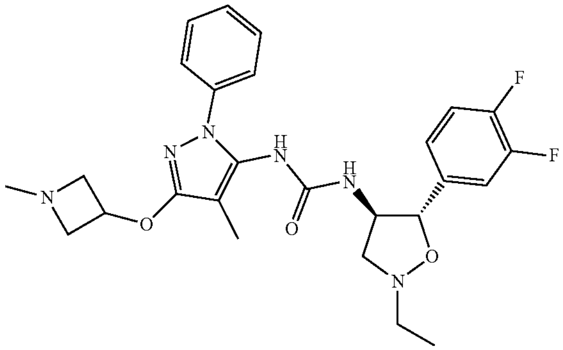 [SMILES: CCN1C[C@@H](NC(=O)Nc2c(C)c(OC3CN(C)C3)nn2-c2ccccc2)[C@H](c2ccc(F)c(F)c2)O1] | 3 | 1.87 | 513 | racemate |
| I-633 | 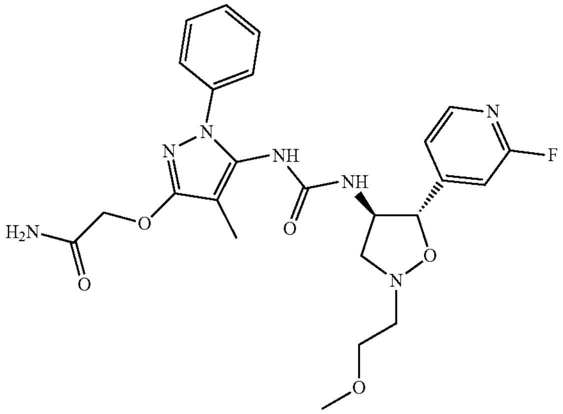 [SMILES: COCCN1C[C@@H](NC(=O)Nc2c(C)c(OCC(N)=O)nn2-c2ccccc2)[C@H](c2ccnc(F)c2)O1] | 1 | 1.4 | 514 | racemate |
| I-634 | 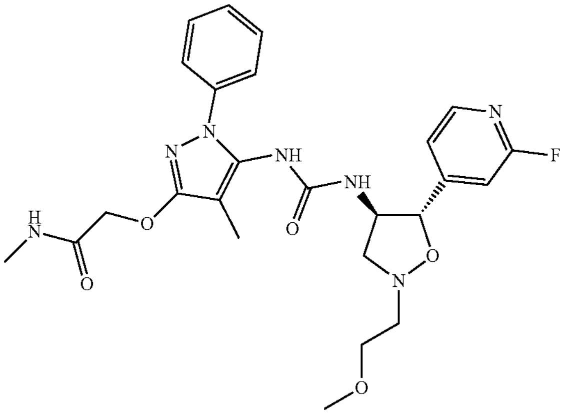 [SMILES: CNC(=O)COc1nn(-c2ccccc2)c(NC(=O)N[C@@H]2CN(CCOC)O[C@H]2c2ccnc(F)c2)c1C] | 1 | 1.46 | 528 | racemate |

TABLE 142
| No. | Structure | LCMS method No. | RT | MS (m/z) | configuration |
|---|---|---|---|---|---|
| I-635 | 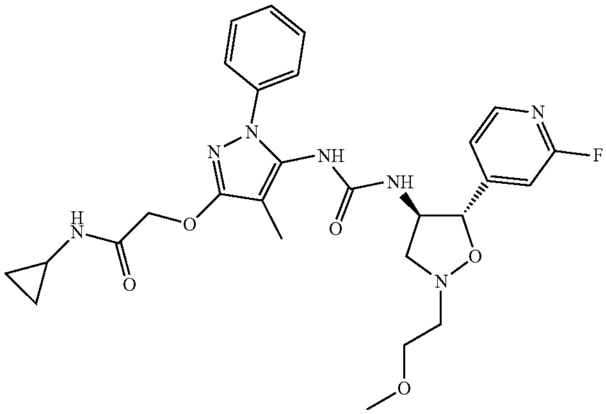 [SMILES: COCCN1C[C@@H](NC(=O)Nc2c(C)c(OCC(=O)NC3CC3)nn2-c2ccccc2)[C@H](c2ccnc(F)c2)O1] | 1 | 1.58 | 554 | racemate |
| I-636 | 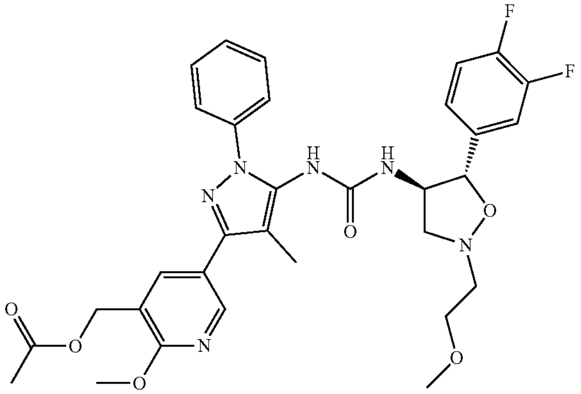 [SMILES: COCCN1C[C@@H](NC(=O)Nc2c(C)c(-c3cnc(OC)c(COC(C)=O)c3)nn2-c2ccccc2)[C@H](c2ccc(F)c(F)c2)O1] | 1 | 2.12 | 637.35 | |
| I-637 | 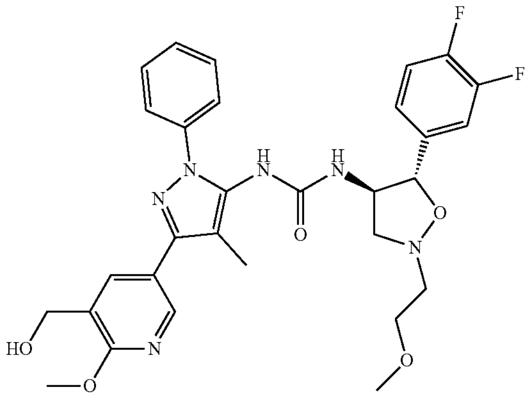 [SMILES: COCCN1C[C@@H](NC(=O)Nc2c(C)c(-c3cnc(OC)c(CO)c3)nn2-c2ccccc2)[C@H](c2ccc(F)c(F)c2)O1] | 1 | 1.81 | 595.35 | |

TABLE 142-continued
| No. | Structure | LCMS method No. | RT | MS (m/z) | configuration |
|---|---|---|---|---|---|
| I-638 | 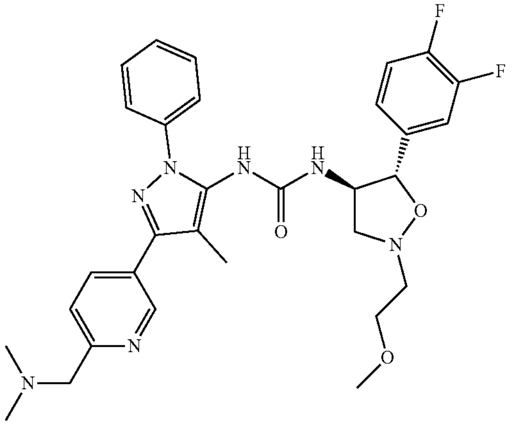 [SMILES: COCCN1C[C@@H](NC(=O)Nc2c(C)c(-c3ccc(CN(C)C)nc3)nn2-c2ccccc2)[C@H](c2ccc(F)c(F)c2)O1] | 1 | 1.36 | 592.35 | |
| I-639 | 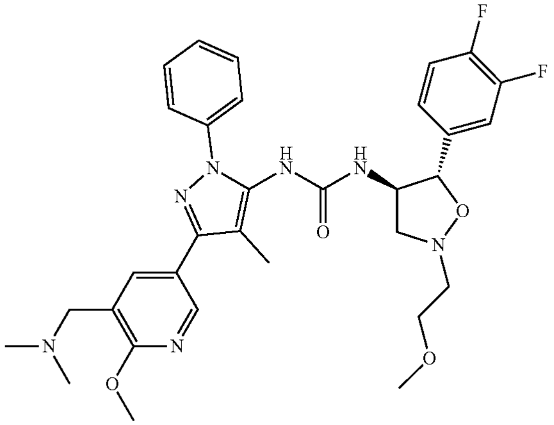 [SMILES: COCCN1C[C@@H](NC(=O)Nc2c(C)c(-c3cnc(OC)c(CN(C)C)c3)nn2-c2ccccc2)[C@H](c2ccc(F)c(F)c2)O1] | 1 | 1.39 | 622.35 | |
TABLE 143
| No. | Structure | LCMS method No. | RT | MS (m/z) | configuration |
|---|---|---|---|---|---|
| I-640 | 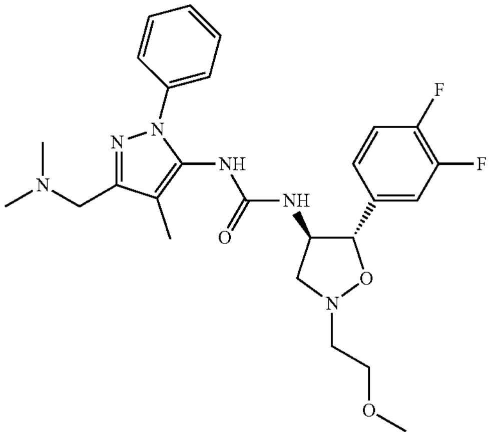 [SMILES: COCCN1C[C@@H](NC(=O)Nc2c(C)c(CN(C)C)nn2-c2ccccc2)[C@H](c2ccc(F)c(F)c2)O1] | 1 | 1.25 | 515.35 | |

TABLE 143-continued
| No. | Structure | LCMS method No. | RT | MS (m/z) | configuration |
|---|---|---|---|---|---|
| I-641 | 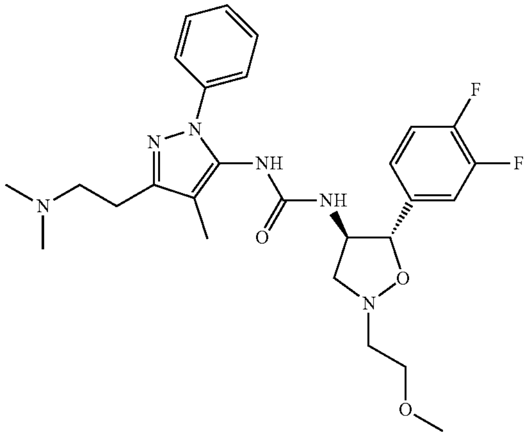 [SMILES: COCCN1C[C@@H](NC(=O)Nc2c(C)c(CCN(C)C)nn2-c2ccccc2)[C@H](c2ccc(F)c(F)c2)O1] | 1 | 1.29 | 529.35 | |
| I-642 | 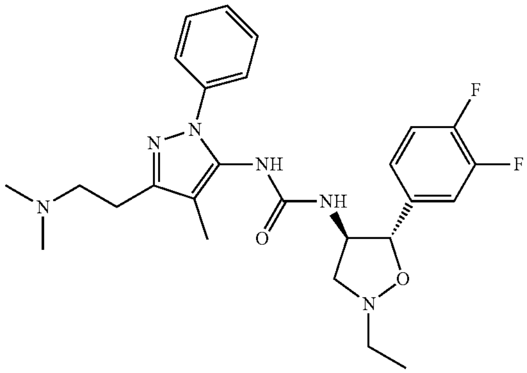 [SMILES: CCN1C[C@@H](NC(=O)Nc2c(C)c(CCN(C)C)nn2-c2ccccc2)[C@H](c2ccc(F)c(F)c2)O1] | 1 | 1.29 | 499.35 | racemate |
| I-643 | 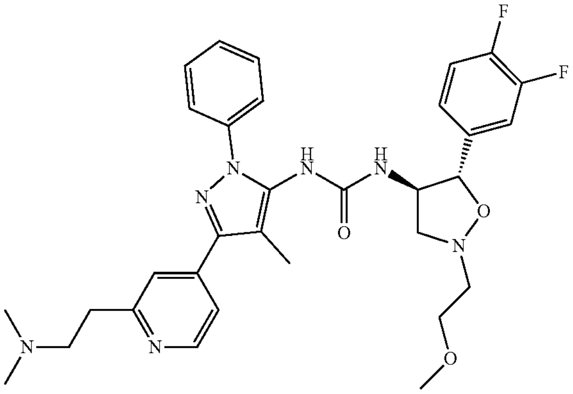 [SMILES: COCCN1C[C@@H](NC(=O)Nc2c(C)c(-c3ccnc(CCN(C)C)c3)nn2-c2ccccc2)[C@H](c2ccc(F)c(F)c2)O1] | 1 | 1.38 | 606.35 | |

TABLE 143-continued
| No. | Structure | LCMS method No. | RT | MS (m/z) | configuration |
|---|---|---|---|---|---|
| I-644 | 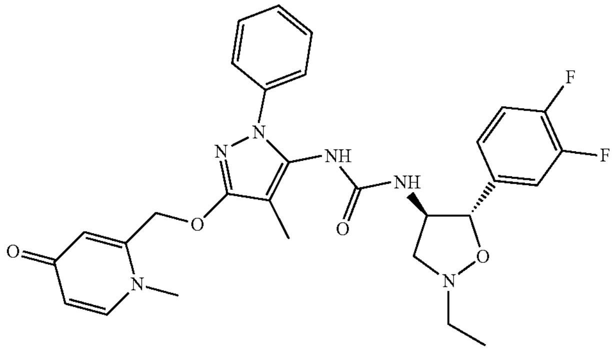 [SMILES: CCN1C[C@@H](NC(=O)Nc2c(C)c(OCc3cc(=O)ccn3C)nn2-c2ccccc2)[C@H](c2ccc(F)c(F)c2)O1] | 1 | 1.59 | 565 | racemate |
TABLE 144
| No. | Structure | LCMS method No. | RT | MS (m/z) | configuration |
|---|---|---|---|---|---|
| I-645 | 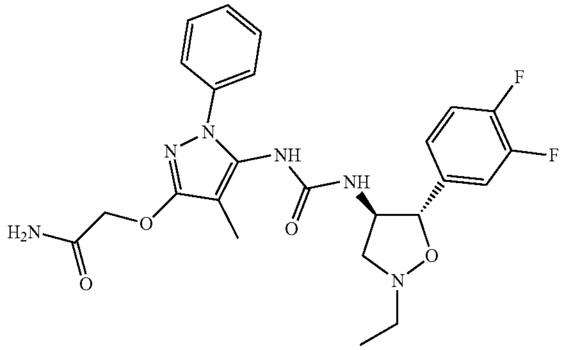 [SMILES: CCN1C[C@@H](NC(=O)Nc2c(C)c(OCC(N)=O)nn2-c2ccccc2)[C@H](c2ccc(F)c(F)c2)O1] | 1 | 1.65 | 501 | racemate |
| I-646 | 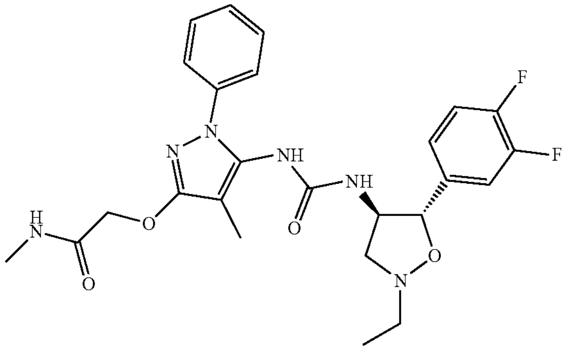 [SMILES: CCN1C[C@@H](NC(=O)Nc2c(C)c(OCC(=O)NC)nn2-c2ccccc2)[C@H](c2ccc(F)c(F)c2)O1] | 1 | 1.72 | 515 | racemate |

TABLE 144-continued
| No. | Structure | LCMS method No. | RT | MS (m/z) | configuration |
|---|---|---|---|---|---|
| I-647 | 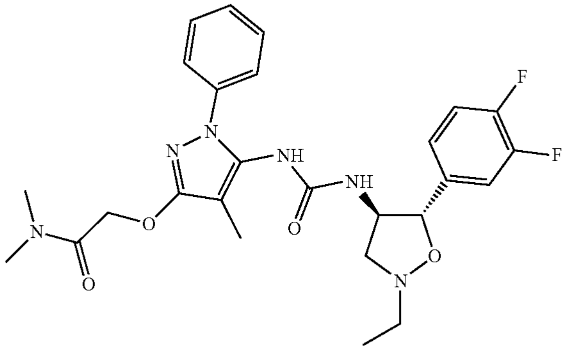 [SMILES: CCN1C[C@@H](NC(=O)Nc2c(C)c(OCC(=O)N(C)C)nn2-c2ccccc2)[C@H](c2ccc(F)c(F)c2)O1] | 1 | 1.77 | 529 | racemate |
| I-648 | 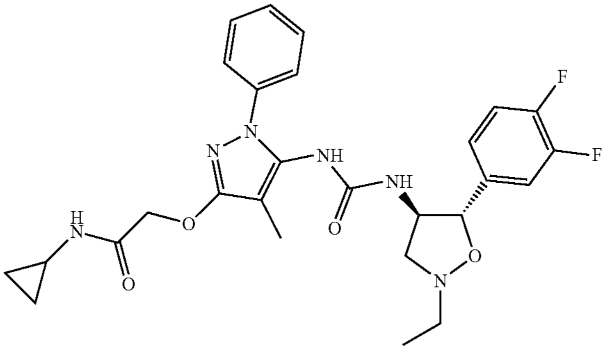 [SMILES: CCN1C[C@@H](NC(=O)Nc2c(C)c(OCC(=O)NC3CC3)nn2-c2ccccc2)[C@H](c2ccc(F)c(F)c2)O1] | 1 | 1.84 | 541 | racemate |
| I-649 | 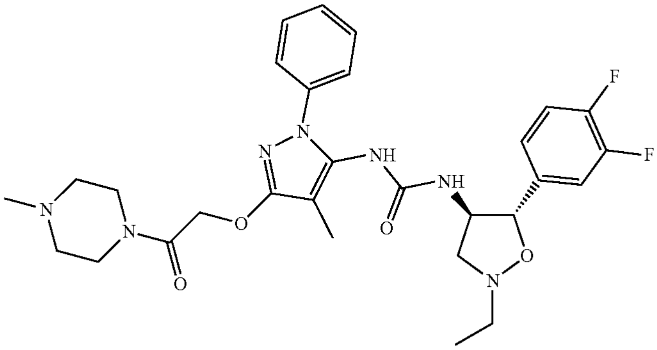 [SMILES: CCN1C[C@@H](NC(=O)Nc2c(C)c(OCC(=O)N3CCN(C)CC3)nn2-c2ccccc2)[C@H](c2ccc(F)c(F)c2)O1] | 1 | 1.4 | 584 | racemate |

TABLE 145
| No. | Structure | LCMS method No. | RT | MS (m/z) | configuration |
|---|---|---|---|---|---|
| I-650 | 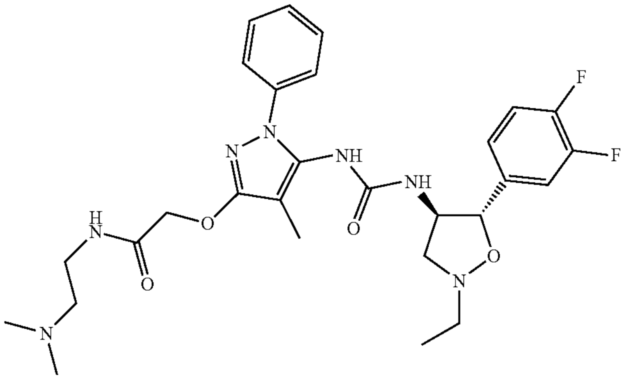 [SMILES: CCN1C[C@@H](NC(=O)Nc2c(C)c(OCC(=O)NCCN(C)C)nn2-c2ccccc2)[C@H](c2ccc(F)c(F)c2)O1] | 1 | 1.44 | 572 | racemate |
| I-651 | 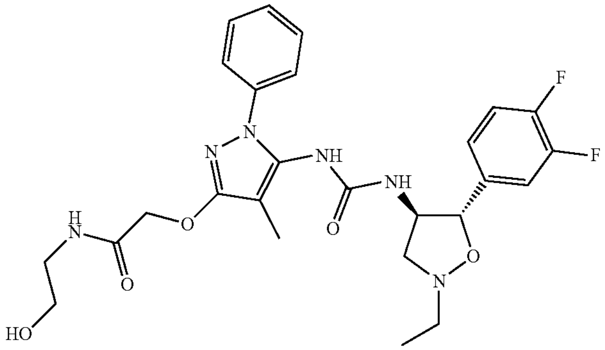 [SMILES: CCN1C[C@@H](NC(=O)Nc2c(C)c(OCC(=O)NCCO)nn2-c2ccccc2)[C@H](c2ccc(F)c(F)c2)O1] | 1 | 1.61 | 545 | racemate |
| I-652 | 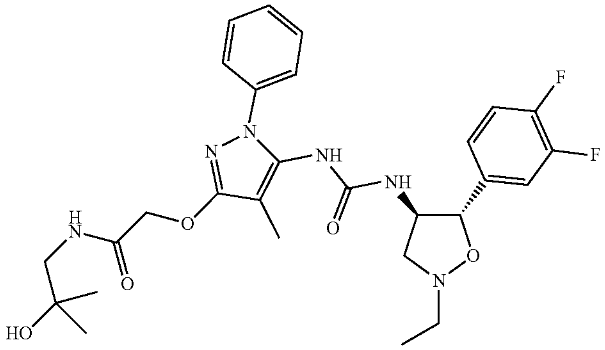 [SMILES: CCN1C[C@@H](NC(=O)Nc2c(C)c(OCC(=O)NCC(C)(C)O)nn2-c2ccccc2)[C@H](c2ccc(F)c(F)c2)O1] | 1 | 1.72 | 573 | racemate |
| I-653 | 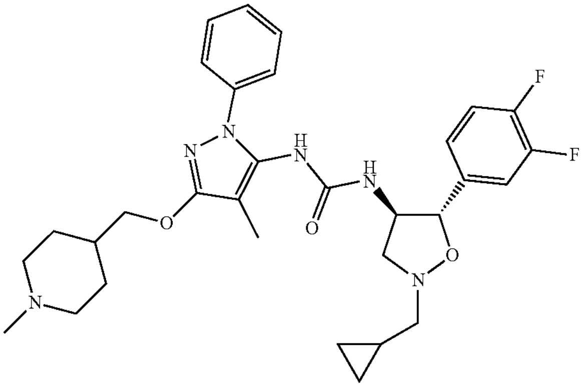 [SMILES: Cc1c(OCC2CCN(C)CC2)nn(-c2ccccc2)c1NC(=O)N[C@@H]1CN(CC2CC2)O[C@H]1c1ccc(F)c(F)c1] | 1 | 1.66 | 581 | racemate |

TABLE 145-continued
| No. | Structure | LCMS method No. | RT | MS (m/z) | configuration |
|---|---|---|---|---|---|
| I-654 | 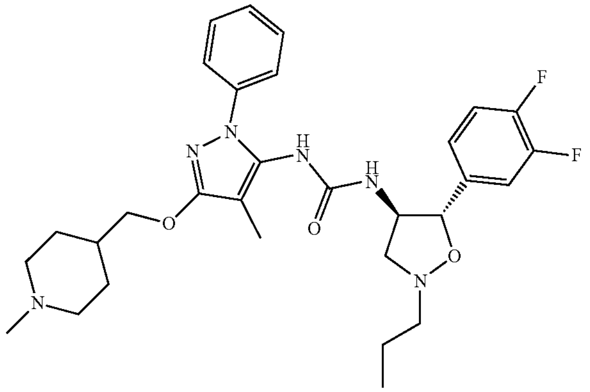 [SMILES: CCCN1C[C@@H](NC(=O)Nc2c(C)c(OCC3CCN(C)CC3)nn2-c2ccccc2)[C@H](c2ccc(F)c(F)c2)O1] | 1 | 1.67 | 569.3 | racemate |
TABLE 146
| No. | Structure | LCMS method No. | RT | MS (m/z) | configuration |
|---|---|---|---|---|---|
| I-655 | 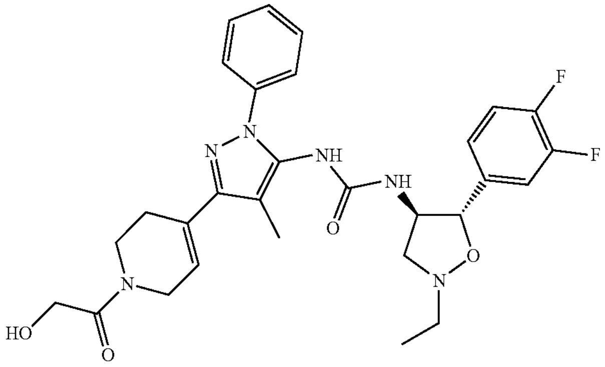 [SMILES: CCN1C[C@@H](NC(=O)Nc2c(C)c(C3=CCN(C(=O)CO)CC3)nn2-c2ccccc2)[C@H](c2ccc(F)c(F)c2)O1] | 1 | 1.75 | 567.2 | racemate |
| I-656 | 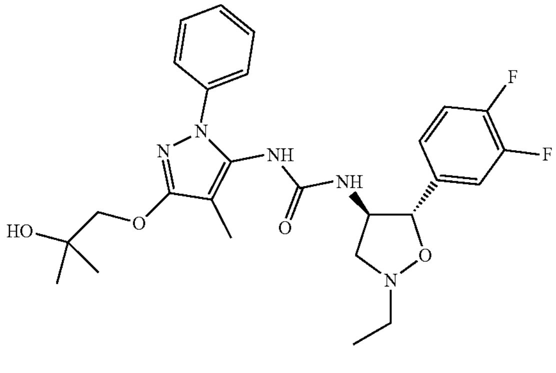 [SMILES: CCN1C[C@@H](NC(=O)Nc2c(C)c(OCC(C)(C)O)nn2-c2ccccc2)[C@H](c2ccc(F)c(F)c2)O1] | 1 | 1.92 | 516.1 | racemate |

TABLE 146-continued
| No. | Structure | LCMS method No. | RT | MS (m/z) | configuration |
|---|---|---|---|---|---|
| I-657 | 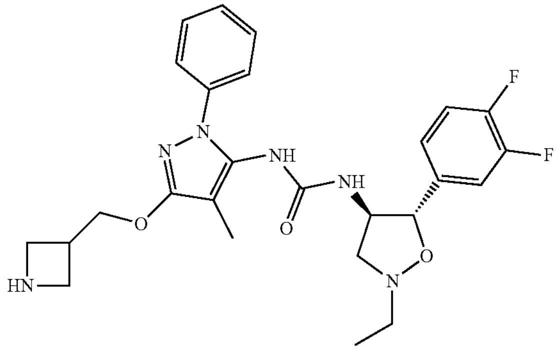 [SMILES: CCN1C[C@@H](NC(=O)Nc2c(C)c(OCC3CNC3)nn2-c2ccccc2)[C@H](c2ccc(F)c(F)c2)O1] | 3 | 1.7 | 513 | racemate |
| I-658 | 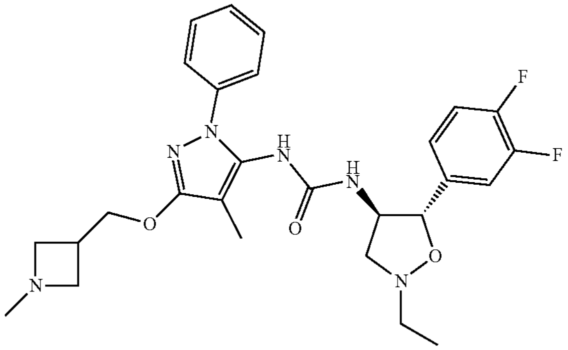 [SMILES: CCN1C[C@@H](NC(=O)Nc2c(C)c(OCC3CN(C)C3)nn2-c2ccccc2)[C@H](c2ccc(F)c(F)c2)O1] | 3 | 1.83 | 527 | racemate |
| I-659 | 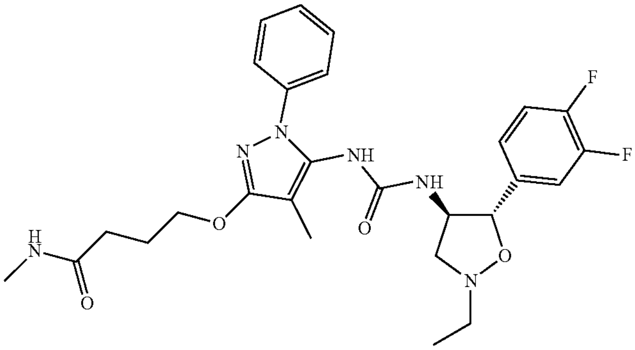 [SMILES: CCN1C[C@@H](NC(=O)Nc2c(C)c(OCCCC(=O)NC)nn2-c2ccccc2)[C@H](c2ccc(F)c(F)c2)O1] | 2 | 1.77 | 543 | racemate |

TABLE 147
| No. | Structure | LCMS method No. | RT | MS (m/z) | configuration |
|---|---|---|---|---|---|
| I-660 | 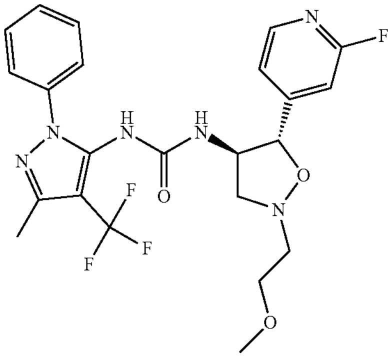 [SMILES: COCCN1C[C@@H](NC(=O)Nc2c(C(F)(F)F)c(C)nn2-c2ccccc2)[C@H](c2ccnc(F)c2)O1] | 1 | 1.79 | 509.25 | racemate |
| I-661 | 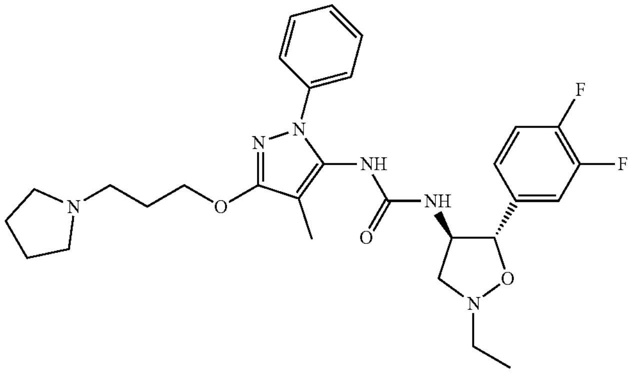 [SMILES: CCN1C[C@@H](NC(=O)Nc2c(C)c(OCCCN3CCCC3)nn2-c2ccccc2)[C@H](c2ccc(F)c(F)c2)O1] | 1 | 1.43 | 555.3 | racemate |
| I-662 | 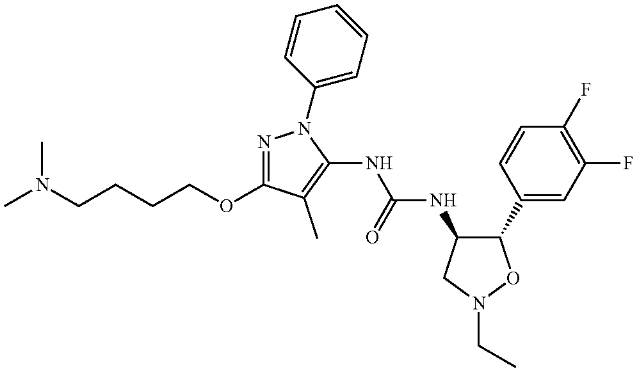 [SMILES: CCN1C[C@@H](NC(=O)Nc2c(C)c(OCCCCN(C)C)nn2-c2ccccc2)[C@H](c2ccc(F)c(F)c2)O1] | 1 | 1.4 | 543.3 | racemate |
| I-663 | 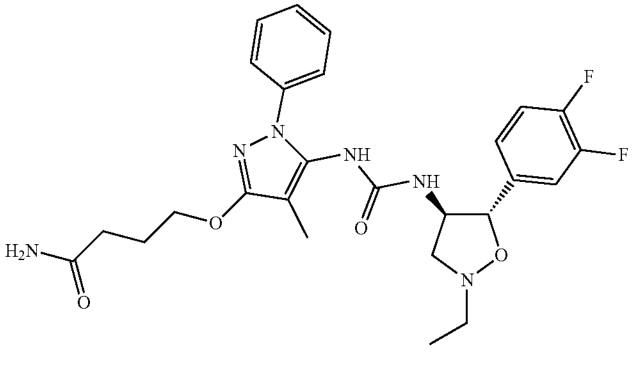 [SMILES: CCN1C[C@@H](NC(=O)Nc2c(C)c(OCCCC(N)=O)nn2-c2ccccc2)[C@H](c2ccc(F)c(F)c2)O1] | 1 | 1.69 | 529.1 | racemate |

TABLE 147-continued
| No. | Structure | LCMS method No. | RT | MS (m/z) | configuration |
|---|---|---|---|---|---|
| I-664 | 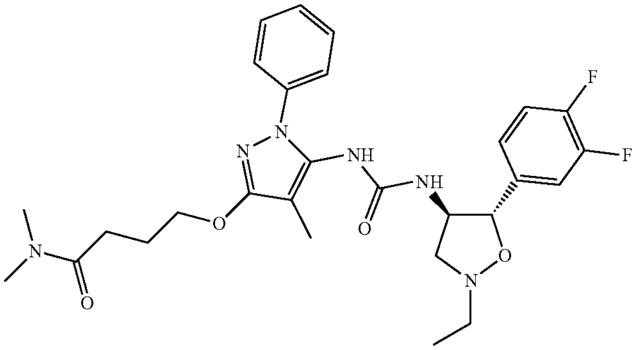 [SMILES: CCN1C[C@@H](NC(=O)Nc2c(C)c(OCCCC(=O)N(C)C)nn2-c2ccccc2)[C@H](c2ccc(F)c(F)c2)O1] | 1 | 1.86 | 557.2 | racemate |
20
TABLE 148
| No. | Structure | LCMS method No. | RT | MS (m/z) | configuration |
|---|---|---|---|---|---|
| I-665 | 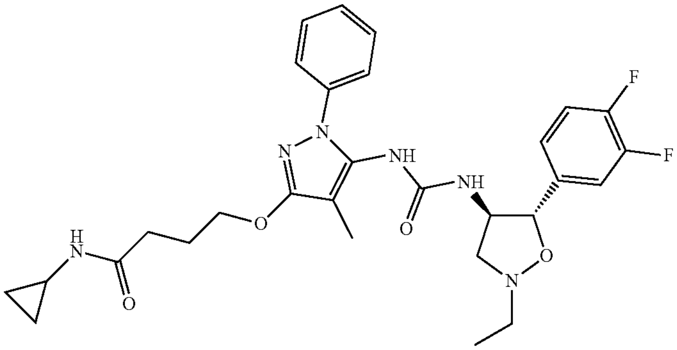 [SMILES: CCN1C[C@@H](NC(=O)Nc2c(C)c(OCCCC(=O)NC3CC3)nn2-c2ccccc2)[C@H](c2ccc(F)c(F)c2)O1] | 1 | 1.86 | 569.2 | racemate |
| I-666 | 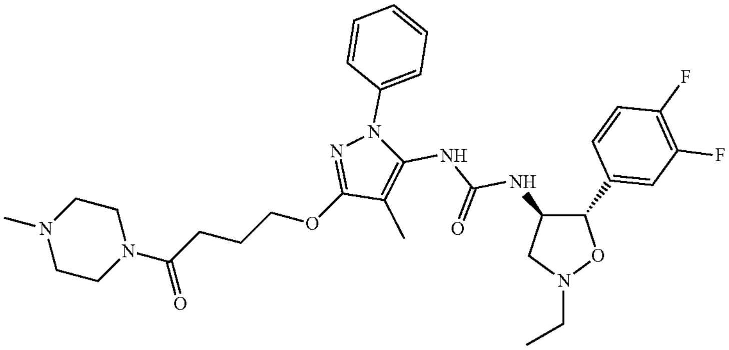 [SMILES: CCN1C[C@@H](NC(=O)Nc2c(C)c(OCCCC(=O)N3CCN(C)CC3)nn2-c2ccccc2)[C@H](c2ccc(F)c(F)c2)O1] | 1 | 1.47 | 612.3 | racemate |

TABLE 148-continued
| No. | Structure | LCMS method No. | RT | MS (m/z) | configuration |
|---|---|---|---|---|---|
| I-667 | 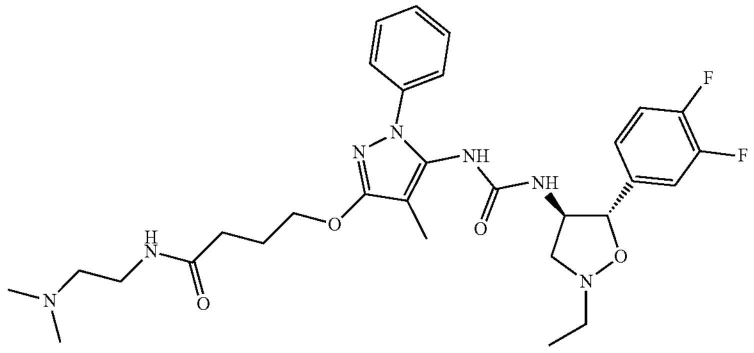 [SMILES: CCN1C[C@@H](NC(=O)Nc2c(C)c(OCCCC(=O)NCCN(C)C)nn2-c2ccccc2)[C@H](c2ccc(F)c(F)c2)O1] | 1 | 1.46 | 600.3 | racemate |
| I-668 | 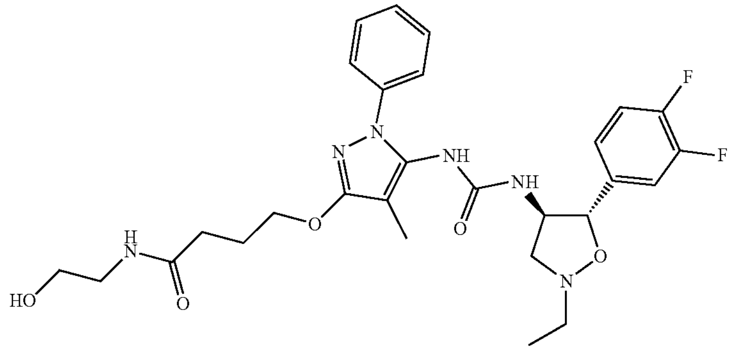 [SMILES: CCN1C[C@@H](NC(=O)Nc2c(C)c(OCCCC(=O)NCCO)nn2-c2ccccc2)[C@H](c2ccc(F)c(F)c2)O1] | 1 | 1.65 | 573.2 | racemate |
| I-669 | 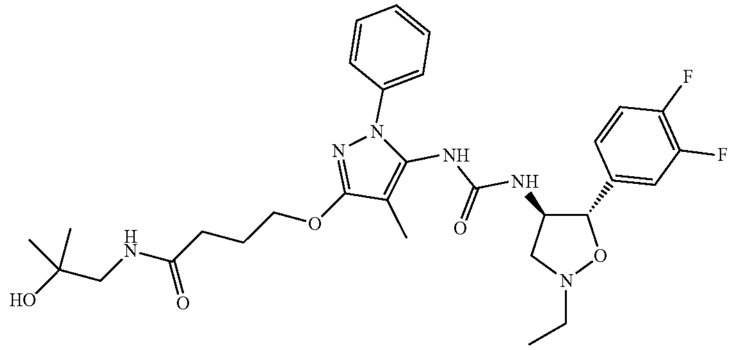 [SMILES: CCN1C[C@@H](NC(=O)Nc2c(C)c(OCCCC(=O)NCC(C)(C)O)nn2-c2ccccc2)[C@H](c2ccc(F)c(F)c2)O1] | 1 | 1.75 | 601.3 | racemate |

TABLE 149
| No. | Structure | LCMS method No. | RT | MS (m/z) | configuration |
|---|---|---|---|---|---|
| I-670 | 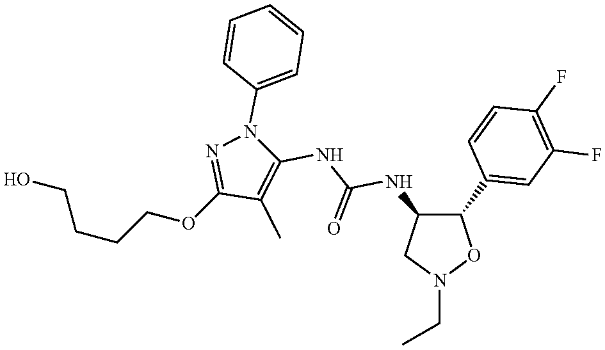 [SMILES: CCN1C[C@@H](NC(=O)Nc2c(C)c(OCCCCO)nn2-c2ccccc2)[C@H](c2ccc(F)c(F)c2)O1] | 2 | 1.88 | 516 | racemate |
| I-671 | 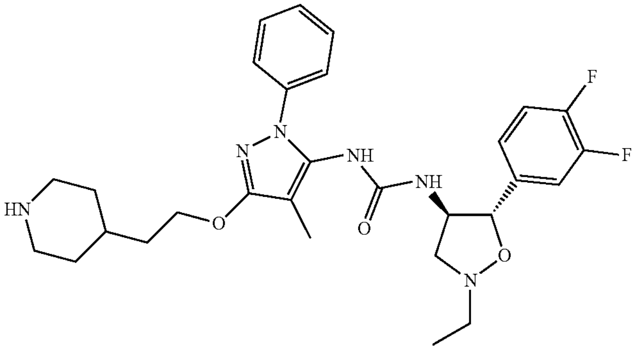 [SMILES: CCN1C[C@@H](NC(=O)Nc2c(C)c(OCCC3CCNCC3)nn2-c2ccccc2)[C@H](c2ccc(F)c(F)c2)O1] | 3 | 1.83 | 555 | racemate |
| I-672 | 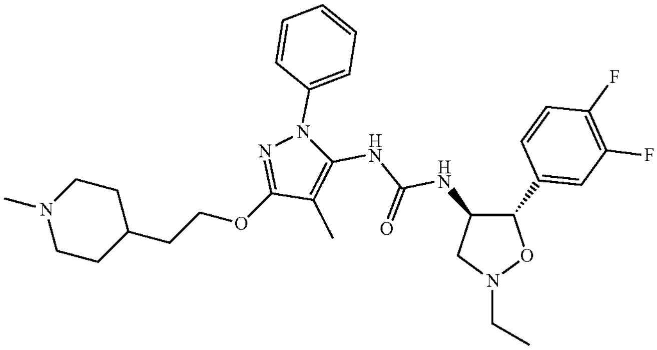 [SMILES: CCN1C[C@@H](NC(=O)Nc2c(C)c(OCCC3CCN(C)CC3)nn2-c2ccccc2)[C@H](c2ccc(F)c(F)c2)O1] | 3 | 1.76 | 569 | racemate |
| I-673 | 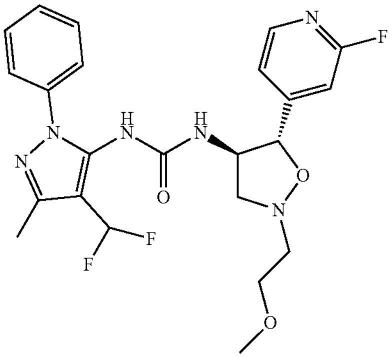 [SMILES: COCCN1C[C@@H](NC(=O)Nc2c(C(F)F)c(C)nn2-c2ccccc2)[C@H](c2ccnc(F)c2)O1] | 1 | 1.66 | 491.30 | racemate |

TABLE 149-continued
| No. | Structure | LCMS method No. | RT | MS (m/z) | configuration |
|---|---|---|---|---|---|
| I-674 | 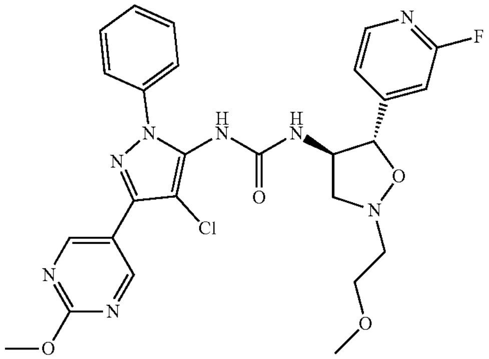 | 1 | 1.72 | 569.25 | racemate |
TABLE 150
| No. | Structure | LCMS method No. | RT | MS (m/z) | configuration |
|---|---|---|---|---|---|
| I-675 | 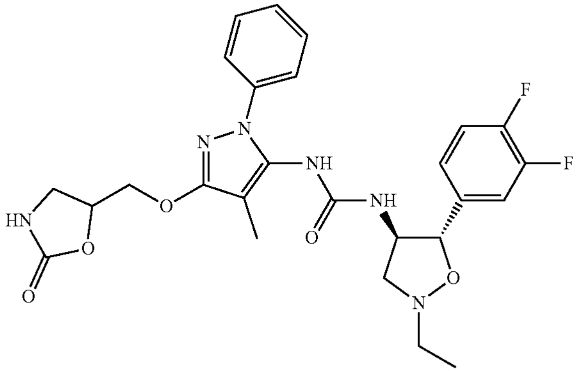 [SMILES: CCN1C[C@@H](NC(=O)Nc2c(C)c(OCC3CNC(=O)O3)nn2-c2ccccc2)[C@H](c2ccc(F)c(F)c2)O1] | 1 | 1.66 | 543.30 | diastereo mixture |
| I-676 | 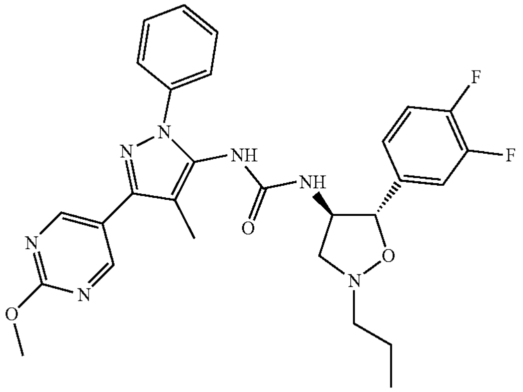 [SMILES: CCCN1C[C@@H](NC(=O)Nc2c(C)c(-c3cnc(OC)nc3)nn2-c2ccccc2)[C@H](c2ccc(F)c(F)c2)O1] | 3 | 2.25 | 550.00 | racemate |

TABLE 150-continued
| No. | Structure | LCMS method No. | RT | MS (m/z) | configuration |
|---|---|---|---|---|---|
| I-677 | 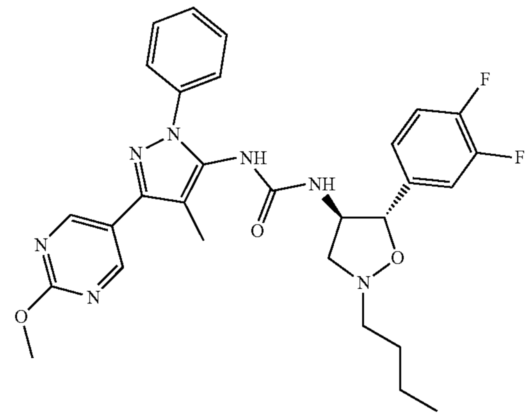 [SMILES: CCCCN1C[C@@H](NC(=O)Nc2c(C)c(-c3cnc(OC)nc3)nn2-c2ccccc2)[C@H](c2ccc(F)c(F)c2)O1] | 3 | 2.41 | 564.00 | racemate |
| I-678 | 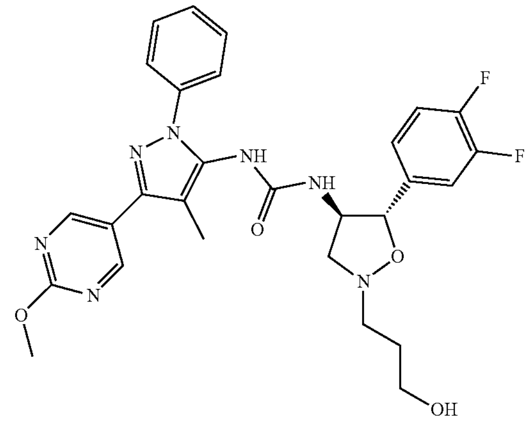 [SMILES: COc1ncc(-c2nn(-c3ccccc3)c(NC(=O)N[C@@H]3CN(CCCO)O[C@H]3c3ccc(F)c(F)c3)c2C)cn1] | 2 | 1.73 | 566.00 | racemate |
| I-679 | 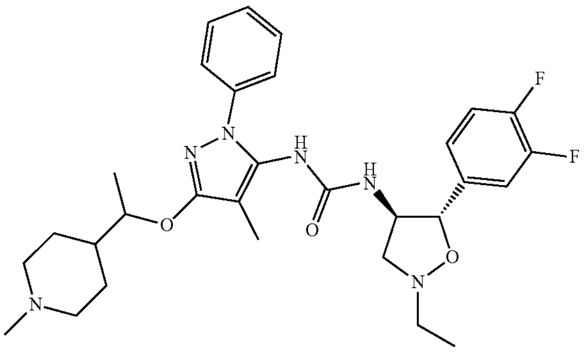 [SMILES: CCN1C[C@@H](NC(=O)Nc2c(C)c(OC(C)C3CCN(C)CC3)nn2-c2ccccc2)[C@H](c2ccc(F)c(F)c2)O1] | 3 | 2.03 | 569.00 | diastereo mixture |

TABLE 151

| No. | Structure | LCMS method No. | RT | MS (m/z) | configuration |
|---|---|---|---|---|---|
| I-680 | 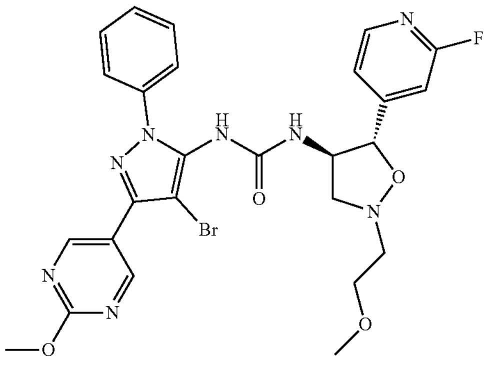 [SMILES: COCCN1C[C@@H](NC(=O)Nc2c(Br)c(-c3cnc(OC)nc3)nn2-c2ccccc2)[C@H](c2ccnc(F)c2)O1] | 1 | 1.73 | 613.20 | racemate |

Test Example 1: The Growth Inhibition Assay Using TF-1 Cells

To produce the stable cells expressing four types of NT receptors (TrkA, TrkB, TrkC and p75) highly and simultaneously, each human NT receptor gene was transfected by a retrovirus vector into human erythroleukemic cell line TF-1 cells (ATCC Number:CRL-2003). The inhibition assay against NGF, BDNF and NT-3 were done in TF-1 cells expressing TrkA+p75, TrkB+p75 and TrkC+p75, respectively. Two hundred nL per well of each compound (final concentration: 20 μmol/L-0.05 nmol/L) dissolved in DMSO was applied in a white 384 well flat-bottom plate. The cells were suspended in RPMI-1640 medium containing 10% fetal bovine serum and seeded in each well at 400 cells for the TF1 cells expressing TrkA and p75 or TrkC and p75, and 800 cells for the TF cells expressing TrkB and p75. Forty μL of human NGF (final concentration: 4 ng/mL), human BDNF (final concentration: 8 ng/mL) or human NT-3 (final concentration: 8 ng/mL) was added in each well and the plate was incubated for 3 days. Then, twenty μL of CellTiter-Glo reagent for CellTiter-Glo Luminescent Cell Viability Assay (manufactured by Promega) was added in each well and chemiluminescence was measured by a microplate reader to evaluate the growth of TF-1 cells. Luminescence value in the well incubated with or without each growth factor is 0% or 100% inhibition, respectively. The inhibitory activity of each compound was calculated by the following formula.

Inhibition (%)=(1−(luminescence value with compound−luminescence value of 100% inhibitory activity)/(luminescence value of 0% inhibitory activity−luminescence value of 100% inhibitory activity))×100

The 50% inhibitory concentration (IC50) was determined by the logistic regression using the inhibition data in 10 points of 3-fold dilution series at a compound concentration range of 20 μmol/L to 1 nmol/L or 10 points of 3-fold dilution series at a range of 1 μmol/L to 0.05 nmol/L.

Test Example 2: Human TrkA Inhibition Assay

Seven point five μL per well of human TrkA (PV3144, Lifetechnologies, final concentration: 1 nmol/L) suspended in the assay buffer (100 mmol/L 4-(2-hydroxyethyl)-1-piperazineethanesulfonic acid (HEPES), 10 mmol/L magnecium chloride, 0.003 vol % Brij-35, 0.004 vol % Tween20 and 1 mmol/L dithiothreitol (DTT)) was applied in a 384 well plate and the plate was pre-incubated for 15 min at room temperature with 0.4 μL of each compound (final concentration: 200 μmol/L-1 pmol/L) dissolved in DMSO. Then, fluorescent substrate (FL-peptide 27, 760424, PerkinElmer, final concentration: 1.5 μmol/L) and ATP (final concentration 500 μmol/L) dissolved in the assay buffer was added in each well. After the incubation of 120 min at 37° C., fifteen μL of termination buffer (100 mmol/L HEPES, 40 mmol/L ethylenediaminetetraacetic acid (EDTA), 10 mmol/L magnecium chloride, 0.003 vol % Brij-35, 0.004 vol % Tween20, 1 mmol/L DTT and 0.16 vol % Coating Reagent 3) was added in each well to stop the enzyme reaction. Fluorescent intensities (FI) of phosphorylated and non-phosphorylated fluorescent substrates were measured by LabChip EZReader II (Caliper LifeSciences, Inc.), and conversion ratio (CR) was calculated by the following formula-1. The CR in the well applied with DMSO alone was used as a negative control and the CR in the well without applying TrkA was used as a positive control. The inhibitory effect of each compound on TrkA phosphorylation was calculated by the following formula-2.

CR (%)=(FI of phosphorylated substrate/(FI of phosphorylated substrate+FI of non-phosphorylated substrate))×100 (Formula-1)

Phosphorylation inhibition (%)=(1−(CR with compound treatment−CR of positive control)/(CR of negative control−CR of positive control))×100 (Formula-2)

IC50 values (nmol/L) were determined by the logistic regression using the inhibition data in 10 points of 3-fold dilution series at a compound concentration range of 20 nmol/L to 1 pmol/L, or 10 points of 3-fold dilution series at the range of 2 μmol/L to 0.1 nmol/L, or 10 points of 3-fold dilution series at the range of 200 μmol/L to 10 nmol/L, or 15 points of 3-fold dilution series at the range of 200 μmol/L to 0.04 nmol/L.

(Result)

The evaluation results of the compounds in the present invention are indicated as follows. IC50 values of 0 to 100 nM, 100 to 1000 nM and over 1000 nM were shown as “A”, “B” and “C”, respectively.

IC50 values of the compounds in the present invention are as follows.

Compound I-1: 5200 nM,
Compound I-3: 120 nM,
Compound I-7: 6.1 nM,
Compound I-10: 170 nM,
Compound I-22: 0.81 nM,
Compound I-25: 2.9 nM,
Compound I-28: 2.5 nM,
Compound I-31: 0.78 nM,
Compound I-36: 1.4 nM,
Compound I-39: 0.48 nM,
Compound I-40: 1.6 nM,
Compound I-47: 4.0 nM,
Compound I-57: 2.2 nM,
Compound I-65: 0.92 nM,
Compound I-66: 1.6 nM,
Compound I-73: 1.2 nM,
Compound I-79: 1.5 nM,
Compound I-82: 22.0 nM,
Compound I-96: 15.0 nM,
Compound I-108: 1.0 nM,
Compound I-119: 4.0 nM,
Compound I-122: 2.7 nM,
Compound I-135: 0.52 nM,
Compound I-136: 30.0 nM,
Compound I-145: 0.87 nM,
Compound I-146: 330 nM,
Compound I-159: 2.1 nM,
Compound I-165: 5.3 nM,
Compound I-166: 4.8 nM,
Compound I-190: 2.1 nM,
Compound I-193: 4.0 nM,
Compound I-211: 1.5 nM,
Compound I-217: 4.6 nM,
Compound I-232: 4.2 nM,
Compound I-233: 1.5 nM,
Compound I-236: 1.4 nM,
Compound I-237: 8.1 nM,
Compound I-239: 3.8 nM,
Compound I-241: 3.2 nM,
Compound I-244: 17.0 nM,
Compound I-245: 3.0 nM,
Compound I-253: 1.3 nM,
Compound I-258: 0.48 nM,
Compound I-268: 0.55 nM,
Compound I-273: 4.7 nM,
Compound I-275: 3.0 nM,
Compound I-278: 3.7 nM,
Compound I-279: 2.0 nM,
Compound I-285: 2.7 nM,
Compound I-291: 2.0 nM,
Compound I-298: 0.6 nM,
Compound I-299: 2.1 nM,
Compound I-302: 8.2 nM,
Compound I-303: 1.5 nM,
Compound I-309: 2.0 nM,
Compound I-313: 3.6 nM,
Compound I-315: 0.76 nM,
Compound I-319: 1.2 nM,
Compound I-322: 2.4 nM,
Compound I-325: 2.5 nM,
Compound I-329: 1.7 nM,
Compound I-332: 1.2 nM,
Compound I-344: 0.97 nM,
Compound I-356: 1.5 nM,
Compound I-392: 6.8 nM, Compound I-406: 2.2 nM,
Compound I-413: 2.5 nM,
Compound I-431: 3.1 nM,
Compound I-436: 4.0 nM,
Compound I-458: 0.52 nM,
Compound I-508: 1.1 nM,
Compound I-0509: 1.3 nM,
Compound I-526: 22 nM,
Compound I-536: 4.0 nM,
Compound I-552: 1.7 nM,
Compound I-555: 0.93 nM,
Compound I-620: 6.8 nM,
Compound I-627: 4.8 nM,
Compound I-638: 1.4 nM,
Compound I-639: 0.52 nM,
Compound I-645: 68 nM,
Compound I-655: 5 nM,
Compound I-660: 70 nM,
Compound I-674: 5.8 nM.

TABLE 152

| No. | IC50_nM |
|---|---|
| I-2 | B |
| I-4 | A |
| I-5 | A |
| I-6 | A |
| I-8 | A |
| I-9 | A |
| I-11 | A |
| I-12 | A |
| I-13 | A |
| I-14 | A |
| I-15 | A |
| I-16 | A |
| I-17 | C |
| I-18 | A |
| I-19 | A |
| I-20 | A |
| I-21 | A |
| I-23 | A |
| I-24 | C |
| I-26 | A |
| I-27 | A |
| I-29 | A |
| I-30 | A |
| I-32 | A |
| I-33 | A |
| I-34 | A |
| I-35 | A |
| I-38 | C |
| I-41 | A |
| I-42 | A |
| I-43 | A |
| I-44 | A |

TABLE 153

| No. | IC50 (nM) |
|---|---|
| I-45 | A |
| I-46 | A |
| I-48 | A |
| I-49 | A |
| I-50 | A |
| I-51 | A |
| I-52 | A |
| I-53 | A |
| I-54 | A |
| I-55 | A |
| I-56 | A |
| I-58 | B |
| I-59 | A |

TABLE 153-continued

| No. | IC50 (nM) |
|---|---|
| I-60 | A |
| I-61 | A |
| I-62 | A |
| I-63 | A |
| I-64 | A |
| I-67 | A |
| I-68 | A |
| I-69 | A |
| I-70 | A |
| I-71 | A |
| I-72 | A |
| I-74 | A |
| I-75 | A |
| I-76 | A |
| I-77 | A |
| I-78 | A |
| I-80 | A |
| I-81 | A |
| I-83 | C |
| I-84 | A |
| I-85 | A |
| I-86 | A |
| I-87 | A |
| I-88 | C |
| I-89 | A |
| I-90 | A |
| I-91 | A |
| I-92 | A |
| I-93 | A |
| I-94 | C |
| I-95 | C |
| I-97 | A |
| I-98 | A |
| I-99 | A |
| I-100 | A |
| I-101 | A |
| I-102 | A |
| I-103 | A |
| I-104 | A |
| I-105 | A |
| I-106 | A |
| I-107 | A |
| I-109 | A |
| I-110 | A |
| I-111 | A |
| I-112 | A |
| I-113 | A |
| I-114 | A |
| I-115 | A |
| I-116 | A |
| I-117 | A |
| I-118 | A |
| I-120 | A |
| I-121 | A |
| I-123 | A |
| I-124 | A |
| I-125 | A |
| I-126 | A |
| I-127 | A |
| I-128 | A |
| I-129 | A |
| I-130 | C |
| I-131 | A |
| I-132 | A |
| I-133 | A |
| I-134 | A |
| I-137 | A |
| I-138 | A |
| I-139 | A |
| I-140 | A |
| I-141 | A |
| I-142 | A |
| I-143 | A |
| I-144 | A |
| I-147 | A |
| I-148 | A |
| I-149 | A |

TABLE 153-continued

| No. | IC50 (nM) |
|---|---|
| I-150 | A |
| I-151 | A |
| I-152 | A |
| I-153 | A |
| I-154 | A |
| I-155 | A |
| I-156 | A |
| I-157 | A |
| I-158 | A |
| I-160 | A |
| I-161 | A |
| I-162 | A |
| I-163 | A |
| I-164 | A |
| I-167 | A |
| I-168 | A |
| I-169 | A |
| I-170 | A |
| I-171 | A |
| I-172 | A |
| I-173 | A |
| I-174 | A |
| I-175 | A |
| I-176 | A |

TABLE 154

| No. | IC50 (nM) |
|---|---|
| I-177 | A |
| I-178 | A |
| I-179 | A |
| I-180 | A |
| I-181 | A |
| I-182 | A |
| I-183 | A |
| I-184 | A |
| I-185 | A |
| I-186 | A |
| I-187 | A |
| I-188 | A |
| I-189 | A |
| I-191 | A |
| I-192 | A |
| I-194 | A |
| I-195 | A |
| I-196 | A |
| I-197 | A |
| I-198 | A |
| I-199 | A |
| I-200 | A |
| I-201 | A |
| I-202 | B |
| I-203 | B |
| I-204 | B |
| I-205 | B |
| I-206 | B |
| I-207 | A |
| I-208 | A |
| I-209 | A |
| I-210 | A |
| I-212 | A |
| I-213 | A |
| I-214 | A |
| I-215 | A |
| I-216 | A |
| I-218 | A |
| I-219 | A |
| I-220 | A |
| I-221 | A |
| I-222 | A |
| I-223 | A |
| I-224 | A |

TABLE 154-continued

| No. | IC50 (nM) |
|---|---|
| I-225 | A |
| I-226 | A |
| I-227 | A |
| I-228 | A |
| I-229 | A |
| I-230 | A |
| I-231 | A |
| I-234 | A |
| I-235 | A |
| I-238 | A |
| I-240 | A |
| I-242 | A |
| I-243 | A |
| I-246 | A |
| I-247 | A |
| I-248 | A |
| I-249 | A |
| I-250 | A |
| I-251 | A |
| I-252 | A |
| I-254 | A |
| I-255 | A |
| I-256 | A |
| I-257 | A |
| I-259 | A |
| I-260 | A |
| I-261 | A |
| I-262 | A |
| I-263 | B |
| I-264 | A |
| I-265 | A |
| I-266 | A |
| I-267 | A |
| I-269 | A |
| I-270 | A |
| I-271 | A |
| I-272 | A |
| I-274 | A |
| I-276 | A |
| I-277 | A |
| I-280 | A |
| I-281 | A |
| I-282 | A |
| I-283 | A |
| I-284 | A |
| I-286 | A |
| I-287 | A |
| I-288 | A |
| I-289 | A |
| I-290 | A |
| I-292 | A |
| I-293 | A |
| I-294 | A |
| I-295 | B |
| I-296 | A |
| I-297 | A |
| I-300 | A |
| I-301 | A |
| I-304 | B |
| I-305 | A |
| I-306 | A |
| I-307 | A |
| I-308 | A |
| I-310 | A |
| I-311 | A |
| I-312 | A |
| I-314 | A |
| I-316 | A |
| I-317 | A |
| I-318 | A |

TABLE 155

| No. | IC50 (nM) |
|---|---|
| I-320 | A |
| I-321 | A |
| I-323 | A |
| I-324 | A |
| I-326 | A |
| I-327 | A |
| I-328 | A |
| I-330 | A |
| I-331 | A |
| I-333 | A |
| I-334 | A |
| I-335 | A |
| I-336 | A |
| I-337 | A |
| I-338 | A |
| I-339 | A |
| I-340 | A |
| I-341 | A |
| I-342 | A |
| I-343 | A |
| I-345 | A |
| I-346 | A |
| I-347 | A |
| I-348 | A |
| I-349 | A |
| I-350 | A |
| I-351 | A |
| I-352 | A |
| I-353 | A |
| I-354 | A |
| I-355 | A |
| I-357 | A |
| I-358 | A |
| I-359 | A |
| I-360 | A |
| I-361 | A |
| I-362 | C |
| I-363 | A |
| I-364 | A |
| I-365 | A |
| I-366 | A |
| I-367 | A |
| I-368 | A |
| I-369 | A |
| I-370 | A |
| I-371 | A |
| I-372 | A |
| I-373 | A |
| I-374 | A |
| I-375 | A |
| I-376 | A |
| I-377 | A |
| I-378 | A |
| I-379 | A |
| I-380 | A |
| I-381 | A |
| I-382 | A |
| I-383 | A |
| I-384 | A |
| I-385 | A |
| I-386 | C |
| I-387 | B |
| I-388 | C |
| I-389 | A |
| I-390 | A |
| I-391 | A |
| I-393 | A |
| I-394 | A |
| I-395 | A |
| I-396 | A |
| I-397 | A |
| I-398 | A |
| I-399 | A |
| I-400 | A |
| I-401 | A |
| I-402 | A |
| I-403 | A |
| I-404 | A |

TABLE 155-continued

| No. | IC50 (nM) |
|---|---|
| I-405 | A |
| I-407 | A |
| I-408 | A |
| I-409 | A |
| I-410 | A |
| I-411 | A |
| I-412 | A |
| I-414 | A |
| I-415 | A |
| I-416 | A |
| I-417 | A |
| I-418 | A |
| I-419 | A |
| I-420 | A |
| I-421 | A |
| I-422 | A |
| I-423 | A |
| I-424 | A |
| I-425 | A |
| I-426 | A |
| I-427 | A |
| I-428 | A |
| I-429 | A |
| I-430 | A |
| I-432 | A |
| I-433 | A |
| I-434 | A |
| I-435 | A |
| I-437 | A |
| I-438 | A |
| I-439 | A |
| I-440 | A |
| I-441 | B |
| I-442 | B |
| I-443 | A |
| I-444 | A |
| I-445 | A |
| I-446 | A |
| I-447 | A |
| I-448 | B |
| I-449 | A |
| I-450 | A |
| I-451 | A |
| I-452 | A |
| I-453 | A |
| I-454 | A |
| I-455 | A |
| I-456 | A |
| I-457 | A |
| I-459 | A |
| I-460 | A |
| I-461 | A |
| I-462 | A |
| I-463 | A |
| I-464 | A |
| I-465 | A |
| I-466 | A |
| I-467 | A |
| I-468 | A |
| I-469 | A |
| I-470 | A |
| I-471 | A |
| I-472 | A |
| I-473 | A |
| I-474 | B |
| I-475 | A |
| I-476 | A |
| I-477 | A |
| I-478 | A |
| I-479 | A |
| I-480 | A |
| I-481 | A |
| I-482 | A |
| I-483 | A |
| I-484 | A |
| I-485 | A |
| I-486 | A |
| I-487 | A |

TABLE 155-continued

| No. | IC50 (nM) |
|---|---|
| I-488 | A |
| I-489 | A |
| I-490 | A |
| I-491 | A |
| I-492 | C |
| I-493 | C |
| I-494 | C |
| I-495 | A |
| I-496 | A |
| I-497 | A |
| I-498 | A |
| I-499 | A |
| I-500 | A |
| I-501 | A |
| I-502 | A |
| I-503 | A |
| I-504 | A |
| I-505 | A |
| I-506 | A |
| I-507 | A |
| I-510 | A |
| I-511 | A |
| I-512 | A |
| I-513 | A |

TABLE 156

| No. | IC50 (nM) |
|---|---|
| I-514 | A |
| I-515 | A |
| I-516 | A |
| I-517 | A |
| I-518 | A |
| I-519 | A |
| I-520 | A |
| I-521 | A |
| I-522 | A |
| I-523 | A |
| I-524 | A |
| I-525 | A |
| I-527 | A |
| I-528 | A |
| I-529 | A |
| I-530 | A |
| I-531 | A |
| I-532 | A |
| I-533 | A |
| I-534 | A |
| I-535 | C |
| I-537 | A |
| I-538 | A |
| I-539 | A |
| I-540 | A |
| I-541 | A |
| I-542 | A |
| I-543 | A |
| I-544 | A |
| I-545 | A |
| I-546 | A |
| I-547 | A |
| I-548 | A |
| I-549 | A |
| I-550 | A |
| I-551 | A |
| I-553 | A |
| I-554 | A |
| I-556 | A |
| I-557 | A |
| I-558 | A |
| I-559 | A |
| I-560 | A |
| I-561 | A |
| I-562 | A |
| I-563 | A |

TABLE 156-continued

| No. | IC50 (nM) |
|---|---|
| I-564 | A |
| I-565 | A |
| I-566 | A |
| I-567 | A |
| I-568 | A |
| I-569 | A |
| I-570 | A |
| I-571 | A |
| I-572 | A |
| I-573 | A |
| I-574 | A |
| I-575 | A |
| I-576 | A |
| I-577 | A |
| I-578 | A |
| I-579 | A |
| I-580 | A |

TABLE 157

| No. | IC50 (nM) |
|---|---|
| I-581 | A |
| I-582 | A |
| I-583 | A |
| I-584 | A |
| I-585 | A |
| I-586 | A |
| I-587 | A |
| I-588 | A |
| I-589 | A |
| I-590 | A |
| I-591 | A |
| I-592 | A |
| I-593 | A |
| I-594 | A |
| I-595 | A |
| I-596 | A |
| I-597 | A |
| I-598 | A |
| I-599 | A |
| I-600 | A |
| I-601 | A |
| I-602 | A |
| I-603 | A |
| I-604 | A |
| I-605 | B |
| I-606 | A |
| I-607 | A |
| I-608 | A |
| I-609 | A |
| I-610 | A |
| I-611 | A |
| I-612 | A |
| I-613 | A |
| I-614 | A |
| I-615 | A |
| I-616 | A |
| I-617 | A |
| I-618 | A |
| I-619 | A |
| I-621 | C |
| I-622 | C |
| I-623 | B |
| I-624 | A |
| I-625 | A |
| I-626 | A |
| I-628 | A |
| I-629 | A |
| I-630 | A |
| I-631 | A |
| I-632 | B |
| I-633 | A |
| I-634 | A |

TABLE 157-continued

| No. | IC50 (nM) |
|---|---|
| I-635 | A |
| I-636 | A |
| I-637 | A |
| I-640 | B |
| I-641 | A |
| I-642 | B |
| I-643 | A |
| I-644 | A |
| I-646 | A |
| I-647 | A |
| I-648 | A |
| I-649 | A |
| I-650 | B |
| I-651 | A |
| I-652 | A |
| I-653 | A |
| I-654 | A |
| I-656 | B |
| I-657 | A |
| I-658 | A |
| I-659 | A |
| I-661 | A |
| I-662 | A |
| I-663 | A |
| I-664 | A |
| I-665 | A |
| I-666 | A |
| I-667 | A |
| I-668 | A |
| I-669 | A |
| I-670 | A |
| I-671 | A |
| I-672 | A |
| I-673 | B |
| I-675 | A |
| I-676 | A |
| I-677 | A |
| I-678 | B |
| I-679 | A |
| I-680 | A |

Test Example 3: hERG Test

For the purpose of assessing risk of an electrocardiogram QT interval prolongation of the compound of the present invention, effects of the compound of the present invention on delayed rectifier $K^+$ current ($I_{Kr}$), which plays an important role in the ventricular repolarization process, was studied using CHO cells expressing human ether-a-go-go related gene (hERG) channel.

After a cell was retained at a membrane potential of −80 mV by whole cell patch clamp method using an automated patch clamp system (QPatch; Sophion Bioscience A/S) and gave a leak potential of −50 mV, IKr induced by depolarization pulse stimulation at +20 mV for 2 seconds, and further, repolarization pulse stimulation at −50 mV for 2 seconds, was recorded. A vehicle, which is the 0.1-0.3% dimethyle sulfoxide solution in extracellular solution (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid): 10 mmol/L, pH7.4), or the compound of the present invention had been dissolved at an objective concentration in the extracellular solution is applied to the cell at room temperature for 7 minutes or more. From the recording $I_{Kr}$, an absolute value of the tail peak current was measured based on the current value at the resting membrane potential using analysis software (QPatch assay software; Sophion Bioscience A/S). Further, the % inhibition of tail peak current for the compound of the present invention relative to the tail peak current after application of the vehicle is calculated to assess influence of the compound of the present invention on $I_{Kr}$.

(Result) % inhibition was shown at 5 mol/L of test compound.

Compound I-4: 14.1%

Compound I-6: 8.9%

Compound I-7: 4.2%

Compound I-12: 17.6%

Test Example 4: CYP Inhibition Test

Using commercially available pooled human liver microsomes, an inhibitory degree of each metabolite production amount by the compound of the present invention is assessed as marker reactions of human main five CYP isoforms (CYP1A2, 2C9, 2C19, 2D6, and 3A4), 7-ethoxyresorufin O-deethylation (CYP1A2), tolbutamide methylhydroxylation (CYP2C9), mephenytoin 4'-hydroxylation (CYP2C19), dextromethorphan O-demethylation (CYP2D6), and terfenedine hydroxylation.

The reaction conditions are as follows: substrate, 0.5 μmol/L ethoxyresorufin (CYP1A2), 100 μmol/L tolbutamide (CYP2C9), 50 μmol/L S-mephenitoin (CYP2C19), 5 mol/L dextromethorphan (CYP2D6), 1 μmol/L terfenedine (CYP3A4); reaction time, 15 minutes; reaction temperature, 37° C.; enzyme, pooled human liver microsomes 0.2 mg protein/mL; concentrations of the compound of the present invention, 1.0, 5.0, 10, 20 μmol/L (four points).

Each five kinds of substrates, human liver microsomes, or compound of the present invention in 50 mmol/L Hepes buffer are added to a 96-well plate at the composition as described above, and NADPH, as a cofactor is added to initiate metabolism reactions. After the incubation at 37° C. for 15 minutes, a methanol/acetonitrile=1/1 (v/v) solution is added to stop the reaction. After the centrifugation at 3000 rpm for 15 minutes, resorufin (CYP1A2 metabolite) in the supernatant is quantified by a fluorescent multilabel counter or LC/MS/MS and hydroxytolbutamide (CYP2C9 metabolite), 4' hydroxymephenytoin (CYP2C19 metabolite), dextromethorphan (CYP2D6 metabolite), and terfenadine alcohol metabolite (CYP3A4 metabolite) are quantified by LC/MS/MS.

The sample adding only DMSO as a solvent to a reaction system instead of a solution dissolving a compound of the present invention is adopted as a control (100%). Remaining activity (%) is calculated and $IC_{50}$ is calculated by reverse presumption by a logistic model using a concentration and an inhibition rate.

Test Example 5: CYP3A4 (MDZ) MBI Test

CYP3A4 (MDZ) MBI test is a test of investigating mechanism based inhibition potential on CYP3A4 by the enhancement of inhibitory degree of a metabolic reaction caused by the compound of the present invention. CYP3A4 inhibition is evaluated using pooled human liver microsomes by 1-hydroxylation reaction of midazolam (MDZ) as a marker reaction.

The reaction conditions are as follows: substrate, 10 μmol/L MDZ; pre-reaction time, 0 or 30 minutes; substrate reaction time, 2 minutes; reaction temperature, 37° C.; protein content of pooled human liver microsomes, at pre-reaction time 0.5 mg/mL, at reaction time 0.05 pmg/mL (at 10-fold dilution); concentrations of the compound of the present invention, 1, 5, 10, 20 μmol/L (four points).

Pooled human liver microsomes and a solution of the compound of the present invention in K-Pi buffer (pH 7.4) as a pre-reaction solution are added to a 96-well plate at the composition of the pre-reaction. A part of pre-reaction solution is transferred to another 96-well plate, and 1/10 diluted by K-Pi buffer containing a substrate. NADPH as a co-factor is added to initiate a reaction as a marker reaction (preincubation 0 min). After a predetermined time of a reaction, methanol/acetonitrile=1/1 (v/v) solution is added to stop the reaction. In addition, NADPH is added to a remaining pre-reaction solution to initiate a pre-reaction (preincubation 30 min). After a predetermined time of a pre-reaction, a part is transferred to another 96-well plate, and 1/10 diluted by K-Pi buffer containing a substrate to initiate a reaction as a marker reaction. After a predetermined time of a reaction, methanol/acetonitrile=1/1 (v/v) solution is added to stop the reaction. After centrifuged at 3000 rpm for 15 minutes, 1-hydroxymidazolam in the supernatant is quantified by LC/MS/MS.

The sample adding DMSO as a solvent to a reaction system instead of a solution dissolving the compound of the present invention is adopted as a control (100%). Remaining activity (%) is calculated at each concentration of the compound of the present invention compared to a control, and IC value is calculated by reverse-presumption by a logistic model using a concentration and an inhibition rate. Shifted IC value is calculated as "IC of preincubation at 0 min/IC of preincubation at 30 min". When a shifted IC is 1.5 or more, this is defined as positive. When a shifted IC is 1.0 or less, this is defined as negative.

Test Example 6: BA Test

Materials and Methods for Experiments to Evaluate Oral Absorption (1) Experimental animals: SD rats are used.

(2) Rearing condition: SD rats are allowed free access to solid feed and sterilized tap water.

(3) Setting of dosage and grouping: Oral administration and intravenous administration are performed with the predetermined dosage. Grouping is set as below. (Dosage is changed per compound)

Oral administration 1 mg/kg or 2 μmol/kg (n=2)

Intravenous administration 0.5 mg/kg or 1 μmol/kg (n=2)

(4) Preparation of administration solutions: Oral administration is performed as suspension or solution by using 0.5% methylcellulose solution or dimethyl sulfoxide/0.5% methyl cellulose solution=1/4 solution. Intravenous administration is performed after solubilization by using dimethylacetamide/propylene glycol=1/1 or dimethyl sulfoxide/propylene glycol=1/1 as the solvent.

(5) Routes of administration: Oral administration is performed mandatory into the stomach by oral sonde. Intravenous administration is performed from caudal vein by syringes with needle.

(6) Evaluation items: Blood is collected serially and concentration of a compound of the present invention in plasma is measured by LC/MS/MS.

(7) Statistical analysis: About transition of concentration of a compound of the present invention in plasma, the area under the plasma concentration versus time curve (AUC) is calculated by non-linear least-squares method program, WinNonlin (a registered trademark), and bioavailability (BA) of a compound of the present invention is calculated from AUCs of the oral administration group and the intravenous administration group.

Test Example 7: Clearance Test

Materials and Methods for Experiments
(1) Experimental animals: SD rats were used.
(2) Rearing condition: SD rats were allowed free access to solid feed and sterilized tap water.
(3) Setting of dosage and grouping: Intravenous administration was performed with the predetermined dosage. Grouping was set as below. (Dosage is changed per compound) Intravenous administration 0.5 mg/kg or 1 μmol/kg (n=2)
(4) Preparation of administration solutions: Administration was performed after solubilization by using dimethylacetamide/propylene glycol=1/1 or dimethyl sulfoxide/propylene glycol=1/1 as the solvent.
(5) Routes of administration: Intravenous administration was performed from caudal vein by syringes with needle.
(6) Evaluation items: Blood was collected serially and concentration of a compound of the present invention in plasma was measured by LC/MS/MS.
(7) Statistical analysis: About transition of concentration of a compound of the present invention in plasma, Total Clearance (CLtot) of a compound of the present invention was calculated by non-linear least-squares method program, WinNonlin (a registered trademark).
(Result)
Compound I-12: 13.6 mL/min/kg
Compound I-19: 15.6 mL/min/kg
Compound I-040: 2.82 mL/min/kg
Compound I-057: 7.93 mL/min/kg
Compound I-090: 6.35 mL/min/kg
Compound I-275: 3.73 mL/min/kg Test Example 8: Fluctuation Ames Test Mutagenicity of Compounds of the Present Invention is Evaluated.

A 20 μL of freezing-stored *Salmonella typhimurium* (TA98 strain, TA100 strain) is inoculated on 10 mL of a liquid nutrient medium (2.5% Oxoid nutrient broth No. 2), and this is incubated at 37° C. for 10 hours under shaking. The 7.70 mL of TA98 culture medium is centrifuged (2000×g, 10 minutes) and TA98 is suspended in 7.70 mL Micro F buffer (K2HPO4: 3.5 g/L, KH2PO4: 1 g/L, (NH4)2SO4: 1 g/L, trisodium citrate dehydrate: 0.25 g/L, MgSO4.7H2O: 0.1 g/L) after removing the culture medium. The TA98 suspension is mixed with 120 mL Exposure medium (Micro F buffer containing Biotin: 8 μg/mL, histidine: 0.2 μg/mL, glucose: 8 mg/mL). The 3.42 mL of TA100 culture medium strain is mixed with 130 mL Exposure medium. Each 12 μL of DMSO solution of the compound of the present invention (several stage dilution from maximum dose 50 mg/mL at 2 to 3 fold ratio), DMSO as a negative control, and 50 μg/mL of 4-nitroquinoline 1-oxide DMSO solution for the TA98 strain and 0.25 μg/mL of 2-(2-furyl)-3-(5-nitro-2-furyl)acrylamide DMSO solution for the TA100 strain in the assay without metabolic activation, 40 μg/mL of 2-aminoanthracene DMSO solution for the TA98 strain and 20 μg/mL of 2-aminoanthracene DMSO solution for the TA100 strain in the assay with metabolic activation as a positive control, and 588 μL of the test bacterial suspension (498 μL and 90 μL of S9 mixture in the case of metabolic activation assay) are mixed, and this is incubated at 37° C. for 90 minutes under shaking. A 460 μL of the mixture is mixed with 2300 μL of Indicator medium (Micro F buffer containing 8 μg/mL biotin, 0.2 μg/mL histidine, 8 mg/mL glucose, 37.5 μg/mL bromocresol purple), each 50 μL is dispensed to microplate 48 wells/dose, and this is incubated at 37° C. for 3 days. Since the wells containing the bacteria which gained growth ability by point mutation in amino acid (histidine) synthesizing enzyme gene turns from purple to yellow due to a pH change, the number of yellow wells in 48 wells is counted per dose, and is compared with the negative control group. (−) and (+) means negative and positive in mutagenicity respectively.

Test Example 9: Metabolism Stability Test

Using commercially available pooled human hepatic microsomes, a compound of the present invention is reacted for a constant time, and a remaining rate is calculated by comparing a reacted sample and an unreacted sample, thereby, a degree of metabolism in liver is assessed.

A reaction is performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution is added to 100 μL of a methanol/acetonitrile=1/1 (v/v), mixed and centrifuged at 3000 rpm for 15 minutes. The compound of the present invention in the supernatant is quantified by LC/MS/MS or Solid Phase Extraction (SPE)/MS, and a remaining amount of the compound of the present invention after the reaction is calculated, letting a compound amount at 0 minute reaction time to be 100%.

Test Example 10: Powder Solubility Test

Appropriate quantity of the compound of the present invention is put in a suitable container and 200 μL of pH 4 citrate buffer (100 mmol/L citric acid monohydrate aqueous solution and 100 mmol/L trisodium citrate dihydrate aqueous solution are mixed in appropriate quantity to adjust pH to 4) or JP-2 fluid (1 volume of water is added to 1 volume of the solution in which 3.40 g of potassium dihydrogen phosphate and 3.55 g of anhydrous disodium hydrogen phosphate are dissolved in water to reach 1000 mL) is independently added to each container. When total amount is dissolved after adding the test reagent, the compound of the present invention is added appropriately. After sealing and shaking at 25° C. or 37° C. for 1 hour, solution is filtrated and 100 μL of methanol is added to 100 μL of each filtrate to dilute two-fold. The dilution rate is changed as necessary. After checking that there is no bubble and precipitate, the container is sealed and shaken. The compound of the present invention is measured using HPLC by absolute calibration curve method.

Test Example 11: Solubility Test

The solubility of the compound of the present invention is determined under 1% DMSO addition conditions. A 10 mmol/L solution of the compound is prepared with DMSO, and 2 μL of the solution of the compound of the present invention is added, respectively, to 198 μL of JP-2 fluid (see below). The mixture is shaked for 1 hour at a room temperature, and the mixture is filtered. The filtrate is ten or hundred-fold diluted with methanol/water=1/1(v/v) or acetonitrile/methanol/water=1/1/2(V/V/V) and the compound concentration in the filtrate is measured with LC/MS or Solid Phase Extraction (SPE)/MS by the absolute calibration method.

A: 3.40 g of potassium dihydrogen phosphate and 3.55 g of anhydrous disodium hydrogen phosphate is dissolved in water to reach 1000 mL.

B: 1 volume of water is added 1 volume of the solution that 3.40 g of potassium dihydrogen phosphate and 3.55 g of sodium dihydrogen phosphate anhydrous are dissolved in water to be 1000 mL.

Formulation Example

The following Formulation Examples are only exemplified and not intended to limit the scope of the invention.

Formulation Example 1: Tablets

The compounds of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2: Capsules

The compounds of the present invention, lactose and calcium stearate are mixed uniformly to obtain powder medicines in the form of powders or fine granules. The powder medicines are filled into capsule containers to give capsules.

Formulation Example 3: Granules

The compounds of the present invention, lactose and calcium stearate are mixed uniformly and the mixture is compressed and molded. Then, it is crushed, granulated and sieved to give suitable sizes of granules.

Formulation Example 4: Orally Disintegrating Tablets

The compounds of the present invention and crystalline cellulose are mixed, granulated and tablets are made to give orally disintegrating tablets.

Formulation Example 5: Dry Syrups

The compounds of the present invention and lactose are mixed, crushed, granulated and sieved to give suitable sizes of dry syrups.

Formulation Example 6: Injections

The compounds of the present invention and phosphate buffer are mixed to give injection.

Formulation Example 7: Infusions

The compounds of the present invention and phosphate buffer are mixed to give injection.

Formulation Example 8: Inhalations

The compound of the present invention and lactose are mixed and crushed finely to give inhalations.

Formulation Example 9: Ointments

The compounds of the present invention and petrolatum are mixed to give ointments.

Formulation Example 10: Patches

The compounds of the present invention and base such as adhesive plaster are mixed to give patches.

INDUSTRIAL APPLICABILITY

The compound of the present invention has TrkA inhibitory activity and it can be useful for a TrkA mediated disorder such as pain associated with osteoarthritis, rheumatoid arthritis, fracture, interstitial cystitis, chronic pancreatitis and prostate inflammation; and nociceptive pain as typified by chronic low back pain, diabetic peripheral neuropathy pain, postoperative pain, pelvic pain and cancer pain; neuropathic pain, acute pain, chronic pain, cancer, inflammatory disease, allergic disease, dermatological disease and the like.

What is claimed is:

1. A compound represented by Formula (I):

(I)

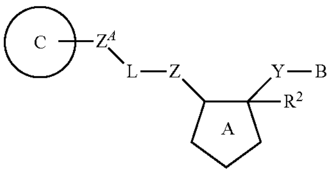

wherein the group represented by Formula:

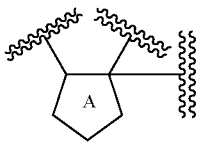

is a group represented by Formula:

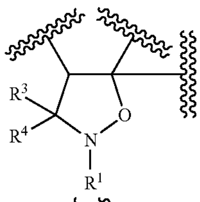
,
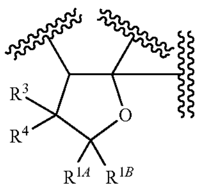
,
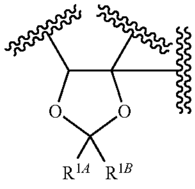
,
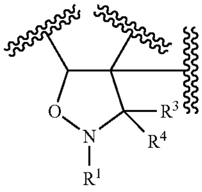
,

-continued

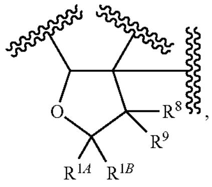

,

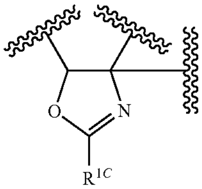

or

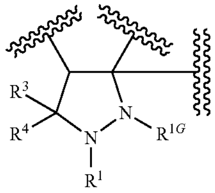

wherein $R^1$ is a hydrogen atom, cyano, substituted or unsubstituted alkyl, substituted or unsubstituted alkenyl, substituted or unsubstituted acyl, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

each of $R^{1A}$ and $R^{1C}$ is substituted or unsubstituted alkyl, substituted or unsubstituted alkenyl, substituted or unsubstituted acyl, substituted or unsubstituted alkyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted amino, substituted or unsubstituted alkyl sulfonyl, substituted or unsubstituted alkenylsulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, carboxy, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{1B}$ is a hydrogen atom, hydroxy, halogen, substituted or unsubstituted alkyl, substituted or unsubstituted alkenyl, substituted or unsubstituted acyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or $R^{1A}$ and $R^{1B}$ may be taken together to form a group represented by $=CR^{1D}R^{1E}$, a group represented by $=N—O—R^{1F}$, a substituted or unsubstituted non-aromatic carbocycle, or a substituted or unsubstituted non-aromatic heterocycle;

$R^{1D}$ and $R^{1E}$ are each independently hydrogen, substituted or unsubstituted alkyl, substituted or unsubstituted alkyloxy, or substituted or unsubstituted alkyloxycarbonyl;

$R^{1F}$ is a hydrogen atom, substituted or unsubstituted alkyl, substituted or unsubstituted alkenyl, or substituted or unsubstituted alkynyl;

$R^{1G}$ is a hydrogen atom or substituted or unsubstituted alkyl;

$R^3$ and $R^4$ are each independently a hydrogen atom, substituted or unsubstituted alkyl, substituted or unsubstituted alkenyl, substituted or unsubstituted alkynyl, substituted or unsubstituted alkyloxycarbonyl, or substituted or unsubstituted carbamoyl;

$R^8$ is a hydrogen atom, halogen, hydroxy, substituted or unsubstituted alkyl, substituted or unsubstituted alkenyl, substituted or unsubstituted alkynyl, or substituted or unsubstituted alkyloxy; and $R^9$ is a hydrogen atom, halogen, hydroxy, substituted or unsubstituted alkyl, substituted or unsubstituted alkenyl, substituted or unsubstituted alkynyl, or substituted or unsubstituted alkyloxy, or $R^8$ and $R^9$ may be taken together to form oxo;

-L- is $—C(=X)—$ or $—SO_2—$;

$=X$ is $=O$, $=S$, $=NR^{10}$ or $=CR^{11}R^{12}$;

$—Z—$ is $—NR^5—$, $—O—$ or $—CR^6R^7—$;

$—Z^A—$ is $—NR^{5A}—$ or $—CR^{6A}R^{7A}—$;

$—Y—$ is a single bond;

B is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

the ring C is a substituted or unsubstituted aromatic heterocycle or a substituted or unsubstituted non-aromatic heterocycle;

$R^2$ is a hydrogen atom, substituted or unsubstituted alkyl, substituted or unsubstituted alkyloxy, cyano, carboxy, substituted or unsubstituted alkyloxycarbonyl, substituted or unsubstituted carbamoyl, halogen or hydroxy;

$R^5$ and $R^{5A}$ are each independently a hydrogen atom or substituted or unsubstituted alkyl;

$R^6$, $R^{6A}$, $R^7$ and $R^{7A}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, or substituted or unsubstituted amino;

$R^{10}$ is substituted or unsubstituted alkyl, substituted or unsubstituted acyl, substituted or unsubstituted alkyloxycarbonyl, substituted or unsubstituted alkylsulfonyl, nitro, substituted or unsubstituted alkyloxy, or hydroxy;

$R^{11}$ is a hydrogen atom, cyano, substituted or unsubstituted acyl, substituted or unsubstituted alkyloxycarbonyl, substituted or unsubstituted carbamoyl, substituted or unsubstituted alkylsulfonyl, or nitro; and $R^{12}$ is a hydrogen atom or cyano;

provided that the ring C is not

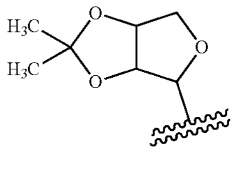

when —Z— is —O—, -L is —C(═O)—, and —$Z^A$— is —$CH_2$—, or a pharmaceutically acceptable salt thereof.

2. The compound according to claim 1, wherein —Y— is a single bond, -L- is —C(═X)—, and $R^1$ is cyano, substituted or unsubstituted alkyl, substituted or unsubstituted alkenyl, substituted or unsubstituted acyl, substituted or unsubstituted alkylsulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

3. The compound according to claim 2, wherein —Z— is —$NR^5$— or —$CR^6R^7$—, or a pharmaceutically acceptable salt thereof.

4. The compound according to claim 3, wherein —Z— is —$NR^5$—, -L- is —C(═O)—, and —$Z^A$— is —$NR^{5A}$—, or a pharmaceutically acceptable salt thereof.

5. The compound according to claim 4, wherein each of $R^5$ and $R^{5A}$ is a hydrogen atom, or a pharmaceutically acceptable salt thereof.

6. The compound according to claim 2, wherein B is substituted or unsubstituted aromatic carbocyclyl or substituted or unsubstituted aromatic heterocyclyl, or a pharmaceutically acceptable salt thereof.

7. The compound according to claim 2, wherein $R^2$ is a hydrogen atom or substituted or unsubstituted alkyl, or a pharmaceutically acceptable salt thereof.

8. The compound according to claim 2, wherein the group represented by Formula:

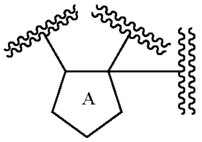

is represented by Formula:

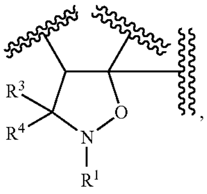
,
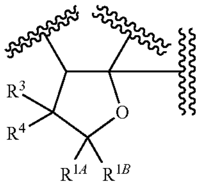
or

-continued

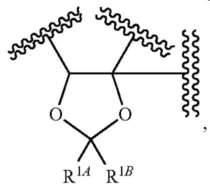
, wherein $R^1$, $R^{1A}$, $R^{1B}$, $R^3$ and $R^4$ are the same as claim 1, or a pharmaceutically acceptable salt.

9. The compound according to claim 2, wherein $R^1$ is substituted or unsubstituted alkyl, $R^{1A}$ is substituted or unsubstituted alkyl, and $R^{1B}$ is a hydrogen atom, or a pharmaceutically acceptable salt.

10. The compound according to claim 2, wherein each of $R^3$ and $R^4$ is a hydrogen atom, or a pharmaceutically acceptable salt.

11. The compound according to claim 2, wherein the ring C is a substituted or unsubstituted aromatic heterocycle, or a pharmaceutically acceptable salt thereof.

12. The compound according to claim 2, wherein the ring C is substituted or unsubstituted pyrazole, or a pharmaceutically acceptable salt thereof.

13. The compound according to claim 12, wherein the ring C is a ring represented by Formula:

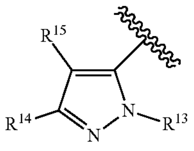

wherein $R^{13}$ is a hydrogen atom, substituted or unsubstituted alkyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

$R^{14}$ is a hydrogen atom, hydroxy, halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted carbamoyl, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl; and $R^{15}$ is a hydrogen atom, halogen, cyano, substituted or unsubstituted alkyl, substituted or unsubstituted alkyloxy, substituted or unsubstituted alkenyloxy, substituted or unsubstituted alkynyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl; or $R^{14}$ and $R^{15}$ are taken together to form a substituted or unsubstituted aromatic carbocycle, a substituted or unsubstituted aromatic heterocycle, a substituted or unsubstituted non-aromatic carbocycle, or a substituted or unsubstituted non-aromatic heterocycle, or a pharmaceutically acceptable salt thereof.

14. The compound according to claim 13, wherein $R^{13}$ is substituted or unsubstituted aromatic carbocyclyl, substituted or unsubstituted alkyl, or substituted or unsubstituted non-aromatic carbocyclyl, $R^{14}$ is substituted or unsubstituted aromatic heterocyclyl, substituted or unsubstituted alkyloxy, substituted or unsubstituted aromatic carbocyclyl, or substituted or unsubstituted non-aromatic heterocyclyl, and $R^{15}$ is a hydrogen atom or substituted or unsubstituted alkyl, or a pharmaceutically acceptable salt thereof.

15. The compound according to claim 1, wherein the compound is selected from the group consisting of,

I-65

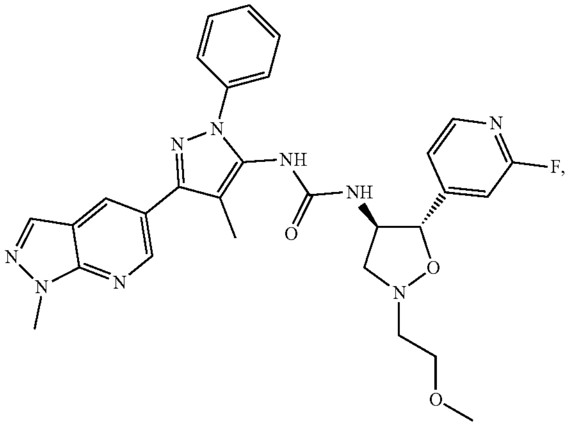

-continued

I-211

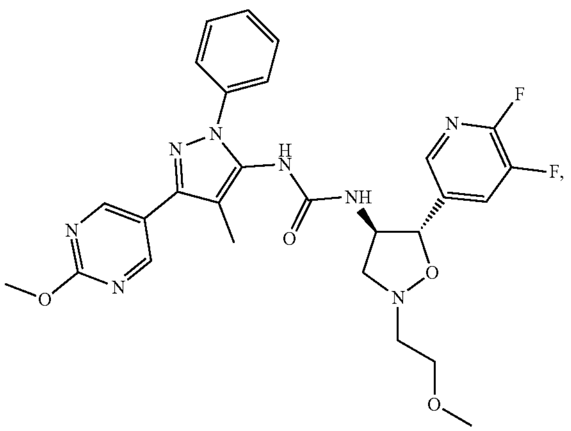

I-236

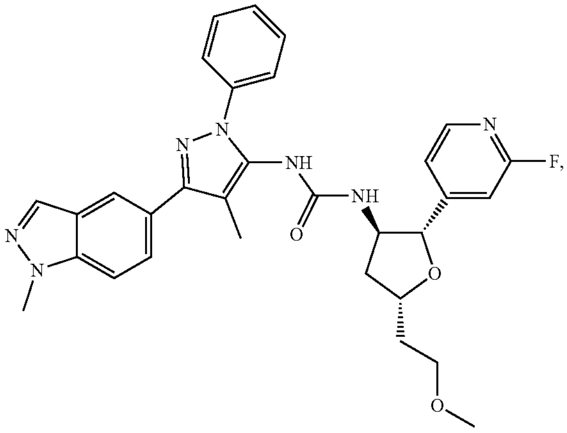

I-237

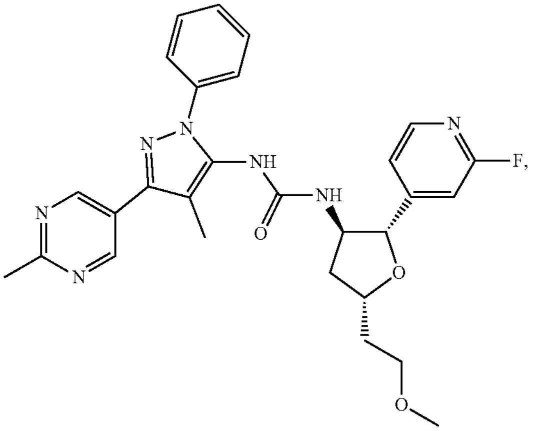

-continued

I-319

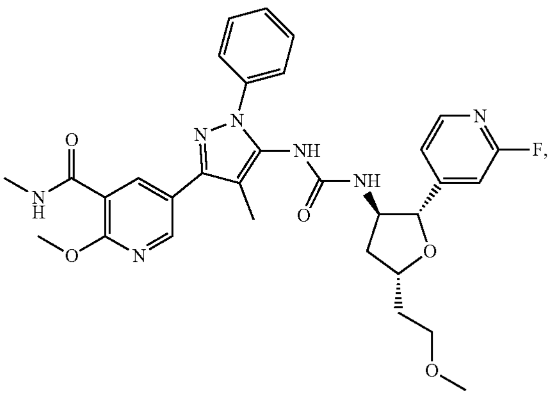

I-325

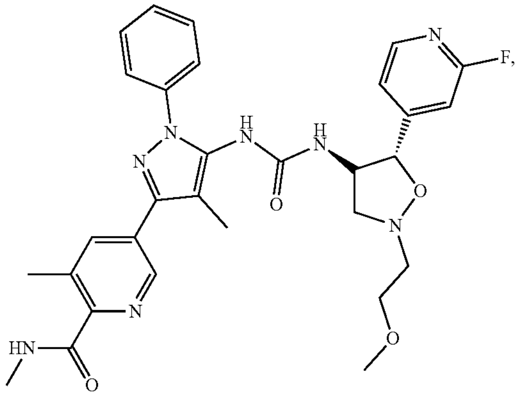

I-536

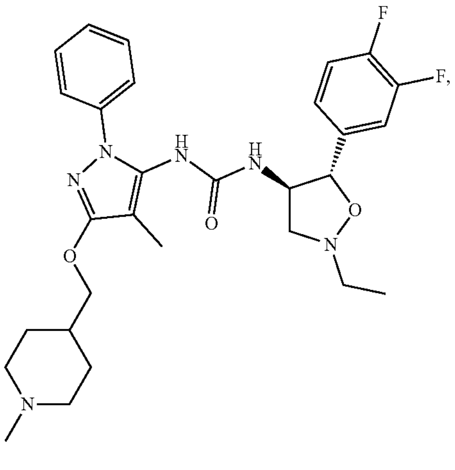

-continued

I-551

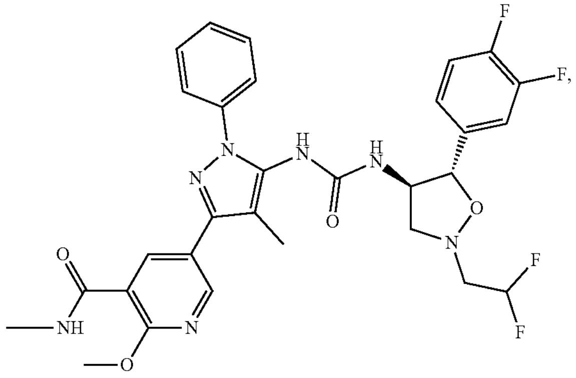

I-556

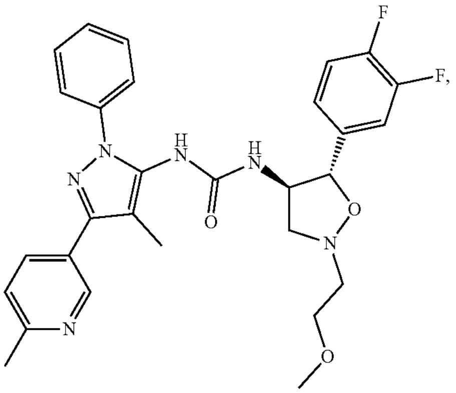

and

I-558

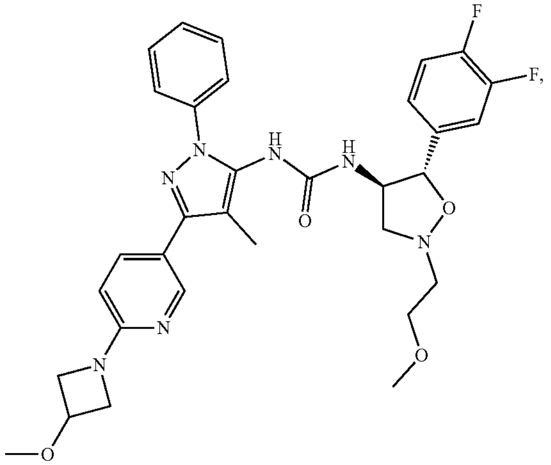

or a pharmaceutically acceptable salt thereof.

16. A pharmaceutical composition comprising the compound according claim 1, or a pharmaceutically acceptable salt thereof.

17. A method for treating a disease related to TrkA comprising administering the compound according to claim 1, or a pharmaceutically acceptable salt thereof, wherein the disease related to TrkA is one or more of pain associated with osteoarthritis, rheumatoid arthritis, fracture, interstitial cystitis, chronic pancreatitis and prostate inflammation; nociceptive pain as typified by chronic low back pain, diabetic peripheral neuropathy pain, postoperative pain, pelvic pain and cancer pain; neuropathic pain; acute pain;

chronic pain; cancer; an inflammatory disease; an allergic disease; or a dermatological disease.

18. The compound according to claim 2, wherein the group represented by Formula:

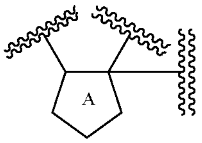

is represented by Formula:

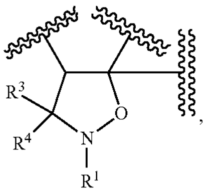

wherein $R^1$, $R^3$ and $R^4$ are the same as claim 1, or a pharmaceutically acceptable salt.

19. The compound according to claim 13, wherein the group represented by Formula:

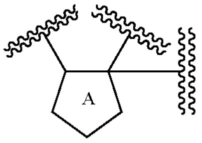

is represented by Formula:

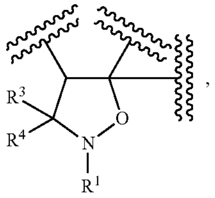

wherein $R^1$ is substituted or unsubstituted alkyl;

each of $R^3$ and $R^4$ is a hydrogen atom;

L- is —C(=O)—;

each of —Z— and —$Z^A$— is —NH—;

—Y— is a single bond;

B is substituted or unsubstituted aromatic carbocyclyl or substituted or unsubstituted aromatic heterocyclyl; and $R^2$ is a hydrogen atom, or a pharmaceutically acceptable salt.

20. The compound according to claim 14, wherein the group represented by Formula:

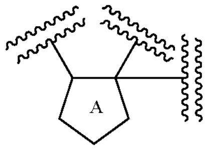

is represented by Formula:

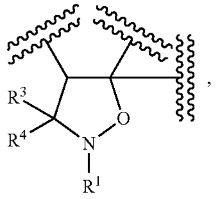

wherein $R^1$ is substituted or unsubstituted alkyl;

each of $R^3$ and $R^4$ is a hydrogen atom;

-L- is —C(=O)—;

each of —Z— and —$Z^A$— is —NH—;

—Y— is a single bond;

B is substituted or unsubstituted phenyl or substituted or unsubstituted pyridyl; and $R^2$ is a hydrogen atom, or a pharmaceutically acceptable salt.

* * * * *